US007560463B2

(12) United States Patent
Mitch et al.

(10) Patent No.: US 7,560,463 B2
(45) Date of Patent: Jul. 14, 2009

(54) DIARYL ETHERS AS OPIOID RECEPTOR ANTAGONISTS

(75) Inventors: Charles Howard Mitch, Columbus, IN (US); Michael Angelo Statnick, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/052,994

(22) Filed: Mar. 21, 2008

(65) Prior Publication Data

US 2008/0255152 A1 Oct. 16, 2008

Related U.S. Application Data

(63) Continuation of application No. 10/526,960, filed as application No. PCT/US2003/026300 on Sep. 17, 2003, now Pat. No. 7,381,719.

(60) Provisional application No. 60/412,158, filed on Sep. 19, 2002.

(51) Int. Cl.
*A61K 31/4965* (2006.01)
(52) U.S. Cl. .................................. 514/255.05
(58) Field of Classification Search ............... None
See application file for complete search history.

(56) References Cited

U.S. PATENT DOCUMENTS

| | | | |
|---|---|---|---|
| 4,191,771 A | 3/1980 | Zimmerman | |
| 4,891,379 A | 1/1990 | Zimmerman et al. | |
| 6,140,352 A | 10/2000 | Crowell et al. | |
| 6,436,959 B1 | 8/2002 | Carson et al. | |
| 7,196,100 B2 | 3/2007 | Benesh et al. | |
| 7,288,543 B2 | 10/2007 | Broughton et al. | |
| 7,378,448 B2 | 5/2008 | Mitch et al. | |
| 7,381,750 B2 | 6/2008 | De La Torre et al. | |
| 7,396,943 B2 | 7/2008 | Benesh et al. | |
| 7,399,774 B2 | 7/2008 | Siegel et al. | |
| 7,414,132 B2 | 8/2008 | Le La Torre et al. | |
| 2007/0155793 A1 | 7/2007 | Benesh | |

FOREIGN PATENT DOCUMENTS

| | | |
|---|---|---|
| EP | 0 921 120 | 9/1999 |
| EP | 0 827 746 | 4/2002 |
| WO | WO 97/10825 | 3/1997 |
| WO | WO 99/67204 | 12/1999 |
| WO | WO 00/40560 | 7/2000 |
| WO | WO 02/06276 | 1/2002 |
| WO | WO 02/38544 | 5/2002 |
| WO | WO 02/078693 | 10/2002 |

OTHER PUBLICATIONS http://content.nejm.org/cgi/reprint/358/16/1692.pdf, last accessed Jul. 31, 2008.*

Wentland, et al., "8-Carboxamidocyclazocine Analogues: Redefining the Structure-Activity Relationships of 2,6-Methano-3-Benzazocines," *Bioorganic & Medicinal Chemistry Letters*, vol. 11, pp. 623-626 (2001).

Wentland, et al., "3-Carboxamido Analogues of Morphine and Naltrexone: Synthesis and Opioid Receptor Binding Properties," *Bioorganic & Medicinal Chemistry Letters*, vol. 11, pp. 1717-1721 (2001).

McGraw-Hill, "Opioid Analgesics and Antagonists," *Goodman & Gilmans's The Pharmacological Basis of Therapeutics*, Ninth Edition, Chapter 23, pp. 521-555 (1996).

Michael Camilleri, "Serotonergic drugs: emerging therapies for IBS," *Management and Pharmacological Therapy of IBS*, Section 5, Chapter 19, pp. 179-190.

Roy, et al., "μ-Opioid receptor-knockout mice: the role of μ-opioid receptor in gastrointestinal transit," *Molecular Brain Research*, vol. 56, pp. 281-283 (1998).

Yuan, et al., "Effects of intravenous methylnaltrexone on opioid-induced gut motility and transit time changes in subjects receiving chronic methadone therapy: a pilot study," *Pain*, vol. 83, pp. 631-635 (1999).

Yuan, et al., "Methylnaltrexone for Reversal of Constipation Due to Chronic Methadone Use," *JAMA*, vol. 283, No. 3, pp. 367-372 (2000).

Schmidt, et al., "Alvimopan (ADL 8-2698) Is a Novel Peripheral Opioid Antagonist," *The American Journal of Surgery*, vol. 182, 27s-38S (2001).

Zimmerman, et al., "Discovery of a Potent, Peripherally Selective trans-3,4-Dimethyl-4-(3-hydroxyphenyl)piperidine Opioid Antagonist for the Treatment of Gastrointestinal Motility Disorders," *J. Med. Chem.*, vol. 37, pp. 2262-2265 (1994).

Broccardo, et al., "Antidiarrheal and colonic antipropulsive effects of spinal and supraspinal adminstration of the natural δ opioid receptor agonist, [D-Ala$^2$]deltorphin II, in the rat," *European Journal of Pharmacology*, vol. 218, pp. 69-73 (1992).

Chamouard, et al., "δ-Opioid receptor agonists inhibit neuromuscular transmission in human colon," *European Journal of Pharmacology*, vol. 262, pp. 33-39 (1994).

Riviere, "Peripheral kappa-opioid agonists for visceral pain," *British Journal of Pharmacology*, vol. 141, pp. 1331-1334 (2004).

Riviere, et al., "Fedotozine Reverses Ileus Induced by Surgery or Peritonitis: Action at Peripheral κ-Opioid Receptors," *Gastroenterology*, vol. 104, pp. 724-731 (1993).

Kariv, et al., "Low-Dose Naltrexone for the Treatment of Irritable Bowel Syndrome," *AJG*, vol. 98, No. 9, Supplement (2003); S268 Abstracts.

Zimmerman, et al., "LY246736 Dihydrate," *Drugs of the Future*, vol. 19, No. 12, pp. 1078-1083 (1994).

* cited by examiner

*Primary Examiner*—James O Wilson
*Assistant Examiner*—Jeffrey H Murray
(74) *Attorney, Agent, or Firm*—John C. Demeter; Francis O. Ginah

(57) ABSTRACT

Compound 5-(2-Methoxy-4-{[2-(tetrahydro-pyran-4-yl)-ethylamino]-methyl}-phenoxy)-pyrazine-2-carboxamide or a pharmaceutically acceptable salt thereof, useful for the treatment of irritable bowel syndrome.

2 Claims, No Drawings

DIARYL ETHERS AS OPIOID RECEPTOR ANTAGONISTS

This application is a continuation of U.S. patent application Ser. No. 10/526,960, filed Mar. 3, 2005 now U.S. Pat. No. 7,381,719, which is a national phase application under 35 U.S.C. Section 371 for PCT/US2003/026300, filed Sep. 17, 2003, which claims the benefit under 35 U.S.C. Section 119 (e) of U.S. provisional patent application 60/412,158, filed Sep. 19, 2002.

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure:

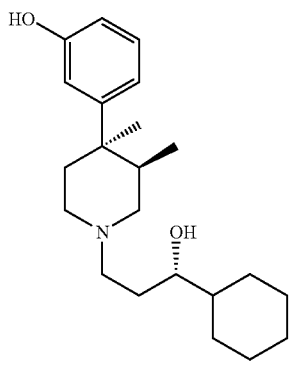

U.S. Pat. No. 4,191,771 also disclosed compounds useful as opioid antagonists. Also, bicyclic analogs of phenyl piperidine have been prepared and reported as opioid antagonists in Wentland, et al., Biorganic and Medicinal Chemistry Letters 11 (2001) 623-626; see also Wentland, et al., Bioorganic and Medicinal Chemistry Letters 11 (2001) 1717-1721. Finally, European Patent application number EP 1 072592A2 filed May 18, 2000, discloses phenylpiperidine compounds of formula 1

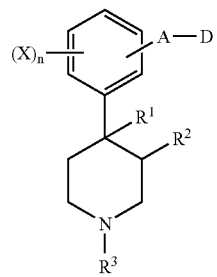

wherein A, D, $R^1$, $R^2$, $R^3$, X, and n have meanings given in the description, which are useful in the prophylaxis and in the treatment of diseases mediated by opioid receptors such as pruritus.

U.S. Pat. No. 6,140,352 and related patents disclose the compound of formula Formula 1

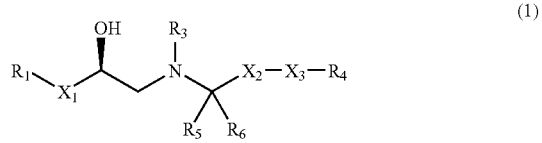

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

Regardless of these and other disclosures of compounds useful as opioid receptor antagonists, or useful for the treatment of obesity, and/or diabetes by other mechanisms, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula (I)

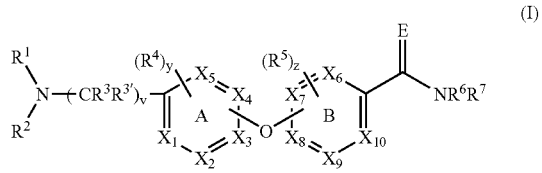

wherein each of $X_1$, $X_2$, $X_3$, $X_4$, $X_5$, $X_6$, $X_7$, $X_8$, $X_9$ and $X_{10}$ is C, CH, or N; provided that each of rings A or B has no more than 2 nitrogen atoms, E is O or NH;

v is 1, 2, or 3;

$R^1$ and $R^2$ are independently selected from hydrogen, $C_1$-$C_8$ alkyl, $C_2$-$C_8$ alkenyl, $C_2$-$C_8$ alkynyl, aryl, $C_3$-$C_8$ cycloalkyl, —$C_1$-$C_{10}$ alkylaryl, heterocyclyl, —$C_1$-$C_{10}$ alkylheterocyclic, -arylheterocyclyl, —$C_3$-$C_8$ cycloalkylheterocyclyl, —$C_1$-$C_8$ alkylC(O)$C_1$-$C_8$ alkyl, aryl C(O) $C_1$-$C_8$ alkyl-, $C_3$-$C_8$ cycloalkylC(O)(CH$_2$)$_n$—, —$C_2$-$C_8$ alkylCH(OH)aryl, —$C_2$-$C_8$alkylCH(OH)cycloalkyl, —$C_2$-$C_8$ alkylCH(OH)heterocyclyl $C_2$-$C_8$ alkylCH(OH) aryl —$C_1$-$C_8$ alkylC(O)heterocyclic, —$C_1$-$C_8$ alkylC(O) aryl, aryloxy$C_1$-$C_8$ alkyl-, benzhydryl, fused bicyclic, $C_1$-$C_8$ alkylfused bicyclic, phenylC(O)—, phenylC(O)$C_1$-$C_8$ alkyl-, $C_1$-$C_8$ alkoxy$C_1$-$C_8$ alkyl-, —CO(O)$C_1$-$C_8$alkyl, —SO$_2$$C_1$-$C_8$alkyl, —SO$_2$$C_1$-$C_{10}$ alkylaryl, —SO$_2$$C_1$-$C_8$ alkylheterocyclic, —$C_1$-$C_8$ alkylcycloalkyl, —(CH$_2$)$_n$C(O)OR$^8$, —(CH$_2$)$_n$C(O)R$^8$, —(CH$_2$)$_m$C(O)NR$^8$R$^8$, and —(CH$_2$)$_m$NSO$_2$R$^8$; wherein each of the alkyl, alkenyl, cycloalkyl, heterocyclic, and aryl groups are optionally substituted with one to five groups independently selected from halo, $C_1$-$C_8$ haloalkyl, $C_1$-$C_8$ thioalkyl, $C_1$-$C_8$ alkyl, $C_2$-$C_8$ alkenyl, aryl, —$C_1$-$C_8$ alkylaryl, —C(O)$C_1$-$C_8$ alkyl, —CO(O)$C_1$-$C_8$ alkyl, —SO$_2$$C_1$-$C_8$ alkyl, —SO$_2$$C_1$-$C_8$ alkylaryl, —SO$_2$$C_1$-$C_8$ alkylheterocyclic, —$C_1$-$C_8$ alkylcycloalkyl, —(CH$_2$)$_n$C(O)OR$^8$, —(CH$_2$)$_n$C(O)R$^8$; and wherein $R^1$ and $R^2$ may optionally combine with each other, or with 1, or 2 atoms adjacent to the nitrogen atom to form a 4, 5, 6, or 7-membered nitrogen-containing heterocycle which nitrogen-containing heterocycle may further have substituents selected from the group consisting of amino, $C_1$-$C_8$ alkyl, $C_2$-$C_8$ alkenyl, $C_2$-$C_8$ alkynyl, aryl, $C_1$-$C_8$ alkylaryl, —C(O)$C_1$-$C_8$ alkyl, —CO(O)$C_1$-$C_8$ alkyl, halo, oxo, $C_1$-$C_8$ haloalkyl; and wherein $R^1$ and $R^2$ may independently attach to the A ring to form a 4, 5, 6, or 7-member nitrogen-containing bicyclic heterocycle which nitrogen-containing bicyclic heterocycle may further have substituents selected from the group consisting of oxo, amino, —$C_1$-$C_8$ alkyl, —$C_2$-$C_8$ alkenyl, —$C_2$-$C_8$ alkynyl, aryl, —$C_1$-$C_8$ alkylaryl, —C(O)$C_1$-$C_8$ alkyl, —CO(O)$C_1$-$C_8$ alkyl, halo, and $C_1$-$C_8$ haloalkyl; and wherein $R^1$ and $R^2$ are not simultaneously hydrogen; and provided that when v is 2, and $R^3$ and $R^{3'}$ are both hydrogen or CH$_3$, and both A and B rings are phenyl, then the group —NR$^1$R$^2$ is not equal to —NHCH$_2$Phenyl; and further provided that when one of $R^1$ or $R^2$ is —CH$_2$CH$_2$-optionally substituted phenyl or —CH$_2$CH$_2$-optionally substituted naphthyl, or —Cl$_2$CH$_2$-optionally substituted 5 or 6 member monocyclic heterocyclic aromatic, and v is 1, and both A and B rings are phenyl, then $R^6$ and $R^7$ are not simultaneously hydrogen;

$R^3$ and $R^{3'}$ are each independently selected from hydrogen, $C_1$-$C_8$ alkyl, $C_2$-$C_8$ alkenyl, $C_2$-$C_8$ alkynyl, aryl, —$C_1$-$C_8$ alkylcycloalkyl, and —$C_1$-$C_8$ alkylaryl;

$R^4$ and $R^5$ are each independently selected from hydrogen, $C_1$-$C_8$ alkyl, $C_2$-$C_8$ alkenyl, —$C_2$-$C_8$ alkynyl, —$C_1$-$C_8$ alkoxyalkyl, $C_1$-$C_8$ thioalkyl, halo, $C_1$-$C_8$ haloalkyl, —$C_1$-$C_8$ alkoxyhaloalkyl, aryl, —$C_1$-$C_8$ alkylaryl, —C(O)$C_1$-$C_8$ alkyl, or —C(O)O$C_1$-$C_8$ alkyl, —$C_1$-$C_8$ alkylamino, —$C_1$-$C_8$ alkylcycloalkyl, —(CH$_2$)$_m$C(O)$C_1$-$C_8$ alkyl, and (CH$_2$)$_n$ NR$^8$R$^8$, wherein each $R^4$ or $R^5$ is attached to its respective ring only at carbon atoms, and wherein y is 0, 1, 2, or 3; and wherein z is 0, 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, —C(O)$C_1$-$C_8$ alkyl, hydroxy, $C_1$-$C_8$ alkoxy, —SO$_2$$C_1$-$C_8$ alkyl, SO$_2$$C_1$-$C_8$ alkylaryl, —SO$_2$$C_1$-$C_8$ alkylheterocyclic, aryl, —$C_1$-$C_8$ alkylaryl, $C_3$-$C_7$ cycloalkyl, —$C_1$-$C_6$ alkylcycloalkyl, —(CH$_2$)$_n$C(O)R$^8$, —(CH$_2$)$_m$C(O)NR$^8$R$^8$, and —(CH$_2$)$_m$NSO$_2$R$^8$; wherein each of the alkyl, alkenyl, and aryl groups are optionally substituted with one to five groups independently selected from $C_1$-$C_8$ alkyl, $C_2$-$C_8$ alkenyl, aryl, and $C_1$-$C_8$ alkylaryl; and wherein $R^6$ and $R^7$ may independently combine with each other, and with the nitrogen atom to which they are attached or with 1, or 2 atoms adjacent to the nitrogen atom to form a 4, 5, 6, or 7-membered nitrogen containing heterocycle which nitrogen containing heterocycle may optionally have substituents selected from the group consisting of oxo, $C_1$-$C_8$ alkyl, $C_2$-$C_8$ alkenyl, $C_2$-$C_8$ alkynyl, aryl, —$C_1$-$C_8$ alkylaryl, —C(O)$C_1$-$C_8$ alkyl, —CO(O)$C_1$-$C_8$ alkyl, hydroxy, $C_1$-$C_8$ alkoxy, —$C_1$-$C_8$ alkylamine, amino, halo, and haloalkyl;

$R^8$ is hydrogen, $C_1$-$C_8$ alkyl, $C_2$-$C_8$ alkenyl, $C_1$-$C_8$ alkylaryl, —C(O)$C_1$-$C_8$ alkyl, or —C(O)O$C_1$-$C_8$ alkyl; and wherein n is 0, 1, 2, 3 or 4 and m is 1, 2 or 3;

or a pharmaceutically acceptable salt, solvate, enantiomer, racemate, diastereomer or mixture of diastereomers thereof.

The present invention also provides a method for the prevention, treatment and/or amelioration of the symptoms of obesity and Related Diseases comprising administering a therapeutically effective amount of a compound of formula II to a patient in need thereof wherein formula II is represented by the structure

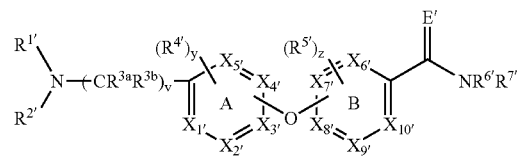

(II)

wherein each of $X_{1'}$, $X_{2'}$, $X_{3'}$, $X_{4'}$, $X_{5'}$, $X_{6'}$, $X_{7'}$, $X_{8'}$, $X_{9'}$, and $X_{10'}$ is C, CH, or N; provided that each of rings A' or B' has no more than 2 nitrogen atoms;

E' is O or NH;

v is 0, 1, 2 or 3;

$R^{1'}$ and $R^{2'}$ are independently selected from hydrogen, $C_1$-$C_8$ alkyl, $C_2$-$C_8$ alkenyl, $C_2$-$C_8$ alkynyl, aryl, $C_3$-$C_8$ cycloalkyl, —$C_1$-$C_{10}$ alkylaryl, heterocyclyl, —$C_1$-$C_{10}$ alkylheterocyclic, -arylheterocyclyl, —$C_3$-$C_8$ cycloalkylheterocyclyl, —$C_1$-$C_8$ alkylC(O)$C_1$-$C_8$ alkyl, aryl C(O) $C_1$-$C_8$ alkyl-, $C_3$-$C_8$ cycloalkylC(O)(CH$_2$)$_n$—, —$C_2$-$C_8$ alkylCH(OH)aryl, —$C_2$-$C_8$alkylCH(OH)cycloalkyl, —$C_2$-$C_8$ alkylCH(OH)heterocyclyl $C_2$-$C_8$ alkylCH(OH) aryl, —$C_1$-$C_8$ alkylC(O)heterocyclic, —$C_1$-$C_8$ alkyl, C(O) aryl, aryloxy$C_1$-$C_8$ alkyl, benzhydryl, fused bicyclic, $C_1$-$C_8$ alkylfused bicyclic, phenylC(O)—, phenylC(O)$C_1$-$C_8$ alkyl-, $C_1$-$C_8$ alkoxy$C_1$-$C_8$ alkyl-, —CO(O)$C_1$-$C_8$alkyl, —SO$_2$$C_1$-$C_8$alkyl, —SO$_2$$C_1$-$C_{10}$ alkylaryl, —SO$_2$$C_1$-$C_8$ alkylheterocyclic, —$C_1$-$C_8$ alkylcycloalkyl, —(CH$_2$)$_n$C(O)OR$^8$, —(CH$_2$)$_n$C(O)R$^8$, —(CH$_2$)$_m$C(O)NR$^8$R$^8$, and —(CH$_2$)$_m$NSO$_2$R$^8$; wherein each of the alkyl, alkenyl, cycloalkyl, heterocyclic, and aryl groups are optionally substituted with one to five groups independently selected from halo, $C_1$-$C_8$ haloalkyl, $C_1$-$C_8$ thioalkyl, $C_1$-$C_8$ alkyl, $C_2$-$C_8$ alkenyl, aryl, —$C_1$-$C_8$ alkylaryl, —C(O)$C_1$-$C_8$ alkyl, —CO(O)$C_1$-$C_8$ alkyl, —SO$_2$$C_1$-$C_8$ alkyl, —SO$_2$$C_1$-$C_8$ alkylaryl, —SO$_2$$C_1$-$C_8$ alkylheterocyclic, —$C_1$-$C_8$ alkylcycloalkyl, —(CH$_2$)$_n$C(O)OR$^8$, —(CH$_2$)$_n$C(O)R$^8$;

and wherein $R^{1'}$ and $R^{2'}$ may optionally combine with each other, or with 1, or 2 atoms adjacent to the nitrogen atom to form a 4, 5, 6, or 7-membered nitrogen-containing heterocycle which nitrogen-containing heterocycle may further have substituents selected from the group consisting of amino, $C_1$-$C_8$ alkyl, $C_2$-$C_8$ alkenyl, $C_2$-$C_8$ alkynyl, aryl, $C_1$-$C_8$ alkylaryl, —C(O)$C_1$-$C_8$ alkyl, —CO(O)$C_1$-$C_8$ alkyl, halo, oxo, $C_1$-$C_8$ haloalkyl; and wherein $R^{1'}$ and $R^{2'}$ may independently attach to the A' ring to form a 4, 5, 6, or 7-member nitrogen-containing bicyclic heterocycle which nitrogen-containing bicyclic heterocycle may further have substituents selected from the group consisting of oxo, amino, —$C_1$-$C_8$ alkyl, —$C_2$-$C_8$ alkenyl, —$C_2$-$C_8$ alkynyl, aryl, —$C_1$-$C_8$ alkylaryl, —C(O)$C_1$-$C_8$ alkyl, —CO(O)$C_1$-$C_8$ alkyl, halo, and $C_1$-$C_8$ haloalkyl; provided that $R^{1'}$ and $R^{2'}$ are not simultaneously hydrogen; and provided that when v is 2, and $R^{3a}$ and $R^{3b}$ are both hydrogen or $CH_3$, and both A' and B' rings are phenyl, then the group —$NR^{1'}R^{2'}$ is not equal to —$NHCH_2$Phenyl; and further provided that when one of $R^{1'}$ or $R^{2'}$ is —$CH_2CH_2$-optionally substituted phenyl or —$CH_2CH_2$-optionally substituted naphthyl, or —$CH_2CH_2$-optionally substituted 5 or 6 member monocyclic heterocyclic aromatic, and v is 1, and both A' and B' rings are phenyl, then $R^{6'}$ and $R^{7'}$ are not simultaneously hydrogen;

$R^{3a}$ and $R^{3b}$ are each independently selected from hydrogen, $C_1$-$C_8$ alkyl, $C_2$-$C_8$ alkenyl, $C_2$-$C_8$ alkynyl, aryl, —$C_1$-$C_8$ alkylcycloalkyl, aryl, and —$C_1$-$C_8$ alkylaryl;

$R^{4'}$ and $R^{5'}$ are each independently selected from hydrogen, $C_1$-$C_8$ alkyl, $C_2$-$C_8$ alkenyl, —$C_2$-$C_8$ alkynyl, —$C_1$-$C_8$ alkoxyalkyl, $C_1$-$C_8$ thioalkyl, halo, $C_1$-$C_8$ haloalkyl, —$C_1$-$C_8$ alkoxyhaloalkyl, aryl, —$C_1$-$C_8$ alkylaryl, —C(O)$C_1$-$C_8$ alkyl, or —C(O)O$C_1$-$C_8$ alkyl, —$C_1$-$C_8$ alkylamino, —$C_1$-$C_8$ alkylcycloalkyl, —$(CH_2)_m$C(O)$C_1$-$C_8$ alkyl, and —$(CH_2)_n$$NR^8R^8$, wherein each $R^{4'}$ and $R^{5'}$ is attached to its respective ring only at carbon atoms, and wherein y is 0, 1, 2, or 3; and wherein z is 0, 1, 2, or 3;

$R^{6'}$ and $R^{7'}$ are each independently selected from hydrogen, $C_1$-$C_8$ alkyl, $C_2$-$C_8$ alkenyl, $C_2$-$C_8$ alkynyl, —C(O)$C_1$-$C_8$ alkyl, hydroxy, $C_1$-$C_8$ alkoxy, —$SO_2C_1$-$C_8$ alkyl, $SO_2C_1$-$C_8$ alkylaryl, —$SO_2C_1$-$C_8$ alkylheterocyclic, aryl, —$C_1$-$C_8$ alkylaryl, $C_3$-$C_7$ cycloalkyl, —$C_1$-$C_6$ alkylcycloalkyl, —$(CH_2)_n$C(O)$R^8$, —$(CH_2)_m$C(O)$NR^8R^8$, and —$(CH_2)_m$$NSO_2R^8$; wherein each of the alkyl, alkenyl, and aryl groups are optionally substituted with one to five groups independently selected from $C_1$-$C_8$ alkyl, $C_2$-$C_8$ alkenyl, aryl, and $C_1$-$C_8$ alkylaryl; and wherein $R^{6'}$ and $R^{7'}$ may independently combine together, and with the nitrogen atom to which they are attached or with 1, or 2 atoms adjacent to the nitrogen atom to form a 4, 5, 6, or 7-membered nitrogen containing heterocycle which nitrogen containing heterocycle may further have substituents selected from the group consisting of $C_1$-$C_8$ alkyl, $C_2$-$C_8$ alkenyl, $C_2$-$C_8$ alkynyl, phenyl, —$C_1$-$C_8$ alkylaryl, —C(O)$C_1$-$C_8$ alkyl, —CO(O)$C_1$-$C_8$ alkyl, hydroxy, —$C_1$-$C_8$ alkoxy, halo, and haloalkyl;

$R^8$ is hydrogen, $C_1$-$C_8$ alkyl, $C_2$-$C_8$ alkenyl, $C_1$-$C_8$ alkylaryl, —C(O)$C_1$-$C_8$ alkyl, or —C(O)O$C_1$-$C_8$ alkyl wherein n is 0, 1, 2, 3 or 4 and wherein m is 1, 2 or 3;

or a pharmaceutically acceptable salt, solvate, enantiomer, racemate, diastereomers or mixtures thereof.

The present invention also provides a pharmaceutical formulation comprising a compound of formula I or II in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression related to obesity, anxiety related to obesity, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, hyperliproteinemia, substance abuse, drug overdose, compulsive behavior disorders (such as paw licking in dog), and addictive behaviors such as for example, gambling, and alcoholism, comprising administering a therapeutically effective amount of a compound of formula I or formula II or a pharmaceutically acceptable salt, solvate, enantiomer, racemate, diastereomer or mixture of diastereomers thereof.

The present invention provides a compound of formula (I) or (II) useful for the manufacture of a medicament for the treatment, prevention and/or amelioration of symptoms associated with obesity and Related Diseases.

In another embodiment, the present invention provides a compound of formula I or II or a pharmaceutically acceptable salt, solvate, enantiomer, racemate, diastereomer or mixtures thereof, useful as an appetite suppressant.

In another embodiment, the present invention provides a method of achieving weight loss while maintaining or minimizing the loss of lean muscle mass, comprising administering a compound of formula I or II or a pharmaceutically acceptable salt, solvate enantiomer, racemate, diastereomer or mixtures thereof, to a patient in need thereof.

DETAILED DESCRIPTION OF THE INVENTION

As used herein the term "obesity" has its commonly understood meaning such as "excessively fat" and includes the clinical designation of being obese as defined in and by the medical literature and brochures of support or public health organizations. For example, *Dorland's Illustrated Medical Dictionary* (29th edition, W.B. Saunders Company, Philadelphia USA.) defines obesity as an increase in bodyweight beyond the limitation of skeletal and physical requirements, as the result of an excessive accumulation of fat in the body." Because the decision of suitability for treatment of a patient with compound(s) of the present invention to a patient is to be made by a qualified physician or care giver, the patient is inherently deemed suitable or obese by the administering caregiver.

As used herein, the term "patient" includes human and nonhuman animals such as companion animals (dogs and cats) and livestock animals.

The preferred patient of treatment, amelioration and/or prevention of obesity and Related Diseases is human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of the symptoms associated with obesity and Related Diseases in a patient afflicted with same or reducing the likelihood that the recipient of a compound of formula I or II will incur or develop any of the pathological conditions, or sequela thereof, described herein.

As used herein, the term "effective amount" is synonymous with "effective dose" and means an amount of a compound of formula I or II that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or II or a combination of compounds of formula I or II or a combination of a compound of formula I or II and a co-antagonist of the opioid receptor or a combination of a compound of formula I and/or II in addition to other effective anti-obesity, weight loss or anti-diabetic agent.

The term "formulation", as in pharmaceutical formulation, or "pharmaceutical composition" is intended to encompass a product comprising the Active Ingredient (as defined supra), and the inert ingredient(s) that make up the carrier, or other components of the drug as administered, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I or II and a pharmaceutically acceptable co-antagonist of opioid receptors useful for the treatment and/or prevention of obesity or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, obesity related depression, obesity related anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinemia. As used herein the terms obesity related depression and obesity related anxiety are conditions of depression and anxiety respectively, that are symptomatic of certain obese patients and possibly brought on by the awareness or self-consciousness of the condition of being obese and possibly coupled with the real or perceived reaction of acceptance or disapproval by the certain individual, individuals or the public at large. Obesity related depression or anxiety may generally be alleviated or treated as the condition of being obese is treated and/or prevented by administration of a compound of formula I or II.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a aromatic or non-aromatic, monocyclic or bicyclic ring system which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds.

The term "$C_1$-$C_8$ alkyl" or $C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkyaryl, means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc. In general, where necessary a dash (-) has been placed by certain groups that may require it to indicate the point of attachement for clarity.

The term "cycloalkane" or "cycloalkyl' means cycloalkanes having from 3 to 8 carbon atoms i.e. from cyclopropane to cyclooctane.

The term "hal" or "halo" as used herein refers to a halogen including fluorine, chlorine, bromine or iodine.

The term "haloalkane" or "haloalkyl' means haloalkanes having from 1 to 8 carbon atoms, and from 1 to 3 halogen atoms as allowed by valency considerations. Examples include chloroethyl, trifluoromethyl, 2-chloropropyl, etc.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes for example, phenyl, benzyl, naphthyl, tetrahydronaphthyl, benzothiophene, etc, but excludes carbazoles and other fused tricyclic ring structures.

As used herein the term "aroxy" or "aryloxy" refers to the group "O-aryl" wherein aryl is as defined previously.

As used herein the term "fused bicyclic" means a fused cycloalkane ring system wherein each ring has from 4 to 8 carbon atoms (i.e. $C_8$-$C_{16}$ fused bicyclic) and the fused ring system has from 0 to 3 bridgehead carbon atoms. One or both of the fused rings may contain zero or one double bond. Examples of fused bicyclics include but are not limited to bicyclo[2,2,1]heptyl, bicyclo[2,2,1]heptenyl.

As used herein the term "heterocyclic" or heterocyclyl" or "heterocycle" are used interchangeably and has its usual meaning and includes mono, bi or tricyclic or spirocyclic heterocyclic groups unless otherwise specified. Heterocycles as used herein may contain 1, 2, or 3 heteroatoms selected independently from nitrogen, oxygen or sulfur, unless otherwise specified. Examples of heterocylclic groups applicable to the present invention include but are not limited to pyranyl, piparazinyl, pyrrolidinyl, azapanyl, azaflorenyl, isoquinolinyl, indolinyl, thiopheneyl, benzthiopheneyl, oxazolyl, morphorlinyl, thiomorphorlinyl, and piperidinyl. Each of the heterocyclic groups may be substituted mono or di or as specified with for example, alkyl, cycloalkyl, aryl, among others as defined. Furthermore, substitution may be at the 1-position or heteroatom as in piperazine, pyrrolidine or at a carbon atom or both.

As used herein, the term "protecting group" refers to a groups useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, 3$^{rd}$ edition, Greene, T. W.; Wuts, P. G. M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I or II and a solvent. Typical solvating solvents include for example, water, methanol ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromidse salt, the bisulfate salt, the methane sulfonic acid salt, the p-toluenesulfonic acid salt, bitartrate, the acetate and the citrate salt.

A compound of the invention as illustrated by formula I or II may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

PCT international application WO 02/078693 A2 published Oct. 10, 2002 discloses compounds of the formula

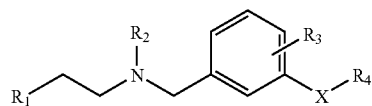

wherein $R_1$, $R_2$, $R_3$, $R_4$ and X are as described therein, as antagonists of the 5-HT$_6$ receptor for the treatment of disorders including cognitive disorders, age related disorders, mood disorders, psychosis, etc. The compounds of the present invention however, are useful for the treatment and/or prevention of obesity and Related Diseases. The compounds of the present invention have also shown inhibition of orexigenic effects, and are thus useful as appetite suppressants either as a single therapy or as combination therapy in conjunction with exercise and other effective appetite suppressing or weight loss medications.

The efficacy of compounds of the present invention have been shown by their activity in several biological models including a scintillation proximity assay (SPA GTP-gamma binding assay), an opioid receptor ex-vivo binding assay, a rat obesity in-vivo assay and an indirect calorimetry assay that measurers energy balance and respiratory quotient. In these models, sample compounds of the present invention performed better than or about equal to reference compounds. The primary reference compound is a highly potent former clinical trial candidate LY 255582 disclosed in U.S. Pat. No. 4,891,379, which development was discontinued for lack of satisfactory human oral bioavailability. Oral administration of the opioid receptor antagonist LY255582 has been shown to produce robust reductions in food intake following acute and chronic treatment in rats. Moreover, chronic treatment with LY255582 produced a sustained negative energy balance leading to a decrease in total body mass in dietary induced obese rats fed a high fat diet. Interestingly sample compounds of the present invention have been found to produce similar or better beneficial effects compared to LY255582. Also interesting is the secondary observation that tested sample compounds of the present invention performed better in our tests when compared with Naltrexone HCl®.

PREFERRED EMBODIMENTS OF THE INVENTION

A compound of formula I preferably exists as the free base or a pharmaceutically acceptable salt. More preferred is the hydrochloride salt, the bisulfate salt, mesylate or the oxalic acid salt of the compound of formula I or II.

Preferred embodiments of the compound of formula I include the substructures Ia, Ib and Ic as shown below:

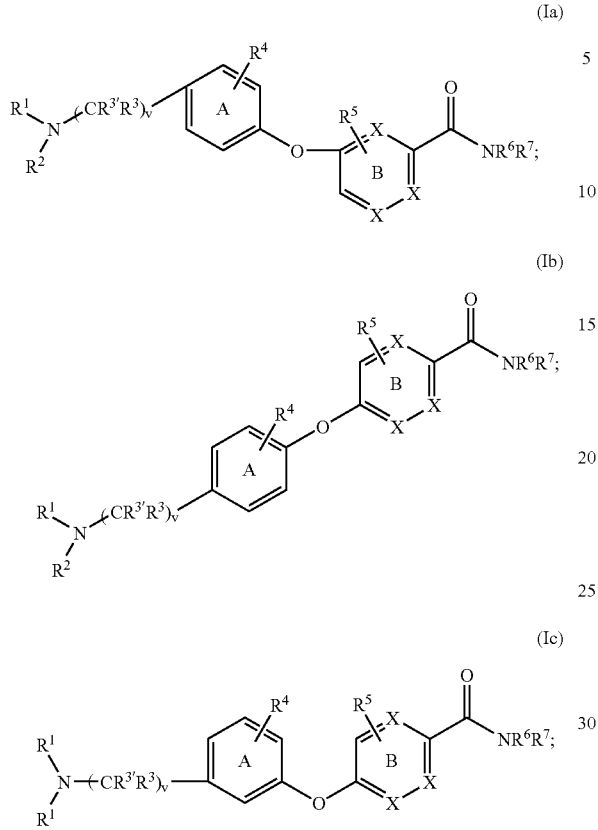

(Ia)

(Ib)

(Ic)

provided that $R^1$ and $R^2$ are not simultaneously hydrogen and provided that when v is 2, and $R^3$ and $R^{3'}$ are both hydrogen or methyl, and the A ring is phenyl, the group —$NR^1R^2$ is not equal to —$NHCH_2Ph$.

For the Groups $R^1$ and $R^2$

Preferred $R^1$ and $R^2$ groups are independently selected from the group consisting of hydrogen, methyl, ethyl, propyl, pentyl, phenyl, naphthyl, benzothiophene, and isopropyl provided that $R^1$ and $R^2$ are not simultaneously hydrogen, and provided that when v is 2, and $R^3$ and $R^{3'}$ are both hydrogen or $CH_3$, and both A and B rings are phenyl, then the group —$NR^1R^2$ is not equal to —$NHCH_2Phenyl$; and further provided that when one of $R^1$ or $R^2$ is —$CH_2CH_2$-optionally substituted phenyl or —$CH_2CH_2$-optionally substituted naphthyl, or —$CH_2CH_2$-optionally substituted 5 or 6 member monocyclic heterocyclic aromatic, and v is 1, and both A and B rings are phenyl, then $R^6$ and $R^7$ are not simultaneously hydrogen;

Also preferred are $R^1$ and $R^2$ groups independently selected from the group consisting of methyl, ethyl, propyl, isopropyl, phenyl,

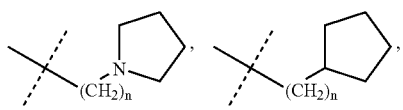

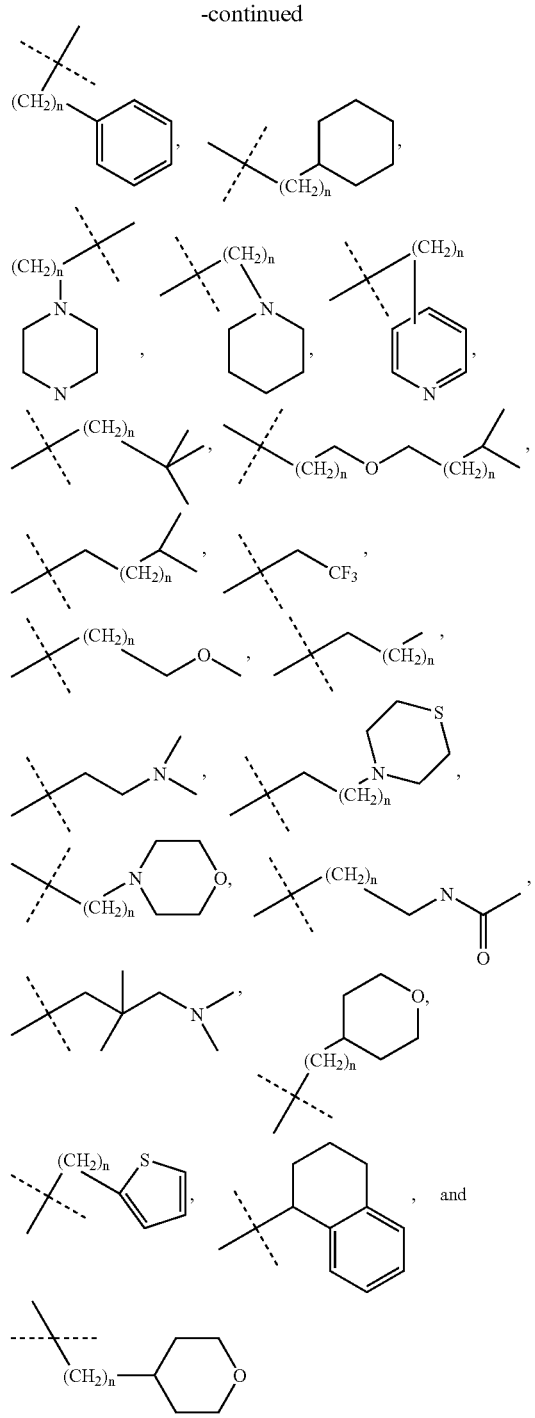

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or —$C_1$-$C_4$ alkylheterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle, and wherein n is preferably 1, 2, or 3; and provided that when v is 2, and $R^3$ and $R^{3'}$ are both hydrogen or CH$_3$, and both A and B rings are phenyl, then the group —NR$^1$R$^2$ is not equal to —NHCH$_2$Phenyl; and further provided that when one of R$^1$ or R$^2$ is —CH$_2$CH$_2$-optionally substituted phenyl or —CH$_2$CH$_2$-optionally substituted naphthyl, or —CH$_2$CH$_2$-optionally substituted 5 or 6 member monocyclic heterocyclic aromatic, and v is 1, and both A and B rings are phenyl, then R$^6$ and R$^7$ are not simultaneously hydrogen;

The broken (dashed) bond indicates the point of attachment to the substrate.

Also preferred are R$^1$ and R$^2$ groups that combine with each other or with 1 or 2 atoms adjacent to the nitrogen atom to form a group selected from the group consisting of

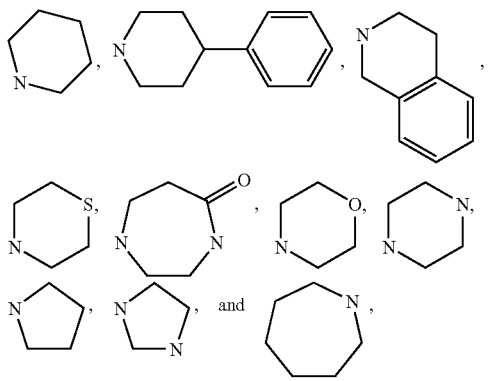

each of which is optionally substituted with a group selected from the group consisting of halogen, amino, C$_1$-C$_8$ alkyl, C$_1$-C$_8$ haloalkyl, C$_1$-C$_8$ thioalkyl, —C$_1$-C$_8$ alkylamino, phenyl, C$_1$-C$_8$ alkylsubstituted phenyl, C$_4$-C$_8$ heterocycle or —C$_1$-C$_4$ alkylheterocycle.

Preferred R$^3$ and R$^{3'}$ Groups

A preferred R$^3$ is hydrogen. A preferred R$^{3'}$ group is selected from hydrogen, methyl, ethyl, propyl, isopropyl, butyl, isobutyl, phenyl and benzyl.

Preferred R$^4$ Groups

A preferred R$^4$ group is selected from the group consisting of hydrogen, halo, C$_1$-C$_5$ alkyl, C$_1$-C$_5$ haloalkyl, C$_1$-C$_5$ alkoxy, —C$_1$-C$_5$ alkylamino, —N(C$_1$-C$_5$ alkyl)$_2$, —NHC$_1$-C$_5$ alkyl, —C$_1$-C$_5$ alkyl N(C$_1$-C$_5$ alkyl)$_2$, —C$_1$-C$_5$ alkyl-NHC$_1$-C$_5$ alkyl, phenyl, —C$_1$-C$_5$ alkylphenyl, —C$_1$-C$_5$ alkylcycloalkyl, and C$_1$-C$_5$ thioalkyl. More preferred is a —R$^4$ group selected from the group consisting of hydrogen, methyl, ethyl, isopropyl, chloro, fluoro, trifluoromethyl, methoxy, ethoxy, thiomethyl, phenyl, and benzyl. Most preferred is an R$^4$ group selected from the group consisting of hydrogen, methyl, ethyl, isopropyl, fluoro, chloro, trifluoromethyl, methoxy, ethoxy, propoxy, isopropoxy, and benzyl.

Though the groups R$^4$ and a R$^5$ may exist as multiple substituents on their respective ring substrates, a preferred embodiment of the invention involves compounds wherein each of R$^4$, and R$^5$ are independently singly or doubly substituted on their respective ring substrates.

Preferred R$^5$ Groups

A preferred R$^5$ group is selected from the group consisting of hydrogen, halo, C$_1$-C$_5$ alkyl, C$_1$-C$_5$ haloalkyl, C$_1$-C$_5$ alkoxy, —C$_1$-C$_5$ alkylamino, —N(C$_1$-C$_5$ alkyl)$_2$, —NHC$_1$-C$_5$ alkyl, —C$_1$-C$_5$ alkylN(C$_1$-C$_5$ alkyl)$_2$, —C$_1$-C$_5$ alkyl-NHC$_1$-C$_5$ alkyl, phenyl, —C$_1$-C$_5$ alkylphenyl, —C$_1$-C$_5$ alkylcycloalkyl, and C$_1$-C$_5$ thioalkyl. More preferred is an R$^5$ group selected from the group consisting of hydrogen, methyl, ethyl, isopropyl, chloro, fluoro, trifluoromethyl, methoxy, ethoxy, thiomethyl, phenyl, and benzyl. A most preferred R$^5$ group is selected from the group consisting of hydrogen, methyl, ethyl, isopopropyl, fluoro, chloro, trifluoromethyl, methoxy, ethoxy, trifluoromethoxy, and benzyl.

Preferred R$^6$ and R$^7$ Groups

Preferred are R$^6$ and R$^7$ groups independently selected from the group consisting of hydrogen, methyl, ethyl, propyl, pentyl, isopropyl, phenyl and benzyl, provided that when one of R$^1$ or R$^2$ is —CH$_2$CH$_2$-optionally substituted phenyl or —CH$_2$CH$_2$-optionally substituted naphthyl, or —CH$_2$CH$_2$-optionally substituted 5 or 6 member monocyclic heterocyclic aromatic, and v is 1, and both A and B rings are phenyl, then R$^6$ and R$^7$ are not simultaneously hydrogen.

Also preferred are compounds of formula I wherein R$^6$ and R$^7$ may independently combine with each other, and with the nitrogen atom to which they are attached or with 1, or 2 atoms adjacent to the nitrogen atom to form a 4, 5, 6, or 7-membered nitrogen containing heterocycle which nitrogen containing heterocycle may optionally have substituents selected from the group consisting of oxo amino, C$_1$-C$_8$ alkyl, C$_2$-C$_8$ alkenyl, C$_2$-C$_8$ alkynyl, phenyl, —C$_1$-C$_8$ alkylaryl, —C(O)C$_1$-C$_8$ alkyl —CO(O)C$_1$-C$_8$ alkyl, hydroxy, C$_1$-C$_8$ alkoxy, halo, and haloalkyl.

Most preferred are compounds of the invention wherein R$^6$ and R$^7$ are both hydrogen except as provided for previously.

Preferred E Group

A most preferred E group is an oxygen atom (O).

Preferred A-ring

A preferred A-ring is a phenyl ring or a pyridine ring.

Preferred B-ring

A preferred B-ring is a phenyl ring, a pyrazine ring, a pyrimidine ring or a pyridine ring. Most preferred B ring is a phenyl, pyrazine or pyridine ring.

Preferred Values for v, n and m

A preferred value for v is 1, or 2.
A preferred value for n is 1, 2 or 3.
A preferred value for m is 1 or 2.

For the Groups R$^{1'}$ and R$^{2'}$

Preferred R$^{1'}$ and R$^{2'}$ groups are independently selected from the group consisting of hydrogen, methyl, ethyl, propyl, pentyl, and isopropyl provided that R$^{1'}$ and R$^{2'}$ are not simultaneously hydrogen, and provided that when v is 2, and R$^{3a}$ and R$^{3b}$ are both hydrogen or CH$_3$, and both A' and B' rings are phenyl, then the group —NR$^{1'}$R$^{2'}$ is not equal to —NHCH$_2$Phenyl; and further provided that when one of R$^{1'}$ or R$^{2'}$ is —CH$_2$CH$_2$-optionally substituted phenyl or —CH$_2$CH$_2$-optionally substituted naphthyl, or —CH$_2$CH$_2$-optionally substituted 5 or 6 member monocyclic heterocyclic aromatic, and v is 1, and both A' and B' rings are phenyl, then R$^{6'}$ and R$^{7'}$ are not simultaneously hydrogen; Also preferred are R$^{1'}$ and R$^{2'}$ groups independently selected from the group consisting of hydrogen, methyl, ethyl, propyl, isopropyl, phenyl,

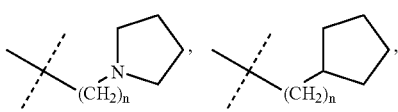

-continued

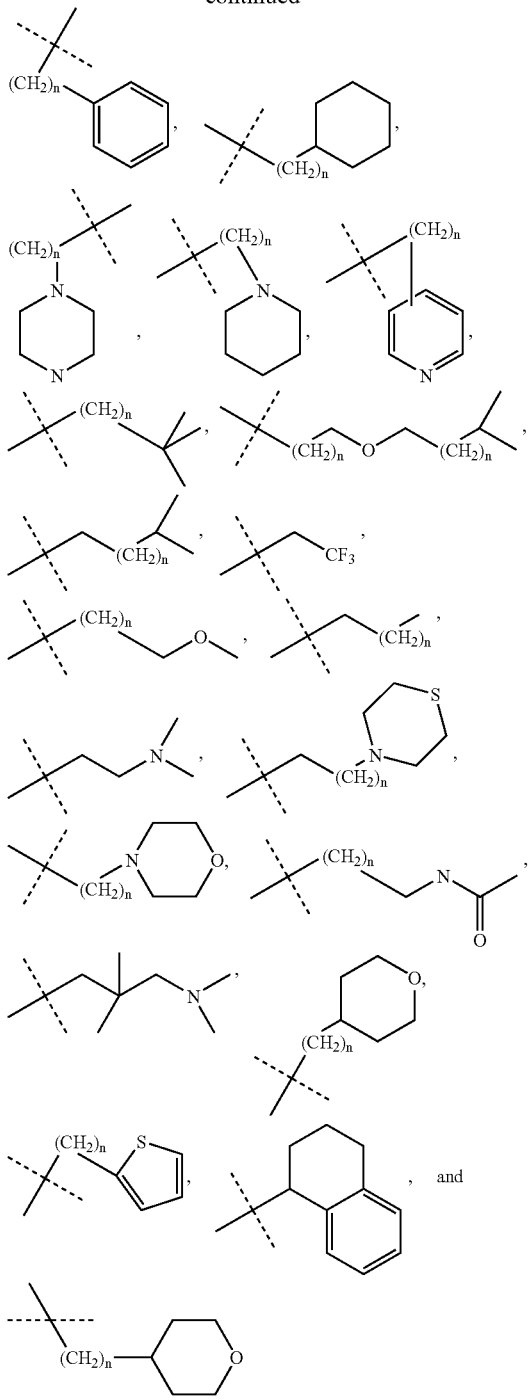

each of which is optionally substituted with a group selected from halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle, and wherein n is preferably 1, 2 or 3; and and provided that when v is 2, and $R^{3a}$ and $R^{3b}$ are both hydrogen or $CH_3$, and both A' and B' rings are phenyl, then the group —$NR^{1'}R^{2'}$ is not equal to —$NHCH_2$Phenyl; and further provided that when one of $R^{1'}$ or $R^{2'}$ is —$CH_2CH_2$-optionally substituted phenyl or —$CH_2CH_2$-optionally substituted naphthyl, or —$CH_2CH_2$-optionally substituted 5 or 6 member monocyclic heterocyclic aromatic, and v is 1, and both A' and B' rings are phenyl, then $R^{6'}$ and $R^{7'}$ are not simultaneously hydrogen.

Also preferred are $R^{1'}$ and $R^{2'}$ groups which combine with each other or with 1 or 2 atoms adjacent to the nitrogen atom to form a group selected from the group consisting of:

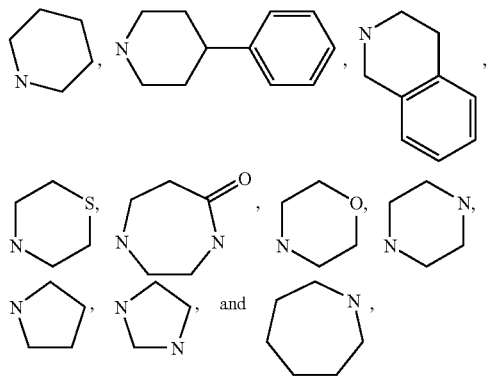

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^{3a}$ and $R^{3b}$ Groups

A preferred $R^{3a}$ is hydrogen. A preferred $R^{3b}$ group is selected from hydrogen, methyl, ethyl, propyl, isopropyl, phenyl and benzyl.

Preferred $R^{4'}$ Groups

A preferred $R^{4'}$ group is selected from the group consisting of hydrogen, halo, $C_1$-$C_5$ alkyl, $C_1$-$C_5$ haloalkyl, $C_1$-$C_5$ alkoxy, —$C_1$-$C_5$ alkylamino, —$N(C_1$-$C_5$ alkyl$)_2$, —$NHC_1$-$C_5$ alkyl, —$C_1$-$C_5$ alkylN($C_1$-$C_5$ alkyl$)_2$, —$C_1$-$C_5$ alkyl-$NHC_1$-$C_5$ alkyl, phenyl, —$C_1$-$C_5$-alkylphenyl, —$C_1$-$C_5$ alkylcycloalkyl, and $C_1$-$C_5$ thioalkyl. More preferred is a $R^{4'}$ group selected from the group consisting of hydrogen, methyl, ethyl, isopropyl, chloro, fluoro, trifluoromethyl, methoxy, ethoxy, thiomethyl, phenyl, and benzyl. A most preferred $R^{4'}$ group is selected from the group consisting of hydrogen, methyl, ethyl, isopropyl, fluoro, chloro, trifluoromethyl, methoxy, ethoxy, propoxy, isopropoxy, and benzyl.

Though the groups $R^{4'}$ and $R^{5'}$ may exist as multiple substituents on their respective ring substrates, a preferred embodiment of the invention involves compounds wherein each of $R^{4'}$, and $R^{5'}$ are singly or doubly substituted on their respective ring substrates.

Preferred $R^{5'}$ Groups

A preferred $R^{5'}$ group is selected from the group consisting of hydrogen, halo, $C_1$-$C_5$ alkyl, $C_1$-$C_5$ haloalkyl, $C_1$-$C_5$ alkoxy, —$C_1$-$C_5$ alkylamino, —$N(C_1$-$C_5$ alkyl$)_2$, —$NHC_1$-$C_5$ alkyl, —$C_1$-$C_5$ alkylN($C_1$-$C_5$ alkyl$)_2$, —$C_1$-$C_5$ alkyl-$NHC_1$-$C_5$ alkyl, phenyl, —$C_1$-$C_5$ alkylphenyl, —$C_1$-$C_5$ alkylcycloalkyl, and $C_1$-$C_5$ thioalkyl. More preferred is an $R^{5'}$ group selected from the group consisting of hydrogen, methyl, ethyl, isopropyl, chloro, fluoro, trifluoromethyl, trifluoromethoxy, methoxy, ethoxy, thiomethyl, phenyl, and benzyl. A most preferred $R^{5'}$ group is selected from the group consisting of hydrogen, methyl, ethyl, isopropyl, fluoro, chloro, trifluoromethyl, methoxy, ethoxy, trifluoromethoxy, and benzyl.

Preferred $R^{6'}$ and $R^{7'}$ Groups

Preferred are $R^{6'}$ and $R^{7'}$ groups independently selected from the group consisting of hydrogen, methyl, ethyl, propyl, pentyl, isopropyl, phenyl and benzyl provided that when one of $R^{1'}$ or $R^{2'}$ is —CH$_2$CH$_2$-optionally substituted phenyl or —CH$_2$CH$_2$-optionally substituted naphthyl, or —CH$_2$CH$_2$-optionally substituted 5 or 6 member monocyclic heterocyclic aromatic, and v is 1, and both A' and B' rings are phenyl, then $R^{6'}$ and $R^{7'}$ are not simultaneously hydrogen.

Also preferred are compounds of formula II wherein $R^{6'}$ and $R^{7'}$ may independently combine with each other, and with the nitrogen atom to which they are attached or with 1, or 2 atoms adjacent to the nitrogen atom to form a 4, 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, —$C_1$-$C_8$ alkylaryl, —C(O)$C_1$-$C_8$ alkyl, —CO(O)$C_1$-$C_8$ alkyl, hydroxy, $C_1$-$C_8$ alkoxy, halo, and haloalkyl.

Most preferred are compounds of formula II wherein $R^{6'}$ and $R^{7'}$ are both hydrogen provided that when one of $R^{1'}$ or $R^{2'}$ is —CH$_2$CH$_2$-optionally substituted phenyl or —CH$_2$CH$_2$-optionally substituted naphthyl, or —CH$_2$CH$_2$-optionally substituted 5 or 6 member monocyclic heterocyclic aromatic, and v is 1, and both A' and B' rings are phenyl, then $R^{6'}$ and $R^{7'}$ are not simultaneously hydrogen.

Preferred E' Group

A most preferred E' group is an oxygen atom (O).

Preferred A'-ring

A preferred A'-ring is a phenyl ring or a pyridine ring.

Preferred B'-ring

A preferred B'-ring is a phenyl ring, a pyrazine ring, a pyrimidine ring or a pyridine ring. Most preferred B' ring is a phenyl, pyrazine or pyridine ring.

A preferred compound according to the present invention is a compound selected from the group consisting of:

6-[4-(2-Benzylamino-ethyl)-phenoxy]-nicotinamide.
6-{4-[2-(Benzyl-phenethyl-amino)-ethyl]-phenoxy}-nicotinamide,
6-(4-{2-[Benzyl-(3-phenyl-propyl)-amino]-ethyl}-phenoxy)-nicotinamide,
6-{4-[2-(Benzyl-hexyl-amino)-ethyl]-phenoxy}-nicotinamide,
6-{4-[2-(Benzyl-heptyl-amino)-ethyl]-phenoxy}-nicotinamide,
6-(4-{2-[Benzyl-(5-methyl-hexyl)-amino]-ethyl}-phenoxy)-nicotinamide,
6-[4-(2-{Benzyl-[2-(3-chloro-phenyl)-ethyl]-amino}-ethyl)-phenoxy]-nicotinamide,
6-(4-{2-[Benzyl-(3-cyclohexyl-propyl)-amino]-ethyl}-phenoxy)-nicotinamide,
6-(4-{2-[Benzyl-(3-o-tolyl-propyl)-amino]-ethyl}-phenoxy)-nicotinamide,
6-(4-{2-[Benzyl-(3-thiophen-2-yl-propyl)-amino]-ethyl}-phenoxy)-nicotinamide,
6-{4-[2-(Benzyl-pentyl-amino)-ethyl]-phenoxy}-nicotinamide,
6-(4-{2-[Benzyl-(3-cyclopentyl-propyl)-amino]-ethyl}-phenoxy)-nicotinamide,
6-[4-(2-{Benzyl-[2-(2-fluoro-phenyl)-ethyl]-amino}-ethyl)-phenoxy]-nicotinamide,
6-[4-(2-Dibenzylamino-ethyl)-phenoxy]-nicotinamide,
6-(4-{2-[Benzyl-(3-oxo-3-phenyl-propyl)-amino]-ethyl}-phenoxy)-nicotinamide,
6-(4-{2-[Benzyl-(3-oxo-3-thiophen-2-yl-propyl)-amino]-ethyl}-phenoxy)-nicotinamide,
6-(4-{2-[Benzyl-(3-cyclohexyl-3-oxo-propyl)-amino]-ethyl}-phenoxy)-nicotinamide,
6-(4-{2-[Benzyl-(3-hydroxy-3-phenyl-propyl)-amino]-ethyl}-phenoxy)-nicotinamide,
6-(4-{2-[Benzyl-(3-hydroxy-3-thiophen-2-yl-propyl)-amino]-ethyl}-phenoxy)-nicotinamide,
6-(4-{2-[Benzyl-(3-cyclohexyl-3-hydroxy-propyl)-amino]-ethyl}-phenoxy)-nicotinamide,
6-{4-[2-(3-Phenyl-propylamino)-ethyl]-phenoxy}-nicotinamide,
6-[4-(2-Phenethylamino-ethyl)-phenoxy]-nicotinamide,
6-[4-(2-Hexylamino-ethyl)-phenoxy]-nicotinamide,
6-[4-(2-Heptylamino-ethyl)-phenoxy]-nicotinamide,
6-[4-(2-Pentylamino-ethyl)-phenoxy]-nicotinamide,
6-{4-[2-(5-Methyl-hexylamino)-ethyl]-phenoxy}-nicotinamide,
6-(4-{2-[2-(3-Chloro-phenyl)-ethylamino]-ethyl}-phenyloxy)-nicotinamide,
6-{4-[2-(3-Cyclopentyl-propylamino)-ethyl]-phenoxy}-nicotinamide,
6-{4-[2-(3-Cyclohexyl-propylamino)-ethyl]-phenoxy}-nicotinamide,
6-(4-{2-[2-(3-Fluoro-phenyl)-ethylamino]-ethyl}-phenoxy)-nicotinamide,
6-{4-[2-(3-o-Tolyl-propylamino)-ethyl]-phenoxy}-nicotinamide,
6-{4-[2-(3-Thiophen-2-yl-propylamino)-ethyl]-phenoxy}-nicotinamide,
6-[4-(2-Amino-ethyl)-phenoxy]-nicotinamide,
6-{4-[2-(2-Methoxy-benzylamino)-ethyl]-phenoxy}-nicotinamide,
6-{4-[2-(3-Fluoro-benzylamino)-ethyl]-phenoxy}-nicotinamide,
6-{4-[2-(3-Chloro-benzylamino)-ethyl]-phenoxy}-nicotinamide,
6-{4-[2-(3,4-Dichloro-benzylamino)-ethyl]-phenoxy}-nicotinamide,
6-{4-[2-(3-Trifluoromethyl-benzylamino)-ethyl]-phenoxy}-nicotinamide,
6-{4-[2-(4-Cyano-benzylamino)-ethyl]-phenoxy}-nicotinamide,
6-{4-[2-(4-Fluoro-benzylamino)-ethyl]-phenoxy}-nicotinamide,
6-{4-[2-(4-Methyl-benzylamino)-ethyl]-phenoxy}-nicotinamide,
6-{4-[2-(3,5-Bis-trifluoromethyl-benzylamino)-ethyl]-phenoxy}-nicotinamide,
6-{4-[2-(2,6-Difluoro-benzylamino)-ethyl]-phenoxy}-nicotinamide
6-{4-[2-(3,5-Difluoro-benzylamino)-ethyl]-phenoxy}-nicotinamide,
6-{4-[2-(4-Acetylamino-benzylamino)-ethyl]-phenoxy}-nicotinamide,
6-{4-[2-(2-Trifluoromethyl-benzylamino)-ethyl]-phenoxy}-nicotinamide,
6-{4-[2-(2-Methyl-benzylamino)-ethyl]-phenoxy}-nicotinamide,
6-{4-[2-(3-Methoxy-benzylamino)-ethyl]-phenoxy}-nicotinamide, 6-{4-[2-(4-Chloro-benzylamino)-ethyl]-phenoxy}-nicotinamide,
6-{4-[2-(4-Phenoxy-benzylamino)-ethyl]-phenoxy}-nicotinamide,
6-{4-[2-(4-Methoxy-benzylamino)-ethyl]-phenoxy}-nicotinamide,
6-{4-[2-(4-Trifluoromethyl-benzylamino)-ethyl]-phenoxy}-nicotinamide,
6-{4-[2-(3-Oxo-2,3-dihydro-1H-isoindol-1-ylamino)-ethyl]-phenoxy}-nicotinamide,
6-{4-[2-(4-Trifluoromethoxy-benzylamino)-ethyl]-phenoxy}-nicotinamide,
6-{4-[2-(3-Trifluoromethoxy-benzylamino)-ethyl]-phenoxy}-nicotinamide,
6-(4-{2-[(Thiophen-2-ylmethyl)-amino]-ethyl}-phenoxy)-nicotinamide,
6-(4-{2-[(Furan-2-ylmethyl)-amino]-ethyl}-phenoxy)-nicotinamide,
6-[4-(2-Octylamino-ethyl)-phenoxy]-nicotinamide,
6-[4-(2-Cyclohexylamino-ethyl)-phenoxy]-nicotinamide,
6-{4-[2-(Cyclohexylmethyl-amino)-ethyl]-phenoxy}-nicotinamide,
6-[4-(2-Propylamino-ethyl)-phenoxy]-nicotinamide,
6-[4-(2-Butylamino-ethyl)-phenoxy]-nicotinamide,
6-[4-(2-Isopropylamino-ethyl)-phenoxy]-nicotinamide,
6-[4-(2-Isobutylamino-ethyl)-phenoxy]-nicotinamide,
6-{4-[2-(3-Methyl-butylamino)-ethyl]-phenoxy}-nicotinamide,
6-(4-{2-[(Pyridin-4-ylmethyl)-amino]-ethyl}-phenoxy)-nicotinamide,
6-(4-{2-[(Pyridin-2-ylmethyl)-amino]-ethyl}-phenoxy)-nicotinamide,
6-(4-{2-[(5-Methyl-furan-2-ylmethyl)-amino]-ethyl}-phenoxy)-nicotinamide,
6-(4-{2-[(3-Methyl-thiophen-2-ylmethyl)-amino]-ethyl}-phenoxy)-nicotinamide,
6-(4-{2-[(5-Methyl-thiophen-2-ylmethyl)-amino]-ethyl}-phenoxy)-nicotinamide,
6-(4-{2-[(Thiophen-3-ylmethyl)-amino]-ethyl}-phenoxy)-nicotinamide,
6-[4-(2-Ethylamino-ethyl)-phenoxy]-nicotinamide,
6-{4-[2-(4-Hydroxy-benzylamino)-ethyl]-phenoxy}-nicotinamide,
6-{4-[2-(3-Hydroxy-benzylamino)-ethyl]-phenoxy}-nicotinamide,
6-{4-[2-(3-Phenyl-prop-2-ynylamino)-ethyl]-phenoxy}-nicotinamide,
6-(4-{2-[(Furan-3-ylmethyl)-amino]-ethyl}-phenoxy)-nicotinamide,
6-(4-{2-[(Benzofuran-2-ylmethyl)-amino]-ethyl}-phenoxy)-nicotinamide,
6-(4-{2-[(5-Ethyl-furan-2-ylmethyl)-amino]-ethyl}-phenoxy)-nicotinamide,
6-(4-{2-[(5-Chloro-thiophen-2-ylmethyl)-amino]-ethyl}-phenoxy)-nicotinamide,
6-(4-{2-[(4,5-Dimethyl-furan-2-ylmethyl)-amino]-ethyl}-phenoxy)-nicotinamide,
6-(4-{2-[(4-Chloro-1-methyl-1H-pyrazol-3-ylmethyl)-amino]-ethyl}-phenoxy)-nicotinamide,
6-(4-{2-[(Triazol-2-ylmethyl)-amino]-ethyl}-phenoxy)-nicotinamide,
6-(4-{2-[(2-Methyl-1H-imidazol-4-ylmethyl)-amino]-ethyl}-phenoxy)-nicotinamide,
6-{4-[2-(3,5-Di-tert-butyl-4-hydroxy-benzylamino)-ethyl]-phenoxy}-nicotinamide,
6-{4-[2-(2-Fluoro-benzylamino)-ethyl]-phenoxy}-nicotinamide,
6-{4-[2-(3-Phenoxy-benzylamino)-ethyl]-phenoxy}-nicotinamide,
6-{4-[2-(2-Chloro-benzylamino)-ethyl]-phenoxy}-nicotinamide,
6-{4-[2-(3-Cyano-benzylamino)-ethyl]-phenoxy}-nicotinamide,
6-{4-[2-(3-Methyl-benzylamino)-ethyl]-phenoxy}-nicotinamide.
6-(4-{2-[(1H-Imidazol-4-ylmethyl)-amino]-ethyl}-phenoxy)-nicotinamide.
6-(4-{2-[(Pyridin-3-ylmethyl)-amino]-ethyl}-phenoxy)-nicotinamide,
6-{4-[2-(2-Phenoxy-ethylamino)-ethyl]-phenoxy}-nicotinamide,
6-{4-[2-(3-Fluoro-4-hydroxy-benzylamino)-ethyl]-phenoxy}-nicotinamide,
6-(4-{2-[(2-Butyl-1H-imidazol-4-ylmethyl)-amino]-ethyl}-phenoxy)-nicotinamide,
6-(4-{2-[(Benzo[b]thiophen-3-ylmethyl)-amino]-ethyl}-phenoxy)-nicotinamide,
6-(4-{2-[(3-Phenyl-1H-pyrazol-4-ylmethyl)-amino]-ethyl}-phenoxy)-nicotinamide,
6-[4-(2-Allylamino-ethyl)-phenoxy]-nicotinamide,
6-{4-[2-(4-Imidazol-1-yl-benzylamino)-ethyl]-phenoxy}-nicotinamide,
6-(4-{2-[(3-Methyl-benzo[b]thiophen-2-ylmethyl)-amino]-ethyl}-phenoxy)-nicotinamide,
6-{4-[2-(4-Methyl-pent-2-enylamino)-ethyl]-phenoxy}-nicotinamide,
6-{4-[2-(2-Trifluoromethoxy-benzylamino)-ethyl]-phenoxy}-nicotinamide,
6-(4-{2-[(2-Piperidin-1-yl-thiazol-5-ylmethyl)-amino]-ethyl}-phenoxy)-nicotinamide,
6-{4-[2-(4-Cyclohexyl-butylamino)-ethyl]-phenoxy}-nicotinamide,
6-{4-[2-(2-Cyclohexyl-ethylamino)-ethyl]-phenoxy}-nicotinamide,
6-{4-[2-(2-Chloro-6-fluoro-benzylamino)-ethyl]-phenoxy}-nicotinamide,
6-{4-[2-(Cyclopropylmethyl-amino)-ethyl]-phenoxy}-nicotinamide,
6-(4-{2-[(Naphthalen-1-ylmethyl)-amino]-ethyl}-phenoxy)-nicotinamide,
6-(4-{2-[(Bicyclo[2.2.1]hept-5-en-2-ylmethyl)-amino]-ethyl}-phenoxy)-nicotinamide,
6-(4-{2-[(Naphthalen-2-ylmethyl)-amino]-ethyl}-phenoxy)-nicotinamide,
6-(4-{2-[(Quinolin-4-ylmethyl)-amino]-ethyl}-phenoxy)-nicotinamide,
6-{4-[2-(2,6-Dichloro-benzylamino)-ethyl]-phenoxy}-nicotinamide,
6-{4-[2-(Indan-1-ylamino)-ethyl]-phenoxy}-nicotinamide,
6-{4-[2-(2-Hydroxy-5-methoxy-benzylamino)-ethyl]-phenoxy}-nicotinamide,
6-{4-[2-(3-Bromo-4-fluoro-benzylamino)-ethyl]-phenoxy}-nicotinamide,
6-{4-[2-(4-Fluoro-2-trifluoromethyl-benzylamino)-ethyl]-phenoxy}-nicotinamide,
6-{4-[2-(3-Chloro-4-fluoro-benzylamino)-ethyl]-phenoxy}-nicotinamide,
6-[4-(2-Cyclooctylamino-ethyl)-phenoxy]-nicotinamide,
6-{4-[2-(2-Phenoxy-benzylamino)-ethyl]-phenoxy}-nicotinamide,
6-{4-[2-(Cyclobutylmethyl-amino)-ethyl]-phenoxy}-nicotinamide,
6-{4-[2-(Cycloheptylmethyl-amino)-ethyl]-phenoxy}-nicotinamide, 6-(4-{2-[(2-Morpholin-4-yl-thiazol-5-ylmethyl)-amino]-ethyl}-phenoxy)-nicotinamide,
6-(4-{2-[(2,4-Dichloro-thiazol-5-ylmethyl)-amino]-ethyl}-phenoxy)-nicotinamide,
6-(4-{2-[(2-Chloro-thiazol-5-ylmethyl)-amino]-ethyl}-phenoxy)-nicotinamide,
6-{4-[2-(Cyclopentylmethyl-amino)-ethyl]-phenoxy}-nicotinamide,
6-(4-{2-[(3,5-Dimethyl-isoxazol-4-ylmethyl)-amino]-ethyl}-phenoxy)-nicotinamide,
6-(4-{2-[(5-Methyl-isoxazol-3-ylmethyl)-amino]-ethyl}-phenoxy)-nicotinamide,
6-(4-{2-[(3-Phenyl-isoxazol-5-ylmethyl)-amino]-ethyl}-phenoxy)-nicotinamide,
6-[4-(2-{[3-(4-Chloro-phenyl)-[1,2,4]oxadiazol-5-ylmethyl]-amino}-ethyl)-phenoxy]-nicotinamide,
6-(4-{2-[(5-p-Tolyl-[1,3,4]oxadiazol-2-ylmethyl)-amino]-ethyl}-phenoxy)-nicotinamide,
6-{4-[2-(1-Phenyl-ethylamino)-ethyl]-phenoxy}-nicotinamide,
6-[4-(3-Benzylamino-propyl)-phenoxy]-nicotinamide,
6-{4-[3-(Benzyl-pentyl-amino)-propyl]-phenoxy}-nicotinamide,
6-{4-[3-(Benzyl-phenethyl-amino)-propyl]-phenoxy}-nicotinamide,
6-(4-{3-[Benzyl-(3-cyclopentyl-propyl)-amino]-propyl}-phenoxy)-nicotinamide,
6-[4-(3-{Benzyl-[2-(3-fluoro-phenyl)-ethyl]-amino}-propyl)-phenoxy]-nicotinamide,
6-[4-(3-Pentylamino-propyl)-phenoxy]-nicotinamide,
6-[4-(3-Phenethylamino-propyl)-phenoxy]-nicotinamide,
6-{4-[3-(3-Cyclopentyl-propylamino)-propyl]-phenoxy}-nicotinamide,
6-(4-{3-[2-(3-Fluoro-phenyl)-ethylamino]-propyl}-phenoxy)-nicotinamide,
(R)-6-[4-(2-Benzylamino-propyl)-phenoxy]-nicotinamide,
(R)-6-[4-(2-Dibenzylamino-propyl)-phenoxy]-nicotinamide,
6-[4-(2-Benzylamino-2-methyl-propyl)-phenoxy]-nicotinamide,
6-[4-(2-Methyl-2-pentylamino-propyl)-phenoxy]-nicotinamide,
6-[4-(2-Methyl-2-phenethylamino-propyl)-phenoxy]-nicotinamide,
6-(4-{2-[2-(3-Fluoro-phenyl)-ethylamino]-2-methyl-propyl}-phenoxy)-nicotinamide,
6-{4-[2-(3-Cyclopentyl-propylamino)-2-methyl-propyl]-phenoxy}-nicotinamide,
6-[4-(3-Benzylamino-butyl)-phenoxy]-nicotinamide,
6-[4-(3-Pentylamino-butyl)-phenoxy]-nicotinamide,
6-[4-(3-Propylamino-butyl)-phenoxy]-nicotinamide,
6-[4-(3-Methylamino-butyl)-phenoxy]-nicotinamide,
6-[4-(3-Phenethylamino-butyl)-phenoxy]-nicotinamide,
6-(4-{3-[2-(3-Fluoro-phenyl)-ethylamino]-butyl}-phenoxy)-nicotinamide,
6-(4-{3-[2-(3-Chloro-phenyl)-ethylamino]-butyl}-phenoxy)-nicotinamide,
6-(4-{3-[(Furan-2-ylmethyl)-amino]-butyl}-phenoxy)-nicotinamide,
6-{4-[3-(2-Thiophen-2-yl-ethylamino)-butyl]-phenoxy}-nicotinamide,
6-{4-[3-(Cyclopropylmethyl-amino)-butyl]-phenoxy}-nicotinamide,
6-{4-[3-(3-Trifluoromethyl-benzylamino)-butyl]-phenoxy}-nicotinamide,
6-{4-[3-(4-Fluoro-benzylamino)-butyl]-phenoxy}-nicotinamide,
6-{4-[3-(3-Fluoro-benzylamino)-butyl]-phenoxy}-nicotinamide,
6-[4-(3-Allylamino-butyl)-phenoxy]-nicotinamide,
6-{4-[3-(4-Chloro-benzylamino)-butyl]-phenoxy}-nicotinamide,
6-{4-[3-(4-Methoxy-benzylamino)-butyl]-phenoxy}-nicotinamide,
6-{4-[3-(4-Trifluoromethyl-benzylamino)-butyl]-phenoxy}-nicotinamide,
6-{4-[3-(4-Trifluoromethoxy-benzylamino)-butyl]-phenoxy}-nicotinamide,
6-{4-[3-(3-Trifluoromethoxy-benzylamino)-butyl]-phenoxy}-nicotinamide,
(1R)-6-{4-[3-(1-Phenyl-ethylamino)-butyl]-phenoxy}-nicotinamide,
(1S)-6-{4-[3-(1-Phenyl-ethylamino)-butyl]-phenoxy}-nicotinamide,
6-[4-(2-Benzylamino-propyl)-phenoxy]-nicotinamide,
6-[4-(2-Pentylamino-propyl)-phenoxy]-nicotinamide,
6-[4-(2-Propylamino-propyl)-phenoxy]-nicotinamide,
6-[4-(2-Methylamino-propyl)-phenoxy]-nicotinamide,
6-[4-(2-Phenethylamino-propyl)-phenoxy]-nicotinamide,
6-(4-{2-[2-(3-Fluoro-phenyl)-ethylamino]-propyl}-phenoxy)-nicotinamide,
6-(4-{2-[2-(3-Chloro-phenyl)-ethylamino]-propyl}-phenoxy)-nicotinamide,
6-(4-{2-[(Furan-2-ylmethyl)-amino]-propyl}-phenoxy)-nicotinamide,
6-{4-[2-(2-Thiophen-2-yl-ethylamino)-propyl]-phenoxy}-nicotinamide,
6-{4-[2-(Cyclopropylmethyl-amino)-propyl]-phenoxy}-nicotinamide,
6-{4-[2-(3-Trifluoromethyl-benzylamino)-propyl]-phenoxy}-nicotinamide,
6-{4-[2-(4-Fluoro-benzylamino)-propyl]-phenoxy}-nicotinamide,
6-{4-[2-(3-Fluoro-benzylamino)-propyl]-phenoxy}-nicotinamide,
6-[4-(2-Allylamino-propyl)-phenoxy]-nicotinamide,
6-{4-[2-(4-Chloro-benzylamino)-propyl]-phenoxy}-nicotinamide,
6-{4-[2-(4-Trifluoromethyl-benzylamino)-propyl]-phenoxy}-nicotinamide,
6-{4-[2-(4-Methoxy-benzylamino)-propyl]-phenoxy}-nicotinamide,
6-{4-[2-(4-Trifluoromethoxy-benzylamino)-propyl]-phenoxy}-nicotinamide,
6-{4-[2-(3-Trifluoromethoxy-benzylamino)-propyl]-phenoxy}-nicotinamide,
(1S)-6-{4-[2-(1-Phenyl-ethylamino)-propyl]-phenoxy}-nicotinamide,
(1R)-6-{4-[2-(1-Phenyl-ethylamino)-propyl]-phenoxy}-nicotinamide,
6-[4-(2-Benzylamino-1-methyl-ethyl)-phenoxy]-nicotinamide,
6-{4-[2-(Benzyl-pentyl-amino)-1-methyl-ethyl]-phenoxy}-nicotinamide,
6-[4-(1-Methyl-2-pentylamino-ethyl)-phenoxy]-nicotinamide,
6-[4-(2-Benzylamino-1,1-dimethyl-ethyl)-phenoxy]-nicotinamide,
6-{4-[2-(Cyclohexylmethyl-amino)-1,1-dimethyl-ethyl]-phenoxy}-nicotinamide,
6-{4-[2-(2-Chloro-benzylamino)-1,1-dimethyl-ethyl]-phenoxy}-nicotinamide,
6-{4-[2-(3-Fluoro-benzylamino)-1,1-dimethyl-ethyl]-phenoxy}-nicotinamide, 6-[4-(3-Phenylamino-propyl)-phenoxy]-nicotinamide,
6-[4-(2-Dimethylamino-ethyl)-phenoxy]-nicotinamide,
6-[4-(2-Piperidin-1-yl-ethyl)-phenoxy]-nicotinamide,
6-[4-(2-Morpholin-1-yl-ethyl)-phenoxy]-nicotinamide,
6-{4-[2-(3,4-Dihydro-1H-isoquinolin-2-yl)-ethyl]-phenoxy}-nicotinamide,
6-{4-[2-(4-Benzoyl-piperidin-1-yl)-ethyl]-phenoxy}-nicotinamide,
6-{4-[2-(3-Methyl-piperidin-1-yl)-ethyl]-phenoxy}-nicotinamide,
6-{4-[2-(3,5-Dimethyl-piperidin-1-yl)-ethyl]-phenoxy}-nicotinamide,
6-{4-[2-(4-Benzhydryl-piperidin-1-yl)-ethyl]-phenoxy}-nicotinamide,
6-{4-[2-(4-Phenyl-piperidin-1-yl)-ethyl]-phenoxy}-nicotinamide,
6-(4-{2-[3-Fluoro-phenyl)-piperidin-1-yl]-ethyl}-phenoxy)-nicotinamide,
6-[4-(2-Azepan-1-yl-ethyl)-phenoxy]-nicotinamide,
6-{4-[2-(Benzyl-methyl-amino)-ethyl]-phenoxy}-nicotinamide,
6-{4-[2-(Benzyl-ethyl-amino)-ethyl]-phenoxy}-nicotinamide,
6-{4-[2-(Benzyl-propyl-amino)-ethyl]-phenoxy}-nicotinamide,
6-{4-[2-(Benzyl-butyl-amino)-ethyl]-phenoxy}-nicotinamide,
6-{4-[2-(Benzyl-cyclopropylmethylamino)-ethyl]-phenoxy}-nicotinamide,
6-{4-[2-(Benzyl-isobutyl-amino)-ethyl]-phenoxy}-nicotinamide,
6-{4-[2-(Benzyl-(3-methyl-butyl)-amino)-ethyl]-phenoxy}-nicotinamide,
6-[4-(2-Benzoylamino-ethyl)-phenoxy]-nicotinamide,
4-[4-(2-Benzylamino-ethyl)-phenoxy]-2-fluoro-benzamide,
2-[4-(2-Benzylamino-ethyl)-phenoxy]-4-fluoro-benzamide,
4-[4-(2-Benzylamino-ethyl)-phenoxy]-2-chloro-benzamide,
6-[4-(2-Benzylamino-ethyl)-2-methyl-phenoxy]-nicotinamide,
6-[2-Methyl-4-(phenethylamino-methyl)-phenoxy]nicotinamide,
6-[2-Fluoro-4-(phenethylamino-methyl)-phenoxy]nicotinamide,
6-[2-Ethoxy-4-(phenethylamino-methyl)-phenoxy]nicotinamide,
6-[2-Chloro-4-(phenethylamino-methyl)-phenoxy]nicotinamide,
6-[3-Chloro-4-(phenethylamino-methyl)-phenoxy]nicotinamide,
6-[2-Methyl-4-(3-methyl-butylamino-methyl)-phenoxy]nicotinamide,
6-[2-Fluoro-4-(3-methyl-butylamino-methyl)-phenoxy]nicotinamide,
6-[2-Chloro-4-(3-methyl-butylamino-methyl)-phenoxy]nicotinamide,
6-[2-Ethoxy-4-(3-methyl-butylamino-methyl)-phenoxy]nicotinamide,
6-{4-[2-Cyclopentyl-ethylamino)-methyl]-2-methyl-phenoxy}-nicotinamide,
6-{4-[2-Cyclopentyl-ethylamino)-methyl]-2-fluoro-phenoxy}-nicotinamide,
6-{2-Chloro-4-[2-Cyclopentyl-ethylamino)-methyl]-phenoxy}-nicotinamide,
6-{4-[2-Cyclopentyl-ethylamino)-methyl]-2-ethoxy-phenoxy}-nicotinamide,
6-{2-Methyl-4-[2-thiophen-2-yl-ethylamino)-methyl]-phenoxy}-nicotinamide,
6-(4-{[2-(3-Fluoro-phenyl)-ethylamino]-methyl}-2-methyl-phenoxy)-nicotinamide,
6-{2-Methyl-4-[(2-o-tolyl-ethylamino)-methyl]-phenoxy}-nicotinamide,
6-{4-[(3,3-Dimethyl-butylamino)-methyl]-2-methyl-phenoxy}-nicotinamide,
6-(4-{[2-(3-Chloro-phenyl)-ethylamino]-methyl}-2-methyl-phenoxy)-nicotinamide,
6-(4-Butylaminomethyl-2-methyl-phenoxy)-nicotinamide,
6-(2-Methyl-4-{[methyl-(3-methyl-butyl)-amino]-methyl}-phenoxy)-nicotinamide,
6-{2-Methyl-4-[(methyl-phenethyl-amino)-methyl]-phenoxy}-nicotinamide,
3-Fluoro-4-[4-(phenethylamino-methyl)-phenoxy]-benzamide,
3-Chloro-4-[4-(phenethylamino-methyl)-phenoxy]-benzamide,
2-Chloro-4-[4-(phenethylamino-methyl)-phenoxy]-benzamide,
3-Fluoro-4-{2-methyl-4-[(3-methyl-butylamino)-methyl]-phenoxy}-benzamide,
4-(4-Benzylamino-phenoxy)-benzamide,
4-(4-Phenethylamino-phenoxy)-benzamide,
6-[4-(Benzylamino-methyl)-phenoxy]-nicotinamide,
6-(4-Allylaminomethyl-phenoxy)-nicotinamide,
6-{4-[(4-Methoxy-benzylamino)-methyl]-phenoxy}-nicotinamide,
6-{4-[(3-Trifluoromethyl-benzylamino)-meth-yl]-phenoxy}-nicotinamide,
6-{4-[(2-Thiophen-2-yl-ethylamino)-methyl]-phenoxy}-nicotinamide,
6-{4-[(3-Fluoro-benzylamino)-methyl)]-phenoxy}-nicotinamide,
6-(4-{[(Furan-2-ylmethyl)-amino]-methyl}-phenoxy)-nicotinamide,
6-(4-{[2-(3-Fluoro-phenyl)-ethylamino]-methyl}-phenoxy)-nicotinamide,
6-{4-[(4-Trifluoromethoxy-benzylamino)-methyl]-phenoxy}-nicotinamide,
6-[4-(Phenethylamino-methyl)-phenoxy]-nicotinamide,
6-(4-{[2-(3-Chloro-phenyl)-ethylamino]-methyl}-phenoxy)-nicotinamide,
6-(4-{[2-(4-Sulfamoyl-phenyl)-ethylamino]-methyl}-phenoxy)-nicotinamide,
6-{4-[(3-Phenyl-propylamino)-methyl]-phenoxy}-nicotinamide,
6-{4-[(3,3-Diphenyl-propylamino)-methyl]-phenoxy}-nicotinamide,
6-{4-[(3,3-Dimethyl-butylamino)-methyl]-phenoxy}-nicotinamide,
6-(4-{[2-(2-Methoxy-phenyl)-ethylamino]-methyl}-phenoxy)-nicotinamide,
6-{4-[(2-Phenylamino-ethylamino)-methyl]-phenoxy}-nicotinamide,
6-{4-[(2-Phenyl-propylamino)-methyl]-phenoxy}-nicotinamide,
6-{4-[(2-Pyridin-2-yl-ethylamino)-methyl]-phenoxy}-nicotinamide,
6-(4-{[2-(2-Chloro-phenyl)-ethylamino]-methyl}-phenoxy)-nicotinamide,
6-{4-[(2-Pyridin-3-yl-ethylamino)-methyl]-phenoxy}-nicotinamide,
6-{4-[(2,2-Diphenyl-ethylamino)-methyl]-phenoxy}-nicotinamide,
6-{4-[(3-Methyl-butylamino)-methyl]-phenoxy}-nicotinamide, 6-{4-[(2-Cyclohexyl-ethylamino)-methyl]-phenoxy}-nicotinamide,
6-{4-[(2-Methylsulfanyl-ethylamino)-methyl]-phenoxy}-nicotinamide,
6-{4-[(6-Hydroxy-hexylamino)-methyl]-phenoxy}-nicotinamide,
6-{4-[(2-Dimethylamino-ethylamino)-methyl]-phenoxy}-nicotinamide,
6-(4-Decylaminomethyl-phenoxy)-nicotinamide,
6-{4-[(2-Ethyl-hexylamino)-methyl]-phenoxy}-nicotinamide,
6-(4-{[(Tetrahydro-furan-2-ylmethyl)-amino]-methyl}-phenoxy)-nicotinamide,
6-{4-[(2-Pyrrolidin-1-yl-ethylamino)-methyl]-phenoxy}-nicotinamide,
6-(4-{[2-(1-Methyl-pyrrolidin-2-yl)-ethylamino]-methyl}-phenoxy)-nicotinamide,
6-(4-{[2-(1H-Imidazol-4-yl)-ethylamino]-methyl}-phenoxy)-nicotinamide,
6-(4-{[3-(2-Methyl-piperidin-1-yl)-propylamino]-methyl}-phenoxy)-nicotinamide,
6-{4-[(2-Diisopropylamino-ethylamino)-methyl]-phenoxy}-nicotinamide,
6-{4-[(2-Cyclohex-1-enyl-ethylamino)-methyl]-phenoxy}-nicotinamide,
6-(4-Pentylaminomethyl-phenoxy)-nicotinamide,
4-{4-[(4-Trifluoromethoxy-benzylamino)-methyl]-phenoxy}-benzamide,
4-(4-{[2-(3-Chloro-phenyl)-ethylamino]-methyl}-phenoxy)-benzamide,
4-{4-[(4-Trifluoromethyl-benzylamino)-methyl]-phenoxy}-benzamide,
4-{4-[(4-Fluoro-benzylamino)-methyl]-phenoxy}-benzamide,
4-(4-Pentylaminomethyl-phenoxy)-benzamide,
4-{4-[(2-Phenyl-propylamino)-methyl]-phenoxy}-benzamide,
4-(4-{[2-(2-Chloro-phenyl)-ethylamino]-methyl}-phenoxy)-benzamide,
4-(4-{[2-(2,4-Dichloro-phenyl)-ethylamino]-methyl}-phenoxy)-benzamide,
4-(4-{[2-(4-Fluoro-phenyl)-ethylamino]-methyl}-phenoxy)-benzamide,
4-(4-{[2-(3-Fluoro-phenyl)-ethylamino]-methyl}-phenoxy)-benzamide,
4-(4-{[2-(2-Fluoro-phenyl)-ethylamino]-methyl}-phenoxy)-benzamide,
4-(4-{[2-(2,5-Dimethoxy-phenyl)-ethylamino]-methyl}-phenoxy)-benzamide,
4-(4-{[2-(2,6-Dichloro-phenyl)-ethylamino]-methyl}-phenoxy)-benzamide,
4-{4-[(2-o-Tolyl-ethylamino)-methyl]-phenoxy}-benzamide,
4-{4-[(2,2-Diphenyl-ethylamino)-methyl]-phenoxy}-benzamide,
4-[4-(3-Phenyl-propylamino)-phenoxy]-benzamide,
4-{4-[(2-Cyclopentyl-ethylamino)-methyl]-phenoxy}-benzamide,
4-{4-[(2,6-Dichloro-benzylamino)-methyl]-phenoxy}-benzamide,
4-(4-{[(Furan-2-ylmethyl)-amino]-methyl}-phenoxy)-benzamide,
6-(4-{[2-(3,4-Dichloro-phenyl)-ethylamino]-methyl}-phenoxy)-nicotinamide,
6-(4-{[2-(2-Ethoxy-phenyl)-ethylamino]-methyl}-phenoxy)-nicotinamide,
6-{4-[(2-o-Tolyl-ethylamino)-methyl]-phenoxy}-nicotinamide,
6-(4-{[2-(2-Phenoxy-phenyl)-ethylamino]-methyl}-phenoxy)-nicotinamide,
6-[4-((2-Thiophenyl-ethylamino)-methyl)-2-ethoxy phenoxy]nicotinamide,
6-[4-((3-Methyl-butylamino)-methyl)-2-ethoxy phenoxy]nicotinamide methanesulfonate salt,
6-[4-((3-Dimethyl-butylamino)-methyl)-2-ethoxy phenoxy]nicotinamide,
6-[4-(Butylamino-methyl)-2-ethoxy phenoxy]nicotinamide,
6-[4-((2-Phenyl-ethylamino)-methyl)-2,5-dimethyl phenoxy]nicotinamide,
6-[4-((2-Cyclopentyl-ethylamino)-methyl)-2-ethoxy phenoxy]nicotinamide methanosulfonate salt,
6-[4-((3-Methyl-butylamino)-methyl)-2,5-dimethyl phenoxy]nicotinamide
6-(4-Iodo-phenoxy)-nicotinamide,
(±)-6-(4-Piperidin-3-yl-phenoxy)-nicotinamide,
(±)-6-[4-(1-Benzyl-piperidin-3-yl)-phenoxy]-nicotinamide,
(±)-6-[4-(1-Cyclohexylmethyl-piperidin-3-yl)-phenoxy]-nicotinamide,
(±)-6-[4-(1-Methyl-piperidin-3-yl)-phenoxy]-nicotinamide,
(±)-6-[4-(1-(3-Fluoro-benzyl)-piperidin-3-yl)-phenoxy]-nicotinamide,
(±)-6-[4-(1-(2-Fluoro-benzyl)-piperidin-3-yl)-phenoxy]-nicotinamide,
(±)-6-[4-(1-Hexyl-piperidin-3-yl)-phenoxy]-nicotinamide,
(±)-6-{4-[1-(3-Methyl-butyl)-piperidin-3-yl]-phenoxy}-nicotinamide,
(±)-6-[4-(1-Phenethyl-piperidin-3-yl)-phenoxy]-nicotinamide,
(±)-6-{4-[1-(2-Cyclohexyl-ethyl)-piperidin-3-yl]-phenoxy}-nicotinamide,
6-[4-(4-Benzyl-piperazin-1-ylmethyl)-phenoxy]-nicotinamide,
6-[4-(4-Phenethyl-piperazin-1-ylmethyl)-phenoxy]-nicotinamide,
6-[4-(4-Cyclopentyl-piperazin-1-ylmethyl)-phenoxy]-nicotinamide,
(±)-6-{4-[4-(1-Phenyl-ethyl)-piperazin-1-ylmethyl]-phenoxy}-nicotinamide,
6-[4-(4-Benzhydryl-piperazin-1-ylmethyl)-phenoxy]-nicotinamide,
6-{4-[4-(4-Fluoro-phenyl)-piperazin-1-ylmethyl]-phenoxy}-nicotinamide,
6-[4-(4-Phenyl-piperazin-1-ylmethyl)-phenoxy]-nicotinamide,
6-[4-(4-Cyclohexyl-piperazin-1-ylmethyl)-phenoxy]-nicotinamide,
6-[4-(4-Isopropyl-piperazin-1-ylmethyl)-phenoxy]-nicotinamide,
(3R)-6-{4-[(1-Benzyl-pyrrolidin-3-ylamino)-methyl]-phenoxy}-nicotinamide,
(3S)-6-{4-[(1-Benzyl-pyrrolidin-3-ylamino)-methyl]-phenoxy}-nicotinamide,
(±)-6-[4-(2-Phenyl-piperidin-1-ylmethyl)-phenoxy]-nicotinamide,
(±)-6-[4-(2-Phenyl-pyrrolidin-1-ylmethyl)-phenoxy]-nicotinamide, hydrochloric acid salt,
(±)-6-[4-(3-Phenyl-pyrrolidin-1-ylmethyl)-phenoxy]-nicotinamide,
6-[4-(4-Phenyl-piperidin-1-ylmethyl)-phenoxy]-nicotinamide,
(±)-6-[4-(3-Phenyl-azepan-1-ylmethyl)-phenoxy]-nicotinamide, (±)-6-[4-(4-Phenyl-azepan-1-ylmethyl)-phenoxy]-nicotinamide,
6-[4-(4,4-Diphenyl-piperidin-1-ylmethyl)-phenoxy]-nicotinamide,
6-[4-(3,3-Diphenyl-pyrrolidin-1-ylmethyl)-phenoxy]-nicotinamide,
6-[4-(2,2-Diphenyl-pyrrolidin-1-ylmethyl)-phenoxy]-nicotinamide,
6-(4-Piperidin-1-ylmethyl-phenoxy)-nicotinamide,
(±)-6-[4-(1,2,4,4a,9,9a-Hexahydro-3-aza-fluoren-3-ylmethyl)-phenoxy]-nicotinamide.
(±)-6-{4-[3-(2-Chloro-phenyl)-piperidin-1-ylmethyl]-phenoxy}-nicotinamide,
(±)-6-{4-[3-(3-Chloro-phenyl)-piperidin-1-ylmethyl]-phenoxy}-nicotinamide,
(±)-6-{4-[3-(3-Trifluoromethyl-phenyl)-piperidin-1-ylmethyl]-phenoxy}-nicotinamide,
(±)-6-[4-(3-Methyl-piperidin-1-ylmethyl)-phenoxy]-nicotinamide,
(±)-6-[4-(3-Phenethyl-piperidin-1-ylmethyl)-phenoxy]-nicotinamide,
(±)-6-[4-(3-Phenpropyl-piperidin-1-ylmethyl)-phenoxy]-nicotinamide,
(±)-6-[4-(3-Benzyl-piperidin-1-ylmethyl)-phenoxy]-nicotinamide,
(±)-6-[4-(3-Phenyl-piperidin-1-ylmethyl)-phenoxy]-nicotinamide,
(±)-6-{4-[3-(4-Fluoro-phenyl)-piperidin-1-ylmethyl]-phenoxy}-nicotinamide, hydrochloric acid salt,
(±)-6-{4-[3-(2-Fluoro-phenyl)-piperidin-1-ylmethyl]-phenoxy}-nicotinamide, hydrochloric acid salt,
(±)-6-[4-(3-Cyclohexyl-piperidin-1-ylmethyl)-phenoxy]-nicotinamide, hydrochloric acid salt,
(±)-6-[2-Methyl-4-(3-phenyl-piperidin-1ylmethyl)-phenoxy]-nicotinamide, hydrochloric acid salt,
(±)-6-[2-Methyl-4-(3-phenyl-azepan-1ylmethyl)-phenoxy]-nicotinamide, hydrochloric acid salt,
(±)-6-[2-Methyl-4-(4-phenyl-azepan-1ylmethyl)-phenoxy]-nicotinamide,
(±)-1-{6-[2-Methyl-4-(3-phenyl-pyrrolidin-1-ylmethyl)-phenoxy]-pyridin-3-yl}-ethanone,
(±)-5-(1,1-Difluoro-ethyl)-2-[2-methyl-4-(3-phenyl-pyrrolidin-1-ylmethyl)-phenoxy]-pyridine hydrochloric acid salt,
(±)-6-[2-Fluoro-4-(3-phenyl-pyrrolidin-1-ylmethyl)-phenoxy]-nicotinamide,
(±)-6-[2-Ethoxy-4-(3-phenyl-pyrrolidin-1-ylmethyl)-phenoxy]-nicotinamide,
(±)-6-[2-Chloro-4-(3-phenyl-pyrrolidin-1-ylmethyl)-phenoxy]-nicotinamide,
6-(3-Phenethyl-2,3,4,5-tetrahydro-1H-benzo[d]azepin-7-yloxy)nicotinamide,
6-(3-Benzyl-2,3,4,5-tetrahydro-1H-benzo[d]azepin-7-yloxy)-nicotinamide,
6-[4-(Phenethylaminomethyl)phenoxy]nicotinamide,
{2-[4-(5-Aminomethylpyridin-2-yloxy)phenyl]ethyl}benzylamine,
5-[4-(Phenethylaminomethyl)phenoxy]pyridine-2-carboxyamide,
2-[4-(2-Benzylaminoethyl)phenoxy]nicotinamide,
6-[4-(2-Benzylaminoethyl)phenoxy]pyridine-2-carboxamide,
2-[4-(2-Benzylaminoethyl)phenoxy]isonicotinamide,
N-Methyl-{6-[4-(phenethylaminomethyl)phenoxy]nicotinamide,
5-[4-(Phenethylaminomethyl)phenoxy]pyrazine-2-carboxamide,
5-(4-{[2-(4-Fluorophenyl)ethylamino]methyl}phenoxy)pyridine-2-carboxamide,
5-{4-[(3-Methylbutylamino)methyl]phenoxy}pyridine-2-carboxamide methanesulfonate,
5-{2-Methyl-4-[(3-methylbutylamino)methyl]phenoxy}pyridine-2-carboxamide methanesulfonate,
5-{2-Methoxy-4-[(3-methylbutylamino)methyl]phenoxy}pyridine-2-carboxamide methanesulfonate,
5-(4-{[2-(3-Trifluoromethylphenyl)ethylamino]methyl}phenoxy)pyridine-2-carboxamide methanesulfonate,
5-{4-[(2-Thiophen-2-ylethylamino)methyl]phenoxy}pyridine-2-carboxamide methanesulfonate,
5-{2-Methyl-4-[(2-thiophen-2-ylethylamino)methyl]phenoxy}pyridine-2-carboxamide methanesulfonate,
5-{2-Methoxy-4-[(2-thiophen-2-ylethylamino)methyl]phenoxy}pyridine-2-carboxamide methanesulfonate,
5-{4-[(2-Cyclopentylethylamino)methyl]phenoxy}pyridine-2-carboxamide methanesulfonate,
5-{4-[(2-Cyclopentylethylamino)methyl]-2-methylphenoxy}pyridine-2-carboxamide methanesulfonate,
5-{4-[(2-Cyclopentylethylamino)methyl]-2-methoxyphenoxy}pyridine-2-carboxamide methanesulfonate,
5-(4-{[(Benzo[b]thiophen-3-ylmethyl)amino]methyl}phenoxy)pyridine-2-carboxamide methanesulfonate,
5-(4-{[2-(4-Methoxyphenyl)ethylamino]methyl}phenoxy)pyridine-2-carboxamide methanesulfonate,
5-(4-{[2-(3-Fluorophenyl)ethylamino]methyl}phenoxy)pyridine-2-carboxamide methanesulfonate,
5-(4-{[2-(2-Fluorophenyl)ethylamino]methyl}phenoxy)pyridine-2-carboxamide methanesulfonate,
5-{2-Fluoro-4-[(3-methylbutylamino)methyl]phenoxy}pyridine-2-carboxamide methanesulfonate,
5-{2-Methyl-4-[(3-methylbutylamino)methyl]phenoxy}pyrazine-2-carboxamide methanesulfonate,
5-(2-Fluoro-4-pentylaminomethylphenoxy)pyridine-2-carboxamide
5-{2-Fluoro-4-[(2-thiophen-2-ylethylamino)methyl]phenoxy}pyridine-2-carboxamide,
5-{2-Fluoro-4-[(2-pyridin-3-ylethylamino)methyl]phenoxy}pyridine-2-carboxamide,
5-{2-Fluoro-4-[(2-m-tolylethylamino)methyl]phenoxy}pyridine-2-carboxamide,
5-(2-Fluoro-4-{[2-(4-fluorophenyl)ethylamino]methyl}phenoxy)pyridine-2-carboxamide,
5-{2-Chloro-4-[(3-methylbutylamino)methyl]phenoxy}pyridine-2-carboxamide,
5-(2-Chloro-4-(pentylaminomethyl)phenoxy)pyridine-2-carboxamide,
5-{2-Chloro-4-[(2-thiophen-2-ylethylamino)methyl]phenoxy}pyridine-2-carboxamide,
5-{2-Chloro-4-[(2-pyridin-3-ylethylamino)methyl]phenoxy}pyridine-2-carboxamide,
6-{2-Methoxy-4-[(3-methylbutylamino)methyl]phenoxy}nicotinamide,
5-(2-Fluoro-4-{[2-(tetrahydropyran-4-yl)ethylamino]methyl}phenoxy)pyridine-2-carboxamide,
5-{2-Fluoro-4-[(2-o-tolylethylamino)methyl]phenoxy}pyridine-2-carboxamide,
5-{4-[(2-Naphthalen-2-ylethylamino)methyl]phenoxy}pyridine-2-carboxamide,
5-{4-[(2-Naphthalen-1-ylethylamino)methyl]phenoxy}pyridine-2-carboxamide, 5-{4-[(2-Benzo[b]thiophen-3-ylethylamino)methyl]phenoxy}pyridine-2-carboxamide,
6-(2-Methoxy-4-pentylaminomethylphenoxy)nicotinamide,
6-{2-Methoxy-4-[(2-thiophen-2-ylethylamino)methyl]phenoxy}nicotinamide,
6-{2-Methoxy-4-[(2-o-tolylethylamino)methyl]phenoxy}nicotinamide,
6-{2-Methoxy-4-[(2-m-tolylethylamino)methyl]phenoxy}nicotinamide,
6-{4-[(3,3-Dimethylbutylamino)methyl]-2-methoxyphenoxy}nicotinamide,
6-{2-Methoxy-4-[(2-pyridin-3-ylethylamino)methyl]phenoxy}nicotinamide,
6-(4-Butylaminomethyl-2-methoxyphenoxy)nicotinamide,
6-(2-Methoxy-4-{[2-(tetrahydropyran-4-yl)ethylamino]methyl}phenoxy)nicotinamide,
6-{2-Methoxy-4-[(2-morpholin-4-ylethylamino)methyl]phenoxy}nicotinamide,
6-{4-[(2-Ethylbutylamino)methyl]-2-methoxyphenoxy}nicotinamide,
6-(4-{[2-(4-Fluorophenyl)ethylamino]methyl}-2-methoxyphenoxy)nicotinamide,
6-(4-{[2-(2-Fluorophenyl)ethylamino]methyl}-2-methoxyphenoxy)nicotinamide,
6-(4-Hexylaminomethyl-2-methoxyphenoxy)nicotinamide,
6-{2-Methoxy-4-[(4-methylpentylamino)methyl]phenoxy}nicotinamide methanesulfonate,
6-{2-Methoxy-4-[(2-p-tolylethylamino)methyl]phenoxy}nicotinamide methanesulfonate,
5-(2-Methyl-4-{[2-(tetrahydropyran-4-yl)ethylamino]methyl}phenoxy)pyrazine-2-carboxamide,
5-{4-[(3,3-Dimethylbutylamino)methyl]-2-methylphenoxy}pyrazine-2-carboxamide,
5-{4-[(3-Methylbutylamino)methyl]phenoxy}pyrazine-2-carboxamide,
5-(4-{[2-(Tetrahydropyran-4-yl)ethylamino]methyl}phenoxy)pyrazine-2-carboxamide,
5-{4-[(3,3-Dimethylbutylamino)methyl]phenoxy}pyrazine-2-carboxamide,
6-(2-Methoxy-4-{[2-(tetrahydropyran-4-yl)ethylamino]methyl}phenoxy)nicotinamide methanesulfonate,
6-(4-Hexylaminomethyl-2-methoxyphenoxy)nicotinamide methanesulfonate,
6-(2-Methoxy-4-pentylaminomethylphenoxy)nicotinamide methanesulfonate,
6-(4-Butylaminomethyl-2-methoxyphenoxy)nicotinamide methanesulfonate,
6-{2-Methoxy-4-[(2-pyridin-3-ylethylamino)methyl]phenoxy}nicotinamide methanesulfonate,
6-{4-[(2-Ethylbutylamino)methyl]-2-methoxyphenoxy}nicotinamide methanesulfonate,
6-{4-[(3,3-Dimethylbutylamino)methyl]-2-methoxyphenoxy}nicotinamide methanesulfonate,
6-{2-Methoxy-4-[(3-methylbutylamino)methyl]phenoxy}nicotinamide methanesulfonate,
6-(2)-Phenethyl-2,3,4,5-tetrahydro-1H-benzo[c]azepin-7-yloxy)nicotinamide,
6-[2-(3-Methylbutyl)-2,3,4,5-tetrahydro-1H-benzo[c]azepin-7-yloxy]nicotinamide,
6-[2-(3-Methylpentyl)-2,3,4,5-tetrahydro-1H-benzo[c]azepin-7-yloxy]nicotinamide,
(±)-6-{4-[2-(2-Hydroxycyclohexylamino)ethyl]phenoxy}nicotinamide,
(±)-(cis)-6-{4-[2-(3-Hydroxycyclohexylamino)ethyl]phenoxy}nicotinamide,
(±)-(trans)-6-{4-[2-(3-Hydroxycyclohexylamino)ethyl]phenoxy}nicotinamide,
(±)-6-{4-[2-((trans)-4-Hydroxycyclohexylamino)ethyl]phenoxy}nicotinamide,
(±)-6-{4-[2-((trans)-2-Hydroxycyclopentylamino)ethyl]phenoxy}nicotinamide,
4-[5-(Phenethylamino-methyl)-pyridin-2-yloxy]-benzamide dihydrochloride 4-{5-[(3-Trifluoromethyl-benzylamino)-methyl]-pyridin-2-yloxy}-benzamide 4-{5-[(3-Phenyl-propylamino)-methyl]-pyridin-2-yloxy}-benzamide
4-{5-[(4-Fluoro-benzylamino)-methyl]-pyridin-2-yloxy}-benzamide 4-[5-(Isobutylamino-methyl)-pyridin-2-yloxy]-benzamide 4-{5-[(2-Thiophen-2-yl-ethylamino)-methyl]-pyridin-2-yloxy}-benzamide
4-(5-{[2-(3-Fluoro-phenyl)-ethylamino]-methyl}-pyridin-2-yloxy)-benzamide
4-(5-{[2-(2-Methoxy-phenyl)-ethylamino]-methyl}-pyridin-2-yloxy)-benzamide 4-(5-{[2-(2-Chloro-phenyl)-ethylamino]-methyl}-pyridin-2-yloxy)-benzamide 4-[5-(3-Phenyl-pyrrolidin-1-ylmethyl)-pyridin-2-yloxy]-benzamide 4-{5-[(3,3-Dimethyl-butylamino)-methyl]-pyridin-2-yloxy}-benzamide 4-{5-[(3-Methyl-butylamino)-methyl]-pyridin-2-yloxy}-benzamide
4-{3-Chloro-5-[(2-thiophen-2-yl-ethylamino)-methyl]-pyridin-2-yloxy}-benzamide
4-(3-Chloro-5-{[2-(3-chloro-phenyl)-ethylamino]-methyl}-pyridin-2-yloxy)-benzamide and pharmaceutically acceptable salts, solvates, enantiomers, and mixtures of diastereomers thereof.

Also particularly preferred is a compound selected from the group consisting of:
6-[2-Chloro-4-(3-methyl-butylamino-methyl)-phenoxy]nicotinamide,
6-(2-Methoxy-4-pentylaminomethylphenoxy)nicotinamide,
6-{2-Methoxy-4-[(3-methylbutylamino)methyl]phenoxy}nicotinamide,
6-{4-[(3,3-Dimethyl-butylamino)-methyl]-2-methyl-phenoxy}-nicotinamide,
6-{4-[(3,3-Dimethylbutylamino)methyl]-2-methoxyphenoxy}nicotinamide,
5-(2-Fluoro-4-pentylaminomethylphenoxy)pyridine-2-carboxamide,
6-(4-{[2-(2-Fluorophenyl)ethylamino]methyl}-2-methoxyphenoxy)nicotinamide,
4-(4-{[2-(4-Fluoro-phenyl)-ethylamino]-methyl}-phenoxy)-benzamide,
6-(4-{[2-(3-Fluoro-phenyl)-ethylamino]-methyl}-phenoxy)-nicotinamide, a combination of one or more of the above and a pharmaceutically acceptable salt, solvate, enantiomer, diastereomer and diastereomeric mixture thereof.

Most preferred is a compound selected from the group consisting of:
5-{2-Fluoro-4-[(3-methyl-butylamino)-methyl]-phenoxy}-pyrazine-2-carboxamide

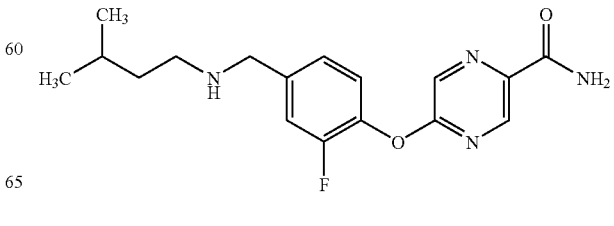

5-(2-Methoxy-4-pentylaminomethyl-phenoxy)-pyrazine-2-carboxamide

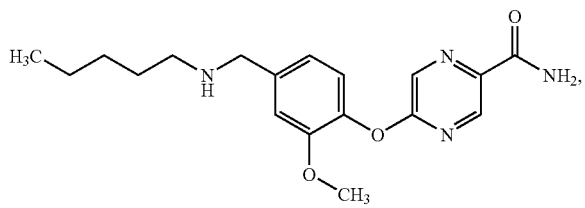

6-(2-Fluoro-4-{[2-(tetrahydro-pyran-4-yl)-ethylamino]-methyl}-phenoxy)-nicotinamide; methanesulfonic acid salt

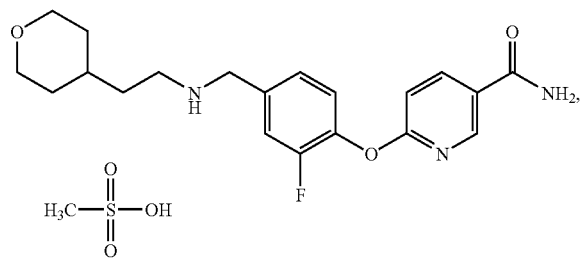

6-(2,3-Difluoro-4-pentylaminomethyl-phenoxy)-nicotinamide

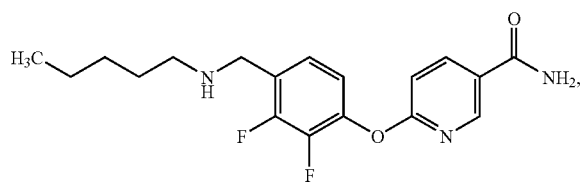

5-(4-{[2-(4-Fluoro-phenyl)-ethylamino]-methyl}-2-methoxy-phenoxy)-pyrazine-2-carboxamide

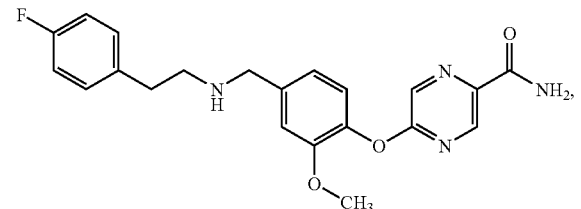

6-{4-[(3-Methyl-butylamino)-methyl]-phenoxy}-nicotinamide

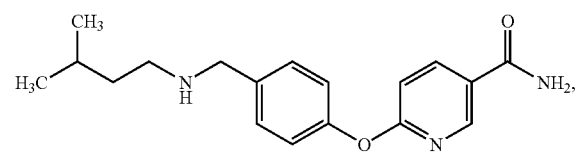

5-{4-[(4,4-Dimethyl-pentylamino)-methyl]-2-methoxy-phenoxy}-pyrazine-2-carboxamide

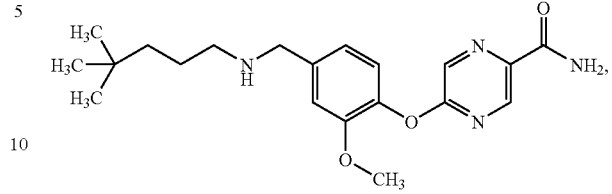

5-(2-Methoxy-4-{[2-(tetrahydro-pyran-4-yl)-ethylamino]-methyl}-phenoxy)-pyrazine-2-carboxamide

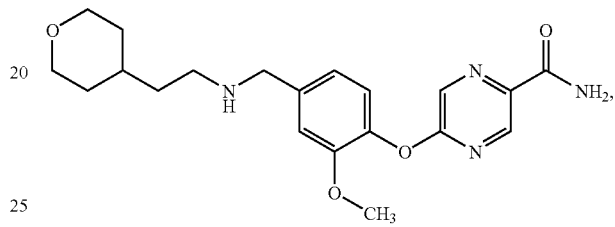

5-{4-[(3,3-Dimethyl-butylamino)-methyl]-2-fluoro-phenoxy}-pyrazine-2-carboxamide

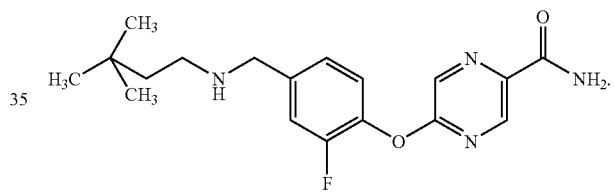

5-(2-Fluoro-4-{[2-(tetrahydro-pyran-4-yl)-ethylamino]-methyl}-phenoxy)-pyrazine-2-carboxamide

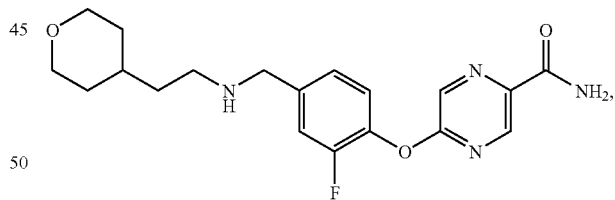

6-{2-Methyl-4-[(3-methyl-butylamino)-methyl]-phenoxy}-nicotinamide; methanesulfonic acid salt

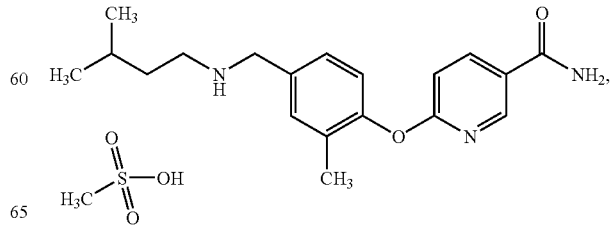

5-(2-Methyl-4-{[2-(tetrahydro-pyran-4-yl)-ethylamino]-methyl}-phenoxy)-pyrazine-2-carboxamide,

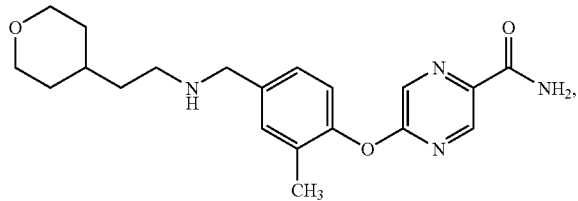

6-{4-[(3,3-Dimethyl-butylamino)-methyl]-2-fluoro-6-methoxy-phenoxy}-nicotinamide,

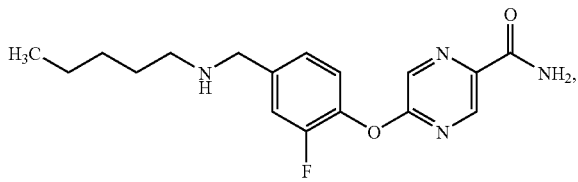

5-(2-Fluoro-4-pentylaminomethyl-phenoxy)-pyrazine-2-carboxamide


3-Chloro-4-{4-[(3,3-dimethyl-butylamino)-methyl]-phenoxy}-benzamide

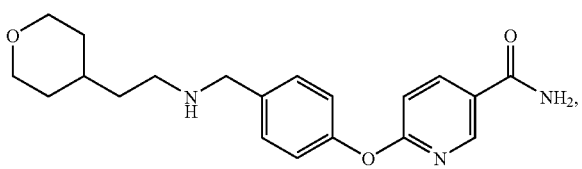

6-(4-{[2-(Tetrahydro-pyran-4-yl)-ethylamino]-methyl}-phenoxy)-nicotinamide

6-{4-[2-(3,3-Dimethyl-butylamino)-ethyl]-2,6-difluoro-phenoxy}-nicotinamide

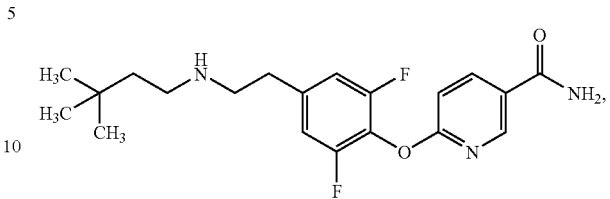

6-{2-Chloro-4-[(3-methyl-butylamino)-methyl]-phenoxy}-nicotinamide

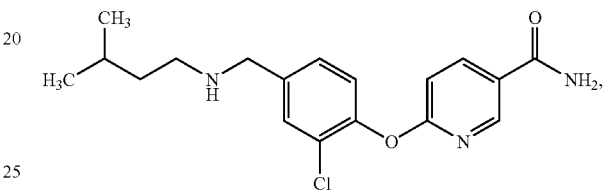

3,5-Difluoro-4-{4-[(3-methyl-butylamino)-methyl]-phenoxy}-benzamide

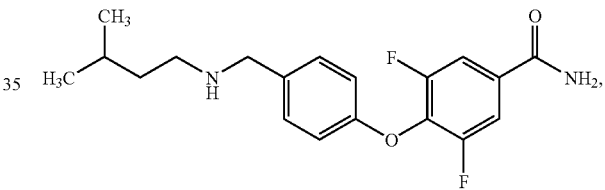

6-{2,3,6-Trifluoro-4-[(3-methyl-butylamino)-methyl]-phenoxy}-nicotinamide

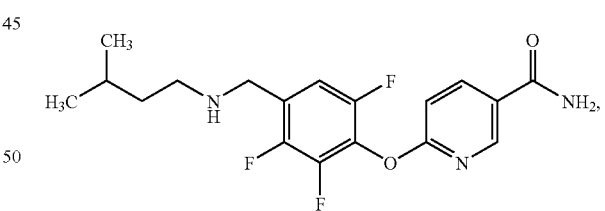

6-{2,6-Difluoro-4-[(3-methyl-butylamino)-methyl]-phenoxy}-nicotinamide

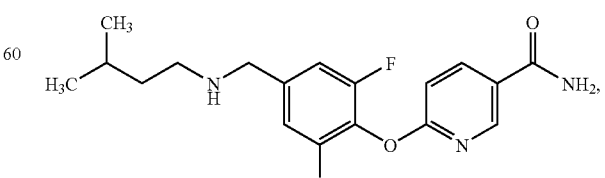

3-Fluoro-4-{4-[(3-methyl-butylamino)-methyl]-phenoxy}-benzamide

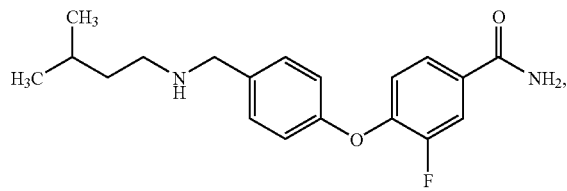

and a pharmaceutically acceptable salt, solvate, enantiomer, diastereomer and diastereomeric mixture thereof.

PREPARING COMPOUNDS OF THE INVENTION

In a typical protocol, an optionally substituted benzonitrile or pyridine carboxamide or synthon thereof, having a leaving group such as halogen, preferably fluoro, bromo, or chloro, or an alkylsulfonyl or other suitable leaving group is reacted with a nucleophilic group such as for example, hydroxy phenylcarboxaldelhyde or synthon or derivative thereof. For example according to Scheme 1, involves the use of potassium carbonate in dimethylacetamide at temperatures of about 60 to 100° C.

The nitrile compound of formula 3 is converted to the carboxamide 4 by hydrolysis procedures known to one of skill in the art. For example, the compound of formula 3 is reacted with potassium carbonate or other suitable base in the presence of hydrogen peroxide in a suitable organic solvent i.e. DMSO or DMF. The resulting amide compound 4 is reductively aminated with a suitably substituted amine. The reductive amination may be performed in two steps or a single step depending on the stability of the intermediate imine. The compound 4 is reacted with a primary or secondary amine (primary amine shown) in methanol as solvent. Molecular sieves may be added to enhance the efficiency of the imine formation. In a second step the reducing agent, typically, sodium borohydride or other hydride reducing agent is added to the reaction mixture. The progress of the reaction may be monitored by TLC, HPLC, LC-MS or other analytical technique known to one of skill in the art to determine the substantial completion of each step and timing for the addition of the next reagent. The reductive amination of compound 4 results in the compound of formula 5, which is a compound of the invention. Analogues of compounds 3 and 5 having one or more substituent R groups may be prepared by using appropriately substituted starting materials or by inter-conversion

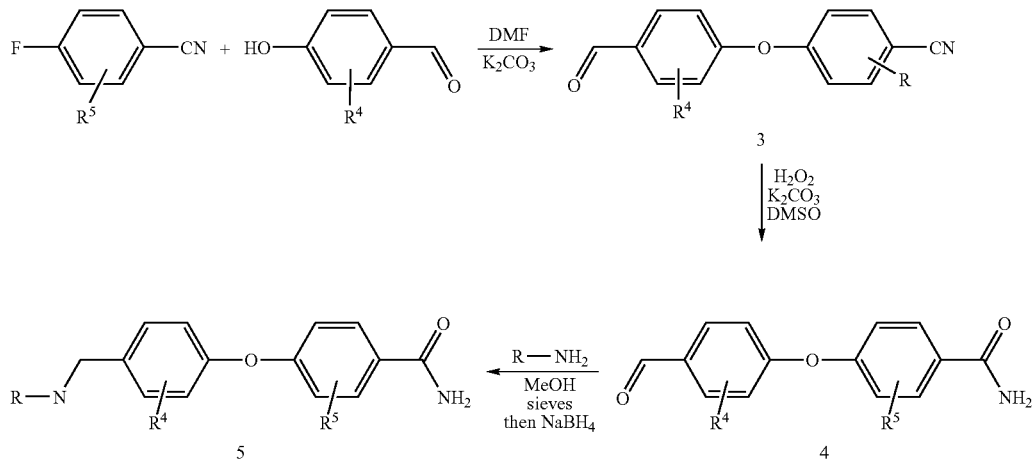

optionally substituted 4-fluorobenzonitrile is reacted with optionally substituted 4-hydroxybenzaldehyde to afford the ether, compound 3, under basic conditions. Basic conditions include the use of bases selected from inorganic and organic bases. Examples of useful inorganic bases include but are not limited to potassium carbonate, sodium hydride, sodium carbonate, sodium hydroxide, potassium hydroxide, calcium carbonate and cesium carbonate. Examples of organic bases include but are not limited to potassium hexamethyl disilazide, n-butyl lithium, Hexamethylphophoroustriamide, (HMPT), and the like. The basic conditions are complemented by the presence of a solvent, preferably an organic solvent. Preferred organic solvents include protic solvents or polar aprotic solvents. Most preferred solvents include dimethylformamide, methanol, dimethylacetamide (DMA), dimethylsulfoxide. A most preferred basic reaction condition of substituent functionality. For example an initial substituent R group may be protected and deprotected appropriately to achieve the desired end substituent R. Alternatively an initial substituent, R may be converted by known 1, 2 or 3 step reactions to other desired R substituents.

An alternate protocol illustrated in Scheme 2 shows the use of the carboxamide starting material to prepare, for example, compounds having the pyridinyl B-ring.

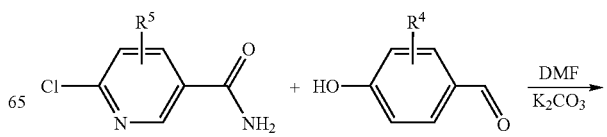

-continued

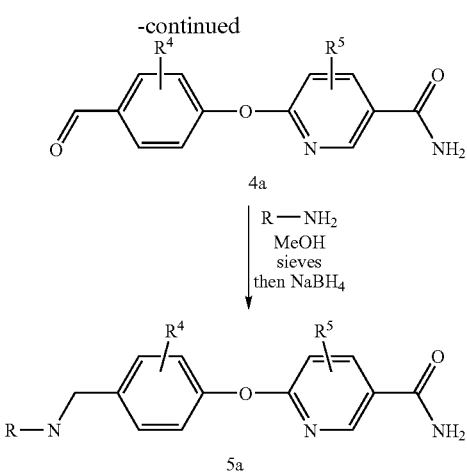

The use of the carboxamide starting material is particularly preferred for compounds of the invention where the B-ring is pyridinyl, pyridazinyl, pyrazinyl or pyrimidinyl group. The carboxamide may be introduced as part of the starting material where the appropriate surrogate for the B-ring is commercially available or may be prepared for certain groups as discussed in the examples. For example, the use of pyridine carboxamide, nicotinamide or substituted analogs thereof, results in substituted derivatives or analogs of compounds of formula 4a or 5a, which are also compounds of the present invention. Primary and secondary amines are useful for the reductive amination to convert compound (4a) to compound (5a). Examples of useful amines include but are not limited to phenethylamine, 3-methylbutylamine, propylamine, isopropylamine, benzylamine and isopentylamine.

Compounds prepared by this and other schemes disclosed herein or known to one of skill in the art may further be converted to the acid addition salt as shown for example, in Scheme 2A.

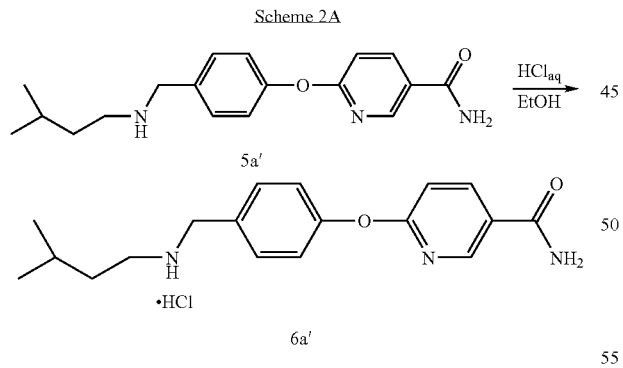

Scheme 2A shows preparation of the hydrochloride salt (6a') of compound 5a of Scheme 2 wherein $RNH_2$ is 3-methylbutylamine or other amine group and $R^4$ and $R^5$ are both hydrogen. The compound 5a' is dissolved in ethanol and a slight excess (e.g 1.0 to 1.5 mo.ar equivalents) of 1N hydrochloric acid is added at temperatures ranging from about 0° C. to room temperature. The mixture may be allowed to crystallize over time with or without cooling, or may be evaporated to afford the hydrochloride salt, which may be further purified by trituration with a suitable organic solvent such as toluene, hexanes, diethylether or mixtures thereof. Alternatively, anhydrous HCl may be bubbled into a cold solution of compound 5a' until the reaction is complete or the solution is saturated, and the mixture worked up as appropriate. One of skill in the art is aware of the nuances and the varied techniques for preparing, isolating and purifying acid addition salts, and should achieve comparable results using methods appropriate for the particular substrate without undue experimentation.

A modified protocol for preparing compounds of the invention is provided in Scheme 3 wherein the nucleophilic displacement reaction to form the ether linkage is performed towards the end of the synthesis rather than early on.

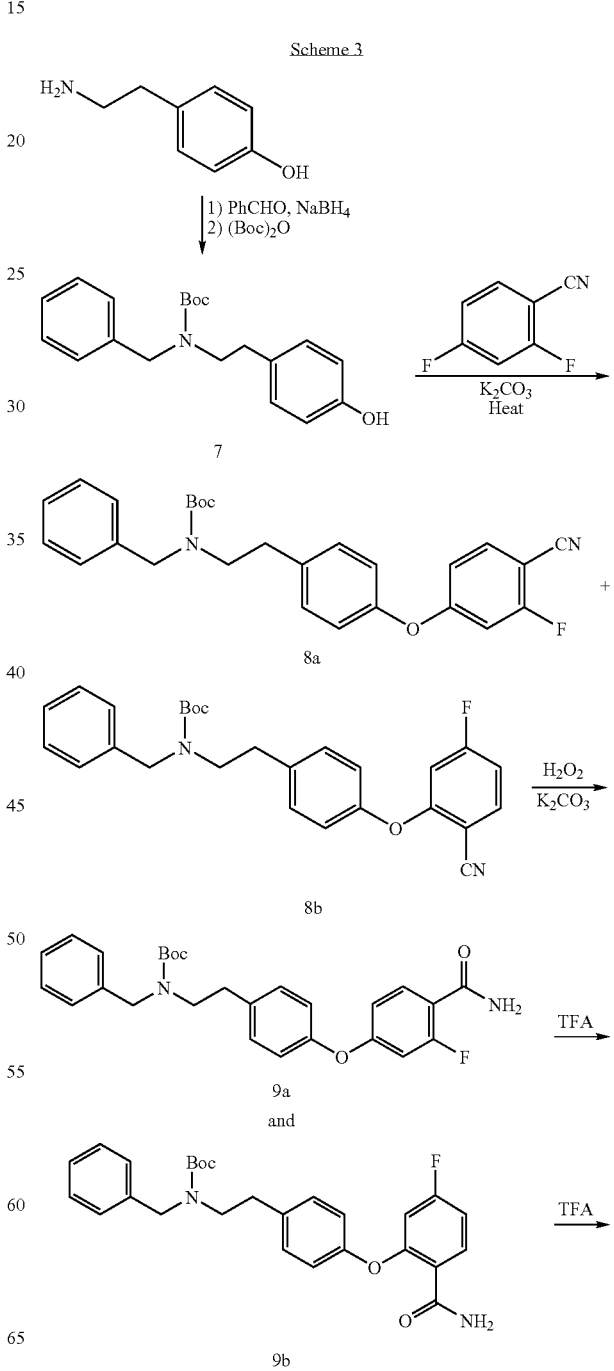

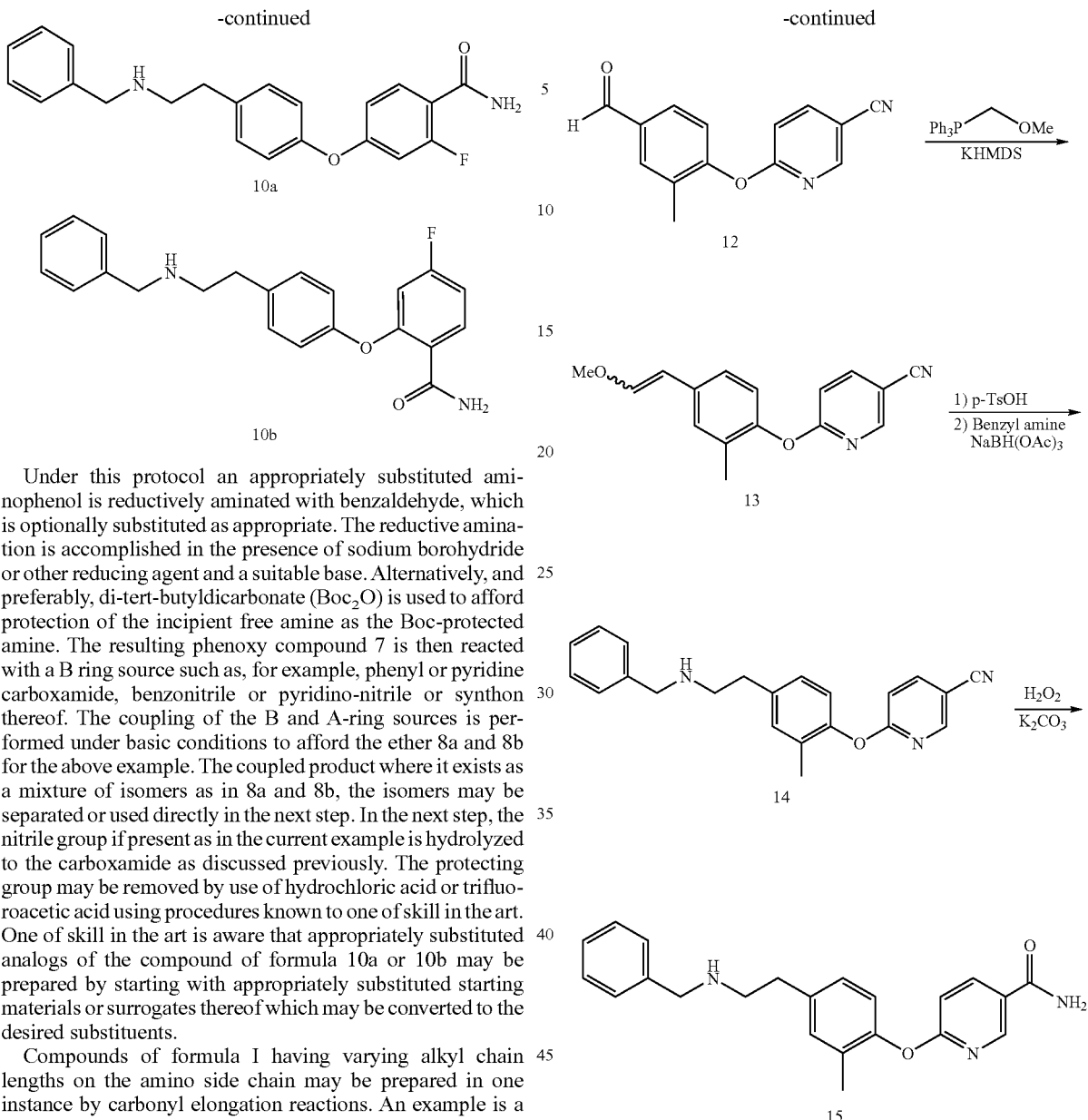

Under this protocol an appropriately substituted aminophenol is reductively aminated with benzaldehyde, which is optionally substituted as appropriate. The reductive amination is accomplished in the presence of sodium borohydride or other reducing agent and a suitable base. Alternatively, and preferably, di-tert-butyldicarbonate ($Boc_2O$) is used to afford protection of the incipient free amine as the Boc-protected amine. The resulting phenoxy compound 7 is then reacted with a B ring source such as, for example, phenyl or pyridine carboxamide, benzonitrile or pyridino-nitrile or synthon thereof. The coupling of the B and A-ring sources is performed under basic conditions to afford the ether 8a and 8b for the above example. The coupled product where it exists as a mixture of isomers as in 8a and 8b, the isomers may be separated or used directly in the next step. In the next step, the nitrile group if present as in the current example is hydrolyzed to the carboxamide as discussed previously. The protecting group may be removed by use of hydrochloric acid or trifluoroacetic acid using procedures known to one of skill in the art. One of skill in the art is aware that appropriately substituted analogs of the compound of formula 10a or 10b may be prepared by starting with appropriately substituted starting materials or surrogates thereof which may be converted to the desired substituents.

Compounds of formula I having varying alkyl chain lengths on the amino side chain may be prepared in one instance by carbonyl elongation reactions. An example is a modified Wittig type reaction as shown in Scheme 4.

Scheme 4

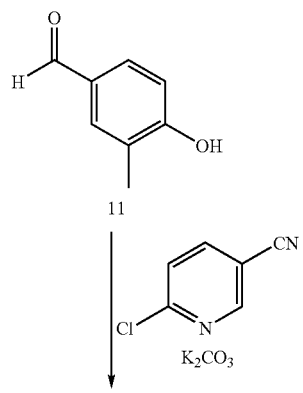

The protocol of Scheme 4 and known variations thereof allow manipulation of the amino side chain for chain length and/or substituents. Under this protocol, optionally substituted 4-hydroxy benzaldehyde i.e. compound 11 is reacted with optionally substituted benzonitrile having a suitable leaving group, e.g. halo, alkylsulfonyl, etc. The nicotinonitrile 12 or analog thereof, is then subjected to a carbonyl elongation reaction such as, for example, the Wittig reaction and variations thereof. (see *Organophosphorus Agents in Organic Synthesis*, J. I. G. Cadogan, Ed., Academic Press London (1979); see also, J. March, Advanced Organic Chemistry, $3^{rd}$ Edition, Wiley Interscience, New York N.Y., (1995). In the example given, the aldehyde 12 is reacted with methoxymethyl triphenylphosphine (available from Aldrich chemical Company, Milwaukee, USA) using a strong base such as, for example, n-butyl lithium, sec-butyl lithium and the like, to generate the incipient carbanion. The resulting vinylmethyl ether 13 is hydrolyzed using a strong acid such as, p-toluenesulfonic acid, HCl or sulfuric acid to generate the new aldehyde. The aldehyde is then reacted with a suitable amine followed by reduction to afford the reductive amination product 14. Details of each step in the schemes disclosed herein are provided in the experimental section, or may be found in reference organic synthesis texts or are known to one of skill in the art. Some reactions such as the formation of the ylide specie for the Wittig and related reactions perform better at reduced temperatures ranging from about −10° C. to about −70° C. Other reactions perform better at elevated temperatures ranging from about 30° C. to about 150° C., and yet other reactions perform better at ambient temperature ranging from about 15° C. to about 30° C.

Compounds of the invention wherein the groups $R^1$ and $R^2$ combine with each other and with the nitrogen atom to form a nitrogen containing heterocycle may be prepared, for example, according to scheme 5.

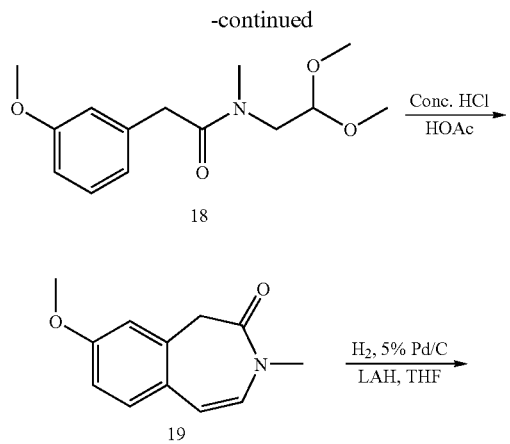

Scheme 5

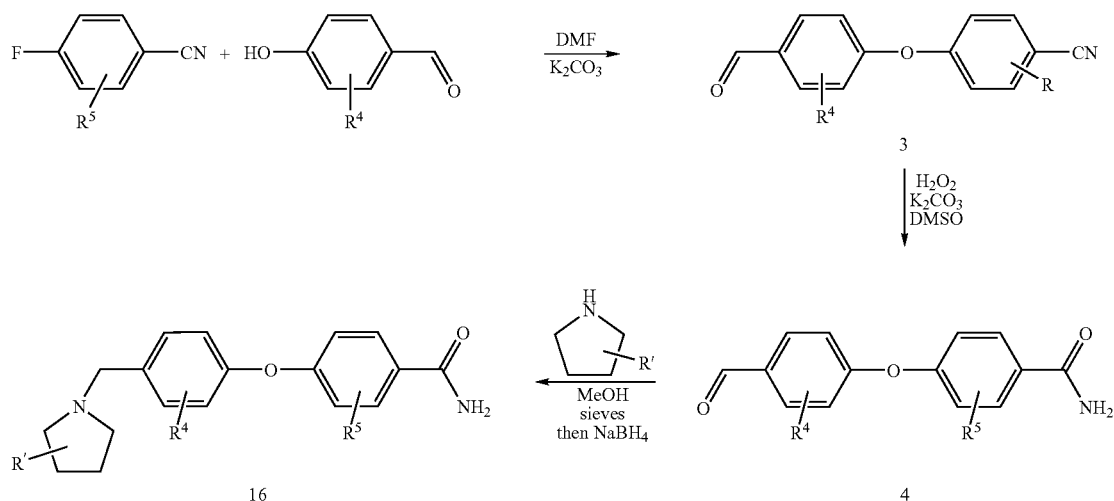

According to Scheme 5, the reductive amination of aldehyde with amine is performed using a cyclic amine having the desired ring size and/or substituents. For example, the reaction of compound optionally substituted cyclic amine such as for example, optionally substituted pyrrolidine (as shown) with the aldehyde 4 results in the formation of compound 16 having the $R^1$ and $R^2$ combine together to form the nitrogen containing heterocyclic amine.

Compounds of formula I wherein $R^1$ or $R^2$ combines with the A ring to form a nitrogen containing heterocycle may be prepared as shown in the following scheme 6.

Scheme 6

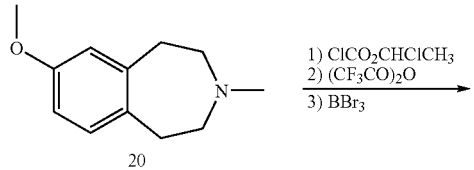

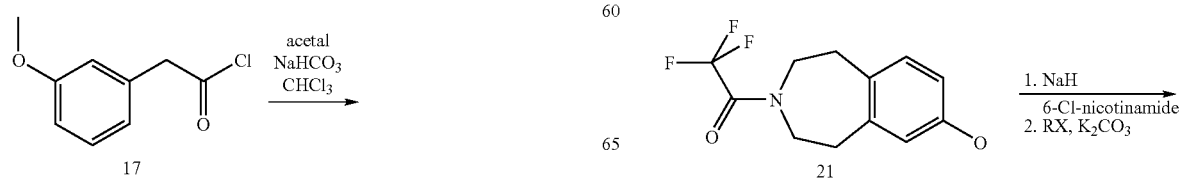

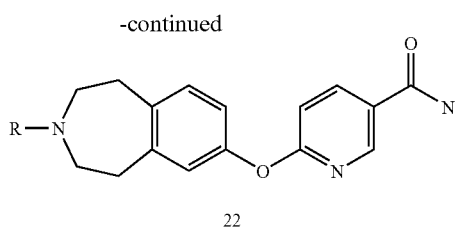

The scheme above, shows the preparation of the benzo[d] azepine ring as a representative example. As shown the reaction of 3-methoxyphenacetyl chloride (17) with methylamino acetaldehyde dimethylacetal results in the formation of compound 18. Compound (18) is cyclized to the azepin-2-one compound 19. Compound 19 is reduced to the tetrahydrobenzo[d]azepin-2-one compound using, for example, lithium aluminum hydride in THF or 5% palladium on carbon in ethyl acetate. The compound is further deoxygenated and reduced to the tetrahydrobenzo[d]azepine compound 20. Compound 20 is first protected as the trifluoroacetamide, de-methylated with boron tribromide in a suitable polar aprotic solvent, and then reacted with 6-chloronicotinamide, for example, to form the corresponding ether product. The trifluoroacetamide protecting group is removed by basic hydrolysis, i.e. ammonia in methanol, and substitution on the azepine nitrogen results in compounds of the invention 22. Such substitutions may be effected by using a base such as sodium or potassium carbonate in the presence of the electrophile i.e. alkyl, benzyl or aryl halide. Detailed procedures for the practice of the above protocol, as with other protocols described above may be found in the experimental section. Also details for individual steps of protocols disclosed herein may be found in the literature or are known to one of skill in the art.

Compounds of formula I wherein the B-ring is a positional isomer of pyridine may be prepared as shown for example in Scheme 7.

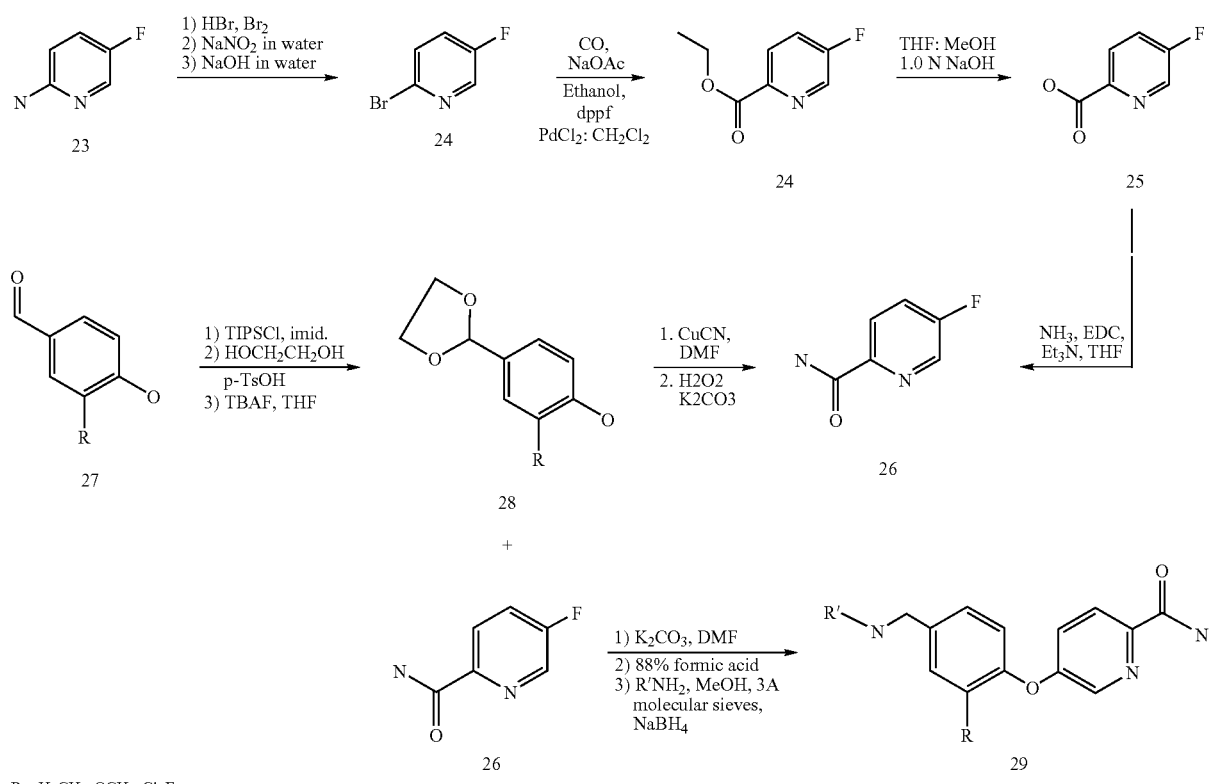

R = H, CH₃, OCH₃, Cl, F

As shown above, diazotization followed by bromination of 2-amino-5-fluoropyridine (23) affords the 2-bromo-5-fluoropyridine compound 24. The 2-bromo-5-fluoropyridine compound is converted to the ethoxycarbonyl derivative via a hydroxycarbonylation reaction followed by esterification of the incipient carboxylic group. The palladium catalyzed hydroxycarbonylation reaction is known to one of skill in the art and is also disclosed in general organic chemistry reference text. For a variant of the hydroxycarbonylation reaction using the triflate leaving group see Sandro Sacchi and Alessandro Lupi, *Palladium Catalyzed Hydroxycarbonylation of Vinyl and Aryl Triflates: Synthesis of α,β-Unsaturated and Aromatic Carboxylic Acids*, Tetrahedron Letters, Vol. 33, No. 27, pp. 3939-3942, (1992). The resulting ester may be hydrolyzed to the acids which is then converted to the carboxamide via a coupling reaction facilitated by a coupling agent such as EDCI for example. Alternatively the 2-bromo-5-fluoropyridine compound may be converted to the nitrile by reaction with copper cyanide in a polar aprotic solvent such as DMF. The nitrile is then hydrolyzed as discussed previously to afford the corresponding carboxamide 26. One of skill in the art is aware that palladium catalyzed cyanation reactions using copper cyanide, palladium source and ligand are available to effect the cyanation reaction discussed above with similar or possibly improved yields. The carboxamide compound 26 is reacted with a substituted or unsubstituted 4-hydroxybenzaldehyde protected as the acetal 28. The resulting etherification product is then reductively aminated with an amine in the presence of sodium borohydride or other suitable reducing agent to afford the compound of the invention 29 as shown.

Compounds of formula I wherein the B ring is pyrazinyl may be prepared, for example, according to scheme (8) below:

Scheme 8

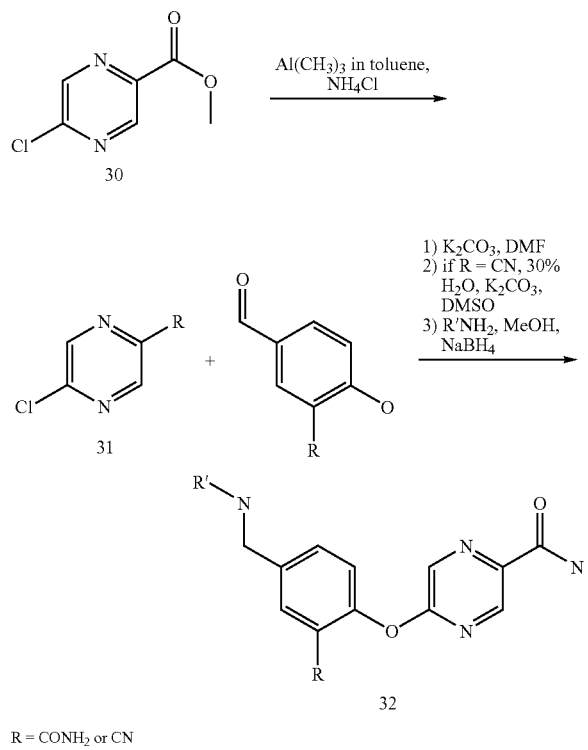

R = CONH₂ or CN

Compounds wherein R¹ and/or R² is independently a cyclic group, i.e. saturated of unsaturated monocyclic carbocycle may be prepared as shown below in Scheme 9. Scheme 9 is affected by reacting the amine 33 incorporating the A-ring, with a halogeno-nicotinamide e.g., 6-chloronicotinamide or a halogeno-nicotinonitrile to form the compound of the invention 34.

Scheme 9

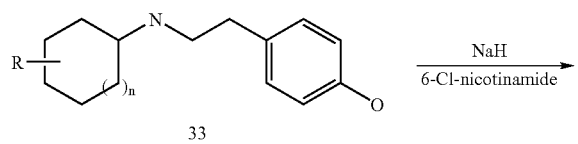

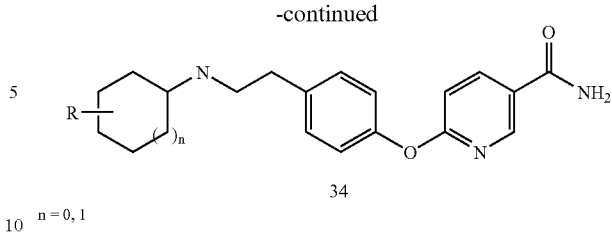

n = 0, 1

Where a halogeno-nicotinonitrile is used the hydrolysis of the resulting nitrile to form the amide derivative has been disclosed previously. The amine 33 is itself prepared by reductive amination of 4-hydroxy phenacetaldehyde and the respective amine. The phenacetaldehyde may itself be purchased or prepared from the corresponding benzaldehyde by carbonyl elongation reactions i.e. by the Wittig or modified Wittig reaction as discussed previously.

An alternative protocol is shown in Scheme 10.

Scheme 10

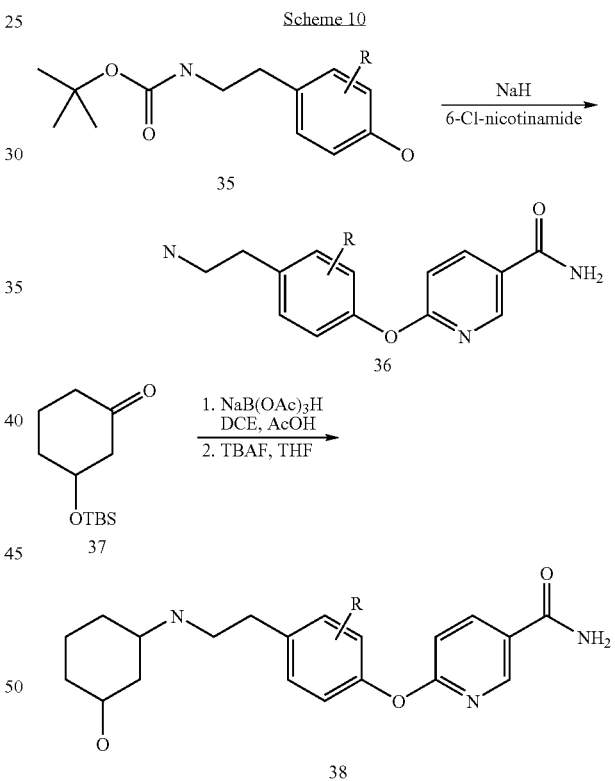

As shown in Scheme 10, an amine substrate having the A-ring, i.e., 4-hydroxyphenethyl amine is protected at the amine using, for example, the Boc-protecting group or other typical amino protecting groups. The Boc-protected amine 35 is coupled to the B-ring component, i.e., 6-chloronicotinamide (shown) or nicotinonitrile or benzonitrile or analog or derivative thereof. The coupled product is then de-protected and reductively aminated with a cyclic ketone having the desired R¹ and/or R² group per the structure and scope of formula I. For the example shown, tertiary butyl dimethyl silyl (TBDMS) protected 3-hydroxycyclohexanone 37 is reacted with the amine 36 having the A and B rings already in place, to form the desired compound of the invention 38 upon desilylation.

The preferred reaction conditions for each step of the reactions or schemes disclosed herein are provided in the experimental section, or known to one of skill in the art, or suggested in the literature or ascertainable with minimal routine experimentation by one of skill in the art following some or all the teachings disclosed and/or referenced herein. Substituents such as "R" and "R" groups used in the schemes are for illustration purposes only and are not intended to limit the scope of the number and/or type of substituents. One of skill in the art is aware of substituent-types and multiplicities thereof that are suitable and/or possible for a particular position. In general, while a particular substrate or compound is used for illustration purposes, no limitation is implied the workability of the particular scheme for other compounds within the ambit of the invention unless so stated. One of skill in the art is aware that compounds of formula II may also be prepared by the schemes above and by procedures disclosed in the experimental section.

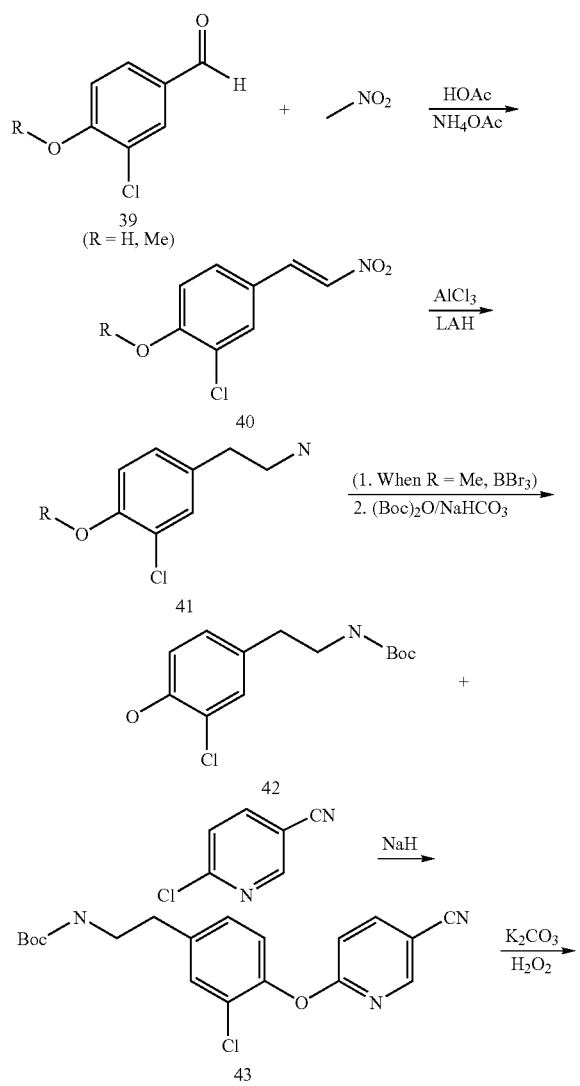

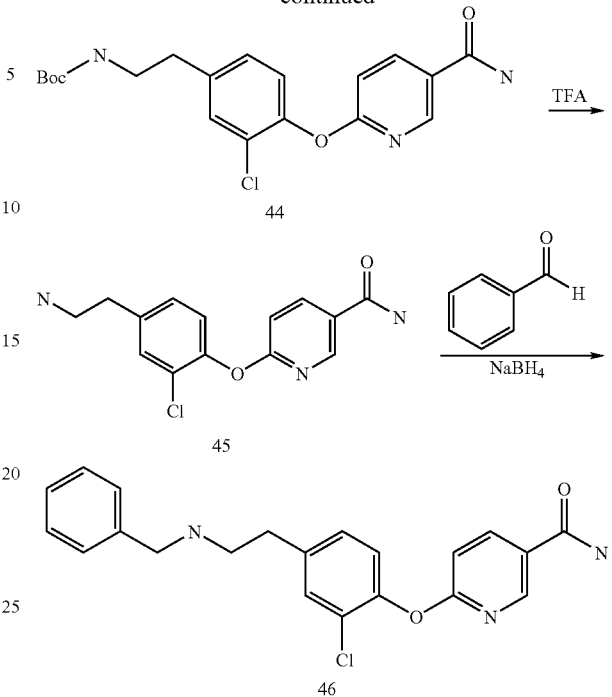

Certain compounds of the invention may also be accessed by protocols such as Scheme 11. For example, compounds of formula I or II having "y" groups other than hydrogen may be more readily accessed by a Michael addition of nitromethane on an aldehyde e.g., aldehyde 39, having the desired A ring substituents. The resulting product is reduced to afford the saturated amine. When r is methyl the product 41 is deprotected by reaction with BBr$_3$, following procedures disclosed herein and/or known to one of skill in the art. The resulting hydoprxyamine is optionally protected for example by use of a Boc-group to afford the compound 42. The protected amino compound 42 is then reacted with appropriately substituted benzamide or nicotinonitrile or nicotinamide to afford a compound of formula I or II after further processing as described previously.

METHOD OF USING THE INVENTION

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I or II.

The term "receptor blocking dose", as used herein, means an amount of a compound of formula I or II necessary to block a mu, kappa, or delta receptor or receptor v combination (heterodimer) thereof following administration to a mammal requiring blocking of a mu, kappa, or delta receptor or receptor combination (heterodimer) thereof.

The compounds of formula I or II or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof, such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof. The compounds of the present invention have been found to display excellent activity in an opioid receptor binding assay which measures the ability of the compounds to block the mu, kappa, delta or receptor combination (heterodimer) thereof.

GTP-γ-S Binding Assay

An SPA—based GTP-γ-S assay format was developed based on previous opioid (Emmerson et al., J. Pharm Exp Ther 278, 1121, 1996; Horng et al., Society for Neuroscience Abstracts, 434.6, 2000) and muscarinic (DeLapp et al., JPET 289, 946, 1999) assay formats. Membranes were re-suspended in 20 mM HEPES, 100 mM NaCl, 5 mM $MgCl_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a representative sample of compounds of the invention in the GTP-γ-S Binding Assay are shown in table 1 below.

TABLE 1

| Compound # | Mu (nM) | Kb (nM) Kappa | Delta (nM) |
|---|---|---|---|
| | | In Vitro Antagonism GTP-γ-S | |
| 475 | 0.843 | 7.859 | 17.489 |
| 476 | 0.281 | 3.378 | 8.900 |
| 478 | 0.410 | 4.498 | 5.779 |
| 271 | 0.200 | 0.400 | 4.400 |
| 479 | 0.503 | 6.855 | 30.101 |
| 252 | 0.177 | 2.166 | 14.121 |

TABLE 1-continued

| Compound # | Mu (nM) | Kb (nM) Kappa | Delta (nM) |
|---|---|---|---|
| | | In Vitro Antagonism GTP-γ-S | |
| 253 | 0.068 | 0.355 | 0.708 |
| 256 | 0.072 | 0.894 | 0.677 |

Ex-Vivo Receptor Binding

In order to bridge in vitro binding affinity and antagonist potency to in vivo potency and efficacy applicants have developed an ex vivo receptor binding assay in rat brain. This assay measures the difference in association (binding) of a high affinity nonselective opioid receptor radioligand (3H-diprenorphine) in brain tissue isolated from animals receiving vehicle versus compound treatment (less binding of 3H-diprenorphine=greater compound association with opioid receptors). Studies using the ex-vivo receptor binding assay have demonstrated a positive correlation between activity (potency and duration of activity) which also correlates to 24 hour efficacy in dietary induced obese rats.

Methods. An opioid receptor ex vivo binding assay measures 3H-diprenorphine binding (0.1-0.4 nM affinity radioligand for mu, delta and kappa receptors) in rat striatum/nucleus accumbens; a region of the brain that contains a high density of mu, delta and kappa receptors, following oral administration of compounds. Experimentally, a screening dose of 7 mg/kg, p.o. of compound or vehicle is administered to rats. Six hours following compound administration, the animals are sacrificed and the striatum/nucleus accumbens is isolated and homogenized in 10 volumes (weight/volume) binding buffer. The homogenate is then used in a homogenate binding assay using a saturating concentration of 3H-diprenorphine for 30 minutes. The homogenization and assay is performed at 4° C., to minimize compound redistribution in the in vitro binding portion of the assay. Results are reported (Table 2) as % inhibition of diprenorphine binding, based on the difference in specific binding between compound treated animals versus control animals treated with vehicle alone.

TABLE 2

| Compound of Example No. | Ex Vivo Binding [3H]-Diprenorphine % Inhibition of at 6 hours 7 mg/kg of test compound |
|---|---|
| 228 | >65% |
| 309 | >60% |
| 271 | >40% |
| 253 | >40% |
| 481 | 83% |
| 229 | 77% |
| 420 | 75% |
| 447 | 62% |
| 263 | 62% |
| 238 | 59% |
| 446 | 55% |
| 227 | 55% |
| 405 | 55% |
| 431 | 54% |
| 294 | 50% |
| 256 | 40% |
| 272 | 79% |

TABLE 2-continued

| Compound of Example No. | Ex Vivo Binding [3H]-Diprenorphine % Inhibition of at 6 hours 7 mg/kg of test compound |
|---|---|
| 246 | 58% |
| 240 | 38% |
| LY255582 | >40% |
| Naltrexone ® | <40% |

Acute Feeding Assay (Rat Obesity Assay)

The efficacy of compounds of the present invention has been further verified by the results of a Rat Obesity assay shown in Table 3. The assay results show that compounds of the present invention achieve inhibition of opioid receptors at a level comparable to or superior to that achieved with a previous clinical candidate compound LY255582 disclosed and claimed in U.S. Pat. No. 4,891,379.

TABLE 3

| Compound of Example No. | Doses in ug/kg to achieve effective inhibition |
|---|---|
| 290 | 3 |
| 227 | 0.3 |
| 228 | 0.3 |
| 271 | 0.3 |
| 263 | ≦3 |
| 309 | ≦3 |
| 253 | ≦3 |
| LY255582 | 1 |
| Naltrexone ® | >10 |

Indirect Calorimetry Assay

Twenty-four-hour energy expenditure (EE) and respiratory quotient (RQ) were measured by indirect calorimetry using an open circuit calorimetry system (Oxymax, Columbus Instruments Int. Corp., USA). RQ is the ratio of the volume of $CO_2$ produced ($VCO_2$) to the volume of $O_2$ consumed ($VO_2$). EE was calculated as the product of calorific value of oxygen (CV) and $VO_2$ per kilogram of body weight, where CV=3.815+1.232 (RQ). Total calories expended were calculated to determine daily fuel utilization. To calculate the proportion of protein, fat and carbohydrate that is used during that 24-hour period, we used Flatt's proposal (see, Flatt J P 1991 Assessment of daily and cumulative carbohydrate and fat balances in mice. J Nutr Biochem 2:193-202.) and formulae as well as other derived constants (see Elia M, Livesey G 1992 Energy expenditure and fuel selection in biological systems: the theory and practice of calculations based on indirect calorimetry and tracer methods. World Rev Nutr Diet 70:68-131.). Food consumption over the 24-hour period was also measured. The minimum effective dose (MED) for inhibition of food consumption is reported as the lowest dose that caused a reduction in food consumption that was significantly different from vehicle treated controls. Results obtained for a sample of compounds of the invention with the indirect calorimetry assay are shown below in Table 4.

TABLE 4

| Compound of Example | Inhibition of Feeding Diet Induced Obese Rat Minimum Effective Dose (MED) mg/kg, p.o. | Energy Balance* Diet Induced Obese Rat test dose 3 mg/kg, p.o. kcal/kg/day |
|---|---|---|
| 290 | 3 | −65 |
| 227 | 0.3 | −68 |
| 228 | 0.3 | −81 |
| 271 | 0.3 | −35 |
| 263 | ≦3 | −56 |
| 309 | ≦3 | −39 |
| 253 | ≦3 | −19 |
| LY255582 | 1 | −36 |
| Naltrexone ® | >10 | Not significant |

*Energy balance = caloric intake minus utilization (kcal/kg/day)

The indirect calorimetry assay above shows that the minimum effective dose to inhibit food consumption at a level significantly different from the level achieved with a vehicle control dose was comparable or better for compounds of the present invention compared to a reference compound.

FORMULATION

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active ingredient). As such, the present invention also provides pharmaceutical formulations comprising a compound of the invention and a pharmaceutically acceptable carrier, diluent or excipient thereof.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
|---|---|---|
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50-60° C. and passed through a No. 18 mesh U.S. sieve. The sodium carboxylmethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
|---|---|
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxylmethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
| --- | --- |
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

EXAMPLE 1

6-[4-(2-Benzylamino-ethyl)-phenoxy]-nicotinamide

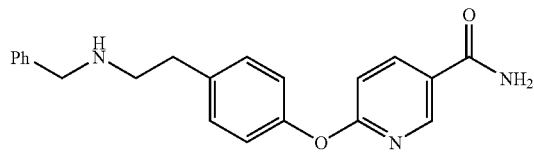

Step 1

4-(2-Benzylamino-ethyl)-phenol

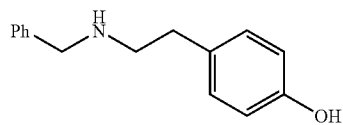

Add benzaldehyde (7.5 mL, 74 mmol) to a stirred solution of tyramine (10.00 g, 73 mmol) and anhydrous methanol (90 mL). Heat reaction to reflux for 1 h under nitrogen. Cool reaction to 0° C. and slowly add sodium borohydride (2.84 g, 75 mmol). Stir for 1 h at room temperature and then concentrate on a rotary evaporator. Add water (100 mL) and stir for 1.5 h at room temperature. Filter and wash with water to yield 10.11 g (61%) of 4-(2-benzylamino-ethyl)-phenol: mass spectrum (ion spray): m/z=228.1 (M+1); $^1$H NMR (DMSO-$d_6$): 9.14 (br s, 1H), 7.29-7.18 (m, 5H), 6.96 (d, 2H), 6.65 (d, 2H), 3.69 (s, 2H), 2.67-2.60 (m, 4H), 2.02 (br s, 1H).

Step 2

Add 6-chloronicotinamide (7.03 g, 44.90 mmol) to a stirred solution of 4-(2-benzylamino-ethyl)-phenol (10.10 g, 44.43 mmol), potassium carbonate (15.35 g, 111.1 mmol), dimethylacetamide (138 mL), and isooctane (16 mL). Using a Dean-Stark trap, heat the reaction to reflux under nitrogen for 6 h. Cool the reaction mixtures to room temperature, filter off the solids, and concentrate most of the solvent off on a rotary evaporator. Take the residue up in ethyl acetate (200 mL) and add 1N hydrochloric acid (200 mL). Stir for 15 minutes and filter off the precipitate washing with ethyl acetate. Dissolve the solid in 400 mL of boiling 1:1 methanol/water. To this solution add 5N sodium hydroxide (35 mL) and allow the solution to cool to room temperature. Filter and wash with water to yield 19.74 g (83%) of 6-[4-(2-benzylamino-ethyl)-phenoxy]-nicotinamide: mass spectrum (ion spray): m/z=348.1 (M+1); $^1$H NMR (CDCl$_3$): 8.58 (d, 1H), 8.15 (dd, 1H), 7.34-7.24 (m, 7H), 7.06 (d, 2H), 6.93 (d, 1H), 6.08 (br s, 2H), 3.82 (s, 2H), 2.92 (t, 2H), 2.84 (t, 2H), 1.33 (br s, 1H).

EXAMPLE 2

6-{4-[2-(Benzyl-phenethyl-amino)-ethyl]-phenoxy}-nicotinamide

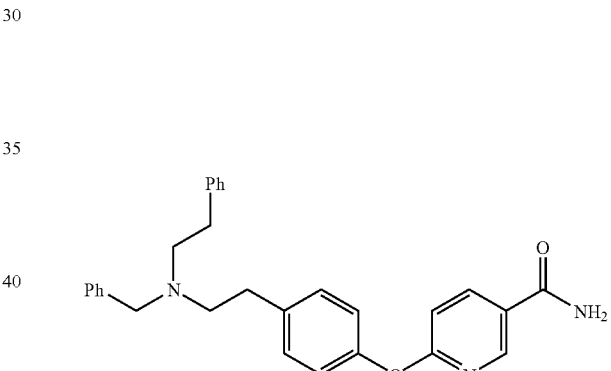

Add sodium bicarbonate (0.0823 g, 0.0980 mmol) to a stirred solution of 6-[4-(2-benzylamino-ethyl)-phenoxy]-nicotinamide (0.3061 g, 0.0881 mmol), (2-bromoethyl)benzene (0.135 mL, 0.988 mmol), and DMF (5 mL). Heat the reaction to reflux for 3 h under nitrogen and then cool to room temperature. Pour the reaction into water (50 mL) and extract with diethyl ether (3×50 mL). Dry the diethyl ether extracts over magnesium sulfate and then filter off the magnesium sulfate. Concentrate on a rotary evaporator and purify the crude product by flash chromatography on silica gel eluting with 90% ethyl acetate/hexanes to yield 0.1538 g (39%) of 6-{4-[2-(benzyl-phenethyl-amino)-ethyl]-phenoxy}-nicotinamide: mass spectrum (ion spray): m/z=452.1 (M+1); $^1$H NMR (CDCl$_3$): 8.55 (d, 1H), 8.13 (dd, 1H), 7.29-7.11 (m, 14H), 7.01 (d, 2H), 6.92 (d, 1H), 3.71 (s, 1H), 2.94-2.77 (m, 9H).

By the method of example 1 the following compounds were prepared:

| Example | Name | Mass spectrum (ion spray): m/z (M + 1) | $^1$H NMR (CDCl$_3$) |
|---|---|---|---|
| 3 | 6-(4-{2-[Benzyl-(3-phenyl-propyl)-amino]-ethyl}-phenoxy)-nicotinamide | 466.1 | 8.53 (d, 1H), 8.11 (dd, 1H), 7.29-7.11 (m, 14H), 7.03-7.00 (m, 2H), 6.91 (d, 1H), 3.63 (s, 2H), 2.77-2.68 (m, 4H), 2.59-2.52 (m, 4H), 1.83-1.75 (m, 2H) |
| 4 | 6-{4-[2-(Benzyl-hexyl-amino)-ethyl]-phenoxy}-nicotinamide | 433.1 | 8.56 (d, 1H), 8.13 (dd, 1H), 7.29-7.15 (m, 9H), 7.01 (d, 2H), 6.92 (dd, 1H), 3.62 (s, 2H), 2.78-2.66 (m, 4H), 2.48 (t, 2H), 1.48-1.43 (m, 2H), 1.30-1.23 (m, 6H), 0.86 (t, 3H) |
| 5 | 6-{4-[2-(Benzyl-heptyl-amino)-ethyl]-phenoxy}-nicotinamide | 446.2 | 8.56 (d, 1H), 8.13 (dd, 1H), 7.31-7.15 (m, 7H), 7.01 (d, 2H), 6.91 (d, 1H), 5.85 (br s, 2H), 3.62 (s, 2H), 2.78-2.66 (m, 4H), 2.48 (t, 2H), 1.48-1.45 (m, 2H), 1.29-1.24 (m, 8H), 0.86 (t, 3H) |
| 6 | 6-(4-{2-[Benzyl-(5-methyl-hexyl)-amino]-ethyl}-phenoxy)-nicotinamide | 446.1 | 8.55 (dd, 1H), 8.13 (dd, 1H), 7.29-7.16 (m, 9H), 7.03-6.98 (m, 2H), 6.92 (dd, 1H), 3.62 (s, 2H), 2.78-2.67 (m, 4H), 2.48 (t, 2H), 1.52-1.41 (m, 3H), 1.29-1.21 (m, 2H), 1.15-1.10 (m, 2H), 0.84 (d, 6H) |
| 7 | 6-[4-(2-{Benzyl-[2-(3-chloro-phenyl)-ethyl]-amino}-ethyl)-phenoxy]-nicotinamide | 486.2 | 8.55 (dd, 1H), 8.14 (dd, 1H), 7.28-6.91 (m, 16H), 3.69 (s, 2H), 2.78-2.69 (m, 8H) |
| 8 | 6-(4-{2-[Benzyl-(3-cyclohexyl-propyl)-amino]-ethyl}-phenoxy)-nicotinamide | 472.2 | 8.55 (d, 1H), 8.13 (dd, 1H), 7.29-7.15 (m, 9H), 7.01 (d, 2H), 6.92 (d, 1H), 3.62 (s, 2H), 2.78-2.67 (m, 4H), 2.46 (t, 2H), 1.67-1.46 (m, 7H), 1.19-1.12 (m, 6H), 0.87-0.82 (m, 2H) |
| 9 | 6-(4-{2-[Benzyl-(3-o-tolyl-propyl)-amino]-ethyl}-phenoxy)-nicotinamide | 480.0 | 8.54 (d, 1H), 8.13 (dd, 1H), 7.31-7.00 (m, 15H), 6.93 (d, 1H), 3.67 (s, 2H), 2.78-2.74 (m, 4H), 2.62-2.55 (m, 4H), 2.28 (s, 3H), 1.80-1.73 (m, 2H) |
| 10 | 6-(4-{2-[Benzyl-(3-thiophen-2-yl-propyl)-amino]-ethyl}-phenoxy)-nicotinamide | 472.1 | 8.55 (dd, 1H), 8.14 (dd, 1H), 7.31-6.72 (m, 15H), 3.65 (s, 2H), 2.83-2.71 (m, 6H), 2.58 (t, 2H), 1.89-1.60 (m, 2H) |

By the method of example 2 the following compounds were prepared:

| | | Data | | |
|---|---|---|---|---|
| | | | HPLC (30/70 to 90/10 ACN/(0.1% TFA in water) Zorbax SB-Phenyl Column 4.6 mm × 15 cm × 5 micron | |
| Example | Name | Mass spectrum (ion spray): m/z (M + 1) | Purity | Retention Time (minutes) |
| 11 | 6-{4-[2-(Benzyl-pentyl-amino)-ethyl]-phenoxy}-nicotinamide | 418.1 | 98.0 | 8.28 |
| 12 | 6-(4-{2-[Benzyl-(3-cyclopentyl-propyl)-amino]-ethyl}-phenoxy)-nicotinamide | 458.4 | 96.6 | 8.94 |
| 13 | 6-[4-(2-{Benzyl-[2-(2-fluoro-phenyl)-ethyl]-amino}-ethyl)-phenoxy]-nicotinamide | 470.3 | 98.0 | 8.44 |

EXAMPLE 14

6-[4-(2-Dibenzylamino-ethyl)-phenoxy]-nicotinamide

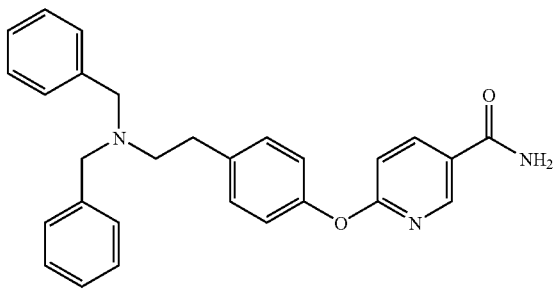

Compound of Example 14 is prepared by the method of Example 2.

EXAMPLES 15A-15E

Step 1

1-(2-Bromo-ethyl)-3-chloro-benzene-

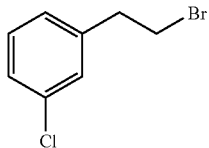

Add triphenylphoshpine (3.90 g, 14.9 mmol) to a stirred solution of 3-chlorophenethyl alcohol (2.0 mL, 14.8 mmol), carbon tetrabromide (4.91 g, 14.8 mmol) and anhydrous dichloromethane (100 mL). Stir for 5 h under nitrogen at room temperature, and then wash with water (100 mL) and brine (100 mL). Dry the dichloromethane layer over magnesium sulfate, filter, and concentrate on a rotary evaporator to give the crude product. The crude product is purified by flash chromatography on silica gel eluting with 100% hexanes to yield 2.30 g (71%) of 1-(2-bromo-ethyl)-3-chloro-benzene: TLC: $R_f$ in 100% hexanes: 0.27; $^1$H NMR (CDCl$_3$): 7.26-7.11 (m, 3H), 7.09-7.07 (m, 1H), 3.54 (t, 2H), 3.12 (t, 2H).

Step 2

Add sodium triacetoxyborohydride (0.2600 g, 1.227 mmol) to a stirred solution of 6-[4-(2-benzylamino-ethyl)-phenoxy]-nicotinamide (0.3058 g, 0.8802 mmol), benzaldehyde (0.092 mL, 0.905 mmol), glacial acetic acid (0.052 mL, 0.908 mmol) and 1,2-dichloroethane (8 mL). Stir for 18 h at room temperature under nitrogen. Pour the reaction into 1N sodium hydroxide (50 mL) and extract with diethyl ether (3×50 mL). Wash the diethyl ether extracts with brine, dry over magnesium sulfate, filter, and concentrate on a rotary evaporator to give the crude product. The crude product is purified by flash chromatography on silica gel eluting with 75% ethyl acetate/hexanes to yield 0.2501 g (65%) of 6-[4-(2-dibenzylamino-ethyl)-phenoxy]-nicotinamide: HPLC (30/70 to 90/10 ACN/(0.1% TFA in water) Zorbax SB-Phenyl Column 4.6 mm×5 cm×5 micron: Retention time: 8.14 minutes, Purity: 99.7%; mass spectrum (ion spray): m/z=438.0 (M+1).

The following compounds (Examples 15A-15E) were prepared from the corresponding commercially available alcohols except examples 1-(3-bromo-propyl)-2-methyl-benzene and 2-(3-bromo-propyl)-thiophene in which the starting alcohols were synthesized:

| Example No. | Name | TLC: $R_f$ in 100% Hexanes | $^1$H NMR (CDCl$_3$) |
|---|---|---|---|
| 15A | (3-Bromo-propyl)-cyclopentane | 0.55 | 3.38 (t, 2H), 1.89-1.38 (m, 11H), 1.11-1.02 (m, 2H) |
| 15B | (3-Bromo-propyl)-cyclohexane | 0.55 | 3.37 (t, 2H), 1.87-1.81 (m, 2H), 1.69-1.59 (m, 5H), 1.31-1.06 (m, 6H), 0.91-0.83 (m, 2H) |
| 15C | 1-(2-Bromo-ethyl)-3-fluoro-benzne | 0.28 | 7.30-7.24 (m, 1H), 6.98-6.89 (m, 3H), 3.55 (t, 2H), 3.15 (t, 2H) |
| 15D | 1-(3-Bromo-propyl)-2-methyl-benzene | 0.22 | 7.17-7.12 (m, 4H), 3.45 (t, 2H), 2.78 (t, 2H), 2.33 (s, 3H), 2.17-2.10 (m, 2H) |
| 15E | 2-(3-Bromo-propyl)-thiophene | 0.2 | 7.16-7.13 (m, 1H), 6.95-6.92 (m, 1H), 6.85-6.83 (m, 1H), 3.44 (t, 2H), 3.02 (t, 2H), 2.25-2.18 (m, 2H) |

Preparing Alcohol Starting Material for Example 15D 3-o-Tolyl-propan-1-ol

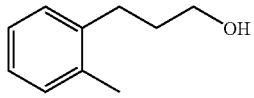

Add 2-methylhydrocinnamic acid (18.4 mmol) to anhydrous tetrahydrofuran (100 mL) and cool to 0° C. Slowly add lithium aluminum hydride (2.20 g, 58.0 mmol) and remove the ice bath after 20 minutes. Stir at room temperature under nitrogen for 18 h. Cool the reaction to 0° C. and quench the reaction by slowly adding water (2.2 mL), 15% sodium hydroxide (2.2 mL), and water (6.6 mL). Filter off the aluminum salts. Add brine (100 mL) and 5 N sodium hydroxide (30 mL) to the filtrate and extract with ethyl acetate (3×100 mL). Dry the ethyl acetate extracts with magnesium sulfate, filter, and concentrate on a rotary evaporator to yield 2.65 g (96%) of 3-o-tolyl-propan-1-ol: $^1$H NMR (CDCl$_3$): 7.18-7.10 (m, 4H), 3.72 (t, 2H), 2.72-2.69 (m, 2H), 2.33 (s, 3H), 1.90-1.83 (m, 2H), 1.60 (br s, 1H).

Preparing Alcohol Starting Material for Example 15E

3-Thiophen-2-yl-propan-1-ol

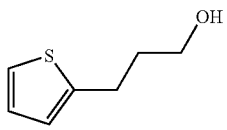

Using a method similar to example 15D, using 3-(2-thienyl)propanoic acid affords the title compound: $^1$H NMR (CDCl$_3$): 7.12 (dd, 1H), 6.92 (dd, 1H), 6.82-6.80 (m, 1H), 3.70 (t, 2H), 2.96-2.92 (m, 2H), 1.98-1.91 (m, 2H), 1.67 (br s, 1H).

EXAMPLE 16

6-(4-{2-[Benzyl-(3-oxo-3-phenyl-propyl)-amino]-ethyl}-phenoxy)-nicotinamide

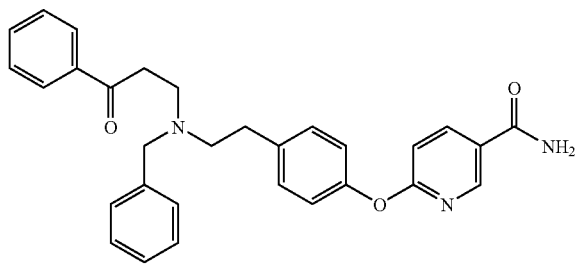

Step 1

3-Trimethylammonium-1-phenyl-propan-1-one iodide

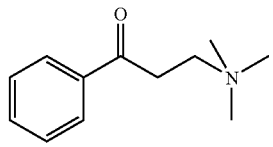

Add concentrated hydrochloric acid (0.090 mL, 1.1 mmol) to a stirred solution of acetophenone (5.0 mL, 43 mmol), paraformaldehyde (2.15 g), dimethylamine hydrochloride (4.54 g, 56 mmol), and ethanol (15 mL). Heat the reaction to reflux for 18 h under nitrogen. Cool the reaction to room temperature, pour it into 1 N sodium hydroxide (150 mL), and extract with diethyl ether (3×150 mL). Dry the diethyl ether extracts over magnesium sulfate, filter, and concentrate on a rotary evaporator to give the crude product. Dissolve the crude product in ethanol (70 mL) and add iodomethane (3.2 mL, 51 mmol). Stir the reaction at room temperature for 18 h under nitrogen. Filter and wash with ethanol followed by diethyl ether to yield 12.56 g (92%) of 3-trimethylammonium-1-phenyl-propan-1-one iodide: mass spectrum (ion spray): m/z=193.0 (M+1); $^1$H NMR (DMSO-d$_6$): 8.08-8.06 (m, 2H), 7.72-7.67 (m, 1H), 7.60-7.55 (m, 2H), 3.70 (s, 4H), 3.14 (s, 6H), 3.11 (s, 3H).

Step 2

Add 3-trimethylammonium-1-phenyl-propan-1-one iodide (0.3612 g, 1.132 mmol) to a stirred solution of 6-[4-(2-benzylamino-ethyl)-phenoxy]-nicotinamide (0.3041 g, 0.8753 mmol), sodium carbonate (0.1862 g, 1.757 mmol), and dimethylformamide (5 mL). Bubble nitrogen through the reaction for 18 h at room temperature. Pour the reaction into 1 N sodium hydroxide (50 mL) and extract with diethyl ether (3×50 mL). Dry the diethyl ether extracts over magnesium sulfate, filter, and concentrate on a rotary evaporator to give the crude product. The crude product is purified by flash chromatography on silica gel eluting with 90% ethyl acetate/hexanes to yield 0.1910 g (46%) of 6-(4-{2-[benzyl-(3-oxo-3-phenyl-propyl)-amino]-ethyl}-phenoxy)-nicotinamide: mass spectrum (ion spray): m/z=480.1 (M+1); $^1$H NMR (CDCl$_3$): 8.57 (d, 1H), 8.15 (dd, 1H), 7.90-7.88 (m, 2H), 7.57-7.53 (m, 1H), 7.46-7.42 (m, 2H), 7.28-7.15 (m, 9H), 7.04-7.00 (m, 2H), 6.93 (d, 1H), 3.71 (s, 2H), 3.13-3.01 (m, 4H), 2.78 (s, 4H).

EXAMPLE 17

6-(4-{2-[Benzyl-(3-oxo-3-thiophen-2-yl-propyl)-amino]-ethyl}-phenoxy)-nicotinamide

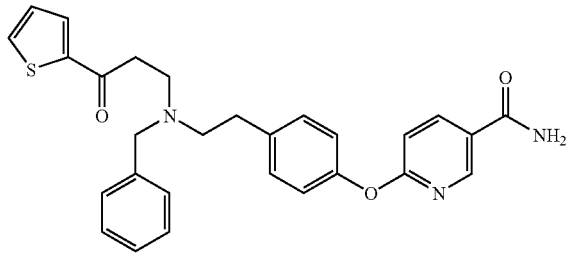

Step 1

3-Trimethylammonium-1-thiophen-2-yl-propan-1-one iodide

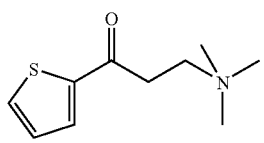

Using a method similar to example 16, using 2-acetylthiophene affords the title compound: mass spectrum (ion spray): m/z=199.0 (M+1); $^1$H NMR (DMSO-d$_6$): 8.12-8.04 (m, 2H), 7.32-7.28 (m, 1H), 3.70-3.61 (m, 4H), 3.11 (s, 6H), 3.09 (s, 3H).

Step 2

Using a method similar to example 16, using 3-trimethylammonium-1-thiophen-2-yl-propan-1-one iodide affords the title compound: mass spectrum (ion spray): m/z=486.3 (M+1), $^1$H NMR (CDCl$_3$): 8.57 (d, 1H), 8.15 (dd, 1H), 7.63-7.60 (m, 2H), 7.29-7.01 (m, 12H), 6.93 (d, 1H), 3.71 (s, 2H), 3.04 (s, 4H), 2.178 (br s, 4H).

EXAMPLE 18

6-(4-{2-[Benzyl-(3-cyclohexyl-3-oxo-propyl)-amino]-ethyl}-phenoxy)-nicotinamide

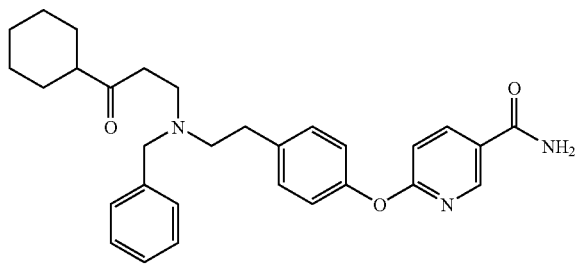

Step 1

1-Cyclohexyl-3-trimethylammonium-propan-1-one iodide

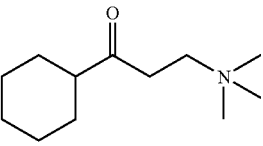

Using a method similar to example 16, using cyclohexyl methyl ketone affords the title compound: mass spectrum (ion spray): m/z=198.2 (M+1); $^1$H NMR (DMSO-d$_6$): 3.51-3.47 (m, 4H), 3.11 (s, 6H), 3.05 (s, 3H), 2.49-2.42 (m, 1H), 1.87-1.84 (m, 2H), 1.73-1.60 (m, 3H), 1.31-1.12 (m, 5H).

Step 2

Using a method similar to example 16, using 1-cyclohexyl-3-trimethylammonium-propan-1-one iodide affords the title compound. Mass spectrum (ion spray): m/z=486.1 (M+1); $^1$H NMR (CDCl$_3$): 8.58 (d, 1H), 8.15 (dd, 1H), 7.31-7.15 (m, 9H), 7.04-7.01 (m, 2H), 6.93 (d, 1H), 3.63 (s, 2H), 2.87-2.57 (m, 5H), 2.30-2.24 (m, 1H), 1.81-1.64 (m, 5H), 1.33-1.15 (m, 5H).

EXAMPLE 19

6-(4-{2-[Benzyl-(3-hydroxy-3-phenyl-propyl)-amino]-ethyl}-phenoxy)-nicotinamide

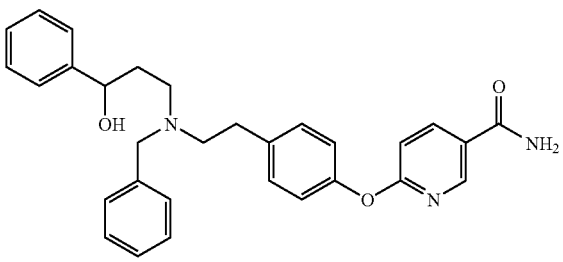

Add methanol (10 mL) to 6-(4-{2-[benzyl-(3-oxo-3-phenyl-propyl)-amino]-ethyl}-phenoxy)-nicotinamide (0.1871 g, 0.3901 mmol) and cool to 0° C. Add sodium borohydride (0.0664 g, 1.756 mmol) and stir for 1.5 h at (0° C. under nitrogen. Pour the reaction into brine (50 mL) and extract with diethyl ether (3×50 mL). Dry the diethyl ether extracts over magnesium sulfate, filter, and concentrate on a rotary evaporator to give the crude product. The crude product is purified by flash chromatography on silica gel eluting with 100% ethyl acetate to yield 0.0239 g (13%) of 6-(4-{2-[benzyl-(3-hydroxy-3-phenyl-propyl)-amino]-ethyl}-phenoxy)-nicotinamide: HPLC (30/70 to 90/10 ACN/(0.1% TFA in water) Zorbax SB-Phenyl Column 4.6 mm×15 cm×5 micron:

Retention time: 8.07 minutes, Purity: 99.9%; mass spectrum (ion spray): m/z=482.3 (M+1).

EXAMPLE 20

6-(4-{2-[Benzyl-(3-hydroxy-3-thiophen-2-yl-propyl)-amino]-ethyl}-phenoxy)-nicotinamide

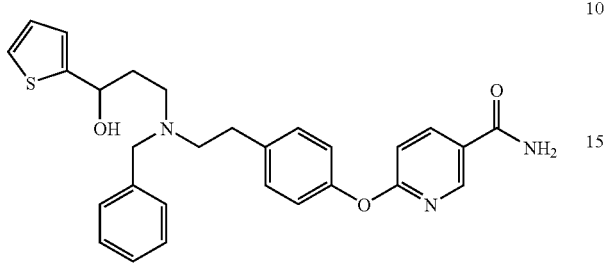

Using a method similar to example 19, using 6-(4-{2-[benzyl-(3-oxo-3-thiophen-2-yl-propyl)-amino]-ethyl}-phenoxy)-nicotinamide affords the title compound: HPLC (30/70 to 90/10 ACN/(0.1% TFA in water) Zorbax SB-Phenyl Column 4.6 mm×15 cm×5 micron: Retention time: 7.93 minutes, Purity: 99.2%; mass spectrum (ion spray): m/z=488.0 (M+1).

EXAMPLE 21

6-(4-{2-[Benzyl-(3-cyclohexyl-3-hydroxy-propyl)-amino]-ethyl}-phenoxy)-nicotinamide

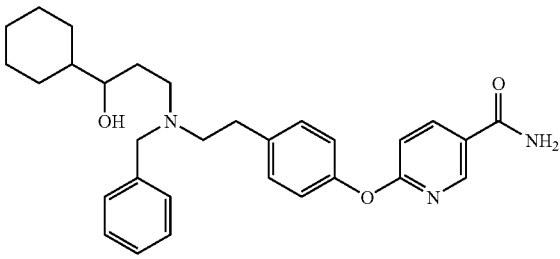

Using a method similar to example 19, using 6-(4-{2-[benzyl-(3-cyclohexyl-3-oxo-propyl)-amino]-ethyl}-phenoxy)-nicotinamide affords the title compound: HPLC (30/70 to 90/10 ACN/(0.1% TFA in water) Zorbax SB-Phenyl Column 4.6 mm×15 cm×5 micron: Retention time: 8.49 minutes, Purity: 99.0%; mass spectrum (ion spray): m/z=488.1 (M+1).

EXAMPLE 22

6-{4-[2-(3-Phenyl-propylamino)-ethyl]-phenoxy}-nicotinamide

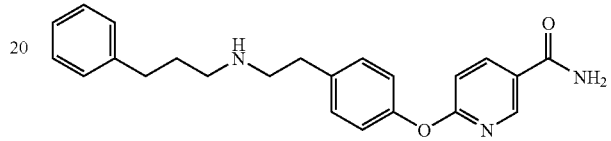

Add 1-chloroethylchloroformate (0.056 mL, 0.52 mmol) to a stirred solution of 6-(4-{2-[benzyl-(3-phenyl-propyl)-amino]-ethyl}-phenoxy)-nicotinamide (0.1211 g, 0.2603 mmol) (Example 3) and 1,2-dichloroethane (5 mL). Heat the reaction to reflux under nitrogen for 1.5 h. Add methanol (7 mL) and heat at reflux under nitrogen for 1 h. Cool the reaction to room temperature and add 2 M ammonia in methanol (5 mL). Concentrate on a rotary evaporator to give the crude product. The crude product is purified by flash chromatography on silica gel eluting with 1% concentrated ammonium hydroxide/10% ethanol/chloroform to yield 0.0654 g (67%) of 6-{4-[2-(3-phenyl-propylamino)-ethyl]-phenoxy}-nicotinamide: HPLC (30/70 to 90/10 ACN/(0.1% TFA in water) Zorbax SB-Phenyl Column 4.6 mm×15 cm×5 micron: Retention time: 7.48 minutes, Purity: 99.2%; mass spectrum (ion spray): m/z=376.2 (M+1).

By the method of example 22 the following compounds were prepared from the corresponding compounds prepared in examples 2-14:

| | | Data | | |
|---|---|---|---|---|
| | | Mass spectrum (ion spray): m/z | HPLC (30/70 to 90/10 ACN/ (0.1% TFA in water) Zorbax SB-Phenyl Column 4.6 mm × 15 cm × 5 micron | |
| Example | Name | (M + 1) | Purity | Retention Time (minutes) |
| 23 | 6-[4-(2-Phenethylamino-ethyl)-phenoxy]-nicotinamide | 362.1 | 98.9 | 5.28 |
| 24 | 6-[4-(2-Hexylamino-ethyl)-phenoxy]-nicotinamide | 342.1 | 99.2 | 7.01 |
| 25 | 6-[4-(2-Heptylamino-ethyl)-phenoxy]-nicotinamide | 356.2 | 99.8 | 8.13 |
| 26 | 6-[4-(2-Pentylamino-ethyl)-phenoxy]-nicotinamide | 328.1 | 98.7 | 4.44 |

-continued

| Example | Name | Mass spectrum (ion spray): m/z (M + 1) | HPLC (30/70 to 90/10 ACN/ (0.1% TFA in water) Zorbax SB-Phenyl Column 4.6 mm × 15 cm × 5 micron | |
|---|---|---|---|---|
| | | | Purity | Retention Time (minutes) |
| 27 | 6-{4-[2-(5-Methyl-hexylamino)-ethyl]-phenoxy}-nicotinamide | 356.1 | 99.9 | 7.78 |
| 28 | 6-(4-{2-[2-(3-Chloro-phenyl)-ethylamino]-ethyl}-phenoxy)-nicotinamide | 396.0 | 99.3 | 7.71 |
| 29 | 6-{4-[2-(3-Cyclopentyl-propylamino)-ethyl]-phenoxy}-nicotinamide | 368.2 | 98.4 | 7.99 |
| 30 | 6-{4-[2-(3-Cyclohexyl-propylamino)-ethyl]-phenoxy}-nicotinamide | 382.1 | 98.1 | 8.29 |
| 31 | 6-(4-{2-[2-(3-Fluoro-phenyl)-ethylamino]-ethyl}-phenoxy)-nicotinamide | 380.1 | 99.1 | 1.43 |
| 32 | 6-{4-[2-(3-o-Tolyl-propylamino)-ethyl]-phenoxy}-nicotinamide | 390.1 | 99.1 | 7.88 |
| 33 | 6-{4-[2-(3-Thiophen-2-yl-propylamino)-ethyl]-phenoxy}-nicotinamide | 382.1 | 98.6 | 5.4 |

EXAMPLE 34

6-[4-(2-Amino-ethyl)-phenoxy]-nicotinamide

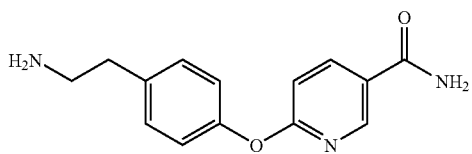

Step 1

[2-(4-Hydroxy-phenyl)-ethyl]-carbamic acid tert-butyl ester

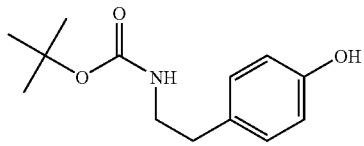

Add di-tert-butyl dicarbonate (9.75 g, 44.7 mmol) to a stirred solution of tyramine (5.00 g, 36.5 mmol) and anhydrous tetrahydrofuran. Stir the reaction at room temperature for 18 h under nitrogen. Concentrate the reaction to give the crude product. The crude product is purified by flash chromatography on silica gel eluting with 35% ethyl acetate/hexanes to yield 7.56 g (87%) of [2-(4-hydroxy-phenyl)-ethyl]-carbamic acid tert-butyl ester: mass spectrum (ion spray): m/z=236.1 (M−1); $^1$H NMR (CDCl$_3$): 7.01 (d, 2H), 6.77 (d, 2H), 6.10 (br s, 1H), 4.61 (br s, 1H), 3.34-3.32 (m, 2H), 2.72-2.68 (m, 2H), 1.44 (s, 9H).

Step 2

{2-[4-(5-Carbamoyl-pyridin-2-yloxy)-phenyl]-ethyl}-carbamic acid tert-butyl ester

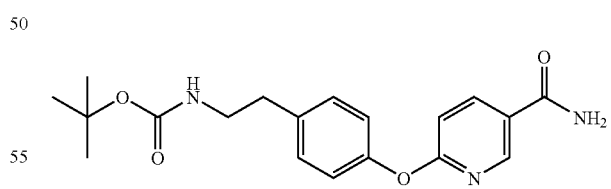

Add potassium tert-butoxide (4.28 g, 36.2 mmol) to a stirred solution of [2-(4-hydroxy-phenyl)-ethyl]-carbamic acid tert-butyl ester (6.40 g, 27.0 mmol) and anhydrous tetrahydrofuran (120 mL). Stir for 30 minutes under nitrogen at room temperature. Add 6-chloronicotinamide (4.27 g, 27.2 mmol) and heat to reflux for 18 h under nitrogen. Cool to room temperature pour the reaction mixture into 150 mL), and extract with diethyl ether (3×150 mL). Dry the diethyl ether extracts over magnesium sulfate, filter, and concentrate on a rotary evaporator to give the crude product. The crude product is purified by flash chromatography on silica gel eluting with 0.7% concentrated ammonium hydroxide/7% ethanol/chloroform to yield 4.46 g (46%) of {2-[4-(5-carbamoyl-pyridin-2-yloxy)-phenyl]-ethyl}-carbamic acid tert-butyl ester: mass spectrum (ion spray): m/z=358.1 (M+1); $^1$H NMR (DMSO-d$_6$): 8.58 (d, 1H), 8.22 (dd, 1H), 8.02 (br s, 1H), 7.46 (br s, 1H), 7.23 (d, 2H), 7.06-7.02 (m, 3H), 6.92-6.89 (m, 1H), 3.17-3.12 (m, 2H), 2.69 (t, 2H), 1.35 (s, 9H).

Step 3

Add dichloromethane (60 mL) to the compound of Example 33 Step 2 (5.12 g, 14.3 mmol). To this slurry add trifluoroacetic acid (32.0 mL, 415 mmol) and stir under nitrogen for 1.5 h. Divide the reaction into three equal aliquots and load each aliquot onto a 10 g prepacked SCX cartridge. Wash with methanol (200 mL) and elute the product off the cartridge with 2 M ammonia in methanol (100 mL). Combine the 2 M ammonia in methanol washes from the three cartridges and concentrate on a rotary evaporator to give 3.11 g (84%) of 6-[4-(2-amino-ethyl)-phenoxy]-nicotinamide: mass spectrum (ion spray): m/z=258.1 (M+1); $^1$H NMR (DMSO-d$_6$): 8.61 (d, 1H), 8.25 (dd, 1H), 8.04 (s, 1H), 7.49 (s, 1H), 7.30-7.23 (m, 2H), 7.11-7.03 (m, 3H), 2.80-2.63 (m, 4H), 1.89 (br s, 2H).

EXAMPLE 35

6-{4-[2-(2-Methoxy-benzylamino)-ethyl]-phenoxy}-nicotinamide

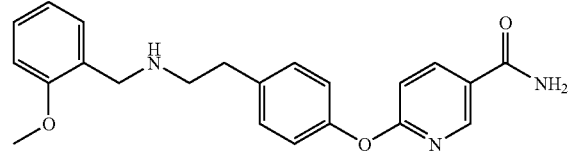

Add three-angstrom molecular sieves to a stirred solution of 6-[4-(2-amino-ethyl)-phenoxy]-nicotinamide (0.1000 g, 0.3887 mmol) (compound of example 33), 2-methoxybenzaldehyde (0.047 mL, 0.39 mmol), and methanol (5 mL). Agitate the reaction for 18 h on a platform shaker at room temperature. Add sodium borohydride and agitate for 1 h at room temperature. Filter to remove the molecular sieves and load the reaction mixture directly onto a 10 g prepacked SCX cartridge. Flush with methanol (150 mL) and elute the product off the SCX cartridge with 2 M ammonia in methanol (50 mL). Concentrate on a rotary evaporator to give 0.1253 g (85%) of 6-{4-[2-(2-methoxy-benzylamino)-ethyl]-phenoxy}-nicotinamide: HPLC (30/70 to 90/10 ACN/(0.1% TFA in water) Zorbax SB-Phenyl Column 4.6 mm×15 cm×5 micron: Retention time: 4.14 minutes, Purity: 97.9%; mass spectrum (ion spray): m/z=378.1 (M+1).

By the method of example 34 the following compounds were prepared:

| Example | Name | Mass spectrum (ion spray): m/z (M + 1) | HPLC (30/70 to 90/10 ACN/(0.1% TFA in water) Zorbax SB-Phenyl Column 4.6 mm × 15 cm × 5 micron | |
|---|---|---|---|---|
| | | | Purity | Retention Time (minutes) |
| 36 | 6-{4-[2-(3-Fluoro-benzylamino)-ethyl]-phenoxy}-nicotinamide | 366.1 | 99.0 | 3.69 |
| 37 | 6-{4-[2-(3-Chloro-benzylamino)-ethyl]-phenoxy}-nicotinamide | 382.0 | 99.2 | 5.22 |
| 38 | 6-{4-[2-(3,4-Dichloro-benzylamino)-ethyl]-phenoxy}-nicotinamide | 416.0 | 99.0 | 7.73 |
| 39 | 6-{4-[2-(3-Trifluoromethyl-benzylamino)-ethyl]-phenoxy}-nicotinamide | 416.1 | 99.1 | 7.52 |
| 40 | 6-{4-[2-(4-Cyano-benzylamino)-ethyl]-phenoxy}-nicotinamide | 373.1 | 90.8 | 3.00 |
| 41 | 6-{4-[2-(4-Fluoro-benzylamino)-ethyl]-phenoxy}-nicotinamide | 366.1 | 100.0 | 3.76 |
| 42 | 6-{4-[2-(4-Methyl-benzylamino)-ethyl]-phenoxy}-nicotinamide | 362.1 | 98.6 | 4.92 |
| 43 | 6-{4-[2-(3,5-Bis-trifluoromethyl-benzylamino)-ethyl]-phenoxy}-nicotinamide | 484.0 | 98.7 | 8.30 |
| 44 | 6-{4-[2-(2,6-Difluoro-benzylamino)-ethyl]-phenoxy}-nicotinamide | 384.1 | 100.0 | 3.13 |
| 45 | 6-{4-[2-(3,5-Difluoro-benzylamino)-ethyl]-phenoxy}-nicotinamide | 384.1 | 98.4 | 4.25 |

-continued

| Example | Name | Mass spectrum (ion spray): m/z (M + 1) | HPLC (30/70 to 90/10 ACN/(0.1% TFA in water) Zorbax SB-Phenyl Column 4.6 mm × 15 cm × 5 micron | |
|---|---|---|---|---|
| | | | Purity | Retention Time (minutes) |
| 46 | 6-{4-[2-(4-Acetylamino-benzylamino)-ethyl]-phenoxy}-nicotinamide | 405.1 | 99.3 | 2.12 |
| 47 | 6-{4-[2-(2-Trifluoromethyl-benzylamino)-ethyl]-phenoxy}-nicotinamide | 416.1 | 99.1 | 5.87 |
| 48 | 6-{4-[2-(2-Methyl-benzylamino)-ethyl]-phenoxy}-nicotinamide | 362.1 | 98.7 | 4.13 |
| 49 | 6-{4-[2-(3-Methoxy-benzylamino)-ethyl]-phenoxy}-nicotinamide | 378.1 | 98.5 | 3.70 |
| 50 | 6-{4-[2-(4-Chloro-benzylamino)-ethyl]-phenoxy}-nicotinamide | 382.0 | 99.4 | 5.11 |
| 51 | 6-{4-[2-(4-Phenoxy-benzylamino)-ethyl]-phenoxy}-nicotinamide | 440.1 | 99.4 | 8.19 |
| 52 | 6-{4-[2-(4-Methoxy-benzylamino)-ethyl]-phenoxy}-nicotinamide | 378.1 | 98.7 | 3.56 |
| 53 | 6-{4-[2-(4-Trifluoromethyl-benzylamino)-ethyl]-phenoxy}-nicotinamide | 416.1 | 99.4 | 7.46 |
| 54 | 6-{4-[2-(3-Oxo-2,3-dihydro-1H-isoindol-1-ylamino)-ethyl]-phenoxy}-nicotinamide | 389.1 | 95.8 | 2.05 |
| 55 | 6-{4-[2-(4-Trifluoromethoxy-benzylamino)-ethyl]-phenoxy}-nicotinamide | 432.1 | 99.5 | 7.79 |
| 56 | 6-{4-[2-(3-Trifluoromethoxy-benzylamino)-ethyl]-phenoxy}-nicotinamide | 432.1 | 99.3 | 7.72 |
| 57 | 6-(4-{2-[(Thiophen-2-ylmethyl)-amino]-ethyl}-phenoxy)-nicotinamide | 354.0 | 99.1 | 2.63 |
| 58 | 6-(4-{2-[(Furan-2-ylmethyl)-amino]-ethyl}-phenoxy)-nicotinamide | 338.1 | 99.0 | 2.27 |
| 59 | 6-[4-(2-Octylamino-ethyl)-phenoxy]-nicotinamide | 370.2 | 96.7 | 8.34 |
| 60 | 6-[4-(2-Cyclohexylamino-ethyl)-phenoxy]-nicotinamide | 340.2 | 90.4 | 3.04 |
| 61 | 6-{4-[2-(Cyclohexylmethyl-amino)-ethyl]-phenoxy}-nicotinamide | 354.2 | 98.7 | 5.10 |
| 62 | 6-[4-(2-Propylamino-ethyl)-phenoxy]-nicotinamide | 300.1 | 96.8 | 2.07 |
| 63 | 6-[4-(2-Butylamino-ethyl)-phenoxy]-nicotinamide | 314.1 | 97.3 | 2.57 |
| 64 | 6-[4-(2-Isopropylamino-ethyl)-phenoxy]-nicotinamide | 300.1 | 83.0 | 1.99 |
| 65 | 6-[4-(2-Isobutylamino-ethyl)-phenoxy]-nicotinamide | 314.1 | 97.0 | 2.40 |
| 66 | 6-{4-[2-(3-Methyl-butylamino)-ethyl]-phenoxy}-nicotinamide | 328.2 | 98.1 | 3.44 |
| 67 | 6-(4-{2-[(Pyridin-4-ylmethyl)-amino]-ethyl}-phenoxy)-nicotinamide | 349.1 | 96.8 | 1.54 |
| 68 | 6-(4-{2-[(Pyridin-2-ylmethyl)-amino]-ethyl}-phenoxy)-nicotinamide | 349.1 | 84.4 | 2.07 |
| 69 | 6-(4-{2-[(5-Methyl-furan-2-ylmethyl)-amino]-ethyl}-phenoxy)-nicotinamide | 352.1 | 98.5 | 2.98 |
| 70 | 6-(4-{2-[(3-Methyl-thiophen-2-ylmethyl)-amino]-ethyl}-phenoxy)-nicotinamide | 368.1 | 93.8 | 3.45 |

-continued

| | | Data | | |
|---|---|---|---|---|
| | | Mass spectrum (ion spray): m/z | HPLC (30/70 to 90/10 ACN/(0.1% TFA in water) Zorbax SB-Phenyl Column 4.6 mm × 15 cm × 5 micron | |
| Example | Name | (M + 1) | Purity | Retention Time (minutes) |
| 71 | 6-(4-{2-[(5-Methyl-thiophen-2-ylmethyl)-amino]-ethyl}-phenoxy)-nicotinamide | 368.1 | 97.9 | 3.80 |
| 72 | 6-(4-{2-[(Thiophen-3-ylmethyl)-amino]-ethyl}-phenoxy)-nicotinamide | 354.1 | 98.5 | 2.80 |
| 73 | 6-[4-(2-Ethylamino-ethyl)-phenoxy]-nicotinamide | 286.1 | 100.0 | 2.43 |
| 74 | 6-{4-[2-(4-Hydroxy-benzylamino)-ethyl]-phenoxy}-nicotinamide | 364.2 | 98.9 | 2.42 |
| 75 | 6-{4-[2-(3-Hydroxy-benzylamino)-ethyl]-phenoxy}-nicotinamide | 364.2 | 99.4 | 2.43 |
| 76 | 6-{4-[2-(3-Phenyl-prop-2-ynylamino)-ethyl]-phenoxy}-nicotinamide | 372.2 | 96.9 | 6.41 |
| 77 | 6-(4-{2-[(Furan-3-ylmethyl)-amino]-ethyl}-phenoxy)-nicotinamide | 338.2 | 99.7 | 2.47 |
| 78 | 6-(4-{2-[(Benzofuran-2-ylmethyl)-amino]-ethyl}-phenoxy)-nicotinamide | 388.2 | 98.4 | 5.48 |
| 79 | 6-(4-{2-[(5-Ethyl-furan-2-ylmethyl)-amino]-ethyl}-phenoxy)-nicotinamide | 366.2 | 99.2 | 4.62 |
| 80 | 6-(4-{2-[(5-Chloro-thiophen-2-ylmethyl)-amino]-ethyl}-phenoxy)-nicotinamide | 388.1 | 99.1 | 4.54 |
| 81 | 6-(4-{2-[(4,5-Dimethyl-furan-2-ylmethyl)-amino]-ethyl}-phenoxy)-nicotinamide | 366.2 | 99.8 | 4.51 |
| 82 | 6-(4-{2-[(4-Chloro-1-methyl-1H-pyrazol-3-ylmethyl)-amino]-ethyl}-phenoxy)-nicotinamide | 386.1 | 99.6 | 2.42 |
| 83 | 6-(4-{2-[(Thiazol-2-ylmethyl)-amino]-ethyl}-phenoxy)-nicotinamide | 355.1 | 87.4 | 2.02 |
| 84 | 6-(4-{2-[(2-Methyl-1H-imidazol-4-ylmethyl)-amino]-ethyl}-phenoxy)-nicotinamide | 352.2 | 100.0 | 100.00 |
| 85 | 6-{4-[2-(3,5-Di-tert-butyl-4-hydroxy-benzylamino)-ethyl]-phenoxy}-nicotinamide | 476.2 | 88.0 | 8.77 |
| 86 | 6-{4-[2-(2-Fluoro-benzylamino)-ethyl]-phenoxy}-nicotinamide | 366.1 | 98.3 | 3.21 |
| 87 | 6-{4-[2-(3-Phenoxy-benzylamino)-ethyl]-phenoxy}-nicotinamide | 440.1 | 94.1 | 8.20 |
| 88 | 6-{4-[2-(2-Chloro-benzylamino)-ethyl]-phenoxy}-nicotinamide | 382.0 | 91.3 | 4.04 |
| 89 | 6-{4-[2-(3-Cyano-benzylamino)-ethyl]-phenoxy}-nicotinamide | 373.1 | 96.4 | 3.25 |
| 90 | 6-{4-[2-(3-Methyl-benzylamino)-ethyl]-phenoxy}-nicotinamide | 362.1 | 92.8 | 4.80 |
| 91 | 6-(4-{2-[(1H-Imidazol-4-ylmethyl)-amino]-ethyl}-phenoxy)-nicotinamide | 338.1 | 90.5 | 1.53 |
| 92 | 6-(4-{2-[(Pyridin-3-ylmethyl)-amino]-ethyl}-phenoxy)-nicotinamide | 349.1 | 95.5 | 1.56 |
| 93 | 6-{4-[2-(2-Phenoxy-ethylamino)-ethyl]-phenoxy}-nicotinamide | 378.1 | 85.7 | 4.67 |
| 94 | 6-{4-[2-(3-Fluoro-4-hydroxy-benzylamino)-ethyl]-phenoxy}-nicotinamide | 382.0 | 83.3 | 2.49 |
| 95 | 6-(4-{2-[(2-Butyl-1H-imidazol-4-ylmethyl)-amino]-ethyl}-phenoxy)-nicotinamide | 394.1 | 94.2 | 1.60 |

-continued

| | | | HPLC (30/70 to 90/10 ACN/(0.1% TFA in water) Zorbax SB-Phenyl Column 4.6 mm × 15 cm × 5 micron | |
|---|---|---|---|---|
| | | Mass spectrum (ion spray): m/z | | |
| Example | Name | (M + 1) | Purity | Retention Time (minutes) |
| 96 | 6-(4-{2-[(Benzo[b]thiophen-3-ylmethyl)-amino]-ethyl}-phenoxy)-nicotinamide | 404.0 | 89.1 | 6.70 |
| 97 | 6-(4-{2-[(3-Phenyl-1H-pyrazol-4-ylmethyl)-amino]-ethyl}-phenoxy)-nicotinamide | 414.1 | 99.4 | 2.96 |
| 98 | 6-[4-(2-Allylamino-ethyl)-phenoxy]-nicotinamide | 297.8 | 98.6 | 1.68 |
| 99 | 6-{4-[2-(4-Imidazol-1-yl-benzylamino)-ethyl]-phenoxy}-nicotinamide | 414.1 | 98.4 | 1.58 |
| 100 | 6-{4-{2-[(3-Methyl-benzo[b]thiophen-2-ylmethyl)-amino]-ethyl}-phenoxy)-nicotinamide | 418.1 | 99.5 | 7.76 |
| 101 | 6-{4-[2-(4-Methyl-pent-2-enylamino)-ethyl]-phenoxy}-nicotinamide | 340.1 | 59.2 | 4.74 |
| 102 | 6-{4-[2-(2-Trifluoromethoxy-benzylamino)-ethyl]-phenoxy}-nicotinamide | 432.1 | 92.2 | 7.13 |
| 103 | 6-(4-{2-[(2-Piperidin-1-yl-thiazol-5-ylmethyl)-amino]-ethyl}-phenoxy)-nicotinamide | 438.1 | 95.8 | 1.65 |
| 104 | 6-{4-[2-(4-Cyclohexyl-butylamino)-ethyl]-phenoxy}-nicotinamide | 396.2 | 76.1 | 8.61 |
| 105 | 6-{4-[2-(2-Cyclohexyl-ethylamino)-ethyl]-phenoxy}-nicotinamide | 368.2 | 90.6 | 7.78 |
| 106 | 6-{4-[2-(2-Chloro-6-fluoro-benzylamino)-ethyl]-phenoxy}-nicotinamide | 400.0 | 91.9 | 3.40 |
| 107 | 6-{4-[2-(Cyclopropylmethyl-amino)-ethyl]-phenoxy}-nicotinamide | 312.1 | 90.0 | 2.14 |
| 108 | 6-(4-{2-[(Naphthalen-1-ylmethyl)-amino]-ethyl}-phenoxy)-nicotinamide | 398.1 | 92.0 | 6.42 |
| 109 | 6-(4-{2-[(Bicyclo[2.2.1]hept-5-en-2-ylmethyl)-amino]-ethyl}-phenoxy)-nicotinamide | 364.1 | 97.5 | 4.63 |
| 110 | 6-(4-{2-[(Naphthalen-2-ylmethyl)-amino]-ethyl}-phenoxy)-nicotinamide | 398.1 | 61.2 | 7.30 |
| 111 | 6-(4-{2-[(Quinolin-4-ylmethyl)-amino]-ethyl}-phenoxy)-nicotinamide | 399.1 | 55.3 | 1.54 |
| 112 | 6-{4-[2-(2,6-Dichloro-benzylamino)-ethyl]-phenoxy}-nicotinamide | 416.0 | 72.3 | 4.39 |
| 113 | 6-{4-[2-(Indan-1-ylamino)-ethyl]-phenoxy}-nicotinamide | 374.1 | 96.0 | 4.23 |
| 114 | 6-{4-[2-(2-Hydroxy-5-methoxy-benzylamino)-ethyl]-phenoxy}-nicotinamide | 394.1 | 94.8 | 2.81 |
| 115 | 6-{4-[2-(3-Bromo-4-fluoro-benzylamino)-ethyl]-phenoxy}-nicotinamide | 446.0 | 93.9 | 5.97 |
| 116 | 6-{4-[2-(4-Fluoro-2-trifluoromethyl-benzylamino)-ethyl]-phenoxy}-nicotinamide | 434.1 | 97.7 | 6.18 |
| 117 | 6-{4-[2-(3-Chloro-4-fluoro-benzylamino)-ethyl]-phenoxy}-nicotinamide | 400.0 | 92.0 | 5.36 |
| 118 | 6-[4-(2-Cyclooctylamino-ethyl)-phenoxy]-nicotinamide | 368.2 | 90.5 | 5.97 |

-continued

| | | Data | | |
|---|---|---|---|---|
| | | Mass spectrum (ion spray): m/z | HPLC (30/70 to 90/10 ACN/(0.1% TFA in water) Zorbax SB-Phenyl Column 4.6 mm × 15 cm × 5 micron | |
| Example | Name | (M + 1) | Purity | Retention Time (minutes) |
| 119 | 6-{4-[2-(2-Phenoxy-benzylamino)-ethyl]-phenoxy}-nicotinamide | 440.1 | 93.3 | 8.09 |

By the method of example 35 the following compounds were prepared:

| Example | Name | Mass Spectrum (ion spray) m/z (M + 1) | $^1$H NMR (CDCl$_3$) |
|---|---|---|---|
| 120 | 6-{4-[2-(Cyclobutylmethyl-amino)-ethyl]-phenoxy}-nicotinamide | 326.1 | 8.58 (d, 1H), 8.16 (dd, 1H), 7.27-7.25 (m, 4H), 7.07 (d, 2H), 6.96 (d, 1H), 2.90-2.82 (m, 4H), 2.67 (d, 2H), 2.48-2.42 (m, 1H), 2.06-1.61 (m, 7H) |
| 121 | 6-{4-[2-(Cycloheptylmethyl-amino)-ethyl]-phenoxy}-nicotinamide | 368.2 | 8.58 (d, 1H), 8.16 (dd, 1H), 7.27-7.24 (m, 4H), 7.09-7.06 (m, 2H), 6.99-6.94 (m, 1H), 2.96-2.75 (m, 4H), 2.49 (d, 2H), 1.74-1.12 (m, 14H) |
| 122 | 6-(4-{2-[(2-Morpholin-4-yl-thiazol-5-ylmethyl)-amino]-ethyl}-phenoxy)-nicotinamide | 440.1 | 8.57 (d, 1H), 8.16 (dd, 1H), 7.26-7.24 (m, 4H), 7.07 (d, 2H), 6.99-6.95 (m, 2H), 3.86 (s, 2H), 3.82-3.79 (m, 4H), 3.44-3.42 (m, 4H), 2.92 (t, 2H), 2.82 (t, 2H), 1.25 (s, 1H) |
| 123 | 6-(4-{2-[(2,4-Dichloro-thiazol-5-ylmethyl)-amino]-ethyl}-phenoxy)-nicotinamide | 423.0 | 8.57 (d, 1H), 8.19-8.15 (m, 1H), 7.27-7.24 (m, 4H), 7.11-7.07 (m, 2H), 6.99-6.96 (m, 1H), 3.91 (s, 2H), 2.98-2.93 (m, 2H), 2.84-2.81 (m, 2H), 1.64 (br s, 1H) |
| 124 | 6-(4-{2-[(2-Chloro-thiazol-5-ylmethyl)-amino]-ethyl}-phenoxy)-nicotinamide | 389.0 | 8.57 (d, 1H), 8.17 (dd, 1H), 7.34 (s, 1H), 7.26-7.24 (m, 4H), 7.09-7.07 (m, 2H), 6.97 (d, 1H), 3.94 (d, 2H), 2.93 (t, 2H), 2.82 (t, 2H), 1.55 (br s, 1H) |
| 125 | 6-{4-[2-(Cyclopentylmethyl-amino)-ethyl]-phenoxy}-nicotinamide | 340.1 | 8.58 (d, 1H), 8.16 (dd, 1H), 7.27-7.24 (m, 4H), 7.09-7.05 (m, 2H), 6.95 (d, 1H), 2.92-2.81 (m, 4H), 2.57 (d, 2H), 2.04-1.96 (m, 1H), 1.78-1.48 (m, 7H), 1.16-1.08 (m, 2H) |

Preparing Aldehyde Intermediates

4-Cyclohexyl-butyraldehyde

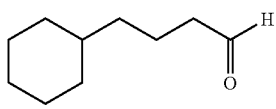

Add Dess-Martin reagent (7.02 g, 16.6 mmol) to a stirred solution of 4-cyclohexyl-1-butanol (2.5 mL, 14.4 mmol) in anhydrous dichloromethane (120 mL). Stir for 3 h at room temperature under nitrogen. Add diethyl ether (200 mL) and 1N sodium hydroxide (150 mL) and stir for 10 minutes. Separate the layers and extract a second time with diethyl ether (100 mL). Combine the diethyl ether extracts, wash with 1N sodium hydroxide (100 mL), dry over magnesium sulfate, filter, and concentrate on a rotary evaporator to yield 2.01 g (90%) of 4-cyclohexyl-butyraldehyde: $^1$H NMR (CDCl$_3$): 9.76 (s, 1H), 2.41-2.37 (m, 2H), 1.71-1.58 (m, 7H), 1.27-1.07 (m, 6H), 0.93-0.82 (m, 2H).

3-Cyclohexyl-propionaldehyde

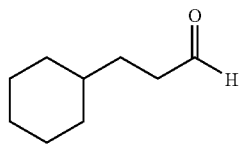

Using a method similar alcohol oxidation method as above, 3-cyclohexyl-1-propanol gives the title compound: $^1$H NMR (CDCl₃): 9.76 (s, 1H), 2.47-2.39 (m, 2H), 1.71-1.49 (m, 7H), 1.27-1.07 (m, 4H), 0.93-0.84 (m, 2H).

Cyclohexyl-acetaldehyde

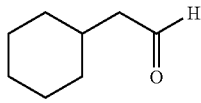

Using a similar the alcohol oxidation method as above, using 2-cyclohexylethanol gives the title compound: ¹H NMR (CDCl₃): 9.75 (s, 1H), 2.32-2.21 (m, 2H), 1.93-1.62 (m, 6H), 1.34-0.94 (m, 5H).

Cycloheptanecarbaldehyde

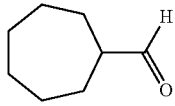

Using a similar alcohol oxidation method as above, cycloheptymethanol gives the title compound: ¹H NMR (CDCl₃): 9.63 (s, 1H), 2.39-2.33 (m, 1H), 1.99-1.90 (m, 2H), 1.83-1.46 (m, 10H).

Cyclobutanecarbaldehyde

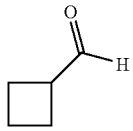

Using a similar alcohol oxidation method as above, using cyclobutylmethanol gives the title compound: ¹H NMR (CDCl₃): 9.73 (s, 1H), 3.20-3.14 (m, 1H), 2.32-1.86 (m, 6H).

Cyclopentanecarbaldehyde

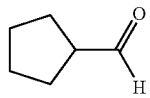

Using a method as above, using cyclopentylmethanol gives the title compound: ¹H NMR (CDCl₃): 9.60 (s, 1H), 2.76-2.68 (m, 1H), 1.87-1.74 (m, 4H), 1.65-1.54 (m, 4H).

EXAMPLE 126

6-(4-{2-[(3,5-Dimethyl-isoxazol-4-ylmethyl)-amino]-ethyl}-phenoxy)-nicotinamide

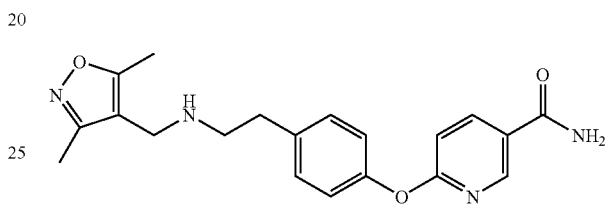

Add sodium bicarbonate (0.0481 g, 0.573 mmol) to a stirred solution of 4-(chloromethyl)-3,5-dimethylisoxazole (0.054 mL, 0.435 mmol), and 6-[4-(2-amino-ethyl)-phenoxy]-nicotinamide (0.1004 g, 0.390 mmol) in dimethylformamide (4 mL). Heat the reaction to reflux under nitrogen for 4 h. Cool to room temperature, pour the reaction mixture into 1 N sodium hydroxide (50 mL), extract with diethyl ether (3×50 mL), dry the extracts over magnesium sulfate, filter, and concentrate on a rotary evaporator to give the crude product. The crude product is purified by flash chromatography on silica gel eluting with 0.8% concentrated ammonium hydroxide/8% ethanol/chloroform to yield 0.0843 g (59%) of 6-(4-{2-[(3,5-dimethyl-isoxazol-4-ylmethyl)-amino]-ethyl}-phenoxy)-nicotinamide: mass spectrum (ion spray): m/z=367.1 (M+1); ¹H NMR (CDCl₃): 8.57 (dd, 1H), 8.16 (dd, 1H), 7.26-7.22 (m, 4H), 7.09-7.05 (m, 2H), 6.96 (d, 1H), 3.54 (s, 2H), 2.88-2.79 (m, 4H), 2.33 (s, 3H), 2.20 (s, 3H), 1.50 (br s, 1H).

By the method of example 126 the following compounds were prepared:

| Example | Name | ¹H NMR (CDCl₃) |
|---|---|---|
| 127 | 6-(4-{2-[(5-Methyl-isoxazol-3-ylmethyl)-amino]-ethyl}-phenoxy)-nicotinamide | 8.57 (d, 1H), 8.16 (dd, 1H), 7.26-7.24 (m, 4H), 7.09-7.06 (m, 2H), 6.96 (d, 1H), 5.93 (s, 1H), 3.84 (s, 2H), 2.93 (t, 2H), 2.83 (t, 2H), 2.40 (d, 3H), 1.59 (br s, 1H) |
| 128 | 6-(4-{2-[(3-Phenyl-isoxazol-5-ylmethyl)-amino]-ethyl}-phenoxy)-nicotinamide | 8.56 (d, 1H), 8.16 (dd, 1H), 7.80-7.76 (m, 2H), 7.46-7.42 (m, 3H), 7.28-7.26 (m, 4H), 7.10-7.08 (m, 2H), 6.96 (d, 1H), 6.43 (s, 1H), 3.99 (s, 2H), 2.99 (t, 2H), 2.86 (t, 2H), 1.61 (br s, 1H) |

| Example | Name | ¹H NMR (CDCl₃) |
|---|---|---|
| 129 | 6-[4-(2-{[3-(4-Chloro-phenyl)-[1,2,4]oxadiazol-5-ylmethyl]-amino}-ethyl)-phenoxy]-nicotinamide | 8.56 (d, 1H), 8.17 (dd, 1H), 8.02 (d, 2H), 7.46 (d, 2H), 7.27-7.26 (m, 3H), 7.09 (d, 2H), 6.97 (d, 2H), 4.14 (s, 2H), 3.03-2.88 (m, 4H), 1.59 (br s, 1H) |
| 130 | 6-(4-{2-[(5-p-Tolyl-[1,3,4]oxadiazol-2-ylmethyl)-amino]-ethyl}-phenoxy)-nicotinamide | 8.57 (d, 1H), 8.16 (dd, 1H), 7.92 (d, 2H), 7.31-7.25 (m, 6H), 7.08-7.06 (m, 2H), 6.95 (d, 1H), 4.12 (s, 2H), 3.02 (t, 2H), 2.87 (t, 2H), 2.42 (s, 3H), 1.65 (br s, 1H) |
| 131 | 6-{4-[2-(1-Phenyl-ethylamino)-ethyl]-phenoxy}-nicotinamide | 8.57 (d, 1H), 8.16 (dd, 1H), 7.41-7.20 (m, 9H), 7.04 (d, 2H), 6.95 (d, 1H), 3.83-3.78 (m, 1H), 2.87-2.68 (m, 4H), 1.65 (br s, 1H), 1.36 (d, 3H) |

EXAMPLE 132

6-[4-(3-Benzylamino-propyl)-phenoxy]-nicotinamide

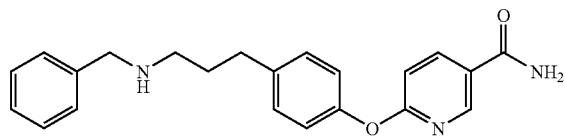

Step 1

N-Benzyl-3-(4-hydroxy-phenyl)-propionamide

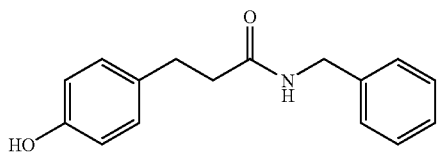

Add benzylamine (32.0 mL, 293 mmol) to methyl 3-(4-hydroxyphenyl)propionate (7.01 g, 38.9 mmol) and heat to 150° C. for 18 h under nitrogen. Cool to room temperature and pour the reaction mixture into 5 N hydrochloric acid (200 mL) and extract with ethyl acetate (3×150 mL). Wash the ethyl acetate extracts with 5 N hydrochloric acid (200 mL), dry the extracts over magnesium sulfate, filter, and concentrate on a rotary evaporator to yield 9.74 g (98%) of N-benzyl-3-(4-hydroxy-phenyl)-propionamide: mass spectrum (ion spray): m/z=256.2 (M+1); ¹H NMR (DMSO-d₆): 9.15 (s, 1H), 8.28 (t, 1H), 7.39-6.96 (m, 7H), 6.66-6.63 (m, 2H), 4.23 (d, 2H), 2.72 (t, 2H), 2.37 (t, 2H).

Step 2

4-(3-Benzylamino-propyl)-phenol

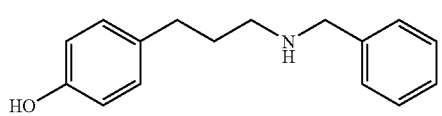

Add lithium aluminum hydride (8.00 g, 211 mmol) to anhydrous tetrahydrofuran (150 mL) and cool to 0° C. under nitrogen. Add N-benzyl-3-(4-hydroxy-phenyl)-propionamide (9.74 g, 38.2 mmol) to anhydrous tetrahydrofuran (80 mL) and add this solution slowly via cannula to the lithium aluminum hydride/tetrahydrofuran mixture at 0° C. under nitrogen. Once this addition is complete, remove the ice bath and heat to reflux for 18 h under nitrogen. Cool the reaction to 0° C. and slowly quench with water (200 mL). Adjust the pH of the solution to pH=8 with 4 M hydrochloric acid. Saturate this solution with sodium chloride, extract with ethyl acetate (3×100 mL), dry the extracts over magnesium sulfate, filter, and concentrate on a rotary evaporator to yield 9.00 g (98%) of 4-(3-benzylamino-propyl)-phenol: mass spectrum (ion spray): m/z=242.1 (M+1); ¹H NMR (DMSO-d₆): 7.31-7.16 (m, 6H), 6.95-6.92 (m, 2H), 6.66-6.62 (m, 2H), 3.65 (s, 2H), 2.48-2.43 (m, 5H), 1.68-1.60 (m, 2H).

Step 3

Using a method similar to example 1, step 2, using 4-(3-benzylamino-propyl)-phenol and purifying by flash chromatography on silica gel eluting with 1% concentrated ammonium hydroxide/10% ethanol/chloroform gives the title compound: HPLC (30/70 to 90/10 ACN/(0.1% TFA in water) Zorbax SB-Phenyl Column 4.6 mm×15 cm×5 micron: Retention time: 3.91 minutes, Purity: 98.9%; mass spectrum (ion spray): m/z=362.2 (M+1).

EXAMPLE 133

6-{4-[3-(Benzyl-pentyl-amino)-propyl]-phenoxy}-nicotinamide

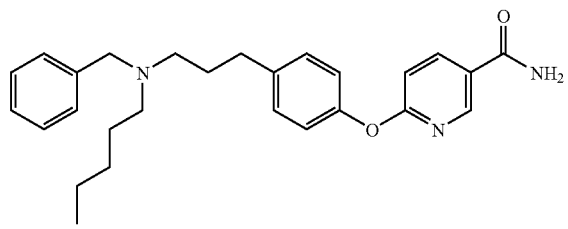

Using a method similar to example 2, using 6-[4-(3-benzylamino-propyl)-phenoxy]-nicotinamide (Step 3, Example 131) and 1-bromopentane gives the title compound: HPLC (30/70 to 90/10 ACN/(0.1% TFA in water) Zorbax SB-Phenyl Column 4.6 mm×15 cm×5 micron: Retention time: 8.40 minutes, Purity: 99.8%; mass spectrum (ion spray): m/z=432.3 (M+1).

By the method of example 132 the following compounds were prepared:

| Example | Name | Mass spectrum (ion spray): m/z (M + 1) | Data HPLC (30/70 to 90/10 ACN/(0.1% TFA in water) Zorbax SB-Phenyl Column 4.6 mm × 15 cm × 5 micron | |
|---|---|---|---|---|
| | | | Purity | Retention Time (minutes) |
| 134 | 6-{4-[3-(Benzyl-phenethyl-amino)-propyl]-phenoxy}-nicotinamide | 466.3 | 99.5 | 8.50 |
| 134 | 6-(4-{3-[Benzyl-(3-cyclopentyl-propyl)-amino]-propyl}-phenoxy)-nicotinamide | 472.4 | 97.6 | 9.00 |
| 135 | 6-[4-(3-{Benzyl-[2-(3-fluoro-phenyl)-ethyl]-amino}-propyl)-phenoxy]-nicotinamide | 484.3 | 98.9 | 8.54 |

EXAMPLE 137

6-[4-(3-Pentylamino-propyl)-phenoxy]-nicotinamide-

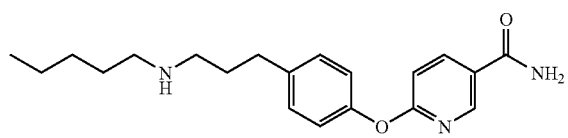

Using a method similar to example 132, adding pentyl amine to 3-(4-hydroxyphenyl)propionate affords the intermediate N-pentyl-3-(4-hydroxyphenyl)-propionate. The N-pentyl-3-(4-hydroxyphenyl)-propionate is reduced and displaced with 6-chloronicotinamide to form the desired product. HPLC (30/70 to 90/10 ACN/(0.1% TFA in water) Zorbax SB-Phenyl Column 4.6 mm×15 cm×5 micron: Retention time: 4.77 minutes, Purity: 99.5%; mass spectrum (ion spray): m/z=342.3 (M+1).

By the method of example 137 the following compounds were prepared:

| Example | Name | Mass spectrum (ion spray): m/z (M + 1) | Data HPLC (30/70 to 90/10 ACN/(0.1% TFA in water) Zorbax SB-Phenyl Column 4.6 mm × 15 cm × 5 micron | |
|---|---|---|---|---|
| | | | Purity | Retention Time (minutes) |
| 138 | 6-[4-(3-Phenethylamino-propyl)-phenoxy]-nicotinamide | 376.3 | 100 | 5.94 |
| 139 | 6-{4-[3-(3-Cyclopentyl-propylamino)-propyl]-phenoxy}-nicotinamide | 382.3 | 97.5 | 8.20 |

-continued

| Example | Name | Mass spectrum (ion spray): m/z (M + 1) | Data HPLC (30/70 to 90/10 ACN/(0.1% TFA in water) Zorbax SB-Phenyl Column 4.6 mm × 15 cm × 5 micron | |
|---|---|---|---|---|
| | | | Purity | Retention Time (minutes) |
| 140 | 6-(4-{3-[2-(3-Fluoro-phenyl)-ethylamino]-propyl}-phenoxy)-nicotinamide | 394.2 | 99.9 | 7.02 |

EXAMPLE 141

(R)-6-[4-(2-Benzylamino-propyl)-phenoxy]-nicotinamide

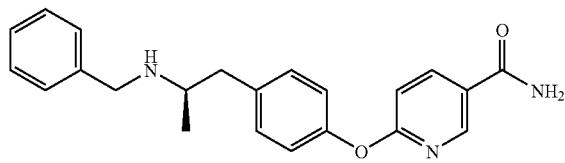

Using a method similar to example 2, using (R)-6-[4-(2-amino-propyl)-phenoxy]-nicotinamide and benzyl bromide gives the title product: HPLC (30/70 to 90/10 ACN/(0.1% TFA in water) Zorbax SB-Phenyl Column 4.6mm×15 cm×5 micron: Retention time: 3.46 minutes, Purity: 97.9%; mass spectrum (ion spray): m/z=362.2 (M+1).

EXAMPLE 142

(R)-6-[4-(2-Dibenzylamino-propyl)-phenoxy]-nicotinamide

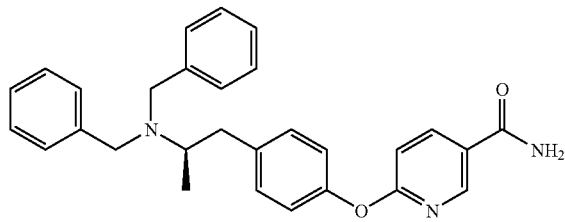

Using a method similar to example 2, using (R)-6-[4-(2-amino-propyl)-phenoxy]-nicotinamide and benzyl bromide gives the title product: HPLC (30/70 to 90/10 ACN/(0.1% TFA in water) Zorbax SB-Phenyl Column 4.6 mm×15 cm×5 micron: Retention time: 8.04 minutes, Purity: 99.8%; mass spectrum (ion spray): m/z=452.4 (M+1).

EXAMPLE 143

6-[4-(2-Benzylamino-2-methyl-propyl)-phenoxy]-nicotinamide

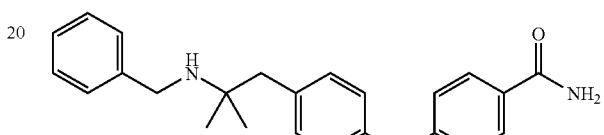

Using a method similar to example 2, using 6-[4-(2-amino-2-methyl-propyl) phenoxy]-nicotinamide and benzyl bromide gives the title product: HPLC (30/70 to 90/10 ACN/(0.1% TFA in water) Zorbax SB-Phenyl Column 4.6 mm×15 cm×5 micron: Retention time: 3.96 minutes, Purity: 100%; mass spectrum (ion spray): m/z=376.2 (M+1).

By the method of example 142 the following compounds were prepared:

| | | Data | | |
|---|---|---|---|---|
| | | Mass spectrum (ion spray): m/z | HPLC (30/70 to 90/10 ACN/(0.1% TFA in water) Zorbax SB-Phenyl Column 4.6 mm x 15 cm x 5 micron | |
| Example | Name | (M + 1) | Purity | Retention Time (minutes) |
| 144 | 6-[4-(2-Methyl-2-pentylamino-propyl)-phenoxy]-nicotinamide | 356.3 | 99.7 | 5.46 |
| 145 | 6-[4-(2-Methyl-2-phenethylamino-propyl)-phenoxy]-nicotinamide | 390.3 | 97.5 | 6.94 |
| 146 | 6-(4-{2-[2-(3-Fluoro-phenyl)-ethylamino]-2-methyl-propyl}-phenoxy)-nicotinamide | 408.2 | 98.2 | 7.63 |
| 147 | 6-{4-[2-(3-Cyclopentyl-propylamino)-2-methyl-propyl]-phenoxy}-nicotinamide | 396.3 | 96.6 | 8.23 |

EXAMPLE 148

(+-)-6-[4-(3-Benzylamino-butyl)-phenoxy]-nicotinamide

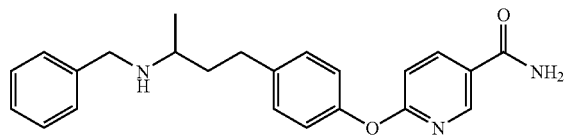

Step 1

6-[4-(3-Oxo-butyl)-phenoxy]-nicotinamide

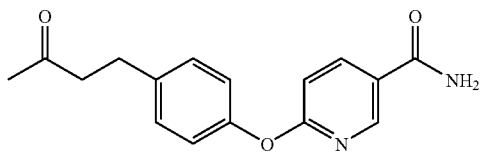

Add potassium carbonate (6.31 g, 45.7 mmol) to a stirred solution of 4-(4-hydroxyphenol)-2-butanone (3.00 g, 18.3 mmol), and 6-chloronicotinamide (2.87 g, 18.3 mmol) in dimethylacetamide (60 mL) and isooctane (10 mL). Equip with a Dean-Stark trap and heat the reaction to reflux for 6 h under nitrogen. Cool the reaction mixture to room temperature, filter off the solids, and concentrate the filtrate on a rotary evaporator to give the crude product. The crude product is purified by flash chromatography on silica gel eluting with 0.7% concentrated ammonium hydroxide/7% ethanol/chloroform to yield 3.49 g (67%) of 6-[4-(3-oxo-butyl)-phenoxy]-nicotinamide: mass spectrum (ion spray): m/z=285.2 (M+1); $^1$H NMR (CDCl$_3$): 8.58 (d, 1H), 8.16 (dd, 1H), 7.26-7.22 (m, 4H), 7.07-7.04 (m, 2H), 6.95 (d, 1H), 2.93-2.90 (m, 2H), 2.81-2.77 (m, 2H), 2.16 (s, 3H).

Step 2

Add sodium triacetoxyborohydride (0.2301 g, 1.086 mmol) to a stirred solution of 6-[4-(3-oxo-butyl)-phenoxy]-nicotinamide (0.2051 g, 0.7214 mmol), benzylamine (0.079 mL, 0.723 mmol), glacial acetic acid (0.045 ml 0.786 mmol), and 1,2-dichloroethane (7 mL). Stir the reaction for 18 h at room temperature under nitrogen. Add methanol (1.5 mL) and load the reaction mixture directly onto a 2 g prepacked SCX cartridge. Wash the cartridge with methanol (100 mL) and elute the product off of the cartridge with 2 M ammonia in methanol (50 mL). Concentrate the eluant on a rotary evaporator to yield 0.1863 g (69%) of 6-[4-(3-benzylamino-butyl)-phenoxy]-nicotinamide: HPLC (30/70 to 90/10 ACN/(0.1% TFA in water) Zorbax SB-Phenyl Column 4.6 mm×15 cm×5 micron: Retention time: 4.09 minutes, Purity: 99.9%; mass spectrum (ion spray): m/z=376.4 (M+1).

By the method of example 148 the following compounds were prepared:

| | | Data | | |
|---|---|---|---|---|
| | | | HPLC (30/70 to 90/10 ACN/(0.1% TFA in water) Zorbax SB-Phenyl Column 4.6 mm × 15 cm × 5 micron | |
| | | Mass spectrum (ion spray): m/z | | |
| Example | Name | (M + 1) | Purity | Retention Time (minutes) |
| 149 | 6-[4-(3-Pentylamino-butyl)-phenoxy]-nicotinamide | 356.5 | 100.0 | 5.19 |
| 150 | 6-[4-(3-Propylamino-butyl)-phenoxy]-nicotinamide | 328.3 | 82.8 | 2.52 |
| 151 | 6-[4-(3-Methylamino-butyl)-phenoxy]-nicotinamide | 300.2 | 52.2 | 1.94 |
| 152 | 6-[4-(3-Phenethylamino-butyl)-phenoxy]-nicotinamide | 390.2 | 97.7 | 6.48 |
| 153 | 6-(4-{3-[2-(3-Fluoro-phenyl)-ethylamino]-butyl}-phenoxy)-nicotinamide | 408.5 | 100.0 | 7.69 |
| 154 | 6-(4-{3-[2-(3-Chloro-phenyl)-ethylamino]-butyl}-phenoxy)-nicotinamide | 424.1 | 99.9 | 8.01 |
| 155 | 6-(4-{3-[(Furan-2-ylmethyl)-amino]-butyl}-phenoxy)-nicotinamide | 366.4 | 89.5 | 89.50 |
| 156 | 6-{4-[3-(2-Thiophen-2-yl-ethylamino)-butyl]-phenoxy}-nicotinamide | 396.5 | 99.0 | 5.30 |
| 157 | 6-{4-[3-(Cyclopropylmethyl-amino)-butyl]-phenoxy}-nicotinamide | 340.2 | 88.2 | 2.76 |
| 158 | 6-{4-[3-(3-Trifluoromethyl-benzylamino)-butyl]-phenoxy}-nicotinamide | 444.2 | 99.3 | 7.95 |
| 159 | 6-{4-[3-(4-Fluoro-benzylamino)-butyl]-phenoxy}-nicotinamide | 394.2 | 99.3 | 4.92 |

-continued

| Example | Name | Mass spectrum (ion spray): m/z (M + 1) | Purity | HPLC (30/70 to 90/10 ACN/(0.1% TFA in water) Zorbax SB-Phenyl Column 4.6 mm × 15 cm × 5 micron Retention Time (minutes) |
|---|---|---|---|---|
| 160 | 6-{4-[3-(3-Fluoro-benzylamino)-butyl]-phenoxy}-nicotinamide | 394.4 | 99.7 | 5.03 |
| 161 | 6-[4-(3-Allylamino-butyl)-phenoxy]-nicotinamide | 326.2 | 72.6 | 2.40 |
| 162 | 6-{4-[3-(4-Chloro-benzylamino)-butyl]-phenoxy}-nicotinamide | 410.1 | 92.7 | 6.78 |
| 163 | 6-{4-[3-(4-Methoxy-benzylamino)-butyl]-phenoxy}-nicotinamide | 406.2 | 99.9 | 5.09 |
| 164 | 6-{4-[3-(4-Trifluoromethyl-benzylamino)-butyl]-phenoxy}-nicotinamide | 444.2 | 54.8 | 7.95 |
| 165 | 6-{4-[3-(4-Trifluoromethoxy-benzylamino)-butyl]-phenoxy}-nicotinamide | 460.2 | 99.9 | 8.09 |
| 166 | 6-{4-[3-(3-Trifluoromethoxy-benzylamino)-butyl]-phenoxy}-nicotinamide | 460.1 | 100.0 | 8.09 |
| 167 | (1R)-6-{4-[3-(1-Phenyl-ethylamino)-butyl]-phenoxy}-nicotinamide | 390.2 | 71.0 | 5.30 |
| 168 | (1S)-6-{4-[3-(1-Phenyl-ethylamino)-butyl]-phenoxy}-nicotinamide | 390.2 | 69.3 | 5.26 |

EXAMPLE 169

6-[4-(2-Benzylamino-propyl)-phenoxy]-nicotinamide

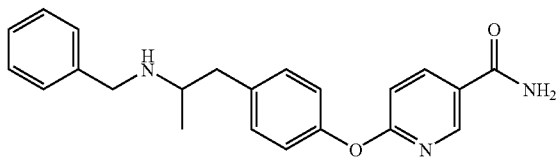

Step 1

6-[4-(2-Oxo-propyl)-phenoxy]-nicotinamide

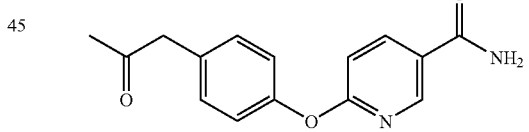

Using a method similar to example 148 Step 1, using 4-hydroxyphenylacetone and purifying by flash chromatography on silica gel eluting with 0.5% concentrated ammonium hydroxide/5% ethanol/chloroform gives the title compound: mass spectrum (ion spray): m/z=271.2 (M+1); $^1$H NMR (CDCl$_3$): 8.59 (d, 1H), 8.18 (dd, 1H), 7.27-7.24 (m, 4H), 7.14-7.10 (m, 2H), 6.98 (d, 1H), 3.73 (s, 2H), 2.21 (s, 3H).

Step 2

Using a method similar to example 148 Step 2, using 6-[4-(2-oxo-propyl)-phenoxy]-nicotinamide gives the title compound: mass spectrum (ion spray): HPLC (30/70 to 90/10 ACN/(0.1% TFA in water) Zorbax SB-Phenyl Column 4.6 mm×15 cm×5 micron: Retention time: 3.47 minutes, Purity: 99.5%; mass spectrum (ion spray): m/z=362.4 (M+1).

By the method of example 169 the following compounds were made:

| | | Data | | |
|---|---|---|---|---|
| | | Mass spectrum (ion spray): | HPLC (30/70 to 90/10 ACN/(0.1% TFA in water) Zorbax SB-Phenyl Column 4.6 mm × 15 cm × 5 micron | |
| Example | Name | m/z (M + 1) | Purity | Retention Time (minutes) |
| 170 | 6-[4-(2-Pentylamino-propyl)-phenoxy]-nicotinamide | 342.2 | 99.4 | 4.67 |
| 171 | 6-[4-(2-Propylamino-propyl)-phenoxy]-nicotinamide | 314.2 | 68.8 | 2.26 |
| 172 | 6-[4-(2-Methylamino-propyl)-phenoxy]-nicotinamide | 286.1 | 59.4 | 1.54 |
| 173 | 6-[4-(2-Phenethylamino-propyl)-phenoxy]-nicotinamide | 376.2 | 98.9 | 5.35 |
| 174 | 6-(4-{2-[2-(3-Fluoro-phenyl)-ethylamino]-propyl}-phenoxy)-nicotinamide | 394.2 | 98.6 | 6.14 |
| 175 | 6-(4-{2-[2-(3-Chloro-phenyl)-ethylamino]-propyl}-phenoxy)-nicotinamide | 410.1 | 52.4 | 7.63 |
| 176 | 6-(4-{2-[(Furan-2-ylmethyl)-amino]-propyl}-phenoxy)-nicotinamide | 352.1 | 77.2 | 2.49 |
| 177 | 6-{4-[2-(2-Thiophen-2-yl-ethylamino)-propyl]-phenoxy}-nicotinamide | 382.1 | 98.2 | 4.21 |
| 178 | 6-{4-[2-(Cyclopropylmethyl-amino)-propyl]-phenoxy}-nicotinamide | 326.2 | 74.6 | 2.36 |
| 179 | 6-{4-[2-(3-Trifluoromethyl-benzylamino)-propyl]-phenoxy}-nicotinamide | 430.1 | 88.4 | 7.00 |
| 180 | 6-{4-[2-(4-Fluoro-benzylamino)-propyl]-phenoxy}-nicotinamide | 380.1 | 98.3 | 4.04 |
| 181 | 6-{4-[2-(3-Fluoro-benzylamino)-propyl]-phenoxy}-nicotinamide | 380.1 | 96.8 | 3.81 |
| 182 | 6-[4-(2-Allylamino-propyl)-phenoxy]-nicotinamide | 312.2 | 60.4 | 2.09 |
| 183 | 6-{4-[2-(4-Chloro-benzylamino)-propyl]-phenoxy}-nicotinamide | 396.1 | 98.5 | 5.87 |
| 184 | 6-{4-[2-(4-Trifluoromethyl-benzylamino)-propyl]-phenoxy}-nicotinamide | 392.2 | 82.2 | 7.06 |
| 185 | 6-{4-[2-(4-Methoxy-benzylamino)-propyl]-phenoxy}-nicotinamide | 430.1 | 98.3 | 4.18 |
| 186 | 6-{4-[2-(4-Trifluoromethoxy-benzylamino)-propyl]-phenoxy}-nicotinamide | 446.1 | 99.0 | 7.97 |
| 187 | 6-{4-[2-(3-Trifluoromethoxy-benzylamino)-propyl]-phenoxy}-nicotinamide | 446.1 | 100.0 | 7.93 |
| 188 | (1S)-6-{4-[2-(1-Phenyl-ethylamino)-propyl]-phenoxy}-nicotinamide | 376.2 | 98.6 | 4.26 |

-continued

| | | Data | |
|---|---|---|---|
| Example | Name | Mass spectrum (ion spray): m/z (M + 1) | HPLC (30/70 to 90/10 ACN/(0.1% TFA in water) Zorbax SB-Phenyl Column 4.6 mm × 15 cm × 5 micron |
| | | | Purity | Retention Time (minutes) |
| 189 | (1R)-6-{4-[2-(1-Phenyl-ethylamino)-propyl]-phenoxy}-nicotinamide | 376.2 | 98.6 | 4.27 |

EXAMPLE 190

6-[4-(2-Benzylamino-1-methyl-ethyl)-phenoxy]-nicotinamide

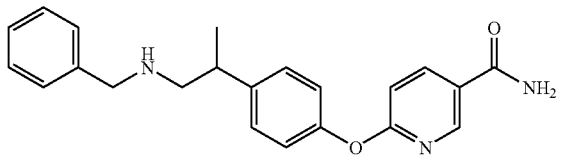

Step 1

N-Benzyl-2-(4-hydroxy-phenyl)-propionamide

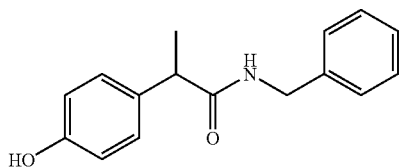

Using a method similar to example 132 Step 1, using (4-hydroxyphenyl)-2-propanoic acid gives the title compound: mass spectrum (ion spray): m/z=256.0 (M+1); $^1$H NMR (DMSO-d$_6$): 9.23 (s, 1H), 8.36 (t, 1H), 7.29-7.05 (m, 7H), 6.72-6.67 (m, 2H), 4.23 (d, 2H), 3.57-3.51 (m, 1H), 1.30 (d, 3H).

Step 2

4-(2-Benzylamino-1-methyl-ethyl)-phenol

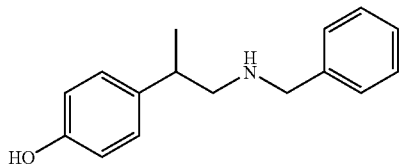

Dissolve N-benzyl-2-(4-hydroxy-phenyl)-propionamide (13.25 g, 51.9 mmol) in anhydrous tetrahydrofuran (100 mL) and add via a cannula to borane-tetrahydrofuran complex (1.0M in tetrahydrofuran, 300 mL, 300 mmol) under nitrogen. Heat the reaction to reflux for 18 h under nitrogen. Cool the reaction to 0° C. and quench with 6 M hydrochloric acid. Concentrate the tetrahydrofuran on a rotary evaporator to give the crude product. Add water (50 mL) and tetrahydrofuran (30 mL) to the crude product and heat the reaction to reflux for 1 h. Cool the reaction to room temperature and adjust the pH to pH=8 with 5 N sodium hydroxide. Add brine (200 mL) and extract with ethyl acetate (3×200 mL). Dry the ethyl acetate extracts over magnesium sulfate, filter, and concentrate on a rotary evaporator to give the crude product. Purify the crude product by flash chromatography on silica gel eluting with 0.7% concentrated ammonium hydroxide/7% ethanol/chloroform to yield 6.55 g (52%) of 4-(2-benzylamino-1-methyl-ethyl)-phenol: HPLC (30/70 to 90/10 ACN/(0.1% TFA in water) Zorbax SB-Phenyl Column 4.6 mm×15 cm×5 micron: Retention time: 3.08 minutes, Purity: 99.6%; mass spectrum (ion spray): m/z=242.1 (M+1).

Step 3

Using a method similar to example 1,4-(2-benzylamino-1-methyl-ethyl)-phenol is reacted with 6-chloronicotinamide to afford the title compound. The crude product is purified by flash chromatography on silica gel eluting with 0.7% concentrated ammonium hydroxide/7% ethanol/chloroform gives the title compound: HPLC (30/70 to 90/10 ACN/(0.1% TFA in water) Zorbax SB-Phenyl Column 4.6 mm×15 cm×5 micron: Retention time: 4.52 minutes, Purity: 99.1%; mass spectrum (ion spray): m/z=362.2 (M+1).

EXAMPLE 191

6-{4-[2-(Benzyl-pentyl-amino)-1-methyl-ethyl]-phenoxy}-nicotinamide

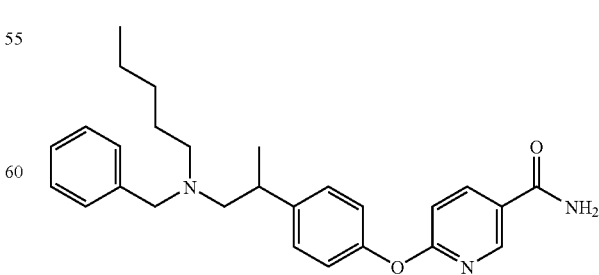

Using a method similar to example 3, using 6-[4-(2-benzylamino-1-methyl-ethyl)-phenoxy]-nicotinamide (example

EXAMPLE 192

6-[4-(1-Methyl-2-pentylamino-ethyl)-phenoxy]-nicotinamide

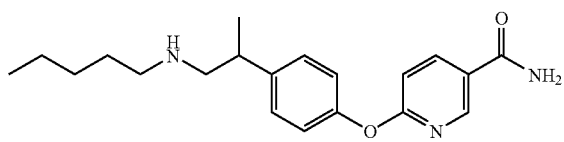

Using a method similar to example 22, using 6-{4-[2-(benzyl-pentyl-amino)-1-methyl-ethyl)]-phenoxy}-nicotinamide gives the title compound: HPLC (30/70 to 90/10 ACN/(0.1% TFA in water) Zorbax SB-Phenyl Column 4.6 mm×15 cm×5 micron: Retention time: 5.31 minutes. Purity: 100%; mass spectrum (ion spray): m/z=342.2 (M+1).

EXAMPLE 193

6-[4-(2-Amino-1,1-dimethyl-ethyl)-phenoxy]-nicotinamide

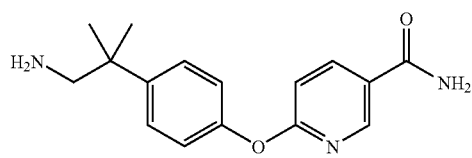

Step 1

2-(4-Methoxy-phenyl)-2-methyl-propionitrile

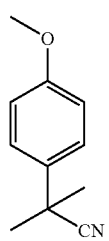

Add potassium bis(trimethylsilyl)amide (39.90 g, 200 mmol) to a stirred solution of 4-fluoroanisole (15.0 mL, 133 mmol), isobutyronitrile (49.0 mL, 539 mmol) and anhydrous tetrahydrofuran (150 mL). Heat the reaction to reflux under nitrogen for 72 h. Cool the reaction to room temperature, pour it into 1 N hydrochloric acid (300 mL), and extract with diethyl ether (3×100 mL). Wash the diethyl ether extracts with brine (100 mL), dry the extracts over magnesium sulfate, filter, and concentrate on a rotary evaporator to give the crude product. The crude product is purified by flash chromatography on silica gel eluting with 10% ethyl acetate/hexanes to yield 12.13 g (52%) of 2-(4-methoxy-phenyl)-2-methyl-propionitrile: TLC: R$_f$ in 10% ethyl acetate/hexanes: 0.30; $^1$H NMR (CDCl$_3$): 7.40-7.37 (m, 2H), 6.92-6.90 (m, 2H), 3.81 (s, 3H), 1.70 (s, 6H).

Step 2

2-(4-Hydroxy-phenyl)-2-methyl-propionitrile

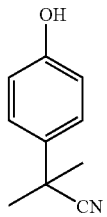

Add anhydrous dichloromethane (400 mL) to 2-(4-methoxy-phenyl)-2-methyl-propionitrile (11.93 g, 68.1 mmol) and cool to −78° C. under nitrogen. Then add boron tribromide (33.0 mL, 349 mmol) and stir at −78° C. for 30 minutes. Remove the dry ice/acetone bath and allow the reaction to warm to room temperature. Stir for 3 h and then pour the reaction onto ice. Extract with ethyl acetate (2×150 mL), dry the extracts over magnesium sulfate, filter, and concentrate on a rotary evaporator to give the crude product. The crude product is purified by flash chromatography on silica gel eluting with 35% ethyl acetate/hexanes to yield 9.79 g (89%) of 2-(4-hydroxy-phenyl)-2-methyl-propionitrile: TLC: R$_f$ in 40% ethyl acetate/hexanes: 0.38; $^1$H NMR (CDCl$_3$): 7.34-7.32 (m, 2H), 6.86-6.83 (m, 2H), 5.23 (s, 1H), 1.70 (s, 6H).

Step 3

[2-(4-Hydroxy-phenyl)-2-methyl-propyl]-carbamic acid tert-butyl ester

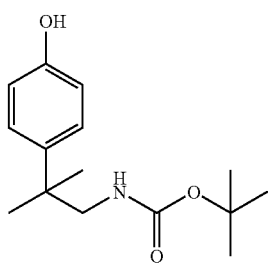

Add lithium aluminum hydride (10.00 g, 264 mmol) to anhydrous tetrahydrofuran (250 mL) and cool the slurry to 0° C. Dissolve 2-(4-hydroxy-phenyl)-2-methyl-propionitrile (9.90 g, 61.4 mmol) in anhydrous tetrahydrofuran (100 mL) and slowly, via cannula add this solution to the above slurry at 0° C. under nitrogen. Allow the reaction to warm to room temperature and stir for 2 h under nitrogen. Then heat the reaction to reflux. After 15 minutes cool the reaction to 0° C. and slowly quench with a saturated solution of ammonium chloride. Adjust the pH to pH=8 with 4 M hydrochloric acid and filter to remove the aluminum salts. Add brine (300 mL)

to the filtrate and extract with ethyl acetate (6×150 mL). Combine the ethyl acetate extracts and wash them with 1 N hydrochloric acid (2×150 mL). Combine and adjust the pH of the 1 N hydrochloric acid washes to pH=8 with sodium bicarbonate and then saturate this solution with sodium bicarbonate. Then extract the saturated sodium bicarbonate solution with ethyl acetate (5×150 mL) and with chloroform (5×150 mL). Combine the organic extracts, dry with magnesium sulfate, filter, and concentrate on a rotary evaporator to yield 2.78 g of the crude product. Add anhydrous tetrahydrofuran (150 mL) to the crude product. Then add di-tert-butyl dicarbonate (5.00 g, 22.9 mmol) to the reaction mixture and stir for 18 h at room temperature under nitrogen. Concentrate on a rotary evaporator to give the crude product. The crude product is purified by flash chromatography on silica gel eluting with 25% ethyl acetate/hexanes to yield 0.86 g (5%) of [2-(4-hydroxy-phenyl)-2-methyl-propyl]-carbamic acid tert-butyl ester: mass spectrum (ion spray): m/z=266.1 (M+1); $^1$H NMR (CDCl$_3$): 7.20 (d, 2H), 6.80 (d, 2H), 4.31 (br s, 1H), 3.28 (d, 2H), 1.40 (s, 10H), 1.28 (s, 6H).

Step 4

{2-[4-(5-Carbamoyl-pyridin-2-yloxy)-phenyl]-2-methyl-propyl}-carbamic acid tert-butyl ester

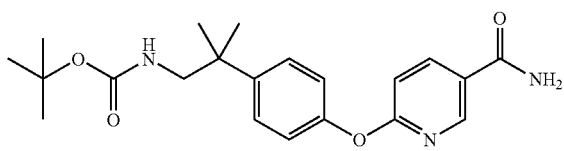

Add cesium carbonate (2.15 g, 6.60 mmol) to a stirred solution of [2-(4-hydroxy-phenyl)-2-methyl-propyl]-carbamic acid tert-butyl ester (0.86 g, 3.24 mmol) in dimethylformamide (20 mL). Stir for 30 minutes under nitrogen at room temperature. Then add 6-chloronicotinamide (0.51 g, 3.26 mmol) and heat to 100° C. under nitrogen for 6 h. Cool the reaction to room temperature, pour into brine (100 mL), extract with ethyl acetate (3×75 mL), dry the ethyl acetate extracts over magnesium sulfate, filter, and concentrate on a rotary evaporator to give the crude product. The crude product is purified by flash chromatography on silica gel eluting with 0.7% concentrated ammonium hydroxide/7% ethanol/chloroform to yield 0.5043 g (40%) of {2-[4-(5-carbamoyl-pyridin-2-yloxy)-phenyl]-2-methyl-propyl}-carbamic acid tert-butyl ester: mass spectrum (ion spray): m/z=386.2 (M+1); $^1$H NMR (CDCl$_3$): 8.64 (d, 1H), 8.20 (dd, 1H), 7.40 (d, 2H), 7.12 (d, 2H), 6.98 (d, 1H), 4.38 (br s, 1H), 3.34 (d, 2H), 1.75 (br s, 2H), 1.41 (s, 9H), 1.34 (s, 6H).

Step 5

6-[4-(2-Amino-1,1-dimethyl-ethyl)-phenoxy]-nicotinamide

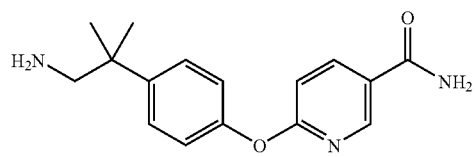

Add trifluoroacetic acid (2.0 mL, 26.0 mmol) to a stirred solution of {2-[4-(5-carbamoyl-pyridin-2-yloxy)-phenyl]-2-methyl-propyl}-carbamic acid tert-butyl ester (0.5000 g, 1.297 mmol) in dichloromethane (8 mL). Stir the reaction at room temperature under nitrogen for 2.5 h. Load the reaction contents directly onto a 10 g prepacked SCX cartridge, flush with methanol (200 mL), and elute the product with 2 M ammonia in methanol (75 mL). Concentrate the eluant on a rotary evaporator to give the crude product. The crude product is purified by flash chromatography on silica gel eluting with 1.5% concentrated ammonium hydroxide/15% ethanol/chloroform to yield 0.2626 g (71%) of 6-[4-(2-amino-1,1-dimethyl-ethyl)-phenoxy]-nicotinamide: mass spectrum (ion spray): m/z=286.1 (M+1); $^1$H NMR (DMSO-d$_6$): 8.59 (d, 1H), 8.23 (dd, 1H), 8.01 (s, 1H), 7.46 (s, 1H), 7.40-7.36 (m, 2H), 7.08-7.02 (m, 3H), 3.32 (br s, 2H), 2.64 (s, 2H), 1.22 (s, 6H).

EXAMPLE 194

6-[4-(2-Benzylamino-1,1-dimethyl-ethyl)-phenoxy]-nicotinamide

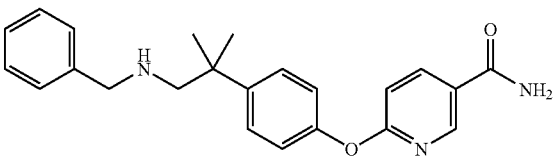

Using a method similar to example 35, using 6-[4-(2-amino-1,1-dimethyl-ethyl)-phenoxy]-nicotinamide (example 193), and benzaldehyde affords the title compound: HPLC (5/95 to 95/5 ACN/(0.1% TFA in water) Zorbax SB-Phenyl Column 4.6 mm×15 cm×5 micron: Retention time: 6.01 minutes, Purity: 95.6%; mass spectrum (ion spray): m/z=376.1 (M+1).

By the method of example 194 the following compounds were prepared:

| | | Data | |
|---|---|---|---|
| | Mass spectrum (ion spray): m/z | HPLC (5/95 to 95/5 ACN/(0.1% TFA in water) Zorbax SB-Phenyl Column 4.6 mm × 15 cm × 5 micron | |
| Example Name | (M + 1) | Purity | Retention Time (minutes) |
| 195 6-{4-[2-(Cyclohexylmethyl-amino)-1,1-dimethyl-ethyl]-phenoxy}-nicotinamide | 382.1 | 90.7 | 6.16 |
| 196 6-{4-[2-(2-Chloro-benzylamino)-1,1-dimethyl-ethyl]-phenoxy}-nicotinamide | 410.0 | 95.5 | 6.08 |
| 197 6-{4-[2-(3-Fluoro-benzylamino)-1,1-dimethyl-ethyl]-phenoxy}-nicotinamide | 394.1 | 97.5 | 6.04 |

EXAMPLE 198

6-[4-(3-Phenylamino-propyl)-phenoxy]-nicotinamide

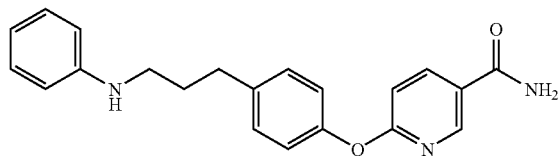

Step 1

6-[4-(3-Hydroxy-propyl)-phenoxy]-nicotinamide

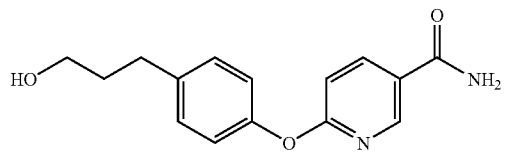

Add potassium carbonate (2.2821 g, 16.51 mmol) to a stirred solution of 3-(4-hydroxyphenyl)-1-propanol (1.0041 g, 6.598 mmol), 6-chloronicotinamide (1.0038 g, 6.411 mmol), dimethylacetamide (21 mL) and isooctane (3 mL). Equip the reaction setup with a Dean-Stark trap and heat the reaction to reflux under nitrogen for 6 h. Cool the reaction to room temperature and filter off the solids. Concentrate on a rotary evaporator to give the crude product. Take the crude product up in 1 N sodium hydroxide (250 mL), extract with ethyl acetate (4×100 mL), dry the extracts over magnesium sulfate, filter, and concentrate on a rotary evaporator to give the crude product. The crude product is purified by flash chromatography on silica gel eluting with 1.5% concentrated ammonium hydroxide/15% ethanol/chloroform to yield 1.5188 g (87%) of 6-[4-(3-hydroxy-propyl)-phenoxy]-nico- tinamide: mass spectrum (ion spray): m/z=273.2 (M+1); $^1$H NMR (DMSO-$d_6$): 8.61 (d, 1H), 8.24 (dd, 1H), 8.03 (s, 1H), 7.48 (s, 1H), 7.25 (d, 2H), 7.07-7.03 (m, 3H), 4.50 (t, 1H), 3.46-3.41 (m, 2H), 2.63 (t, 2H), 1.77-1.70 (m, 2H).

Step 2

6-[4-(3-Oxo-propyl)-phenoxy]-nicotinamide

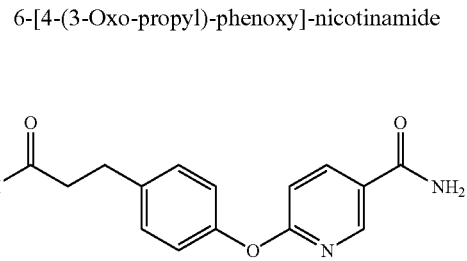

Add 6-[4-(3-hydroxy-propyl)-phenoxy]-nicotinamide (0.4051 g, 1.488 mmol) to a stirred solution of triethylamine (0.620 mL, 4.45 mmol) and anhydrous dimethylsulfoxide (4.5 mL). Dissolve pyridine sulfur trioxide (0.7023 g, 4.413 mmol) in anhydrous dimethylsulfoxide (4.5 mL) and add this solution via a cannula to the above stirred solution under nitrogen. Stir the reaction at room temperature for 1 h under nitrogen. Pour the reaction into ice water (50 mL), extract with ethyl acetate (3×50 mL), dry the ethyl acetate extracts over magnesium sulfate, filter, and concentrate on a rotary evaporator to give the crude product. The crude product is purified by flash chromatography on silica gel eluting with 100% ethyl acetate to yield 0.1428 g (36%) of 6-[4-(3-oxo-propyl)-phenoxy]-nicotinamide: mass spectrum (ion spray): m/z=271.2 (M+1); $^1$H NMR (CDCl$_3$): 9.84 (t, 1H), 8.58 (d, 1H), 8.16 (dd, 1H), 7.26-7.23 (m, 2H), 7.09-7.05 (m, 2H), 6.95 (d, 1H), 6.02 (br s, 2H), 2.98 (t, 2H), 2.82 (t, 2H).

Step 3

Add sodium triacetoxyborohydride (0.1633 g, 0.7705 mmol) to a stirred solution of 6-[4-(3-oxo-propyl)-phenoxy]-nicotinamide (0.1341 g, 0.4962 mmol), aniline (0.047 mL, 0.5158 mmol), and 1,2-dichloroethane (7 mL). Stir the reaction for 18 h at room temperature under nitrogen. Pour the reaction mixture into 1 N sodium hydroxide (50 mL), extract with dichloromethane (3×50 mL), dry the dichloromethane extracts over magnesium sulfate, filter, and concentrate on a rotary evaporator to give the crude product. The crude product is purified by flash chromatography on silica gel eluting with 0.6% concentrated ammonium hydroxide/6% ethanol/chloroform to yield 0.0142 g (8%) of 6-[4-(3-phenylamino-propyl)-phenoxy]-nicotinamide: mass spectrum (ion spray): m/z=348.1 (M+1); $^1$H NMR (CDCl$_3$): 8.58 (d, 1H), 8.16 (dd, 1H), 7.26-7.18 (m, 7H), 7.10-7.04 (m, 2H), 6.97-6.94 (m, 1H), 6.79-6.51 (m, 2H), 3.19 (t, 2H), 2.76 (t, 2H), 2.04-1.97 (m, 3H).

EXAMPLE 199

6-[4-(2-Dimethylamino-ethyl)-phenoxy]-nicotinamide

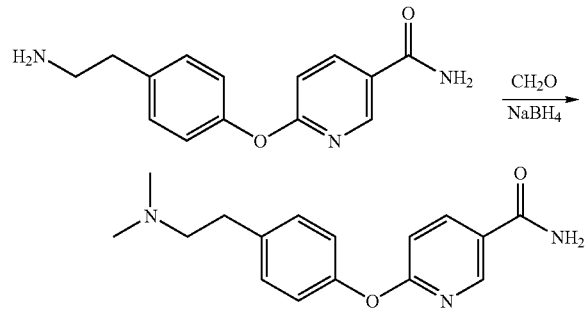

Combine amine (50 mg, 0.19 mmol) from Example 34, and formaldehyde 38% (260 μL, 3.1 mmol) in MeOH (1 mL). Stir the mixture at room temperature for 2 hours. Add NaBH$_4$ (60 mg, 1.55 mmol) and stir overnight. Evaporate the solvent in the rotatory evaporator, dissolve the crude product in CH$_2$Cl$_2$ and wash with H$_2$O. Extract the aqueous layer with CH$_2$Cl$_2$. Combine organic layers and dry over MgSO$_4$. Eliminate the solvent and purify by flash chromatography oil silica gel (eluent: CHCl$_3$/10% EtOH/1% NH$_4$OH) to give the title compound (32 mg, 58%). Electrospray MS M+1 ion=286, $^1$H-NMR (methanol-d$_4$, 300 MHz): 8.62 (d, 1H, J=2.5 Hz), 8.23 (dd, 1H, J=2.5 and 8.7 Hz), 7.31-7.27 (m, 2H), 7.08-7.04 (m, 2H), 6.96 (d, 1H, J=8.5 Hz), 2.86-2.78 (m, 2H), 2.61-2.54 (m, 2H), 2.32 (s, 6H).

EXAMPLE 200

6-[4-(2-Piperidin-1-yl-ethyl)-phenoxy]-nicotinamide

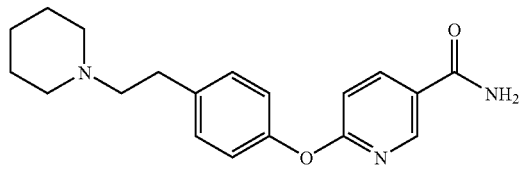

Step 1

6-[4-(2-Hydroxy-ethyl)-phenoxy]-nicotinamide

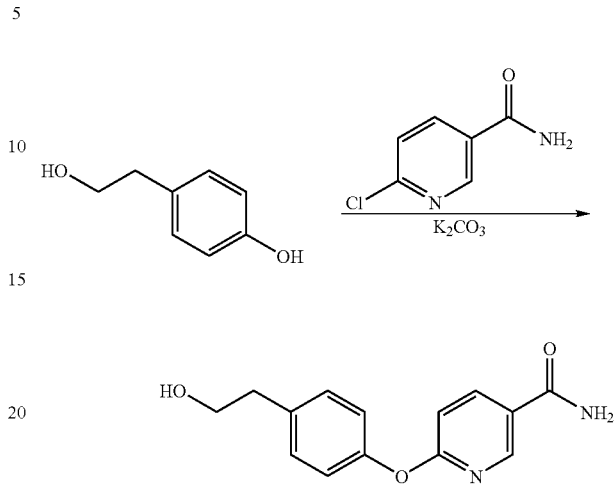

Combine 4-(2-hydroxy-ethyl)-phenol (2.0 g, 14.5 mmol), 6-chloronicotinamide (2.3 g, 14.5 mmol) and K$_2$CO$_3$ (5.0 g, 36.2 mmol) in DMF (40 mL) under nitrogen, stir and heat at 120° C. overnight. Cool to ambient temperature and pour into water, extract the aqueous layer with ethyl acetate. Combine the organic layers and dry over Na$_2$SO$_4$. Eliminate the solvent and purify by flash chromatography on silica gel (eluent: CHCl$_3$/7% EtOH/0.7% NH$_4$OH) to give the title compound (1.8 g, 49%). Electrospray MS M+1 ion=259, $^1$H-NMR (DMSO-d$_6$, 400 MHz): 8.58 (d, 1H, J=2.7 Hz), 8.22 (dd, 1H, J=2.7 and 8.8 Hz), 8.00 (bs, 1H), 7.46 (bs, 1H), 7.25 (m, 2H), 7.05-7.02 (m, 3H), 4.65 (t, 1H, J=5.3 Hz), 3.63-3.58 (m, 2H), 2.72 (t, 2H, J=6.9 Hz).

Step 2

Dissolve 6-[4-(2-hydroxy-ethyl)-phenoxy]-nicotinamide (100 mg, 0.38 mmol) under N$_2$ atmosphere in dry DMF (4 mL). Add Et$_3$N (1108 μL, 0.77 mmol) then cool the mixture at 0° C., add MsCl (29 μL, 0.38 mmol), allow the mixture to warm to room temperature. After 1 hour add piperidine (76 μL, 0.77 mmol) and heat the mixture at 90° C. for 1 hour. Cool to ambient temperature and pour into water. Extract the aqueous layer with EtOAc. Dry the organic layer over MgSO$_4$. Eliminate the solvent. Purify by flash chromatography on silica gel (eluent: CHCl$_3$/5% EtOH/0.5% NH$_4$OH) to give the title compound (65 mg, 55%). Electrospray MS M+1 ion=326, $^1$H-NMR (CDCl$_3$, 400 MHz): 8.58 (d, 1H, J=2.4 Hz), 8.14 (dd, 1H, J=2.4 end 8.5 Hz), 7.25-7.23 (m, 2H), 7.07-7.03 (m, 2H), 6.93 (d, 1H, J=8.5 Hz), 6.12 (bs, 2H), 2.88-2.80 (m, 2H), 2.68-2.65 (m, 2H), 2.53-2.44 (m, 4H), 1.67-1.59 (m, 4H), 1.51-1.43 (m, 2H).

By the method of example 200 the following compounds (examples 201-209) were prepared. All samples were purified following the same procedure described for example 200 except where noted.

EXAMPLE 201

6-[4-(2-Morpholin-1-yl-ethyl)-phenoxy]-nicotinamide

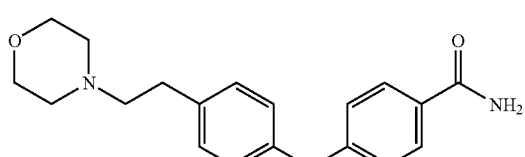

Electrospray MS M+1 ion=328, ¹H-NMR (CDCl₃, 400 MHz): 8.51 (d, 1H, J=2.4 Hz), 8.09 (dd, 1H, J=2.4 and 8.8 Hz), 7.21-7.17 (m, 2H), 7.02-6.98 (m, 2H), 6.88 (d, 1H, J=8.8 Hz), 5.91 (bs, 2H), 3.72-3.67 (m, 4H), 2.80-2.74 (m, 2H), 2.61-2.54 (m, 2H), 2.52-2.45 (m, 4H).

EXAMPLE 202

6-{4-[2-(3,4-Dihydro-1H-isoquinolin-2-yl)-ethyl]-phenoxy}-nicotinamide

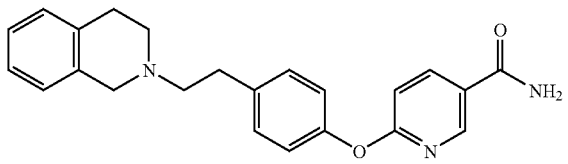

Electrospray MS M+1 ion=374, ¹H-NMR (CDCl₃, 400 MHz): 8.52 (d, 1H, J=2.4 Hz), 8.10 (dd, 1H, J=2.4 and 8.8 Hz), 7.25-7.22 (m, 2H), 7.10-6.97 (m, 6H), 6.89 (d, 1H, J=8.8 Hz), 3.74 (bs, 2H), 2.96-2.76 (m, 8H).

EXAMPLE 203

6-{4-[2-(4-Benzoyl-piperidin-1-yl)-ethyl]-phenoxy}-nicotinamide

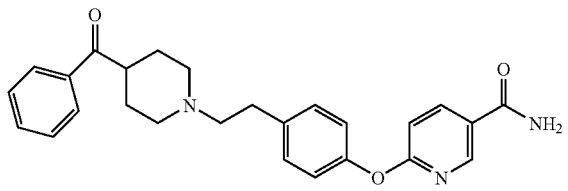

Electrospray MS M+1 ion=430, ¹H-NMR (CDCl₃, 400 MHz): 8.52 (d, 1H, J=2.4 Hz), 8.10 (dd, 1H, J=2.4 and 8.5 Hz), 7.88 (d, 2H, J=7.5 Hz), 7.52-7.47 (m, 1H), 7.43-7.38 (m, 2H), 7.22-7.19 (m, 2H), 7.01-6.98 (m, 2H), 6.89 (d, 1H, J=8.5 Hz), 3.22 (m, 1H), 3.07-3.00 (m, 2H), 2.82-2.76 (m, 2H), 2.63-2.56 (m, 2H), 2.19-2.09 (m, 2H), 1.88-1.79 (m, 4H).

EXAMPLE 204

6-{4-[2-(3-Methyl-piperidin-1-yl)-ethyl]-phenoxy}-nicotinamide

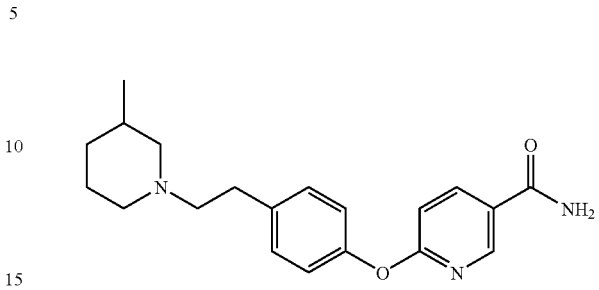

Electrospray MS M+1 ion=340, ¹H-NMR (CDCl₃ 400 MHz): 8.58 (d, 1H, J=2.3 Hz), 8.16 (dd, 1H, J=2.4 and 8.2 Hz), 7.26-7.24 (m, 2H), 7.07-7.03 (m, 2H), 6.95 (d, 1H, J=8.2 Hz), 3.48 (d, 1H, J=6.3 Hz), 3.00-2.81 (m, 4H), 2.62-2.57 (m, 2H), 1.96-1.87 (m, 1H), 1.75-1.60 (m, 5H), 0.88 (d, 3H, J=6.3 Hz).

EXAMPLE 205

6-{4-[2-(3,5-Dimethyl-piperidin-1-yl)-ethyl]-phenoxy}-nicotinamide

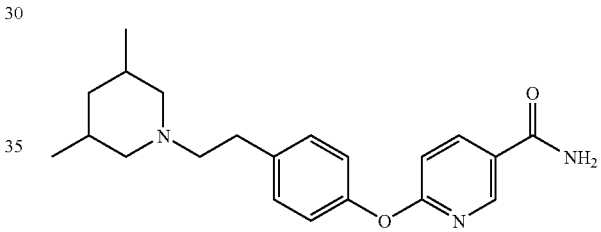

Electrospray MS M+1 ion=354, ¹H-NMR (metanol-d₄, 400 MHz): 8.61 (d, 1H, J=2.7 Hz), 8.24 (dd, 1H, J=2.7 and 8.5 Hz), 7.32-7.28 (m, 2H), 7.08-7.05 (m, 2H), 6.96 (d, 1H) J=8.5 Hz), 3.02-2.98 (m, 2H), 2.90-2.84 (m, 2H), 2.67-2.61 (m, 2H), 1.80-1.59 (m, 6H), 0.91 (t, 6H, J=6.5 Hz).

EXAMPLE 206

6-{4-[2-(4-Benzhydryl-piperidin-1-yl)-ethyl]-phenoxy}-nicotinamide

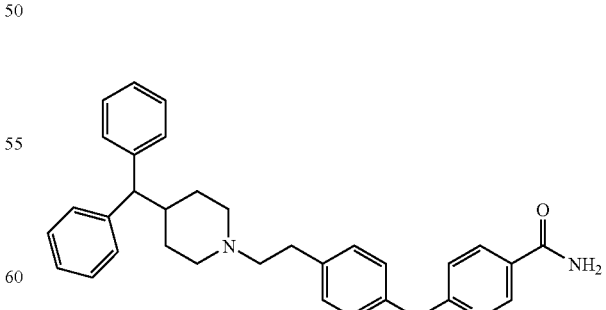

Purification: 5-95% gradient 3 ml/min (ACN&H₂O with 6.5 nM NH₄OAc) on a 4.6×50 mm Symmetry Column. Electrospray MS M+1 ion=492, ¹H-NMR (methanol-d₄, 400 MHz): 8.61 (d, 1H, J=2.5 Hz), 8.23 (dd, 1H, J=2.5 and 8.9

Hz), 7.34-7.22 (m, 10H), 7.15-7.10 (m, 2H), 7.06-7.03 (m, 2H), 6.95 (d, 1H, J=8.9 Hz), 3.53 (d, 1H, J=10.3 Hz), 3.07-3.02 (m, 2H), 2.87-2.82 (m, 2H), 2.68-2.63 (m, 2H), 2.31-2.13 (m, 3H), 1.62-1.57 (m, 2H), 1.32-1.22 (m, 2H).

EXAMPLE 207

6-{4-[2-(4-Phenyl-piperidin-1-yl)-ethyl]-phenoxy}-nicotinamide

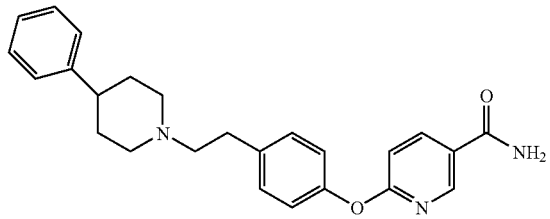

Electrospray MS M+1 ion=402, $^1$H-NMR (CDCl$_3$, 400 MHz): 8.51 (d, 1H, J=2.4 Hz), 8.10 (dd, 1H, J=2.4 and 8.7 Hz), 7.27-7.11 (m, 7H), 7.02-6.99 (m, 2H), 6.89 (d, 1H, J=8.7 Hz), 3.13-3.07 (m, 2H), 2.86-2.79 (m, 2H), 2.64-2.57 (m, 2H), 2.52-2.41 (m, 1H), 2.14-2.05 (m, 2H), 1.84-1.75 (m, 4H).

EXAMPLE 208

6-(4-{2-[3-Fluoro-phenyl)-piperidin-1-yl]-ethyl}-phenoxy)-nicotinamide

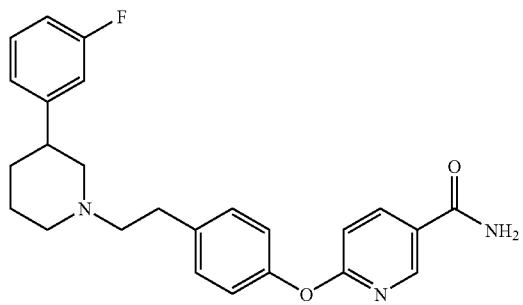

Purification: 5-95% gradient 3 ml/min (ACN&H$_2$O with 6.5 nM NH$_4$OAc) oil a 4.6×50 mm Symmetry Column. Electrospray MS M+1 ion=420, $^1$H-NMR (methanol-d$_4$, 400 MHz): 8.61 (d, 1H, J=2.4 Hz), 8.23 (dd, 1H, J=2.4 and 8.6 Hz), 7.33-7.26 (m, 4H), 7.09-7.00 (m, 4H), 6.96 (d, 1H, J=8.6 Hz), 3.28-3.17 (m, 2H), 2.96-2.81 (m, 5H), 2.40-2.30 (m, 2H), 1.97-1.74 (m, 3H), 1.63-1.52 (m, 1H).

EXAMPLE 209

6-[4-(2-Azepan-1-yl-ethyl)-phenoxy]-nicotinamide

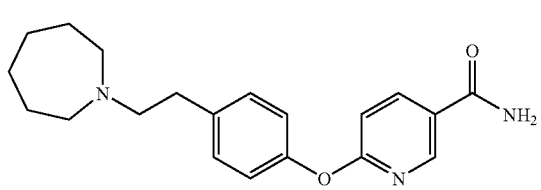

Electrospray MS M+1 ion=340, $^1$H-NMR (CDCl$_3$, 400 MHz): 8.58 (d, 1H, J=2.6 Hz), 8.16 (dd, 1H, J=2.6 and 8.8 Hz), 7.26-7.23 (m, 2H), 7.07-7.03 (m, 2H), 6.94 (d, 1H, J=8.8 Hz), 2.84-2.72 (m, 8H), 1.73-1.59 (m, 8H).

EXAMPLE 210

6-{4-[2-(Benzyl)-methyl-amino)-ethyl]-phenoxy}-nicotinamide

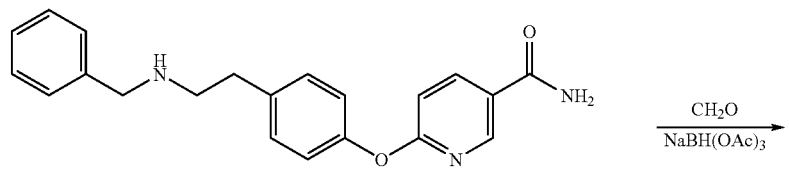

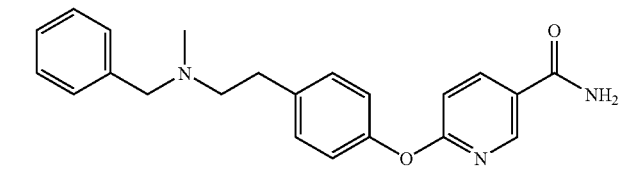

Combine amine (65 mg, 0.20 mmol) from example 1, AcOH (70 μL, 1.2 mmol), formaldehyde (0.6 mmol) and NaBH(OAc)₃ (0.40 mmol) in 1,2-DCE (2 mL). Stir the mixture at room temperature overnight. Dilute the mixture with CH₂Cl₂ and wash with NaHCO₃ sat. Extract the aqueous layer with CH₂Cl₂, combine the organic layers and dry over Na₂SO₄. Purify by flash chromatography on silica gel (eluent: EtOAc). Electrospray MS M+1 ion=362, ¹H-NMR (CDCl₃, 400 MHz): 8.58 (d, 1H, J=2.6 Hz), 8.15 (dd, 1H, J=2.6 and 8.6 Hz), 7.32-7.22 (m, 7H), 7.06-7.04 (m, 2H), 6.95 (d, 1H, J=8.6 Hz), 3.61 (bs, 2H), 2.91-2.84 (m, 2H), 2.74-2.66 (m, 2H), 2.32 (s, 3H).

By method of example 210 the following compounds were prepared: examples 211-216.

EXAMPLE 211

6-{4-[2-(Benzyl-ethyl-amino)-ethyl]-phenoxy}-nicotinamide

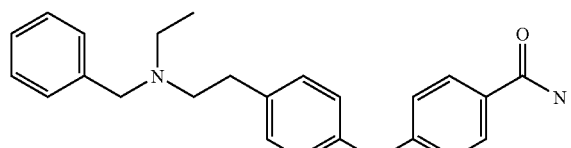

Electrospray MS M+1 ion=376, ¹H-NMR (CDCl₃, 400 MHz): 8.58 (d, 1H, J=2.5 Hz), 8.14 (dd, 1H, J=2.5 and 8.7 Hz), 7.33-7.18 (m, 7H), 7.04-7.01 (m, 2H), 6.92 (d, 1H, J=8.7 Hz), 6.17 (bs, 2H), 3.66 (s, 2H), 2.82-2.72 (m, 4H), 2.62 (c, 2H, J=7.1 Hz), 1.08 (t, 3H, J=7.1 Hz).

EXAMPLE 212

6-{4-[2-(Benzyl-propyl-amino)-ethyl]-phenoxy}-nicotinamide

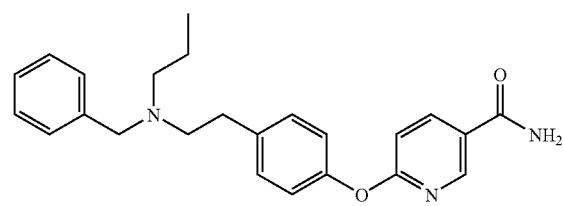

Electrospray MS M+1 ion=390, ¹H-NMR (CDCl₃, 400 MHz): 8.58 (d, 1H, J=2.4 Hz), 8.14 (dd, 1H, J=2.4 and 8.3 Hz), 7.35-7.15 (m, 7H), 7.14-7.00 (m, 2H), 6.92 (d, 1H, J=8.3 Hz), 3.66 (bs, 2H), 2.82-2.69 (m, 4H), 2.49 (t, 2H, J=7.1 Hz), 1.52 (m, 2H), 0.87 (t, 3H, J=7.1 Hz).

EXAMPLE 213

6-{4-[2-(Benzyl-butyl-amino)-ethyl]-phenoxy}-nicotinamide

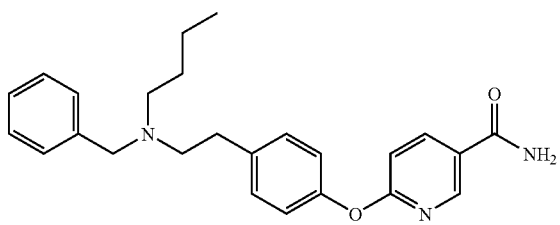

Electrospray MS M+1 ion=404, ¹H-NMR (CDCl₃, 400 MHz): 8.58 (d, 1H, J=2.4 Hz), 8.15 (dd, 1H, J=2.4 and 8.3 Hz), 7.35-7.16 (m, 7H), 7.05-7.00 (m, 2H), 6.92 (d, 1H, J=8.3 Hz), 3.65 (bs, 2H), 2.83-2.68 (m, 4H), 2.52 (t, 2H, J=1.1 Hz), 1.48 (m, 2H), 1.30 (m, 2H), 0.88 (t, 3H, J=7.1 Hz).

EXAMPLE 214

6-{4-[2-(Benzyl)-cyclopropylmethylamino)-ethyl]-phenoxy}-nicotinamide

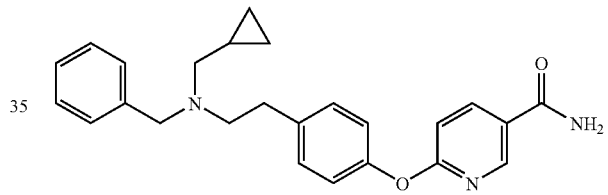

Electrospray MS M+1 ion=402, ¹H-NMR (CDCl₃ 400 MHz): 8.47 (d, 1H, J=2.5 Hz), 8.05 (dd, 1H, J=2.5 and 8.7 Hz), 7.27-7.07 (m, 7H), 6.96-6.91 (m, 2H), 6.84 (d, 1H, J=8.7 Hz), 3.64 (bs, 2H), 2.72 (m, 4H), 2.34 (m, 2H), 0.80 (m, 1H), 0.40 (m, 2H), 0.00 (m, 2H).

EXAMPLE 215

6-{4-[2-(Benzyl)-isobutyl-amino)-ethyl]-phenoxy}-nicotinamide

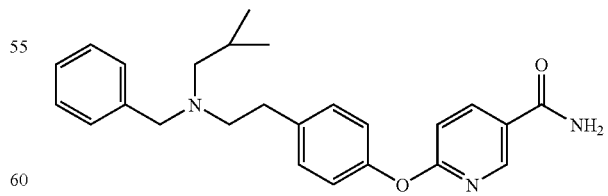

Electrospray MS M+1 ion=404, ¹H-NMR (CDCl₃, 400 MHz): 8.57 (d, 1H, J=2.3 Hz), 8.15 (dd, 1H, J=2.3 and 8.6 Hz), 7.34-7.15 (m, 7H), 7.04-6.99 (m, 2H), 6.92 (d, 1H, J=8.6 Hz), 3.61 (s, 2H), 2.80-2.64 (m, 4H), 2.24 (d, 2H, J=7.0 Hz), 1.78 (m, 1H), 0.87 (t, 6H, J=7.0 Hz).

EXAMPLE 216

6-{4-[2-(Benzyl-(3-methyl-butyl)-amino)-ethyl]-phenoxy}-nicotinamide

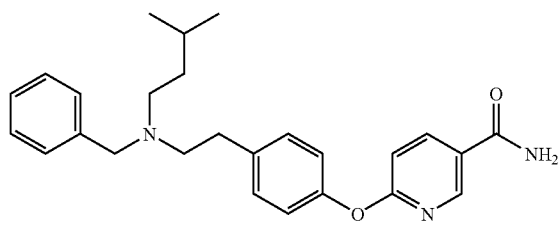

Electrospray MS M+1 ion=418, $^1$H-NMR (CDCl$_3$, 400 MHz): 8.51 (d, 1H, J=2.5 Hz), 8.08 (dd, 1H, J=2.5 and 8.0 MHz), 7.26-7.15 (m, 5H), 7.13-7.10 (m, 2H), 6.97-6.94 (m, 2H), 6.87 (d, 1H, J=8.8 Hz), 3.57 (s, 2H), 2.74-2.61 (m, 4H), 2.46 (t, 2H, J=7.4 Hz), 1.56-1.46 (m, 1H), 1.31 (c, 2H, J=7.1 Hz), 0.79 (d, 6H, J=7.1 Hz).

EXAMPLE 217

Synthesis of 6-[4-(2-Benzoylamino-ethyl)-phenoxy]-nicotinamide

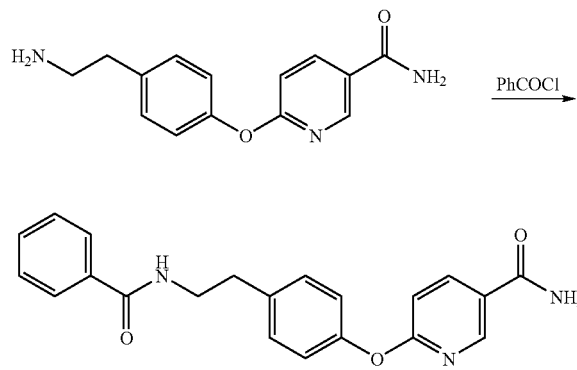

Combine amine starting material of Example 34 (100 mg, 0.39 mmol), benzoyl chloride (50 μL, 0.43 mmol) and Et$_3$N (120 μL, 0.86 mmol) in THF (4 mL) and DMF (0.5 mL). Stir the mixture at room temperature for 3 hours. Eliminate the solvent and purify by flash chromatography on silica gel (eluent: EtOAc/hexane 75/25) to give the title compound. (90 mg, 65%). Electrospray MS M+1 ion=362, $^1$H-NMR (methanol-d$_4$, 400 MHz): 8.62 (d, 1H, J=2.8 Hz), 8.24 (dd, 1H, J=2.8 and 9.0 Hz), 7.79-7.76 (m, 2H), 7.55-7.42 (m, 5H), 7.09-7.06 (m, 2H), 6.96 (d, 1H, J=9.0 Hz), 3.62 (t, 2H, J=7.3 Hz), 2.95 (t, 2H, J=7.3 Hz).

Synthesis of 4-[4-(2-Benzylamino-ethyl)-phenoxy]-2-fluoro-benzamide (example 218) and 2-[4-(2-Benzylamino-ethyl)-phenoxy]-4-fluoro-benzamide (example 219)

EXAMPLE 218

4-[4-(2-Benzylamino-ethyl)-phenoxy]-2-fluoro-benzamide

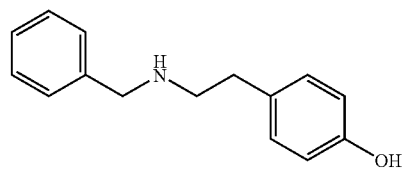

Step 1

4-(2-Benzylamino-ethyl)-phenol

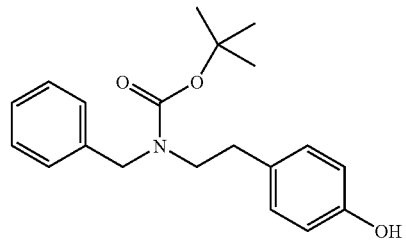

Combine tyramine (5.0 g, 36.4 mmol), benzaldehyde (3.8 ml, 37.2 mmol) in MeOH (46 mL), heat at reflux for 2 h. Cool the mixture at 0° C. and add NaBH$_4$ (1.44 g, 38.2 mmol). Stir at room temperature overnight. Remove most of MeOH, add H$_2$O and stir for 2 h. Filter the mixture and wash the white solid with water. Dry the solid precipitate under vacuum at 40° C. overnight to afford the title compound (7.53 g, 91%). Electrospray MS M+1 ion=228. $^1$H-NMR (methanol-d$_4$, 300 MHz): 7.40-7.20 (m, 5H), 7.03-6.95 (m, 2H), 6.73-6.65 (m, 2H), 3.75 (s, 2H), 2.85-2.65 (m, 4H).

Step 2

Benzyl-[2-(4-hydroxy-phenyl)-ethyl]-carbamic acid tert-butyl ester

Combine the product of step 1 (2.0 g, 8.8 mmol) and di-tert-butyl dicarbonate (2.11 g, 9.6 mmol) in THF (120 mL), stir the mixture at room temperature overnight. Eliminate the solvent and purify on silica gel (eluent: gradient from hexane to hexane/EtOAc 20/80) to afford the title compound (2.0 g, 68%). Electrospray MS M−1 ion=326, ¹H-NMR (methanol-$d_4$, 400 MHz): 7.34-7.15 (m, 5H), 7.05-6.90 (m, 2H), 6.75-6.65 (m, 2H), 4.40-4.25 (m, 2H), 3.40-3.25 (m, 2H), 2.65-2.60 (m, 2H), 1.20 (s, 9H).

Step 3

Benzyl-{2-[4-(4-cyano-3-fluoro-phenoxy)-phenyl]-ethyl}-carbamic acid tert-butyl ester and Benzyl-{2-[4-(2-cyano-5-fluoro-phenoxy)-phenyl]-ethyl}-carbamic acid tert-butyl ester

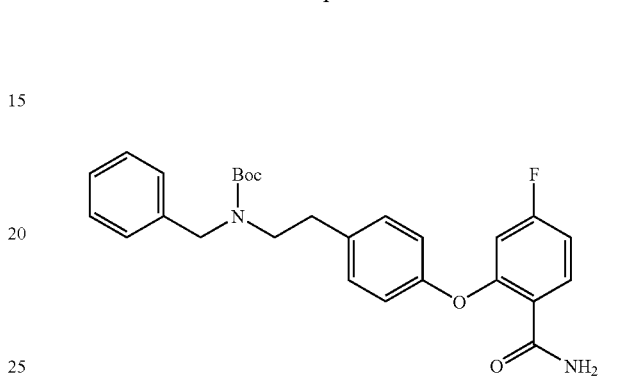

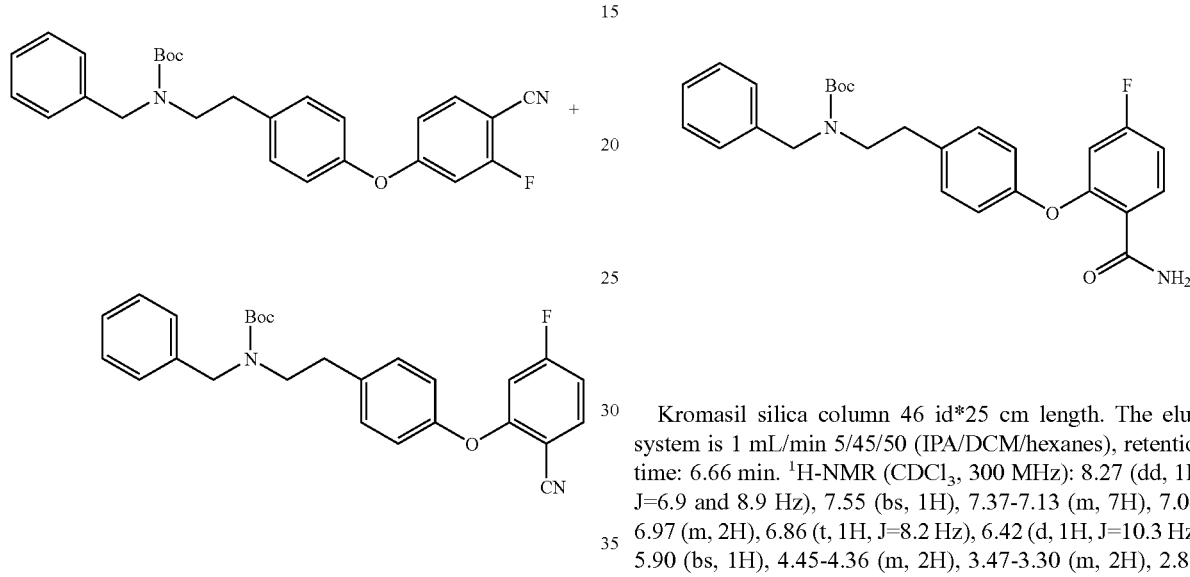

Combine benzyl-[2-(4-hydroxy-phenyl)-ethyl]-carbamic acid tert-butyl ester (400 mg, 1.23 mmol) and $K_2CO_3$ (187 mg, 1.35 mmol) in DMF (6 mL), stir the mixture at room temperature for 30 min and then add 2,4-difluoro-benzonitrile (188 mg, 1.35 mmol), heat at 100° C. overnight. Cool the mixture to about room temperature and pour it into water. Extract the aqueous layer with EtOAc. Dry the organic layer over $Na_2SO_4$ and eliminate the solvent in the rotatory evaporator. Purify on silica gel (eluent: EtOAc/hexanes 15/85) to get the mixture of both regioisomers (400 mg, 73%). Electrospray MS M−1 ion=445, ¹H-NMR ($CDCl_3$, 400 MHz, mixture of the two regioisomers): 7.36 (dd, 1H, J=5.3 and 8.2 Hz), 7.51 (t, 1H, J=7.6 Hz), 7.36-7.13 (m, 17H), 7.01 (d, 1H, J=8.2 Hz), 6.97 (d, 1H, J=8.2 Hz), 6.83-6.76 (m, 1H), 6.68 (d, 1H, J=10.0 Hz), 6.46 (d, 1H, J=10.0 Hz), 4.46-4.34 (m, 4H), 3.48-3.32 (m, 4H), 2.88-2.73 (m, 4H), 1.50-1.45 (m, 18H).

Step 4

Benzyl-{2-[4-(2-carbamoyl-5-fluoro-phenoxy)-phenyl]-ethyl}-carbamic acid tert-butyl ester and benzyl-{2-[4-(4-carbamoyl-3-fluoro-phenoxy)-phenyl]-ethyl}-carbamic acid tert-butyl ester Combine benzyl-{2-[4-(4-cyano-3-fluoro-phenoxy)-phenyl]-ethyl}-carbamic acid tert-butyl ester and benzyl-{2-[4-(2-cyano-5-fluoro-phenoxy)-phenyl]-ethyl}-carbamic acid tert-butyl ester, a mixture of both regioisomers, (100 mg, 0.22 mmol), $H_2O_2$ (26 μL), and $K_2CO_3$ (16 mg, 0.11 mmol) in DMSO (0.8 mL). Stir the mixture at room temperature for 3 hours and add water. Extract the aqueous layer with EtOAc. Dry the organic layer over $MgSO_4$. Eliminate the solvent and purify by flash chromatography (eluent: AcOEt/hexane 40/60) to give the mixture of regioisomeric carboxamides (90 mg, 85%). The regioisomers were separated by HPLC (Kromasil silica column 10 um silica particle size, 5 cm id*25 cm length. The elute system is 120 mL/min 5/45/50 (IPA/DCM/hexanes), 30 mg loading in 100% DCM).

Step 5a

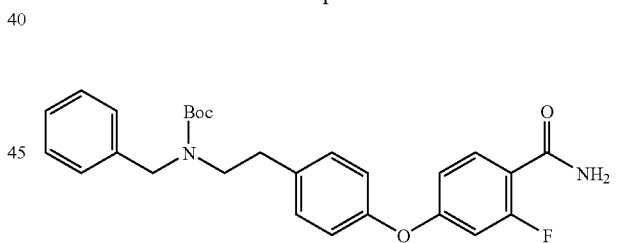

Kromasil silica column 46 id*25 cm length. The elute system is 1 mL/min 5/45/50 (IPA/DCM/hexanes), retention time: 6.66 min. ¹H-NMR ($CDCl_3$, 300 MHz): 8.27 (dd, 1H, J=6.9 and 8.9 Hz), 7.55 (bs, 1H), 7.37-7.13 (m, 7H), 7.04-6.97 (m, 2H), 6.86 (t, 1H, J=8.2 Hz), 6.42 (d, 1H, J=10.3 Hz), 5.90 (bs, 1H), 4.45-4.36 (m, 2H), 3.47-3.30 (m, 2H), 2.88-2.71 (m, 2H), 1.53-1.41 (m, 9H).

Step 5b

Kromasil silica column 46 id*25 cm length. The elute system is 1 ml/min 5/45/50 (IPA/DCM/HEXANE), retention time: 7.68 min. ¹H-NMR ($CDCl_3$, 400 MHz): 8.00 (t, 1H, J=9.7 Hz), 7.30-7.04 (m, 7H), 6.94-6.90 (m, 2H), 6.75 (dd, 1H, J=2.4 and 8.4 Hz), 6.58 (dd, 1H, J=2.4 and 13.9 Hz), 6.52 (m, 1H), 5.69 (bs, 1H), 4.38-4.28 (m, 2H), 3.40-3.25 (m, 2H), 2.79-2.65 (m, 2H), 1.45-1.35 (m, 9H).

Dissolve compound of step 5b (23 mg, 0.049 mmol) in $CH_2Cl_2$ (2 mL) and add trifluoroacetic acid (99 μL, 1.29 mmol), stir the mixture at room temperature for 5 h. Eliminate the solvent and purify on a SCX column to afford the title compound (18 mg, 99%). Electrospray MS M+1 ion=365. ¹H-NMR ($CDCl_3$, 400 MHz): 8.06 (t, 1H, J=8.4 Hz), 7.35-7.22 (m, 7H), 7.01-6.98 (m, 2H), 6.82 (dd, 1H, J=2.4 and 8.9 Hz), 6.66 (dd, 1H, J=2.4 and 13.6 Hz), 6.60 (bd, 1H), 6.00 (bd, 1H), 3.82 (s, 2H), 2.95-2.90 (m, 2H), 2.87-2.82 (m, 2H).

EXAMPLE 219

2-[4-(2-Benzylamino-ethyl)-phenoxy]-4-fluoro-benzamide

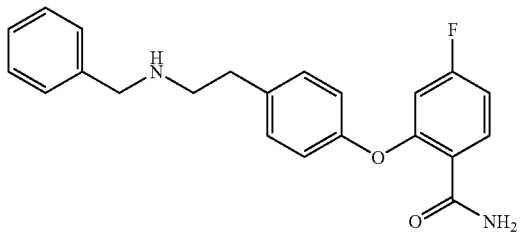

The title compound was prepared from the compound of example 218 step 5a following the same acidic hydrolysis described above.

Electrospray MS M+1 ion=365. $^1$H-NMR (CDCl$_3$, 400 MHz): 8.28 (dd, 1H, J=6.6 and 8.0 Hz), 7.55 (bs, 1H), 7.35-7.23 (m, 7H), 7.05-7.00 (m, 2H), 6.86 (ddd, 1H, J=2.2, 8.0 and 10.0 Hz), 6.46 (dd, 1H, J=2.2 and 10.0 Hz), 5.89 (bs, 1H), 3.83 (s, 2H), 2.95-2.90 (m, 2H), 2.88-2.83 (m, 2H).

EXAMPLE 220

4-[4-(2-Benzylamino-ethyl)-phenoxy]-2-chloro-benzamide

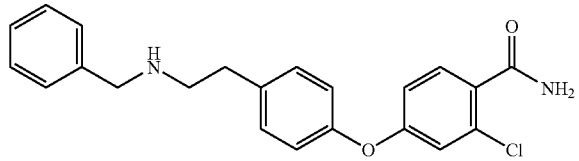

Step 1

Benzyl-{2-[4-(3-chloro-4-cyano-phenoxy)-phenyl]-ethyl}-carbamic acid tert-butyl ester

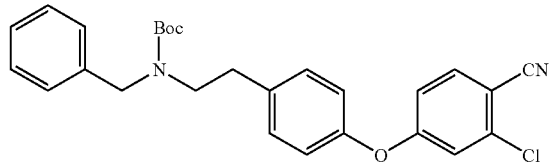

Combine the compound from Example 218 step 2 (692 mg, 2.12 mmol) and K$_2$CO$_3$ (323 mg, 2.33 mmol) in DMF (9 mL), stir the mixture at room temperature for 30 min and then add 2-chloro-4-fluoro-benzonitrile (330 mg, 2.12 mmol), and heat at 100° C. overnight. Cool to ambient temperature and pour into water. Extract the aqueous layer with EtOAc. Dry the organic layer over Na$_2$SO$_4$ and eliminate the solvent. Purify by flash chromatography on silica gel (eluent: EtOAc/hexane 15/85) to obtain the title compound (940 mg, 95%). Electrospray MS M−1 ion=461, $^1$H-NMR (CDCl$_3$, 400 MHz): 7.57 (d, 1H, J=7.8 Hz), 7.36-7.13 (m, 7H), 7.00-6.85 (m, 4H), 4.44-4.36 (m, 2H), 3.49-3.32 (m, 2H), 2.83-2.73 (m, 2H), 1.51-1.43 (m, 9H).

Step 2

Combine the compound of step 1 (95 mg, 0.21 mmol), H$_2$O$_2$ (25 µl) and K$_2$CO$_3$ (15 mg, 0.10 mmol) in DMSO (0.8 mL), and stir the mixture at room temperature overnight. Add water and extract the aqueous layer with EtOAc. Dry the organic layer over Na$_2$SO$_4$ and eliminate the solvent. Purify by flash chromatography (EtOAc/hexane 50/50) to give a yellow oil. Dissolve the oil in CH$_2$Cl$_2$ (3 mL) and add trifluoroacetic acid (240 µL), and stir the mixture at room temperature for 4 hour. Eliminate the solvent. Purify by an SCX column to give the title compound (57 mg, 76%). Electrospray MS M+1 ion=381. $^1$H-NMR (CDCl$_3$, 400 MHz): 7.82 (d, 1H, J=8.5 Hz), 7.35-7.20 (m, 7H), 6.99-6.95 (m, 3H), 6.90 (dd, 11, J=2.5 and 8.5 Hz), 6.53 (m, 2H), 3.83 (s, 2H), 2.95-2.89 (m, 2H), 2.86-2.81 (m, 2H).

EXAMPLE 221

6-[4-(2-Benzylamino-ethyl)-2-methyl-phenoxy]-nicotinamide

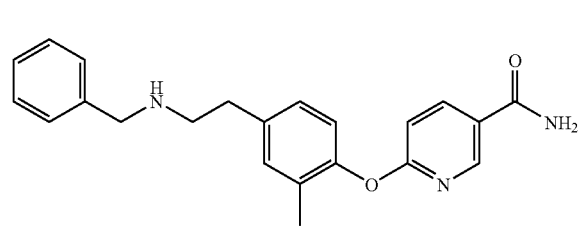

Step 1

6-(4-Formyl-2-methyl-phenoxy)-nicotinonitrile

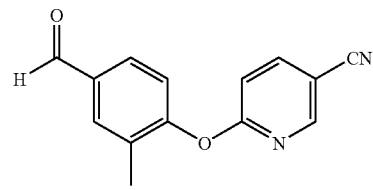

Combine 4-hydroxy-3-methyl-benzaldehyde (401 mg, 2.94 mmol), K$_2$CO$_3$ (570 mg, 4.12 mmol) and 6-chloronicotinonitrile (408 mg, 2.94 mmol) in DMF (6 ml), heat at 100° C. After 4 h cool to ambient temperature and pour into water. Extract the aqueous layer with EtOAc. Dry the organic layer over Na$_2$SO$_4$ and eliminate the solvent. Dry under vacuum at 45° C. overnight to get the title compound (680 mg, 97%). $^1$H-NMR (CDCl$_3$, 400 MHz): 9.99 (s, 1H), 8.43 (d, 1H, J=2.5 Hz), 7.97 (dd, 1H, J=2.5 and 8.8 Hz), 7.84 (bs, 1H), 7.80 (dd, 1H, J=2.5 and 8.8 Hz), 7.22 (d, 1H, J=8.4 Hz), 7.11 (d, 1H, J=8.4 Hz), 2.24 (s, 3H).

Step 2

6-[4-(2-Methoxy-vinyl)-2-methyl-phenoxy]-nicotinonitrile

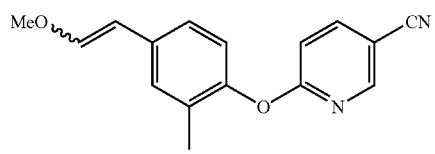

Suspend (methoxymethyl)triphenylphosphonium chloride (1.14 g, 3.34 mmol) in THF (11 mL) under N₂ and cool the mixture at 0° C., add slowly 0.5M KHMDS in toluene (6.7 mL, 3.34 mmol) and stir at 0° C. for 30 min. Cool the mixture at −78° C. and add a solution of aldehyde from step 1 above (663 mg, 2.78 mmol) in THF (2 mL). Warm the mixture slowly to room temperatures and stir for 1 h. Add water and extract the aqueous layer with Et₂O. Dry the organic layer over MgSO₄. Eliminate the solvent and purify by flash chromatography on silica gel (eluent: gradient from EtOAc/hexane 10/90 to 20/80) to get the title compound (530 mg, 76%). Electrospray MS M+1 ion=267. ¹H-NMR (CDCl₃, 300 MHz, mixture of isomers): 8.47-8.45 (m, 2H), 7.92-7.86 (m, 2H), 7.50-7.45 (m, 1H), 7.15-6.93 (m, 5H), 6.14 (d, 1H, J=7.1 Hz), 5.79 (d, 1H, J=13.2 Hz), 5.20 (d, 1H, J=7.1 Hz), 3.78 (s, 3H), 3.68 (s, 3H), 2.11 (s, 3H), 2.10 (s, 3H).

Step 3

6-[4-(2-Benzylamino-ethyl)-2-methyl-phenoxy]-nicotinonitrile

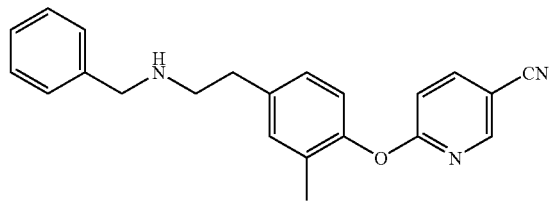

Combine the compound of example 221, step 2 (6-[4-(2-methoxy-vinyl)-2-methyl-phenoxy]-nicotinamide) (125 mg, 0.50 mmol) and p-TsOH (9 mg, 0.05 mmol) in i-PrOH (0.7 mL) and H₂O (0.7 mL). Heat the mixture at reflux for 4 hours. Cool the reaction mixture to about room temperature. Add NaHCO₃ (sat) and extract the aqueous layer with Et₂O. Dry the organic layer over MgSO₄ to afford an oil (120 mg). Dissolve the oil (66 mg) in 1,2-DCE (3.2 mL) and add benzylamine (40 μL), AcOH (97 μL) and NaBH(OAc)₃ (119 mg), stir the mixture at room temperature overnight. Dilute with CH₂Cl₂ and add saturated NaHCO3, extract the aqueous layer with CH₂Cl₂ combine organic layers and dry over Na₂SO₄. Eliminate the solvent and purify by flash chromatography on silica gel (eluent: EtOAc/hexane 75/25) to afford the title compound (16 mg). Electrospray MS M+1 ion=344. ¹H-NMR (CDCl₃, 400 MHz): 8.45 (d, 1H, J=2.5 Hz), 7.89 (dd, 1H, J=2.5 and 8.9 Hz), 7.35-7.23 (m, 5H), 7.13-7.07 (m, 2H), 7.00-6.94 (m, 2H), 3.82 (s, 2H), 2.92 (t, 2H, J=7.4 Hz), 2.82 (t, 2H, J=7.4 Hz), 2.10 (s, 3H).

Step 4

Combine nitrile, 6-[4-(2-benzylamino-ethyl)-2-methyl-phenoxy]-nicotinonitrile (compound of example 219, step 3) (13 mg, 0.04 mmol), H₂O₂ (5 μL) and K₂CO₃ (3 mg, 0.02 mmol) in DMSO (0.2 mL), and stir the mixture at room temperature overnight. Add water and extract the aqueous layer with EtOAc. Dry the organic layer over Na₂SO₄ and eliminate the solvent. Purify by flash chromatography (eluent: CHCl₃/0.5% EtOH/0.05% NH₄OH) to give the title compound (7 mg, 52%). Electrospray MS M+1 ion=362. ¹H-NMR (methanol-d₄, 300 MHz): 8.59 (d, 1H, J=2.5 Hz), 8.24 (dd, 1H, J=2.5 and 8.0 Hz), 7.33-7.21 (m, 5H), 7.15-7.07 (m, 2H), 6.98-6.93 (m, 2H), 3.78 (s, 2H), 2.83 (s, 4H), 2.09 (s, 3H).

EXAMPLE 222

Synthesis of 6-[2-Methyl-4-(phenethylamino-methyl)-phenoxy]nicotinamide

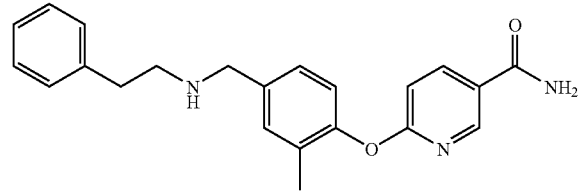

Step 1

Synthesis of 6-(4-Formyl-2-methyl-phenoxy)-nicotinamide

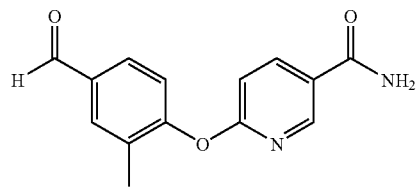

A solution of 4-hydroxy-3-methylbenzaldehyde (1.0 equiv) in DMF (0.2 M solution) was treated with K₂CO₃ (1.5 equiv) and 6-chloronicotinamide (1.0 equiv). The reaction mixture was placed inside the microwave oven and then irradiated for 5 min. Upon completion of the reaction, the mixture was cooled, poured into H₂O and extracted with ethyl acetate, and the combined organic layers were washed twice with water and brine. After drying the extracts over magnesium sulfate and evaporation under vacuum the crude product was purified by silica gel chromatography using CHCl₃:EtOH 7%:NH₄OH 0.7% to afford the title compound as a solid.

40% yield ¹H NMR (CD₃OD, 200 MHz) δ: 9.94 (s, 1H), 8.59 (d, J=2.2 Hz, 1H), 8.29 (dd, J=8.8, 2.6 Hz, 1H), 7.86 (s, 1H), 7.80 (dd, J=8.4, 1.8 Hz, 1H), 7.22 (d, J=8.4 Hz, 1H), 7.10 (d, J=8.8 Hz, 1H), 2.22 (s, 3H). ¹³C NMR (CD₃OD, 200

MHz) δ: 191.6, 167.3, 165.3, 157.2, 147.6, 140.0, 134.1, 133.4, 132.2, 129.5, 125.0, 122.7, 111.6, 16.8.

Step 2

A mixture of aldehyde from step 1 above (1 equiv), phenethylamine (1 equiv), 4A molecular sieves (10% weight) in methanol (0.1 M) was stirred overnight under nitrogen atmosphere at room temperature. The following day NaBH$_4$ (5 equiv) was added and the reaction mixture was stirred for 3 hours. The reaction can be monitored by electrospray MS. The reaction mixture was filtered off and the solvent evaporated to yield a residue, which was purified by SCX or flash chromatography.

99% yield $^1$H NMR (CD$_3$OD, 200 MHz) δ: 8.60 (d, J=2.7 Hz, 1H), 8.24 (dd, J=8.9, 2.7 Hz, 1H), 7.30 (dd, J=8.6, 1.6 Hz, 2H), 7.27 (d, J=17.5 Hz, 3H), 7.22 (d, J=14.2 Hz, 3H), 7.02-6.93 (m, 2H), 3.77 (s, 2H), 2.85 (s, 4H), 2.12 (s, 3H). $^{13}$C NMR (CD$_3$OD, 200 MHz) δ: 168.2, 165.5, 150.7, 147.4, 139.5, 139.4, 136.6, 131.2, 130.3, 128.2, 128.1, 127.1, 125.8, 124.3, 121.4, 109.7, 52.2, 49.9, 35.2, 14.9. MS (APCI): (M$^+$+1) 362.2.

EXAMPLE 223

Synthesis of 6-[2-Fluoro-4-(phenethylamino-methyl)-phenoxy]nicotinamide

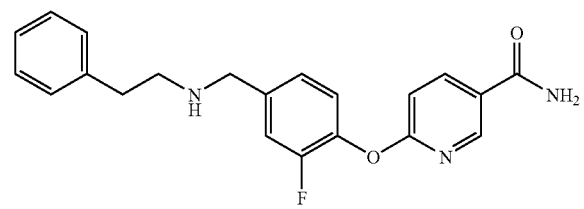

Step 1

Synthesis of 6-(2-Fluoro-4-formyl-phenoxy)-nicotinamide

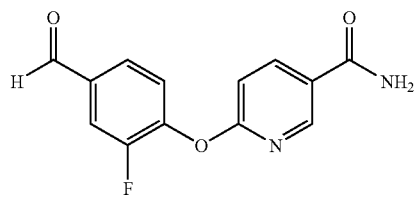

Using a procedure similar to that of example 221 step 1, and using 4-hydroxy-3-fluoro-benzaldehyde the above compound was prepared in 38% yield $^1$H NMR (CDCl$_3$, 200 MHz) δ: 9.99 (s, 1H), 8.52 (d, J=1.9 Hz, 1H), 8.25 (dd, J=8.6, 2.4 Hz, 1H), 7.76-7.71 (m, 2H), 7.47-7.40 (m, 1H), 7.14 (d, J=8.6 Hz, 1H). MS (Electrospray): (M$^+$+1) 261.1.

Step 2

The compound of example 221 step 1 was reductively aminated with phenethylamine using procedures similar to those previously described to afford the title compound in 8% Yield $^1$H NMR (CD$_3$OD, 200 MHz) δ: 8.57 (dd, J=2.4, 0.8 Hz, 1H), 8.27 (dd, J=8.6, 2.4 Hz, 1H), 7.32-7.14 (m, 9H), 7.08 (dd, J=8.6, 0.8 Hz, 1H), 3.79 (s, 2H), 2.84 (s, 4H). $^{13}$C NMR (CD$_3$OD, 200 MHz) δ: 168.7, 165.3, 154.9 (d, $^1$J$_{CF}$=246.5), 147.6, 139.9, 139.8, 139.2 (d, $^3$J$_{CF}$=6.2), 128.7, 128.5, 127.1, 126.3, 124.9 (d, $^3$J$_{CF}$=3.4), 123.9, 116.7 (d, $^2$J$_{CF}$=18.6), 110.3, 52.4, 50.4, 35.8. MS (Electrospray): (M$^+$+1) 366

EXAMPLE 224

Synthesis of 6-[2-Ethoxy-4-(phenethylamino-methyl)-phenoxy]nicotinamide

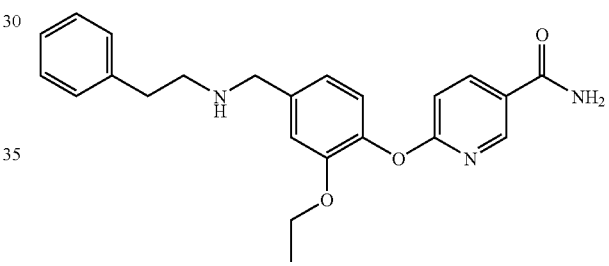

Step 1

Synthesis of 6-(2-Ethoxy-4-formyl-phenoxy)-nicotinamide

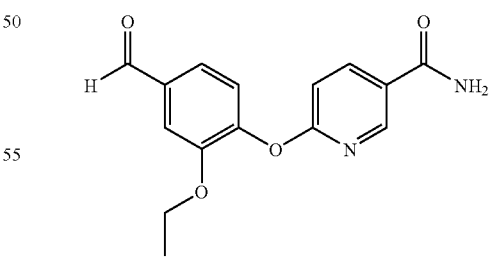

Using a procedure similar to that of example 221 step 1, and using 4-ethoxy-3-fluoro-benzaldehyde the above compound was prepared in 35% yield $^1$H NMR (CD$_3$OD, 300 MHz) δ: 9.97 (s, 1H), 8.59 (dd, J=2.4, 0.8 Hz, 1H), 8.29 (dd, J=8.6, 2.7 Hz, 1H), 7.64-7.61

(m, 2H), 7.39 (d, J=8.3 Hz, 1H), 7.09 (dd, J=8.6, 0.5 Hz, 1H), 4.07 (q, J=7.0 Hz, 2H), 1.14 (t, J=7.0 Hz, 3H).

Step 2

The compound of example 224 step 1 was reductively aminated with phenethylamine using procedures similar to those previously described to afford the title compound in 99% yield.

$^1$H NMR (CD$_3$OD, 200 MHz) δ: 8.58 (dd, J=2.4, 0.5 Hz, 1H), 8.21 (dd, J=8.6, 2.4 Hz, 1H), 7.32-7.17 (m, 6H), 7.10-7.05 (m, 2H), 6.94-6.88 (m, 2H), 3.94 (q, J=7.0 Hz, 2H), 3.77 (s, 2H), 2.84 (s, 4H), 1.09 (t, J=7.0 Hz, 3H). $^{13}$C NMR (CD$_3$Cl, 300 MHz) δ: 166.5, 165.0, 149.7, 146.2, 140.2, 138.9, 138.0, 137.6, 127.7, 127.5, 125.2, 122.8, 121.6, 119.5, 112.8, 109.4, 63.3, 52.5, 49.5, 35.2, 28.7, 13.6. MS (Electrospray): (M$^+$+1) 392.2. MS (APCI): (M$^+$+1)

EXAMPLE 225

Synthesis of 6-[2-Chloro-4-(phenethylamino-methyl)-phenoxy]nicotinamide

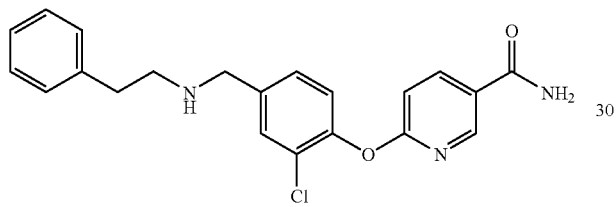

Step 1

Synthesis of 6-(2-Chloro-4-formyl-phenoxy)-nicotinamide

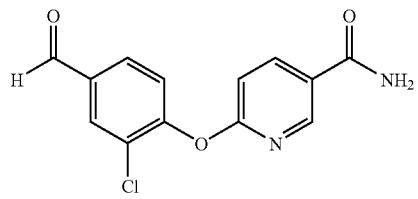

7.4% yield $^1$H NMR (CD$_3$OD, 200 MHz) δ: 9.95 (s, 1H), 8.56 (d, J=2.9 Hz, 1H), 8.34-8.28 (m, 1H), 8.05 (d, J=1.8 Hz, 1H), 7.92 (dd, J=8.4, 1.8 Hz, 1H), 7.46 (d, J=8.4 Hz, 1H), 7.20-7.15 (m, 1H). MS (Electrospray): (M$^+$+1) 277.2

Step 2

The compound of example 225 step 1 is reductively aminated with phenethyl amine using procedures similar to those previously described to afford the title compound in 87% yield.

$^1$H NMR (CD$_3$OD, 200 MHz) δ: 8.57 (d, J=2.4 Hz, 1H), 8.27 (dd, J=8.6, 2.4 Hz, 1H), 7.49 (d, J=1.9 Hz, 1H), 7.34-7.18 (m, 8H), 7.05 (dd, J=8.6, 0.5 Hz, 1H), 3.78 (s, 2H), 2.83 (s, 4H). $^{13}$C NMR (CD$_3$OD, 300 MHz) δ: 168.6, 165.3, 148.6, 147.6, 140.0, 139.9, 139.0, 130.5, 128.7, 128.6, 128.5, 127.2, 126.3, 125.3, 124.0, 110.5, 52.2, 50.4, 35.7. MS (APCI): (M$^+$+1) 382.1.

EXAMPLE 226

Synthesis of 6-[3-Chloro-4-(phenethylamino-methyl)-phenoxy]nicotinamide

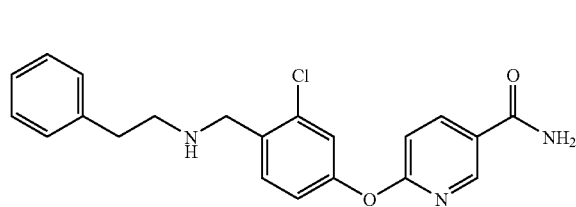

Step 1

Synthesis of 6-(3-Chloro-4-formyl-phenoxy)-nicotinamide

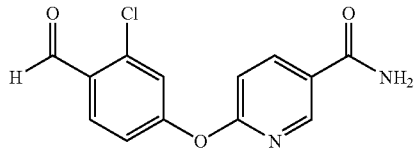

7% yield $^1$H NMR (CD$_3$OD, 200 MHz) δ: MS (APCI): (M$^+$+1)

Step 2

The compound of example 226 step 1 is reductively aminated with phenethylamine using procedures similar to those previously described to afford the title compound in 51% yield.

$^1$H NMR (CD$_3$OD, 200 MHz) δ: 8.62 (dd, J=2.4, 0.5 Hz, 1H), 8.27 (dd, J=8.6, 2.4 Hz, 1H), 7.45 (d, J=8.3 Hz, 1H), 7.32-7.17 (m, 7H), 7.11-7.02 (m, 2H), 3.89 (s, 2H), 2.86 (s, 4H). $^{13}$C NMR (CD$_3$OD, 300 MHz) δ: 168.1, 165.0, 153.2, 147.2, 139.4, 139.3, 133.9, 133.3, 131.1, 128.2, 128.1, 125.9, 125.1, 122.1, 119.8, 110.8, 49.8, 49.5, 35.1. MS (APCI): (M$^+$+1) 382.1.

EXAMPLE 227

Synthesis of 6-[2-Methyl-4-(3-methyl-butylamino-methyl)-phenoxy]nicotinamide

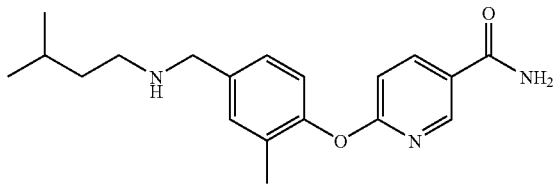

Using the aldehyde of Example 222 step 1, and using 3-methylbutylamine in place of phenethylamine affords the title compound.

99% yield $^1$H NMR (CD$_3$OD, 200 MHz) δ: 8.58 (dd, J=2.6, 0.7 Hz, 1H); 8.22 (dd, J=8.4, 2.2 Hz, 1H); 7.28 (s, 1H); 7.22 (dd, J=8.0, 1.8 Hz, 1H); 7.01-6.90 (m, 2H); 3.73 (s, 2H); 2.63 (d, J=7.7 Hz, 1H); 2.59 (d, J=9.1 Hz, 1H); 2.11 (s, 3H); 1.67-1.51 (m, 1H); 1.48-1.36 (m, 2H); 0.89 (d, J=6.6 Hz, 6H). $^{13}$C NMR (CDCl$_3$, 300 MHz) δ: 166.2, 164.9, 149.4, 146.4, 138.3, 137.0, 130.2, 129.5, 125.9, 122.8, 120.7, 109.4, 52.7, 46.9, 38.2, 25.1, 21.7, 15.3. MS (APCI): (M$^+$+1) 328.1.

EXAMPLE 228

Synthesis of 6-[2-Fluoro-4-(3-methyl-butylamino-methyl)-phenoxy]nicotinamide

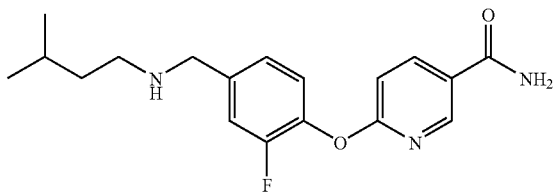

Using the compound of Example 223, step 1, and using 3-methylbutylamine, the title compound was prepared by reductive amination as described previously.

99% yield $^1$H NMR (CD$_3$OD, 200 MHz) δ: 8.58 (dd, J=2.7, 0.8 Hz, 1H), 8.28 (dd, J=8.6, 2.4 Hz, 1H), 7.30-7.21 (m, 3H), 7.09 (dd, J=8.9, 0.8 Hz, 1H), 3.77 (s, 2H), 2.65-2.57 (m, 2H), 1.70-1.53 (m, 1H), 1.49-1.38 (m, 2H), 0.91 (d, J=6.4 Hz, 7H). $^{13}$C NMR (CD$_3$OD, 200 MHz) δ: 168.7, 165.3, 154.9 (d, $^1$J$_{CF}$=246.2), 147.7, 139.8, 139.6, 139.4 (d, $^3$J$_{CF}$=6.2), 125.4, 124.9 (d, $^3$J$_{CF}$=3.4), 123.9, 116.7 (d, $^2$J$_{CF}$=18.9), 110.3, 52.7, 38.6, 26.5, 22.1. MS (APCI): (M$^+$+1) 332.1

EXAMPLE 229

Synthesis of 6-[2-Chloro-4-(3-methyl-butylamino-methyl)-phenoxy]nicotinamide

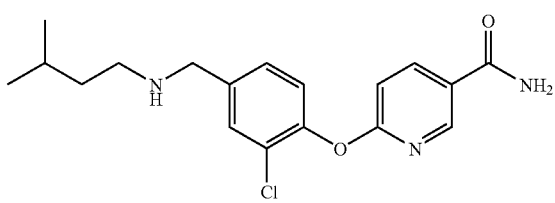

Using the compound of Example 225, step 1, and using 3-methylbutylamine, affords the title compound.

73% yield. $^1$H NMR (CD$_3$OD, 200 MHz) δ: 8.57 (dd, J=2.4, 0.8 Hz, 1H), 8.28 (dd, J=8.6, 2.4 Hz, 1H), 7.54 (d, J=2.2 Hz, 1H), 7.36 (dd, J=8.3, 1.9 Hz, 1H), 7.22 (d, J=8.1 Hz, 1H), 7.06 (dd, J=8.9, 0.8 Hz, 1H), 3.78 (s, 2H), 2.62 (t, J=7.8 Hz, 2H), 1.63 (hep, J=6.7 Hz, 1H), 1.49-1.38 (m, 2H), 0.91 (d, J=6.4 Hz, 6H). $^{13}$C NMR (CD$_3$OD, 300 MHz) δ: 167.2, 163.9, 147.2, 146.3, 138.4, 137.6, 129.1, 127.1, 123.9, 122.6, 109.1. MS (APCI): (M$^+$+1) 348.1

EXAMPLE 230

Synthesis of 6-[2-Ethoxy-4-(3-methyl-butylamino-methyl)-phenoxy]nicotinamide

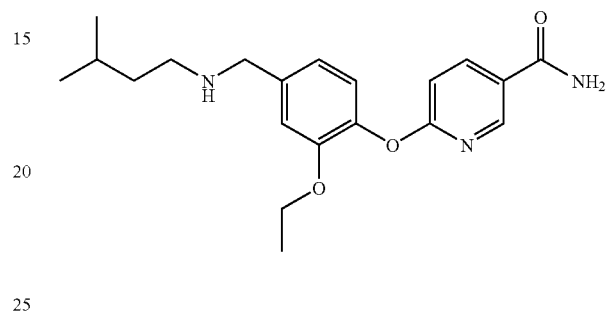

Using the compound of example 224, step 1, and using 3-methoxybutylamine, the title compound is prepared by reductive amination as described previously 76% yield.

$^1$H NMR (CD$_3$OD, 200 MHz) δ: 8.55 (d, J=1.9 Hz, 1H), 8.12 (dd, J=8.3, 2.1 Hz, 1H), 7.10-6.90 (m, 4H), 6.25 (s, 2H), 3.96 (q, J=7.0 Hz, 2H), 3.77 (s, 2H), 2.69-2.62 (m, 2H), 1.70-1.53 (m, 1H), 1.45-1.35 (m, 2H), 1.11 (t, J=7.0 Hz, 3H), 0.88 (d, J=6.7 Hz, 6H). $^{13}$C NMR (CD$_3$OD, 300 MHz) δ: 166.4, 165.0, 149.7, 146.1, 140.1, 138.1, 138.0, 122.8, 121.5, 119.5, 112.9, 109.4, 63.3, 53.0, 46.8, 38.2, 25.2, 21.7, 13.6. MS (Electrospray): (M$^+$+1) 358.1

EXAMPLE 231

Synthesis of 6-{4-[2-Cyclopentyl-ethylamino)-methyl]-2-methyl-phenoxy}-nicotinamide

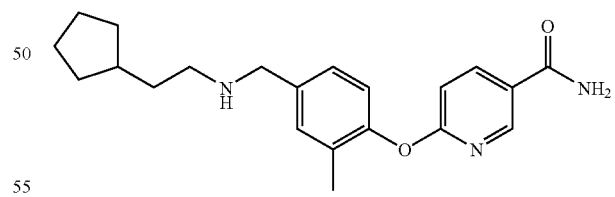

Using the compound of Example 220 step 1 and 2-cyclopentylethylamine, the title compound is prepared by reductive amination.

78% yield. $^1$H NMR (CD$_3$OD, 200 MHz) δ: 8.60 (dd, J=2.4, 0.5 Hz, 1H), 8.24 (dd, J=8.6, 2.4 Hz, 1H), 7.29-7.20 (m, 2H), 7.01 (d, J=8.1 Hz, 1H), 6.94 (dd, J=8.9, 0.8 Hz, 1H), 3.74 (s, 2H), 2.65-2.57 (m, 2H), 2.12 (s, 3H), 1.85-1.68 (m, 4H), 1.66-1.50 (m, 7H). $^{13}$C NMR (CD$_3$OD, 300 MHz) δ:

170.1, 167.4, 152.6, 149.3, 141.3, 138.5, 133.2, 132.2, 129.0, 126.2, 123.3, 111.6, 54.3, 39.8, 37.2, 34.2, 26.5, 16.8. MS (APCI): (M$^+$+1) 354.5

EXAMPLE 232

Synthesis of 6-{4-[2-Cyclopentyl-ethyl amino)-methyl]-2-fluoro-phenoxy}-nicotinamide

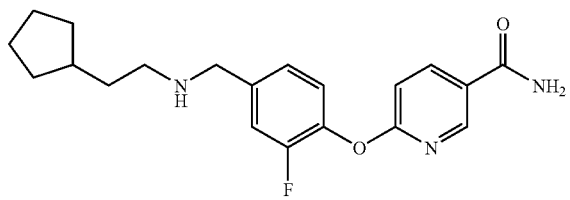

Reductive amination of 2-cyclopentylethylamine and the compound of Example 223, step 1, affords the title compound.

84% yield. $^1$H NMR (CD$_3$OD, 200 MHz) δ: 8.57 (dd, J=2.4, 0.8 Hz, 1H), 8.27 (dd, J=8.6, 2.4 Hz, 1H), 7.30-7.17 (m, 3H), 7.08 (dd, J=8.6, 0.5 Hz, 1H), 3.77 (s, 2H), 2.65-2.57 (m, 2H), 1.90-1.71 (m, 4H), 1.63-1.52 (m, 8H). $^{13}$C NMR (CD$_3$OD, 300 MHz) δ: 168.6, 165.3, 154.9 (d, $^1J_{CF}$=246.5), 147.6, 139.8, 139.7 (d, $^2J_{CF}$=13.0), 139.3 (d, $^3J_{CF}$=6.0), 125.4, 124.9 (d, $^3J_{CF}$=3.4), 123.9, 116.7 (d, $^2J_{CF}$=18.6), 110.3, 52.6, 38.4, 35.9, 32.7, 25.1. MS (APCI): (M$^+$+1) 358.2

EXAMPLE 233

Synthesis of 6-{2-Chloro-4-[2-Cyclopentyl-ethylamino)-methyl]-phenoxy}-nicotinamide

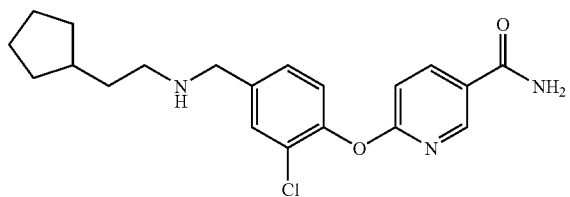

Title compound is prepared by reductive amination of 2-cyclopentylamine and the compound of Example 225, step 1.

67% yield. $^1$H NMR (CD$_3$OD, 200 MHz) δ: 8.57 (dd, J=2.7, 0.8 Hz, 1H), 8.27 (dd, J=8.6, 2.4 Hz, 1H), 7.53 (d, J=1.9 Hz, 1H), 7.39-7.19 (m, 2H), 7.05 (dd, J=8.6, 0.8 Hz, 1H), 3.76 (s, 2H), 2.69-2.57 (m, 2H), 1.80-1.74 (m, 5H), 1.61-1.54 (m, 8H). $^{13}$C NMR (CD$_3$OD, 300 MHz): 167.2, 164.0, 147.2, 146.3, 138.4, 137.7, 129.1, 127.1, 125.8, 123.9, 122.6, 109.1, 51.0, 37.0, 34.5, 31.3, 31.3, 23.7.

EXAMPLE 234

Synthesis of 6-{4-[2-Cyclopentyl-ethylamino)-methyl]-2-ethoxy-phenoxy}-nicotinamide

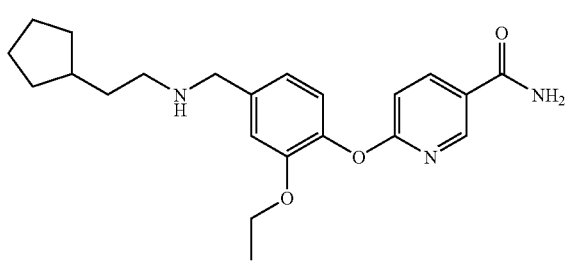

Reductive amination of 2-cyclopentylamine and the compound of Example 224, step 1 affords the title compound 91% yield.

$^1$H NMR (CD$_3$OD, 200 MHz) δ: 8.57 (dd, J=2.7, 0.8 Hz, 1H), 8.23 (dd, J=8.6, 2.4 Hz, 1H), 7.14-7.10 (m, 2H), 7.01 (d, J=1.9 Hz, 1H), 6.94 (dd, J=8.6, 0.3 Hz, 1H), 3.99 (q, J=7.3 Hz, 2H), 3.83 (s, 2H), 2.73-2.65 (m, 2H), 1.81-1.76 (m, 4H), 1.65-1.54 (m, 7H), 1.11 (t, J=7.0 Hz, 3H). $^{13}$C NMR (CD$_3$OD, 300 MHz) δ: 167.3, 164.9, 149.8, 146.2, 140.4, 138.1, 136.6, 123.3, 121.2, 119.8, 113.1, 108.7, 63.0, 51.8, 37.0, 34.3, 31.3, 23.7, 12.6. MS (APCI): (M$^+$+1) 384.2.

EXAMPLE 235

Synthesis of 6-{2-Methyl-4-[2-thiophen-2-yl-ethylamino)-methyl]-phenoxy}nicotinamide

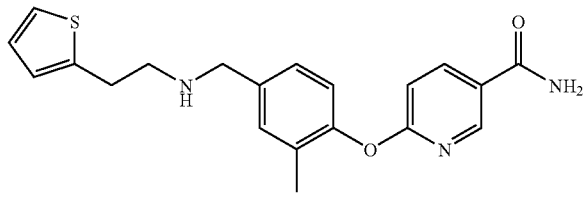

Reductive amination of 2-thiophen-2-yl-ethylamine and the compound of Example 222, step 1 affords the title compound following the procedure of example 222, step 2.

30% yield. $^1$H NMR (CD$_3$OD, 300 MHz) δ: 8.62 (d, J=2.2 Hz, 1H), 8.26 (dd, J=8.7, 2.4 Hz, 1H), 7.28-7.21 (m, 3H), 7.03-6.87 (m, 4H), 3.78 (s, 2H), 3.10-3.05 (m, 2H), 2.90 (t, J=7.1 Hz, 3H), 2.13 (s, 3H). $^{13}$C NMR (CD$_3$OD, 300 MHz) δ: 168.2, 165.5, 150.7, 147.4, 141.7, 139.4, 136.7, 131.2, 130.2, 127.1, 126.4, 126.2, 124.7, 124.3, 123.1, 121.4, 109.6, 52.1, 50.0, 29.2, 14.9. MS (APCI): (M$^+$+1) 368.1.

EXAMPLE 236

Synthesis of 6-(4-{[2-(3-Fluoro-phenyl)-ethylamino]-methyl}-2-methyl-phenoxy)-nicotinamide

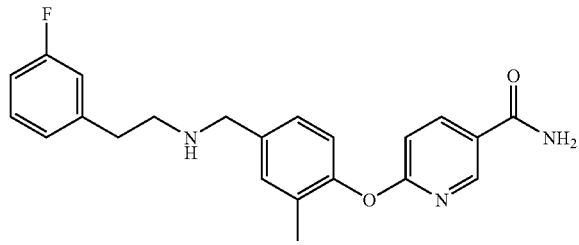

The compound of example 222, step 1 is reductively aminated with 2-(3-fluoro-phenyl)-ethylamine following the procedure of example 222, step 2 to afford the title compound.

55% yield. $^1$H NMR (CD$_3$OD, 200 MHz) δ: 8.60 (d, J=2.4 Hz, 1H), 8.24 (dd, J=8.6, 2.4 Hz, 1H), 7.33-7.18 (m, 3H), 7.04-6.87 (m, 5H), 3.76 (s, 2H), 2.84 (s, 4H), 2.10 (s, 3H). $^{13}$C NMR (CD$_3$OD, 300 MHz) δ: 167.3, 164.6, 162.0 (d, $^1J_{CF}$=242.7), 149.8, 146.5, 141.6 (d, $^3J_{CF}$=7.4), 138.5, 135.7, 130.3, 129.4, 128.8 (d, $^3J_{CF}$=8.3), 126.2, 123.4, 123.2 (d, $^4J_{CF}$=2.8), 120.5, 114.0 (d, $^2J_{CF}$=20.8), 111.5 (d, $^2J_{CF}$=21.1), 108.8, 51.3, 48.6, 34.0 (d, $^4J_{CF}$=1.4), 14.0. MS (APCI): (M$^+$+1) 380.2.

EXAMPLE 237

Synthesis of 6-{2-Methyl-4-[(2-o-tolyl-ethylamino)-methyl]-phenoxy}-nicotinamide

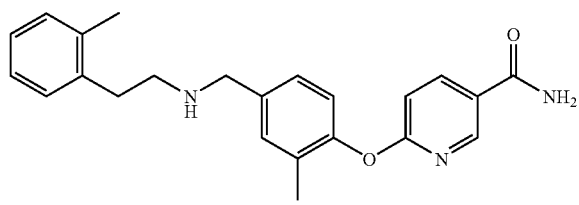

The titled compound results from the reductive amination reaction of the compound of example 222, step 1 and 2-o-tolyl-ethylamine following the procedure of example 222, step 2.

78% yield. $^1$H NMR (CD$_3$OD, 300 MHz) δ: 8.62 (dd, J=1.6, 0.6 Hz, 1H), 8.25 (dd, J=8.9, 2.6 Hz, 1H), 7.27-7.09 (m, 6H), 7.01 (d, J=8.3 Hz, 1H), 6.94 (dd, J=8.7, 1.0 Hz, 1H), 3.78 (s, 2H), 2.88-2.77 (m, 4H), 2.30 (s, 3H), 2.12 (s, 3H). $^{13}$C NMR (CD$_3$OD, 300 MHz) δ: 167.3, 164.6, 149.8, 146.5, 138.5, 136.6, 135.7, 134.8, 130.3, 129.4, 128.9, 127.9, 126.1, 125.0, 124.7, 123.4, 120.5, 108.7, 51.3, 31.7, 17.0, 14.0. MS (APCI): (M$^+$+1) 376.1

EXAMPLE 238

Synthesis of 6-{4-[(3,3-Dimethyl-butylamino)-methyl]-2-methyl-phenoxy}-nicotinamide

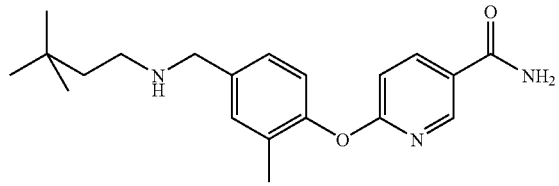

The reaction of the compound of Example 222, step 1 and 3,3-dimethyl-butylamine following the procedure of example 222, step 2 affords the title compound.

61% yield. $^1$H NMR (CD$_3$OD, 200 MHz) δ: 8.60 (dd, J=2.4, 0.5 Hz, 1H), 8.24 (dd, J=8.9, 2.7 Hz, 1H), 7.29-7.21 (m, 2H), 7.01 (d, J=8.1 Hz, 1H), 6.93 (dd, J=8.9, 0.8 Hz, 1H), 3.74 (s, 2H), 2.67-2.59 (m, 2H), 2.12 (s, 3H), 1.51-1.43 (m, 2H), 0.92 (s, 9H). $^{13}$C NMR (CD$_3$OD, 300 MHz) δ: 168.2, 165.5, 150.7, 147.5, 139.4, 136.7, 131.3, 130.3, 127.1, 124.32, 121.4, 109.6, 52.6, 44.7, 42.7, 29.1, 28.5, 14.9.

EXAMPLE 239

Synthesis of 6-(4-{[2-(3-Chloro-phenyl)-ethylamino]-methyl}-2-methyl-phenoxy)-nicotinamide

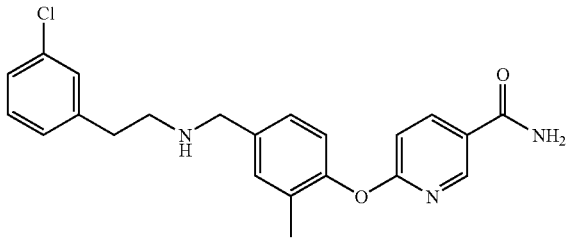

The reaction of the compound of Example 222, step 1 and 3-chloro-phenethylamine affords the title compound following the procedure of example 222, step 2.

55% yield. $^1$H NMR (CD$_3$OD, 200 MHz) δ: 8.60 (dd, J=2.7, 0.8 Hz, 1H), 8.24 (dd, J=8.6, 2.4 Hz, 1H), 7.31-7.11 (m, 7H), 7.00 (d, J=8.3 Hz, 1H), 6.94 (dd, J=8.9, 0.8 Hz, 1H), 3.76 (s, 2H), 2.83 (s, 4H), 2.12 (s, 3H). $^{13}$C NMR (CD$_3$OD, 300 MHz) δ: 167.3, 164.6, 149.8, 146.5, 141.2, 138.5, 135.8, 132.9, 130.3, 129.4, 128.6, 127.4, 126.2, 125.8, 125.0, 123.4, 120.5, 108.7, 51.3, 48.6, 34.0, 14.0. MS (APCI): (M$^+$+1) 396.1

EXAMPLE 240

Synthesis of 6-(4-Butylaminomethyl-2-methyl-phenoxy)-nicotinamide

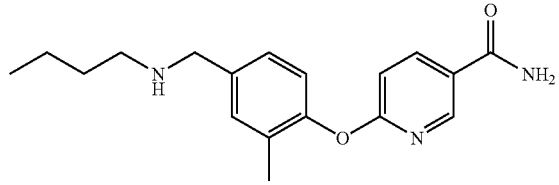

The reductive amination of the compound of Example 222, step 1 and butylamine following the procedure of example 222, step 2, affords the title compound 56% yield.

$^1$H NMR (CD$_3$OD, 200 MHz) δ: 8.61 (dd, J=2.7, 0.8 Hz, 1H), 8.25 (dd, J=8.9, 2.7 Hz, 1H), 7.29-7.20 (m, 2H), 7.00 (d, J=8.3 Hz, 1H), 6.93 (dd, J=8.9, 0.8 Hz, 1H), 3.73 (s, 2H), 2.63-2.55 (m, 2H), 2.12 (s, 3H), 1.65-1.46 (m, 2H), 1.41-1.24 (m, 2H), 0.93 (t, J=7.3 Hz, 3H). $^{13}$C NMR (CD$_3$OD, 300 MHz) δ: 167.3, 164.6, 149.8, 146.5, 138.4, 135.9, 130.3, 129.3, 126.2, 123.4, 120.4, 108.7, 51.5, 30.2, 19.2, 14.0, 12.0. MS (APCI): (M$^+$+1) 314.2

EXAMPLE 241

Synthesis of 6-(2-Methyl-4-{[methyl-(3-methyl-butyl)-amino]-methyl}-phenoxy)-nicotinamide

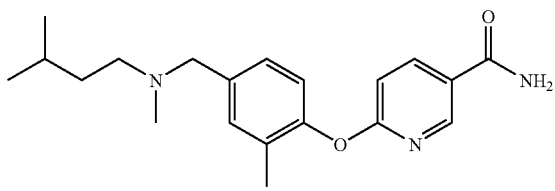

A solution of Example 227 (1.0 equiv) in MeOH (0.2 M solution) was treated with formaldehyde (5 equiv) and stirred at room temperature (r.t.) for 2 hours. Sodium Borohydride was added and stirred at r.t. overnight. The solvent was removed under vacuum and crude residue was purified by silica gel chromatography using the appropriate eluent (typically mixtures CHCl$_3$/EtOH 7%/NH4OH 0.7%) to afford the title compound as a solid.

20% yield. $^1$H NMR (CD$_3$OD, 200 MHz) δ: 8.61 (dd, J=2.7, 0.8 Hz, 1H), 8.25 (dd, J=8.6, 2.4 Hz, 1H), 7.28-7.19 (m, 2H), 7.01 (d, J=8.3 Hz, 1H), 6.95 (dd, J=8.6, 0.8 Hz, 1H), 3.53 (s, 2H), 2.48-2.41 (m, 2H), 2.23 (s, 3H), 2.13 (s, 3H), 1.66-1.53 (m, 1H), 1.51-1.40 (m, 2H), 0.91 (d, J=6.2 Hz, 6H). $^{13}$C NMR (CD$_3$OD, 200 MHz) δ: 167.3, 164.6, 150.0, 146.5, 138.5, 134.2, 131.4, 129.2, 127.33, 123.4, 120.3, 108.8, 60.1, 54.3, 39.95, 34.5, 25.4, 20.7, 13.9. MS (APCI): (M$^+$+1) 342.2

EXAMPLE 242

Synthesis of 6-{2-Methyl-4-[(methyl-phenethyl-amino)-methyl]-phenoxy}-nicotinamide

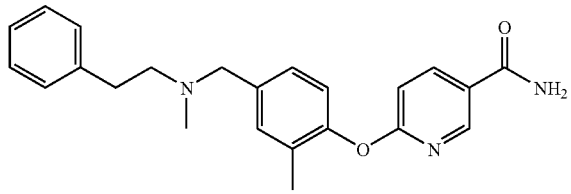

N-methyl-phenethylamine when reacted with the compound of Example 220, step 1 following the procedure of example 222, step 2 affords the title compound.

47% yield. $^1$H NMR (CD$_3$OD, 200 MHz) δ: 8.62-8.59 (m, 1H), 8.25 (dd, J=8.9, 2.7 Hz, 1H), 7.29-7.10 (m, 7H), 6.95 (dd, J=11.0, 8.3 Hz, 1H), 6.92 (d, J=8.6 Hz, 1H), 3.56 (s, 2H), 2.87-2.77 (m, 2H), 2.71-2.60 (m, 2H), 2.30 (s, 3H), 2.10 (s, 3H). $^{13}$C NMR (CD$_3$OD, 300 MHz) δ: 167.2, 164.6, 150.0, 146.5, 139.0, 138.5, 134.2, 131.3, 129.2, 127.4, 127.2, 127.0, 124.7, 123.4, 123.1, 120.3, 108.8, 59.8, 57.6, 39.9, 31.8, 14.0. MS (APCI): (M$^+$+1) 376.2

EXAMPLE 243

Synthesis of 3-Fluoro-4-[4-(phenethylamino-methyl)-phenoxy]-benzamide

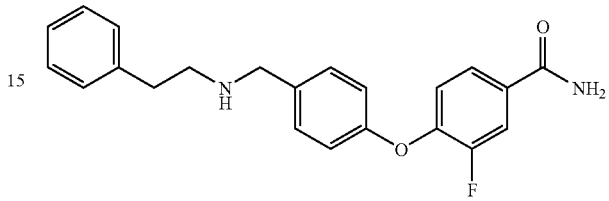

Step 1

Synthesis of 3-Fluoro-4-(4-formyl-phenoxy)-benzonitrile

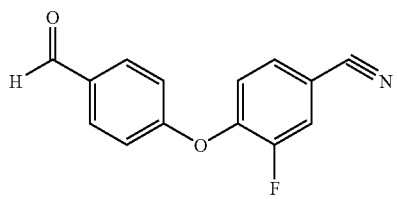

Basic displacement reaction of 4-hydroxy benzaldehyde and 3,4 difluorobenzonitrile using potassium carbonate in anhydrous DMF at reflux temperatures affords the above compound.

32% Yield $^1$H NMR (CDCl$_3$, 200 MHz) δ: 9.92 (s, 1H), 7.95 (d, J=8.8 Hz, 2H), 7.76 (dd, J=10.2, 1.8 Hz, 1H), 7.64-7.58 (m, 1H), 7.34 (d, J=8.4 Hz, 1H), 7.18 (d, J=8.8 Hz, 2H). MS (APCI): (M$^+$–1) 240.0.

Step 2

Synthesis of 3-Fluoro-4-(4-formyl-phenoxy)-benzamide

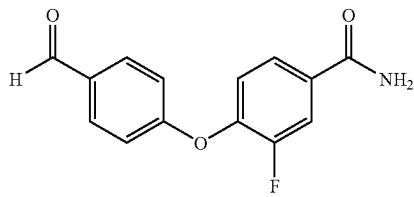

Hydrolysis of the compound of step 1 using hydrogen peroxide and potassium carbonate in DMSO as described previously afford the above compound in 99% yield.

$^1$H NMR (CD$_3$OD, 200 MHz) δ: 9.89 (s, 1H), 7.94-7.89 (m, 2H), 7.84-7.71 (m, 2H), 7.32-7.23 (m, 1H), 7.12 (d, J=8.8 Hz, 2H). MS (APCI): (M$^+$+1) 260.1

Step 3

The reaction of phenethylamine and the compound of Example 243, step 2 under reductive amination conditions affords the title compound.

47% yield. $^1$H NMR (CD$_3$OD, 200 MHz) δ: 11.68 (dd, J=11.5, 2.0 Hz, 1H), 11.52 (ddd, J=8.5, 1.8, 1.0 Hz, 1H), 11.03-10.74 (m, 7H), 10.61-10.47 (m, 3H), 5.65 (s, 2H), 4.25 (s, 4H). $^{13}$C NMR (CD$_3$OD, 300 MHz) δ: 167.8, 154.4, 152.2 (d, $^1J_{CF}$=247.0), 146.4 (d, $^2J_{CF}$=11.4), 138.6, 134.1, 128.9, 128.8, 127.3, 127.2, 124.9, 123.2 (d, $^3J_{CF}$=3.7), 118.8, 116.9, 115.2 (d, $^2J_{CF}$=19.7), 51.2, 49.0, 34.2.

EXAMPLE 244

Synthesis of 3-Chloro-4-[4-(phenethylamino-methyl)-phenoxy]-benzamide

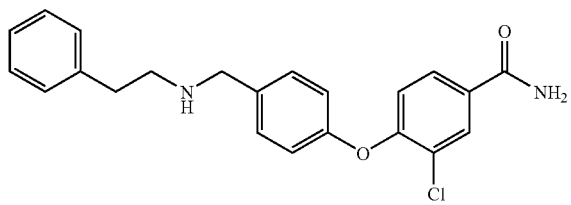

Step 1

Synthesis of 3-Chloro-4-(4-formyl-phenoxy)-benzonitrile

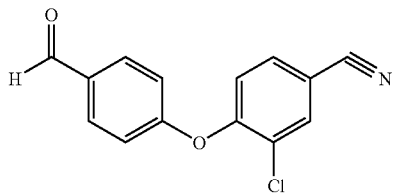

The above compound is prepared by nucleophilic displacement reaction of 4-hydroxy benzaldehyde and 3-chloro-4-fluorobenzonitrile under basic conditions as described in Example 243, step 1.91% yield.

$^1$H NMR (CDCl$_3$, 200 MHz) δ: 9.96 (s, 1H), 7.91 (dd, J=6.9, 2.2 Hz, 2H), 7.79 (d, J=1.8 Hz, 1H), 7.56 (dd, J=8.4, 2.2 Hz, 1H), 7.11-7.07 (m, 2H). MS (Electrospray): (M$^+$+1) 258.0

Step 2

Synthesis of 3-Chloro-4-(4-formyl-phenoxy)-benzamide

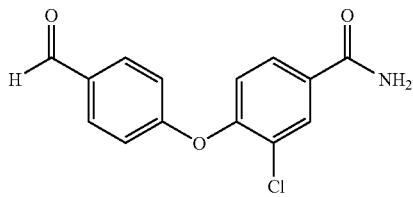

99% Yield. $^1$H NMR (CD$_3$OD, 200 MHz) δ: 9.96 (s, 1H), 8.00 (d, J=2.1 Hz, 1H), 7.89 (d, J=8.9 Hz, 2H), 7.73 (s, 1H), 7.15 (d, J=8.6 Hz, 1H), 7.06 (d, J=8.6 Hz, 2H). MS (APCI): (M$^+$+1) 276.0

Step 3

The reductive amination reaction of the compound of Example 242, step 2 (as described above) with phenethylamine affords the title compound.

48% yield. $^1$H NMR (CD$_3$OD, 200 MHz) δ: 8.04 (d, J=2.1 Hz, 1H), 7.77 (dd, J=8.6, 2.4 Hz, 1H), 7.38-7.18 (m, 7H), 7.00-6.93 (m, 3H), 3.80 (s, 2H), 2.85 (s, 4H). $^{13}$C NMR (CD$_3$OD, 200 MHz) δ: 170.5, 157.5, 157.0, 141.2, 136.7, 132.0, 131.9, 131.5, 130.1, 130.0, 129.3, 127.8, 126.4, 120.4, 53.9, 51.7, 36.8. MS (APCI): (M$^+$+1) 381.2

EXAMPLE 245

Synthesis of 2-Chloro-4-[4-(phenethylamino-methyl)-phenoxy]-benzamide

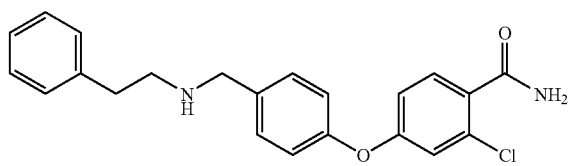

Step 1

Synthesis of 2-Chloro-4-(4-formyl-phenoxy)-benzonitrile

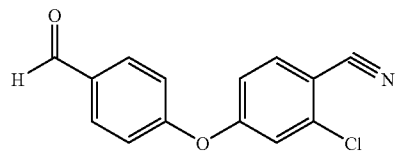

4-Hydroxy benzaldehyde (1 equiv), 2-chloro-4-fluorobenzonitrile (1 equiv) and K$_2$CO$_3$ (2.5 equiv) in anhydrous DMF (0.2 M) were heated at 110° C. under nitrogen during 1 hour (the reaction can be monitored by tlc). After cooling down to room temperature, the reaction mixture was poured into water and extracted with ethyl acetate (3×50 mL). The combined organic layer was dried over Na$_2$SO$_4$, filtered and concentrated under vacuum (toluene was added to aid DMF evaporation). The crude mixture was purified by flash chromatography using hexanes/ethyl acetate (4:1) as eluent.

84% yield. $^1$H NMR (CDCl$_3$, 200 MHz) δ: 9.99 (s, 1H), 7.94 (d, J=8.4 Hz, 2H), 7.65 (d, J=8.4 Hz, 1H), 7.19 (s, 1H), 7.15-7.13 (m, 2H), 6.99 (dd, J=8.4, 2.2 Hz, 1H). MS (Electrospray): (M$^+$+1) 258.1.

Step 2

Synthesis of 2-Chloro-4-(4-formyl-phenoxy)-benzamide

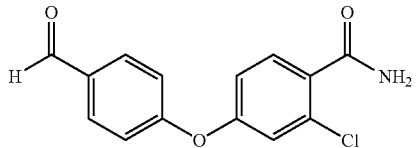

A solution of 2-chloro-4-(4-formylphenoxy)benzonitrile (1.0 equiv) in DMSO (0.2 M solution) was treated with K$_2$CO$_3$ (0.5 equiv) and 33% H$_2$O$_2$. After 12 h, the reaction mixture was poured into H$_2$O and extracted with ethyl acetate. The combined organic layers were washed twice with water and brine. After drying the extracts over magnesium sulfate and evaporation under vacuum, the crude product was purified by silica gel chromatography using the appropriate eluent (typically mixtures of hexanes/ethyl acetate) to afford the title compound as a solid.

99% Yield $^1$H NMR (CD$_3$OD, 200 MHz) δ: 9.92 (s, 1H), 7.97-7.92 (m, 2H), 7.57 (d, J=8.4 Hz, 1H), 7.19-7.15 (m, 3H), 7.07 (dd, J=8.4, 2.2 Hz, H). MS (Electrospray): (M$^+$+1) 276.0.

Step 3

Reacting phenethylamine with the compound of Example 245, step 2 under reductive amination conditions (described previously) affords the title compound.

34% yield. $^1$H NMR (CD$_3$OD, 200 MHz) δ: 6.12 (d, J=8.6 Hz, 1H) 5.99 (d, J=8.6 Hz, 2H), 5.88-5.79 (m, 5H), 5.66-5.51 (m, 4H), 2.42 (s, 2H), 1.46 (s, 4H). $^{13}$C NMR (CD$_3$OD, 300 MHz): 170.6, 159.8, 155.1, 39.5, 135.3, 132.1, 130.5, 130.3, 128.5, 128.4, 126.2, 119.8, 118.9, 116.1, 52.2, 50.1, 35.2. MS (APCI): (M$^+$+1) 380.9.

EXAMPLE 246

Synthesis of 3-Fluoro-4-{2-methyl-4-[(3-methyl-butylamino)-methyl]-phenoxy}-benzamide

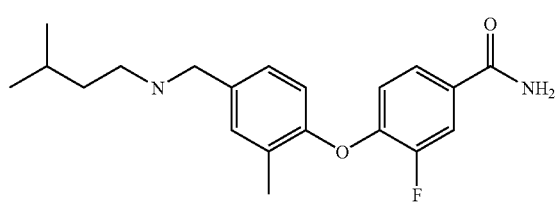

Step 1

Synthesis of 3-Fluoro-4-(4-formyl-2-methyl-phenoxy)-benzonitrile

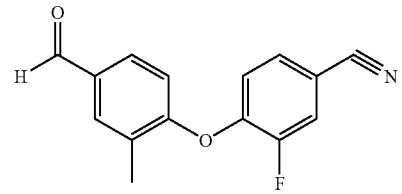

38% yield. $^1$H NMR (CDCl$_3$, 300 MHz) δ: 9.95 (s, 1H), 7.83 (s, 1H), 7.71 (dd, J=8.3, 1.6 Hz, 1H), 7.53 (dd, J=9.9, 1.9 Hz, 1H), 7.47-7.43 (m, 1H), 7.02 (t, J=8.3 Hz, 1H), 6.93 (d, J=8.3 Hz, 1H), 2.37 (s, 3H). $^{13}$C NMR (CDCl$_3$, 300 MHz) δ: 189.9, 157.4, 152.0 (d, $^1J_{CF}$=252.1), 146.9 (d, $^2J_{CF}$=11.0), 132.2, 122.0, 229.8, 128.7, 128.6, 120.3, 120.0, 119.9 (d, $^3J_{CF}$=1.4), 116.7, 116.3 (d, $^3J_{CF}$=2.3), 107.1 (d, $^2J_{CF}$=8.1), 15.0.

Step 2

Synthesis of 3-Fluoro-4-(4-formyl-2-methyl-phenoxy)-benzamide

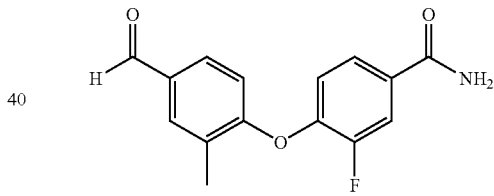

88% yield. $^1$H NMR (CD$_3$OD, 200 MHz) δ: 9.87 (s, 1H), 7.84-7.82 (m, 2H), 7.77-7.68 (m, 2H), 7.14 (t, J=8.0 Hz, 1H), 6.87 (d, J=8.4 Hz, 1H), 2.37 (s, 3H). MS (Electrospray): (M$^+$+1) 274.0

Step 3

The reaction of 3-methylbutylamine and the compound of Example 246, step 2 under reductive amination conditions affords the title compound.

68% Yield $^1$H NMR (CD$_3$OD, 200 MHz) δ: 7.76 (dd, J=11.6, 1.6 Hz, 1H), 7.61 (d, J=8.1 Hz, 1H), 7.29 (s, 1H), 7.19 (d, J=7.8 Hz, 1H), 6.89-6.75 (m, 2H), 3.71 (s, 2H), 2.64-2.56 (m, 2H), 2.21 (s, 3H), 1.68-1.51 (m, 1H), 1.48-1.37 (m, 2H), 0.90 (d, J=6.5 Hz, 6H). $^{13}$C NMR (CD$_3$OD, 200 MHz) δ: 167.2, 150.8 (d, $^1J_{CF}$=245.8), 150.9, 146.6 (d, $^2J_{CF}$=11), 134.5, 130.0, 127.6, 127.2 (d, $^3J_{CF}$=5.5), 125.7, 122.5 (d, $^3J_{CF}$=3.1), 117.2, 116.0, 114.4 (d, $^2J_{CF}$=19.6), 50.9, 45.2, 36.4, 24.5, 20.0, 13.0. MS (Electrospray): (M$^+$+1) 345.4.

EXAMPLE 247

4-(4-Benzylaminomethylphenoxy)-benzamide

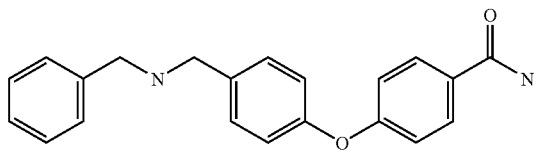

Step 1

4-(4-Formyl-phenoxy)-benzonitrile

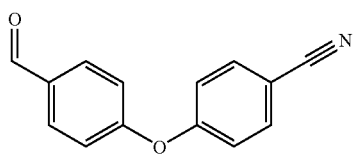

Combine 4-fluorobenzonitrile (3.96 g, 32.7 mmol), 4-hydroxybenzaldehyde (3.99 g, 32.7 mmol), dimethyl acetamide (100 mL), and potassium carbonate (6.8 g, 49 mmol), stir, and heat to 130° C. After 18 h, cool to ambient temperature, partially remove the solvent in vacuo, and dilute with 100 mL of water. Extract the aqueous solution with diethyl ether (3×150 mL), wash the organic phase with water (2×100 mL), and brine (100 mL). Dry the organic phase over magnesium sulfate, filter, and concentrate under vacuum. Purify via a Biotage Flash 40L system, using a gradient: 5:95 hexanes/ethyl acetate to 50:50 hexanes/ethyl acetate to give the title compound (3.6 g, 49%) as a white solid: $^1$H NMR (chloroform-d): 9.95 (s, 1H), 7.92 (d, 2H), 7.68 (d, 2H), 7.14 (m, 4H).

Step 2

4-(4-Formyl-phenoxy)-benzamide

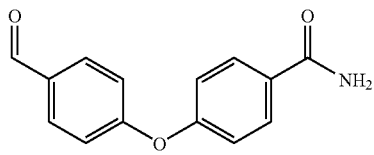

Combine 4-(4-Formyl-phenoxy)-benzonitrile (3.6 g, 16.1 mmol), dimethylsulfoxide (25 mL), potassium carbonate (2.1 g, 15.2 mmol), and 3 mL of 30% hydrogen peroxide solution. Stir 18 h at ambient temperature. Dilute with 100 mL of water, extract with ethyl acetate (3×100 mL). Wash the organic phase with 100 mL of water, and 50 mL of brine. Dry the organic phase over sodium sulfate, filter, and concentrate under vacuum. Purify via a Biotage Flash 40L system using 75:25 hexanes/ethyl acetate as eluting solvent to give 3.0 g (77%) of the title compound: $^1$H NMR (chloroform-d): 9.95 (s, 1H), 7.88 (m, 4H), 7.12 (m, 4H), 5.29-5.14 (br m, 2H).

Step 3

Combine 4-(4-Formyl-phenoxy)-benzamide from Example 247, step 2 (0.1 g, 0.41 mmol), benzylamine (0.040 g, 0.38 mmol), 4 Å molecular sieves (1 g) in methanol (5 mL), and stir for 18 h at ambient temperature. Add sodium borohydride (0.058 g, 1.52 mmol), agitate 66 h at ambient temperature. Filter through a 5 g SCX column, eluting first with 1:1 dichloromethane/methanol. Discard the first washings, then elute with 1:1 dichloromethane/2 M ammonia in methanol. Collect the eluants and concentrate in vacuo. Purify by Chromatotron, on a 2 mm silica plate, eluting with 90:10:1 dichloromethane/ethanol/ammonium hydroxide to afford the title compound (0.058 g, 46%): mass spectrum (ion spray): m/z=333.06 (M+1); $^1$H NMR (DMSO-$d_6$): 7.82 (m, 3H), 7.39-7.18 (m, 5H), 7.02-6.97 (m, 4H), 3.67-3.66 (2s, 4H).

EXAMPLE 248

4-(4-Phenethylaminomethylphenoxy)-benzamide

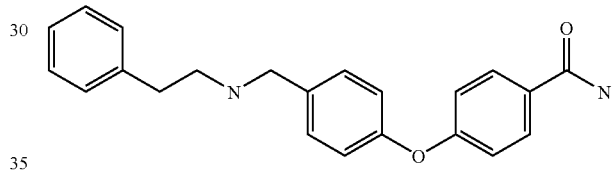

Combine 4-(4-Formyl-phenoxy)-benzamide (from Example 247, step 2) (0.39 g, 1.6 mmol), phenethylamine (0.15 g, 1.2 mmol), 20 mL of methanol and 2 g of 3 Å molecular sieves, and stir at ambient temperature ambient under nitrogen for 5 h. Add sodium borohydride (0.18 g, 4.8 mmol), and stir at ambient temperature for 18 h at ambient temperature. Filter the reaction mixture through Celite, and adsorb on silica gel. Purify by Biotage Flash 40S, eluting with 95:5:0.5 chloroform/ethanol/ammonium hydroxide to afford 0.27 g (93%) of the title compound: mass spectrum (ion spray): m/z=347.28 (M+1); HPLC retention time: 6.01 min (HPLC method in this experiment and subsequent experiments: 5:95-95:5 ACN/0.1% TFA in water over 10 minutes using a 15 cm Zorbax column, running at 1 mL/minute, ultraviolet detector set at 254 nM).

EXAMPLE 249

6-[4-(Benzylamino-methyl)-phenoxy]-nicotinamide

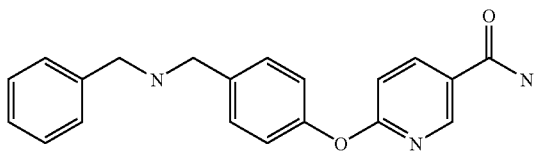

Step 1

6-(4-Formyl-phenoxy)-nicotinamide

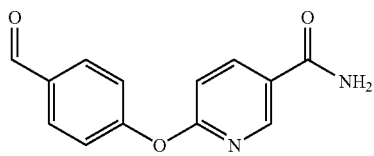

Combine 6-chloronicotinamide (4.53 g, 28.9 mmol), 4-hydroxybenzaldehyde (3.5 g, 28.9 mmol), potassium carbonate (6 g, 43.4 mmol), and dimethylformamide (200 mL). Heat the reaction mixture to 130° C. under nitrogen, and stir for 18 h. Dilute the reaction mixture with 200 mL of water, extract with diethyl ether (4×100 mL) and dichloroethane (2×100 mL). Combine the organics, and dry over magnesium sulfate. Filter, and concentrate in vacuo. Adsorb the residue on silica, and purify by Biotage Flash 40L (elute with 50:50 hexanes/ethyl acetate to 100% ethyl acetate) to afford the title compound as a white solid (3.2 g, 46%): $^1$H NMR (DMSO-$d_6$): 10.0 (s, 1H), 8.59 (d, 1H), 8.26-8.22 (dd, 1H), 7.98-7.95 (m, 2H), 7.10-7.07 (d, 1H), 6.15-5.65 (br m, 2H).

Step 2

Combine 6-(4-Formyl-phenoxy)-nicotinamide (0.097 g, 0.4 mmol) in 5 mL of methanol with benzylamine (0.4 mmol), and 1 g of 3 Å molecular sieves. Stir for 18 h. Add sodium borohydride (0.076 g, 2 mmol), and stir for 18 h. Flush the reactions down through a 5 g SCX column, first wash with 1:1 chloroform/methanol, then collect washes with 1:1 chloroform/2 M ammonia in methanol. Adsorb the collected material on silica, then purify via a ISCO® Combiflash 16x system (use a 10 g silica cartridge, and elute with 98:2:2 chloroform/ethanol/ammonium hydroxide, gradient to 90:10:1 chloroform/ethanol/ammonium hydroxide). $^1$H NMR (DMSO-$d_6$): 8.58 (d, 1H), 8.22 (m, 1H), 8.0 (s, 1H), 7.46 (s, 1H), 7.27-7.38 (m, 6H), 7.20 (m, 1H), 7.02-7.08 (m, 3H), 3.67-3.68 (d, 4H). TLC $R_f$ (90:10:1 chloroform/ethanol/ammonium hydroxide): 0.31.

The following examples were synthesized in a manner similar to Example 249:

| Example | Name | mass spec (M+) | HPLC r.t., min | % purity |
|---|---|---|---|---|
| 250 | 6-(4-Allylaminomethyl-phenoxy)-nicotinamide | 284 | 3.87 | 99 |
| 251 | 6-{4-[(4-Methoxy-benzylamino)-methyl]-phenoxy}-nicotinamide | 364 | 0.79 | 99 |
| 252 | 6-{4-[(3-Trifluoromethyl-benzylamino)-methyl]-phenoxy}-nicotinamide | 364 | 0.87 | 99 |
| 253 | 6-{4-[(2-Thiophen-2-yl-ethylamino)-methyl]-phenoxy}-nicotinamide | 353 | 0.78 | 99 |
| 254 | 6-{4-[(3-Fluoro-benzylamino)-methyl]-phenoxy}-nicotinamide | 351 | 0.78 | 99 |
| 255 | 6-(4-{[(Furan-2-ylmethyl)-amino]-methyl}-phenoxy)-nicotinamide | 324 | 0.74 | 100 |
| 256 | 6-(4-{[2-(3-Fluoro-phenyl)-ethylamino]-methyl}-phenoxy)-nicotinamide | 366 | 0.83 | 100 |
| 257 | 6-{4-[(4-Trifluoromethoxy-benzylamino)-methyl]-phenoxy}-nicotinamide | 418 | 0.89 | 99.6 |
| 258 | 6-[4-(Phenethylamino-methyl)-phenoxy]-nicotinamide | 348 | 5.87 | 91.2 |
| 259 | 6-(4-{[2-(3-Chloro-phenyl)-ethylamino]-methyl}-phenoxy)-nicotinamide | 382 | 6 | 98.9 |
| 260 | 6-(4-{[2-(4-Sulfamoyl-phenyl)-ethylamino]-methyl}-phenoxy)-nicotinamide | 427 | 5.65 | 89 |
| 261 | 6-{4-[(3-Phenyl-propylamino)-methyl]-phenoxy}-nicotinamide | 362 | 5.94 | 99 |
| 262 | 6-{4-[(3,3-Diphenyl-propylamino)-methyl]-phenoxy}-nicotinamide | 438 | 6.23 | 98.7 |
| 263 | 6-{4-[(3,3-Dimethyl-butylamino)-methyl]-phenoxy}-nicotinamide | 328 | 5.87 | 97.2 |
| 264 | 6-(4-{[2-(2-Methoxy-phenyl)-ethylamino]-methyl}-phenoxy)-nicotinamide | 378 | 5.91 | 98.9 |
| 265 | 6-{4-[(2-Phenylamino-ethylamino)-methyl]-phenoxy}-nicotinamide | 363 | 5.87 | 99.2 |
| 266 | 6-{4-[(2-Phenyl-propylamino)-methyl]-phenoxy}-nicotinamide | 362 | 5.94 | 98.4 |
| 267 | 6-{4-[(2-Pyridin-2-yl-ethylamino)-methyl]-phenoxy}-nicotinamide | 349 | 5.49 | 98.5 |
| 268 | 6-(4-{[2-(2-Chloro-phenyl)-ethylamino]-methyl}-phenoxy)-nicotinamide | 382 | 5.96 | 98.7 |
| 269 | 6-{4-[(2-Pyridin-3-yl-ethylamino)-methyl]-phenoxy}-nicotinamide | 349 | 5.47 | 90.9 |

-continued

| Example | Name | mass spec (M+) | HPLC r.t., min | % purity |
|---|---|---|---|---|
| 270 | 6-{4-[(2,2-Diphenyl-ethylamino)-methyl]-phenoxy}-nicotinamide | 424 | 6.16 | 99 |
| 271 | 6-{4-[(3-Methyl-butylamino)-methyl]-phenoxy}-nicotinamide | 314 | 5.79 | 99 |
| 272 | 6-{4-[(2-Cyclohexyl-ethylamino)-methyl]-phenoxy}-nicotinamide | 354 | 6.05 | 96 |
| 273 | 6-{4-[(2-Methylsulfanyl-ethylamino)-methyl]-phenoxy}-nicotinamide | 317 | 5.56 | 99.6 |
| 274 | 6-{4-[(6-Hydroxy-hexylamino)-methyl]-phenoxy}-nicotinamide | 344 | 5.51 | 99.9 |
| 275 | 6-{4-[(2-Dimethylamino-ethylamino)-methyl]-phenoxy}-nicotinamide | 315 | 5.4 | 99.9 |
| 276 | 6-(4-Decylaminomethyl-phenoxy)-nicotinamide | 384 | 6.37 | 98.7 |
| 277 | 6-{4-[(2-Ethyl-hexylamino)-methyl]-phenoxy}-nicotinamide | 356 | 6.07 | 99.7 |
| 278 | 6-(4-{[(Tetrahydro-furan-2-ylmethyl)-amino]-methyl}-phenoxy)-nicotinamide | 328 | 5.54 | 99.9 |
| 279 | 6-{4-[(2-Pyrrolidin-1-yl-ethylamino)-methyl]-phenoxy}-nicotinamide | 341 | 5.41 | 99.9 |
| 280 | 6-(4-{[2-(1-Methyl-pyrrolidin-2-yl)-ethylamino]-methyl}-phenoxy)-nicotinamide | 356 | 5.42 | 99.8 |
| 281 | 6-(4-{[2-(1H-Imidazol-4-yl)-ethylamino]-methyl}-phenoxy)-nicotinamide | 338 | 5.4 | 99.7 |
| 282 | 6-(4-{[3-(2-Methyl-piperidin-1-yl)-propylamino]-methyl}-phenoxy)-nicotinamide | 383 | 5.46 | 99.9 |
| 283 | 6-{4-[(2-Diisopropylamino-ethylamino)-methyl]-phenoxy}-nicotinamide | 371 | 5.46 | 99.9 |
| 284 | 6-{4-[(2-Cyclohex-1-enyl-ethylamino)-methyl]-phenoxy}-nicotinamide | 352 | 5.93 | 99.6 |
| 285 | 6-(4-Pentylaminomethyl-phenoxy)-nicotinamide | 313 | 5.94 | 98 |

The following examples were synthesized in a manner similar to Example 248:

| Example | Name | mass spec (M+) | HPLC r.t., min | % purity |
|---|---|---|---|---|
| 286 | 4-{4-[(4-Trifluoromethoxy-benzylamino)-methyl]-phenoxy}-benzamide | 417 | 1.02 | 94 |
| 287 | 4-(4-{[2-(3-Chloro-phenyl)-ethylamino]-methyl}-phenoxy)-benzamide | 381 | 0.95 | 96.7 |
| 288 | 4-{4-[(4-Trifluoromethyl-benzylamino)-methyl]-phenoxy}-benzamide | 401 | 0.98 | 93.4 |
| 289 | 4-{4-[(4-Fluoro-benzylamino)-methyl]-phenoxy}-benzamide | 351 | 0.84 | 90 |
| 290 | 4-(4-Pentylaminomethyl-phenoxy)-benzamide | 351 | 0.84 | 95.5 |
| 291 | 4-{4-[(2-Phenyl-propylamino)-methyl]-phenoxy}-benzamide | 361 | 6.11 | 97.6 |
| 292 | 4-(4-{[2-(2-Chloro-phenyl)-ethylamino]-methyl}-phenoxy)-benzamide | 381 | 6.09 | 99.1 |
| 293 | 4-(4-{[2-(2,4-Dichloro-phenyl)-ethylamino]-methyl}-phenoxy)-benzamide | 415 | 6.2 | 99.9 |
| 294 | 4-(4-{[2-(4-Fluoro-phenyl)-ethylamino]-methyl}-phenoxy)-benzamide | 365 | 6.02 | 99.8 |
| 295 | 4-(4-{[2-(3-Fluoro-phenyl)-ethylamino]-methyl}-phenoxy)-benzamide | 365 | 6.02 | 99.9 |
| 296 | 4-(4-{[2-(2-Fluoro-phenyl)-ethylamino]-methyl}-phenoxy)-benzamide | 365 | 6.05 | 99.7 |
| 297 | 4-(4-{[2-(2,5-Dimethoxy-phenyl)-ethylamino]-methyl}-phenoxy)-benzamide | 407 | 6.07 | 99.3 |
| 298 | 4-(4-{[2-(2,6-Dichloro-phenyl)-ethylamino]-methyl}-phenoxy)-benzamide | 415 | 6.2 | 99.8 |

-continued

| Example | Name | mass spec (M+) | HPLC r.t., min | % purity |
|---|---|---|---|---|
| 299 | 4-{4-[(2-o-Tolyl-ethylamino)-methyl]-phenoxy}-benzamide | 361 | 6.11 | 99.6 |
| 300 | 4-{4-[(2,2-Diphenyl-ethylamino)-methyl]-phenoxy}-benzamide | 423 | 6.26 | 99.9 |
| 301 | 4-[4-(3-Phenyl-propylamino)-phenoxy]-benzamide | 347 | 1.54 | 93 |
| 302 | 4-{4-[(2-Cyclopentyl-ethylamino)-methyl]-phenoxy}-benzamide | 339 | 6.13 | 97 |
| 303 | 4-{4-[(2,6-Dichloro-benzylamino)-methyl]-phenoxy}-benzamide | 401 | 6.02 | 98.8 |

EXAMPLE 304

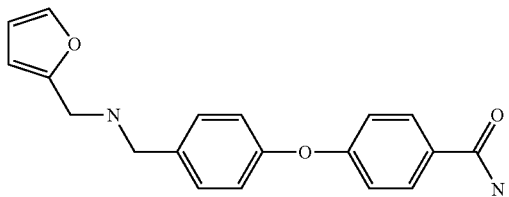

Combine 4-(4-Formyl-phenoxy)-benzamide (from example 247, step 2) (0.12 g, 0.5 mmol) in 3 mL of methanol with Furan-2-yl-methylamine (0.024 g, 0.25 mmol), and 0.5 g of 3 Å molecular sieves. Stir for 18 h. Add to this sodium borohydride (0.046 g, 1.25 mmol), stir for 18 h. Elute down through a 5 g SCX column, first wash with 1:1 chloroform/methanol (discard these washes), then with 1:1 chloroform/2 N NH$_3$ in MeOH, with the washings being collected. Adsorb on silica gel, purify by ISCO® 1000 (10 g silica column) and elute with 95:5:0.5 chloroform/ethanol/ammonium hydroxide to afford 34 mg of product. TLC R$_f$(95:5:0.5 chloroform/ethanol/ammonium hydroxide): 0.25. $^1$H NMR (DMSO-d$_6$): 7.86 (d, 4H), 7.54 (s, 1H), 7.36 (d, 2H), 7.27 (s, 1H), 7.0 (m, 4H), 6.37 (s, 1H), 6.24 (s, 1H), 3.66 (s, 2H), 3.64 (s, 2H).

The following examples were synthesized in a manner similar to Example 304

| Example | Name | mass spec (M+) | HPLC r.t., min | % purity |
|---|---|---|---|---|
| 305 | 6-(4-{[2-(3,4-Dichloro-phenyl)-ethylamino]-methyl}-phenoxy)-nicotinamide | 416 | 6.06 | 99.4 |
| 306 | 6-(4-{[2-(2-Ethoxy-phenyl)-ethylamino]-methyl}-phenoxy)-nicotinamide | 392 | 6.04 | 99.3 |
| 307 | 6-{4-[(2-o-Tolyl-ethylamino)-methyl]-phenoxy}-nicotinamide | 362 | 5.95 | 99.6 |
| 308 | 6-(4-{[2-(2-Phenoxy-phenyl)-ethylamino]-methyl}-phenoxy)-nicotinamide | 440 | 6.19 | 94.7 |

EXAMPLE 309

6-{4-[(2-Cyclopentyl-ethylamino)-methyl]-phenoxy}-nicotinamide

Combine 6-(4-formyl-phenoxy)-nicotinamide (0.61 g, 2.54 mmol) with 2-Cyclopentyl-ethylamine (0.38 g, 3.3 mmol), 2 g of 3 Å molecular sieves, and 10 mL of methanol. Stir for 18 h under nitrogen. Add sodium borohydride (0.5 g, 13.2 mmol), and stir for 24 h. Filter through Celite, remove the solvent in vacuo. Partition the residue between water (50 mL) and ethyl acetate (100 mL). Dry the organic phase (sodium sulfate), filter, and concentrate in vacuo. Adsorb on silica, and purify on an ISCO® 100 g system (eluting with 95:5:0.5 to 90:10:1 chloroform/ethanol/ammonium hydroxide) to afford 0.45 g of product. HPLC retention time: 5.93 min (98.7% purity), ESMS (M+): 340.

General Procedures and Intermediates

General Procedure for Nucleophilic Aromatic Substitutions

Dissolve the corresponding aldehyde (1 equiv), 6-chloronicotinonitrile (1 equiv) and K$_2$CO$_3$ (2.5 equiv) in anhydrous DMF (0.2 M) and heat at about 110° C. under nitrogen for about 1 hour (the reaction can be monitored by tlc). After cooling down to room temperature, the reaction mixture is poured into water and extracted with ethyl acetate (3×50 mL). The combined organic layer is dried over Na$_2$SO$_4$, filtered and concentrated under vacuum (toluene may be added to aid DMF evaporation). The crude mixture is purified by flash chromatography using hexanes/ethyl acetate (4:1) as eluant.

6-(2-Ethoxy-4-formyl-phenoxy)nicotinonitrile

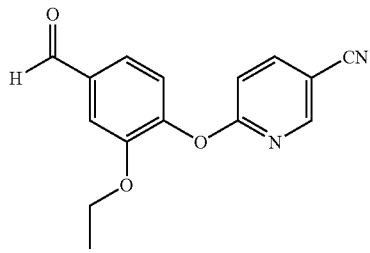

90% yield. $^1$H NMR (CHCl$_3$-d$_3$) δ: 9.95 (s, 1H, CHO), 8.37 (dd, 1H, J=2.6, 0.7 Hz), 7.90 (dd, 1H, J=8.8, 2.6 Hz), 7.50-7.33 (m, 2H), 7.32 (m, 1H), 7.10 (dd, 1H, J=8.8, 0.7 Hz), 4.03 (q, 2H, J=7.0 Hz), 1.14 (t, 3H, J=7.0 Hz). $^{13}$C NMR (CHCl$_3$-d$_3$) δ: 190.9, 164.9, 151.3, 151.7, 146.8, 142.1, 135.0, 124.8, 123.1, 116.6, 112.0, 111.6, 104.3, 64.4, 14.3.

6-(2,6-Dimethyl-4-formyl-phenoxy)nicotinonitrile

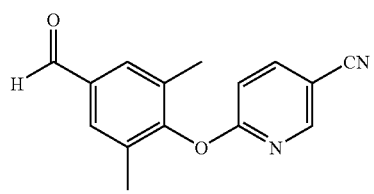

88% yield. $^1$H NMR (CHCl$_3$-d$_3$) δ: 9.93 (s, 1H, CHO), 8.37 (dd, 1H, J=2.4, 0.7 Hz), 7.92 (dd, 1H, J=8.8, 2.4 Hz), 7.64 (s, 2H), 7.09 (dd, 1H, J=8.8, 0.7 Hz), 2.14 (s, 6H). $^{13}$C NMR (CHCl$_3$-d$_3$) δ: 191.3, 164.2, 154.4, 152.2, 142.5, 134.0, 132.0, 130.4, 116.5, 111.1, 104.3, 16.4.

6-(5-Methoxy-4-formyl-phenoxy)nicotinonitrile

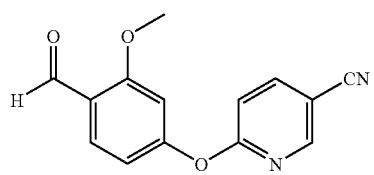

12% Yield. $^1$H NMR (CHCl$_3$-d$_3$) δ: 10.38 (s, 1H, CHO), 8.44 (dd, 1H, J=2.7, 0.7 Hz), 7.92 (dd, 1H, J=2.7, 8.8 Hz), 7.84 (d, 1H, J=8.8 Hz), 7.05 (dd, 1H, J=8.8, 0.7 Hz), 6.78 (m, 2H), 3.89 (s, 3H). $^{13}$C NMR (CHCl$_3$-d$_3$): 187.4, 163.7, 162.2, 157.8, 151.0, 141.6, 129.2, 121.5, 115.4, 112.7, 111.5, 104.2, 104.0, 54.9.

General Procedure: Nucleophilic Aromatic Substitution 6-chloronicotinamide

A solution of 4-hydroxy-3-methylbenzaldehyde (1.0 equiv) in DMF (0.2 M solution) was treated with K$_2$CO$_3$ (1.5 equiv) and 6-chloronicotinamide (1.0 equiv). The reaction mixture was placed inside the microwave oven and then irradiated for 5 min. Upon completion of the reaction, the mixture was cooled, poured into H$_2$O and extracted with ethyl acetate, and the combined organic layers were washed twice with water and brine. After drying the extracts over magnesium sulfate and evaporation under vacuum the crude product was purified by silica eel chromatography using CHCl$_3$:EtOH 7%:NH$_4$OH 0.7% to afford the title compound as a solid.

6-(4-Formyl-2,5-dimethyl phenoxy)nicotinamide

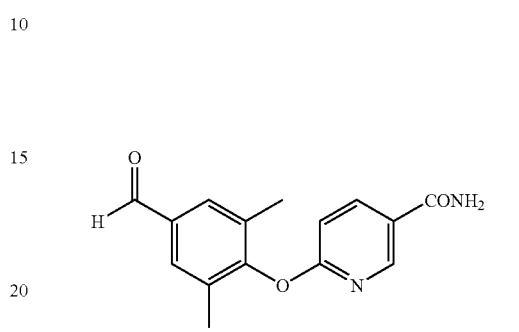

38% Yield. $^1$H NMR (MeOH-d$_4$) δ: 9.90 (s, 1H, CHO), 8.51 (dd, 1H, J=2.6, 0.7 Hz), 8.25 (dd, 1H, J=8.8, 2.6 Hz), 7.68 (s, 2H), 7.10 (dd, 1H, J=8.8, 0.7 Hz), 2.14 (s, 6H). MS (Electrospray): 271.0 (M$^+$+1).

General Procedure: Reductive Amination

A mixture of aldehyde (1 equiv), amine (1 equiv), 4 Å molecular sieves (1000% weight) in methanol (0.1 M) was stirred overnight under nitrogen atmosphere at room temperature. The following day NaBH$_4$ (5 equiv) was added and the reaction mixture was stirred for 3 hours. The reaction can be monitored by electrospray MS. The reaction mixture was filtered off and the solvent evaporated to yield a residue which was purified by SCX or flash chromatography depending on the case.

General Procedure: Nitrile Hydrolysis to Carboxamide

A solution of the corresponding nitrile (1.0 equiv) in DMSO (0.2 M solution) was treated with K$_2$CO$_3$ (0.5 equiv) and 33% H$_2$O$_2$ (1.0-2.0 equiv) at 0° C. The reaction was monitored by TLC and more H$_2$O$_2$ was added if required. After 12 h, the reaction was poured into H$_2$O and extracted with ethyl acetate and the combined organic layers were washed twice with water and brine. After drying over sodium sulfate and evaporation under vacuum the crude product was purified by silica gel chromatography using the appropriate eluant (typically chloroform/ethanol/NH$_4$OH, 92.3/7/0.7) to afford the title compound as a solid.

General Procedure: Methanesulfonate Salt

To a solution of the corresponding organic compound (1.0 equiv) in THF (0.1 M solution) was treated with methanesulfonic acid (1 equiv) to afford the desired sulfonate salt after purification.

EXAMPLE 310

6-[4-((2-Cyclopentyl-ethylamino)-methyl)-2-ethoxyphenoxy]nicotinamide

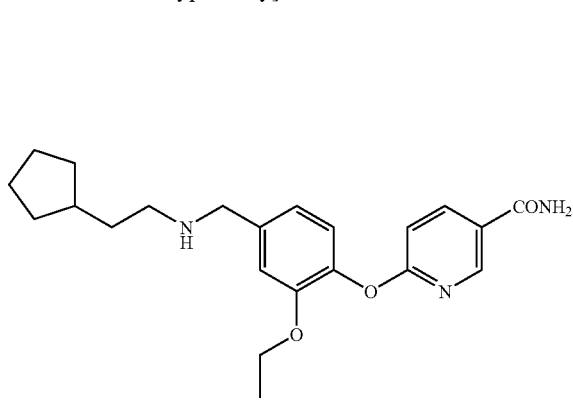

Step 1

6-[4-((2-Cyclopentyl-ethylamino)-methyl)-2-ethoxyphenoxy]nicotinonitrile

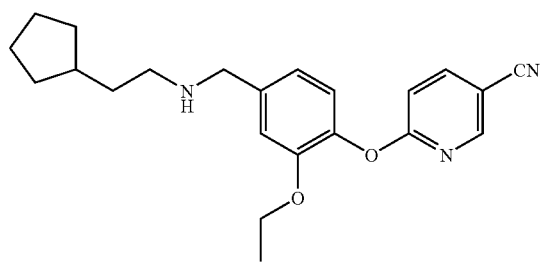

The above compound was obtained following the applicable general procedures described above and using the corresponding intermediates and reagents.

20% yield. $^1$H NMR (MeOH-d$_4$) δ: 8.41 (dd, 1H, J=2.1, 0.5 Hz), 8.07 (dd, 1H, J=8.8, 2.1 Hz), 7.15-6.90 (m, 4H), 4.01 (q, 2H, J=7.0 Hz), 3.77 (s, 2H), 2.63 (t, 2H, J=7.0 Hz), 1.80 (m, 3H), 1.55 (m, 6H), 1.11 (m, 5H). $^{13}$C NMR (MeOH-d$_4$) δ: 166.2, 152.0, 151.0, 142.8, 141.3, 138.4, 122.5, 121.1, 116.8, 114.3, 111.4, 104.0, 64.3, 53.2, 49.3, 38.4, 35.7, 32.1, 25.1, 14.0. MS (Electrospray): 366.5 (M$^+$+1).

Step 2

The title compound may be prepared by basic hydrolysis of the nitrile group to form the amide as has been described previously.

EXAMPLE 311

6-[4-((3,3-Dimethyl-butylamino)-methyl)-2-ethoxyphenoxy]nicotinamide

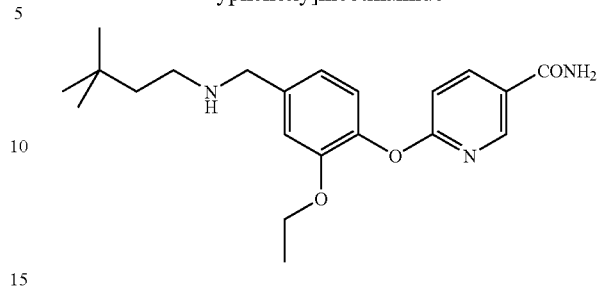

Step 1

6-[4-((3,3-Dimethyl-butylamino)-methyl)-2-ethoxyphenoxy]nicotinonitrile

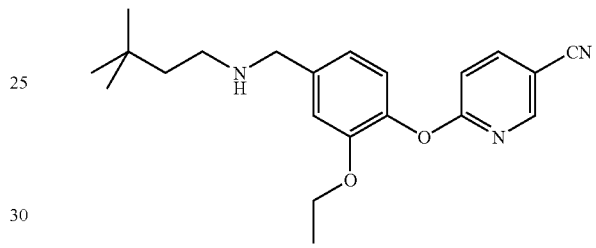

The above compound was obtained in quantitative yield following the applicable general procedures described above and using the corresponding intermediates and reagents.

$^1$H NMR (MeOH-d$_4$) δ: δ: 8.42 (dd, 1H, J=0.8, 2.4 Hz), 8.10 (dd, 1H, J=8.6, 2.4 Hz), 7.15-6.85 (m, 4H), 4.01 (q, 2H, J=7.0 Hz), 3.76 (s, 2H), 2.65 (t, 2H, J=8.0 Hz), 1.43 (t, 2H, J=8.0 Hz), 1.12 (t, 3H, J=7.0 Hz), 0.91 (s, 9H). $^{13}$C NMR (MeOH-d$_4$) δ: 165.8, 151.4, 150.5, 142.3, 140.7, 138.3, 122.0, 113.8, 110.9, 103.5, 63.8, 52.9, 48.4, 44.6, 42.7, 28.5, 13.5. MS (Electrospray): 354.2 (M$^+$+1).

Step 2

The title amide may be obtained via basic hydrolysis reaction of the nitrile from step 1 following procedures described previously.

EXAMPLE 312

6-[4-((3-Methyl-butylamino)-methyl)-2,5-dimethylphenoxy]nicotinamide

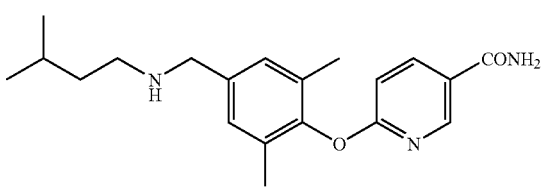

Step 1

6-[4-((3-Methyl-butylamino)-methyl)-2,5-dimethylphenoxy]nicotinonitrile

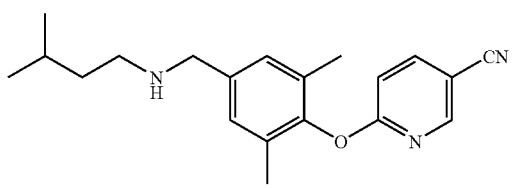

The above compound was obtained in quantitative yield following the applicable general procedures described above and using the corresponding intermediates and reagents.

$^1$H NMR (MeOH-d$_4$) δ: 8.43 (dd, 1H, J=2.4, 0.8 Hz), 8.11 (dd, 1H, J=8.6, 2.4 Hz), 7.13-7.05 (m, 3H), 3.69 (s, 2H), 2.60 (t, 2H, J=7.0 Hz), 2.05 (s, 6H), 1.65-1.51 (m, 1H), 1.51-1.35 (m, 2H), 0.90 (d, 6H, J=6.9 Hz). $^{13}$C NMR (MeOH-d$_4$) δ: 164.1, 151.0, 147.7, 141.9, 136.0, 129.3, 127.7, 127.6, 115.3, 109.6, 102.7, 51.6, 47.5, 37.1, 25.1, 20.7, 14.0, 14.1. MS (Electrospray): 324.5 (M$^+$+1).

Step 2

The title amide may be obtained via basic hydrolysis reaction of the nitrile from step 1 following procedures described previously.

EXAMPLE 313

6-[4-((2-Phenyl-ethylamino)-methyl)-2,5-dimethylphenoxy]nicotinamide

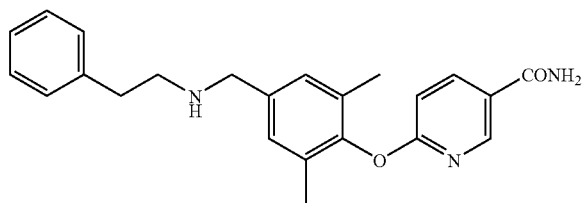

Step 1

6-[4-((2-Phenyl-ethylamino)-methyl)-2,5-dimethylphenoxy]nicotinonitrile

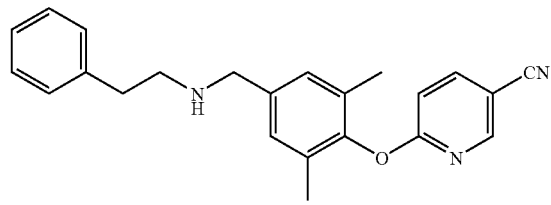

The above compound was obtained following the applicable general procedures described above and using the corresponding intermediates and reagents.

Quantitative yield. $^1$H NMR (MeOH-d$_4$) δ: 8.43 (dd, 1H, J=2.1, 0.5 Hz), 8.15 (dd, 1H, J=8.6, 2.1 Hz), 7.35-7.05 (m, 8H), 3.71 (s, 2H), 2.82 (s, 4H), 2.04 (s, 6H). $^{13}$C NMR (MeOH-d$_4$) δ: 164.9, 151.9, 148.7, 142.8, 139.5, 136.7, 130.3, 128.5, 128.2, 128.1, 125.8, 116.2, 110.5, 163.6, 52.2, 49.9, 35.2, 15.0. MS (Electrospray): 358.1 (M$^+$+1).

Step 2

The title amide may be obtained via basic hydrolysis reaction of the nitrile from step 1.

EXAMPLE 314

6-[4-((2-Thiophen-2-yl-ethylamino)-1-ethyl)-2-ethoxyphenoxy]nicotinamide

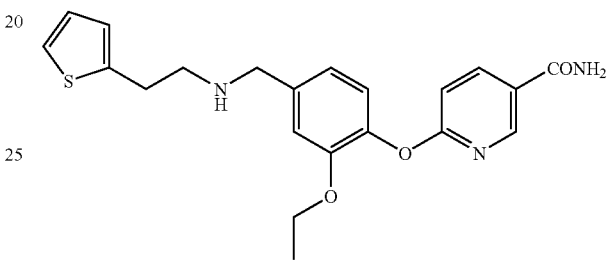

The above compound was obtained following the applicable general procedures described above and using the corresponding intermediates and reagents.

94% yield. $^1$H NMR (MeOH-d$_4$) δ: 8.60 (d, 1H, J=2.2 Hz), 8.24 (dd, 1H, J=8.7, 2.4 Hz), 7.21 (d, 1H, J=5.0 Hz), 7.11 (m, 2H), 7.00-6.90 (m, 4H), 4.15 (q, 2H, J=6.8 Hz), 3.80 (s, 2H), 3.07 (t, 2H, J=7.5 Hz), 2.90 (t, 2H, J=7.5 Hz), 1.11 (t, 3H, J=6.8 Hz). $^{13}$C NMR (MeOH-d$_4$): 167.4, 164.9, 149.8, 146.2, 140.9, 138.1, 137.0, 125.5, 123.8, 123.2, 122.2, 121.2, 119.7, 112.9, 108.6, 62.9, 51.6, 49.0, 28.3, 12.6. MS (Electrospray): 398.0 (M$^+$+1).

EXAMPLE 315

6-[4-((3-Methyl-butylamino)-methyl)-2-ethoxyphenoxy]nicotinamide methanesulfonate salt

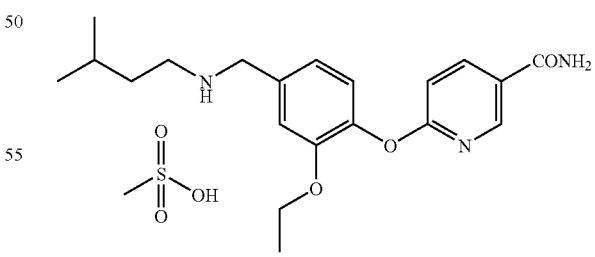

The above compound was obtained following the applicable general procedures described above and using the corresponding intermediates and reagents.

Quantitative yield. $^1$H NMR (MeOH-d$_4$) δ: 8.60 (s, 1H), 8.32 (dt, 1H, J=6.4, 2.2 Hz), 7.35-7.01 (m, 4H), 4.26 (s, 2H), 4.06 (q, 2H, J=6.8 Hz), 3.14 (t, 2H, J=8.0 Hz), 2.72 (s, 3H), 1.80-1.60 (m, 3H), 1.14 (t, 3H, J=6.8 Hz), 1.00 (d, 6H, J=6.0

Hz). $^{13}$C NMR (MeOH-d$_4$) δ: 166.8, 164.1, 150.0, 145.5, 141.8, 138.5, 128.7, 123.4, 121.9, 121.2, 114.2, 109.0, 63.1, 49.5, 44.7, 37.1, 33.3, 24.7, 20.1, 12.3. MS (Electrospray): 358.5 (M$^+$+1).

EXAMPLE 316

6-[4-((3,3-Dimethyl-butylamino)-methyl)-2-ethoxyphenoxy]nicotinamide

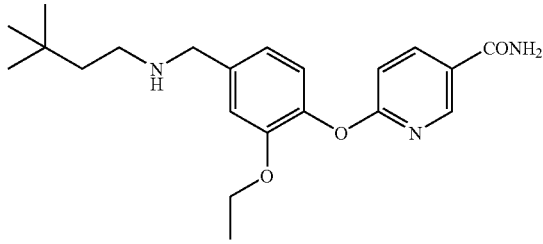

The above compound was obtained following the applicable general procedures described above and using the corresponding intermediates and reagents.

Quantitative yield. $^1$H NMR (MeOH-d$_4$) δ: 8.60 (d, 1H, J=2.4 Hz), 8.24 (dt, 1H, J=8.6, 2.2 Hz), 7.15 (m, 2H), 7.00-6.90 (m, 2H), 4.01 (q, 2H, J=7.0 Hz), 3.78 (s, 2H), 2.65 (t, 2H, J=8.0 Hz), 1.49 (t, 2H, J=8.0 Hz), 1.12 (t, 3H, J=7.0 Hz), 0.93 (s, 9H). $^{13}$C NMR (MeOH-d$_4$) δ: 167.3, 164.9, 149.7, 146.2, 140.3, 138.1, 137.1, 123.2, 121.2, 119.7, 113.1, 108.6, 62.9, 52.0, 43.7, 41.8, 28.2, 27.6, 12.6. MS (Electrospray): 372.3 (M$^+$+1).

EXAMPLE 317

6-[4-(Butylamino-methyl)-2-ethoxyphenoxy]nicotinamide

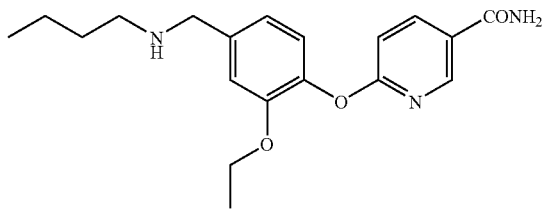

The above compound was obtained following the applicable general procedures described above and using the corresponding intermediates and reagents.

Quantitative yield. $^1$H NMR (MeOH-d$_4$) δ: 8.61 (d, 1H, J=2.4 Hz), 8.24 (dd, 1H, J=8.6, 2.4 Hz), 7.14 (m, 2H), 7.00-6.90 (m, 2H), 4.01 (q, 2H, J=7.0 Hz), 3.78 (s, 2H), 2.63 (t, 2H, J=7.2 Hz), 1.56 (m, 2H), 1.40 (m, 2H), 1.13 (t, 3H, J=7.0 Hz), 0.96 (t, 3H, J=7.0 Hz). $^{13}$C NMR (MeOH-d$_4$) δ: 167.3, 164.9, 149.7, 146.3, 140.3, 138.1, 137.1, 123.3, 121.2, 119.7, 113.0, 108.6, 62.9, 51.9, 47.5, 30.2, 19.2, 12.6, 12.0. MS (Electrospray): 344.2 (M$^+$+1).

EXAMPLE 318

6-[4-((2-Phenyl-ethylamino)-methyl)-2,5-dimethylphenoxy]nicotinamide

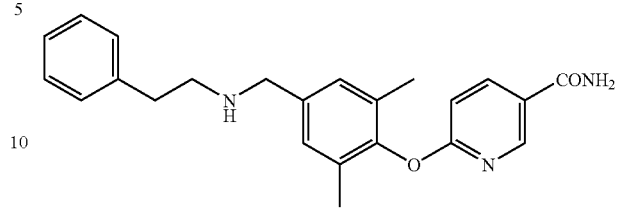

The above compound was obtained following the applicable general procedures described above and using the corresponding intermediates and reagents.

Quantitative yield. $^1$H NMR (MeOH-d$_4$) δ: 8.61 (dd, 1H, J=2.4, 0.5 Hz), 8.24 (dd, 1H, J=8.6, 2.4 Hz), 7.35-7.10 (m, 5H), 7.04 (s, 2H), 6.92 (dd, 1H, J=8.6, 0.5 Hz), 3.70 (s, 2H), 2.82 (s, 4H), 2.05 (s, 6H). $^{13}$C NMR (MeOH-d$_4$) δ: 167.3, 164.0, 148.0, 146.8, 138.6, 135.6, 129.5, 127.6, 127.2, 124.9, 123.3, 108.0, 51.4, 49.0, 34.3, 14.2. MS (Electrospray): 376.1 (M$^+$+1).

EXAMPLE 319

6-[4-((2-Cyclopentyl-ethylamino)-methyl)-2-ethoxyphenoxy]nicotinamide methanosulfonate salt

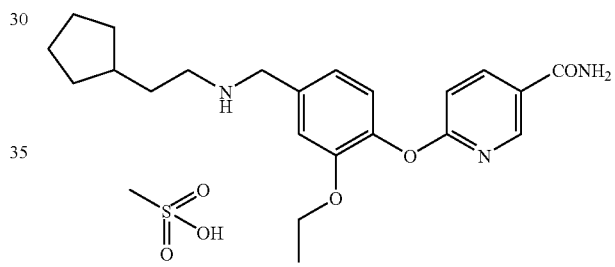

The above compound was obtained following the applicable general procedures described above and using the corresponding intermediates and reagents.

89% yield. $^1$H NMR (MeOH-d$_4$) δ: 8.53 (dd, 1H, J=2.3, 0.5 Hz), 8.25 (dd, 1H, J=8.6, 2.3 Hz), 7.28-7.21 (m, 2H), 7.25 (dd, 1H, J=8.3, 1.9 Hz), 7.05 (dd, 1H, J=8.6, 0.5 Hz), 4.21 (s, 2H), 4.01 (q, 2H, J=7.0 Hz), 3.08 (t, 2H, J=8.0 Hz), 2.69 (s, 3H), 1.90-1.50 (m, 10H), 1.12 (m, 4H). $^{13}$C NMR (MeOH-d$_4$) δ: 167.2, 164.4, 150.3, 146.0, 142.3, 138.2, 128.5, 123.6, 122.1, 121.2, 114.2, 109.1, 63.2, 49.7, 37.1, 36.3, 31.0, 30.9, 23.6, 12.4. MS (Electrospray): 384.2 (M$^+$+1).

EXAMPLE 320

6-[4-((3-Methyl-butylamino)-1-ethyl)-2,5-dimethylphenoxy]nicotinonamide

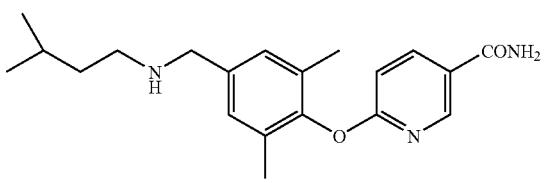

62% yield. $^1$H NMR (MeOH-d$_4$) δ: 8.56 (dd, 1H, J=2.4, 0.5 Hz), 8.23 (dd, 1H, J=8.6, 2.4 Hz), 7.11 (s, 2H), 6.90 (dd, 1H, J=8.6, 0.5 Hz), 3.70 (s, 2H), 2.61 (t, 2H, J=7.5 Hz), 2.07 (s, 6H), 1.75-1.51 (m, 1H), 1.51-1.35 (m, 2H), 0.90 (d, 6H, J=6.5 Hz). $^{13}$C NMR (MeOH-d$_4$) δ: 167.3, 164.1, 148.0, 146.6, 138.6, 135.7, 129.5, 127.7, 123.3, 108.1, 51.6, 45.8, 37.1, 25.1, 20.6, 14.1. MS (Electrospray): 342.3 (M$^+$+1).

3-Substituted Piperidine Series

General Methods

Reagents obtained from commercial suppliers were used without further purification unless otherwise noted. Solvents were purchased as anhydrous and used without further purification. All air and water sensitive reactions were performed in heat-dried glassware under a nitrogen atmosphere. $^1$H NMR spectra were recorded on a Varian spectrometer at 400 MHz using CD$_3$OD, CDCl$_3$, or DMSO-d$_6$. All preparative reverse-phase high-performance liquid chromatography (RP-HPLC) was performed using a Kromasil® column (50.8 mm×25 cm) with a gradient of 95:5→20:80, 0.03% aqueous hydrochloric acid:acetonitrile at 10 mL/min over 70 min. time. Analytical thin layer chromatography was performed on Whatman plates (2.5×7.5 mm) and visualized using para-anisaldehyde or potassium permanganate stain followed by heating. Silica gel chromatography was performed using Biotage prepacked silica gel columns (KP-sil, 60 Å).

EXAMPLE 321

6-[4-(1-Benzyl-1,2,5,6-tetrahydro-pyridin-3-yl)-phenoxy]-nicotinamide hydrochloride salt

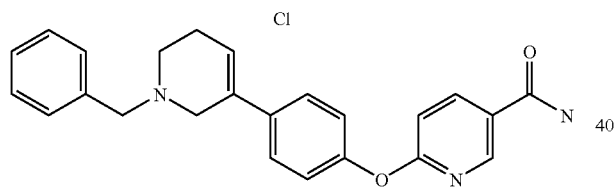

Step 1

6-(4-Iodo-phenoxy)-nicotinamide

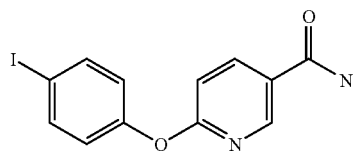

Combine 4-iodophenol (6.31 g, 28.7 mmol), 6-chloro-nicotinamide (4.51 g, 28.8 mmol), potassium carbonate (10.0 g, 72.4 mmol), and dimethylacetamide (145 mL), stir and heat at 200° C. After 3 h. cool to ambient temperature and dilute with water (600 mL), filter, and dry in vacuo to provide 8.27 g (85%) of the title compound as a white/brown solid: mass spectrum (electrospray): m/z=341.0 (M+1); $^1$H NMR (methanol-d$_4$): 8.67 (d, 1H, J=2.4 Hz), 8.31 (dd, 1H, J=2.4, 8.3 Hz), 7.82-7.79 (m, 2H), 7.09 (d, 1H, J=8.8 Hz), 7.03-6.99 (m, 2H).

Step 2

Combine bis(pinacolato)diboron (0.437 g, 1.72 mmol), potassium acetate (0.454 g, 4.62 mmol), 1,1'-bis(diphenylphosphino)ferrocene (0.0273 g, 0.0492 mmol), [1,1'-bis(diphenylphosphino)ferrocene]dichloropalladium(II) complex with dichloromethane (0.0377 g, 0.0461 mmol), flush with nitrogen, treat with a solution of trifluoro-methane-sulfonic acid 1-benzyl-1,2,5,6-tetrahydro-pyridin-3-yl ester (See Zheng, Q.; Yang, Y.; Martin, A. R. *Tetrahedron Lett.* 1993, 34, 2235-2238) (0.503 g, 1.56 mmol) in dioxane (10 mL), stir and heat at 80° C. After 4 h, concentrate the reaction mixture and dry in vacuo. Combine crude boronate, potassium carbonate (0.650 g, 4.70 mmol), [1,1'-bis(diphenylphosphino)ferrocene]dichloropalladium(II) complex with dichloromethane (0.0777 g, 0.0951 mmol), treat with a solution of 6-(4-iodo-phenoxy)-nicotinamide (0.582 g, 1.71 mmol) in dimethylformamide (10 mL), stir and heat at 80° C. After 4.5 h, cool the reaction mixture to ambient temperature, dilute with water (30 mL), and extract with ethyl acetate (3×30 mL). Wash combined organic extracts with brine (1×), dry over anhydrous magnesium sulfate, filter, and concentrate. Purify the residue by silica gel chromatography (10:1 to 5:1 ethyl acetate:methanol), then reverse-phase HPLC to provide 0.175 g (29%) of the title compound as a white solid: mass spectrum (electrospray) m/z=386.2 (M+1); $^1$H NMR (methanol-d$_4$): 8.66 (d, 1H, J=2.4 Hz), 8.32 (dd, 1H, J=2.4, 8.3 Hz), 7.65-7.52 (m, 5H), 7.52-7.48 (m, 2H), 7.22 (d, 1H, J=8.8 Hz), 7.10 (d, 1H, J=8.8 Hz), 6.41 (m, 1H), 4.61 (d, 1H, J=13.2 Hz), 4.52 (d, 1H, J=12.7 HZ), 4.22-4.20 (m, 2H), 3.72-3.67 (m, 1H), 3.36-3.31 (m, 1H), 2.75-2.65 (m, 1H).

EXAMPLE 322

(±)-6-(4-Piperidin-3-yl-phenoxy)-nicotinamide hydrochloride

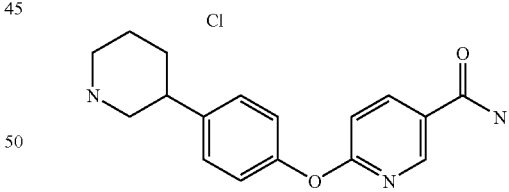

Combine the product of example 321 (0.0421 g, 0.0998 mmol), 10% Pd—C (2 spatula tips), and methanol (2.0 mL). Bubble one balloon of hydrogen gas through solution then stir under ca. 1 atm. After 3.5 h, filter the reaction mixture through Celite®, concentrate, and purify by reverse-phase HPLC to provide 0.0129 g (39%) of the title compound as a white solid: mass spectrum (electrospray): m/z=298.1 (M+1); $^1$H NMR (methanol-d$_4$): 8.86 (s br, 1H), 8.59 (dd, 1H, J=2.0, 8.8 Hz), 7.53 (d, 2H, J=8.3 Hz), 7.32 (d, 2H, J=7.8 Hz), 7.19 (d, 1H, J=8.8 Hz), 3.51 (d, 1H, J=8.3 Hz), 3.25-3.08 (m, 3H), 2.18-2.08 (m, 2H), 2.06-1.84 (m, 2H).

EXAMPLE 323

(±)-6-[4-(1-Benzyl-piperidin-3-yl)-phenoxy]-nicotinamide

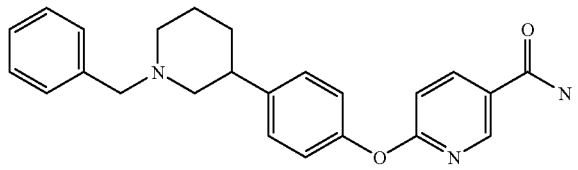

Combine 6-(4-Piperidin-3-yl-phenoxy)-nicotinamide (free base of compound of example 322) (0.0298 g, 0.101 mmol), benzaldehyde (0.0108 mL, 0.106 mmol), and sodium triacetoxyborohydride (0.0310 mg, 0.146 mmol) in acetonitrile (2.0 mL). Add methanol (0.5 mL) to dissolve insoluble starting material. Add benzaldehyde (0.0200 mL, 0.197 mmol) after 15 min. then stir for 4 h. Add sodium borohydride (0.0083 g, 0.219 mmol) and stir for 10 min., concentrate, and purify by silica gel chromatography (30:1 ethyl acetate:hexanes → 20:1 ethyl acetate:methanol) to provide 0.0223 g (57%) of the title compound as a white solid: mass spectrum (electrospray): m/z=388.2 (M+1); $^1$H NMR (CDCl$_3$): 8.56 (d, 1H, J=2.4 Hz), 8.14 (dd, 1H, J=2.4, 8.8 Hz), 7.33-7.29 (m, 4H), 7.27-7.22 (m, 3H), 5.84 (s br, 2H), 3.57 (m, 2H), 3.06-2.83 (m, 3H), 2.10-1.90 (m, 4H), 1.80-1.70 (m, 2H), 1.50-1.37 (m, 1H).

EXAMPLE 324

(±)-6-[4-(1-Cyclohexylmethyl-piperidin-3-yl)-phenoxy]-nicotinamide

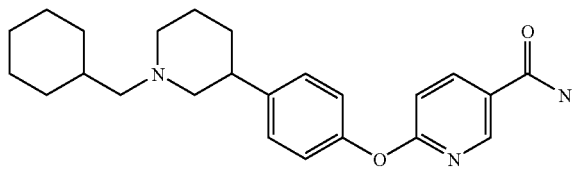

Combine 6-(4-Piperidin-3-yl-phenoxy)-nicotinamide (free base of compound of example 322) (0.96 mL of 0.12 M stock solution in methanol, 0.0344 g, 0.116 mmol) and cyclohexanecarboxaldehyde (0.021 mL, 0.173 mmol), and stir overnight. Add sodium borohydride (0.0108 g, 0.285 mmol), stir for 4.5 h, then concentrate and purify by silica gel chromatography (20:1→10:1 ethyl acetate:methanol) to provide 0.0085 g (19%) of the title compound as a white solid: high resolution mass spectrum (electrospray): m/z calc for $C_{24}H_{32}N_3O_2$ 394.2495, found 394.2488; $^1$H NMR (CDCl$_3$): 8.58 (s, 1H), 8.14 (d, 1H, J=7.8 Hz), 7.27 (d, 2H, J=8.3 Hz), 7.05 (d, 2H, J=7.8 Hz), 6.93 (d, 1H, J=8.8 Hz), 5.89 (s br, 2H), 2.99-2.77 (m, 3H), 2.16-2.06 (m, 2H), 1.97-1.83 (m, 3H), 1.80-1.59 (m, 7H), 1.54-1.34 (m, 2H), 1.29-1.03 (m, 5H), 0.93-0.77 (m, 3H).

EXAMPLE 325

(±)-6-[4-(1-Methyl-piperidin-3-yl)-phenoxy]-nicotinamide

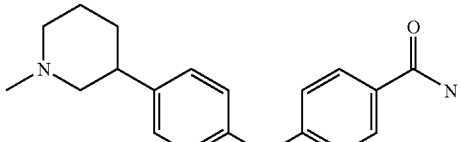

Combine 6-(4-piperidin-3-yl-phenoxy)-nicotinamide (free base of compound of example 322) (0.95 mL of 0.12 M stock solution in methanol, 0.0341 g, 0.115 mmol) and formaldehyde (37% w/w in water, 0.014 mL, 0.156 mmol) and stir overnight. Add sodium borohydride (0.0128 g, 0.338 mmol) and stir. After 4.5 h concentrate the reaction mixture and purify by silica gel chromatography (20:1 ethyl acetate:methanol→2 M ammonia/methanol), then ion exchange chromatography (SCX resin, methanol→2 M ammonia (2M in methanol) to provide 0.02215 g (600%) of the title compound as a white solid: high resolution mass spectrum (electrospray): m/z calc for $C_{18}H_{22}N_3O_2$ 312.1712, found 312.1718; $^1$H NMR (methanol-d$_4$): 8.66 (d, 1H, J=2.4 Hz), 8.29 (dd, 1H, J=2.4, 8.8 Hz), 7.40-7.35 (m, 2H), 7.16-7.11 (m, 2H), 7.02 (d, 1H, J=8.8 Hz), 3.10-3.02 (m, 2H), 2.92 (tt, 1H, J=3.4, 11.7 Hz), 2.43 (s, 3H), 2.27-2.15 (m, 2H), 2.02-1.88 (m, 2H), 1.81 (qt, 1H, J=3.9, 12.7 Hz), 1.57 (dq, 1H, J=3.9, 12.2 Hz).

EXAMPLE 326

(±)-6-[4-(1-(3-Fluoro-benzyl)-piperidin-3-yl)-phenoxy]-nicotinamide

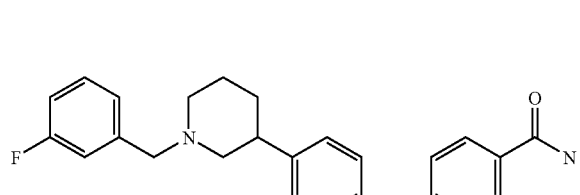

Using a method similar to Example 324, 6-(4-piperidin-3-yl-phenoxy)-nicotinamide (free base of compound of example 322) (0.98 mL of 0.12 M stock solution in methanol, 0.0343 g, 0.115 mmol), 3-fluoro-benzaldehyde (0.0180 mL, 0.170 mmol), and sodium borohydride (0.0102 g, 0.270 mmol) provide 0.0193 g (41%) of the title compound as a white foam: high resolution mass spectrum (electrospray): m/z calc for $C_{24}H_{25}FN_3O_2$ 406.1931, found 406.1917; $^1$H NMR (CDCl$_3$): 8.56 (d, 1H, J=2.4 Hz), 8.14 (dd, 1H, J=2.4, 8.8 Hz), 7.28-7.21 (m, 3H), 7.09-7.02 (m, 4H), 6.95-6.88 (m, 2H), 5.74 (s br, 2H), 3.52 (d, 1H, J=13.7 Hz), 3.50 (d, 1H, J=13.7 Hz), 3.00-2.93 (m, 1H), 2.93-2.80 (m, 2H), 2.06-1.90 (m, 3H), 1.80-1.64 (m, 2H), 1.44 (dq, 1H, J=4.4, 12.2 Hz).

EXAMPLE 327

(±)-6-[4-(1-(2-Fluoro-benzyl)-piperidin-3-yl)-phenoxy]-nicotinamide

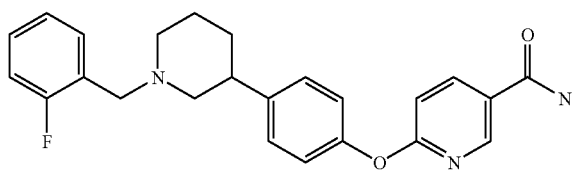

Using a method similar to Example 324, 6-(4-piperidin-3-yl-phenoxy)-nicotinamide (free base of compound of example 322) (0.0305 g, 0.103 mmol), 2-fluoro-benzaldehyde (0.0160 mL, 0.152 mmol), and sodium borohydride (0.0093 g, 0.246 mmol) provide 0.0179 g (43%) of the title compound as a white foam: high resolution mass spectrum (electrospray): m/z calc for $C_{24}H_{25}FN_3O_2$ 406.1931, found 406.1936; $^1$H NMR (CDCl$_3$): 8.56 (d, 1H, J=2.4 Hz), 8.14 (dd, 1H, J=2.4, 8.8 Hz), 7.37 (dt, 1H, J=1.9, 7.3 Hz), 7.27-7.18 (m, 3H), 7.09 (dt, 1H, J=1.0, 7.3 Hz), 7.06-6.97 (m, 3H), 6.93 (dd, 1H, J=1.0, 8.8 Hz), 5.71 (s br, 2H), 3.56 (s, 2H), 3.04-2.97 (m, 1H), 2.93 (d, 1H, J=10.7 Hz), 2.85 (tt, 1H, J=3.4, 11.2 Hz), 2.12-2.01 (m, 2H), 1.96-1.88 (m, 1H), 1.81-1.64 (m, 2H), 1.41 (dq, 1H, J=4.4, 11.7 Hz).

EXAMPLE 328

(±)-6-[4-(1-Hexyl-piperidin-3-yl)-phenoxy]-nicotinamide

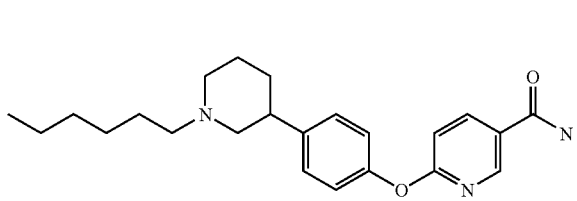

Using a method similar to Example 324, 6-(4-piperidin-3-yl-phenoxy)-nicotinamide (free base of compound of example 322) (0.0260 g, 0.0874 mmol), hexanal (0.0195 mL, 0.162 mmol), and sodium borohydride (0.0076 g, 0.200 mmol) provide 0.0100 g (30%) of the title compound as an off-white foam: high resolution mass spectrum (electrospray): m/z calc for $C_{13}H_{32}N_3O_2$ 382.2495, found 382.2513; $^1$H NMR (methanol-d$_4$): 8.66 (d, 1H, J=2.0 Hz), 8.29 (dd, 1H, J=2.4, 8.8 Hz), 7.41-7.35 (m, 2H), 7.16-7.11 (m, 2H), 7.02 (d, 1H, J=8.3 Hz), 3.23-3.16 (m, 2H), 2.95 (tt, 1H, J=3.4, 11.7 Hz), 2.63-2.56 (m, 2H), 2.35-2.22 (m, 2H), 2.05-1.90 (m, 2H), 1.83 (tq, 1H, J=3.9, 13.7 Hz), 1.70-1.56 (m, 3H), 1.45-1.30 (m, 6H), 0.96 (t, 3H, J=6.3 Hz).

EXAMPLE 329

(±)-6-{4-[1-(3-Methyl-butyl)-piperidin-3-yl]-phenoxy}-nicotinamide

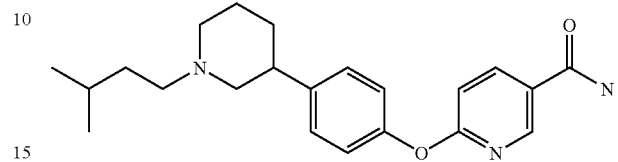

Using a method similar to Example 324, 6-(4-piperidin-3-yl-phenoxy)-nicotinamide (free base of compound of example 322) (0.0252 g, 0.0847 mmol), isovaleraldeldyde (0.0165 mL, 0.154 mmol), and sodium borohydride (0.0082 g, 0.217 mmol) provide 0.0100 g (32%) of the title compound as an off-white foam: high resolution mass spectrum (electrospray): m/z calc for $C_{22}H_{30}N_3O_2$ 368.2338, found 368.2355; $^1$H NMR (methanol-d$_4$): 8.66 (d, 1H, J=2.4 Hz), 8.29 (dd, 1H, J=2.4, 8.8 Hz), 7.41-7.36 (m, 2H), 7.17-7.12 (m, 2H), 7.03 (d, 1H, J=8.8 Hz), 3.28-3.19 (m, 2H), 2.96 (tt, 1H, J=3.4, 11.7 Hz), 2.71-2.63 (m, 2H), 2.43-2.28 (m, 2H), 2.06-1.92 (m, 2H), 1.84 (qt, 1H, J=3.9, 13.2 Hz), 1.71-1.51 (m, 4H), 0.99 (d, 6H, J=6.3 Hz).

EXAMPLE 330

(±)-6-[4-(1-Phenethyl-piperidin-3-yl)-phenoxy]-nicotinamide

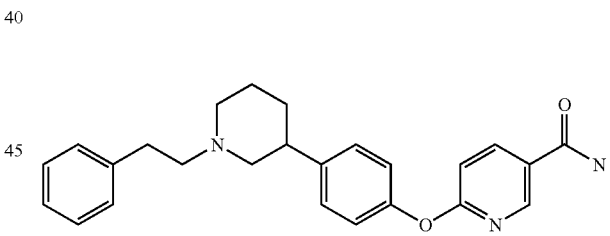

Combine 6-(4-piperidin-3-yl-phenoxy)-nicotinamide (compound of example 322) (0.0237 g, 0.0797 mmol), (2-bromoethyl)benzene (0.0108 mL, 0.0791 mmol), and potassium carbonate (0.0237 g, 0.171 mmol) in dimethylformamide (0.96 mL) and stir for 15 min. Then purify the reaction mixture by ion exchange chromatography (SCX resin, methanol→2 M ammonia in methanol) to provide 0.0204 g (64%) of the title compound as an off-white foam: high resolution mass spectrum (electrospray): m/z calc for $C_{25}H_{28}N_3O_2$ 402.2182, found 402.2182; $^1$H NMR (methanol-d$_4$): 8.66 (d, 1H, J=2.0 Hz), 8.28 (dd, 1H, J=2.9.8.3 Hz), 7.37 (d, 2H, J=7.8 Hz), 7.33-7.27 (m, 2H), 7.27-7.18 (m, 3H), 7.12 (d, 2H, J=8.3 Hz), 7.01 (d, 1H, J=8.8 Hz), 3.15 (d, 2H, J=11.2 Hz), 2.97-2.85 (m, 3H), 2.73-2.65 (m, 2H), 2.19 (q, 2H, J=11.2 Hz), 2.03-1.74 (m, 3H), 1.59 (dq, 1H, J=4.4, 12.7 Hz).

EXAMPLE 331

(±)-6-{4-[1-(2-Cyclohexyl-ethyl)-piperidin-3-yl]-phenoxy}-nicotinamide

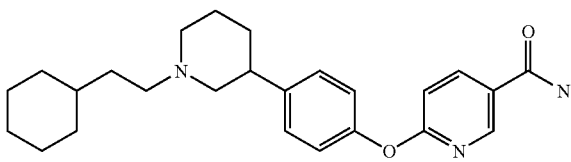

Combine 6-(4-Piperidin-3-yl-phenoxy)-nicotinamide (free base compound of example 322) (0.0255 g, 0.0858 mmol), 1-bromo-2-cyclohexylethane (0.0150 mL, 0.0958 mmol), and potassium carbonate (0.0245 g, 0.177 mmol) in dimethylformamide (1.0 mL) and stir for 10 min. Purify the reaction mixture by ion exchange chromatography (SCX resin, methanol→2 M ammonia/methanol) and silica gel chromatography (15:1→10:1 ethyl acetate:methanol) to provide 0.0146 g (42%) of the title compound as an off-white foam: high resolution mass spectrum (electrospray): m/z calc for $C_{25}H_{34}N_3O_2$ 408.2651, found 408.2661; $^1$H NMR (methanol-$d_4$): 8.61 (s br, 1H), 8.28 (d, 1H, J=7.8 Hz), 7.36 (d, 2H, J=7.8 Hz), 7.12 (d, 2H, J=7.8 Hz), 7.01 (d, 1H, J=8.3 Hz), 3.07 (d, 2H, J=10.2 Hz), 2.89 (t, 1H, J=11.2 Hz), 2.55-2.42 (m, 2H), 2.15-1.93 (m, 4H), 1.93-1.64 (m, 8H), 1.63-1.43 (m, 4H), 1.40-1.15 (m, 8H), 1.07-0.86 (m, 3H).

EXAMPLE 332

6-[4-(4-Benzyl-piperazin-1-ylmethyl)-phenoxy]-nicotinamide

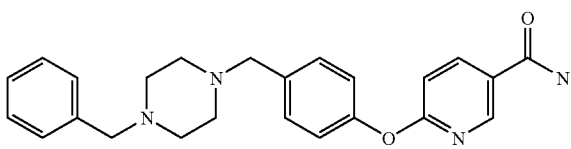

Step 1

6-(4-Formyl-phenoxy)-nicotinamide

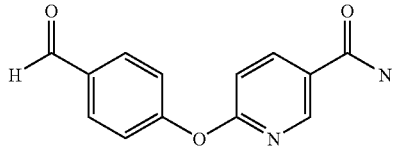

Combine 4-hydroxy benzaldehyde (7.201 g, 59.0 mmol), 6-chloronicotinamide (9.605 g, 57.5 mmol), and potassium carbonate (19.86 g, 143.7 mmol) in dimethylacetamide (190 mL). Stir and heat at 130° C. After 18 h, cool to ambient temperature and dilute with water (600 mL). Extract aqueous layer with ethyl acetate (3×500 mL). Wash combined ethyl acetate extracts with water (1×) and brine (1×), successively, dry over anhydrous magnesium sulfate, filter, and concentrate. Purification by silica gel chromatography (1:1 ethyl acetate:hexanes→ethyl acetate) to provide 6.852 g (49%, 90% pure) of the title compound as a white solid: mass spectrum (electrospray): m/z=243.0 (M+1); $^1$H NMR (methanol-$d_4$): 9.97 (s, 1H), 8.70 (d, 1H, J=2.4 Hz), 8.36 (dd, 1H, J=2.4, 8.8 Hz), 8.06-8.02 (m, 2H), 7.42-7.37 (m, 2H), 7.19 (d, 1H, J=9.3 Hz).

Step 2

6-[4-(4-Benzyl-piperazin-1-ylmethyl)-phenoxy]-nicotinamide

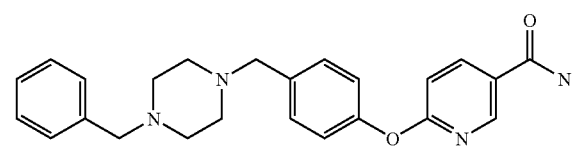

Combine 6-(4-formyl-phenoxy)-nicotinamide (from step 1 above) (0.300 g, 1.24 mmol) and 1-benzylpiperazine (0.35 mL, 2.01 mmol) in methanol (12 mL) and stir at ambient temperature. After 15 h, add sodium borohydride (0.108 g, 2.85 mmol) and stir. After 1 h, filter the white precipitate and dry under vacuum to give 0.283 g (57%) of the title compound as a white solid: high resolution mass spectrum (electrospray): m/z calc for $C_{24}H_{17}N_4O_2$ 403.2134, found 403.2128: $^1$H NMR (DMSO-$d_6$): 8.63 (d, 1H, J=1.5 Hz), 8.27 (dd, 1H, J=2.4, 8.3 Hz), 8.05 (s br, 1H), 7.50 (s br, 1H), 7.39-7.23 (m, 7H), 7.15-7.06 (m, 3H), 3.48 (m, 4H), 2.41 (s br, 8H).

EXAMPLE 333

6-[4-(4-Phenethyl-piperazin-1-ylmethyl)-phenoxy]-nicotinamide

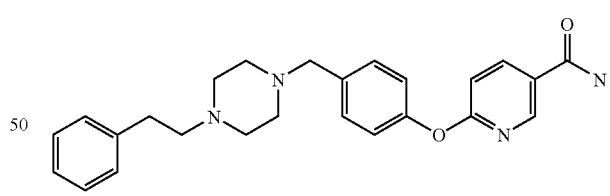

Using a method similar to Example 332, using 6-(4-formyl-phenoxy)-nicotinamide (compound of example 332, step 1) (0.304 g, 1.26 mmol), 1-(2-phenethyl) piperazine (0.360 g, 1.89 mmol), and sodium borohydride (0.109 g, 2.88 mmol) in methanol (10 mL) provides 0.246 g (47%) of the title compound as a white solid: high resolution mass spectrum (electrospray): m/z calc for $C_{25}H_{29}N_4O_2$ 417.2291, found 417.2291; $^1$H NMR (DMSO-$d_6$): 8.60 (d, 1H, J=2.4 Hz), 8.23 (dd, 1H, J=2.4, 8.8 Hz), 7.32 (d, 2H, J=8.8 Hz), 7.28-7.21 (m, 2H), 7.21-7.12 (m, 3H), 7.08 (d, 2H, J=8.8 Hz), 7.03 (d, 1H, J=8.8 Hz), 3.45 (s, 2H), 2.74-2.62 (m, 2H), 2.52-2.26 (m, 10H).

EXAMPLE 334

6-[4-(4-Cyclopentyl-piperazin-1-ylmethyl)-phenoxy]-nicotinamide

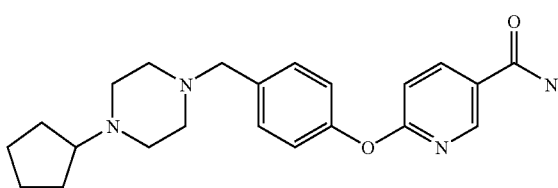

Combine 6-(4-formyl-phenoxy)-nicotinamide (compound of example 332, step 1) (0.303 g, 1.25 mmol) and 1-cyclopentyl piperazine (0.198 g, 1.28 mmol) in methanol (11 mL) and stir. After 15.5 h, add sodium borohydride (0.109 g, 2.88 mmol), and stir at ambient temperature. After 1 h, concentrate the reaction mixture and purify by silica gel chromatography (ethyl acetate→4:1 ethyl acetate:methanol) to provide 0.172 g (36%) of the title compound as an off white solid: high resolution mass spectrum (electrospray): m/z calc for $C_{22}H_{29}N_4O_2$ 381.2291, found 381.2306; $^1$H NMR (DMSO-$d_6$): 8.66 (d, 1H, J=2.4 Hz), 8.30 (dd, 1H, J=2.9, 8.8 Hz), 7.48-7.43 (m, 2H), 7.18-7.13 (m, 2H), 7.04 (d, 1H, J=7.8 Hz), 3.61 (s, 2H), 3.00-2.25 (m, 9H), 2.01-1.88 (m, 2H), 1.82-1.69 (m, 2H), 1.69-1.56 (m, 2H), 1.53-1.38 (m, 2H).

EXAMPLE 335

(±)-6-{4-[4-(1-Phenyl-ethyl)-piperazin-1-ylmethyl]-phenoxy}-nicotinamide

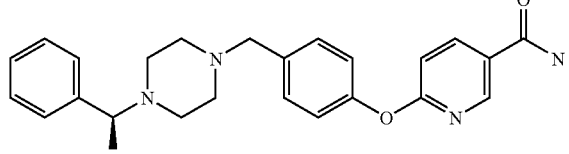

Using a method similar to Example 332, using 6-(4-formyl-phenoxy)-nicotinamide (compound of example 332, step 1) (0.307 g, 1.27 mmol), 1-(1-phenylethyl) piperizine (0.365 g, 1.92 mmol), and sodium borohydride (0.108 g, 2.85 mmol) in methanol (10 mL), after 1 d, provides 0.122 g (23%) of the title compound as a white solid: high resolution mass spectrum (electrospray): m/z calc for $C_{25}H_{29}N_4O_2$ 417.2291, found 417.2298; $^1$H NMR (DMSO-$d_6$): 8.62 (d, 1H, J=2.0 Hz), 8.26 (dd, 1H, J=2.4, 8.8 Hz), 8.01 (s br, 1H), 7.46 (s br, 1H), 7.36-7.28 (m, 6H), 7.27-7.21 (m, 1H), 7.12-7.05 (m, 3H), 3.42 (s, 2H), 3.39 (q, 1H, J=6.8 Hz), 2.51-2.25 (s br, 8H), 1.29 (d, 3H, J=6.8 Hz).

EXAMPLE 336

6-[4-(4-Benzhydryl-piperazin-1-ylmethyl)-phenoxy]-nicotinamide

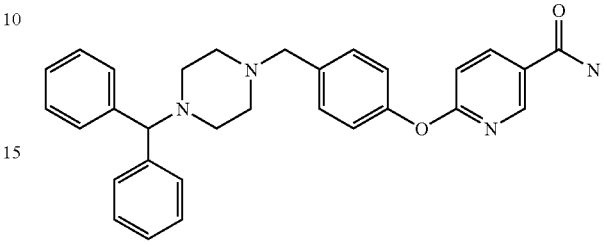

Using a method similar to Example 334, using 6-(4-formyl-phenoxy)-nicotinamide (compound of example 332, step 1) (0.300 g, 1.24 mmol), 1-benzhydryl-piperazine (0.470 g, 1.86 mmol), and sodium borohydride (0.111 g, 2.93 mmol) in methanol (12 mL) after additional purification by reverse-phase HPLC, provides 0.143 g (24%) of the title compound as a yellow foam: high resolution mass spectrum (electrospray): m/z calc for $C_{30}H_{31}N_4O_2$ 479.2447, found 479.2462; $^1$H NMR (methanol-$d_4$): 8.65 (d, 1H, J=2.0 Hz), 8.29 (dd, 1H, J=2.4, 8.8 Hz), 7.49-7.42 (m, 6H), 7.30 (t, 4H, J=7.8 Hz), 7.23-7.17 (m, 2H), 7.14 (d, 2H, J=8.8 Hz), 7.03 (d, 1H, J=8.8 Hz), 4.28 (s, 1H), 3.63 (s, 2H), 2.72-2.30 (m, 8H).

EXAMPLE 337

6-{4-[4-(4-Fluoro-phenyl)-piperazin-1-ylmethyl]-phenoxy}-nicotinamide

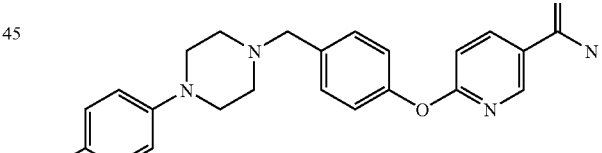

Combine 6-(4-formyl-phenoxy)-nicotinamide (compound of example 332, step 1) (0.299 g, 1.23 mmol), 1-(4-fluorophenyl)-piperizine, bis hydrochloride salt (0.314 g, 1.24 mmol), triethylamine (0.36 mL, 2.58 mmol) in methanol (12 mL) and stir. After 23 h, add sodium borohydride (0.108 g, 2.85 mmol). After 1 d, concentrate and purify the residue by silica gel chromatography (25:1→4:1 methylene chloride:methanol) to provide 0.107 g (21%) of the title compound as a white solid: high resolution mass spectrum (electrospray): m/z calc for $C_{23}H_{24}FN_4O_2$ 407.1883, found 407.1883; $^1$H NMR (methanol-$d_4$): 8.67 (d, 1H, J=2.4 Hz), 8.30 (dd, 1H, J=2.4; 8.8 Hz), 7.52-7.47 (m, 2H), 7.20-7.15 (m, 2H), 7.05 (d, 1H, J=7.8 Hz), 7.01 (d, 1H, J=6.3 Hz), 3.66 (s, 2H), 3.21-3.16 (m, 4H), 2.74-2.68 (m, 4H).

EXAMPLE 338

6-[4-(4-Phenyl-piperazin-1-ylmethyl)-phenoxy]-nicotinamide

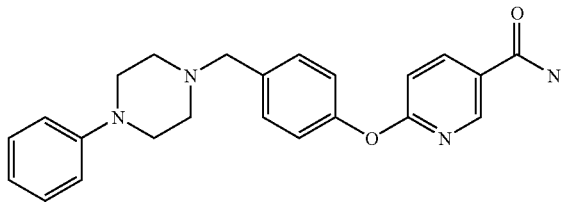

Using a method similar to Example 334, using 6-(4-formyl-phenoxy)-nicotinamide (compound of example 332, step 1) (0.302 g, 1.25 mmol), 1-phenyl-piperazine (0.192 mL, 1.26 mmol), and sodium borohydride (0.110 g, 2.91 mmol) in methanol (12 mL) provides 0.0627 g (13%) of the title compound as a white solid Chromatography solvent: 25:1 methylene chloride:methanol. High resolution mass spectrum (electrospray): m/z calc for $C_{23}H_{25}N_4O_2$ 389.1978, found 389.1993; $^1$H NMR (methanol-$d_4$): 8.67 (d, 1H, J=2.0 Hz), 8.30 (dd, 1H, J=2.9, 8.8 Hz), 7.50 (d, 2H, J=8.8 Hz), 7.27 (dd, 2H, J=7.3, 8.8 Hz), 7.20-7.15 (m, 2H), 7.05 (d, 1H, J=8.3 Hz), 7.03-6.99 (m, 2H), 6.88 (t, 1H, J=7.3 Hz), 3.67 (s, 2H), 3.27-3.21 (m, 4H), 2.74-2.69 (m, 4H).

EXAMPLE 339

6-[4-(4-Cyclohexyl-piperazin-1-ylmethyl)-phenoxy]-nicotinamide

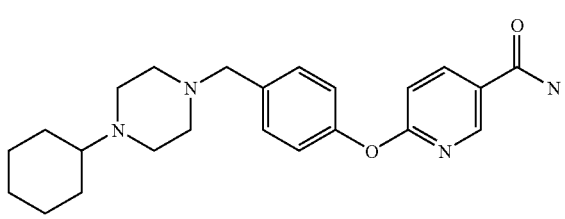

Using a method similar to Example 334, using 6-(4-formyl-phenoxy)-nicotinamide (compound of example 332, step 1) (0.299 g, 1.23 mmol), 1-cyclohexyl-piperazine (0.208 g, 1.24 mmol), and sodium borohydride (0.107 g, 2.83 mmol) in methanol (12 mL) provides 0.158 g (32%) of the title compound as a white solid (chromatography solvent: 20:1→10:1 methylene chloride:methanol). High resolution mass spectrum (electrospray): m/z calc for $C_{23}H_{31}N_4O_2$ 395.2447, found 395.2461; $^1$H NMR (methanol-$d_4$): 8.66 (d, 1H, J=2.0 Hz), 8.30 (dd, 1H, J=2.4, 8.8 Hz), 7.48-7.43 (m, 2H), 7.18-7.13 (m, 2H), 7.04 (d, 1H, J=8.3 Hz), 3.61 (s, 2H), 2.82-2.53 (m, 8H), 2.39-2.29 (m, 1H), 2.03-1.96 (m, 2H), 1.91-1.83 (m, 2H), 1.73-1.66 (m, 1H), 1.40-1.15 (m, 5H).

EXAMPLE 340

6-[4-(4-Isopropyl-piperazin-1-ylmethyl)-phenoxy]-nicotinamide

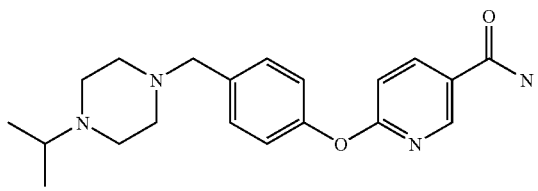

Using a method similar to Example 334, using 6-(4-formyl-phenoxy)-nicotinamide (compound of example 332, step 1) (0.304 g, 1.26 mmol), 1-isopropyl-piperazine (0.161 g, 1.26 mmol), and sodium borohydride (0.108 g, 2.85 mmol) in methanol (12 mL) provides 0.158 g (32%) of the title compound as a white solid (chromatography solvent: ethyl acetate→7:3 ethyl acetate:methanol): high resolution mass spectrum (electrospray): m/z calc for $C_{20}H_{27}N_4O_2$ 355.2134, found 355.2140; $^1$H NMR (methanol-$d_4$): 8.67 (d, 1H, J=2.0 Hz), 8.30 (dd, 1H, J=2.4, 8.8 Hz), 7.48-7.43 (m, 2H), 7.18-7.13 (m, 2H), 7.04 (d, 1H, J=8.3 Hz), 3.56 (s, 2H), 2.79-2.52 (m, 9H), 1.13 (d, 6H, J=6.8 Hz).

EXAMPLE 341

(3R)-6-{4-[(1-Benzyl-pyrolidin-3-ylamino)-methyl]-phenoxy}-nicotinamide

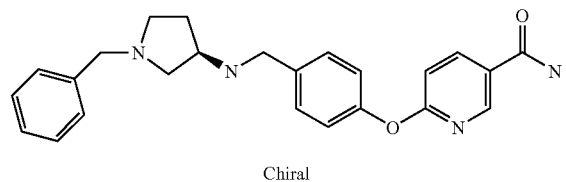

Chiral

Using a method similar to Example 334, using 6-(4-formyl-phenoxy)-nicotinamide (compound of example 332, step 1) (0.300 g, 1.24 mmol), (3R)-1-benzylpyrrolidin-3-yl amine (0.22 mL, 1.27 mmol), and sodium borohydride (0.108 g, 2.85 mmol) in methanol (12 mL) provides 0.154 g (31%) of the title compound as a white foam (chromatography solvent: ethyl acetate→4:1 ethyl acetate:methanol): high resolution mass spectrum (electrospray): m/z calc for $C_{24}H_{27}N_4O$, 403.2134, found 403.2131; $^1$H NMR (methanol-$d_4$): 8.66 (d, 1H, J=2.4 Hz), 8.29 (dd, 1H, J=2.9, 8.8 Hz), 7.48-7.42 (m, 2H), 7.40-7.27 (m, 5H), 7.17-7.12 (m, 2H), 7.02 (d, 1H, J=9.3 Hz), 3.79 (d, 1H, J=13.2 Hz), 3.76 (d, 1H, J=13.7 Hz), 3.69 (d, 1H, J=12.7 Hz), 3.67 (d, 1H, J=-12.7 Hz), 3.44-3.36 (m, 1H), 2.92 (dd, 1H, J=7.3, 9.8 Hz), 2.69 (t, 2H, J=6.8 Hz), 2.44 (dd, 1H, J=6.3, 10.2 Hz), 2.25-2.14 (m, 1H), 1.77-1.67 (m, 1H).

EXAMPLE 342

(3S)-6-{4-[(1-Benzyl-pyrrolidin-3-ylamino)-methyl]-phenoxy}-nicotinamide

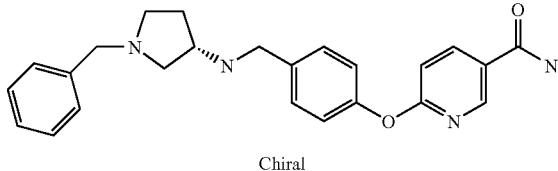

Chiral

Using a method similar to Example 334, and using 6-(4-formyl-phenoxy)-nicotinamide (compound of example 332, step 1) (0.300 g, 1.24 mmol), (3S)-1-benzylpyrrolidin-3yl amine (0.21 mL, 1.22 mmol), and sodium borohydride (0.108 g, 2.85 mmol) in methanol (12 mL) provides 0.214 g (43%) of the title compound as a white foam (chromatography solvent: ethyl acetate→19:1 ethyl acetate:methanol): high resolution mass spectrum (electrospray): m/z calc for $C_{24}H_{27}N_4O_2$ 403.2134, found 403.2144; $^1$H NMR (methanol-$d_4$): 8.66 (d, 1H, J=2.4 Hz), 8.29 (dd, 1H, J=2.9, 8.8 Hz), 7.48-7.42 (m, 2H), 7.40-7.27 (m, 5H), 7.17-7.12 (m, 2H), 7.02 (d, 1H, J=9.3 Hz), 3.79 (d, 1H, J=13.2 Hz), 3.76 (d, 1H, J=13.7 Hz), 3.69 (d, 1H, J=12.7 Hz), 3.67 (d, 1H, J=12.7 Hz), 3.44-3.36 (m, 1H), 2.92 (dd, 1H, J=7.3, 9.8 Hz), 2.69 (t, 2H, J=6.8 Hz), 2.44 (dd, 1H, J=6.3, 10.2 Hz), 2.25-2.14 (m, 1H), 1.77-1.67 (m, 1H).

EXAMPLE 343

(±)-6-[4-(2-Phenyl-piperidin-1-ylmethyl)-phenoxy]-nicotinamide

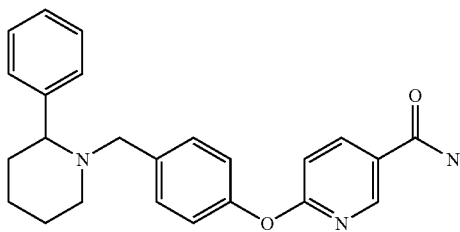

Combine 6-(4-formyl-phenoxy)-nicotinamide (compound of example 332, step 1) (0.152 g, 0.628 mmol), 2-phenyl-piperidine hydrochloride salt (0.122 g, 0.620 mmol), triethylamine (0.178 mL, 1.28 mmol) in methanol (6.0 mL) and stir. After 21 hours, add sodium borohydride (0.108 g, 2.85 mmol). After about 24 hours, concentrate and purify the residue by silica gel chromatography (25:1→4:1 methylene chloride:methanol) then reverse-phase HPLC to provide 0.0047 g (2%) of the title compound as a white solid: mass spectrum (electrospray): m/z=388.2 (M+1); $^1$H NMR (methanol-$d_4$): 8.66 (d, 1H, J=2.4 Hz), 8.29 (dd, 1H, J=2.4, 8.3 Hz), 7.52 (d, 2H, J=7.3 Hz), 7.41 (t, 2H, J=7.3 Hz), 7.37-7.28 (m, 3H), 7.11 (d, 2H, J=8.3 Hz), 7.02 (d, 1H, J=8.8 Hz), 3.81 (d, 1H, J=10.7 Hz), 3.39 (s, 2H), 3.20-2.94 (m, 2H), 2.17 (s br, 1H), 1.93-1.61 (m, 4H), 1.59-1.44 (m, 1H).

EXAMPLE 344

(±)-6-[4-(2-Phenyl-pyrrolidin-1-ylmethyl)-phenoxy]-nicotinamide hydrochloride

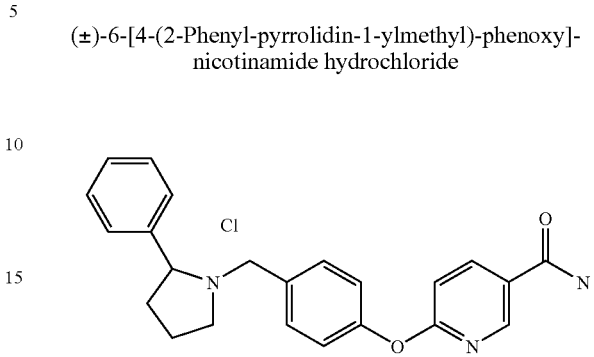

Combine 6-(4-formyl-phenoxy)-nicotinamide (compound of example 332, step 1) (0.150 g, 0.619 mmol), 2-phenyl-pyrrolidine (0.095 g, 0.64 mmol), sodium triacetoxyborohydride (0.194 g, 0.915 mmol) and acetic acid (0.051 mL, 0.891 mmol) in 1,2-dichloroethane (9.0 mL). After about 24 hours, purify the reaction mixture by ion exchange chromatography (SCX resin, methanol→2 M ammonia/methanol) and concentrate. Dissolve the residue in 1,4-dioxane and treated with 4 N hydrochloric acid in dioxane. Isolate the white precipitate by vacuum filtration. The solid became a yellowish syrup after approximately 3 min. on vacuum. Dissolve the residue in 1,4-dioxane and concentrate to provide 0.0100 g (3.9%) of the title compound as a white/yellow foam: high resolution mass spectrum (electrospray): m/z calc for $C_{23}H_{24}N_3O_2$ 374.1869, found 374.1877; $^1$H NMR (methanol-$d_4$): 8.63 (s, 1H), 8.35 (dd, 1H, J=1.5, 7.8 Hz), 7.64-7.44 (m, 7H), 7.24 (d, 2H, J=8.8 Hz), 7.11 (d, 1H, J=8.8 Hz), 4.69-4.60 (m, 1H), 4.28 (s, 2H), 3.75-3.66 (m, 1H), 3.58-3.47 (m, 1H), 2.71-2.60 (m, 1H), 2.45-2.22 (m, 3H).

EXAMPLE 345

(±)-6-[4-(3-Phenyl-pyrrolidin-1-ylmethyl)-phenoxy]-nicotinamide

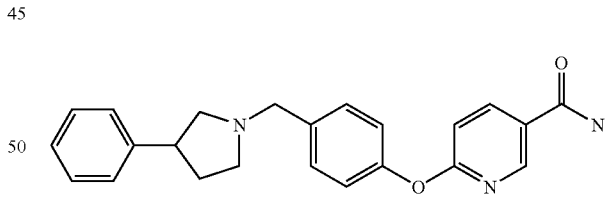

Convert 3-phenyl-pyrrolidine phosphoric acid salt (0.152 g, 1.03 mmol) to the free base by ion exchange chromatography (SCX resin, methanol→2 M ammonia/methanol) and then concentrate. Combine free base with 6-(4-formyl-phenoxy)-nicotinamide (compound of example 332, step 1) (0.150 g, 0.618 mmol), sodium triacetoxyborohydride (0.201 g, 0.948 mmol), and acetic acid (0.053 mL, 0.891 mmol) in 1,2-dichloroethane (9.5 mL) and stir at ambient temperature. After 1 d, purify the reaction mixture by ion exchange chromatography (SCX resin, methanol→2 M ammonia in methanol) and concentrate to provide 0.204 g (88%) of the title compound as a white solid: high resolution mass spectrum (electrospray): m/z calc for $C_{23}H_{24}N_3O_2$ 374.1869, found 374.1887; $^1$H NMR (methanol-$d_4$): 8.67 (dd, 1H, J=1.0, 2.4

Hz), 8.29 (dd, 1H, J=2.4, 8.8 Hz), 7.52-7.47 (m, 2H), 7.34-7.28 (m, 4H), 7.25-7.14 (m, 3H), 7.03 (dd, 1H, J=1.0, 8.8 Hz), 3.80 (d, 1H, J=13.2 Hz), 3.77 (d, 1H, J=12.7 Hz), 3.48-3.38 (m, 1H), 3.16 (dd, 1H, J=7.8, 9.3 Hz), 3.00-2.93 (m, 1H), 2.85-2.77 (m, 1H), 2.58 (t, 1H, J=8.8 Hz), 2.44-2.32 (m, 1H), 2.02-1.91 (m, 1H).

EXAMPLE 346

6-[4-(4-Phenyl-piperidin-1-ylmethyl)-phenoxy]-nicotinamide

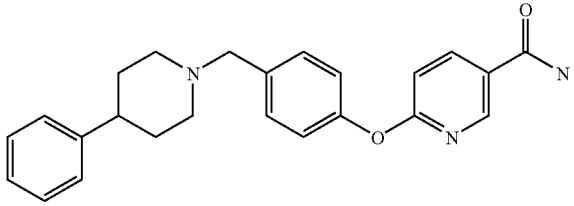

Using a method similar to Example 342, using 4-phenyl-piperidine hydrochloride salt (0.0823 g, 0.416 mmol), 6-(4-formyl-phenoxy)-nicotinamide (compound of example 332, step 1) (0.100 g, 0.415 mmol), sodium triacetoxyborohydride (0.136 g, 0.642 mmol), and acetic acid (0.034 mL, 0.594 mmol) in 1,2-dichloroethane (8.0 mL) provides 0.150 g (94%) of the title compound as a white solid: high resolution mass spectrum (electrospray): m/z calc for $C_{24}H_{26}N_3O_2$ 388.2025, found 388.2039; $^1$H NMR (methanol-$d_4$): 8.67 (d, 1H, J=2.6 Hz), 8.30 (dd, 1H, 2.6, 8.8 Hz), 7.49 (d, 2H, J=8.8 Hz), 7.35-7.25 (m, 4H), 7.23-7.15 (m, 3H), 7.05 (d, 1H, J=8.8 Hz), 3.65 (s, 2H), 3.12 (d, 2H, J=11.9 Hz), 2.65-2.54 (m, 1H), 2.24 (dt, 2H, J=4.0, 11.0 Hz), 1.94-1.78 (m, 4H).

EXAMPLE 347

(±)-6-[4-(3-Phenyl-azepan-1-ylmethyl)-phenoxy]-nicotinamide

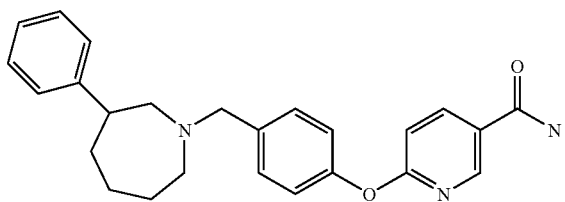

Using a method similar to Example 345, using 3-phenyl-azepane fumaric acid salt (0.122 g, 0.419 mmol), 6-(4-formyl-phenoxy)-nicotinamide (compound of example 332, step 1) (0.100 g, 0.415 mmol), sodium triacetoxyborohydride (0.129 g, 0.609 mmol), and acetic acid (0.034 mL, 0.594 mmol) in 1,2-dichloroethane (8.0 mL) provides 0.154 g (93%) of the title compound as a white solid: high resolution mass spectrum (electrospray): m/z calc for $C_{25}H_{28}N_3O_2$ 402.2182, found 402.2199; $^1$H NMR (DMSO-$d_6$): 8.61 (d, 1H, J=1.8 Hz), 8.25 (dd, 1H, J=2.6, 8.8 Hz), 8.02 (s, 1H), 7.47 (s, 1H), 7.38 (d, 2H, J=8.4 Hz), 7.27-7.02 (m, 5H), 3.70 (d, 1H, J=13.5 Hz), 3.64 (d, 1H, J=13.5 Hz), 2.89-2.63 (m, 5H), 1.81-1.59 (m, 6H).

EXAMPLE 348

(±)-6-[4-(4-Phenyl-azepan-1-ylmethyl)-phenoxy]-nicotinamide

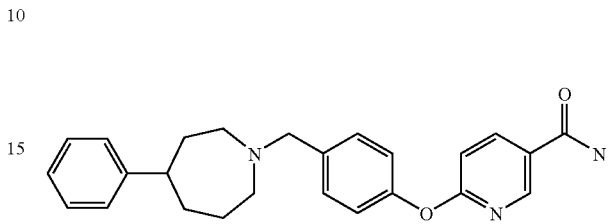

Using a method similar to Example 345, using 3-phenyl-azepane hydrochloric acid salt (0.0874 g, 0.413 mmol), 6-(4-formyl-phenoxy)-nicotinamide (compound of example 332, step 1) (0.101 g, 0.417 mmol), sodium triacetoxyborohydride (0.131 g, 0.618 mmol), and acetic acid (0.035 mL 0.611 mmol) in 1,2-dichloroethane (8.0 mL) provides, after silica gel chromatography (20:1→10:1 methylene chloride:methanol), 0.0368 g (22%) of the title compound as a white solid: high resolution mass spectrum (electrospray): m/z calc for $C_{25}H_{29}N_3O_2$ 402.2182, found 402.2195; $^1$H NMR (methanol-$d_4$): 8.67 (d, 1H, J=2.0 Hz), 8.30 (dd, 1H, J=2.4, 9.3 Hz), 7.52 (d, 2H, J=7.3 Hz), 7.33-7.23 (m, 4H), 7.22-7.15 (m, 3H), 7.06 (d, 1H, J=8.8 Hz), 3.84 (s, 2H), 3.08-2.77 (m, 5H), 2.05-1.78 (m, 6H).

EXAMPLE 349

6-[4-(4,4-Diphenyl-piperidin-1-ylmethyl)-phenoxy]-nicotinamide

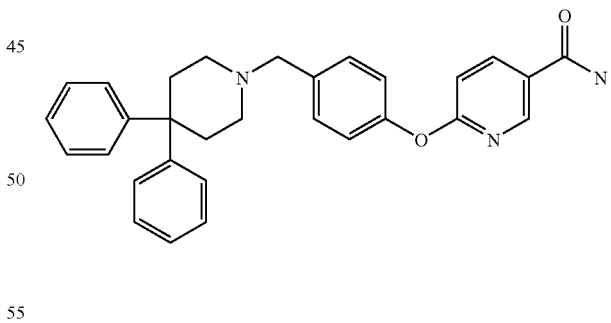

Using a method similar to Example 345, using 4,4-diphenyl-piperidine (0.100 g, 0.421 mmol), 6-(4-formyl-phenoxy)-nicotinamide (compound of example 332, step 1) (0.102 g, 0.419 mmol), sodium triacetoxyborohydride (0.133 g, 0.627 mmol), and acetic acid (0.038 mL, 0.664 mmol) in 1,2-dichloroethane (8.0 mL) provides, after silica gel chromatography (20:1 methylene chloride:methanol), 0.0871 g (45%) of the title compound as a white solid: high resolution mass spectrum (electrospray): m/z calc for $C_{30}H_{30}N_3O_2$ 464.2338, found 464.2357; $^1$H NMR (methanol-$d_4$): 8.67 (d, 1H, J=2.4 Hz), 8.29 (dd, 1H, J=2.0, 7.8 Hz), 7.43 (d, 2H, J=7.8

Hz), 7.38-7.27 (m, 5H), 7.19-7.11 (m, 4H), 7.02 (d, 1H, J=8.8 Hz), 3.55-3.50 (m, 2H), 2.71-2.51 (m, 8H).

EXAMPLE 350

6-[4-(3,3-Diphenyl-pyrrolidin-1-ylmethyl)-phenoxy]-nicotinamide

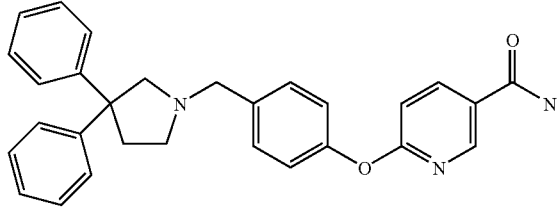

Using a method similar to Example 345, using 3,3-diphenyl-pyrrolidine hydrochloride salt (0.107 g, 0.412 mmol), 6-(4-formyl-phenoxy)-nicotinamide (compound of example 332, step 1) (0.100 g, 0.415 mmol), sodium triacetoxyborohydride (0.133 g, 0.628 mmol), and acetic acid (0.035 mL 0.611 mmol) in 1,2-dichloroethane (8.0 mL) provides 0.196 g (106%) of the title compound as a white solid: high resolution mass spectrum (electrospray): m/z calc for $C_{29}H_{28}N_3O_2$ 450.2182, found 450.2205; $^1$H NMR (methanol-$d_4$): 8.68 (d, 1H, J=2.4 Hz), 8.30 (dd, 1H, J=2.4, 8.8 Hz), 7.46 (d, 2H, J=7.3 Hz), 7.35-7.26 (m, 8H), 7.21-7.12 (m, 4H), 7.04 (d, 1H, J=8.8 Hz), 3.75 (s, 2H), 3.38-3.24 (m, 2H), 2.98-2.91 (m, 2H), 2.71-2.64 (m, 2H).

EXAMPLE 351

6-[4-(2,2-Diphenyl-pyrrolidin-1-ylmethyl)-phenoxy]-nicotinamide

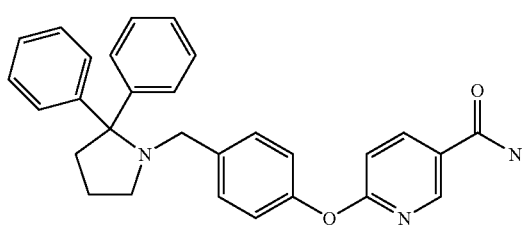

Using a method similar to Example 345, using 3,3-diphenyl-pyrrolidine hydrochloride salt (0.108 g, 0.416 mmol), 6-(4-formyl-phenoxy)-nicotinamide (compound of example 332, step 1) (0.101 g, 0.417 mmol), sodium triacetoxyborohydride (0.132 g, 0.623 mmol) and acetic acid (0.035 mL, 0.611 mmol) in 1,2-dichloroethane (8.0 mL) provides, after silica gel chromatography (20:1 methylene chloride:methanol), 0.0646 g (34%) of the title compound as a white solid: high resolution mass spectrum (electrospray): m/z calc for $C_{29}H_{28}N_3O_2$ 450.2182, found 450.2204; $^1$H NMR (methanol-$d_4$): 8.67 (d, 1H, J=2.4 Hz), 8.29 (dd, 1H, J=2.0, 8.3 Hz), 7.50 (d, 2H, J=8.3 Hz), 7.44-7.35 (m, 8H), 7.34-7.27 (m, 2H), 7.15 (d, 2H, J=8.8 Hz), 7.03 (d, 1H, J=7.8 Hz), 3.30 (s, 2H), 2.70 (t, 2H, J=6.8 Hz), 2.54-2.45 (m, 2H), 2.11-1.99 (m, 2H).

EXAMPLE 352

6-(4-Piperidin-1-ylmethyl-phenoxy)-nicotinamide

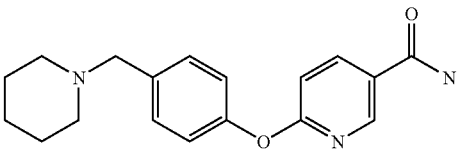

Using a method similar to Example 345, using piperidine (0.041 mL, 0.414 mmol), 6-(4-formyl-phenoxy)-nicotinamide (compound of example 332, step 1) (0.1100 g, 0.413 mmol), sodium triacetoxyborohydride (0.131 g, 0.618 mmol), and acetic acid (0.036 mL, 0.629 mmol) in 1,2-dichloroethane (8.0 mL) provides, after silica gel chromatography (10:1→3:1 methylene chloride:methanol), 0.114 g (88%) of the title compound as a white foam: high resolution mass spectrum (electrospray): m/z calc for $C_{18}H_{22}N_3O_2$ 312.1712, found 312.1722, $^1$H NMR (DMSO-$d_6$): 8.63 (d, 1H, J=2.0 Hz), 8.27 (dd, 1H, J=2.4, 8.8 Hz), 8.06 (s br, 1H), 7.50 (s br, 1H), 7.33 (s, 2H, =8.3 Hz), 7.15-7.06 (m, 3H), 3.44 (s, 2H), 2.35 (s, 4H), 1.57-1.48 (m, 4H), 1.46-1.36 (m, 2H).

EXAMPLE 353

(±)-6-[4-(1,2,4,4a,9,9a-Hexahydro-3-aza-fluoren-3-ylmethyl)-phenoxy]-nicotinamide

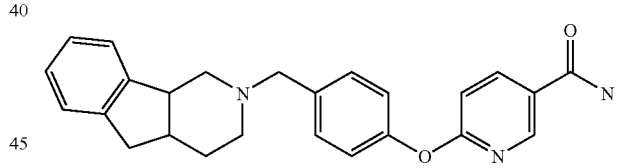

Using a method similar to Example 345, using 4-(1,2,4,4a, 9,9a-hexahydro-3-aza-fluorene hydrochloric acid salt (0.0866 g, 0.413 mmol), 6-(4-formyl-phenoxy)-nicotinamide (compound of example 332, step 1) (0.100 g, 0.413 mmol), sodium triacetoxyborohydride (0.131 g, 0.618 mmol), and acetic acid (0.034 mL, 0.594 mmol) in 1,2-dichloroethane (8.0 mL) provides, after silica gel chromatography (20:1→10:1 methylene chloride:methanol), 0.0966 g (58%) of the title compound as a white foam: high resolution mass spectrum (electrospray): m/z calc for $C_{25}H_{26}N_3O_2$ 400.2025, found 400.2049; $^1$H NMR (DMSO-$d_6$): 8.64 (d, 1H, J=2.4 Hz), 8.27 (dd, 1H, J=2.0, 7.8 Hz), 8.05 (s br, 1H), 7.50 (s br, 1H), 7.36-7.30 (m, 2H), 7.27-7.22 (m, 1H), 7.16-7.06 (m, 6H), 3.53-3.43 (m, 2H), 3.13 (q, 1H, J=5.9 Hz), 2.86 (dd, 1H, J=6.8, 15.6 Hz), 2.72-2.60 (m, 2H), 2.58-2.50 (m, 1H), 2.48-2.39 (m, 2H), 2.31-2.22 (m, 1H), 1.76-1.67 (m, 1H), 1.45-1.34 (m, 1H).

EXAMPLE 354

(±)-6-{4-[3-(2-Chloro-phenyl)-piperidin-1-ylmethyl]-phenoxy}-nicotinamide

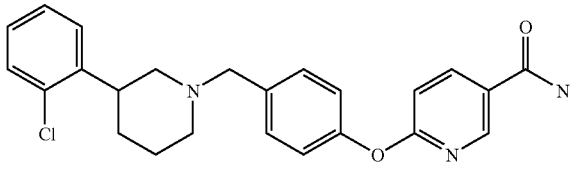

Using a method similar to Example 345, 3-(2-chloro-phenyl)-piperidine fumaric acid salt (0.128 g, 0.410 minor), 6-(4-formyl-phenoxy)-nicotinamide (compound of example 332, step 1) (0.101 g, 0.417 mmol), sodium triacetoxyborohydride (0.129 g, 0.609 mmol), and acetic acid (0.034 mL, 0.594 mmol) in 1,2-dichloroethane (8.0 mL) provides, after silica gel chromatography (20:1→10:1 methylene chloride:methanol) and reverse-phase HPLC, 0.109 g (62%) of the title compound as a white foam: high resolution mass spectrum (electrospray): m/z calc for $C_{24}H_{25}ClN_3O_2$ 422.1635, found 422.1664; $^1$H NMR (methanol-$d_4$): 8.67 (d, 1H, J=2.2 Hz), 8.29 (dd, 1H, J=2.2, 8.3 Hz), 7.47 (d, 2H, J=8.8 Hz), 7.39 (d, 2H, J=7.9 Hz), 7.30 (t, 1H, J=7.0 Hz), 7.21 (dt, 1H, J=1.3, 7.5 Hz), 7.16 (d, 2H, J=8.8 Hz), 7.03 (d, 1H, J=8.3 Hz), 3.71 (d, 1H, J=13.2 Hz), 3.67 (d, 1H, J=13.6 Hz), 3.43 (tt, 1H, J=3.5, 11.9 Hz), 3.12-3.03 (m, 2H), 2.25-2.11 (m, 2H), 1.98-1.76 (m, 3H), 1.58 (dq, 1H, J=4.8, 11.9 Hz).

EXAMPLE 355

(±)-6-{4-[3-(3-Chloro-phenyl)-piperidin-1-ylmethyl]-phenoxy}-nicotinamide

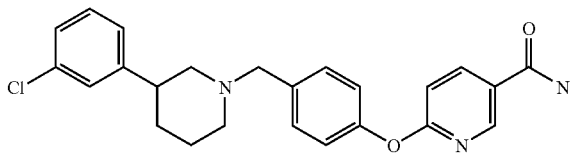

Using a method similar to Example 345, using 3-(3-chloro-phenyl)-piperidine fumaric acid salt (0.129 g, 0.414 mmol), 6-(4-formyl-phenoxy)-nicotinamide (compound of example 332, step 1) (0.100 g, 0.413 mmol) sodium triacetoxyborohydride (0.132 g, 0.623 mmol), and acetic acid (0.035 mL, 0.611 mmol) in 1,2-dichloroethane (8.0 mL) provides, after reverse-phase HPLC, 0.129 g (70%) of the title compound as a white foam: high resolution mass spectrum (electrospray): m/z calc for $C_{24}H_{25}ClN_3O_2$ 422.1635, found 422.1664; $^1$H NMR (methanol-$d_4$): 8.66 (d, 1H, J=2.6 Hz), 8.30 (dd, 1H, J=2.6, 8.8 Hz), 7.47 (d, 2H, J=8.8 Hz), 7.34-7.27 (m, 2H), 7.26-7.19 (m, 2H), 7.16 (d, 2H, J=8.3 Hz), 7.05 (d, 1H, J=8.3 Hz), 3.70 (s, 2H), 3.07 (d, 2H, J=11.4 Hz), 2.89 (tt, 1H, J=4.0, 11.9 Hz), 2.29-2.16 (m, 2H), 2.00-1.72 (m, 3H), 1.56 (dq, 1H, J=4.0, 12.3 Hz).

EXAMPLE 356

(±)-6-{4-[3-(3-Trifluoromethyl-phenyl)-piperidin-1-ylmethyl]-phenoxy}-nicotinamide

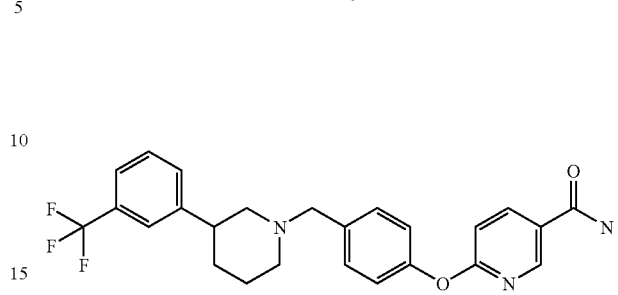

Using a method similar to Example 345, using 3-(3-trifluoromethyl-phenyl)-piperidine, hydrochloric acid salt (0.110 g, 0.414 mmol), 6-(4-formyl-phenoxy)-nicotinamide (compound of example 332, step 1) (0.100 g, 0.413 mmol), sodium triacetoxyborohydride (0.130 g, 0.613 mmol), and acetic acid (0.035 mL, 0.611 mmol) in 1,2-dichloroethane (8.0 mL) provides, after silica gel chromatography (25:1 methylene chloride:methanol), 0.142 g (75%) of the title compound as a white foam: high resolution mass spectrum (electrospray): m/z calc for $C_{25}H_{25}F_3N_3O_2$ 456.1899, found 456.1903; $^1$H NMR (methanol-$d_4$): 8.66 (d, 1H, J=2.4 Hz), 8.29 (dd, 1H, J=2.4, 8.3 Hz), 7.59-7.51 (m, 4H), 7.49-7.44 (m, 2H), 7.18-7.12 (m, 2H), 7.04 (d, 1H, J=9.3 Hz), 3.69-3.61 (m, 2H), 3.08-2.93 (m, 3H), 2.25-2.13 (m, 2H), 2.02-1.93 (m, 1H), 1.91-1.72 (m, 2H), 1.59 (dq, 1H, J=4.4, 12.2 Hz).

EXAMPLE 357

(±)-6-[4-(3-Methyl-piperidin-1-ylmethyl)-phenoxy]-nicotinamide

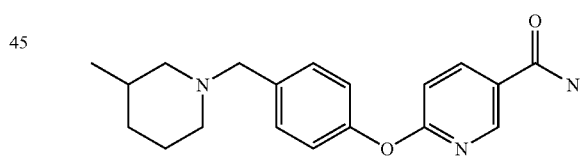

Using a method similar to Example 345, using 3-methyl-piperidine (0.0420 g, 0.423 mmol), 6-(4-formyl-phenoxy)-nicotinamide (compound of example 332, step 1) (0.101 g, 0.417 mmol), sodium triacetoxyborohydride (0.129 g, 0.610 mmol), and acetic acid (0.035 mL, 0.611 mmol) in 1,2-dichloroethane (8.0 mL) provides, after silica gel chromatography (10:1→7:3 methylene chloride:methanol), 0.0400 g (29%) of the title compound as a white foam: high resolution mass spectrum (electrospray): m/z calc for $C_{19}H_{24}N_3O_2$ 326.1869, found 326.1841; $^1$H NMR (DMSO-$d_6$): 8.66 (d, 1H, J=2.2 Hz), 8.29 (dd, 1H, J=2.5, 8.4 Hz), 8.06 (s b, 1H), 7.53 (s br, 1H), 7.38 (d, 2H, J=8.4 Hz), 7.17-7.09 (m, 3H), 3.38-3.28 (m, 2H), 2.83-2.70 (m, 2H), 1.95 (t, 1H, J=10.6 Hz), 1.74-1.41 (m, 5H), 0.97-0.79 (m, 4H).

EXAMPLE 358

(±)-6-[4-(3-Phenethyl-piperidin-1-ylmethyl)-phenoxy]-nicotinamide

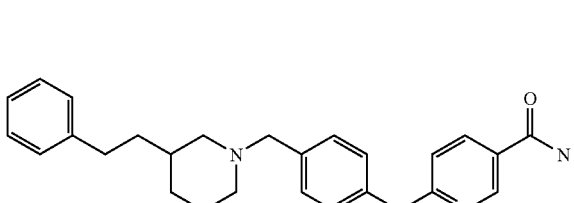

Using a method similar to Example 345, using 3-phenethyl-piperidine (0.0789 g, 0.417 mmol), 6-(4-formyl-phenoxy)-nicotinamide (compound of example 332, step 1) (0.101 g, 0.417 mmol), sodium triacetoxyborohydride (0.129 g, 0.610 mmol), and acetic acid (0.038 mL, 0.664 mmol) in 1,2-dichloroethane (8.0 mL) provides, after silica gel chromatography (25:1→8:1 methylene chloride:methanol), 0.085 g (49%) of the title compound as a white foam: high resolution mass spectrum (electrospray): m/z calc for $C_{26}H_{30}N_3O_2$ 416.2338, found 416.2346; $^1$H NMR (methanol-$d_4$): 8.67 (d, 1H, J=2.0 Hz), 8.30 (dd, 1H, J=2.4, 8.8 Hz), 7.44 (d, 2H, J=8.3 Hz), 7.30-7.24 (m, 2H), 7.20-7.13 (m, 5H), 7.05 (d, 1H, J=7.8 Hz), 3.60 (s, 2H), 3.02-2.90 (m, 2H), 2.71-2.59 (m, 2H), 2.05 (dt, 1H, J=2.0, 11.2 Hz), 1.89 (d, 1H, J=12.2 Hz), 1.82-1.69 (m, 2H), 1.68-1.52 (m, 4H), 1.00 (dq, 1H, J=3.4, 12.2 Hz).

EXAMPLE 359

(±)-6-[4-(3-Phenpropyl-piperidin-1-ylmethyl)-phenoxy]-nicotinamide

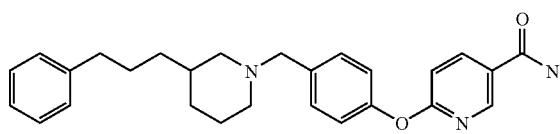

Using a method similar to Example 345, using 3-phenylpropyl-piperidine (0.0993 g, 0.414 mmol), 6-(4-formyl-phenoxy)-nicotinamide (compound of example 332, step 1) (0.100 g, 0.413 mmol), sodium triacetoxyborohydride (0.129 g, 0.610 mmol), and acetic acid (0.038 mL, 0.664 mmol) in 1,2-dichloroethane (8.0 mL) provides, after silica gel chromatography (15:1→8:1 methylene chloride:methanol), 0.0977 g (55%) of the title compound as a white foam: high resolution mass spectrum (electrospray): m/z calc for $C_{27}H_{32}N_3O_2$ 430.2495, found 430.2511; $^1$H NMR (methanol-$d_4$): 8.66 (d, 1H, J=2.4 Hz), 8.31 (dd, 1H, J=2.4, 8.3 Hz), 7.55-7.49 (m, 2H), 7.31-7.15 (m, 7H), 7.09 (d, 1H, J=8.8 Hz), 3.94 (d, 1H, J=13.2 Hz), 3.91 (d, 1H, J=12.7 Hz), 3.18 (d, 2H, J=11.2 Hz), 2.63 (t, 2H, J=7.8 Hz), 2.42 (dt, 1H, J=2.4, 12.2 Hz), 2.14 (t, 1H, J=11.7 Hz), 1.94-1.80 (m, 2H), 1.80-1.59 (m, 4H), 1.38-1.26 (m, 2H), 1.04 (dq, 1H, J=4.4, 13.2 Hz).

EXAMPLE 360

(±)-6-[4-(3-Benzyl-piperidin-1-ylmethyl)-phenoxy]-nicotinamide

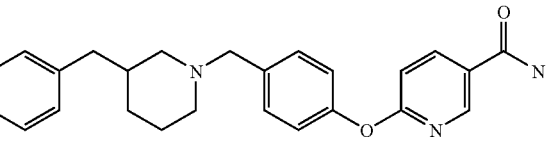

Step 1

(±)-3-Benzyl-piperidine

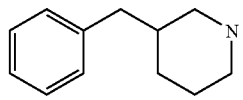

Combine 3-benzyl-pyridine (0.524 g, 3.10 mmol) and 10% palladium on carbon (0.165 g) in acetic acid (30 mL) and stir at 60° C. at a $H_2$ pressure of 60 psi. After 6 h, purify the reaction mixture by ion exchange chromatography (SCX resin, methanol→2 M ammonia/methanol) and silica gel chromatography (10:1→13:1 methylene chloride:methanol) to provide 0.225 g (42%) of the title compound as a yellow oil: $^1$H NMR (DMSO-$d_6$): 7.28 (t, 2H, J=7.3 Hz), 7.22-7.13 (m, 3H), 3.01 (s br, 1H), 2.87-2.76 (m, 2H), 2.50-2.34 (3H), 2.16 (dd, 1H, J=9.3, 11.7 Hz), 1.70-1.49 (m, 3H), 1.29 (tq, 1H, J=3.9, 12.7 Hz), 1.03 (dq, 1H, J=3.9, 12.7 Hz).

Step 2

Using a method similar to Example 345, using 3-benzyl-piperidine (0.0748 g, 0.427 mmol), 6-(4-formyl-phenoxy)-nicotinamide (compound of example 332, step 1) (0.101 g, 0.417 mmol), sodium triacetoxyborohydride (0.130 g, 0.613 mmol), and acetic acid (0.035 mL, 0.611 mmol) in 1,2-dichloroethane (8.0 mL) provides, after silica gel chromatography (15:1→8:1 methylene chloride:methanol), 0.0626 g (37%) of the title compound as a white foam: high resolution mass spectrum (electrospray): m/z calc for $C_{25}H_{28}N_3O_2$ 402.2182, found 402.2192; $^1$H NMR (methanol-$d_4$): 8.67 (d, 1H, J=2.0 Hz), 8.30 (dd, 1H, J=2.4, 8.3 Hz), 7.42 (d, 2H, J=8.8 Hz), 7.28 (t, 2H, J=7.3 Hz), 7.22-7.11 (m, 5H), 7.01 (d, 1H, J=8.3 Hz), 3.62 (d, 1H, J=12.7 Hz), 3.58 (d, 1H, J=12.7 Hz), 2.98-2.88 (m, 2H), 2.55 (d, 2H, J=6.3 Hz), 2.08 (t, 1H, J=11.7 Hz), 1.96-1.81 (m, 2H), 1.80-1.69 (m, 2H), 1.59 (qt, 1H, J=4.4, 12.7 Hz), 1.11-0.98 (m, 1H).

EXAMPLE 361

(±)-6-[4-(3-Phenyl-piperidin-1-ylmethyl)-phenoxy]-nicotinamide

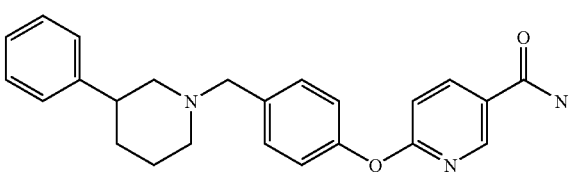

Using a method similar to Example 345, using 3-phenyl-piperidine hydrochloric acid salt (0.413 g, 2.09 mmol), 6-(4-formyl-phenoxy)-nicotinamide (compound of example 332, step 1) (0.50 g, 0.417 mmol), sodium triacetoxyborohydride (0.656 g, 3.10 mmol), and acetic acid (0.172 mL, 3.00 mmol) in 1,2-dichloroethane (20.0 mL) provides, after reverse-phase HPLC, 0.508 g (64%) of the title compound as a white solid: mass spectrum (electrospray): m/z=388.1 (M+1); $^1$H NMR (DMSO-d$_6$): 8.65 (d, 1H, J=2.2 Hz), 8.29 (dd, 1H, J=2.6, 8.8 Hz), 8.05 (s br, 1H), 7.50 (s br, 1H), 7.39 (d, 2H, J=8.4 Hz), 7.35-7.17 (m, 5H), 7.16-7.06 (m, 3H), 3.55 (s, 2H), 2.91 (d, 2H, J=10.6 Hz), 2.80 (t, 1H, J=11.3 Hz), 2.05 (q, 2H, J=8.4 Hz), 1.86 (d, 1H, J=11.3 Hz), 1.81-1.56 (m, 2H), 1.48 (dq, 1H, J=4.0, 12.1 Hz).

EXAMPLE 362

(±)-6-{4-[3-(4-Fluoro-phenyl)-piperidin-1-ylmethyl]-phenoxy}-nicotinamide hydrochloride

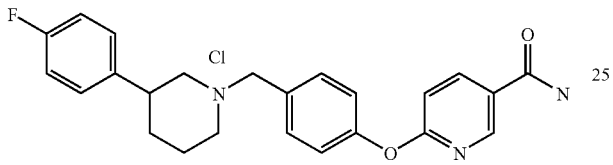

Using a method similar to Example 345, using 3-(4-fluorophenyl)-piperidine (0.117 g, 0.542 mmol), 6-(4-formyl-phenoxy)-nicotinamide (compound of example 332, step 1) (0.111 g, 0.458 mmol), sodium triacetoxyborohydride (0.135 g, 0.637 mmol), and acetic acid (0.034 mL, 0.594 mmol) in 1,2-dichloroethane (8.0 mL) provides, after silica gel chromatography (12:1 methylene chloride:methanol) and reverse-phase HPLC, 0.0938 g (51%) of the title compound as a white solid: high resolution mass spectrum (electrospray): m/z calc for $C_{24}H_{25}FN_3O_2$ 406.1931, found 406.1926; $^1$H NMR (DMSO-d$_6$): 8.64 (d, 1H, J=2.2 Hz), 8.31 (dd, 1H, J=2.6, 8.8 Hz), 8.08 (s br, 1H), 7.68 (d, 2H, J=8.4 Hz), 7.52 (s br, 1H), 7.42-7.08 (m, 5H), 4.33 (s, 2H), 3.50-3.30 (m, 2H), 3.30-2.84 (m, 3H), 2.05-1.79 (m, 3H), 1.75-1.57 (m, 1H).

EXAMPLE 363

(±)-6-{4-[3-(2-Fluoro-phenyl)-piperidin-1-ylmethyl]-phenoxy}-nicotinamide hydrochloride

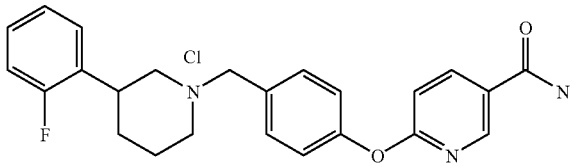

Using a method similar to Example 345, using 3-(4-fluorophenyl)-piperidine (0.118 g, 0.547 mmol), 6-(4-formyl-phenoxy)-nicotinamide (compound of example 332 step 1) (0.109 g, 0.450 mmol), sodium triacetoxyborohydride (0.132 g, 0.623 mmol), and acetic acid (0.035 mL, 0.611 mmol) in 1,2-dichloroethane (8.0 mL) provides, after silica gel chromatography (12:1 methylene chloride:methanol) and reverse-phase HPLC, 0.0511 g (26%) of the title compound as a white solid: high resolution mass spectrum (electrospray): m/z calc for $C_{24}H_{25}FN_3O_2$ 406.1931, found 406.1933; $^1$H NMR (methanol-d$_4$): 8.66 (d, 1H, J=2.0 Hz), 8.36 (dd, 1H, J=2.4, 8.8 Hz), 7.68-7.63 (m, 2H), 7.45-7.31 (m, 4H), 7.28-7.22 (m, 1H), 7.20-7.14 (m, 2H), 4.47 (d, 1H, J=13.2 Hz), 4.43 (d, 1H, J=13.2 Hz), 3.69-3.59 (m, 2H), 3.52-3.43 (m, 1H), 3.27 (t, 1H, J=12.2 Hz), 3.18-3.09 (m, 1H), 2.22-2.15 (m, 1H), 2.10-1.87 (m, 3H).

EXAMPLE 364

(±)-6-[4-(3-Cyclohexyl-piperidin-1-ylmethyl)-phenoxy]-nicotinamide hydrochloride

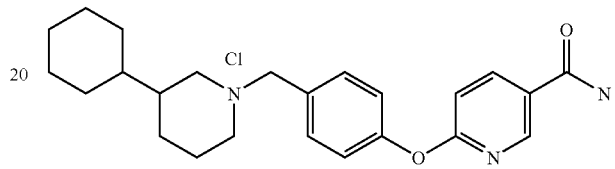

Step 1

(±)-3-Cyclohexyl-piperidin

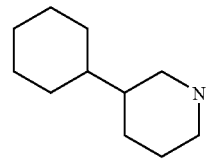

Combine 3-phenyl-piperidine hydrochloride (0.206 g, 1.04 mmol) and 5% rhodium on alumina (0.112 g, 0.0544 mmol) in methanol (50 mL) and stir at 50° C. at a 12 pressure of 60 psi. After 4 d, purify the reaction mixture by ion exchange chromatography (SCX resin, methanol→2 M ammonia/methanol) to provide 0.164 g (3:1 mixture of product:starting material) which was used in the next step without further-purification: mass spectrum (electrospray): m/z=168.1 (M+1-product), 162.1 (M+1-starting material).

Step 2

Using a method similar to Example 345, a mixture of 3-cyclohexyl-piperidine and 3-phenyl piperidine (from step 1 above) (3:1, 0.118 g), 6-(4-formyl-phenoxy)-nicotinamide (compound of example 332, step 1) (0.183 g, 0.755 mmol), sodium triacetoxyborohydride (0.247 g, 1.16 mmol), and acetic acid (0.067 mL, 1.17 mmol) in 1,2-dichloroethane (10.0 mL) provides, after reverse-phase HPLC, 0.155 g (37%) of the title compound as a white solid: high resolution mass spectrum (electrospray): m/z calc for $C_{24}H_{32}N_3O_2$ 394.2495, found 394.2478; $^1$H NMR (methanol-d$_4$): 8.68 (d, 1H, J=2.4 Hz), 8.38 (dd, 1H, J=2.4, 8.3 Hz), 7.69-7.63 (m, 2H), 7.37-7.32 (m, 2H), 7.18 (d, 1H, J=8.8 Hz), 4.42 (d, 1H, J=13.2 Hz), 4.34 (d, 1H, J=13.2 Hz), 3.62-3.55 (m, 1H), 3.54-3.47 (m, 1H), 2.92 (dt, 1H, J=3.4, 13.2 Hz), 2.84 (t, 1H, J=12.2), 2.08-2.00 (m, 1H), 2.00-1.92 (m, 1H), 1.87-1.66 (m, 7H), 1.39-1.02 (m, 7H).

EXAMPLE 365

(±)-6-[2-Methyl-4-(3-phenyl-piperidin-1ylmethyl)-phenoxy]-nicotinamide

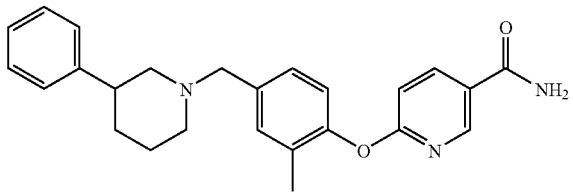

Step 1

6-(4-Formyl-2-methyl-phenoxy)-nicotinonitrile

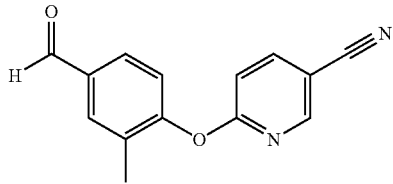

Combine 4-hydroxy-3-methyl-benzaldehyde (0.502 g, 3.69 mmol), 6-chloro-nicotinonitrile (0.510 g, 3.68 mmol), and potassium carbonate (1.28 g, 9.26 mmol) in dimethylacetamide (18 mL) and warm to 100° C. After 1 h. cool to ambient temperature, dilute reaction mixture with water (40 mL), and extract with ethyl acetate (3×50 mL). Wash combined organic extracts with water and brine successively, dry over anhydrous magnesium sulfate, filter, and concentrate. Purify the residue by silica gel chromatography (hexanes→ethyl acetate gradient/1.5 L) to provide 0.784 g (89%) of the title compound as a light brown solid: mass spectrum (electrospray): m/z=239.0 (M+1); $^1$H NMR (CDCl$_3$): 10.01 (s, 1H), 8.44 (d, 1H, J=2.4 Hz), 7.99 (dd, 1H, J=2.0, 8.3 Hz), 7.86 (s, 1H), 7.81 (dd, 1H, J=1.5, 8.3 Hz), 7.23 (d, 1H, J=8.3 Hz), 7.13 (d, 1H, J=8.8 Hz), 2.25 (s, 3H).

Step 2

(±)-6-[2-Methyl-4-(3-phenyl-piperidin-1ylmethyl)-phenoxy]-nicotinonitrile

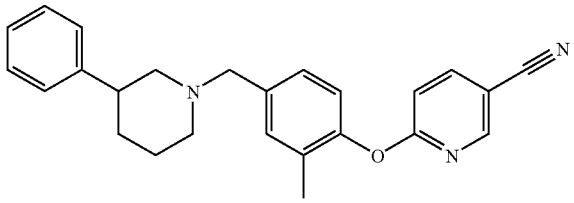

Convert 3-phenyl piperidine hydrochloride (0.652 g, 3.30 mmol) to the free base using ion exchange chromatography (methanol→2 M ammonia/methanol) and concentrate. Combine the free base with 6-(4-formyl-2-methyl-phenoxy)-nicotinonitrile (from step 1 above) (0.748 g, 3.29 mmol), sodium triacetoxyborohydride (1.05 g, 4.95 mmol), and acetic acid (0.30 mL, 5.24 mmol) in 1,2-dichloroethane (33 mL) and stir at ambient temperature. After 17 h, wash reaction mixture with saturated sodium bicarbonate (aq) (2×50 mL), dry over anhydrous magnesium sulfate, filter, and concentrate. Purify the residue by silica gel chromatography (hexanes→2:1 hexanes:ethyl acetate) to provide 0.878 g (70%) of the title compound as a white foam: $^1$H NMR (CDCl$_3$): 8.46 (d, 1H, J=2.9 Hz), 7.91 (dd, 1H, J=2.9, 8.8 Hz), 7.34-7.19 (m, 7H), 6.99 (d, 2H, J=8.8 Hz), 3.52 (s, 2H), 3.06-2.94 (m, 2H), 2.86 (tt, 1H, J=3.9, 11.7 Hz), 2.13 (s, 3H), 2.10-1.91 (m, 3H), 1.84-1.68 (m, 2H), 1.48 (dq, 1H, J=4.9, 12.2 Hz).

Step 3

The nitrile from step 2 may be hydrolyzed to the amide final product as described many times herein.

EXAMPLE 366

(±)-6-[2-Methyl-4-(3-phenyl-pyrolidin-1ylmethyl)-phenoxy]-nicotinamide

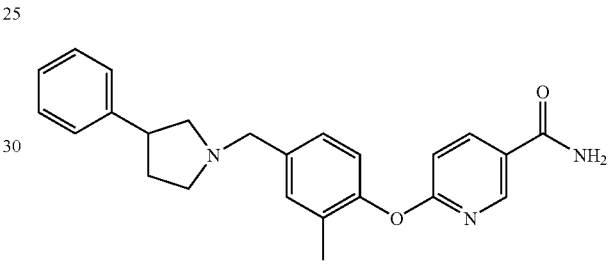

Step 1

(±)-6-[2-Methyl-4-(3-phenyl-pyrolidin-1ylmethyl)-phenoxy]-nicotinonitrile

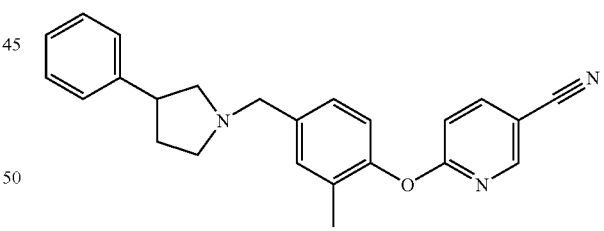

Using a method similar to Example 362, using 3-phenyl-pyrrolidine phosphoric acid salt (1.543 g, 6.29 mmol), 6-(4-formyl-2-methyl-phenoxy)-nicotinonitrile (compound of example 365, step 1) (1.499 g, 6.30 mmol), sodium triacetoxyborohydride (2.00 g, 9.44 mmol) and acetic acid (0.58 mL, 10.1 mmol) in 1,2-dichloroethane (50 mL), after silica gel chromatography (19:1→1:3 hexanes:ethyl acetate) provides 1.65 g (71%) of the title compound as a clear syrup: Mass spectrum (electrospray): m/z=370 (M+1); $^1$H NMR (CDCl$_3$): 8.47 (d, 1H, J=2.4 Hz), 7.91 (dd, 1H, J=2.0, 8.3 Hz), 7.32-7.28 (m, 5H), 7.26-7.17 (m, 2H), 3.67 (s, 2H), 3.45-3.35 (m, 1H), 3.08 (t, 1H, J=9.3 Hz), 2.93-2.85 (m, 1H), 2.72 (dt, 1H, J=5.9, 8.8 Hz), 2.53 (dd, 1H, J=8.3, 9.3 Hz), 2.43-2.32 (m, 1H), 2.14 (s, 3H), 1.99-1.88 (m, 1H).

Step 2

Basic hydrolysis of (±)-6-[2-Methyl-4-(3-phenyl-pyrolidin-1ylmethyl)-phenoxy]-nicotinonitrile as discussed for other nitriles previously is useful to obtain the desired nicotinamide product.

EXAMPLE 367

(±)-6-[2-Methyl-4-(3-phenyl-azepan-1ylmethyl)-phenoxy]-nicotinamide

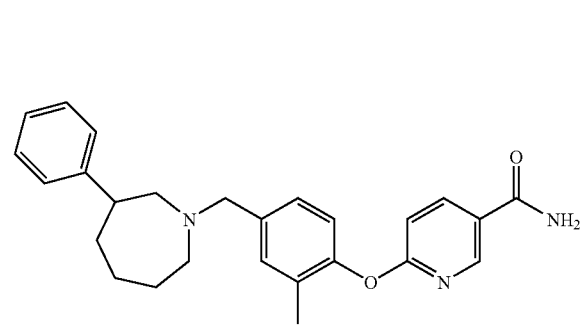

Step 1

(±)-6-[2-Methyl-4-(3-phenyl-azepan-1ylmethyl)-phenoxy]-nicotinonitrile

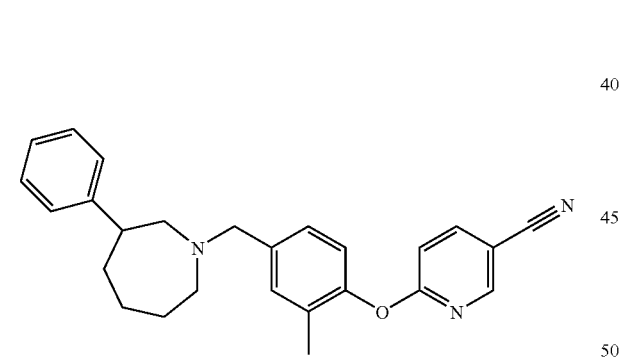

Using a method similar to Example 365 step 2, using 3-phenyl-azapane (0.0610 g, 0.348 mmol), 6-(4-formyl-2-methyl-phenoxy)-nicotinonitrile (compound of example 365 step 1) (0.0816 g, 0.342 mmol), sodium triacetoxyborohydride (0.110 g, 0.519 mmol), and acetic acid (0.032 mL, 0.56 mmol) in 1,2-dichloroethane (4.0 mL), (no aqueous work-up) provides, after ion exchange chromatography (methanol→2 M ammonia/methanol) and silica gel chromatography (4:1→1:1 hexanes:ethyl acetate), 0.0899 g (65%) of the title compound as a yellow oil: Mass spectrum (electrospray): m/z=398.2 (M+1).

Step 2

The nitrile from above is hydrolyzed under basic conditions to afford the target nicotinamide compound.

EXAMPLE 368

(±)-6-[2-Methyl-4-(4-phenyl-azepan-1ylmethyl)-phenoxy]-nicotinamide

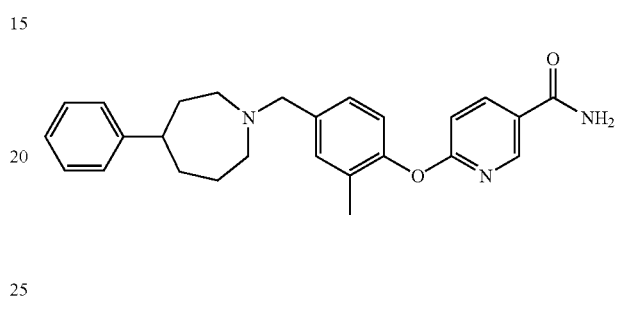

Step 1

(±)-6-[2-Methyl-4-(4-phenyl-azepan-1ylmethyl)-phenoxy]-nicotinonitrile

Using a method similar to Example 365 step 2, using 3-phenyl-azapane (0.0957 g, 0.548 mmol), 6-(4-formyl-2-methyl-phenoxy)-nicotinonitrile (compound of example 365 step 1) (0.103 g, 0.420 mmol), sodium triacetoxyborohydride (0.110 g, 0.651 mmol), and acetic acid (0.03 mL, 0.594 mmol) in 1,2-dichloroethane (5.0 mL), provides, after silica gel chromatography (4:1→1:1 hexanes:ethyl acetate), 0.144 g (84%) of the title compound as a yellow oil: mass spectrum (electrospray): m/z=398.2 (M+1); $^1$H NMR (CDCl$_3$): 8.47 (d, 1H, J=1.5 Hz), 7.91 (dd, 1H, J=1.5, 7.8 Hz), 7.33-7.25 (m, 4H), 7.25-7.21 (m, 2H), 7.21-7.15 (m, 1H), 7.03-6.97 (m, 2H), 3.73-3.67 (m, 2H), 2.90-2.81 (m, 2H), 2.79-2.66 (m, 3H), 2.15 (s, 3H), 2.01-1.67 (m, 6H).

Step 2

The nitrile compound from step 1 is hydrolyzed under basic conditions to afford the corresponding nitrile, as described previously in the general methodology sections.

EXAMPLE 369

(±)-6-[2-Methyl-4-(3-phenyl-piperidin-1ylmethyl)-phenoxy]-nicotinamide methanesulfonate

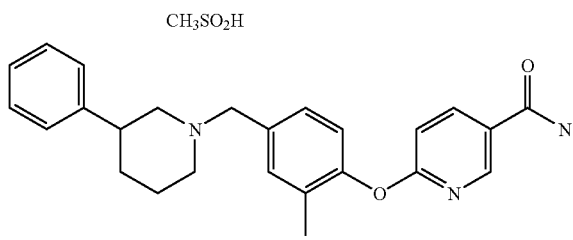

Combine (±)-6-[2-methyl-4-(3-phenyl-piperidinylmethyl)-phenoxy]-nicotinonitrile (compound of example 365, step 2) (0.878 g, 2.29 mmol) and potassium carbonate (0.159 g, 1.15 mmol) in dimethylsulfoxide (11.0 mL,). Treat the mixture with 30% hydrogen peroxide solution (aq) (0.77 mL, 6.79 mmol), and stir at ambient temperature. After 4 h, dilute the reaction mixture with water (25 mL) and extract with ethyl acetate (3×30 mL). Wash combined ethyl acetate extracts with brine, dry over anhydrous magnesium sulfate, filter, and concentrate. Crude product is pure by $^1$H NMR and reverse-phase HPLC. Dissolve product in tetrahydrofuran (12 mL) and treat with methanesulfonic acid (0.148 mL, 2.28 mmol). White precipitate forms and turns oily within 3 minutes. Dissolve residue in tetrahydrofuran and concentrate. Product purity is 82% by reverse-phase HPLC. Purify residue by reverse-phase HPLC. Concentrate fractions containing pure product, recrystallize from methanol:diethyl ether (2:5, 16 mL), and isolate product by vacuum filtration to provide 0.0941 g (10%) of the title compound as white/tan crystals: high resolution mass spectrum (electrospray): m/z calc for $C_{25}H_{28}N_3O_2$ 402.2182, found 402.2172; $^1$H NMR (methanol-$d_4$): 8.62 (d, 1H, J=2.0 Hz), 8.36 (dd, 1H, J=2.4, 8.8 Hz), 7.57-7.54 (m, 1H), 7.48 (dd, 1H, J=1.5, 7.8 Hz), 7.43-7.38 (m, 2H), 7.37-7.30 (m, 3H), 7.23 (d, 1H, J=8.3 Hz), 7.16 (d, 1H, J=8.8 Hz), 4.45-4.36 (m, 2H), 3.63 (t, 2H, J=14.6 Hz), 3.22 (t, 1H, J=12.2 Hz), 3.17-3.07 (m, 2H), 2.23 (s, 3H), 2.20-2.13 (m, 1H), 2.12-2.92 (m, 2H), 1.86 (dq, 1H, J=3.9, 12.2 Hz).

EXAMPLE 370

(±)-6-[2-Methyl-4-(3-phenyl-pyrolidin-1yl-methyl)-phenoxy]-nicotinamide hydrochloride

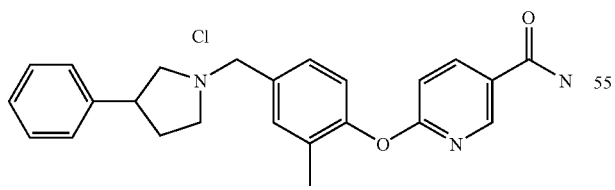

Combine (±)-6-[2-methyl-4-(3-phenyl-pyrolidin-1yl-methyl)-phenoxy]-nicotinonitrile (compound of example 366) (0.642 g, 1.74 mmol) and potassium carbonate (0.125 g, 0.904 mmol) in dimethylsulfoxide (10.0 mL), treat with 30% hydrogen peroxide solution (aq) (0.60 mL, 5.3 mmol), and stir at ambient temperature. After 5 h, dilute the reaction mixture with water (25 mL) and extract with ethyl acetate (3×25 mL). Wash combined ethyl acetate extracts with brine, dry over anhydrous magnesium sulfate, filter, and concentrate to provide 0.660 g (98%) of the title compound (free base) as a white solid. Dissolve product in methylene chloride (10 mL) and treat with 4 N hydrochloric acid/dioxane (0.47 mL, 1.87 mmol). Some decomposition occurs. Purify product by reverse-phase HPLC to provide 0.184 g (25%) of the title compound as a white solid: mass spectrum (electrospray): m/z=388.2 (M+1); $^1$H NMR (methanol-$d_4$): 8.63 (d, 1H, J=1.5 Hz), 8.35 (dd, 1H, J=2.4, 8.8 Hz), 7.61 (d, 1H, J=8.8 Hz), 7.54 (d, 1H, J=8.8 Hz), 7.41 (t, 4H, J=4.4 Hz), 7.38-7.30 (m, 1H), 7.23 (d, 1H, J=8.3 Hz), 7.14 (d, 1H, J=8.8 Hz), 4.59-4.49 (m, 2H), 3.99-3.72 (m, 2H), 3.70-3.41 (m, 2H), 3.48 (t, 1H, J=11.7 Hz), 2.66-2.51 (m, 1H), 2.44-2.15 (m, 4H).

EXAMPLE 371

(±)-6-[2-Methyl-4-(3-phenyl-azepan-1-yl methyl)-phenoxy]-nicotinamide hydrochloride

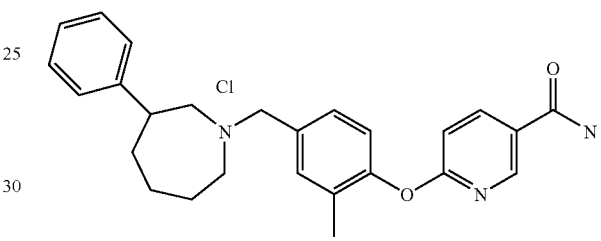

Combine (±)-6-[2-methyl-4-(3-phenyl-azepan-1ylmethyl)-phenoxy]-nicotinonitrile (compound of example 367) (0.0876 g, 0.220 mmol) and potassium carbonate (0.0152 g, 0.11 mmol) in dimethylsulfoxide (2.0 mL), treat with 30% hydrogen peroxide solution (aq) (0.075 mL, 0.66 mmol), and stir at ambient temperature. After 2.5 h, dilute the reaction mixture with water (10 mL) and extract with ethyl acetate (3×10 mL). Wash combined extracts with brine, dry over anhydrous magnesium sulfate, filter, and concentrate. Purify the residue by reverse-phase HPLC to provide 0.0191 g (19%) of the title compound as a white solid: high resolution mass spectrum (electrospray): m/z calc for $C_{26}H_{30}N_3O_2$ 416.2338, found 416.2347; retention time: 3.834 min. The HCl salt of the free base was prepared by known protocols.

EXAMPLE 372

(±)-6-[2-Methyl-4-(4-phenyl-azepan-1ylmethyl)-phenoxy]-nicotinamide

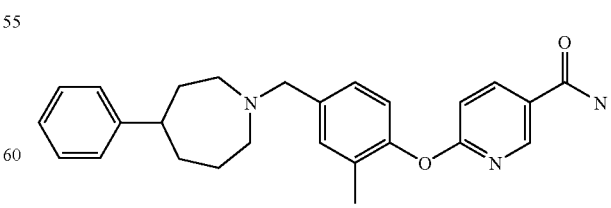

Using a method similar to Example 371, (±)-6-[2-methyl-4-(4-phenyl-azepan-1ylmethyl)-phenoxy]-nicotinonitrile (compound of example 368) (0.246 g, 0.642 mmol), potassium carbonate (0.0429 g, 0.310 mmol), and 30% hydrogen peroxide Solution (aq) (0.220 mL, 1.94 mmol) in dimethylsulfoxide provide, after ion exchange chromatography (methanol→2 M ammonia/methanol), 0.223 g (87%) of the title compound as a while solid: high resolution mass spectrum (electrospray): m/z calc for $C_{25}H_{25}N_3O_2$ 402.2182, found 402.2172; $^1$H NMR (methanol-$d_4$): 8.67 (d, 1H, J=2.0 Hz), 8.36 (dd, 1H, J=2.4, 8.8 Hz), 7.51 (d, 2H, J=8.3 Hz), 7.32-7.22 (m, 4H), 7.20-7.14 (m, 3H), 7.04 (d, 1H, J=8.8 Hz), 3.77 (s, 2H), 2.97 (ddd, 1H, J=3.4, 6.3, 13.2 Hz), 2.92-2.83 (m, 3H), 2.81-2.72 (m, 1H), 2.04-1.76 (m, 6H).

EXAMPLE 373

(±)-6-[2-Fluoro-4-(3-phenyl-pyrrolidin-1-ylmethyl)-phenoxy]-nicotinamide

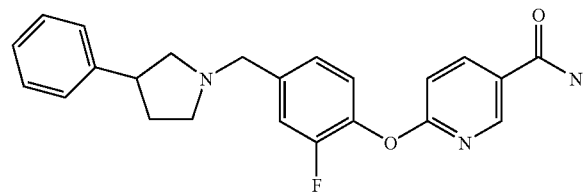

Step 1

6-(2-Fluoro-4-formyl-phenoxy)-nicotinonitrile

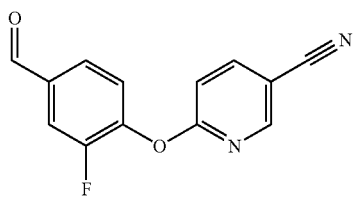

Using a method similar to Example 365, step 1, using 4-hydroxy-3-fluoro-benzaldehyde (3.00 g, 21.4 mmol), 6-chloro-nicotinonitrile (2.98 g, 21.5 mmol), and potassium carbonate (7.40 g, 53.5 mmol) in dimethylacetamide (100 mL) after 6 h at 100° C. provides 3.77 g (73%) of the title compound as a yellow solid (silica gel chromatography conditions: 19:1→1:4 hexanes:ethyl acetate): mass spectrum (electrospray): m/z=243.0 (M+1); $^1$H NMR (CDCl$_3$): 10.00 (d, 1H, J=2.0 Hz), 8.42 (d, 1H, J=1.5 Hz), 8.01 (dd, 1H, J=2.0, 8.3 Hz), 7.80-7.72 (m, 2H), 7.43 (d, 1H, J=7.3 Hz), 7.19 (d, 1H, J=8.8 Hz).

Step 2

(±)-6-[2-Fluoro-4-(3-phenyl-pyrrolidin-1-ylmethyl)-phenoxy]-nicotinonitrile

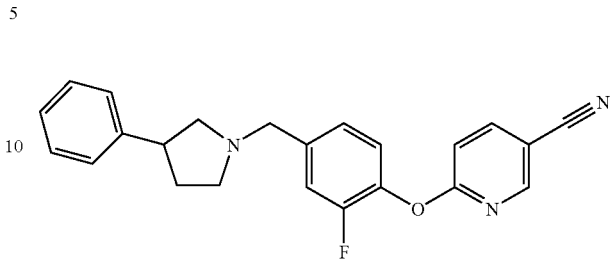

Using a method similar to Example 365 step 2, using 3-phenyl-pyrolidine (0.169 g, 1.15 mmol), 6-(4-formyl-2-fluoro-phenoxy)-nicotinonitrile (compound of example 375 step 1), (0.200 g, 0.826 mmol), sodium triacetoxyborohydride (0.262 g, 1.24 mmol), and acetic acid (0.071 mL, 1.24 mmol) in 1,2-dichloroethane (8.0 mL), after silica gel chromatography (3:1 hexanes:ethyl acetate), provides 0.231 g (75%) of the title compound as a clear syrup: mass spectrum (electrospray): m/z=374.2 (M+1); $^1$H NMR (CDCl$_3$): 8.40 (d, 1H, J=2.9 Hz), 7.91 (dd, 1H, J=2.4, 8.3 Hz), 7.30-7.24 (m, 2H), 7.24-7.21 (m, 3H), 7.20-7.09 (m, 3H), 7.06 (d, 1H, J=8.8 Hz), 3.70-3.61 (m, 2H), 3.40-3.31 (m, 1H), 3.01 (t, 1H, J=8.8 Hz), 2.84-2.77 (m, 1H), 2.75-2.67 (m, 1H), 2.53 (dd, 1H, J=7.8, 9.3 Hz), 2.39-2.28 (m, 1H), 1.95-1.84 (m, 1H).

Step 3

Using a method similar to Example 371, (±)-6-[2-fluoro-4-(3-phenyl-pyrrolidin-1-ylmethyl)-phenoxy]-nicotinonitrile (compound of example 375, step 2) (0.225 g, 0.603 mmol), potassium carbonate (0.0425 g, 0.308 mmol), and 30% hydrogen peroxide solution (aq) (0.203 mL, 1.79 mmol) in dimethylsulfoxide (6.0 mL) provide 0.197 g (83%) of the title compound as a white solid: high resolution mass spectrum (electrospray): m/z calc for $C_{23}H_{23}FN_3O_2$ 392.1774, found 392.1760; $^1$H NMR (methanol-$d_4$): 8.62 (d, 1H, J=2.4 Hz), 8.32 (d, 1H, J=2.9, 8.8 Hz), 7.41-7.25 (m, 7H), 7.25-7.19 (m, 1H), 7.15 (d, 1H, J=8.3 Hz), 3.83 (d, 1H, J=13.2 Hz), 3.80 (d, 1H, J=13.2 Hz), 3.51-3.41 (m, 1H), 3.18 (d, 1H, J=9.3 Hz), 3.02-2.94 (m, 1H), 2.86 (td, 1H, J=5.9, 8.8 Hz), 2.63 (t, 1H, J=8.8 Hz), 2.46-2.35 (m, 1H), 2.05-1.94 (m, 1H).

EXAMPLE 374

6-[2-(5-Methylhexyl)-2,3,4,5-tetrahydro-1H-benzo[c]azepin-7-yloxy]nicotinamide

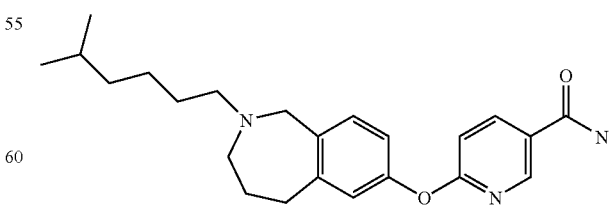

Mix 6-(2,3,4,5-tetrahydro-1H-benzo[c]azepin-7-yloxy) nicotinamide (Example 447, Part E, 0.300 g, 1.06 mmol), K$_2$CO$_3$ (0.366 g, 2.65 mmol), and 1-bromo-5-methylhexane (0.199 g, 1.05 mmol) in DMF (5.3 mL). Heat at 50° C.

overnight, then increase the temperature to 80° C. for 3.5 hours. Cool die reaction mixture to room temperature and add ethyl acetate (100 mL). Wash with water (1×30 mL), brine (1×30 mL), dry the organic layer over Na$_2$SO$_4$, filter and concentrate. Purify by flash chromatography eluting with 6% to 15% (2.0 M NH$_3$ in methanol) in ethyl acetate to give the title compound: MS ES$^+$ 382.2 (M+H)$^+$, HRMS calcd for C$_{23}$H$_{31}$N$_3$O$_2$ 382.2492 (M+H)$^+$, found 382.2495, time 0.46 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], t$_R$=12.4 min, 97.7% purity.

EXAMPLE 375

6-(2-Methoxy-4-{[2-(4-methylcyclohexyl)ethylamino]methyl}phenoxy)nicotinamide methanesulfonate

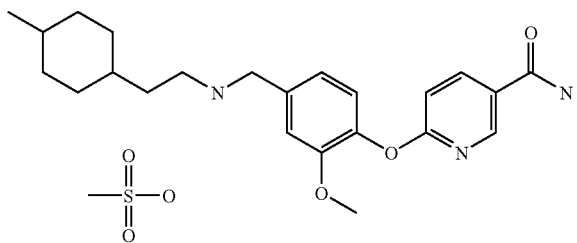

Place 6-(4-formyl-2-methoxyphenoxy)nicotinamide (Ex 414, Part B) (0.100 g, 0.367 mmol), 2-(4-methylcyclohexyl)ethylamine (0.0571 g, 0.404 mmol) and 3 Å molecular-sieves in a vial. Add methanol (3.6 mL), cap and stir the mixture overnight. Add NaBH$_4$ (ca. 3-5 eq in two portions) and stir until the gasses stop evolving. Load the reaction mixture directly onto a 5 g ISCO® pre-load column. Dry the column in a vacuum oven at room temperature. Purify by eluting through a 10 g ISCO® column with 6% to 15% (2.0 M NH$_3$ in methanol) in ethyl acetate to give 6-(2-methoxy-4-{[2-(4-methylcyclohexyl)ethylamino]methyl}phenoxy)nicotinamide. Dissolve the compound in dichloromethane (2.5 mL) and add 1 equivalent of 0.50 M methanesulfonic acid in dichloromethane. Stir the solution for a short time before concentrating to give the title compound: TOF MS ES$^+$ 398.2 (M+H)$^+$, HRMS calcd for C$_{23}$H$_{32}$N$_3$O$_3$ 398.2444 (M+H)$^+$, found 398.2440, time 0.52 min; Anal. Calcd for C$_{23}$H$_{31}$N$_3$O$_3$.0.5H$_2$O: C, 57.35; H, 7.22; N, 8.36. Found: C, 57.33; H, 6.94; N, 8.34.

EXAMPLE 376

(±)-6-[2-Ethoxy-4-(3-phenyl-pyrrolidin-1-ylmethyl)-phenoxy]-nicotinamide

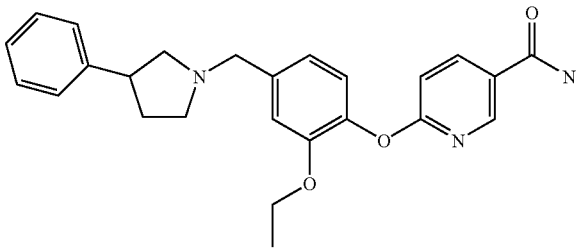

Step 1

6-(2-Ethoxy-4-formyl-phenoxy)-nicotinonitrile

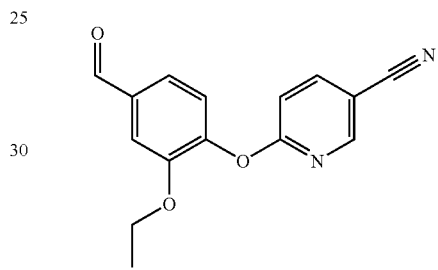

Using a method similar to Example 365, step 1, and using 3-ethoxy-4-hydroxy-benzaldehyde (3.00 g, 18.0 mmol), 6-chloro-nicotinonitrile (2.65 g, 18.0 mmol), and potassium carbonate (6.62 g, 45.2 mmol) in dimethylacetamide (90 mL), after 3 h at 100° C. (no purification) provides 4.52 g (93%) of the title compound as a yellow/white solid: mass spectrum (electrospray): m/z=269.0 (M+1); $^1$H NMR (CDCl$_3$): 9.96 (s, 1H), 8.39 (d, 1H, J=2.0 Hz), 7.95 (dd, 1H, J=2.0, 8.3 Hz), 7.55-7.50 (m, 2H), 7.33 (d, 1H, J=7.8 Hz), 7.11 (d, 1H, J=9.3 Hz), 4.05 (q, 2H, J=6.8 Hz), 1.16 (t, 3H, J=6.8 Hz).

Step 2

(±)-6-[2-Ethoxy-4-(3-phenyl-pyrrolidin-1-ylmethyl)-phenoxy]-nictotinonitrile

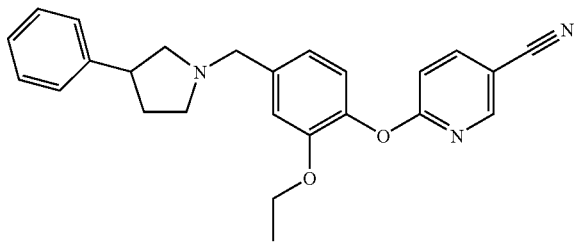

Using a method similar to Example 365 step 2, and using 3-phenyl-pyrolidine (0.150 g, 1.02 mmol), 6-(4-formyl-2- ethoxy-phenoxy)-nicotinonitrile (0.201 g, 0.749 mmol), sodium triacetoxyborohydride (0.237 g, 1.12 mmol), and acetic acid (0.064 mL, 1.12 mmol) in 1,2-dichloroethane (7.5 mL), after silica gel chromatography (1:1 hexanes:ethyl acetate), provides 0.182 g (61%) of the title compound as a clear syrup: mass spectrum (electrospray): m/z=400.2 (M+1); $^1$H NMR (CDCl$_3$): 8.41 (d, 1H, J=2.0 Hz), 7.86 (dd, 1H, J=2.4, 9.3 Hz), 7.29-7.26 (m, 4H), 7.20-7.14 (m, 1H), 7.07-7.03 (m, 2H), 6.99 (d, 1H, J=7.8 Hz), 6.94 (dd, 1H, J=2.0, 7.8 Hz), 4.01-3.92 (m, 2H), 3.69 (d, 1H, J=13.2 Hz), 3.62 (d, 1H, J=13.2 Hz), 3.41-3.31 (m, 1H), 3.99 (dd, 1H, J=7.8, 8.8 Hz), 2.86-2.78 (m, 1H), 2.77-2.70 (m, 1H), 2.54 (dd, 1H, J=7.3, 9.3 Hz), 2.40-2.29 (m, 1H), 1.96-1.85 (m, 1H).

Step 3

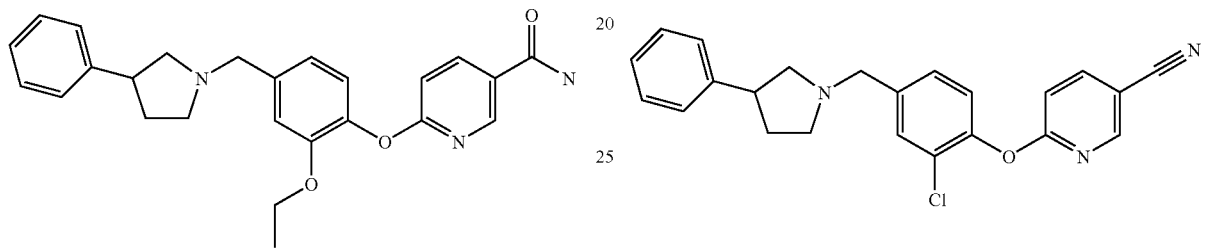

Using a method similar to Example 371, and using (±)-6-[2-Ethoxy-4-(3-phenyl-pyrrolidin-1-ylmethyl)-phenoxy]-nictotinonitrile (step 2 above), potassium carbonate (approx. 0.5 equivalent), and 30% hydrogen peroxide solution (aq) (approx. 3 mole equivalents) in dimethylsulfoxide provides the title compound.

EXAMPLE 377

(±)-6-[2-Chloro-4-(3-phenyl-pyrrolidin-1-ylmethyl)-phenoxy]-nicotinamide

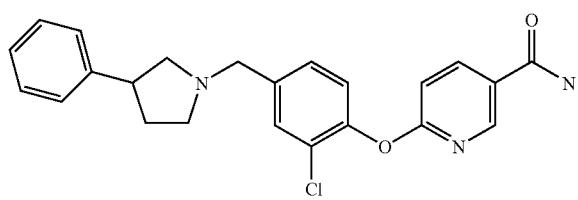

Step 1

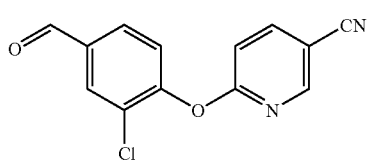

Using a method similar to Example 365, step 1, and using 4-hydro-oxy-3-chloro-benzaldehyde (3.00 g, 19.2 mmol), 6-chloro-nicotinonitrile (2.65 g, 19.1 mmol), and potassium carbonate (6.62 g, 47.9 mmol) in dimethylacetamide (95 mL), after 4 h at 100° C. (silica gel chromatography conditions: 19:1 hexanes:ethyl acetate→ethyl acetate) and recrystallization from 1:1 hexanes:diethylether, provides 2.32 g (47%) of the title compound as a yellow solid: mass spectrum (electrospray): m/z=259.0 (M+1); $^1$H NMR (CDCl$_3$): 10.01 (d, 1H, J=2.0 Hz), 8.42 (d, 1H, J=1.5 Hz), 8.07-8.00 (m, 2H), 7.90 (dd, 1H, J=1.5, 7.8 Hz), 7.42 (d, 1H, J=8.3 Hz), 7.21 (d, 1H, J=8.8 Hz).

Step 2

(±)-6-[2-Chloro-4-(3-phenyl-pyrrolidin-1-ylmethyl)-phenoxy]-nicotinonitrile

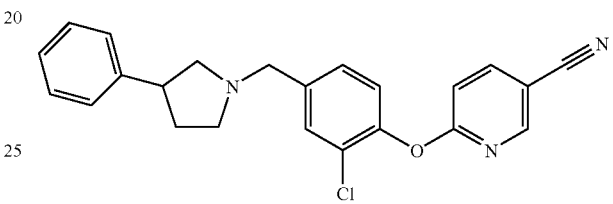

Using a method similar to Example 365, step 2, using 3-phenyl-pyrrolidine (0.160 g, 1.09 mmol), 6-(4-formyl-2-chloro-phenoxy)-nicotinonitrile (0.250 g, 0.966 mmol), sodium triacetoxyborohydride (0.308 g, 1.45 mmol), and acetic acid (0.090 mL, 1.57 mmol) in 1,2-dichloroethane (10.7 mL), after silica gel chromatography (7:3 hexanes:ethyl acetate), provides 0.202 g (54%) of the title compound as a clear syrup: mass spectrum (electrospray): m/z=390.1 (M+1); $^1$H NMR (CDCl$_3$): 8.41 (d, 1H, J=2.4 Hz), 7.92 (dd, 1H, J=2.4, 8.8 Hz), 7.50 (d, 1H, J=2.0 Hz), 7.32 (dd, 1H, J=2.0, 8.3 Hz), 7.30-7.26 (m, 4H), 7.21-7.16 (m, 1H), 7.13 (d, 1H, J=8.3 Hz), 7.07 (d, 1H, J=8.3 Hz), 3.70-3.62 (m, 2H), 3.42-3.32 (m, 1H), 3.03 (t, 1H, J=8.8 Hz), 2.87-2.79 (m, 1H), 2.75-2.68 (m, 1H), 2.54 (t, 1H, J=7.8 Hz), 2.40-2.29 (m, 1H), 1.96-1.85 (m, 1H).

Step 3

Using a similar method to Example 371, and using (±)-6-[2-chloro-4-(3-phenyl-pyrrolidin-1-ylmethyl)-phenoxy]-nicotinonitrile (step 2 above) (0.198 g, 0.508 mmol), potassium carbonate (0.0337 g, 0.244 mmol), and 30% hydrogen peroxide solution (aq) (0.180 mL, 1.59 mmol) in dimethylsulfoxide (5.0 mL) provides 0.126 g (61%) of the title compound as a yellowish syrup: high resolution mass spectrum (electrospray): m/z calc for C$_{23}$H$_{23}$ClN$_3$O, 408.1479, found 408.1449; $^1$H NMR (methanol-d$_4$): 8.61 (d, 1H, J=2.4 Hz), 8.32 (d, 1H, J=2.4, 8.8 Hz), 7.61 (d, 1H, J=2.0 Hz), 7.44 (dd, 1H, J=2.0, 8.3 Hz), 7.35-7.29 (m, 4H), 7.27 (d, 1H, J=8.3 Hz), 7.24-7.18 (m, 1H), 7.11 (d, 1H, J=8.8 Hz), 3.80 (d, 1H, J=13.2 Hz), 3.76 (d, 1H, J=13.2 Hz), 3.50-3.39 (m, 1H), 3.15 (dd, 1H, J=7.8, 9.3 Hz), 2.99-2.91 (m, 1H), 2.82 (td, 1H, J=6.3, 8.8 Hz), 2.60 (t, 1H, J=8.8 Hz), 2.45-2.34 (m, 1H), 2.03-1.92 (m, 1H).

EXAMPLE 378

6-(3-Phenethyl-2,3,4,5-tetrahydro-1H-benzo[d]azepin-7-yloxy)nicotinamide

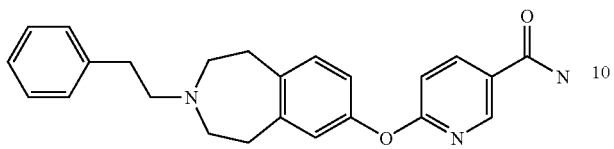

Step 1: N-(2,2-Dimethoxyethyl)-2-(3-methoxyphenyl)-N-methylacetamide

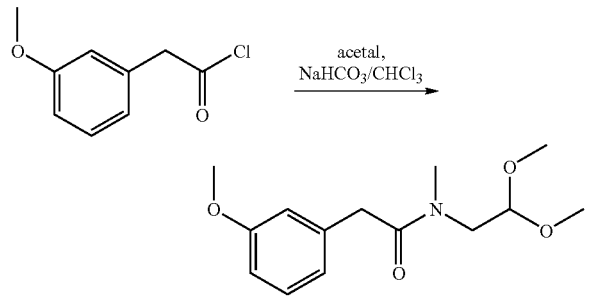

3-methoxyphenylacetyl chloride

Dissolve (methylamino)acetaldehyde dimethyl acetal (365 mL, 2.84 mol, 1.05 eq) in saturated aqueous NaHCO$_3$/CHCl$_3$ (4 L/5.5 L) at room temperature in a 22 L reaction flask. Add 3-methoxyphenacetyl chloride (500 g, 2.71 mol, 10.0 eq) via an addition funnel to the reaction flask over 30 minutes (added at a rate sufficient to control off-gassing). Stir the biphasic mixture for 3 hours vigorously. The reaction is determined to be complete by TLC (hexanes/ethyl acetate). Collect the CHCl$_3$ layer, and dry over sodium sulfate and purify by a silica plug (elute with 1/1 ethyl acetate/hexanes) to obtain N-(2,2-dimethoxyethyl)-2-(3-methoxyphenyl)-N-methylacetamide (product with solvent).
$^1$H NMR (CDCl$_3$): 7.26-7.20 (m, 1H); 6.84-6.77 (m, 3H); 4.52 (t, J=5.6 Hz, 0.7H): 4.4.27 (t, J=5.6 Hz, 0.3H); 3.79 (two singlets, total 3H), 3.77 (s, 0.7H); 3.70 (s, 1.3H), 3.46 (d, J=5.6 Hz, 1.3H); 3.39 (d, J=5.6 Hz, 0.7H); 3.38 (two singlets, total 6H); 3.03 (s, 2H); 2.99 (s, 1H).

Step 2: 8-M ethoxy-3-methyl-1,3-dihydrobenzo[d]azepin-2-one

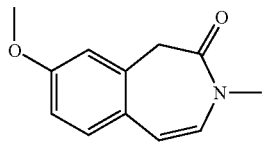

Add concentrated HCl (3.5 L) to a solution of N-(2,2-dimethoxyethyl)-2-(3-methoxyphenyl)-N-methylacetamide (790 g, 2.709 mol, 1.0 eq) dissolved in HOAc (3.5 L). Stir the mixture for 16 hours at room temperature. Dilute the reaction mixture with 4 L of dichloromethane and then quench slowly with 50% NaOH (4.0 L) over 2 hours. Separate the two layers. Collect the organic layer, dry over sodium sulfate and concentrate under vacuum to yield an off-white solid. The solid is put through a silica plug (1/1 hexanes/ethyl acetate) to obtain the product (Cmpd N, 460 g, 84% yield).
MS Found: 204.1 (M+H)$^+$ Step 3: 8-Methoxy-3-methyl-1,3,4,5-tetrahydrobenzo[d]azepin-2-one

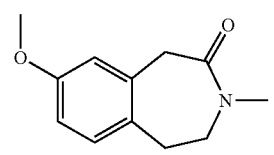

Weigh out 5% Pd on carbon (100 g) to a suitable container and wet the catalyst with ethyl acetate (2 L) while maintaining a nitrogen blanket. Charge the catalyst slurry to a 10-gallon autoclave and rinse the container with ethyl acetate (1 L) while maintaining a nitrogen purge. Add 8-methoxy-3-methyl-1,3-dihydrobenzo[c]azepin-2-one (920 g, 4.5 mol) to the autoclave and rinse with ethyl acetate (4 L). Purge the autoclave with nitrogen, seal the autoclave and pressurize with hydrogen to 50 psi while stirring at 800 rpm and maintaining the reaction temperature between 20-30° C. The reaction is determined to be complete by 1H NMR after 5 hours. Filter the autoclave contents over hyflo and rinse with ethyl acetate, then concentrate the filtrate to obtain the product methoxy-3-methyl-1,3,4,5-tetrahydrobenzo[d]azepin-2-one as an off-white solid (868 g, 93% yield).
MS Found: 206.1 (M+H)$^+$ Step 4: 7-M ethoxy-3-methyl-2,3,4,5-tetrahydro-1H-benzo[d]azepine

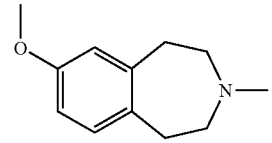

Dissolve methoxy-3-methyl-1,3,4,5-tetrahydrobenzo[d]azepin-2-one (375 g, 183 mmol, 1.0 eq) in THF (2.5 L) and add the solution via an addition funnel over 1 hour to slurry of lithium aluminium hydride (LAH) (175 g, 457 mmol, 2.5 eq) in ether/THF (4.5 L/2 L) in a 22 L reaction vessel under nitrogen while cooled in an ice/acetone bath. Add the starting amide at a rate to maintain the reaction temperature below 30° C. Stir the resulting mixture for 3 hours at room temperature under nitrogen. The reaction is determined to be complete by TLC. Cool the reaction mixture in an ice/acetone bath and quench slowly over 2 hours (off-gassing, exothermic) with water (175 mL) and 5.0 N NaOH solution (350 mL) added in succession. Filter the slurry and wash the solids with THF. Add sodium sulfate to the filtrate to remove any excess water, and then filter. Concentrate the filtrate down under vacuum to a dark oil to obtain the product methoxy-3-methyl-2,3,4,5-tetrahydro-1H-benzo[d]azepine (360 g, quantitative yield).
MS Found: 192.1 (M+H)$^+$

Step 5: 7-Methoxy-2,3,4,5-tetrahydro-1H-benzo[d]azepine hydrochloride

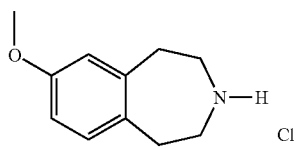

The reactions are set up in a 22 L flask, each equipped with a mechanical stirrer, heating mantle, condenser and nitrogen bubbler. Add 1-chloroethyl chloroformate (620 mL, 5.750 mol, 10.0 eq) over 1 hour to methoxy-3-methyl-2,3,4,5-tetrahydro-1H-benzo[d]azepine (110 g, 575 mmol, 1.0 eq) dissolved in 1,2-dichloroethane (8.0 L) at 60° C. under nitrogen, in a 22 L flask. The solution turns dark purple over the next 2 hours. Heat the mixture to reflux and stir for 16 hours under nitrogen. The reaction is determined to be complete by TLC. Cool the reaction flask and concentrate under vacuum to an oil. Dissolve the oil in methanol (4 L) and add to a 22 L reaction flask and stir for 16 hours at room temperature under nitrogen. Concentrate the resulting solution under vacuum to an off-white solid 220 g, 90% yield).

Step 6: 2,2,2-Trifluoro-1-(7-methoxy-1,2,4,5-tetrahydro-benzo[d]azepin-3-yl)ethanone

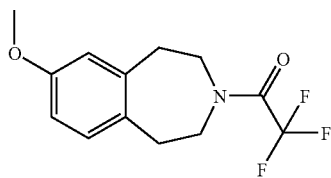

Add trifluoroacetic anhydride (400 mL, 2.780 mol, 1.1 eq) dissolved in dichloromethane (500 mL) to a solution of methoxy-2,3,4,5-tetrahydro-1H-benzo[d]azepine hydrochloride (541 g, 2.530 mol, 1.0 eq) in dichloromethane (7.5 L) and pyridine (450 mL, 5.570 mol, 2.2 eq) at 0° C. Stir the resulting solution for 16 hours at room temperature under nitrogen. The reaction is determined to be complete by TLC. Quench the reaction and wash with 6.0 N HCl (2×1 L). Collect the organic layer and purify using a silica plug (1 kg) with Darco® (approximately 100 g) and elute with dichloromethane. Concentrate the eluant to a solid under vacuum. Place the solid in a vacuum oven for 16 hours at room temperature to give the title compound (605 g, 88% yield).

GC/MS (m/e): 273 (M)$^+$

Step 7: 2,2,2-Trifluoro-1-(7-hydroxy-1,2,4,5-tetrahydro-benzo[d]azepin-3-yl)-ethanone

Dissolve 2,2,2-trifluoro-1-(7-methoxy-1,2,4,5-tetrahydro-benzo[d]azepin-3-yl)ethanone (10.0 g, 36.6 mmol) in dichloromethane (750 mL). Add BBr$_3$ (11.0 mL, 116 mmol) and stir for 4 hours. Quench the reaction mixture with water (350 mL). Filter the suspension, then separate the two layers. Extract the aqueous layer with dichloromethane (2×300 mL). Dry the combined organic extracts over MgSO$_4$, filter and concentrate to give the title compound (8.62 g, 91%): MS ES$^+$ 260 (M+H)$^+$, ES$^-$ 258 (M−H)$^-$; HPLC [YMC-Pack Pro C-18 (150×4.6 mm, S-5 micron) acetonitrile in water containing 0.01% concentrated HCl at 1.0 mL/min, 30-99% over 19 min], $t_R$=8.8 min, 100% purity.

Step 8: 6-[3-(2,2,2-Trifluoroacetyl)-2,3,4,5-tetrahydro-1H-benzo[d]azepin-7-yloxy]nicotinamide

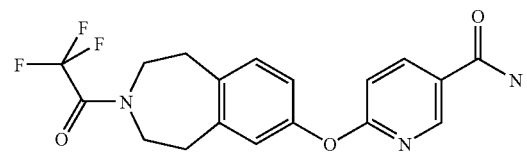

Add 2,2,2-trifluoro-1-(7-hydroxy-1,2,4,5-tetrahydro-benzo[d]azepin-3-yl)ethanone (0.750 g, 2.89 mmol), 6-chloronicotinamide (0.377 g, 2.41 mmol) and K$_2$CO$_3$ (0.833 g, 6.03 mmol) to a round bottom equipped with a Dean-Stark trap. Add toluene (6 mL) and DMF (18 mL). Heat at reflux for two hours. Cool the reaction mixture to 100° C. and stir overnight. Remove the toluene and DMF as an azeotrope with xylenes. Suspend the solid in 5% methanol/ethyl acetate (100 mL) and filter. Wash the filter cake with ethyl acetate. Concentrate the filtrate, then purify by flash chromatography, eluting with 40% ethyl acetate in dichloromethane to give the title compound (0.312 g, 34.0%):

MS ES$^+$ 380 (M+H)$^+$; HPLC [YMC-Pack Pro C-18 (150×4.6 mm, S-5 microm), acetonitrile in water containing 0.01% concentrated HCl at 1.0 mL/min, 30-99% over 19 min], $t_R$=8.5 min, 89% purity.

Step 9: 6-(2,3,4,5-Tetrahydro-1H-benzo[d]azepin-7-yloxy)nicotinamide

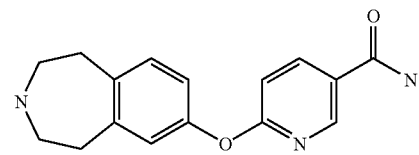

Dissolve 6-[3-(2,2,2-trifluoroacetyl)-2,3,4,5-tetrahydro-1H-benzo[d]azepin-7-yloxy]nicotinamide (0.306 g, 0.806 mmol) in 7.0 M NH$_3$ in methanol (10 mL). Seal the round bottom and allow to sit without stirring. After three hours, concentrate to give the title compound (0.22 g, 100%): MS ES$^+$ 284.1 (M+H)$^+$; HPLC [YMC-Pack Pro C-18 (150×4.6 mm, S-5 microm), acetonitrile in water containing 0.010% concentrated HCl at 1.0 mL/min, 30-99% over 19 min], t$_R$=1.2 min, 93% purity.

Step 10: 6-(3-Phenethyl-2,3,4,5-tetrahydro-1H-benzo[d]azepin-7-yloxy)nicotinamide Take up 6-(2,3,4,5-tetrahydro-1H-benzo[d]azepin-7-yloxy)nicotinamide (0.0500 g, 0.176 mmol) and K$_2$CO$_3$ (0.0488 g, 0.353 mmol) in DMF (1.0 mL). Add 2-bromoethylbenzene (0.0265 mL, 0.194 mmol) and eat to 70° C. overnight. Remove DMF as an azeotrope with xylenes. Purify by 5 g SCX column by washing with methanol and eluting with 2.0 M NH$_3$ in methanol. Then purify by flash chromatography, eluting with 0-10% ethyl acetate and 5% (2.0 M NH$_3$ in methanol) in dichloroethane to give the title compound: MS ES$^+$ 388.1 (M+H)$^+$; HPLC [YMC-Pack Pro C-18 (150×4.6 mm, S-5 microm), acetonitrile in water containing 0.01% concentrated HCl at 1.0 mL/min, 30-99% over 19 min], t$_R$=1.7 min, 100% purity.

EXAMPLE 379

6-(3-Benzyl-2,3,4,5-tetrahydro-1H-benzo[d]azepin-7-yloxy)-nicotinamide

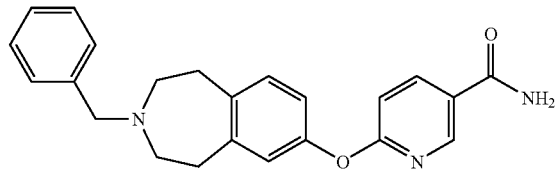

Using a method similar to Example 378, part J, using 6-(2,3,4,5-tetrahydro-1H-benzo[d]azepin-7-yloxy)nicotinamide (Part I) and a slight excess of benzyl bromide affords the title compound (0.0291 g, 44.2%): TOF ES$^+$ 374.2 (M+H)$^+$, HRMS calcd for C$_{23}$H$_{24}$N$_3$O$_2$ 374.1869 (M+H)$^+$, found 374.1870, time 0.41 min; HPLC [YMC-Pack Pro C-18 (150×4.6 mm, S-5 microm) acetonitrile in water containing 0.01% concentrated HCl at 1.0 mL/min, 30-99% over 19 min], t$_R$=1.6 min, 100% purity.

EXAMPLE 380

6-[4-(Phenethylaminomethyl)phenoxy]nicotinamidine

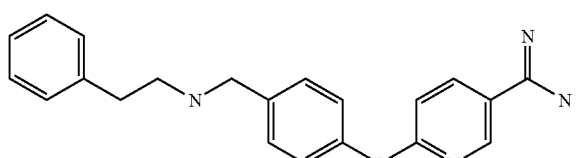

Part A: 4-(Phenethylaminomethyl)phenol

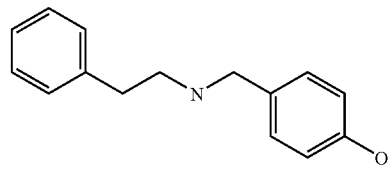

Dissolve 4-hydroxybenzaldehyde (1.00 g, 8.12 mmol) in methanol (40.6 mL). Add 3 Å molecular sieves and phenethylamine (1.02 mL, 8.12 mmol). Stir at room temperature for 17 hours. Add NaBH$_4$ (0.341 g, 9.01 mmol). After five hours, filter and concentrate. Purify by 10 g SCX column washing with methanol and eluting with 2.0 M NH$_3$ in methanol to give the title compound as an off white solid: HRMS calcd for C$_{15}$H$_{18}$NO 228.1388 (M+H)$^+$, found 228.1387, time 0.74 min, MS TOF ES$^+$ 228.1 (M+H)$^+$; HPLC [YMC-Pack Pro C-18 (150×4.6 mm, S-5 microm), acetonitrile in water containing 0.01% concentrated HCl at 1.0 mL/min, 30-99% over 19 min], t$_R$=1.4 min, 100% purity.

Part B: (4-Hydroxybenzyl)phenethylcarbamic acid tert-butyl ester

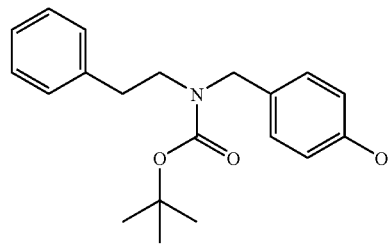

Suspend 4-(phenethylaminomethyl)phenol (0.750 g, 3.30 mmol) in dichloromethane (10 mL). Add a solution of (BOC)$_2$O (1.08 g, 4.95 mmol) in dichloromethane (6.5 mL). Quench with 1.0 N NaOH (75 mL) after 19 hours. Extract with dichloromethane (2×200 mL). Wash the organic layer with brine (1×75 mL), dry over Na$_2$SO$_4$, filter and concentrate. Purify by flash chromatography, eluting with 20-30% ethyl acetate in hexanes to give the title compound (0.570 g, 52.8%): MS ES$^+$ 328.3 (M+H)$^+$, base peak ES$^+$ 272.1 (M+2H—C(CH$_3$)$_3$)$^+$, ES$^-$ 326.3 (M−H)$^-$; HPLC [YMC-Pack Pro C-18 (150×4.6 mm, S-5 microm), acetonitrile in water containing 0.01% concentrated HCl at 1.0 mL/min, 30-99% over 19 min], t$_R$=14.7 min, 100% purity.

Part C: 6-Chloronicotinamidine

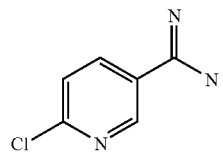

Suspend ammonium chloride (1.16 g, 21.6 mmol) in toluene (10 mL). Cool to 0° C. and slowly add 2.0 M Al(CH$_3$)$_3$ in toluene (10.8 mL, 21.6 mmol) (see Tetrahedron Lett. 1990, 31(14), 1969-1972). After the gas stops evolving, add a solution of 6-chloronicotinonitrile (1.00 g, 7.22 mmol) in toluene (52 mL). Heat to 80° C. overnight. Cool the reaction mixture, then slowly pour into slurry of silica gel (40 g) in CHCl$_3$ (200 mL). Stir for 10 minutes before filtering. Filter and wash the silica plug with methanol (2×100 mL). Concentrate the filtrate and purify by 10 g SCX column washing with methanol and then eluting with 2.0 M NH$_3$ in methanol to give the title compound (0.458 g, 40.8%): MS ES$^+$ 155.9 (M+H)$^+$: HPLC [YMC-Pack Pro C-18 (150×4.6 mm, S-5 microm), acetonitrile in water containing 0.01% concentrated HCl at 1.0 mL/min, 30-99% over 19 min], t$_R$=1.2 min, 97.2% purity.

Part D:
[(6-Chloropyridin-3-yl)iminomethyl]carbamic acid tert-butyl ester

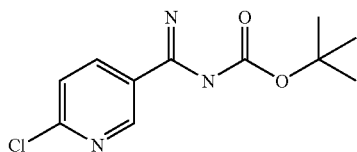

Suspend 6-chloronicotinamidine (0.442 g, 2.84 mmol) in THF (28 mL). Add a solution of (BOC)$_2$O (0.620 g, 5.68 mmol) in THF (4 mL); Concentrate after 16.5 hours. Purify by flash chromatography, eluting with 10-30% ethyl acetate in dichloromethane to give the title compound (0.685 g, 94.3%): MS ES$^+$ 256.0 (M+H)$^+$, base peak ES$^+$ 199.9 (M+2H—C(CH$_3$)$_3$)$^+$, ES$^-$ 254.1 (M−H)$^-$; HPLC [YMC-Pack Pro C-18 (150×4.6 mm, S-5 microm), acetonitrile in water containing 0.01% concentrated HCl at 1.0 mL/min, 30-99% over 19 min], t$_R$=1.5 min., 100% purity.

Part E:
6-[4-(Phenethylaminomethyl)phenoxy]nicotinamidine

Take up (4-hydroxybenzyl)phenethylcarbamic acid tert-butyl ester (0.0900 g, 0.275 mmol), [(6-chloropyridin-3-yl)iminomethyl]carbamic acid tert-butyl ester (0.0703 g, 0.275 mmol) and K$_2$CO$_3$ (0.0950 g, 0.687 mmol) in DMF (2.7 mL). Heat at 60° C. for 3 hours. Then increase the temperature to 80° C. for an additional 22 hours. Concentrate the reaction mixture. Add ethyl acetate to the resulting solid, solid and filter. Concentrate the filtrate. Add dichloromethane (0.50 mL) to the solid, then TFA (0.42 mL). Stir for 3.5 hours at room temperature. Concentrate the reaction mixture. Purify by flash 40 chromatography, eluting with 70% (2.0 M NH$_3$ in methanol) in ethyl acetate. Load the product onto a 5 g SCX column. Wash with methanol and elute with 7.0 M NH$_3$ in methanol to give the title compound (0.0165 g, 17.3%): MS ES$^+$ 347.0 (M+H)$^+$, base peak ES$^-$ 243.0 (M+2H—CH$_2$CH$_2$C$_6$H$_5$)$^+$, HPLC [YMC-Pack Pro C-18 (150×4.6 mm, S-5 microm), acetonitrile in water containing 0.01% concentrated HCl at 1.0 mL/min, 30-99% over 19 min], t$_R$=4.7 min. 100% purity.

EXAMPLE 381

6-[4-(2-Benzylaminoethyl)phenoxy]nicotinonamide

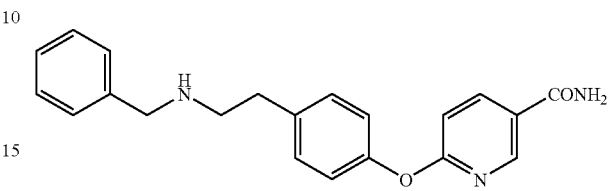

Part A

[2-(4-Hydroxyphenyl)ethyl]carbamic acid tert-butyl ester

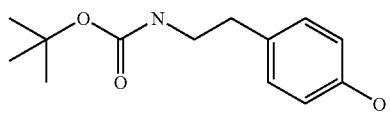

Suspend tyramine (10.0 g, 73.0 mmol) in THF (200 mL). Cool to 0° C. Add a solution of (BOC)$_2$O (31.8 g, 145 mmol) in THF (43 mL). Allow reaction mixture to warm to room temperature overnight. After 20 hours concentrate. Purification through two Waters 500A columns on a Prep LC system 500A to give the title compound: MS FAB ES$^+$ 238.3 (M+H)$^+$, base peak 182.2 (M+2H—C(CH$_3$)$_3$)$^+$; HPLC [YMC-Pack Pro C-18 (150×4.6 mm. S-5 microm), acetonitrile in water containing 0.01% concentrated HCl at 1.0 mL/min. 30-99% over 19 min], t$_R$=8.5 min, 100% purity.

Part B

6-[4-(2-Aminoethyl)phenoxy]nicotinonitrile

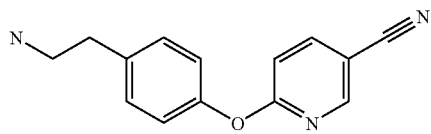

Take up [2-(4-hydroxyphenyl)ethyl]carbamic acid tert-butyl ester (5.00 g, 21.1 mmol), 6-chloronicotinonitrile (2.05 g, 14.8 mmol) and K$_2$CO$_3$ (5.10 g, 36.9 mmol) in toluene (37 mL) and DMF (111 mL). Heat at reflux for 1.5 hours. Then cool to 100° C. and stir overnight at 100° C. Remove solvents as an azeotrope with xylenes.

Suspend the solid in dioxane (73.8 mL). Add 4.0 M HCl in dioxane (73.8 mL). Stir at room temperature for three days. Filter the precipitate. Wash the filter cake with dioxane (1×30 mL), 50% ether in dioxane (1×30 mL) and ether (30 mL). Purify the filter cake using two Waters 500A columns on a Prep LC 500A system to give the title compound: HRMS calcd for C$_{14}$H$_{14}$N$_3$O 240.1137 (M+H)$^+$, found=240.1139, time 0.38 min, MS TOF ES$^+$ 240.1 (M+H)$^+$, base peak 223.1 (M-NH$_2$)$^+$; HPLC [YMC-Pack Pro C-18 (150×4.6 mm, S-5 microm), acetonitrile in water containing 0.01% concentrated HCl at 1.0 mL/min, 30-99% over 19 min], t$_R$=1.6 min, 100% purity.

Part C

6-[4-(2-Benzylaminoethyl)phenoxy]nicotinonitrile

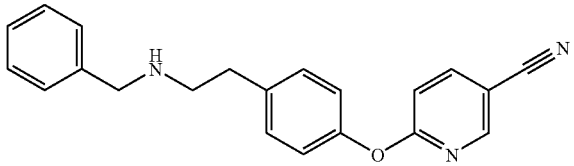

Dissolve 6-[4-(2-aminoethyl)phenoxy]nicotinonitrile (2.09 g, 8.75 mmol) in methanol. Add 3 Å molecular sieves and benzaldehyde (0.89 mL, 8.75 mmol). Stir at room temperature for 18 hours. Add NaBH$_3$CN (1.10 g). After the bubbling subsides, filter. Purify by flash chromatography, eluting with 3% (2.0 M NH$_3$ in methanol) in dichloromethane to give the title compound: HRMS calcd for C$_{22}$H$_{20}$N$_3$O 330.1620 (M+H)$^+$, found 330.1620, time 0.39 min, MS TOF ES$^+$ 330.2 (M+H)$^+$; HPLC [YMC-Pack Pro C-18 (150×4.6 mm, S-5 microm), acetonitrile in water containing 0.01% concentrated HCl at 1.0 mL/min, 30-99% over 19 min], t$_R$=2.4 min, 100% purity.

Part D

{2-[4-(5-Aminomethylpyridin-2-yloxy)phenyl]ethyl}benzylamine

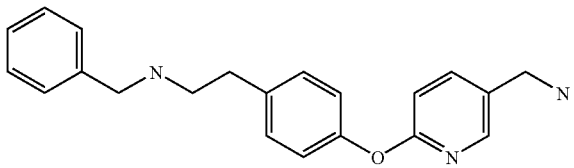

Dissolve 6-[4-(2-benzylaminoethyl)phenoxy]nicotinonitrile 0.0650 g, 0.197 mmol) in THF (2.0 mL). Beat to 65° C. before adding borane-dimethyl sulfide (0.0211 mL, 0.217 mmol). Continue heating for about 2 hours. Then add 5.0 N HCl (0.30 mL). Beat at reflux for 1 hour 20 minutes before cooling to room temperature. Add 1.0 N NaOH until the solution is basic. Extract with ether (3×25 mL). Concentrate the organic layer before purifying by flash chromatography, eluting with 10% (2.0 M NH$_3$ in methanol), 10% methanol and 80% ethyl acetate. Load the product onto a 1 g SCX column with methanol. Wash with methanol and elute with 2.0 M NH$_3$ in methanol. Run a second flash 40 column eluting with 10% (2.0 M NH$_3$ in methanol), 5% methanol and 85% ethyl acetate. Load the product onto a 5 g SCX column with methanol. Wash the column with methanol (4×10 mL) and 25% (2.0 M NH$_3$ in methanol) in methanol (1×10 mL). Then elute with 50% (2.0 M NH$_3$ in methanol) in methanol to give the title compound (0.0141 g, 21.7%): MS ES$^+$ 334.0 (M+H)$^+$, base peak ES$^+$ 227.0 (M-NHCH$_2$C$_6$H$_5$)$^+$; HPLC [YMC-Pack Pro C-18 (150×4.6 mm, S-5 microm), acetonitrile in water containing 0.01% concentrated HCl at 1.0 mL/min, 30-99% over 19 min], t$_R$=4.8 min. 91.2% purity.

Part E

6-[4-(2-Benzylaminoethyl)phenoxy]nicotinonamide

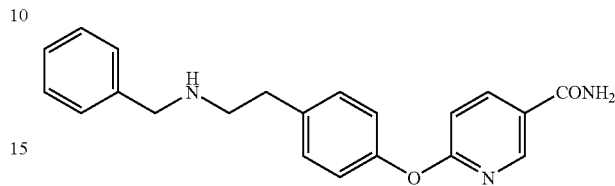

The amide, may be prepared from the nitrile from step C above by following basic hydrolysis procedures described previously.

EXAMPLE 382

5-[4-(Phenethylaminomethyl)phenoxy]pyridine-2-carboxyamide

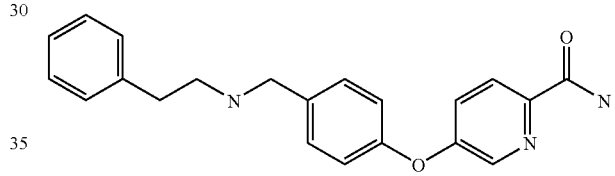

Part A: 2-Bromo-5-fluoropyridine

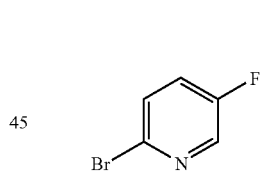

To a 3-neck flask equipped with a dropping funnel and thermometer, add 48% HBr (44.4 mL) and cool to <0° C. in an acetone/CO$_2$ bath. Add 2-amino-5-fluoropyridine (10 g, 89.2 mmol) over 12 minutes. With the temperature <0° C. add Br$_2$ (13.4 mL, 268 mmol) over 20 minutes. Cool the reaction mixture to <−10° C. Add a solution of NaNO$_2$ (15.5 g, 223 nm mol) in water (50 mL) over 1.5 hours. Stir for additional 30 minutes. Add a solution of NaOH (33.6 g, 838 mmol) in water (50 mL) over 30 minutes. Remove the acetone/CO$_2$ bath and allow the reaction mixture to warm to 5° C. Extract the solution with ether (3×150 mL). Wash the organic layer with water (1×75 mL) and brine (1×75 mL). Dry the organic layer over Na$_2$SO$_4$, filter and concentrate to give an orange-red solid as the title compound (14.1 g, 89.8%): TOF MS EI$^+$ 176.9 (M+H)$^+$, HRMS calcd for C$_5$H$_3$NBrF 174.9433, found 174.9438, time 2.27 min; HPLC [YMC-Pack Pro C-18 (150×

Part B: 5-Fluoropyridine-2-carboxamide

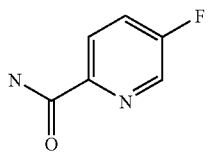

Take up 2-bromo-5-fluoropyridine (0.750 g, 4.26 mmol) and CuCN (0.954 g, 10.7 mmol) in DMF (10.7 mL). Heat to reflux for 5 hours. Cool the reaction mixture to 100° C. Add a solution of FeCl$_3$.6H$_2$O (0.654 g) in 10% HCl solution (30 mL) and stir for 15.5 hours. Cool the reaction mixture to 80° C. and filter. Add 1.0 N NaOH until the reaction mixture becomes basic and extract with dichloromethane (3×200 mL). Wash the organic layer with brine (1×75 mL), dry over Na$_2$SO$_4$, filter and concentrate to give the title compound (0.186 g, 31.2%): TOF MS EI$^+$ 140.0 (M)$^+$, base peak EI$^+$ 97.0 (M-CONH)$^+$, HRMS calcd for C$_6$H$_5$N$_2$OF 140.0386 found 140.0378, time 3.40 min; HPLC [YMC-Pack Pro C-18 (150×4.6 mm, S-5 microm), acetonitrile in water containing 0.01% concentrated HCl at 1.0 mL/min, 30-99% over 19 min], t$_R$=7.5 min, 100% purity.

Part C: [4-(6-Carbaminoylpyridin-3-yloxy)benzyl]phenethylcarbamic acid lei-1-butyl ester

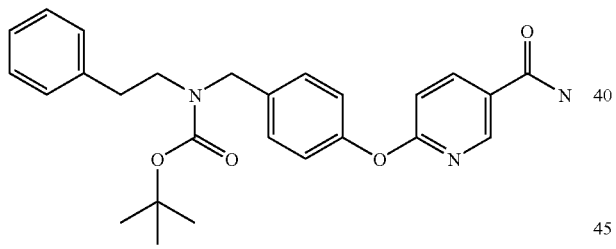

Dissolve (4-hydroxybenzyl)phenethylcarbamic acid tert-butyl ester (0.0915 g, 0.279 mol) in DMF (0.090 mL). Add NaH (80% in mineral oil) (0.0092 g, 0.307 mmol). Stir for 30 minutes before adding 5-fluoropyridine-2-carboxamide (0.0391 g, 0.279 mmol). Heat at 80° C. for 3 days. Load the reaction mixture directly onto a flash 40 column and elute with 35% ethyl acetate, 3% 2.0 M NH$_3$ in methanol and 62% hexanes to give the title compound (0.103 g, 82.4%): MS ES$^+$ 448.5 (M+H)$^+$, base peak ES$^+$ 392.3 (M+2H—C(CH$_3$)$_3$); HPLC [YMC-Pack Pro C-18 (150×4.6 mm, S-5 microm), acetonitrile in water containing 0.01% concentrated HCl at 1.0 mL/min, 5-95% over 19 min, 95% over 19.01-25 min], t$_R$=19.5 min, 100% purity.

Part D: 5-[4-(Phenethylaminomethyl)phenoxy]pyridine-2-carboxyamide

Dissolve [4-(6-carbamoylpyridin-3-yloxy)benzyl]phenethylcarbamic acid tert-butyl ester (0.0979 g, 0.219 mmol) in dichloromethane (2.2 mL). Then add TFA (2.2 mL). Stir at room temperature for 5 hours. Load the reaction mixture directly onto an SCX column. Wash with methanol and 33% (2.0 M NH$_3$ in methanol) in methanol. Elute with 66% (2.0 M NH$_3$ in methanol) in methanol to give the title compound (0.744 g, 97.9%): TOF MS ES$^+$ 348.2 (M+H)$^+$, base peak ES$^+$ 227.1 (M-NHCH$_2$CH$_2$C$_6$H$_5$)$^+$, HRMS calcd for C$_{21}$H$_{22}$N$_3$O$_2$ 348.1712 (M+H)$^+$, found 348.1700, time 0.33 min; HPLC [YMC-Pack Pro C-18 (150×4.6 mm, S-5 microm), acetonitrile in water containing 0.01% concentrated HCl at 1.0 mL/min, 5-95% over 19 min], t$_R$=9.0 min, 100% purity.

EXAMPLE 383

2-[4-(2-Benzylaminoethyl)phenoxy]nicotinamide

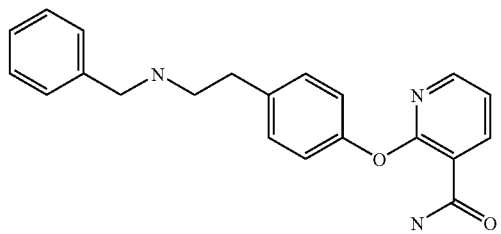

Part A: {2-[4-(3-Carbamoylpyridin-2-yloxy)phenyl]ethyl}carbamic acid tert-butyl ester

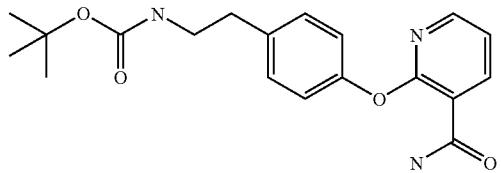

Dissolve [2-(4-hydroxyphenyl)ethyl]carbamic acid tert-butyl ester (Example 377, Part A) (0.500 g, 2.11 mmol) in DMF (10.5 mL). Add NaH (80% in mineral oil) (0.070 g, 2.32 mmol). Stir at room temperature for 30 minutes. Add 2-chloronicotinamide (0.330 g, 2.11 mmol) and heat to 100° C. Remove DMF as an azeotrope with xylenes after 18¾ hours. Take the solid up with ethyl acetate (150 mL) and 1.0 N NaOH (75 mL). Separate the two layers. Extract the aqueous layer with ethyl acetate (1×150 mL). Wash the combined organic layers with brine (1×50 mL), dry over Na$_2$SO$_4$, filter and concentrate. Purify by flash chromatography eluting with 35-45% ethyl acetate in dichloromethane to give the title compound (0.538 g, 71.4%): MS ES$^+$ 358.3 (M+H)$^+$, base peak ES$^-$ 302.1 (M+2H—C(CH$_3$)$_3$)$^+$, MS ES$^-$ 356.4 (M−H)$^-$, HPLC [YMC-Pack Pro C-18 (150×4.6 mm, S-5

Part B: 2-[4-(2-Aminoethyl)phenoxy]nicotinamide

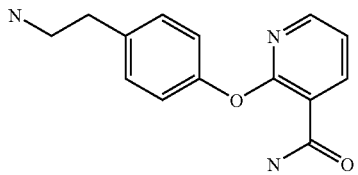

Dissolve {2-[4-(3-carbamoylpyridin-2-yloxy)phenyl]ethyl}carbamic acid tert-butyl ester (0.518 g, 1.45 mmol) in dichloromethane (8.4 mL). Add TFA (8.4 mL) and stir at room temperature for 4 hours. Concentrate the reaction mixture. Load the product onto an SCX column with methanol. Wash the column with methanol then elute with 50% (2.0 M $NH_3$ in methanol) in methanol to give the title compound (0.38 g, 100%): TOF MS $ES^+$ 258.1 $(M+H)^+$, base peak TOF $ES^+$ 241.1 $(M-NH_2)^+$, HRMS calcd for $C_{14}H_{16}N_3O_2$ 258.1243 $(M+H)^+$, found 258.1228, time 0.34 min; HPLC [YMC-Pack Pro C-18 (150×4.6 mm, S-5 microm), acetonitrile in water containing 0.01% concentrated HCl at 1.0 mL/min, 5-95% over 19 min], $t_R$=13.4 min, 100% purity.

Part C:
2-[4-(2-Benzylaminoethyl)phenoxy]nicotinamide

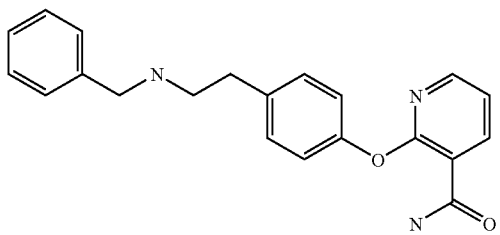

Take up 2-[4-(2-aminoethyl)phenoxy]nicotinamide (0.0555 g, 0.216 mmol) in methanol (2.1 mL). Add benzaldehyde (0.022 mL, 0.216 mmol) and 3 Å molecular sieves. Stir at room temperature overnight. Add $NaBH_4$ (0.0082 g, 0.216 mmol) and stir for 6 hours before loading directly onto an SCX column. Wash the column with methanol then elute with 2.0 M $NH_3$ in methanol. Purify by flash chromatography, eluting with 4% (2.0 M $NH_3$ in methane) in dichloromethane to give the title compound (0.831 g, 79%): TOF MS $ES^+$ 348.2 $(M+H)^+$, HRMS calcd for $C_{21}H_{22}N_3O_2$ 348.1712 $(M+H)^+$, found 348.1721, time 0.35 min; TLC [silica gel 60 $F_{254}$, 5% (2.0 M $NH_3$ in methanol) in dichloromethane] $R_f$=0.20.

EXAMPLE 384

6-[4-(2-Benzylaminoethyl)phenoxy]pyridine-2-carboxamide

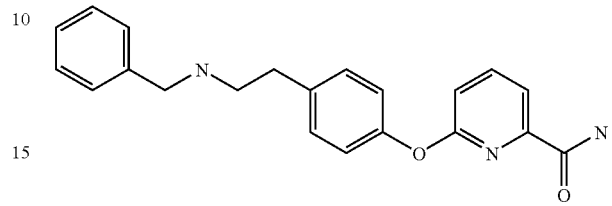

Part A: 6-Bromopyridine-2-carbonitrile

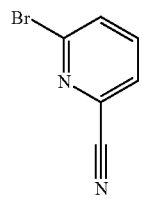

Take up 2,6-dibromopyridine (0.500 g, 2.11 mmol) and CuCN (0.189 g, 2.11 mmol) in DMF (5.3 mL). Heat at 100° C. for 22 hours. Cool to room temperature. Add water (50 mL) and extract with ethyl acetate (3×100 mL). Wash the organic layer with brine (1×75 mL), dry over $Na_2SO_4$, filter and concentrate. Purify by flash chromatography, eluting with 15-40% ethyl acetate in hexanes to give the title compound (0.108 g, 30.0%): GC/MS, MS $ES^+$ 182 $(M-H)^+$, time 8.78 min, % of total 100%; TLC [silica gel 60 $F_{254}$, 30% ethyl acetate in hexanes] $R_f$=0.29.

Part B: {2-[4-(6-Cyanopyridin-2-yloxy)phenyl]ethyl}carbamic acid tert-butyl ester

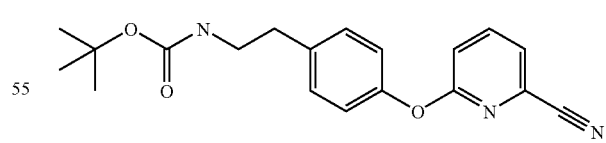

Using a method similar to Example 381 Part A, using [2-(4-hydroxyphenyl)ethyl]carbamic acid tert-butyl ester (0.140 g, 0.588 mmol), NaH (80% in mineral oil) (0.194 g, 0.647 mmol) and 6-bromopyridine-2-carbonitrile (0.107 g, 0.588 minor) gives the title compound (0.0895 g, 44.8%): MS $ES^+$ 340.2 $(M+H)^+$, base peak MS $ES^+$ 284.0 $(M+2H-C(CH_3)_3)^+$, MS $ES^-$ 338.3 $(M-H)^-$, TLC [silica gel 60 $F_{254}$, 40% ethyl acetate in hexanes] $R_f$=0.24.

Part C: {2-[4-(6-Carbamoylpyridin-2-yloxy)phenyl]ethyl}carbamic acid tert-butyl ester

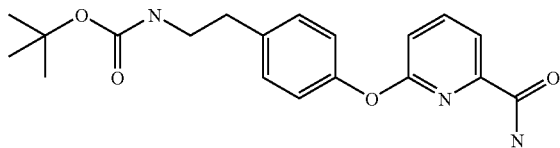

Dissolve {2-[4-(6-cyanopyridin-2-yloxy)phenyl]ethyl}carbamic acid tert-butyl ester (0.814 g, 0.240 mmol) in DMSO (4.8 mL). Add $K_2CO_3$ (0.166 g, 0.120 μmol) and then 30% $H_2O_2$ (0.071 mL 0.624 mmol). Stir at room temperature for 3 hours. Quench the reaction mixture with water (30 mL). Extract with ethyl acetate (1×60 mL). Wash the organic layer with water (1×30 mL), dry over $MgSO_4$, filter and concentrate to give the title compound (68.1 g, 79.5%): MS $ES^+$ 357.9 $(M+H)^+$, base peak $ES^+$ 301.9 $(M+2H—C(CH_3)_3)$, MS $ES^-$ 356.1 $(M-H)^-$; HPLC [YMC-Pack Pro C-18 (150×4.6 mm, S-microm), acetonitrile in water containing 0.01% concentrated HCl at 1.0 mL/min, 30-99% over 19 min], $t_R$=18.5 min, 94.5% purity.

Part D:
6-[4-(2-Aminoethyl)phenoxy]pyridine-2-carboxyamide

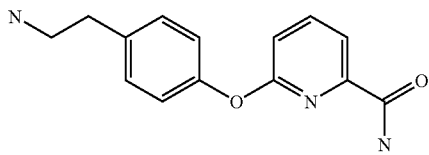

Using a method similar to Example 383 Part B, using {2-[4-(6-carbamoylpyridin-2-yloxy)phenyl]ethyl}carbamic acid tert-butyl ester (0.0631 g, 0.176 mmol) gives the title compound (0.055 g crude): TLC [silica gel 60 $F_{254}$, 10% (2.0 M NH3 in methanol) in dichloromethane] $R_f$=0.13; HPLC [YMC-Pack Pro C-18 (150×4.6 mm, S-5 microm), acetonitrile in water containing 0.01% concentrated HCl at 1.0 mL/min, 30-99% over 19 min], $t_R$=4.8 min, 100% purity.

Part E: 6-[4-(2-Benzylaminoethyl)phenoxy]pyridine-2-carboxamide

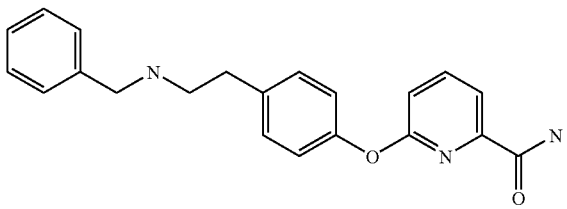

Dissolve 6-[4-(2-aminoethyl)phenoxy]pyridine-2-carboxamide (0.0452 g, 0.176 mmol) in methanol (2.9 mL). Add benzaldehyde (0.018 mL) and 3 Å molecular sieves. Stir at room temperature overnight. Add $NaBH_4$ (0.0066 g, 0.176 mmol). Stir for additional 6.5 hours before filtering and concentrating. Purify by reverse phase chromatography, eluting with 0-99% 0.1% TFA/acetonitrile and 0.1% TFA/water to give the title compound (9.4 mg, 15.4%): MS $ES^-$ 347.9 $(M+H)^+$, HPLC [YMC-Pack Pro C-18 (150×4.6 mm, S-5 microm), acetonitrile in water containing 0.01% concentrated HCl at 1.0 mL/min, 5-95% over 19 min], $t_R$=7.6 min, 100% purity.

EXAMPLE 385

2-[4-(2-Benzylaminoethyl)phenoxy]isonicotinamide

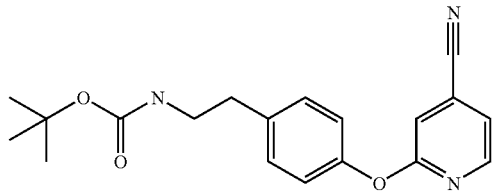

Part A: {2-[4-(4-Cyanopyridin-2-yloxy)phenyl]ethyl}carbamic acid tert-butyl ester

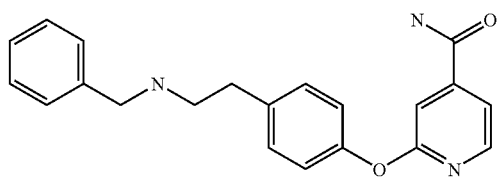

Using a method similar to Example 381, Part A, using 2-chloroisonicotinonitrile (0.500 g, 3.61 mmol) and [2-(4-hydroxyphenyl)ethyl]carbamic acid tert-butyl ester (Example 377, Part A) (0.856 g, 3.61 mmol) gives the title compound (0.947, 77.6%): MS $ES^+$ 340.2 $(M+H)^+$, base peak MS $ES^+$ 284.0 $(M+2H—C(CH_3)_3))^+$; TLC [silica gel 60 $F_{254}$, 40% ethyl acetate in hexanes] $R_f$=0.30.

Part B:
2-[4-(2-Aminoethyl)phenoxy]isonicotinonitrile

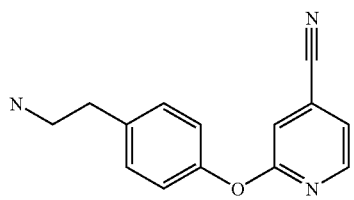

Using a method similar to Example 382, Part D, using {2-[4-(4-cyanopyridin-2-yloxy)phenyl]ethyl}carbamic acid tert-butyl ester (0.200 g, 0.589 mmol) gives the title compound (0.14 g, 100%): TLC [silica gel 60 F$_{254}$, 8% (2.0 M NH$_3$ in methanol) in dichloromethane] R$_f$=0.32.

Part C:
2-[4-(2-Benzylaminoethyl)phenoxy]isonicotinamide

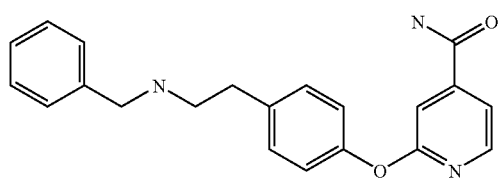

Dissolve 2-[4-(2-aminoethyl)phenoxy]isonicotinonitrile (0.143 g, 0.589 mmol) in methanol (6.0 mL). Add 3 Å molecular sieves and benzaldehyde (0.061 g, 0.598 mmol). Stir at room temperature overnight before adding NaBH$_4$ (0.0226 g, 0.598 mmol). Quench with 1.0 N NaOH (0.5 mL) then concentrate. Purify with a flash 40 column eluting with 5% (2.0 M NH$_3$ in methanol), 35% ethyl acetate and 60% dichloromethane.

Dissolve the product in DMSO (12 mL). Add K$_2$CO$_3$ (0.041 g, 0.299 mmol), then 30% H$_2$O$_2$ (0.18 mL, 1.55 mmol). Stir at room temperature for 1 day. Then heat at 50° C. for 6.5 hours. Allow the reaction mixture to cool down to room temperature overnight. Quench the reaction with 1.0 N NaOH (30 mL). Extract with dichloromethane (1×75 mL), wash the organic layer with brine: 1.0 N NaOH (2:1) (1×30 mL), filter and concentrate. Purify by reverse phase chromatography, eluting with 30-100% 0.10% TFA/acetonitrile in 0.1% TFA/water. Load the product onto an SCX column. Wash with methanol and elute with 2.0 M NH$_3$ in methanol to give the title compound (6.4 mg, 6.1%): MS ES$^+$ 347.9 (M+H)$^+$, MS ES$^-$ 346.2 (M−H)$^-$; HPLC [YMC-Pack Pro C-18 (150×4.6 mm, S-5 microm), 0.1% TFA/acetonitrile in 0.1% TFA/water at 1.0 mL/min, 5-95% over 19 min], t$_R$=8.3 min, 92.2% purity.

EXAMPLE 386

N-Methyl-{6-[4-(phenethylaminomethyl)phenoxy] nicotinamidine

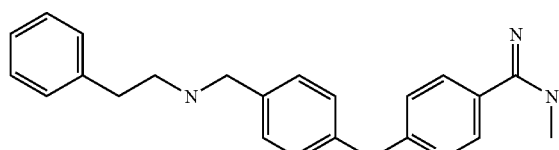

Part A: N-Methyl-6-chloronicotinamidine

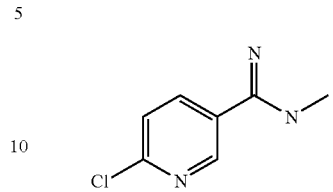

Using a method similar to Example 380, Part D, using 2-chloronicotinonitrile (1.00 g, 7.32 mmol), 2.0 M Al(CH$_3$)$_3$ in toluene (11 mL, 22.0 mmol) and methylamine hydrochloride (1.48 g, 22.0 mmol) gives the title compound (0.952 g, 76.7%): MS ES$^+$ 171.8 (M+H)$^+$, MS ES$^-$ 168.0 (M−H)$^-$; HPLC [YMC-Pack Pro C-18 (150×4.6 mm, S-5 microm), 0.1% TFA/acetonitrile in 0.1% TFA/water at 1.0 mL/min, 5-95% over 19 min], t$_R$=5.0 min, 97.0% purity.

Part B: N-Methyl-6-[4-(phenethylaminomethyl)phenoxy]nicotinamidine

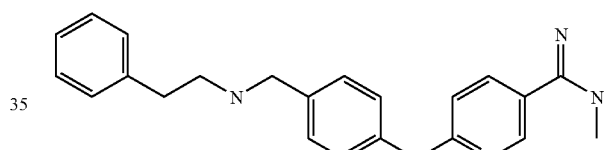

Take up N-methyl-6-chloronicotinamidine (0.0552 g, 0.326 mmol), (4-hydroxybenzyl)phenethylcarbamic acid tert-butyl ester (Example 380, Part B) (0.107 g, 0.326 mmol) and K$_2$CO$_3$ (0.225 g, 1.63 mmol) in DMF (1.6 mL). Beat at 120° C. for 2.5 hours. Then increase the temperature to 140° C. for additional 20 hours. Remove DMF as an azeotrope with xylenes. Take the solid up in dichloromethane:ethyl acetate: methanol (3:5:1) and filter. Load onto an SCX column with methanol. Wash with methanol and elute with 2.0 M NH$_3$ in methanol. Concentrate the eluant to yield the N-BOC protected product.

Dissolve the product in dichloromethane (5.0 mL). Add TFA (5 mL) and stir at room temperature for 6 hours. Concentrate the reaction mixture. Load the product onto an SCX column. Wash with methanol, 33% (2.0 M NH$_3$ in methanol) in methanol and 66% (2.0 M NH$_3$ in methanol) in methanol. Elute with 2.0 M NH$_3$ in methanol to give the title compound (0.0587 g, 50.2%): TOF MS ES$^+$ 361.2 (M+H)$^+$, HRMS calcd for C$_{22}$H$_{25}$N$_4$O 361.2028 (M+H)$^+$, found 361.2048, time 0.47 min; HPLC [YMC-Pack Pro C-18 (150×4.6 mm, S-5 microm), 0.1% TFA/acetonitrile in 0.1% TFA/water at 1.0 mL/min, 5-95% over 19 min], t$_R$=8.1 min, 100% purity; Anal. Calcd for C$_{22}$H$_{24}$Cl$_2$N$_4$O.0.9H$_2$O: C, 70.15; H, 6.90; N, 14.88. Found: C, 70.03; H, 6.71; N, 14.91.

EXAMPLE 387

5-[4-(Phenethylaminomethyl)phenoxy]pyrazine-2-carboxamide

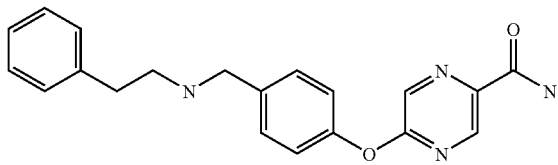

Part A: 5-Chloropyrazine-2-carboxamide

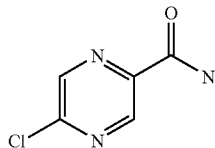

Suspend ammonium chloride (0.465 g, 8.69 mmol) in toluene (14 mL). Cool to 0° C. and slowly add 2.0 M Al(CH$_3$)$_3$ in toluene (4.3 mL, 8.69 mmol). After the gas stops evolving, add 5-chloropyrazine-2-carboxylic acid methyl ester (0.500 g, 2.89 mmol). Heat at 50° C. overnight. Cool the reaction mixture to room temperature, then slowly pour into a slurry of silica gel (10 g) in CHCl$_3$ (50 mL). Stir for 10 minutes before filtering. Wash the silica plug with methanol (2×100 mL) before concentrating. Take the resulting solid up in dichloromethane and wash with water (30 mL) and brine (40 mL). Dry the organic layer over Na$_2$SO$_4$, filter and concentrate. Purify by flash chromatography, eluting with 50% ethyl acetate in hexanes to give the title compound (0.155 g, 34.0%): TOF MS EI$^+$ 157.0 (M$^+$), HRMS calcd for C$_5$H$_4$N$_3$OCl 157.0043 (M+H)$^+$, found 157.0047, time 4.19 min; HPLC [YMC-Pack Pro C-18 (150×4.6 mm, S-5 microm), 0.1% TFA/acetonitrile in 0.1% TFA/water at 1.0 mL/min. 5-95% over 19 min], t$_R$=7.1 min, 100% purity.

Part B: [4-(5-Carbamoylpyrazin-2-yloxy)benzyl]phenethylcarbamic acid tert-butyl ester

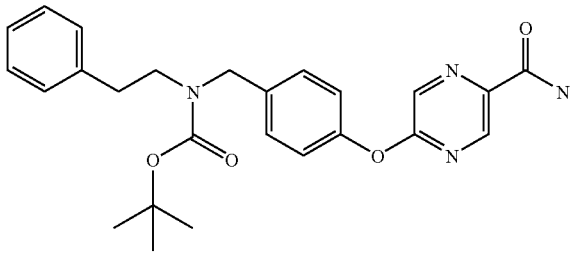

Take up 5-chloropyrazine-2-carboxamide (0.0527 g, 0.334 mmol), (4-hydroxybenzyl)phenethylcarbamic acid tert-butyl ester (Example 380, Part B) (0.110 g, 0.334 mmol) and K$_2$CO$_3$ (0.116 g, 0.836 mmol) in DMF (0.80 mL). Heat at 140° C. for 21.5 hours. Concentrate the reaction mixture then purify by flash chromatography, eluting with 50% ethyl acetate in hexanes to give the title compound (0.019 g, 12.7%):
MS ES$^+$ 448.8 (M+H)$^+$, base peak MS ES$^+$ 392.8 (M-C (CH$_3$)$_3$)$^+$; HPLC [YMC-Pack Pro C-18 (150×4.6 mm, S-5 microm), 0.1% TFA/acetonitrile in 0.1% TFA/water at 1.0 mL/min, 30-99% over 19 min], t$_R$=14.8 min, 100% purity.

Part C: 5-[4-(Phenethylaminomethyl)phenoxy]pyrazine-2-carboxamide

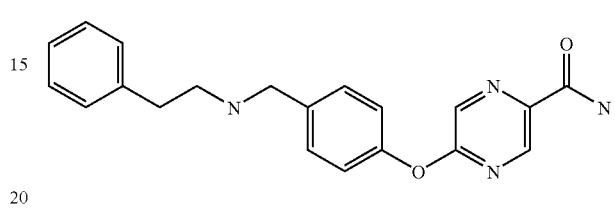

Dissolve [4-(5-carbamoylpyrazin-2-yloxy)benzyl]phenethylcarbamic acid tert-butyl ester (0.015 g, 0.0334 mmol) in dichloromethane (1 mL). Add TFA (1 mL). Stir at room temperature for 6 hours. Load directly onto an SCX (5 g) column. Wash the column with methanol thien elute with 2.0 M NH$_3$ in methanol to give the title compound (11.5 mg, 98%): MS ES$^+$ 348.9 (M+H)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], t$_R$=9.4 min, 98.4 purity.

EXAMPLE 388

5-(4-{[2-(4-Fluorophenyl)ethylamino]methyl}phenoxy)pyridine-2-carboxamide

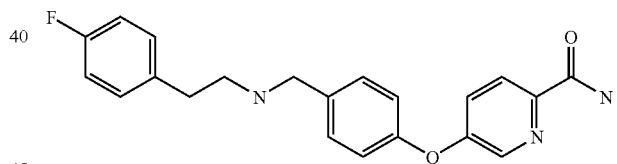

Part A: Ethyl 5-fluoropyridine-2-carboxylate

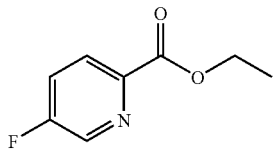

To a Parr shaker add 2-bromo-5-fluoropyridine (Example 382, Part A) (7.00 g, 39.8 mmol), NaOAc (13.1 g, 159 mmol), absolute ethanol (100 mL) and [1,1-bis(diphenylphosphino)ferrocene]dichloropalladium(II):dichloromethane (1.62 g, 1.99 mmol). Charge the reaction vessel with 50 psi of CO. Heat at 90° C. for 18.25 hours. Cool the reaction mixture before filtering through a Celite® pad. Wash the pad with ethyl acetate, then concentrate the filtrate. Purify by flash chromatography, eluting with 25% ethyl acetate in hexanes to give the title compound (4.62 g, 68.6%): MS ES+ 169.9 (M+H)+, base peak MS ES+ 141.8 (M+H—CH2CH3)+; HPLC [YMC-Pack Pro C-18 (150×4.6 mm, S-5 microm), 0.1% TFA/acetonitrile in 0.10% TFA/water at 1.0 mL/min, 5-95% over 19 min], $t_R$=10.3 min, 97.0 purity.

Part B: 5-Fluoropyridine-2-carboxylic acid

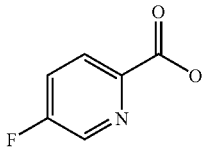

Dissolve ethyl 5-fluoropyridine-2-carboxylate (4.60 g, 27.2 mmol) in THF (34 mL) and methanol (34 mL). Add 1.0 N NaOH (32.6, 32.6 mmol) and stir at room temperature for 1.3 hours. Concentrate the reaction mixture. Then add 1.0 N HCl (32.6 mL) stir and concentrate. Take the solid up in 20% methanol, 3% AcOH and 77% dichloromethane and filter through a silica plug. Wash the plug with the solvent listed above until all of the product elutes off to give the title compound (3.8 g, 100%): MS ES+ 142.03 (M+H)+, HRMS calcd for $C_6H_5NO_2F$ 142.0304 (M+H)+, found 142.0306, time 0.46 min, 0.51; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=6.3 min, 100% purity.

Part C1: 5-Fluoropyridine-2-carboxamide

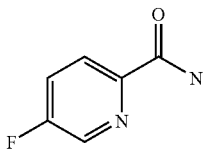

Take up 5-Fluoropyridine-2-carboxylic acid (3.82 g, 27.1 mmol) in THF (67.7 mL). Add N-hydroxysuccinimide (3.43 g, 29.8 mmol) and 1-(3-dimethylaminopropyl)-3-ethylcarbodiimide hydrochloride (5.71 g, 29.8 mmol). Add DMF (15 mL) to dissolve the gum formed. Stir for 3 hours at room temperature before adding ammonium chloride (2.17 g, 40.6 mmol). Bubble in ammonia gas for five minutes. Seal the reaction vessel and stir the reaction mixture overnight before concentrating. Take the solid up in water (150 mL) and extract with ethyl acetate (4×225 mL). Dry the organic layer over $Na_2SO_4$ filter and concentrate. Purify by flash chromatography eluting with 25% ethyl acetate, 1% (2.0 M $NH_3$ in methanol) and 74% dichloromethane to give the title compound (3.06 g, 80.7%): TOF MS EI+ 140.0 (M)+, TOF MS EI+ 97.0 (M+H—CONH2)+, HRMS calcd for $C_6H_5N_2OF$ 140.0386, found 140.0394, time 3.41 min; HPLC [YMC-Pack Pro C-18 (150×4.6 nm, S-5 microm), 0.1% TFA/acetonitrile in 0.1% TFA/water at 1.0 mL/min, 5-95% over 19 min], $t_R$=7.1 min, 100% purity.

Part C2: 4-[1,3]Dioxolan-2-yl-phenol

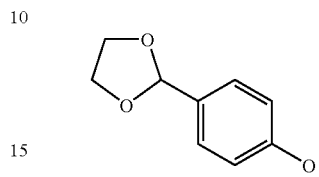

Mix 4-hydroxybenzaldehyde (1.23 g, 10.1 mmol), imidazole (1.37 g, 20.2 mmol), and triisopropylsilyl chloride (2.60 mL, 12.1 mmol) in DMF (10 mL) and stir at room temperature for 2 hours. Quench the reaction with saturated aqueous $NH_4Cl$ (50 mL) and extract with EtOAc (3×100 mL). Wash the organic layers with $H_2O$ and brine (50 mL each). Combine the organic layers, dry over $MgSO_4$, concentrate and purify by flash chromatography, eluting with 2.5% $Et_2O$/hexanes to afford 4-triisopropylsilyloxybenzaldehyde (2.78 g, 99%).

Heat at reflux a mixture of the aldehyde (2.1033 g, 7.55 mmol), p-TsOH.$H_2O$ (14.4 mg, 0.076 mmol), and ethylene glycol (4.2 mL, 75.5 mmol) in benzene (75 mL) overnight, while removing azeotropically the $H_2O$ formed. Cool and wash with 10% $K_2CO_3$ (2×50 mL) and brine which contains 10% $K_2CO_3$ (50 mL). Back-extract the aqueous layers with benzene and $Et_2O$ (100 mL each). Concentrate the combined organic layers after drying over $Na_2SO_4$ to afford (4-[1,3]dioxolan-2-yl-phenoxy)triisopropylsilane.

Dissolve the silyl ether in THF (70 mL) and treat with 1.0 M tetrabutylammonium fluoride (TBAF) in THF (8.0 mL) at room temperature for 1 hour. Concentrate, dissolve the residue in $Et_2O$ (100 mL) and wash with $H_2O$ (2×50 mL) and brine (50 mL). Back-extract the aqueous layers with $Et_2O$ (2×100 mL). Combine the organic layers, dry over $MgSO_4$, concentrate and purify by flash chromatography, eluting with 20-30% EtOAc/hexanes to afford the title compound (0.9799 g, 78%): HRMS calcd for $C_9H_{10}O_3$ 166.0630 (M)+, found 166.0648 time 4.69 min; JR (cm$^{-1}$) 3278 (OH); Anal. Calcd for $C_9H_{10}O_3$.$0.6H_2O$: C, 61.08; H, 6.38. Found: C, 61.21; H, 6.58.

Following 2-substituted-4-[1,3]dioxolan-2-yl-phenols were prepared in a similar manner.

2-Chloro-4-[1,3]dioxolan-2-yl-phenol: HRMS EI+ calcd for $C_9H_9O_3Cl$ 1156.00 (M-$C_2H_4O$)+, found 156.00 time 4.69 min.

4-[1,3]Dioxolan-2-yl-2-fluorophenol: HRMS calcd for $C_9H_9O_3F$ 184.0536 (M)$^4$ found 184.0525, time 4.24 min; IR (cm$^{-1}$) 3573 (OH).

4-[1,3]Dioxolan-2-yl-2-methoxyphenol: HRMS calcd for $C_{10}H_{12}O_4$ 196.0736 (M)+, found 196.0727, time 5.02 min; IR (cm$^{-1}$) 3497 (OH)

4-[1,3]Dioxolan-2-yl-2-methylphenol: HRMS calcd for $C_{10}H_{12}O_3$ 180.0786 (M)+, found 180.0785, time 4.97 min; IR (cm$^{-1}$) 3409 (OH)

4-[1,3]Dioxolan-2-yl-2-ethoxyphenol: HRMS calcd for $C_{11}H_{14}O_4$ 210.0892 (M)$^+$, found 210.0886, time 5.20 min; IR (cm$^{-1}$) 3400 (OH).

Part D:
5-(4-Formylphenoxy)pyridine-2-carboxamide

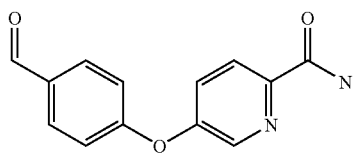

Dissolve 4-[1,3]dioxolan-2-ylphenol (Part C2, 0.471 g, 2.85 mmol) in DMF (89.5 mL). Add NaH (80% in mineral oil) (0.128 g, 4.28 mmol). Stir at room temperature for about an hour before adding 5-fluoropyridine-2-carboxamide (0.400 g, 2.85 mmol). Heat at 80° C. for 4.5 hours before concentrating to dryness to form 5-(4-[1,3]dioxolan-2-ylphenoxy)pyridine-2-carboxamide.

Take up the acetal product in 88% formic acid (9.5 mL). Stir at room temperature for about 3 hours before concentrating. Purify by flash chromatography, eluting with 35% ethyl acetate in dichloromethane to give the title compound (0.744 g): MS ES$^+$ 242.8 (M+H)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=11.0 min, 89.1% purity.

Part E: 5-(4-{[2-(4-Fluorophenyl)ethylamino]methyl}phenoxy)pyridine-2-carboxamide

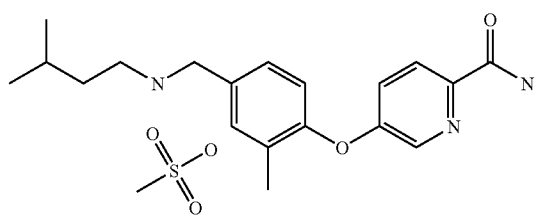

Suspend 5-(4-formylphenoxy)pyridine-2-carboxamide (0.0271 g, 0.112 mmol) In methanol (2.1 mL). Add 4-fluorophenethylamine (0.015 mL, 0.112 mmol) and 3 Å molecular sieves. Stir at room temperature overnight. Add NaBH$_4$ (in small excess) and stir for additional 3 hours. Load the reaction mixture directly onto a 5 g SCX column. Wash the column with methanol and elute with 2.0 M NH$_3$ in methanol. Purify by flash chromatography, eluting with 70% ethyl acetate, 5% (2.0 M NH$_3$ in methanol) and 25% hexanes to give the title compound (0.0370 g, 90.5%): TOF MS ES$^+$ 366.2 (M+H)$^+$, base peak TOF MS ES$^+$ 227.1 (M-NHCH$_2$CH$_2$C$_6$H$_4$F)$^+$, HRMS calcd for $C_{21}H_{21}N_3O_2F$ 366.1618 (M+H)$^+$, found 366.1621, time 0.42 min; HPLC [YMC-Pack Pro C-18 (150× 4.6 mm, S-5 microm), 0.1% TFA/acetonitrile in 0.1% TFA/water at 1.0 mL/min, 5-95°/over 19 min], $t_R$=10.2 min, 100% purity.

EXAMPLE 389

5-{4-[(3-Methylbutylamino)methyl]phenoxy}pyridine-2-carboxamide methanesulfonate

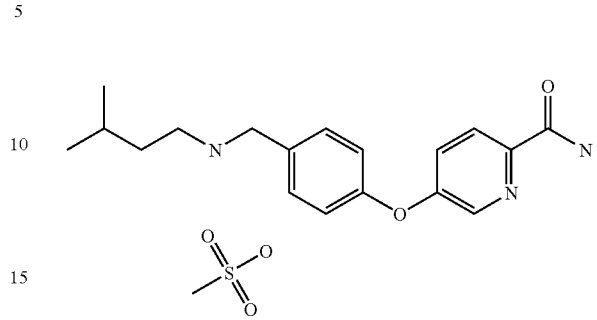

Suspend 5-(4-formylphenoxy)pyridine-2-carboxamide (0.0429 g, 0.160 mmol) in methanol (1.5 mL). Add isoamylamine (0.0185 mL, 0.112 mmol) and 3 Å molecular sieves. Stir at room temperature overnight. Add NaBH$_4$ (in small excess) and stir for additional 3 hours before filtering. Add saturated aqueous NaHCO$_3$ (20 mL) to the filtrate. Extract with dichloromethane (3×50 mL). Dry the organic layer over Na$_2$SO$_4$, filter and concentrate. Purify by flash chromatography, eluting with 5% (2.0 M NH$_3$ in methanol), 70% ethyl acetate and 25% hexanes to give the title compound as a free base (0.0323 g). Redissolve the product in THF (1 mL) and add a solution of 1.27 M methanesulfonate in THF (0.0298 mL) to give the title compound (0.039 g, 64.6%): MS ES$^+$ 314.0 (M+H)$^+$, base peak MS ES$^+$ 226.9 (M-NHCH$_2$CH$_2$CH(CH$_3$)$_2$)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.3 min, 96.0% purity.

EXAMPLE 390

5-{2-Methyl-4-[(3-methylbutylamino)methyl]phenoxy}pyridine-2-carboxamide methanesulfonate

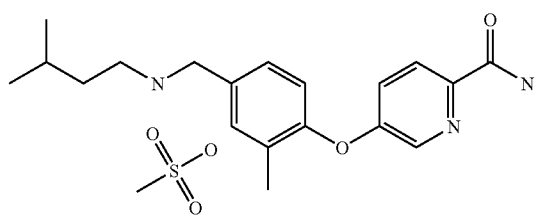

Part A:
5-(4-Formyl-2-methylphenoxy)pyridine-2-carboxamide

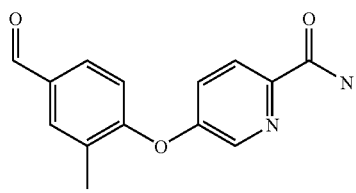

Using a method similar to Example 388 Part D, using 5-fluoropyridine-2-carboxamide (Example 388 Part C) (0.400 g, 2.85 mmol) and 4-[1,3]dioxolan-2-yl-2-methylphenol (Example 388, Part C2) (0.514 g, 2.85 mmol) gives the title compound (0.259 g): TLC [silica gel 60 $F_{254}$, 30% ethyl acetate in dichloromethane] $R_f$=0.20; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=12.1 min, 73.1% purity.

Part B: 5-{2-Methyl-4-[(3-methylbutylamino)methyl]phenoxy}pyridine-2-carboxamide methanesulfonate

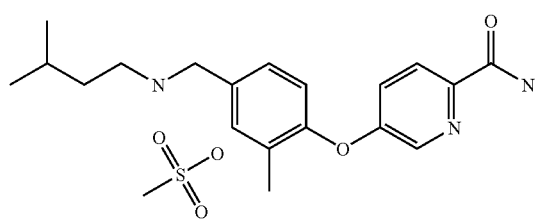

Using a method similar to Example 389 using 5-(4-formyl-2-methylphenoxy(pyridine-2-carboxamide (0.0429 g, 0.160 mmol) and isoamylamine (0.018 L, 0.160 mmol) gives the title compound (0.0576 g, 92.1%): TOF MS ES$^-$ 328.2 (M+H)$^+$, base peak MS ES$^+$ 241.1 (M-NHCH$_2$CH$_2$CH(CH$_3$)$_2$)$^+$, HRMS calcd for $C_{19}H_{26}N_3O_2$ 328.2025 (M+H)$^+$, found 328.2015, time 0.33 min; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.9 min, 100% purity.

EXAMPLE 391

5-{2-Methoxy-4-[(3-methylbutylamino)methyl]phenoxy}pyridine-2-carboxamide methanesulfonate

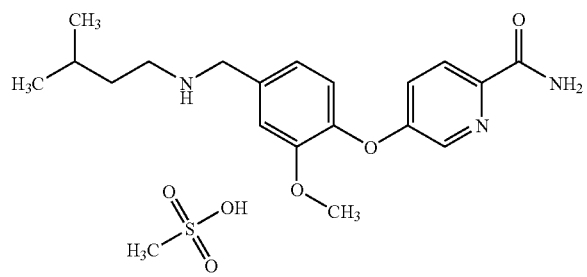

Part A: 5-(4-Formyl-2-methoxyphenoxy)pyridine-2-carboxamide

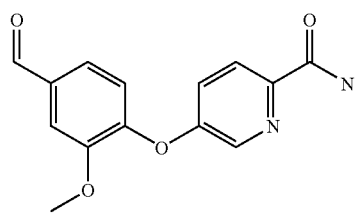

Using a method similar to Example 388 Part D, using 5-fluoropyridine-2-carboxamide (Example 388 Part C) (0.400 g, 2.85 mmol) and 4-[1,3]dioxolan-2-yl-2-methoxyphenol (Example 386, Part C2) (0.560 g, 2.85 mmol) gives the title compound (0.126 g, 16%): MS ES$^+$ 272.9 (M+H)$^+$: HPLC [YMC-Pack Pro C-18 (150×4.6 mm, S-5 microm), 0.1% TFA/acetonitrile in 0.01% TFA/water at 1.0 mL/min. 5-95% over 19 min], $t_R$=11.1 min. 97.2% purity.

Part B: 5-{2-Methoxy-4-[(3-methylbutylamino)methyl]phenoxy}pyridine-2-carboxamide methanesulfonate

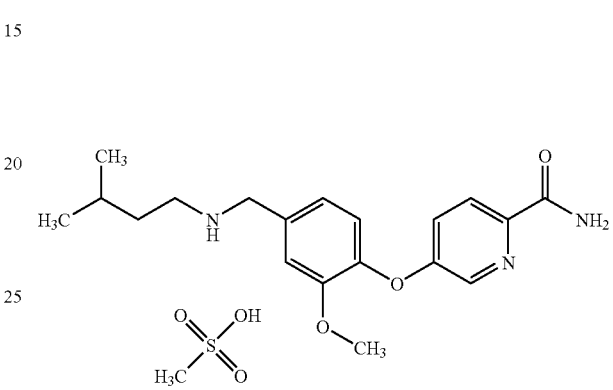

Using a method similar to Example 389 using 5-(4-formyl-2-methoxyl)ethoxy)pyridine-2-carboxamide (0.043 g, 0.160 mmol) and isoamylamine (0.018 mL, 0.160 mmol) gives the title compound (0.055 g, 81.2%): TOF MS ES$^+$ 344.2 (M+H)$^+$, base peak MS ES$^+$ 257.1 (M-NHCH$_2$CH$_2$CH(CH$_3$)$_2$)$^+$, HRMS calcd for $C_{19}H_{26}N_3O_3$ 344.1974 (M+H)$^+$, found 344.1978, time 0.35 min; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.5 min, 97.0% purity.

EXAMPLE 392

5-(4-{[2-(3-Trifluoromethylphenyl)ethylamino]methyl}phenoxy)pyridine-2-carboxamide methanesulfonate

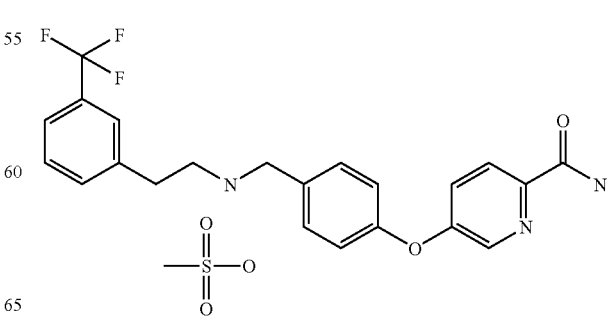

Using a method similar to Example 389, using 5-(4-formylphenoxy)pyridine-2-carboxamide (Example 388, Part D) (0.0337 g, 0.139 mmol) and 2-(3-trifluoromethylphenyl)ethylamine (0.0263 g, 0.139 mmol) gives the title compound (0.0127 g, 18%): MS ES$^+$ 415.9 (M+H)$^+$, base peak MS ES$^+$ 226.9 (M-NHCH$_2$CH$_2$CH(C$_6$H$_4$)CF$_3$)$^+$: HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=11.4 min, 100% purity.

EXAMPLE 393

5-{4-[(2-Thiophen-2-ylethylamino)methyl]phenoxy}pyridine-2-carboxamide methanesulfonate

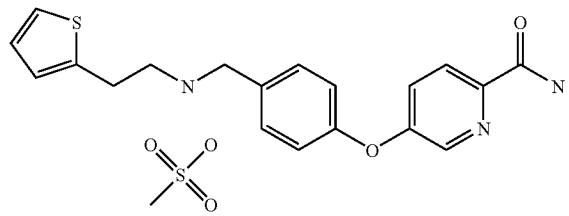

Using a method similar to Example 389, using 5-(4-formylphenoxy)pyridine-2-carboxamide (Example 388, Part D) (0.033 g, 0.136 mmol) and 2-(2-thienyl)ethylamine (0.0208 g, 0.163 mmol) gives the title compound (0.039 g, 64%): TOF MS ES$^+$ 354.1 (M+H)$^+$, base peak MS ES$^+$ 227.1 (M-NHCH$_2$CH$_2$(C$_4$H$_3$S))$^+$, HRMS calcd for C$_{19}$H$_{20}$N$_3$O$_2$S 354.1276 (M+H)$^+$, found 354.1298, time 0.30 min; HPLC [YMC-Pack Pro C-18 (150×4.6 mm, S-5 microm), 0.01% TFA/acetonitrile in 0.1% TFA/water at 1.0 mL/min, 5-95% over 19 min], $t_R$=9.5 min, 98.4% purity.

EXAMPLE 394

5-{2-Methyl-4-[(2-thiophen-2-ylethylamino)methyl]phenoxy}pyridine-9-carboxamide methanesulfonate

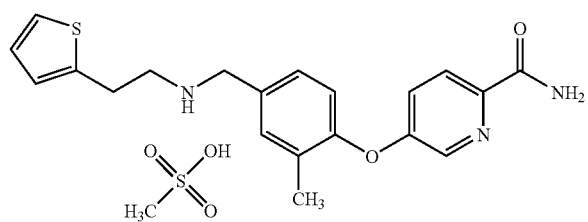

Using a method similar to Example 389, a reaction of 5-(4-formyl-2-methylphenoxy)pyridine-2-carboxamide (Example 390, Part A) (0.0349 g, 0.136 mmol) and 2-(2-thienyl)ethylamine (0.021 mL, 0.163 mmol) gives the title compound (0.0462 g, 73%): TOF MS ES$^+$ 368.1 (M+H)$^+$, base peak MS ES$^+$ 241.1 (M-NHCH$_2$CH$_2$(C$_4$H$_3$S)$^+$, HRMS calcd for C$_{20}$H$_{22}$N$_3$O$_2$S 368.1433 (M+H)$^+$, found 368.1436, time 0.36 min; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=10.0 min, 100% purity.

EXAMPLE 395

5-{2-Methoxy-4-[(2-thiophen-2-ylethylamino)methyl]phenoxy}pyridine-2-carboxamide methanesulfonate

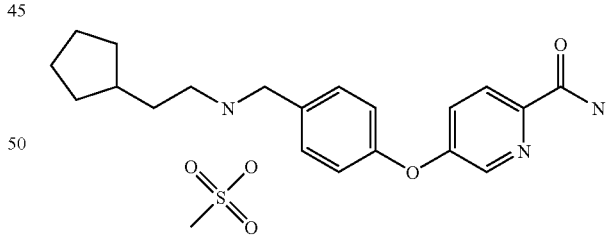

Using a method similar to Example 389, using 5-(4-formyl-2-methoxyphenoxy)pyridine-2-carboxamide (Example 391, Part A) (0.0370 g, 0.136 mmol) and 2-(2-thienyl)ethylamine (0.021 mL, 0.163 mmol) gives the title compound (0.025 g, 38%): TOF MS ES$^+$ 384.1 (M+H)$^+$, base peak MS ES$^+$ 257.1 (M-NHCH$_2$CH$_2$(C$_4$H$_3$S)$^+$, HRMS calcd for C$_{20}$H$_{22}$N$_3$O$_3$S 384.1382 (M+H)$^+$, found 384.1373, time 0.37 min; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.6 min, 100% purity.

EXAMPLE 396

5-{4-[(2-Cyclopentylethylamino)methyl]phenoxy}pyridine-2-carboxamide methanesulfonate Using a method similar to Example 389, and using 5-(4-formylphenoxy)pyridine-2-carboxamide (Example 388, Part D) (0.033 g, 0.138 mmol) and 2-cyclopentylethylamine (0.0156 g, 0.138 mmol) gives the title compound (0.0308 g, 51%): TOF MS ES$^+$ 340.2 (M+H)$^+$, base peak MS ES$^+$ 227.1 (M-NHCH$_2$CH$_2$(C$_5$H$_9$))$^+$, HRMS calcd for C$_{20}$H$_{26}$N$_3$O$_2$ 340.2025 (M+H)$^+$, found 340.2039, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.8 min, 95.9% purity.

EXAMPLE 397

5-{4-[(2-Cyclopentylethylamino)methyl]-2-methylphenoxy}pyridine-2-carboxamide methanesulfonate

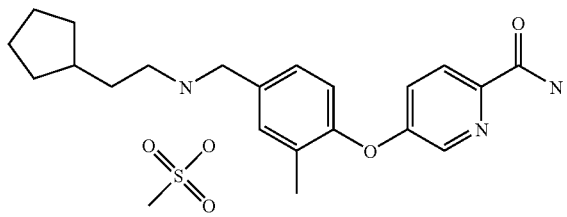

Using a method similar to Example 389, a reaction of 5-(4-formyl-2-methylphenoxy)pyridine-2-carboxamide (Example 390, Part A) (0.0353 g, 0.138 mmol) and 2-cyclopentylethylamine (0.0156 g, 0.138 mmol) gives the title compound (0.0349 g, 56.3%): TOF MS ES$^+$ 354.2 (M+H)$^+$, base peak MS ES$^+$ 241.1 (M-NHCH$_2$CH$_2$(C$_5$H$_9$))$^+$, HRMS calcd for C$_{21}$H$_{28}$N$_3$O$_2$ 354.2182 (M+H)$^+$, found 354.2188, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=8.5 min, 96.0% purity.

EXAMPLE 398

5-{4-[(2-Cyclopentylethylamino)methyl]-2-methoxyphenoxy}pyridine-2-carboxamide methanesulfonate

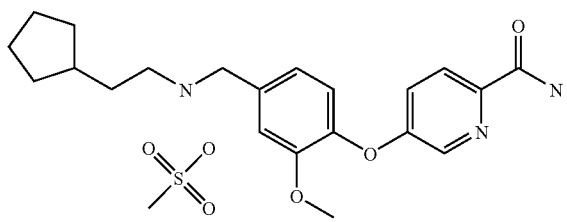

Using a method similar to Example 389, a reaction of 5-(4-formyl-2-methoxyphenoxy)pyridine-2-carboxamide (Example 391, Part A) (0.0375 g, 0.138 mmol) and 2-cyclopentylethylamine (0.0156 g, 0.138 mmol) gives the title compound (0.034 g, 52.9%): TOF MS ES$^+$ 370.2 (M+H)$^+$, base peak MS ES$^+$ 957.1 (M-NHCH$_2$CH$_2$(C$_5$H$_9$))$^+$, HRMS calcd for C$_{21}$H$_{28}$N$_3$O$_3$ 370.2123 (M+H)$^+$, found 370.2155, time 0.38 min; HPLC [YMC-Pack Pro C-18 (150×4.6 mm, S-5 microm), 0.1% TFA/acetonitrile in 0.1% TFA/water at 1.0 mL/min, 5-95% over 19 min], t$_R$=10.5 min. 96.1% purity.

EXAMPLE 399

5-(4-{[(Benzo[b]thiophen-3-ylmethyl)amino]methyl}phenoxy)pyridine-2-carboxamide methanesulfonate

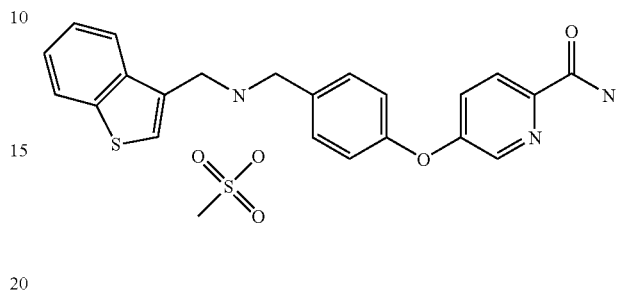

Using a method similar to Example 389, a reaction of 5-(4-formylphenoxy)pyridine-2-carboxamide (Example 388, Part D) (0.037 g, 0.154 mmol) and benzo[b]thiophen-3-ylmethylamine (from the hydrochloride salt freed oil a 1 g SCX column washing with methanol and eluting with 2.0 M NH$_3$ in methanol) (0.0485 g, 0.297 mmol) gives the title compound (0.0398 g, 53%): TOF MS ES$^+$:TIC, 390.1 (M+H)$^+$. HRMS calcd for C$_{22}$H$_{20}$N$_3$O$_2$S 390.1276 (M+H)$^+$, found 390.1261, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=8.0 min, 100% purity; Anal. Calcd for C$_{22}$H$_{19}$N$_3$O$_2$S.1.5CH$_4$OS: C, 52.89; H, 4.72; N, 7.72. Found: C, 52.69; H, 4.56; N, 7.72.

EXAMPLE 400

5-(4-{[2-(4-Methoxyphenyl)ethylamino]methyl}phenoxy)pyridine-2-carboxamide methanesulfonate

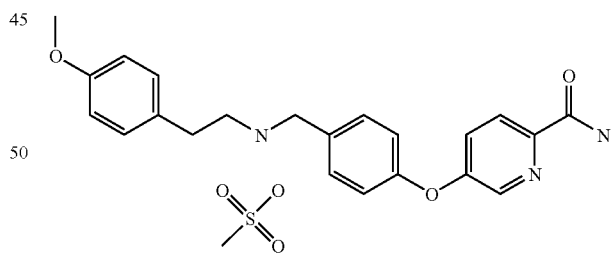

Using a method similar to Example 389, a reaction of 5-(4-formylphenoxy)pyridine-2-carboxamide (Example 388, Part D) (0.039 g, 0.159 mmol) and 4-methoxyphenethylamine (0.023 mL, 0.159 mmol) gives the title compound (0.0241 g, 32%): TOF MS ES$^+$ 378.2 (M+H)$^+$, HRMS calcd for C$_{22}$H$_{24}$N$_3$O$_3$ 378.1818 (M+H)$^+$, found 378.1836, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=7.2 min, 100% purity; Anal. Calcd for C$_{22}$H$_{23}$N$_3$O$_3$.1.1CH$_4$O$_3$S.0.4H$_2$O: C, 56.58; H, 5.80; N, 8.52. Found: C, 56.18; H, 5.67; N, 8.20.

EXAMPLE 401

5-(4-{[2-(3-Fluorophenyl)ethylamino]methyl}phenoxy)pyridine-2-carboxamide methanesulfonate

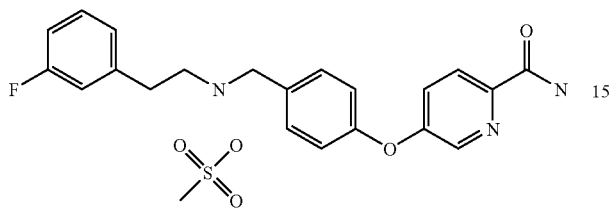

Using a method similar to Example 389, using 5-(4-formylphenoxy)pyridine-2-carboxamide (Example 388, Part D) (0.040 g, 0.164 minor) and 3-fluorophenylethyl amine (0.024 mL, 0.181 mmol) gives the title compound (0.044 g, 58.1%): TOF MS ES$^+$ 366.2 (M+H)$^+$, HRMS calcd for C$_{21}$H$_{21}$N$_3$O$_2$F 366.1618 (M+H)$^4$, found 366.1617, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=7.5 min, 100% purity.

EXAMPLE 402

5-(4-{[2-(2-Fluorophenyl)ethylamino]methyl}phenoxy)pyridine-2-carboxamide methanesulfonate

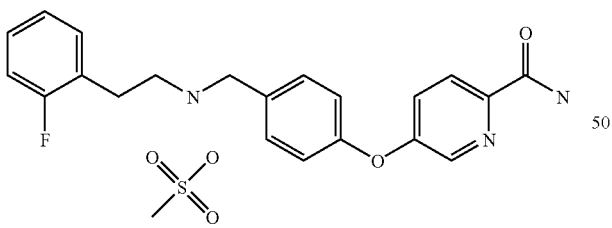

Using a method similar to Example 389, a reaction of 5-(4-formylphenoxy)pyridine-2-carboxamide (Example 388, Part D) (0.040 g, 0.164 mmol) and 2-fluorophenethylamine (0.024 mL, 0.181 mmol) gives the title compound (0.0324 g, 42.8%): TOF MS ES$^+$ 366.2 (M+H)$^+$, HRMS calcd for C$_{21}$H$_{21}$N$_3$O$_2$F 366.1618 (M+H)$^4$, found 366.1623, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=7.3 min, 100% purity.

EXAMPLE 403

5-{2-Fluoro-4-[(3-methylbutylamino)methyl]phenoxy}pyridine-2-carboxamide methanesulfonate

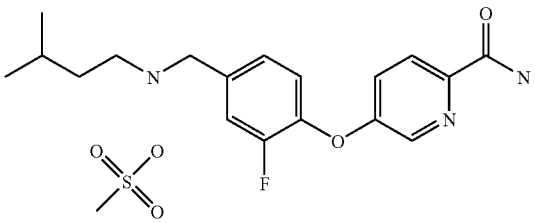

Part A: 5-(4-[1,3]Dioxolan-2-yl-2-fluorophenoxy)pyridine-2-carboxamide

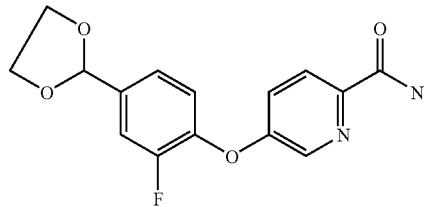

Take up 4-[1,3]dioxolan-2-yl-2-fluorophenol (Example 388, Part C2) (0.400 g, 2.14 mmol), 5-fluoropyridine-2-carboxamide (Example 388, Part C) (0.299 g, 2.14 mmol) and K$_2$CO$_3$ (0.514 g, 2.85 mmol) in DMF (5.3 mL). Heat at 100° C. overnight before concentrating to dryness. Take the black tar up in dichloromethane and filter through a silica gel plug. Wash the plug with ethylacetate (3×150 mL). Concentrate the filtrate. Purify by flash chromatography, eluting with 30-35% ethyl acetate in dichloromethane until the 5-fluoropyridine-2-carboxamide elutes of the column. Then elute with 100% ethyl acetate to give the title compound (0.317 g, 48.8%): MS ES$^+$ 305.0 (M+H)$^+$; TLC [silica gel 60 F$_{254}$, 30% ethyl acetate in dichloromethane] R$_f$=0.16.

Part B:
5-(2-Fluoro-4-formylphenoxy)pyridine-2-carboxamide

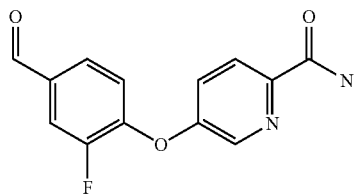

Take up 5-(4-[1,3]dioxolan-2-yl-2-fluorophenoxy)pyridine-2-carboxamide (0.316 g, 1.04 mmol) in 88% formic acid (5.2 mL). Stir at room temperature for 1.25 hours before diluting with water. Extract with dichloroethane (2×50 mL). Wash the organic layer with brine (1×25 mL), dry over Na$_2$SO$_4$, filter and concentrate to give the title compound (0.269 g, 99.6%): TOF MS ES$^+$ 261.1 (M+H)$^+$, HRMS calcd for $C_{13}H_{10}N_2O_3F$ 261.0675 $(M+H)^+$, found 261.0682, time 0.37 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$ 9.0 min, 100% purity.

Part C: 5-{2-Fluoro-4-[(3-methylbutylamino)methyl]phenoxy}pyridine-2-carboxamide methanesulfonate

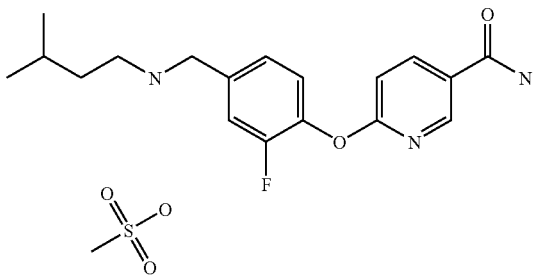

Using a method similar to Example 389, using 5-(2-fluoro-4-formylphenoxy)pyridine-2-carboxamide (0.0326 g, 0.125 mmol) and isoamylamine (0.0145 mL, 0.125 mmol) gives the title compound (0.0412 g, 69%): TOF MS ES+ 332.2 $(M+H)^+$, HRMS calcd for $C_{18}H_{23}N_3O_2F$ 332.1774 $(M+H)^+$, found 332.1787, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.7 min, 100% purity.

EXAMPLE 404

5-{2-Methyl-4-[(3-methylbutylamino)methyl]phenoxy}pyrazine-2-carboxamide methanesulfonate

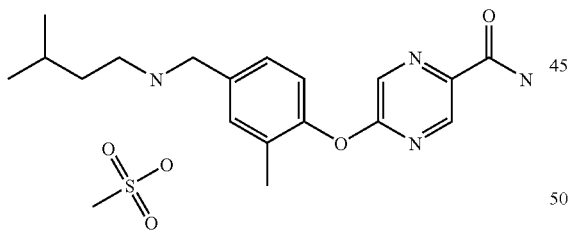

Part A: 5-Chloropyrazine-2-carbonitrile

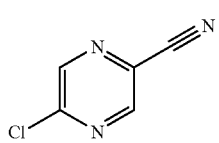

Dissolve 5-chloropyrazine-2-carboxamide (Example 389, Part A) (0.0878 g, 0.557 mmol) in $POCl_3$ (5.6 mL) and heat at reflux for 35 minutes. Concentrate the reaction mixture. Take up the dark oil in saturated aqueous $NaHCO_3$ (15 mL) and extract with dichloromethane (2×25 mL). Wash the organic layer with brine (1×15 mL), dry over $Na_2SO_4$, filter and concentrate. Purify by flash chromatography, eluting with 10% ethyl acetate in hexanes to give the title compound (0.0498 g, 64.0%): GC/MS, MS ES+ 139 $(M)^+$, time 10.6 min % of total 100%; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$ 8.2 min, 100% purity.

Part B: 5-(4-[1,3]dioxolan-2-yl-2-methylphenoxy)pyrazine-2-carbonitrile

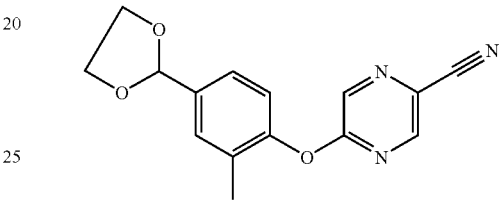

Take up 4-[1,3]dioxolan-2-yl-2-methylphenol (Example 388, Part C2) (0.288 g, 2.06 mmol), 5-chloropyrazine-2-carbonitrile (0.372 g, 2.06 mmol) and $K_2CO_3$ (0.428 g, 3.10 mmol) in DMF (13.8 mL). Beat at 100° C. for 45 minutes. Cool to 80° C. and stir overnight. Dilute the reaction mixture with dichloromethane (100 mL). Wash the organic layer with saturated aqueous $NaHCO_3$ (2×25 mL) and brine (1×25 mL). Dry over $Na_2CO_3$, filter and concentrate. Purify by flash chromatography eluting with 30% ethyl acetate in hexanes to give the title compound (0.560 g, 95.58%): TLC [silica gel 60 $F_{254}$, 30% ethyl acetate in hexanes] $R_f$=0.52.

Part C: 5-(4-[1,3]Dioxolan-2-yl-2-methylphenoxy)pyrazine-2-carboxamide

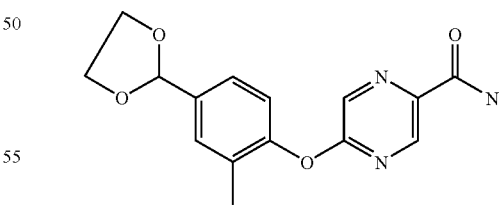

Take up 5-(4-[1,3]dioxolan-2-yl-2-methylphenoxy)pyrazine-2-carbonitrile (0.082 g, 0.305 mmol) and $K_2CO_3$ (0.020 g, 0.152 mmol) in DMSO (3.0 mL). Add 30% $H_2O_2$ (0.090 mL, 0.792 mmol) and stir at room temperature for 1.5 hours before quenching with water (10 mL). Extract with ethyl acetate (50 mL). Wash the organic layer with water (1×10 mL), dry over $Na_2SO_4$, filter and concentrate. Purify by flash chromatography, eluting with 40% ethyl acetate in dichloromethane to give the title compound (0.063 g, 68.6%): MS ES⁺ 302.0 (M+H)⁺; TLC [silica gel 60 F$_{254}$, 40% ethyl acetate in dichloromethane] R$_f$=0.17.

Part D:
5-(4-Formyl-2-methylphenoxy)pyrazine-2-carboxamide

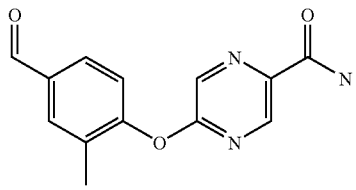

Using a method similar to (Example 403, Part B), a reaction of 5-(4-[1,3]dioxolan-2-yl-2-methylphenoxy)pyrazine-2-carboxamide (0.055 g, 0.183 mmol) gives the title compound (0.047 g, 100%): HPLC [YMC-Pack Pro C-18 (150× 4.6 mm. S-5 microm), 0.1% TFA/acetonitrile in 0.1% TFA/water at 1.0 mL/min, 20-99% over 23 min], t$_R$ 8.6 min, 100% purity; TLC [silica gel 60 F$_{254}$, 30% ethyl acetate in dichloromethane] R$_f$=0.22.

Part E: 5-{2-Methyl-4-[(3-methylbutylamino)methyl]phenoxy}pyrazine-2-carboxamide methanesulfonate

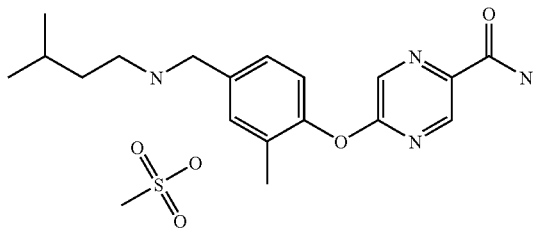

Using a method similar to Example 389, a reaction of 5-(4-formyl-2-methylphenoxy)pyrazine-2-carboxamide (0.0441 g, 0.171 mmol) and isoamylamine (0.020 mL, 0.171 mmol) gives the title compound (0.0563 g, 77.5%): TOF MS ES⁺ 329.2 (M+H)⁺, HRMS calcd for C$_{18}$H$_{25}$N$_4$O$_2$ 329.1978 (M+H)⁺, found 329.1985, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=6.4 min, 94.1% purity.

EXAMPLE 405

5-(2-Fluoro-4-pentylaminomethylphenoxy)pyridine-2-carboxamide

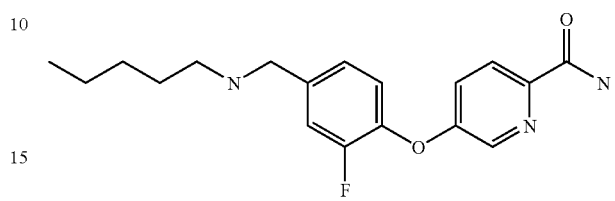

Place 5-(2-fluoro-4-formylphenoxy)pyridine-2-carboxamide (Example 403, Pan B) (0.040 g, 0.154 mmol), amylamine (0.0139 g, 0.154 mmol) and 3 Å molecular sieves in a vial. Add methanol (1.5 mL), cap and stir overnight. Add NaBH$_4$ (in excess over two portions) and stir until the gasses stop evolving. Load directly onto a 5 g SCX column. Wash with methanol (10 mL), then elute with 2.0 M NaBH$_3$ in methanol. Purify by loading the product onto a 5 g loading cartridge and eluting through a 10 g ISCO® column with 50% ethyl acetate, 5% (2.0 M NH$_3$ in methanol) and 45% hexanes to give the title compound (0.0387 g, 76.0%: TOF MS ES⁺ 332.2 (M+H)⁺. HRMS calcd for C$_{18}$H$_{23}$N$_3$O$_2$F 332.1774 (M+H)⁺, found 332.1765, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=6.9 min, 100% purity.

EXAMPLE 406

5-{2-Fluoro-4-[(2-thiophen-2-ylethylamino)methyl]phenoxy}pyridine-2-carboxamide

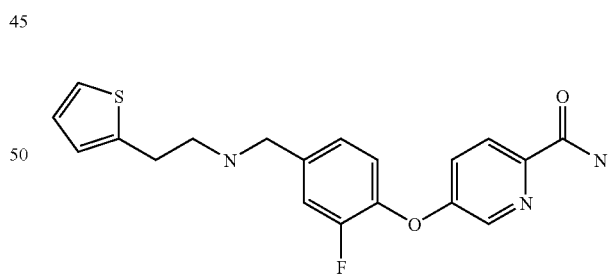

Using a method similar to Example 405, using 5-(2-fluoro-4-formylphenoxy)pyridine-2-carboxamide (Example 403, Part B) (0.040 g, 0.154 mmol) and 2-(2-thienyl)ethylamine (0.0196 g, 0.154 mmol) gives the title compound (0.03444 g, 60.2%): TOF MS ES⁺ 372.1 (M+H)⁺, HRMS calcd for C$_{19}$H$_{19}$N$_3$O$_2$FS 372.1182 (M+H)⁺, found 372.1168, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=6.9 min, 100% purity.

EXAMPLE 407

5-{2-Fluoro-4-[(2-pyridin-3-yl ethylamino)methyl]phenoxy}pyridine-2-carboxamide

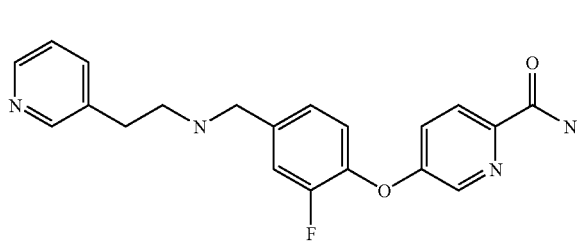

Using a method similar to Example 405, a reaction of 5-(2-fluoro-4-formylphenoxy)pyridine-2-carboxamide (Example 403, Part B) (0.040 g, 0.154 mmol) and 2-(pyridin-3-yl)ethylamine (0.019 g, 0.154 mmol) gives the title compound (0.0463 g, 82.2%): TOF MS ES$^+$ 367.2 (M+H)$^+$, HRMS calcd for $C_{20}H_{20}N_4O_2F$ 367.1570 (M+H)*, found 367.1553, time 0.39 min; HPLC [YMC-Pack Pro C-18 (150× 4.6 mm, S-5 microm), 0.1% TFA/acetonitrile in 0.1% TFA/water at 1.0 mL/min, 5-95% over 19 min], $t_R$=6.9 min. 100% purity.

EXAMPLE 408

5-{2-Fluoro-4-[(2-m-tolylethylamino)methyl]phenoxy}pyridine-2-carboxamide

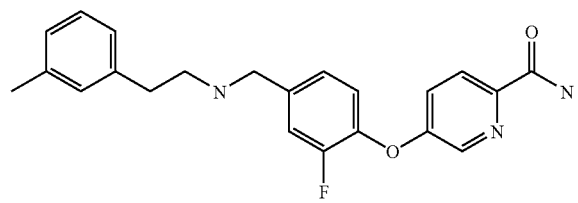

Using a method similar to Example 405, using 5-(2-fluoro-4-formylphenoxy)pyridine-2-carboxamide (Example 405, Part B) (0.040 g, 0.154 mmol) and 3-methylphenethylamine (0.021 g, 0.154 mmol) gives the title compound (0.0306 g, 52.5%): TOF MS ES$^+$ 380.2 (M+H)$^+$, HRMS calcd for $C_{21}H_{23}N_3O_2F$ 380.1774 (M+H)$^+$, found 380.1757, time 0.39 min; HPLC [YMC-Pack Pro C-18 (150×4.6 m, S-5 microm), 0.1% TFA/acetonitrile in 0.1% TFA/water at 1.0 mL/min, 20-99% over 23 min], $t_R$=8.4 min, 100% purity.

EXAMPLE 409

5-(2-Fluoro-4-{[2-(4-fluorophenyl)ethylamino]methyl}phenoxy)pyridine-2-carboxamide

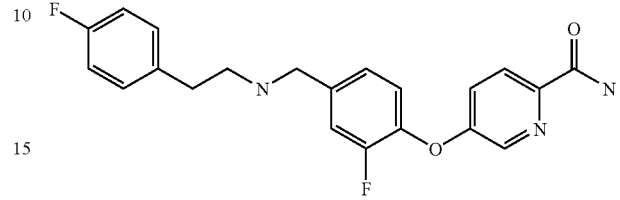

Using a method similar to Example 405, using 5-(2-fluoro-4-formylphenoxy)pyridine-2-carboxamide (Example 403, Part B) (0.040 g, 0.154 mmol) and 4-fluorophenethylamine (0.021 g, 0.154 mmol) gives the title compound (0.0231 g, 39.2%): TOF MS ES$^+$ 384.2 (M+H)$^+$, HRMS calcd for $C_{21}H_{20}N_3O_2F$, 384.1524 (M+H)$^+$, found 384.1509, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.8 min, 100% purity.

EXAMPLE 410

5-{2-Chloro-4-[(3-methylbutylamino)methyl]phenoxy}pyridine-2-carboxamide

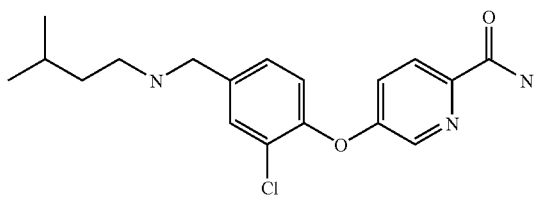

Part A: 5-(2-Chloro-4-[1,3]dioxolan-2-ylphenoxy)pyridine-2-carboxamide

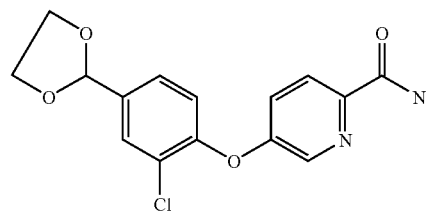

Using a method similar to Example 403, Part A, a reaction of 2-chloro-4-[1,3]dioxolan-2-ylphenol (Example 388, Part C2) (0.429 g, 2.14 mmol) and 5-fluoropyridine-2-carboxamide (Example 388 Part C) (0.299 g, 2.14 mmol) gives the title compound (0.264 g, 38.5%): MS ES⁺ 320.9 (M+H)⁺; TLC [silica gel 60 F$_{254}$, 30% ethyl acetate in dichloromethane] R$_f$=0.19

Part B:
5-(2-Chloro-4-formylphenoxy)pyridine-2-carboxamide

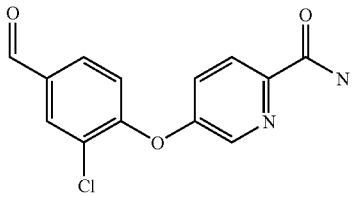

Using a method similar to Example 403, Part B, a reaction of 5-(2-chloro-4-[1,3]dioxolan-2-ylphenoxy)pyridine-2-carboxamide (0.263 g, 0.820 mmol) in 88% formic acid gives the title compound (0.194 g, 85.5%): TOF MS ES⁻ 277.0 (M+H)⁺, HRMS calcd for C$_{13}$H$_{10}$N$_2$O$_3$Cl 277.0380 (M+H)⁺, found 277.0378, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=10.3 min. 100% purity.

Part C: 5-{2-Chloro-4-[(3-methylbutylamino)methyl]phenoxy}pyridine-2-carboxamide

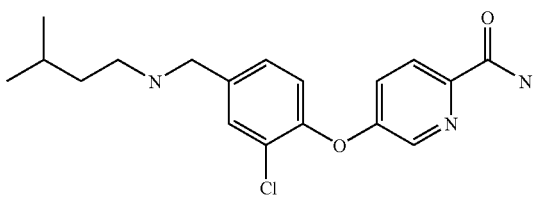

Using a method similar to Example 405, a reaction of 5-(2-chloro-4-formylphenoxy)pyridine-2-carboxamide (0.0388 g, 0.140 mmol) and isoamylamine (0.012 g, 0.140 mmol) gives the title compound (0.0320 g, 65.6%): TOF MS ES⁺ 348.1 (M+H)⁺, HRMS calcd for C$_{18}$H$_{23}$N$_3$O$_2$Cl 348.1479 (M+H)⁺, found 348.1466, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=7.4 min, 100% purity.

EXAMPLE 411

5-(2-Chloro-4-(pentylaminomethyl)phenoxy)pyridine-2-carboxamide

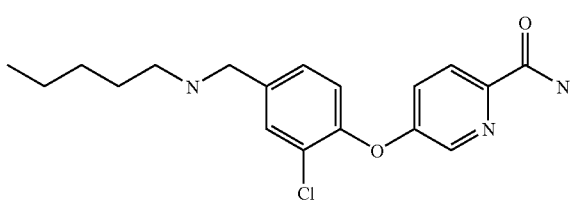

Using a method similar to Example 405, using 5-(2-chloro-4-formylphenoxy)pyridine-2-carboxamide (0.038 g, 0.140 mmol) and amylamine (0.012 g 0.140 mmol) gives the title compound (0.0314 g, 64.3%): TOF MS ES⁺ 348.1 (M+H)⁺, HRMS calcd for C$_{18}$H$_{23}$N$_3$O$_2$Cl 348.1479 (M+H)⁺, found 348.1456, time 0.39 min; HPLC [YMC-Pack Pro C-18 (150× 4.6 mm, S-5 microm), 0.1% TFA/acetonitrile in 0.1% TFA/water at 1.0 mL/min, 20-99% over 23 min], t$_R$=7.6 min, 100% purity.

EXAMPLE 412

5-{2-Chloro-4-[(2-thiophen-2-ylethylamino)methyl]phenoxy}pyridine-2-carboxamide

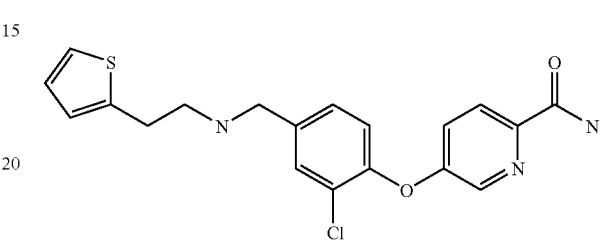

Using a method similar to Example 405, using 5-(2-chloro-4-formylphenoxy)pyridine-2-carboxamide (0.0388 g, 0.140 mmol) and 2-(2-thienyl)ethylamine (0.018 g, 0.140 mmol) gives the title compound (0.0396 g, 72.8%): TOF MS ES⁺ 388.1 (M+H)⁺. HRMS calcd for C$_{19}$H$_{19}$N$_2$O$_2$ClS 388.0887 (M+H)⁺, found 388.0866, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=7.6 min, 100% purity.

EXAMPLE 413

5-{2-Chloro-4-[(2-pyridin-3-yl ethylamino)methyl]phenoxy}pyridine-2-carboxamide

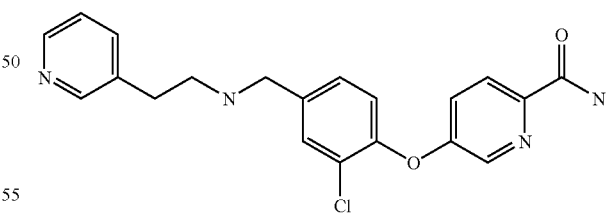

Using a method similar to Example 405, using 5-(2-chloro-4-formylphenoxy)pyridine-2-carboxamide (0.0388 g, 0.140 mmol) and 2-(pyridin-3-yl)ethylamine (0.017 g, 0.140 mmol) gives the title compound (0.0490 g, 91.2%): TOF MS ES⁺ 383.1 (M+H)⁺, HRMS calcd for C$_{20}$H$_{20}$N$_4$O$_2$Cl 1383.1275 (M+H)⁺, found 383.1248, time 0.39 min; Anal. Calcd for C$_{20}$H$_{19}$ClN$_4$O$_2$.0.1CH$_2$Cl$_2$: C, 61.90; H, 5.06; N, 14.38. Found: C, 61.90; H, 5.06; N, 14.38.

EXAMPLE 414

6-{2-Methoxy-4-[(3-methylbutylamino)methyl]phenoxy}nicotinamide

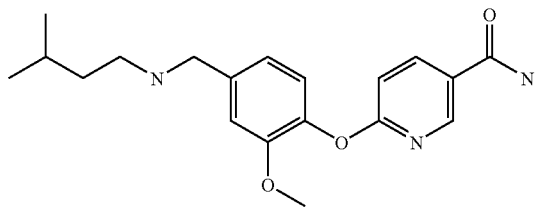

Part A:
6-(4-Formyl-2-methoxyphenoxy)nicotinonitrile

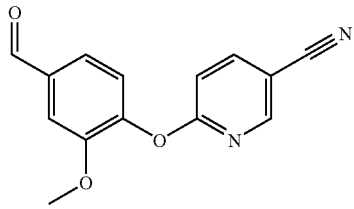

Take up vanillin (1.0 g, 6.57 mmol), 6-chloronicotinonitrile (0.911 g, 6.57 mmol) and $K_2CO_3$ (1.36 g, 9.86 mmol) in DMF (16.4 mL). Stir at room temperature overnight, then heat at 100° C. for 3 hours. Cool the reaction mixture to room temperature before quenching with water (75 mL). Extract with dichloromethane (2×150 mL). Wash the organic layer with brine (1×75 mL), dry over $MgSO_4$, filter and concentrate to give the title compound (1.65 g, 98.8%): TOF MS ES$^+$ 255.1 (M+H)$^+$, HRMS calcd for $C_{14}H_{11}N_2O_3$ 255.0770 (M+H)$^+$, found 255.0776, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=12.2 min, 100% purity.

Part B:
6-(4-Formyl-2-methoxyphenoxy)nicotinamide

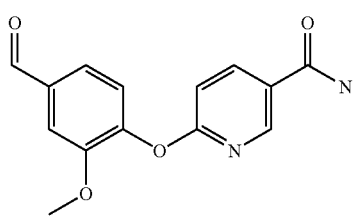

Using a method similar to (Example 404, Part C), 6-(4-formyl-2-methoxyphenoxy)nicotinonitrile (1.53 g, 6.00 mmol) gives the title compound (1.59 g, 97.5%): MS ES$^+$ 273.0 (M+H)$^+$, MS ES$^+$ 271.1 (M−H)$^-$; HPLC [YMC-Pack Pro C-18 (150×4.6 mm. S-5 microm), 0.1% TFA/acetonitrile in 0.1% TFA/water at 1.0 mL/min, 20-99% over 23 min], $t_R$=7.2 min, 98.6% purity.

Part C: 6-{2-Methoxy-4-[(3-methylbutylamino)methyl]phenoxy}nicotinamide

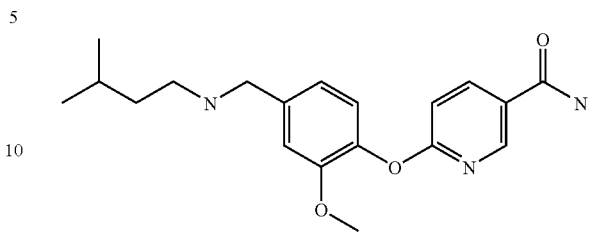

Using a method similar to Example 405, a reaction of 6-(4-formyl-2-methoxyphenoxy)nicotinamide (0.0423 g, 0.155 mmol) and isoamylamine (0.020 g, 0.171 mmol) gives the title compound (0.0162 g, 30.3%): TOF MS ES$^+$ 344.2 (M+H)$^+$, HRMS calcd for $C_{19}H_{26}N_3O_3$ 344.197 (M+H)$^+$, found 344.1949, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=5.9 min, 100% purity.

EXAMPLE 415

5-(2-Fluoro-4-{[2-(tetrahydropyran-4-yl)ethylamino]methyl}phenoxy)pyridine-2-carboxamide

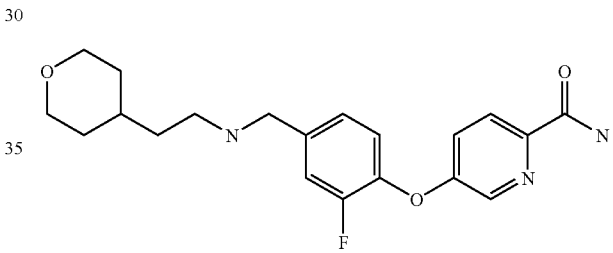

Using a method similar to Example 405, a reaction of 5-(2-fluoro-4-formylphenoxy)pyridine-2-carboxamide (Example 403, Part B) (0.0294 g, 0.113 mmol) and 2-(tetrahydropyran-4-yl)ethylamine (0.016 g, 0.124 mmol) gives the title compound (0.0187 g, 44.2%): TOF MS ES$^+$ 374.2 (M+H)$^+$, HRMS calcd for $C_{20}H_{25}N_3O_3F$ 374.1880 (M+H)$^+$, found 374.1863, time 0.39 min; HPLC [YMC-Pack Pro C-18 (150×4.6 mm, S-5 microm), 0.1% TFA/acetonitrile in 0.1% TFA/water at 1.0 mL/min, 30-99% over 19 min], $t_R$=5.2 min, 95.2% purity.

EXAMPLE 416

5-{2-Fluoro-4-[(2-o-tolylethylamino)-methyl]phenoxy}pyridine-2-carboxamide

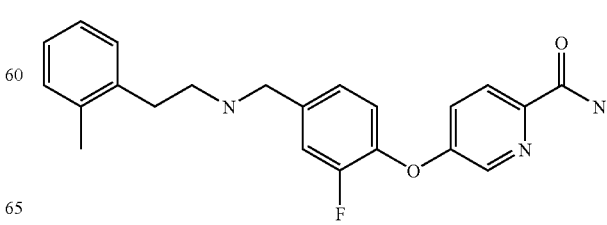

Using a method similar to Example 405, using 5-(2-fluoro-4-formylphenoxy)pyridine-2-carboxamide (Example 403, Part B) (0.0294 g, 0.113 mmol) and 2-methylphenethylamine (0.017 g, 0.124 mmol) gives the title compound (0.0276 g, 65.2%): TOF MS ES$^+$ 380.2 (M+H)$^+$, HRMS calcd for C$_{22}$H$_{23}$N$_3$O$_2$F 380.1774 (M+H)$^+$, found 380.1741, time 0.39 min; HPLC [YMC-Pack Pro C-18 (150×4.6 mm, S-5 microm), 0.1% TFA/acetonitrile in 0.1% TFA/water at 1.0 mL/min, 30-99% over 19 min], t$_R$=8.2 min. 100% purity.

EXAMPLE 417

5-{4-[(2-Naphthalen-2-ylethylamino)methyl]phenoxy}pyridine-2-carboxamide

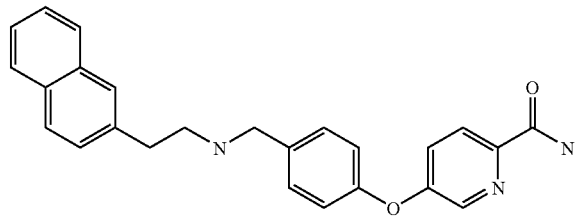

Using a method similar to Example 405, using 5-(4-formylphenoxy)pyridine-2-carboxamide (Example 388, Part D) (0.0366 g, 0.151 mmol) and 2-naphthalen-2-ylethylamine (0.0286 g, 0.166 mmol) gives the title compound (0.0302 g, 50.3%): TOF MS ES$^+$ 398.2 (M+H)$^+$, HRMS calcd for C$_{25}$H$_{24}$N$_3$O$_2$ 398.1869 (M+H)$^+$, found 398.1833, time 0.39 min; HPLC [YMC-Pack Pro C-18 (150×4.6 mm, S-5 microm), 0.1% TFA/acetonitrile in 0.1% TFA/water at 1.0 mL/min, 30-99% over 19 min], t$_R$=9.2 min, 98.0% purity.

EXAMPLE 418

5-{4-[(2-Naphthalen-1-ylethylamino)methyl]phenoxy}pyridine-2-carboxamide

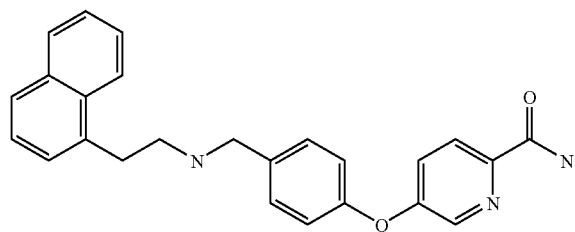

Using a method similar to Example 405, a reaction of 5-(4-formylphenoxy)pyridine-2-carboxamide (Example 388, Part D) (0.0366 g, 0.151 mmol) and 2-naphthalen-1-ylethylamine (0.0285 g, 0.166 mmol) gives the title compound (0.0160 g, 26.7%): TOF MS ES$^+$ 398.2 (M+H)$^+$, HRMS calcd for C$_{25}$H$_{24}$N$_3$O$_2$ 398.1869 (M+H)$^+$, found 398.1855, time 0.39 min; TLC [silica gel 60 F$_{254}$, 4% (2.0 M NH$_3$ in methanol) in ethyl acetate] R$_f$=0.26.

EXAMPLE 419

5-{4-[(2-Benzo[b]thiophen-3-ylethylamino)methyl]phenoxy}pyridine-2-carboxamide

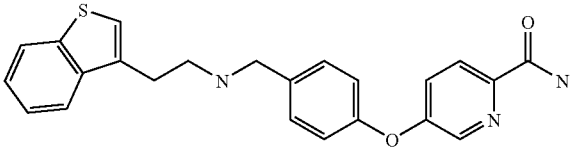

Part A: 2-Benzo[b]thiophen-3-ylethylamine

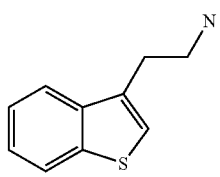

Reduce benzo[b]thiophen-3-yl-acetonitrile (350.9 mg, 2.0 mmol) in Et$_2$O (6.0 mL) with 1.0 M LAH in THF (6.0 mL) at 0-10° C. for 1 hour. Carry out Fieser work-up to remove the LAH. Concentrate and pass through an SCX column washing with MeOH and then eluting with 2.0 M NH$_3$ in MeOH. Concentrate the eluant and purify twice by chromatography, eluting with 75:20:5 EtOAc/hexanes/2.0 M NH$_3$ in MeOH and then with 70:20:10 EtOAc/hexanes/2.0 M NH$_3$ in MeOH to yield the title compound (86.5 mg, 24%): MS ES$^+$ 178.2 (M+H)$^+$, 161.2 (base peak); $^1$H NMR (DMSO-d$_6$) δ 7.94 (d, J=7.3 Hz, 1H), 7.81 (d, J=7.8 Hz, 1H), 7.40-7.33 (m, 3H), 3.32 (br s, 2H), 2.88 (br s, 4H).

Part B: 5-{4-[(2-Benzo[b]thiophen-3-ylethylamino)methyl]phenoxy}pyridine-2-carboxamide Using a method similar to Example 405, a reaction of 5-(4-formylphenoxy)pyridine-2-carboxamide (Example 388, Part D) (0.0366 g, 0.151 mmol) and 2-benzo[b]thiophen-3-ylethylamine (0.0295 g, 0.166 mmol) gives the title compound (0.0306 g, 50.2%): TOF MS ES$^+$ 404.1 (M+H)$^+$, HRMS calcd for C$_{23}$H$_{22}$N$_3$O$_2$S 404.1433 (M+H)$^+$, found 404.1423, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], t$_R$=8.9 min. 100% purity.

EXAMPLE 420

6-(2-Methoxy-4-pentylaminomethylphenoxy)nicotinamide

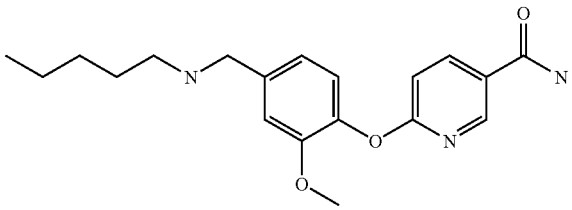

Using a method similar to Example 405, a reaction of 6-(4-formyl-2-methoxyphenoxy)nicotinamide (Example 414, Part B) (0.050 g, 0.184 mmol) and amylamine (0.016 g, 0.184 mmol) gives the title compound (0.0426 g, 67.5%) TOF MS ES+ 344.2 (M+H)+, HRMS calcd for $C_{19}H_{26}N_3O_3$ 344.1974 (M+H)+, found 344.1963, time 0.41 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.1 min, 100% purity.

EXAMPLE 421

6-{2-Methoxy-4-[(2-thiophen-2-ylethylamino)methyl]phenoxy}nicotinamide

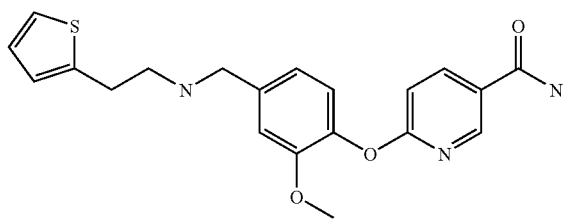

Using a method similar to Example 405, a reaction of 6-(4-formyl-2-methoxyphenoxy)nicotinamide (Example 414, Part B) (0.050 g, 0.184 mmol) and 2-(2-thienyl)ethylamine (0.0234 g, 0.184 mmol) gives the title compound (0.0495 g, 70.3%): TOF MS ES+384.1 (M+H)+, HRMS calcd for $C_{20}H_{22}N_3O_3S$ 384.1382 (M+H)+, found 384.1375, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.1 min, 100% purity.

EXAMPLE 422

6-{2-Methoxy-4-[(2-o-tolylethylamino)methyl]phenoxy}nicotinamide

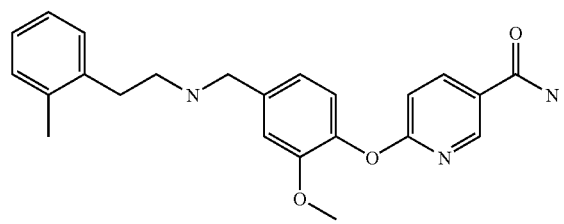

Using a method similar to Example 405, a reaction of 6-(4-formyl-2-methoxyphenoxy)nicotinamide (Example 414, Part B) (0.050 g, 0.184 mmol) and 2-methylphenethylamine (0.0248 g, 0.184 mmol) gives the title compound (0.0584 g, 81.2%): TOF MS ES+ 392.2 (M+H)+, HRMS calcd for $C_{23}H_{26}N_3O_3$ 392.1974 (M+H)+, found 392.1966, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.5 min, 97.6% purity.

EXAMPLE 423

6-{2-Methoxy-4-[(2-m-tolylethylamino)methyl]phenoxy}nicotinamide

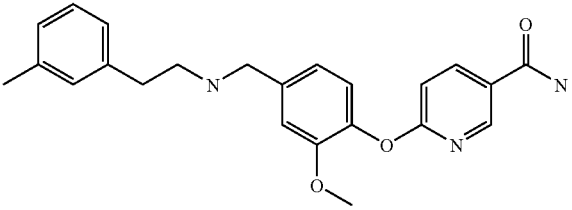

Using a method similar to Example 405, a reaction of 6-(4-formyl-2-methoxyphenoxy)nicotinamide (Example 414, Part B) (0.050 g, 0.184 mmol) and 3-methylphenethylamine (0.0248 g, 0.184 mmol) gives the title compound (0.0568 g, 78.9%): TOF MS ES+ 392.2 (M+H)+, HRMS calcd for $C_{23}H_{26}N_3O_3$ 392.1974 (M+H)+, found 392.1975, time 0.41 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.7 min, 97.6% purity.

EXAMPLE 424

6-{4-[(3,3-Dimethylbutylamino)methyl]-2-methoxyphenoxy}nicotinamide

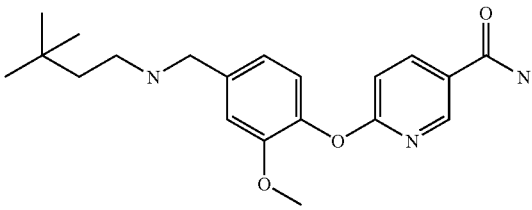

Using a method similar to Example 405, using 6-(4-formyl-2-methoxyphenoxy)nicotinamide (Example 414, Part B) (0.050 g, 0.184 mmol) and 3,3-dimethylbutylamine (0.0186 g, 0.184 mmol) gives the title compound (0.0205 g, 31.3%): TOF MS ES$^r$ 358.2 (M+H)+, HRMS calcd for $C_{20}H_{28}N_3O_3$ 358.2131 (M+H)+, found 358.2131 time 0.41 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.8 min, 100% purity.

EXAMPLE 425

6-{2-Methoxy-4-[(2-pyridin-3-ylethylamino)methyl]phenoxy}nicotinamide

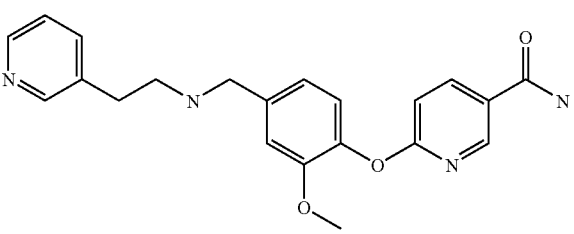

Using a method similar to Example 405, a reaction of 6-(4-formyl-2-methoxyphenoxy)nicotinamide (Example 414, Part B) (0.050 g, 0.184 mmol) and 2-(pyridin-3-yl)ethylamine (0.0224 g, 0.184 mmol) gives the title compound (0.0406 g, 58.4%): TOF MS ES⁺ 379.2 (M+H)⁺, HRMS calcd for $C_{21}H_{23}N_4O_3$ 379.1770 (M+H)⁺, found 379.1759, time 0.41 min.

EXAMPLE 426

6-(4-Butylaminomethyl-2-methoxyphenoxy)nicotinamide

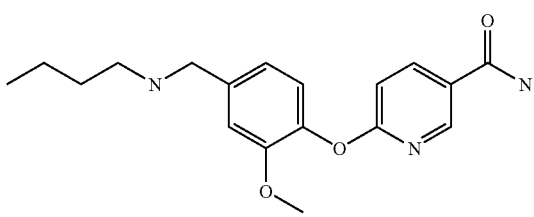

Using a method similar to Example 405, a reaction of 6-(4-formyl-2-methoxyphenoxy)nicotinamide (Example 414, Part B) (0.050 g, 0.184 mmol) and n-butylamine (0.0134 g, 0.184 mmol) gives the title compound (0.0458 g, 75.7%): TOF MS ES⁺ 330.2 (M+H)⁺, HRMS calcd for $C_{18}H_{24}N_3O_3$ 330.1818 (M+H)⁺, found 330.1802, time 0.39 min, HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=4.9 min, 100% purity.

EXAMPLE 427

6-(2-Methoxy-4-{[2-(tetrahydropyran-4-yl)ethylamino]methyl}phenoxy)nicotinamide

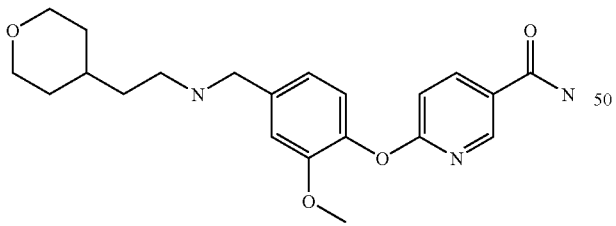

Using a method similar to Example 405, a reaction of 6-(4-formyl-2-methoxyphenoxy)nicotinamide (Example 414, Part B) (0.050 g, 0.184 mmol) and 2-(tetrahydropyran-4-yl)ethylamine (0.0237 g, 0.84 mmol) gives the title compound (0.0545 g, 77.0%): TOF MS ES⁺ 386.2 (M+H)⁺, HRMS calcd for $C_2H_{28}N_3O_4$ 386.2080 (M+H)⁺, found 386.2076, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=4.3 min, 100% purity.

EXAMPLE 428

6-{2-Methoxy-4-[(2-morpholin-4-ylethylamino)methyl]phenoxy}nicotinamide

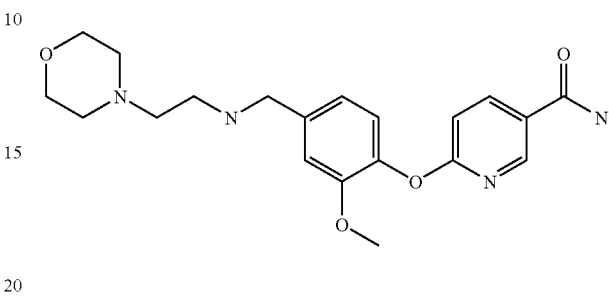

Using a method similar to Example 405, a reaction of 6-(4-formyl-2-methoxyphenoxy)nicotinamide (Example 414, Part B) (0.050 g, 0.184 mmol) and 2-morpholin-4-ylethylamine (0.0224 g, 0.184 mmol) gives the title compound (0.0347 g, 49.0%): TOF MS ES⁺ 387.2 (M+H)⁺, HRMS calcd for $C_{20}H_{27}N_4O_4$ 387.2032 (M+H)⁺, found 387.2023, time 0.41 min; ¹H NMR (DMSO-d₆) δ 8.51 (d, J=2.0 Hz, 1H), 8.19 (dd, J=8.8, 2.4 Hz, 1H), 7.98 (s, 2H), 7.43 (s, 1H), 7.11 (d, J=1.95 Hz, 1H), 7.06 (d, J=8.3 Hz, 1H), 6.98 (d, J=8.3 Hz, 1H), 6.91 (dd, J=8.1, 1.7 Hz, 1H), 3.72 (s, 2H), 3.66 (s, 3H), 3.55 (t, J=4.6 Hz, 4H), 2.63 (t, J=6.6 Hz, 2H), 2.41 (t, J=6.3 Hz, 2H), 2.34 (s, 4H).

EXAMPLE 429

6-{4-[(2-Ethylbutylamino)methyl]-2-methoxyphenoxy}nicotinamide

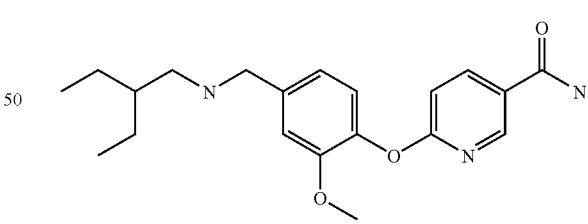

Using a method similar to Example 405, a reaction of 6-(4-formyl-2-methoxyphenoxy)nicotinamide (Example 414, Part B) (0.050 g, 0.184 mmol) and 2-ethylbutylamine (0.0186 g, 0.184 mmol) gives the title compound (0.0450 g, 68.6%): TOF MS ES⁺ 358.2 (M+H)⁺. HRMS calcd for $C_{20}H_{28}N_3O_3$ 358.2131 (M+H)⁺, found 358.2127, time 0.41 ml; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.6 min, 98.8% purity.

EXAMPLE 430

6-(4-{[2-(4-Fluorophenyl)ethylamino]methyl}-2-methoxyphenoxy)nicotinamide

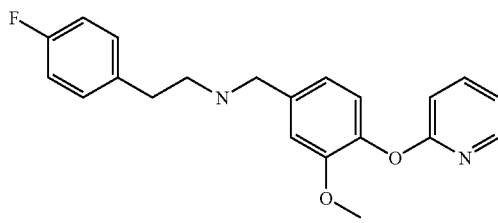

Using a method similar to Example 405, a reaction of 6-(4-formyl-2-methoxyphenoxy)nicotinamide (Example 414, Part B) (0.050 g, 0.184 mmol) and 4-fluorophenethylamine (0.0256 g, 0.184 mmol) gives the title compound (0.0689 g, 94.9%): TOF MS ES$^-$ 396.2 (M+H)$^+$, HRMS calcd for $C_{22}H_{23}N_3O_3F$ 396.1723 (M+H)$^+$, found 396.1714, time 0.41 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.1 ml, 100% purity.

EXAMPLE 431

6-(4-{[2-(2-Fluorophenyl)ethylamino]methyl}-2-methoxyphenoxy)nicotinamide

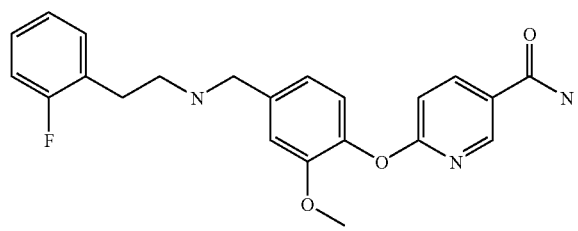

Using a method similar to Example 405, a reaction of 6-(4-formyl-2-methoxyphenoxy)nicotinamide (Example 414, Part B) (0.050 g, 0.184 mmol) and 2-fluorophenethylamine (0.0256 g, 0.184 mmol) gives the title compound (0.0615 g, 84.7%): TOF MS ES$^-$ 396.2 (M+H)$^+$, HRMS calcd for $C_{22}H_{23}N_3O_3F$ 396.1723 (M+H)$^+$, found 396.1722, min 0.39; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.8 min, 98.9% purity.

EXAMPLE 432

6-(4-Hexylaminomethyl-2-methoxyphenoxy)nicotinamide

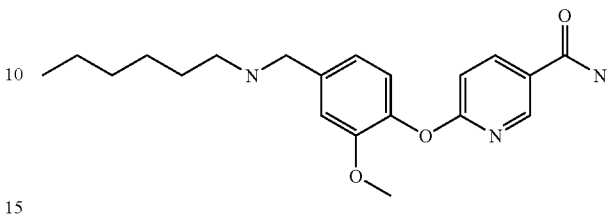

Using a method similar to Example 405, a reaction of 6-(4-formyl-2-methoxyphenoxy)nicotinamide (Example 414, Part B) (0.050 g, 0.184 mmol) and hexylamine (0.0186 g, 0.184 mmol) gives the title compound (0.0479 g, 73.0%): TOF MS ES$^+$ 358.2 (M+H)$^+$, HRMS calcd for $C_{20}H_{28}N_3O_3$ 358.2131 (M+H)$^+$, found 358.2124, time 0.41 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.4 min, 100% purity.

EXAMPLE 433

6-{2-Methoxy-4-[(4-methylpentylamino)methyl]phenoxy}nicotinamide methanesulfonate

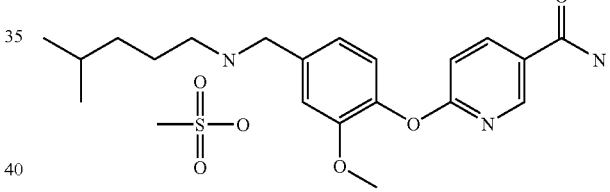

Part A: 4-Methylpentylamine

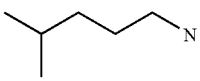

Stir a mixture of 4-methylpentanol (2.0 mL, 16.0 mmol), Et$_3$N (4.5 mL, 32.1 mmol), and TsCl (3.676 g, 19.2 mmol) in CH$_2$Cl$_2$ (30 mL) at room temperature for 2 days. Quench the reaction with H$_2$O, take up the mixture in Et$_2$O (250 mL), and wash with 2.0 N HCl, H$_2$O, 2.0 N NaOH, H$_2$O and brine (100 mL each) consecutively. Back-extract the aqueous washings with Et$_2$O (200 mL). Combine the organic layers, dry over MgSO$_4$ and concentrate.

Dissolve the tosylate obtained in 7.0 N NH$_3$ in MeOH (200 mL) at 0° C. Stir for 5 days, while allowed to warm to room temperature. Concentrate and purify on an SCX column, washing with MeOH, then eluting with 2.0 M NH$_3$ in MeOH. Repeat the process three times till no amine was observed in MeOH washings. Combine the eluants and carefully distill to collect the title amine (610.7 mg, 3704): bp 90-110° C.; GCMS 101 (M)$^+$, 4.46 min.

Part B: 6-{2-Methoxy-4-[(4-methylpentylamino)methyl]phenoxy}nicotinamide methanesulfonate Place 6-(4-formyl-2-methoxyphenoxy)nicotinamide (Example 414, Part B) (0.100 g, 0.367 mmol), 4-methylpentylamine (Part A, 0.0409 g, 0.404 mmol) and 3 Å molecular sieves in a vial. Add methanol (3.6 mL), cap and stir overnight. Add NaBH$_4$ (in excess over two portions) and stir until the gasses stop evolving. Load the reaction mixture directly onto a 5 g ISCO® pre-load column. Dry the column in a vacuum oven at room temperature. Purify by eluting through a 10 g ISCO® column with (2.0 M NH$_3$ in methanol) in ethyl acetate to give 6-{2-methoxy-4-[(4-methylpentylamino)methyl]phenoxy}nicotinamide (0.131 g, 71.8%). Dissolve the compound in dichloromethane (2.5 mL) and add 1 equivalent of 0.50 M methanesulfonic acid in dichloromethane. Stir the solution for a short time before concentrating to give the title compound (0.124 g, 100%): TOF MS ES$^+$ 358.2 (M+H)$^+$, HRMS calcd for $C_{20}H_{28}N_3O_3$ 358.2131 (M+H)$^+$, found 358.2119, time 0.39 mine HPLC [Waters XTerra™ MS C-18 (150×4.6 mm, S-5 microm), 0.1% TFA/acetonitrile in 0.1% TFA/water at 1.0 mL/min, 5-95% over 15 min], $t_R$=8.2 min, 100% purity.

EXAMPLE 434

6-{2-Methoxy-4-[(2-p-tolylethylamino)methyl]phenoxy}nicotinamide methanesulfonate

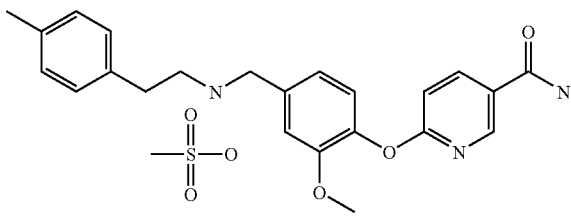

Place 6-(4-formyl-2-methoxyphenoxy)nicotinamide (Example 414, Part B) (0.100 g 0.367 mmol), 2-p-tolylethylamine (0.0546 g, 0.404 mmol) and 3 Å molecular sieves in a vial. Add methanol (3.6 mL), cap and stir overnight. Add NaBH$_4$ (in excess over two portions) and stir until the gasses stop evolving. Load the reaction mixture directly onto a 5 g ISCO® pre-load column. Dry the column in a vacuum oven at room temperature. Purify by eluting through a 10 g ISCO® column with (2.0 M NH$_3$ in methanol) in ethyl acetate to give 6-{2-methoxy-4-[(2-p-tolylethylamino)methyl]phenoxy}nicotinamide (0.143 g, 97.8%). Dissolve the compound in dichloromethane (2.5 mL) and add 1 equivalent of 0.50 M methanesulfonic acid in dichloromethane. Stir the solution for a short time before concentrating to give the title compound (0.168 g, 100%): TOF MS ES$^+$ 392.1 (M+H)$^+$, HRMS calcd for $C_{23}H_{26}N_3O_3$ 392.1974 (M+H)$^+$, found 392.1966, time 0.39 min; HPLC [Waters XTerra™ MS C-18 (150×4.6 mm, S-5 microm), 0.1% TFA/acetonitrile in 0.1% TFA/water at 1.0 mL/min, 5-95% over 15 min], $t_R$=8.4 min, 100% purity.

EXAMPLE 435

5-(2-Methyl-4-{[2-(tetrahydropyran-4-yl)ethylamino]methyl}phenoxy)pyrazine-2-carboxamide

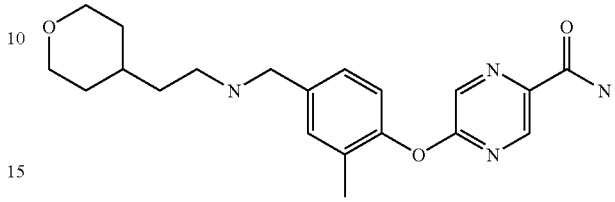

Place 5-(4-formyl-2-methylphenoxy)pyrazine-2-carboxamide (Example 404, Part D) (0.200 g, 0.777 mmol), 2-(tetrahydropyran-4-yl)ethylamine (0.100 g, 0.777 mmol) and 3 Å molecular sieves in a vial. Add methanol (3.8 mL) cap and stir overnight. Add NaBH$_4$ (in excess over two portions) and stir until the gasses stop evolving. Load the reaction mixture directly onto a 5 g ISCO® pre-load column. Dry the pre-loaded column in a vacuum oven at room temperature. Purify by eluting through a 10 g ISCO® column with (2.0 M NH$_3$ in methanol), ethyl acetate and hexanes. After concentrating, take the product up in CH$_2$Cl$_2$ (25 mL) and wash with 1.0 N NaOH solution (2×10 mL). Dry the organic layer over Na$_2$SO$_4$, filter and concentrate to give the title compound (0.121 g, 42.0%): MS ES$^+$ 371.1 (M+H)$^+$, base peak 242.0 (M-C$_7$H$_{14}$NO)$^+$; HPLC [YMC-Pack Pro C-18 (150×4.6 mm, S-5 microm), 0.1% TFA/acetonitrile in 0.1% TFA/water at 1.0 mL/in, 5-95% over 19 min], $t_R$=7.9 min, 100% purity.

EXAMPLE 436

5-{4-[(3,3-Dimethylbutylamino)methyl]-2-methylphenoxy}pyrazine-2-carboxamide

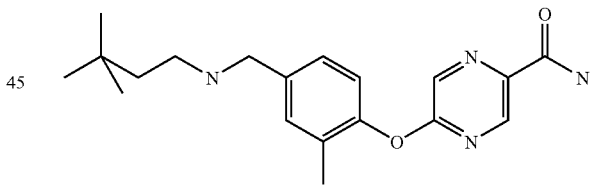

Place 5-(4-formyl-2-methylphenoxy)pyrazine-2-carboxamide (Example 404, Part D) (0.200 g, 0.777 mmol), 3,3-dimethylbutylamine (0.100 g, 0.777 mmol) and 3 Å molecular sieves in a vial. Add methanol (3.8 mL), cap and stir overnight. Add NaBH$_4$ (in excess over two portions) and stir until the gasses stop evolving. Load the reaction mixture directly onto a 5 g ISCO® pre-load column. Dry the pre-loaded column in a vacuum oven at room temperature. Purify by eluting through a 10 g ISCO® column with (2.0 M NH$_3$ in methanol), ethyl acetate and hexanes. After concentrating, take the product up in CH$_2$Cl$_2$ (25 mL) and wash with 1.0 N NaOH solution (2×10 mL). Dry the organic layer over Na$_2$SO$_4$, filter and concentrate to give the title compound (0.110 g, 41.4%): MS ES$^+$ 343.1 (M+H)$^+$, base peak 242.0 (M-C$_6$H$_{14}$N)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.7 min, 94.3% purity.

EXAMPLE 437

5-{4-[(3-Methylbutylamino)methyl]phenoxy}pyrazine-2-carboxamide

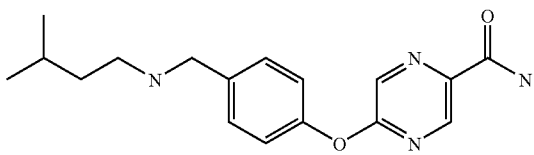

Part A: 5-(4-Formylphenoxy)pyrazine-2-carbonitrile

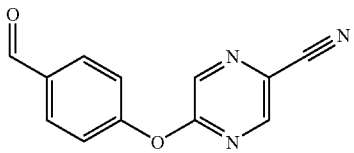

Dissolve 4-[1,3]dioxolan-2-yl-2-phenol (Example 388, Part C2) (1.70 g, 10.2 mmol), 5-chloropyrazine-2-carbonitrile (Example 404, Part A) (1.50 g, 10.7 mmol) and $K_2CO_3$ (3.71 g, 26.9 mmol) in DMA (27.0 mL) and isooctane (13.4 mL). Beat at 110° C. for about 2.25 hours. Cool to room temperature and quench with water (100 mL). Extract with dichloromethane (3×100 mL). Wash the extract with saturated aqueous $NaHCO_3$ (1×50 mL) and brine (1×75 mL). Dry the organic layer over $Na_2SO_4$, filter and concentrate. Purify by flash chromatography, eluting with 0-30% ethyl acetate in hexanes. Concentrate the eluant, then take the solid up in 88% formic acid (46 mL) and stir at room temperature for 4 hours. Dilute the reaction mixture with water (50 mL). Extract with dichloromethane (2×100 mL). Wash the extract with saturated aqueous $NaHCO_3$ (1×50 mL), dry over $Na_2SO_4$, filter and concentrate. Purify by flash chromatography eluting with 30% ethyl acetate in hexanes to give the title compound (1.88 g, 77.7%): TOF MS $ES^+$ 225.1 $(M)^+$, HRMS calcd for $C_{12}H_7N_3O_2$ 225.0538 $(M)^+$, found 225.0527, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=11.5 min, 100% purity.

Part B:
5-(4-Formylphenoxy)pyrazine-2-carboxamide

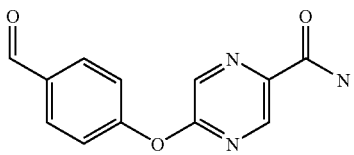

Dissolve 5-(4-formylphenoxy)pyrazine-2-carbonitrile (1.87 g, 8.30 mmol) and $K_2CO_3$ (0.573 g, 4.15 mmol) in DMSO (21 mL). Add 30% $H_2O_2$ (2.4 mL, 20.8 mmol) and stir at room temperature for 22 hours. Add additional $K_2CO_3$ (0.573 g, 4.15 mmol) and heat at 55° C. for about 2.5 hours. Cool the reaction mixture and dilute with $CH_2Cl_2$ (200 mL). Wash with water (1×100 mL) and saturated aqueous $NaHCO_3$ (1×100 mL). Dry the organic layer over $Na_2SO_4$, filter and concentrate. Purify by flash chromatography, eluting with 0-50% ethyl acetate in dichloromethane to give the title compound (0.478 g, 23.7%): TOF MS $ES^+$ 244.1 $(M+H)^+$, HRMS calcd for $C_{12}H_{10}N_3O_3$ 244.0722 $(M+H)^+$, found 244.0709, time 0.38 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=7.2 min, 100% purity.

Part C: 5-{4-[(3-Methylbutylamino)methyl]phenoxy}pyrazine-2-carboxamide Place 5-(4-formylphenoxy)pyrazine-2-carboxamide (0.150 g, 0.617 mmol), 3-methylbutylamine (0.0537 g, 0.617 mmol) and 3 Å molecular sieves in a vial. Add methanol (3.1 mL), cap and stir overnight. Add $NaBH_4$ (in excess over two portions) and stir until the gasses stop evolving. Load the reaction mixture directly onto a 5 g ISCO® pre-load column. Dry the column in a vacuum oven at room temperature. Purify by eluting through a 10 g ISCO®9 column with 2.0 M $NH_3$ in methanol, ethyl acetate and hexanes to give the title compound (0.0606 g, 31.2%): MS $ES^+$ 315.1 $(M+H)^+$, base peak 228.0 $(M-C_5H_{12}N)^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=8.5 min, 96.4% purity.

EXAMPLE 438

5-(4-{[2-(Tetrahydropyran-4-yl)ethylamino]methyl}phenoxy)pyrazine-2-carboxamide

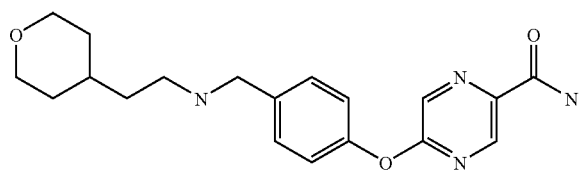

Place 5-(4-formylphenoxy)pyrazine-2-carboxamide (Example 437, Part B) (0.150 g, 0.617 mmol), 2-(tetrahydropyran-4-yl)ethylamine (0.0797 g, 0.617 mmol) and 3 Å molecular sieves in a vial. Add methanol (3.1 mL), cap and stir overnight. Add $NaBH_4$ (in excess over two portions) and stir until the gasses stop evolving. Load the reaction mixture directly onto a 5 g ISCO® pre-load column. Dry the column in a vacuum oven at room temperature. Purify by eluting through a 10 g ISCO®10 column with 2.0 M $NH_3$ in methanol and ethyl acetate. After concentrating, take the product up in dichloromethane (25 mL) and wash with 1.0 N NaOH solution (2×10 mL). Dry the organic layer over $Na_2SO_4$, filter and concentrate to give the title compound (0.0819 g, 37.2%): MS $ES^+$ 357.1 $(M+H)^+$, base peak 228.0 $(M-C_7H_{14}NO)^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=7.4 min, 100% purity.

EXAMPLE 439

5-{4-[(3,3-Dimethylbutylamino)methyl]phenoxy}pyrazine-2-carboxamide

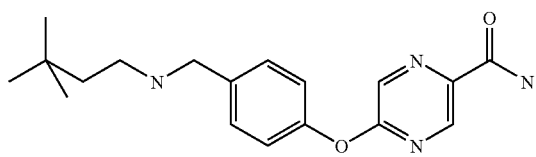

Place 5-(4-formylphenoxy)pyrazine-2-carboxamide (Example 437, Part B) (0.150 g, 0.617 mmol), 3,3-dimethylbutylamine (0.0624 g, 0.617 mmol) and 3 Å molecular sieves in a vial. Add methanol (3.1 mL), cap and stir overnight. Add $NaBH_4$ (in excess over two portions) and stir until the gasses stop evolving. Load the reaction mixture directly onto a 5 g ISCO®0 pre-load column. Dry the column in a vacuum oven at room temperature. Purify by eluting through a 10 g ISCO® column with 2.0 M $NH_3$ in methanol, ethyl acetate and hexanes. After concentrating, take the product up in dichloromethane (25 mL) and wash with 1.0 N NaOH solution (2×10 mL). Dry the organic layer over $Na_2SO_4$, filter and concentrate to give the title compound (0.0687 g, 33.8%): MS $ES^+$ 329.1 $(M+H)^+$, base peak 228.0 $(M-C_6H_{15}N)^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.2 min, 100% purity.

EXAMPLE 440

6-(2-Methoxy-4-{[2-(tetrahydropyran-4-yl)ethylamino]methyl}phenoxy)nicotinamide methanesulfonate

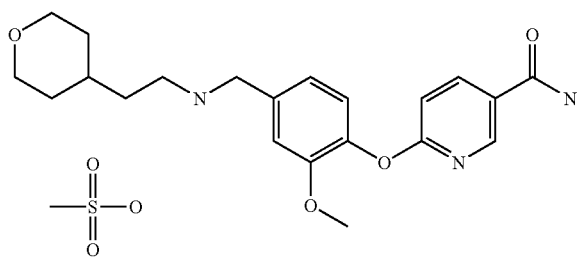

Dissolve 6-(2-methoxy-4-{[2-(tetrahydropyran-4-yl)ethylamino]methyl}phenoxy)nicotinamide (Example 427) (0.612, 1.59 mmol) in THF (4 mL) and few drops of methanol to form a clear solution. Add 1.27 M methanesulfonic acid (1.25 mL, 1.59 mmol) in THF. Stir for 10 minutes, then concentrate to give the title compound (0.749 g, 100%): TOF MS $ES^+$ 386.2 $(M+H)^+$, HRMS calcd for $C_{21}H_{25}N_3O_4$ 386.2080 $(M+H)^+$, found 386.2083, time 0.62 min; HPLC [Waters XTerra™ MS C-18 (150×4.6 mm, S-5 microm), 0.1% TFA/acetonitrile in 0.1% TFA/water at 1.0 mL/min, 5-95% over 15 min], $t_R$=6.6 min, 100% purity.

EXAMPLE 441

6-(4-Hexylaminomethyl-2-methoxyphenoxy)nicotinamide methanesulfonate

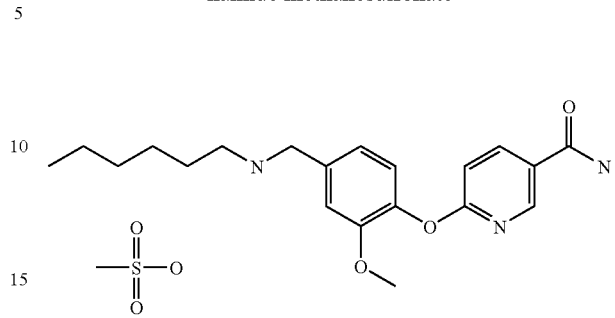

Using a procedure similar to that of Example 440, using 6-(4-hexylaminomethyl-2-methoxyphenoxy)nicotinamide (Example 432) the title compound is obtained.

EXAMPLE 442

6-(2-Methoxy-4-pentylaminomethylphenoxy)nicotinamide methanesulfonate

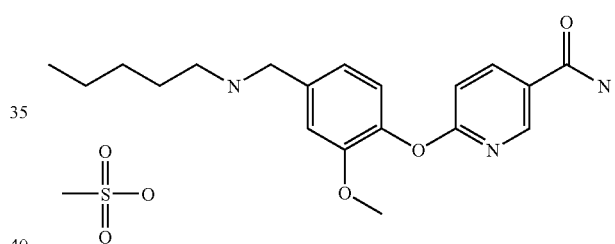

Using a procedure similar to that of Example 440, using 6-(2-methoxy-4-pentylaminomethylphenoxy)nicotinamide (Example 420) the title compound is obtained.

EXAMPLE 443

6-(4-Butylaminomethyl-2-methoxyphenoxy)nicotinamide methanesulfonate

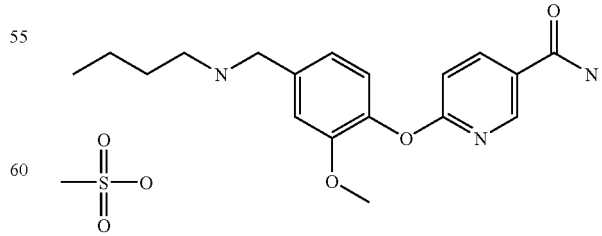

Using a procedure similar to that of Example 440, using 6-(4-butylaminomethyl-2-methoxyphenoxy)nicotinamide (Example 426) the title compound is obtained.

EXAMPLE 444

6-{2-Methoxy-4-[(2-pyridin-3-ylethylamino)methyl]phenoxy}nicotinamide methanesulfonate

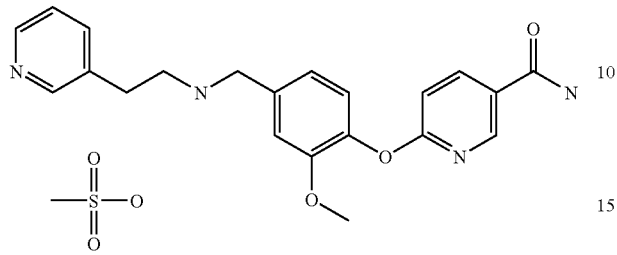

Using a procedure similar to that of Example 440, using 6-{2-methoxy-4-[(2-pyridin-3-ylethylamino)methyl]phenoxy}nicotinamide (Example 425) the title compound is obtained.

EXAMPLE 445

6-{4-[(2-Ethylbutylamino)methyl]-2-methoxyphenoxy}nicotinamide methanesulfonate

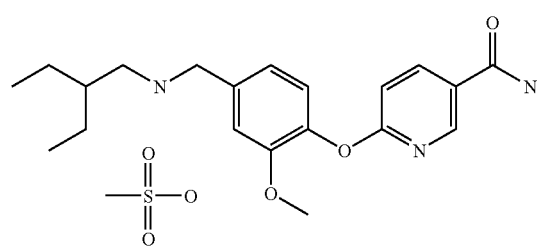

Using a procedure similar to that of Example 440, using 6-{4-[(2-ethylbutylamino)methyl]-2-methoxyphenoxy}nicotinamide Example 429) the title compound is obtained.

EXAMPLE 446

6-{4-[(3,3-Dimethylbutylamino)methyl]-2-methoxyphenoxy}nicotinamide methanesulfonate

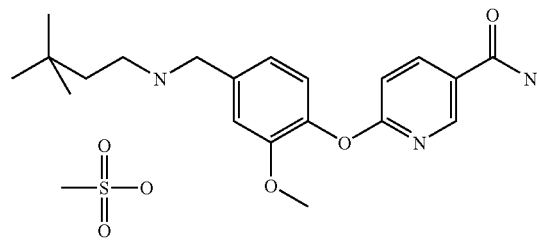

Using a procedure similar to that of Example 440, using 6-{4-[(3,3-dimethylbutylamino)methyl]-2-methoxyphenoxy}nicotinamide (Example 424) the title compound is obtained.

EXAMPLE 446A

6-{2-Methoxy-4-[(3-methylbutylamino)methyl]phenoxy}nicotinamide methanesulfonate

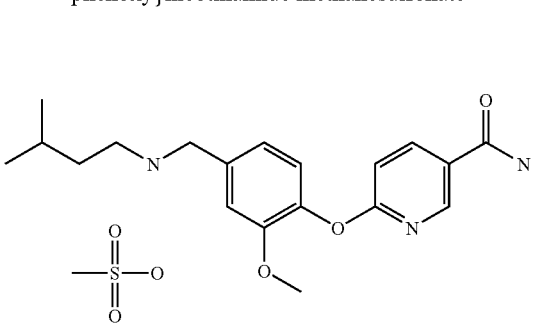

Using a procedure similar to that of Example 440, using 6-{2-methoxy-4-[(3-methylbutylamino)methyl]phenoxy}nicotinamide (Example 414, Part C) the title compound is obtained.

EXAMPLE 447

6-(2-Phenethyl-2,3,4,5-tetrahydro-1H-benzo[c]azepin-7-yloxy)nicotinamide

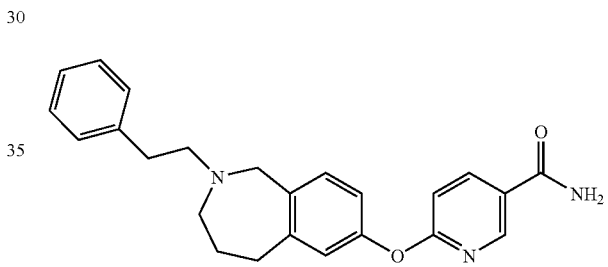

Part A:
7-Methoxy-2,3,4,5-tetrahydro-benzo[c]azepin-1-one

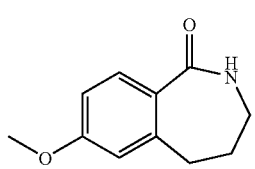

Dissolve 4-hydroxytetralone (50 g, 284 mmol) in methanesulfonic acid (400 mL) and chill to 2° C. in an ice bath. Add sodium azide (24 g, 369 mmol) in 3-gram portions over a period of 3 hours while keeping the temperature below 5° C. Stir the solution cold for an additional hour and allow gradually warm to room temperature by removing the ice bath. Stir the solution for 16 hours. Pour the mixture into 3 L of crushed ice and add saturated aqueous NaHCO$_3$ until a pH of 8 is achieved. Add EtOAc (4 L) and extract 3 times. Dry the organic layer over MgSO$_4$ and concentrate to a white solid. Chromatography on a Biotage® 75 S column (eluant 10:1 hexanes/EtOAc) provides the title compound as a white solid (27.3 g, 50% of theory). $^1$H NMR (DMSO-$d_6$) δ 7.90 (br t, 1H), 7.48 (d, 1H), 6.89 (m, 2H), 3.72 (s, 3H), 2.90 (m, 2H), 2.59 (t, 2H), 1.83 (m, 2H).

Part B:
7-Methoxy-2,3,4,5,5-tetrahydro-benzo[c]azepine

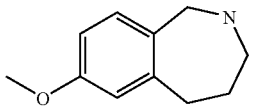

Add 7-methoxy-2,3,4,5-tetrahydro-benzo[c]azepin-1-one from step A (10 g, 53 mmol) to THF (50 mL) under a nitrogen atmosphere. Stir and chill the solution to 0° C. in an ice bath and add drop wise borane-THF complex (156 ml, 1.0 M in THF, 156 mmol). After complete addition, heat the solution at reflux for 2 hours and then cool to room temperature. Quench the reaction with 1.0 N HCl solution. Adjust the pH to 9 with 1.0 N NaOH solution and add 300 mL of EtOAc. Extract the solution, dry the organic layer over MgSO$_4$ and concentrate to a yellow oil. Chromatography on a Biotage® 75 S column ((0% MeOH/DCM) yields the title compound as a white solid (4.2 g; 45% of theory). $^1$H NMR (DMSO-$d_6$) δ 7.00 (d, 1H), 6.63 (s, 1H), 6.59 (dd, 1H), 3.69 (s, 2H), 3.67 (s, 3H), 3.02 (t, 2H), 2.72 (m, 2H), 1.55 (m, 2H). MS (EI) 178.2 m/z (M+1)

Part C: 2,3,4,5-Tetrahydro-1H-benzo[c]azepin-7-ol Hydrobromide

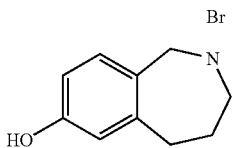

Dissolve product from Step B above (4.2 g, 22 mmol) in CH$_2$Cl$_2$ (50 mL) and add to BBr$_3$ (67 mmol, 6.4 mL) in CH$_2$Cl$_2$ (20 mL) at −78° C. under a nitrogen atmosphere. Stir the reaction mixture at −70° C. for 2 hours and then at room temperature for 16 hours. Cool the clear solution to −78° C. and carefully add methanol (15 mL). Concentrate the solution to a brown solid. Dissolved the solid in methanol (50 mL) and add CH$_2$Cl$_2$ (40 mL). Concentrate the solution to half-volume and add hexanes (40 mL). Concentrate again to half volume and add EtOAc (20 mL). Concentrate to a volume to 20 mL and filter to obtain a white granular solid (4.2 g, 45% of theory): $^1$H NMR (DMSO-$d_6$) δ 9.52 (s, 1H), 8.70 (br, 2H), 7.19 (d, 1H), 6.58 (m, 2H), 4.23 (s, 2H), 3.33 (m, 2H), 2.88 (m, 2H), 1.70 (m, 2H). MS (ES) 164.1 m/z (M+1). Elemental analysis Calc C, 49.19; H, 5.78; N, 5.55. Found C, 49.48; H, 5.78; N, 5.55.

Part D: N-tert-Butoxycarbonyl-2,3,4,5-tetrahydro-1H-benzo[c]azepin-7-ol

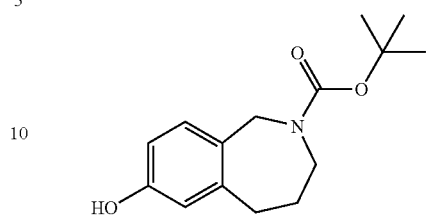

Mix product from Step C above (6.50 g, 26 mmol) with CH$_2$Cl$_2$ (100 mL) to form a slurry. Add triethylamine (79 mmol) and cool the slurry to 5° C. in an ice bath. Dissolve di-tert-butyl dicarbonate in CH$_2$Cl$_2$ (20 mL) and add drop wise to the solution. Remove the ice bath and allow the solution to stir at room temperature for four hours. Concentrate the solution to a brown solid. Add 40 ml of a 1:1 CH$_2$Cl$_2$/EtOAc solution and filter. Concentrate the filtrate to a brown oil and chromatograph (20% EtOAc/hexanes) to give a white solid (6.3 g, 90% of theory): $^1$H NMR (DMSO-$d_6$) δ 9.15 (s, 1H), 6.97 (d, 1H), 6.60 (s, 1H), 6.49 (d, 1H), 4.23 (s, 2H), 3.52 (br m, 2H), 2.72 (br m, 2H), 1.59 (br m, 2H), 1.33 (s, 9H). $^{13}$C NMR (DMSO-$d_6$) δ 156.24, 142.99, 129.41, 116.41, 111.57, 78.29, 50.95, 49.57, 34.58, 28.02. Anal. Calcd for C$_{15}$H$_{21}$NO$_3$: C, 68.42; H, 8.04; N, 5.32. Found: C, 68.54; H, 8.15; N, 5.24.

Part E: 6-(2,3,4,5-Tetrahydro-1H-benzo[c]azepin-7-yloxy)nicotinamide

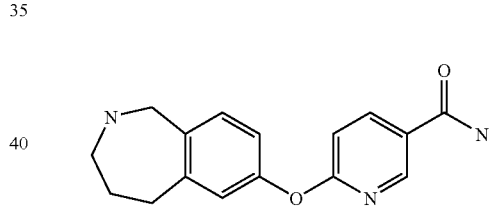

Add 80% NaH in mineral oil (28.3 mg, 0.94 mmol) to a solution of the benzazepinol in Part D (124.3 mg, 0.47 mmol) in anhydrous DMF (2.0 mL) and stir for 30 minutes at room temperature. Add 6-chloronicotinamide (147.8 mg, 0.94 mmol) in one portion and stir overnight at room temperature and then heat at 80° C. for 3 hours. Quench the reaction with water and concentrate. Purify by flash chromatography, eluting with 40% CH$_2$Cl$_2$ in EtOAc.

Dissolve the above-coupled product in CH$_2$Cl$_2$ (2.5 mL) and treat with t-difluoroacetic acid (2.5 mL) at room temperature for one hour. Concentrate the mixture and purify by an SCX column, washing with methanol and then eluting with 2.0 M NH$_3$ in MeOH to yield the title compound (109.3 mg, 82% for 2 steps): MS ES$^+$ 284.0 (M−H)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=6.99 min, 100% purity.

Part F: 6-(2-Phenethyl-2,3,4,5-tetrahydro-1H-benzo[c]azepin-7-yloxy)nicotinamide Mix 6-(2,3,4,5-tetrahydro-1H-benzo[c]azepin-7-yloxy)nicotinamide (Part E, 112.9 mg, 0.40 mmol), K$_2$CO$_3$ (110.1 mg, 0.80 mmol), and phenethyl bromide (82 uL, 0.60 mmol) in DMF (2.0 mL). Heat at 70-80° C. overnight. Remove DMF azeotropically with xylenes. Purify by flash chromatography, eluting with 75:19:6 EtOAc/CH$_2$Cl$_2$/2.0 M NH$_3$ in MeOH and then with 60:30:10 EtOAc/hexanes/2.0 M NH$_3$ in MeOH. Purify by reverse phase chromatography, eluting with 0-99% 0.1% TFA/acetonitrile and 0.1% TFA/water to give the title compound (44.9 mg, 27% from Step D): MS ES$^+$ 284.0 (M−H)$^+$; HPLC [YMC-Pack Pro C-18 (150×4.6 mm, S-5 microm), 0.1% TFA/acetonitrile in 0.1% TFA/water at 1.0 mL/min, 5-95% over 19 min], $t_R$=9.85 min, 100% purity; Anal. Calcd for C$_{24}$H$_{25}$N$_3$O$_2$.0.1H$_2$O.0.1MeOH: C, 73.75; H, 6.57; N, 10.71. Found: C, 73.45; H, 6.62; N, 10.72.

EXAMPLE 448

6-[2-(3-Methylbutyl)-2,3,4,5-tetrahydro-1H-benzo[c]azepin-7-yloxy]nicotinamide

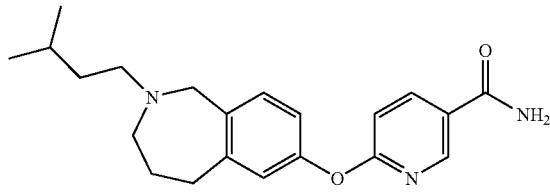

Mix 6-(2,3,4,5-tetrahydro-1H-benzo[c]azepin-7-yloxy)nicotinamide (Example 447, Part E, 50.7 mg, 0.1 mmol), K$_2$CO$_3$ (49.5 mg, 0.36 mmol), and isoamyl bromide (32 uL, 0.27 mmol) in DMF (1.0 mL). Heat at 80° C. for 6 hours. Pass through an SCX column, washing with methanol and then eluting with 2.0 M NH$_3$ in MeOH. Concentrate the eluant and purify by flash chromatography, eluting with 70:22:8 EtOAc/CH$_2$Cl$_2$/2.0 M NH$_3$ in MeOH to afford the title compound (45.7 mg, 72%): MS ES$^+$ 354.0 (M+H)$^+$, HRMS calcd for C$_{21}$H$_{28}$N$_3$O$_2$ 354.2182 (M+H)$^+$, found 354.2182, time 0.39 min; HPLC [YMC-Pack Pro C-18 (150×4.6 mm, S-5 microm), 0.1% TFA/acetonitrile in 0.1% TFA/water at 1.0 mL/min, 20-99% over 23 min], $t_R$=6.39 min, 100% purity; Anal. Calcd for C$_{21}$H$_{27}$N$_3$O$_2$.0.2CH$_2$Cl$_2$.0.1MeOH: C, 69.59; H, 5.98; N, 11.43. Found: C, 69.47; H, 6.25; N, 11.30.

EXAMPLE 449

6-[2-(3-Methylpentyl)-2,3,4,5-tetrahydro-1H-benzo[c]azepin-7-yloxy]nicotinamide

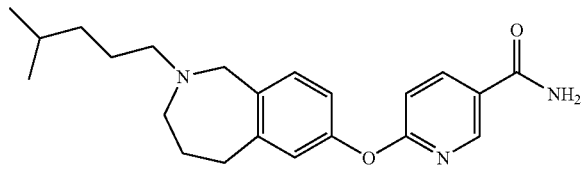

Mix 6-(2,3,4,5-tetrahydro-1H-benzo[c]azepin-7-yloxy)nicotinamide (Example 447, Part E, 55.6 mg, 0.20 mmol), K$_2$CO$_3$ (54.2 mg, 0.39 mmol), and 1-bromo-4-methylpentane (43 uL, 0.29 mmol) in DMF (1.0 mL). Heat at 80° C. overnight. Remove DMF azeotropically with xylenes. Purify by flash chromatography, eluting with 70:25:5 EtOAc/CH$_2$Cl$_2$/2.0 M NH$_3$ in MeOH to afford the title compound (43.1 mg, 60%): MS ES$^+$ 368.4 (M+H)$^+$, HRMS calcd for C$_{22}$H$_{30}$N$_3$O$_2$ 368.2338 (M+H)$^+$, found 368.2330, time 0.39 min; Anal. Calcd for C$_{22}$H$_{29}$N$_3$O$_2$.0.1CH$_2$Cl$_2$.0.1MeOH: C, 70.32; H, 7.87; N, 11.08. Found: C, 70.05; H, 7.52; N, 11.01.

EXAMPLE 450

(±)-6-{4-[2-(2-Hydroxycyclohexylamino)ethyl]phenoxy}nicotinamide

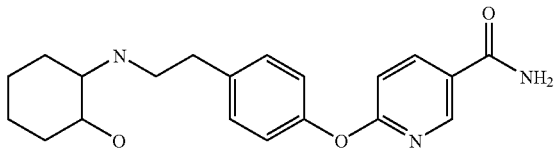

Part A: (±)-4-[2-(2-Hydroxycyclohexylamino)ethyl]phenol

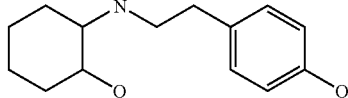

Mix (±)-2-aminocyclohexanol (1.5227 g, 13.2 mmol), K$_2$CO$_3$ (4.56 g, 33.0 mmol), and 1-(2-chloroethyl)-4-methoxybenzene (2.0 mL, 13.2 mmol) in DMF (30 mL). Heat at 100° C. for 24 hours. Cool down to room temperature and filtrate with MeOH wash. Concentrate and remove DMF azeotropically with xylenes. Take up the residue in CH$_2$C$_2$ and H$_2$O (100 mL each). Separate the layers and extract the aqueous layer with CH$_2$Cl$_2$ (2×100 mL). Wash the organic layers with H$_2$O and brine (100 mL each). Dry the combined organic layers over MgSO$_4$, concentrate and purify by flash chromatography, eluting with 50:45:5 EtOAc/CH$_2$Cl/2.0 M NH$_3$ in MeOH to afford 2-(4-methoxyphenethylamino)cyclohexanol. (1.38 g, 42%).

Mix the methoxy ether (505.9 mg, 2.0 mmol) and 1.0 M BBr$_3$ in heptane (4.0 mL, 4.0 mmol) in CH$_2$Cl$_2$ (10 mL in total). Stir the mixture at 0-17° C. for 3 hours. Quench the reaction with saturated aqueous NaHCO$_3$ (30 mL) at 0° C. Take up the mixture in saturated aqueous NaHCO$_3$ (20 mL) and CH$_2$Cl$_2$ (30 mL). Dissolve the precipitate formed with CH$_2$Cl$_2$ and a small amount of MeOH. Separate the layers after vigorously shaking. Wash the organic layer with 1:1 saturated aqueous NaHCO$_3$/brine (50 mL). Back-extract the aqueous layers with CH$_2$Cl$_2$ (2×50 mL) and 10% in MeOH in CH$_2$Cl$_2$ (5 ×). Dry the combined organic layers over MgSO$_4$, concentrate and purify by flash chromatography, eluting with 75:15:10 EtOAc/CH$_2$Cl$_2$/2.0 M NH$_3$ in MeOH (375.8 mg, 79%): MS ES$^+$ 236.1 (M+H)$^+$, ES$^-$ 234.2 (M−H)$^-$; $^1$H NMR (DMSO-d$_6$) δ 9.11 (s, 1H), 6.97 (d, J=8.3 Hz, 2H), 6.93 (d, J=8.3 Hz, 2H), 4.41 (d, J=4.4 Hz, 1H), 3.32 (s, 1H), 3.03 (s, 1H), 2.76 (m, 1H), 2.55 (m, 3H), 2.14 (m, 1H), 1.87 (m, 1H), 1.75 (m, 1H), 1.54 (m, 2H), 1.13 (m, 3H), 0.86 (m, 1H).

Part B: (±)-6-{4-[2-(2-Hydroxycyclohexylamino)ethyl]phenoxy}nicotinamide

Heat a mixture of 4-[2-(2-hydroxycyclohexylamino)ethyl]phenol (152.6 mg, 0.65 mmol), 6-chloronicotinamide (84.6 mg, 0.54 mmol) and K$_2$CO$_3$ (186.7 mg, 1.35 mmol) in 3:1 DMF/toluene (4.0 mL) at 160° C. for 2 hours. Cool to room temperature and filter with thorough MeOH and CH$_2$Cl$_2$ wash. Concentrate the filtrate and remove DMF azeotropically with xylenes. Purify by flash chromatography, eluting with 75:15:10 EtOAc/CH$_2$Cl$_2$/2.0 M NH$_3$ in MeOH (56.3 mg, 29%): MS ES$^+$ 356.1 (M+H)$^+$, HRMS calcd for C$_{20}$H$_{26}$N$_3$O$_3$ 356.1974 (M+H)$^+$, found 356.1966, time 0.37 min; HPLC [YMC-Pack Pro C-18 (150×4.6 mm, S-5 microm), acetonitrile in water containing 0.01% concentrated HCl at 1.0 mL/min, 30-99% over 19 min], t$_R$=1.23 min, 100% purity; Chiralpak AD 225 nm, 60:40 EtOH/heptane at 1.0 mL/min, t$_R$=5.55 min, 50% and t$_R$=7.17 min, 50%; Anal. Calcd for C$_{20}$H$_{25}$N$_3$O$_3$.0.2CH$_2$Cl$_2$.0.2MeOH: C, 64.68; H, 6.97; N, 11.09. Found: C, 64.46; H, 6.84; N, 11.11.

EXAMPLE 451

(±)-(cis)-6-{4-[2-(3-Hydroxycyclohexylamino)ethyl]
phenoxy}nicotinamide

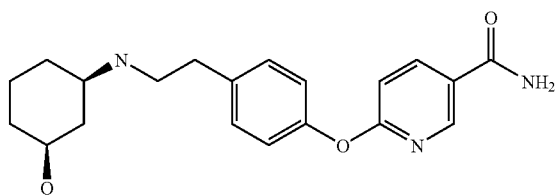

Part A: 3-(tert-Butyldimethylsilyloxy)cyclohexanone

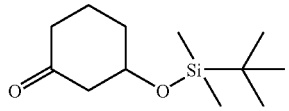

Stir a mixture of 1,3-cyclohexanediol (250.9 mg, 2.16 mmol) and NaH (80% in mineral oil, 71.3 mg, 2.38 mmol) in freshly distilled THF (5.0 mL) for 30 minutes. Add tert-butyldimethylsilyl chloride (325.5 mg, 2.16 mmol) in THF (2.0 mL in total). Stir for 2 hours, add THF (3.0 mL) to the milky solution, and stir overnight. Quench the reaction with brine and extract with EtOAc (3×30 mL). Combine extracts, dry over MgSO$_4$, and concentrate. Flash chromatography, eluting with 30% Et$_2$O/hexanes yields a mono-silyl ether (185.5 mg, 37%).

Add PCC (344 mg, 1.6 mmol) to the mono-protected cyclohexanediol (183.8 mg, 0.8 mmol) in anhydrous CH$_2$Cl$_2$ (10 mL) at room temperature and stir overnight. Filter through a Celite® pad with thorough CH$_2$Cl$_2$ rinse. Wash the filtrate with saturated aqueous NaHCO$_3$ and brine (30 mL each). Back-extract the aqueous layers with CH$_2$Cl$_2$ (2×30 mL). Combine the organic layers, dry over MgSO$_4$, concentrate and purify by flash chromatography, eluting with 20% Et$_2$O/hexanes to afford the title compound (150.7 mg, 83%):

HRMS calcd for C$_{12}$H$_{24}$O$_2$NaSi 251.1443 (M+Na)$^+$, found 251.1432, time 0.43 min; IR (cm$^{-1}$) 1711 (C=O).

Part B: 6-[4-(2-Aminoethyl)phenoxy]nicotinamide

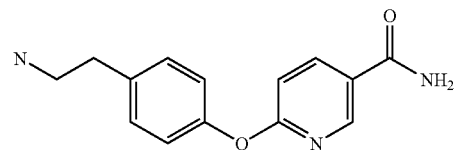

Treat [2-(4-hydroxyphenyl)ethyl]carbamic acid tert-butyl ester (534.3 mg, 2.2 mmol) with NaH (80% in mineral oil, 78.0 mg (2.6 mmol) in anhydrous DMF (10 mL) at room temperature for 30 minutes. Add 6-chloronicotinamide (343.8 mg, 2.2 mmol) and heat the mixture at 80° C. overnight. Quench the reaction with H$_2$O and concentrate to dryness, using xylenes to remove DMF as an azeotrope. Suspend the residue in MeOH and filter with thorough MeOH and CH$_2$Cl$_2$ rinse. Concentrate the filtrate and purify by flash chromatography, eluting with 75:15:10 EtOAc/CH$_2$Cl$_2$/2.0 M NH$_3$ in MeOH. Deprotect the BOC group with 1:1 TFA/CH$_2$Cl$_2$ (16 mL) at room temperature overnight. Concentrate and purify by an SCX column, washing with MeOH and then eluting with 2.0 M NH$_3$ in MeOH: MS ES$^+$ 297.9 (M+H+K)$^+$, HRMS calcd for C$_{14}$H$_{16}$N$_3$O$_2$ 258.1243 (M+H)$^+$, found 258.1235 time 0.40 min; HPLC [YMC-Pack Pro C-18 (150× 4.6 mm, S-5 microm), 0.1% TFA/acetonitrile in 0.1% TFA/water at 1.0 mL/min, 5-95% over 19 min], t$_R$=6.93 min. 100% purity.

Part C: (±)-(cis)- and (trans)-6-(4-{2-[3-(tert-Butyldimethyl-silyloxy)cyclohexylamino]
ethyl}phenoxy)nicotinamide

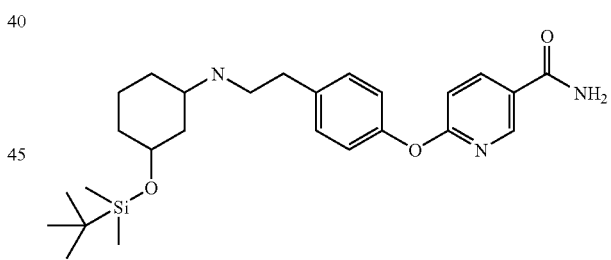

Dissolve 6-[4-(2-aminoethyl)phenoxy]nicotinamide (121.4 mg, 0.472 mmol) in MeOH (0.48 mL) and dichloroethane (1.0 mL). Add 3-(tert-butyldimethylsilyloxy)cyclohexanone (151 mg, 0.66 g mmol) in dichloroethane (2.0 mL). Add the mixture to a solution of NaB(OAc)$_3$H (140 mg, 0.661 mmol) in dichloroethane (1.3 mL). After 10 minutes, add dropwise AcOH (27 uL, 0.472 mmol) and stir the mixture overnight. Quench the reaction with 1.0 N NaOH (4.0 mL) and take up the mixture in Et$_2$O (30 mL). Separate the layers, and extract the aqueous layer with Et$_2$O (3×20 mL). Wash the organic layers with brine (40 mL), dry over MgSO$_4$, and concentrate. Purify by flash chromatography, eluting with 55:40:5 EtOAc/CH$_2$Cl$_2$/2.0 M NH$_3$ in MeOH to afford a diasteremeric mixture of the product (144.7 mg, 65%), which is separable by repeated flash chromatography, eluting with 5-10% 2.0 M NH$_3$ in MeOH/CH$_2$Cl$_2$: MS ES$^+$ 470.1 (M+H)$^+$, ES$^-$ 468.2 (M−H)$^-$.

Part D: (±)-(cis)-6-{4-[2-(3-Hydroxycyclohexylamino)ethyl]phenoxy}nicotinamide Treat (±)-(cis)-6-(4-{2-[3-(tert-butyldimethyl-silyloxy)cyclohexylamino]ethyl}phenoxy)nicotinamide (56.8 mg, 0.12 mmol) in THF (1.0 mL) with 1.0 M tetrabutylammonium fluoride (TBAF) in THF (0.5 eq) for 1 hour. Add another 0.5 eq of 1.0 M TBAF and stir for 4 hours. Add 1.0 eq of 1.0 M TBAF and stir for 2.5 days. Concentrate and purify by flash chromatography, eluting with 10% (2.0 M $NH_3$ in MeOH) in $CH_2Cl_2$. Repeat the chromatography to afford the title compound (29.9 mg, 70%): MS $ES^+$ 356.0 $(M+H)^+$, HRMS calcd for $C_{21}H_{28}N_3O_2$ 356.1974 $(M+H)^+$, found 356.1965, time 0.41 min; HPLC [YMC-Pack Pro C-18 (150×4.6 mm, S-5 microm), 0.1% TFA/acetonitrile in 0.1% TFA/water at 1.0 mL/min, 5-99% over 19 min], $t_R$=7.11 min, 100% purity; Anal. Calcd for $C_{20}H_{25}N_3O_3 \cdot 0.4CH_2Cl_2 \cdot 0.4MeOH$: C, 62.11; H, 6.87; N, 10.45. Found: C, 61.95; H, 6.88; N, 10.36.

EXAMPLE 452

(±)-(trans)-6-{4-[2-(3-Hydroxycyclohexylamino)ethyl]phenoxy}nicotinamide

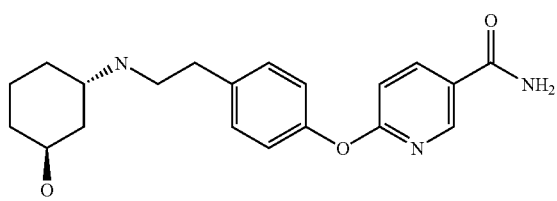

Treat (±)-(trans)-6-(4-{2-[3-(tert-1-butyldimethyl-silyloxy)cyclohexylamino]ethyl}phenoxy)nicotinamide (Example 451, Part C, 63.3 mg, 0.13 mmol) in THF (1.0 mL) with 1.0 M tetrabutylammonium fluoride (TBAF) in THF (0.5 eq) for 1 hour. Add another 0.5 eq of 1.0 M TBAF and stir for 4 hours. Add 1.0 eq of 1.0 M TBAF and stir for 9 days. Add another 1.0 eq of 1.0 M TBAF and stir for 4 days. Concentrate, dissolve the mixture in $CH_2Cl_2$ (20 mL), and wash with $H_2O$ (2×20 mL), saturated aqueous $NaHCO_3$ and brine (20 mL each). Back-extract the aqueous layers with $CH_2Cl_2$ (20 mL). Concentrate the two $H_2O$ washings and purify by flash chromatography, eluting with 15% (2.0 M $NH_3$ in MeOH) in $CH_2Cl_2$ to afford the title compound (42.1 mg, 88%): MS $ES^-$ 356.4 $(M+H)^+$, HRMS calcd for $C_{21}H_{28}N_3O_2$ 356.1974 $(M+H)^+$, found 356.1979, time 0.41 min; HPLC [YMC-Pack Pro C-18 (150×4.6 mm, S-5 microm), 0.1% TFA/acetonitrile in 0.1% TFA/water at 1.0 mL/min, 5-99% over 19 min], $t_R$=7.11 min, 100% purity.

EXAMPLE 453

(±)-6-{4-[2-((trans)-4-Hydroxycyclohexylamino)ethyl]phenoxy}nicotinamide

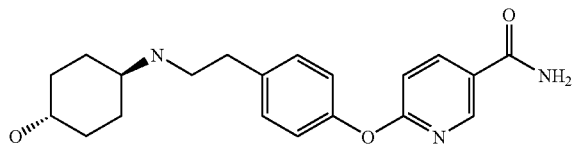

Part A: (±)-(trans)-4-[2-(4-Methoxyphenyl)ethylamino]cyclohexanol

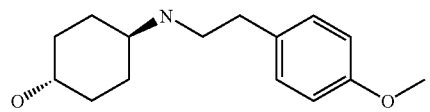

Heat a mixture of (±)-(trans)-4-aminocyclohexanol (607 m, 5.3 mmol), $Cs_2CO_3$ (4.300 g, 13.2 mmol), and 1-(2-chloroethyl)-4-methoxybenzene (0.8 mL) in DMF (10 mL) at 100° C. for 19 hours. Quench the reaction with saturated aqueous $NH_4Cl$ (40 mL). Adjust the pH to alkaline and concentrate to dryness. Suspend the residue in 50:40:10 EtOAc/$CH_2Cl_2$/2.0 M $NH_3$ in MeOH and stir vigorously for 1 hour. Decant the supernatant. Suspend the residue in 10:90 2.0 M $NH_3$ in MeOH/$CH_2Cl_2$ for 30 minutes and filter. Combine the organic layers, concentrate, and purify by flash chromatography, eluting with 75:15:10 EtOAc/$CH_2Cl_2$/2.0 M $NH_3$ in MeOH to afford the title compound (258.3 mg, 20%): MS $ES^+$ 250.0 $(M+H)^+$, HPLC [YMC-Pack Pro C-18 (150×4.6 mm, S-5 microm), acetonitrile in water containing 0.01% concentrated HCl at 1.0 mL/min, 30-99% over 19 min], $t_R$=1.96 min, 100% purity.

Part B: (±)-6-{4-[2-((trans)-4-Hydroxycyclohexylamino)ethyl]phenoxy}nicotinamide Add dropwise 1.0 M $BBr_3$ in heptane (1.35 mL, 1.35 mmol) to a suspension of (±)-(trans)-4-[2-(4-methoxyphenyl)ethylamino]cyclohexanol (Part A, 153.2 mg, 0.61 mmol) in anhydrous $CH_2C_{12}$ (5.0 mL) at 0° C. Add another 1.0 mL of $CH_2Cl_2$ when the compound precipitates out. Stir the mixture at 0° C. for 30 minutes and at room temperature for 2 hours. Quench the reaction with 5 drops of $H_2O$ and concentrate. Purify the residue on an SCX column, washing with MeOH and then eluting with 2.0 M $NH_3$ in MeOH to yield (±)-(trans)-4-[2-(4-hydroxycyclohexylamino)ethyl]phenol (121.2 mg).

Heat a mixture of the phenol (121.2 mg, 0.52 mmol), 6-chloronicotinamide (121.0 mg, 0.77 mmol), and $K_2CO_3$ (213.5 mg, 1.55 mmol) in 3:1 DMF/toluene (6.0 mL) at 165° C. for 3 hours. Quench the reaction with a small amount of $H_2O$ and concentrate to dryness, using xylenes to remove DMF azeotropically. Dissolve the residue in MeOH and filter. Concentrate the filtrate and purify by flash chromatography, eluting with 75:15:10 EtOAc/$CH_2Cl_2$/2.0 M $NH_3$ in MeOH, to afford the title compound (79.1 mg, 43%): MS $ES^+$ 356.0 $(M+H)^+$, HRMS calcd for $C_{20}H_{26}N_3O_3$ 356.1974 $(M+H)^+$, found 356.1959, time 0.34 min; HPLC [YMC-Pack Pro C-18

(150×4.6 mm, S-5 microm), acetonitrile in water containing 0.01% concentrated HCl at 1.0 mL/min, 5-95% over 19 min], $t_R$=5.81 min, 100% purity.

EXAMPLE 454

(±)-6-{4-[2-((trans)-2-Hydroxycyclopentylamino)ethyl]phenoxy}nicotinamide

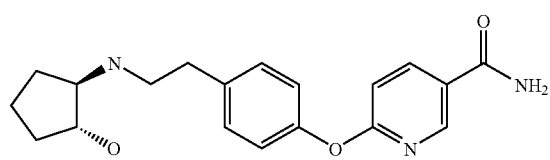

Part A:
4-[2-(2-Hydroxycyclopentylamino)ethyl]phenol

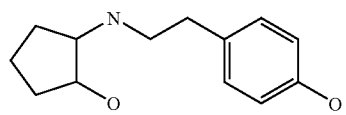

Stir a mixture of cyclopentene oxide (482.0 mg, 5.73 mmol) and tyramine (943.2 mg, 6.88 mmol) in 1.0 N NaOH (20 mL) at room temperature for 64 hours, at 45-55° C. for 6 hours, and at 100° C. for 18 hours. Quench the reaction with saturated aqueous NH$_4$Cl (40 mL) and take it up in EtOAc (50 mL). Separate the layers after shaking. Wash the organic layer with H$_2$O and brine (50 mL each). Back-extract the aqueous layers with CH$_2$Cl$_2$, EtOAc and CH$_2$Cl$_2$ (50 mL each). Adjust the pH of the combined aqueous layers to alkaline and concentrate. Suspend the residue in 10:40:50 2.0 M NH$_3$ in MeOH/CH$_2$Cl$_2$/EtOAc and decant off the supernatant. Dissolve the residual solid in H$_2$O and extract it with 10:40:50 2.0 M NH$_3$ in MeOH/CH$_2$Cl$_2$/EtOAc (100 mL) and 10:90 2.0 M NH$_3$ in MeOH/CH$_2$Cl$_2$. Combine all the organic layers and concentrate. Dissolve the residue in a small amount of MeOH and purify by flash chromatography, eluting with 10:40:50 2.0 M NH$_3$ in MeOH/CH$_1$CL$_2$/EtOAc to afford the title compound as a 1:3 cis/trans isomeric mixture (566 mg, 45%): MS ES$^+$ 222.0 (M+H)$^+$, HPLC [YMC-Pack Pro C-18 (150×4.6 mm, S-5 microm), acetonitrile in water containing 0.01% concentrated HCl at 1.0 mL/min, 5-95% over 19 min], $t_R$=4.72 min, 76% and 6.52 min, 24%.

Part B: (±)-6-{4-[2-((trans)-2-Hydroxycyclopentylamino)ethyl]phenoxy}nicotinamide Heat a mixture of 4-[2-(2-hydroxycyclopentylamino)ethyl]phenol (210.5 mg, 0.95 mmol), K$_2$CO$_3$ (395 mg, 2.85 mmol) and 6-chloronicotinamide (223.4 mg, 1.43 mmol) in 1:3 toluene/DMF (6 mL) at 165° C. for 2 hours, while removing H$_2$O azeotropically with toluene. Remove DMF azeotropically with xylenes and take up the residue in H$_2$O (50 mL) and 10% MeOH in CH$_2$Cl$_2$ (50 mL). Shake and separate the layers. Extract the aqueous layer with 10% MeOH in CH$_2$Cl$_2$ (2×50 mL) and 10% MeOH in EtOAc (50 mL). Combine the organic layers, dry over MgSO$_4$ and concentrate. Concentrate the aqueous layer, which still contains the product by TLC, to dryness and extract the product out with MeOH. Dry the solution with Na$_2$SO$_4$, filter and combine with the organic concentrate above. Concentrate, re-dissolve in MeOH and filter through a Na$_2$SO$_4$ pad. Concentrate and purify by flash chromatography, eluting with 10:15:75 2.0 M NH$_3$ in MeOH/CH$_2$CL$_2$/EtOAc to afford the title compound (137.4 mg) along with the (cis)-isomer of the starting phenol (59.0 mg) recovered: MS ES$^+$ 342.0 (M+H)$^+$, HRMS calcd for C$_{19}$H$_{24}$N$_3$O$_3$ 342.1818 (M+H)$^+$, found 342.1812, time 0.34 min; HPLC [YMC-Pack Pro C-18 (150×4.6 mm, S-5 microm), acetonitrile in water containing 0.01% concentrated HCl at 1.0 mL/min, 5-95% over 19 min], $t_R$=16.76 min, 100% purity; Anal. Calcd for C$_{19}$H$_{23}$N$_3$O$_3$0.1CH$_2$Cl$_2$ 0.1EtOAc: C, 65.29; H, 6.74; N, 11.71. Found: C, 65.35; H, 6.61; N, 11.98.

EXAMPLE 455

4-[5-(Phenethylamino-methyl)-pyridin-2-yloxy]-benzamide dihydrochloride

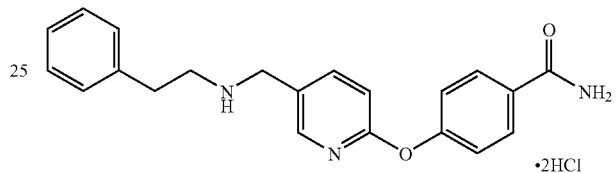

Step 1

4-(5-Cyano-pyridin-2-yloxy)-benzamide

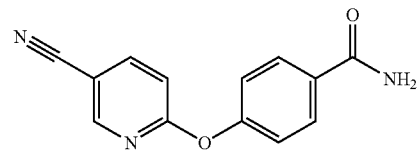

Combine 6-chloro-nicotinonitrile (1.0 g, 7.22 mmol), 4-hydroxybenzamide (1.09 g, 7.94 mmol), and potassium carbonate (1.49 g, 10.83 mmol) in toluene (8 mL). Add DMA (24 mL) to the reaction mixture. Heat the reaction mixture for 1.5 hour at 120° C. Let the reaction mixture cool to room temperature. Pour the reaction mixture onto water and filter the precipitate washing with water. Dry the solid under vacuum to provide the title compound (1.63 g, 94%)

Step 2

4-(5-Aminomethyl-pyridin-2-yloxy)-benzamide

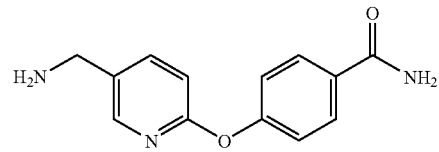

Combine 4-(5-cyano-pyridin-2-yloxy)-benzamide (202 mg, 0.844 mmol), 5% Pd/C (80 mg) and conc. HCl (0.423 mL) in THF (4 mL) and EtOH (4 mL). Run the reaction under hydrogen atmosphere (1 atm) at rt overnight. Add NaOH (5 N, 2 mL) and filter the reaction mixture through Celite®. Concentrate the filtrate. Wash the residue with $H_2O$ (5 mL) and extract with $CH_2Cl_2$ (3×5 mL). Combine the organic layers and purify through an SCX column eluting with 2M ammonia in methanol. Concentrate the fractions to give the title compound (74 mg, 36%).

Step 3

Combine 4-(5-aminomethyl-pyridin-2-yloxy)-benzamide (70 mg, 0.288 mmol) from step 2, methanol (1.8 mL), trimethylorthoformate (1.2 mL), and phenethyl aldehyde (0.034 mL, 0.288 mL). Stir at room temperature for 4 hours, then add sodium borohydride (13 mg, 0.346 mmol). Stir for 4 h. Purify through an SCX column using ammonia (2.0 M in methanol) to give 20 mg (20%) of the free base. Combine the compound with ether (1 mL) and hydrochloric acid (1 M in ether). Triturate and filtrate to give 24 mg of the title compound. Mass spectrum (ion spray): m/z=348.0 (M+1); $^1$H NMR (CDCl$_3$): 8.02 (d, J=1.8 Hz, 1H), 7.77 (d, J=8.6 Hz, 2H), 7.62 (dd, J=2.1 Hz, 8.6 Hz, 1H), 7.25-7.19 (m, 2H), 7.16-7.08 (m, 5H), 6.85 (d, J=8.3 Hz, 1H), 6.18-5.72 (bm, 2H), 3.69 (s, 2H), 2.83 (t, J=6.4 Hz, 2H), 2.75 (t, J=6.4 Hz, 2H), 1.85-1.51 (bs, 1H).

EXAMPLE 456

4-{5-[(3-Trifluoromethyl-benzylamino)-methyl]-pyridin-2-yloxy}-benzamide

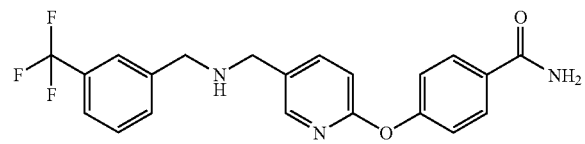

Using a method similar to Example 455, step 3, using 3-trifluoro-benzaldehyde (0.045 mL, 0.339 mmol) gives the title compound (106 mg, 85%). Mass spectrum (ion spray): m/z=401.9 (M+1); $^1$H NMR (DMSO-d$_6$): 8.08 (d, J=2.4 Hz, 1H), 7.97-7.93 (bs, 1H), 7.90 (d, J=8.7 Hz, 2H), 7.85 (dd, J=2.4 Hz, 8.5 Hz, 1H), 7.69 (s, 1H), 7.63 (d, J=7.6 Hz, 1H), 7.58-7.50 (m, 2H), 7.33 (s, 1H), 7.12 (d, J=8.7 Hz, 2H), 7.03 (d, J=8.5 Hz, 1H), 3.76 (s, 2H), 3.66 (s, 2H).

EXAMPLE 457

4-{5-[(3-Phenyl-propylamino)-methyl]-pyridin-2-yloxy}-benzamide

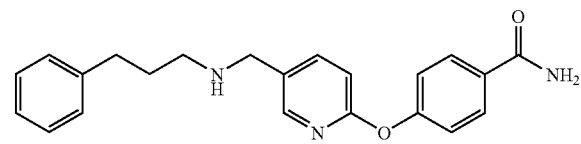

Using a method similar to Example 455, step 3, using 3-phenyl-propyl-aldehyde (0.045 mL, 0.339 mmol) gives the title compound (45 mg, 41%). Mass spectrum (ion spray): m/z=361.9 (M+1); $^1$H NMR (DMSO-d$_6$): 8.07 (d, J=2.1 Hz, 1H), 7.94 (bs, 1H), 7.90 (d, J=8.7 Hz, 2H), 7.82 (dd, J=2.5 Hz, 8.3 Hz, 1H), 7.33 (bs, 1H), 7.24 (t, J=7.4 Hz, 2H), 7.17-7.11 (m, 5H), 7.02 (d, J=8.3 Hz, 1H), 3.64 (s, 2H), 2.58 (t, J=7.6 Hz, 2H), 2.46 (t, J=7.6 Hz, 2H), 1.69 (quintet, J=7.6 Hz, 2H).

EXAMPLE 458

4-{5-[(4-Fluoro-benzylamino)-methyl]-pyridin-2-yloxy}-benzamide

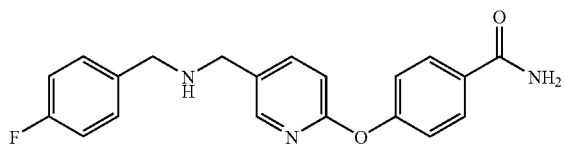

Using a method similar to Example 455, step 3, using 4-fluoro-benzaldehyde (0.036 mL, 0.339 mmol) gives the title compound (97 mg, 90%). Mass spectrum (ion spray): m/z=351.9 (M+1); $^1$H NMR (DMSO-d$_6$): 8.07 (d, J=2.3 Hz, 1H), 7.95 (bs, 1H), 7.90 (d, J=9.0 Hz, 2H), 7.84 (dd, J=2.5 Hz, 8.4 Hz, 1H), 7.37-7.32 (m, 3H), 7.14-7.08 (m, 4H), 7.03 (d, J=8.6 Hz, 1H), 3.64 (s, 2H), 3.63 (s, 2H).

EXAMPLE 459

4-[5-(Isobutylamino-methyl)-pyridin-2-yloxy]-benzamide

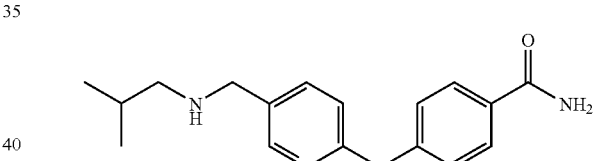

Using a method similar to Example 455, step 3, using isobutylaldehyde (0.031 mL, 0.339 Dinol) gives the title compound (71 mg, 77%). Mass spectrum (ion spray): m/z=300.0 (M+1); $^1$H NMR (DMSO-d$_6$): 8.07 (d, J=2.4 Hz, 1H), 7.94 (bs, 1H), 7.89 (d, J=8.7 Hz, 2H), 7.82 (dd, J=2.4 Hz, 8.2 Hz, 1H), 7.32 (bs, 1H), 7.12 (d, J=8.7 Hz, 2H), 7.03 (d, J=8.2 Hz, 1H), 3.64 (s, 2H), 2.26 (d, J=6.6 Hz, 2H), 1.64 (septet, J=6.6 Hz, 1H), 0.84 (d, J=6.6 Hz, 6H).

EXAMPLE 460

4-{5-[(3,3-Dimethyl-butylamino)-methyl]-pyridin-2-yloxy}-

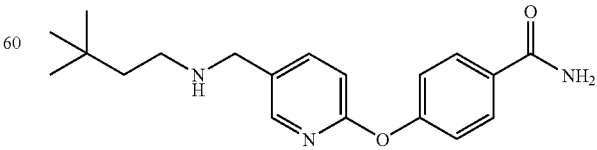

Using a method similar to Example 455, step 3, using 3,3-dimethyl-butyraldehyde (0.062 mL, 0.493 mmol) gives the title compound (111 mg, 82%). Mass spectrum (ion spray): m/z=327.9 (M+1); $^1$H NMR (DMSO-d$_6$): 8.06 (d, J=2.5 Hz, 1H), 7.93 (bs, 1H), 7.88 (d, J=8.5 Hz, 2H), 7.81 (dd, J=2.5 Hz, 8.5 Hz, 1H), 7.31 (bs, 1H), 7.11 (d, J=8.5 Hz, 2H), 7.02 (d, J=8.5 Hz, 1H), 3.63 (s, 2H), 2.46 (t, J=8.7 Hz, 2H), 1.98 (bs, 1H), 1.33 (t, J=8.7 Hz, 2H), 0.84 (s, 9H).

EXAMPLE 461

4-{5-[(3-Methyl-butylamino)-methyl]-pyridin-2-yloxy}-benzamide

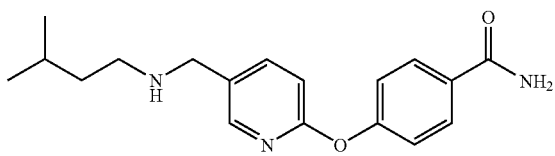

Using a method similar to Example 455, step 3, using 3-methyl-butyraldehyde (0.053 mL, 0.493 mmol) gives the title compound (102 mg, 79%). Mass spectrum (ion spray): m/z=313.9 (M+1); $^1$H NMR (DMSO-d$_6$): 8.06 (d, J=2.5 Hz, 1H), 7.93 (bs, 1H), 7.88 (d, J=8.7 Hz, 2H), 7.81 (dd, J=2.5 Hz, 8.4 Hz, 1H), 7.31 (bs, 1H), 7.11 (d, J=8.7 Hz, 2H), 7.02 (d, J=8.4 Hz, 1H), 3.63 (s, 2H), 2.45 (t, J=7.3 Hz, 2H), 2.02 (bs, 1H), 1.59 (septet, J=6.7 Hz, 1H), 1.28 (q, J=6.9 Hz, 2H), 0.82 (d, J=6.7 Hz, 6H).

EXAMPLE 462

4-{5-[(2-Thiophen-2-yl-ethylamino)-methyl]-pyridin-2-yloxy}-benzamide

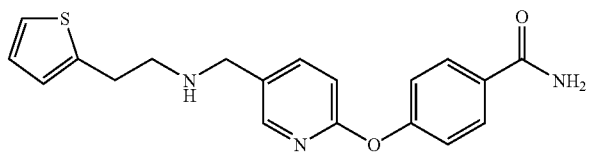

Step 1

4-(5-Formyl-pyridin-2-yloxy)-benzamide

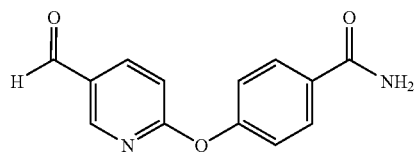

Combine 4-(5-cyano-pyridin-2-yloxy)-benzamide (501 mg, 2.09 mmol) in CH$_2$Cl$_2$ (10 mL) at 0° C. with DIBAL-H (1.0 M in hexanes, 4.2 mL) dropwise. Stir the reaction mixture for 5 h. Pour the reaction mixture onto aqueous NH$_4$Cl and let stir overnight. Filter and redissolve in CHCl$_3$/iPrOH (3:1, 10 mL) and wash with NaOH (1 N, 7 mL). Extract the organic layer, dry over magnesium sulfate, filter and dry under vacuum to provide 4-(5-formyl-pyridin-2-yloxy)-benzamide (312 mg, 62%).

Step 2

Using a method similar to Example 455, step 3, using 2-thiophen-2-yl-ethylamine (0.027 mL, 0.227 mmol) and 4-(5-formyl-pyridin-2-yloxy)-benzamide (58 mg, 0.239 mmol) from step 1 (above) gives the title compound (23 mg, 27%). Mass spectrum (ion spray): m/z=353.9 (M+1); $^1$H NMR (DMSO-d$_6$): 8.08 (d, J=2.1 Hz, 1H), 7.93 (bs, 1H), 7.89 (d, J=8.7 Hz, 2H), 7.82 (dd, J=2.3 Hz, 8.3 Hz, 1H), 7.31 (bs, 1H), 7.27 (dd, J=1.0 Hz, 5.2 Hz, 1H), 7.12 (d, J=8.7 Hz, 2H), 7.02 (d, J=8.3 Hz, 1H), 6.90 (dd, J=3.5 Hz, 5.2 Hz, 1H), 6.84 (d, J=3.3 Hz, 1H), 3.68 (S, 2H), 2.91 (t, J=7.1 Hz, 2H), 2.72 (t, J=7.1 Hz, 2H), 2.25 (bs, N—H).

EXAMPLE 463

4-(5-{[2-(3-Fluoro-phenyl)-ethylamino]-methyl}-pyridin-2-yloxy)-benzamide

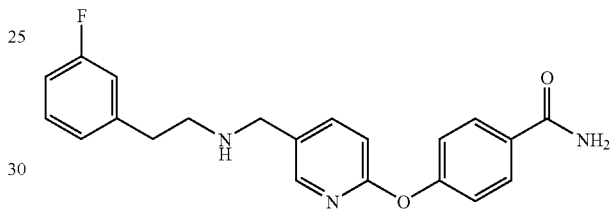

Using a method similar to example 462, step 2, using 3-fluoro-phenyl)-ethylamine (0.026 mL, 0.2 mmol) gives the title compound (14 mg, 18%) Mass spectrum (ion spray): m/z=365.9 (M+1); $^1$H NMR (DMSO-d$_6$): 8.06 (bs, 1H), 7.93 (bs, 1H), 7.88 (d, J=8.6 Hz, 2H), 7.79 (d, J=8.2 Hz, 1H), 7.32-7.24 (m, 2H), 7.11 (d, J=8.2 Hz, 2H), 7.05-6.93 (m, 5H), 3.67 (s, 2H), 2.76-2.64 (m, 4H).

EXAMPLE 464

4-(5-{[2-(2-Methoxy-phenyl)-ethylamino]-methyl}-pyridin-2-yloxy)-benzamide

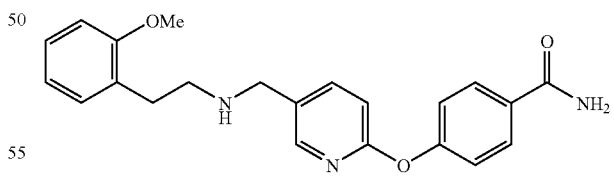

Using a method similar to example 462, step 2, using 2-methoxy-phenyl-ethylamine (0.033 mL, 0.223 mmol) gives the title compound (48 mg, 57%). Mass spectrum (ion spray): m/z=377.9 (M+1); $^1$H NMR (DMSO-d$_6$): 8.06 (d, J=2.1 Hz, 1H), 7.93 (bs, 1H), 7.89 (d, J=8.6 Hz, 2H), 7.79 (dd, J=2.4 Hz, 8.2 Hz, 1H), 7.31 (bs, 1H), 7.17-7.09 (m, 4H), 7.01 (d, J=8.4 Hz, 1H), 6.90 (d, J=8.1 Hz, 1H), 6.82 (t, J=7.5 Hz, 1H), 3.73 (s, 3H), 3.66 (s, 2H), 2.71-2.60 (m, 4H), 2.16 (bs, N—H).

EXAMPLE 465

4-(5-{[2-(2-Chloro-phenyl)-ethylamino]-methyl}-pyridin-2-yloxy)-benzamide

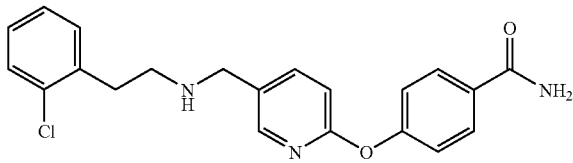

Using a method similar to example 462, step 2, using 2-chloro-phenyl)-ethylamine (0.028 mL, 0.198 mmol) gives the title compound (42 mg, 55%). Mass spectrum (ion spray): m/z=381.8 (M+1); ¹H NMR (DMSO-$d_6$): 8.06 (bs, 1H), 7.93 (bs, 1H), 7.88 (d, J=8.7 Hz, 2H), 7.80 (d, J=8.3 Hz, 1H), 7.40-7.29 (m, 3H), 7.26-7.17 (m, 2H), 7.11 (d, J=8.3 Hz, 2H), 7.01 (d, J=8.3 Hz, 1H), 3.68 (s, 2H), 2.82 (t, J=6.6 Hz, 2H), 2.68 (t, J=6.6 Hz, 2H), 2.27 (bs, N—H).

EXAMPLE 466

(±)-4-[5-(3-Phenyl-pyrolidin-1-ylmethyl)-pyridin-2-yloxy]-benzamide

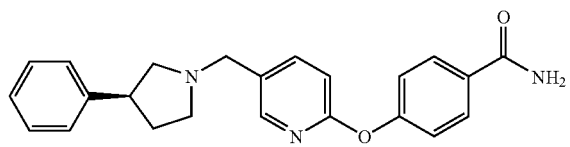

Step 1

4-(5-Formyl-pyridin-2-yloxy)-benzamide

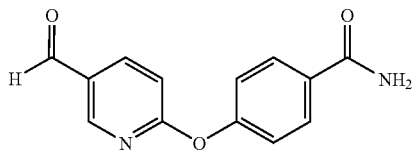

Combine 4-(5-cyano-pyridin-2-yloxy)-benzamide (501 mg, 2.09 mmol) in CH$_2$Cl$_2$ (10 mL) at 0° C. with DIBAL-H (1.0 M in hexanes, 4.2 mL) dropwise. Stir the reaction mixture for 5 h. Pour the reaction mixture onto aqueous NH$_4$Cl and let stir overnight. Filter and redissolve in CHCl$_3$/iPrOH (3:1, 10 mL) and wash with NaOH (1 N, 7 mL). Extract the organic layer, dry over magnesium sulfate, filter and dry under vacuum to provide 4-(5-formyl-pyridin-2-yloxy)-benzamide (312 mg, 62%).

Step 2

Combine 4-(5-formyl-pyridin-2-yloxy)-benzamide (100 mg, 0.413 mmol), (±)-3-phenyl-pyrrolidine (78 mg, 0.318 mmol), sodium triacetoxy-borohydride (101 mg, 0.477 mmol), AcOH (0.018 mL, 0.318 mmol) in CH$_2$Cl$_2$ (5 mL). Stir at rt overnight. Pour the reaction mixture onto an SCX column, eluting with ammonia (2M methanol) followed by chromatography [CH$_2$Cl$_2$:ammonia (2.0 M in methanol) 20:1] to provide the title compound (43 mg, 36%). Mass spectrum (ion spray): m/z=373.9 (M+1); ¹H NMR (DMSO-$d_6$): 8.09 (d, J=1.9 Hz, 1H), 7.93 (bs, 1H), 7.89 (d, J=8.6 Hz, 2H), 7.82 (dd, J=2.2 Hz, 8.6 Hz, 1H), 7.30 (bs, 1H), 7.27-7.24 (m, 4H), 7.17-7.12 (m, 3H), 7.03 (d, J=8.3 Hz, 1H), 3.61 (dd, J=13.1 Hz, 19.5 Hz, 2H), 3.33-3.24 (m, 1H), 2.88 (t, J=8.3 Hz, 1H), 2.66 (t, J=7.0 Hz, 2H), 2.42 (t, J=8.3 Hz, 1H), 2.28-2.18 (m, 1H), 1.79-1.70 (m, 1H).

EXAMPLE 467

4-{5-[(3,3-Dimethyl-butylamino)-methyl]-pyridin-2-yloxy}-benzamide

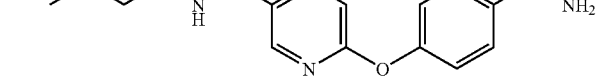

The title compound is prepared following the procedure of Example 462 using the corresponding amine. Mass spectrum (ion spray): m/z=327.9 (M+1); ¹H NMR (DMSO-$d_6$): 8.06 (d, J=2.5 Hz, 1H), 7.93 (bs, 1H), 7.88 (d, J=8.5 Hz, 2H), 7.81 (dd, J=2.5 Hz, 8.5 Hz, 1H), 7.31 (bs, 1H), 7.11 (d, J=8.5 Hz, 2H), 7.02 (d, J=8.5 Hz, 1H), 3.63 (s, 2H), 2.46 (t, J=8.7 Hz, 2H), 1.98 (bs, 1H), 1.33 (t, J=8.7 Hz, 2H), 0.84 (s, 9H).

EXAMPLE 468

4-{5-[(3-Methyl-butylamino)-methyl]-pyridin-2-yloxy}-benzamide

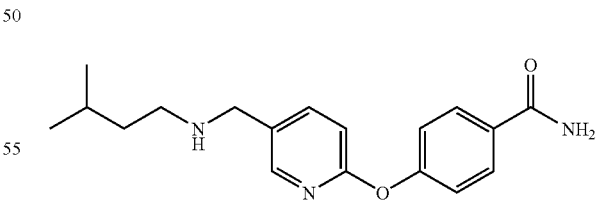

The title compound is prepared following the method of Example 455, step 3 using the corresponding amine. Mass spectrum (ion spray): m/z=313.9 (M+1); ¹H NMR (DMSO-$d_6$): 8.06 (d, J=2.5 Hz, 1H), 7.93 (bs, 1H), 7.88 (d, J=8.7 Hz, 2H), 7.81 (dd, J=2.5 Hz, 8.4 Hz, 1H), 7.31 (bs, 1H), 7.11 (d, J=8.7 Hz, 2H), 7.02 (d, J=8.4 Hz, 1H), 3.63 (s, 2H), 2.45 (t, J=7.3 Hz, 2H), 2.02 (bs, 1H), 1.59 (septet, J=6.7 Hz, 1H), 1.28 (q, J=6.9 Hz, 2H), 0.82 (d, J=6.7 Hz, 6H).

EXAMPLE 469

4-{3-Chloro-5-[(2-thiophen-2-yl-ethylamino)-methyl]-pyridin-2-yloxy}-benzamide

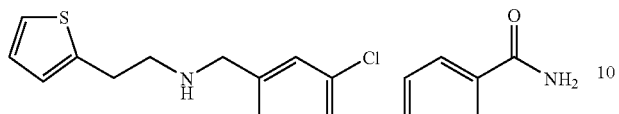

Step 1

5,6-Dichloro-pyridine-3-carbaldehyde

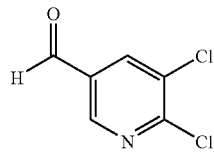

Combine (5,6-dichloro-pyridin-3-yl)-methanol (3.05 g, 17.11 mmol) and manganese dioxide (37.2 g, 427.9 mmol) in $CH_2Cl_2$ (25 mL). Stir the reaction mixture at rt overnight. Filter the reaction mixture through Celite® washing with $CH_2Cl_2$ (2×10 mL). Concentrate the filtrate and dry under vacuum to provide the title compound (1.44 g, 48%).

Step 2

4-(3-Chloro-5-formyl-pyridin-2-yloxy)-benzamide

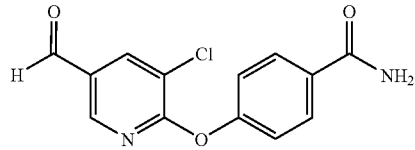

Combine 5,6-dichloro-pyridine-3-carbaldehyde (1.37 g, 7.80 mmol), 4-hydroxy-benzamide (1.18 g, 8.58 mmol), potassium carbonate (1.62 g, 11.7 mmol) in toluene (10 mL) and DMA (30 mL). Stir the reaction mixture at 100° C. for 1 h. Pour the reaction mixture onto $H_2O$ (100 mL) and extract with $Et_2O$ (100 mL). Wash the organic layer with $H_2O$ (2×100 mL), dry the organic phase extracts over magnesium sulfate, filter and concentrate to give the title compound (1.09 g, 51%).

Step 3

Using a method similar to Example 460, using 4-(3-chloro-5-formyl-pyridin-2-yloxy)-benzamide (114 mg, 0.412 mmol) and 2-thiophen-2-yl-ethylamine (0.048 mL, 0.412 mmol) gives the title compound (57 mg, 36%). Mass spectrum (ion spray): m/z=387.9 (M+1); $^1$H NMR (DMSO-$d_6$): 8.37 (bs, 1H), 8.21 (d, J=1.9 Hz, 1H), 7.99 (bs, 1H), 7.93 (d, J=8.7 Hz, 2H), 7.39 (dd, J=1.2 Hz, 5.0 Hz, 1H), 7.36 (bs, 1H), 7.21 (d, J=8.9 Hz, 2H), 6.99-6.94 (m, 2H), 4.16 (s, 2H), 3.26-3.11 (m, 4H).

EXAMPLE 470

4-(3-Chloro-5-{[2-(3-chloro-phenyl)-ethyl amino]-methyl}-pyridin-2-yloxy)-benzamide

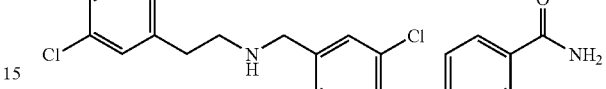

Using a method similar to Example 462, using 4-(3-chloro-5-formyl-pyridin-2-yloxy)-benzamide (101 mg, 0.365 mmol) and 2-(3-chloro-phenyl)-ethylamine (0.056 mL, 0.402 mmol) gives the title compound (57 mg, 36%). Mass spectrum (ion spray): m/z=415.9 (M+1); $^1$H NMR (CDCl$_3$): 7.93 (d, J=1.7 Hz, 1H), 7.86 (d, J=8.7 Hz, 2H), 7.77 (d, J=1.7 Hz, 1H), 7.22-7.17 (m, 4H), 7.07 (d, J=7.0 Hz, 1H), 6.12 (bs, 2H), 3.74 (s, 2H), 2.87 (t, J=6.8 Hz, 2H), 2.78 (t, J=6.8 Hz, 2H), 1.42 (bs, 1H).

General Procedure for Examples 471-474

To a mixture of amine (1 equiv), aldehyde (1.5 equiv) in 5% AcOH/methanol (0.2 M) was added NaCNBH$_4$ (5 equiv) and the resulting reaction mixture was stirred for 2 hours under nitrogen atmosphere at room temperature. The reaction can be monitored by electrospray MS or TLC. Ethyl acetate was added to the reaction mixture and washed twice with saturated aqueous solution of NaHCO$_3$. The organic layer was separated, dried over anhydrous NaSO$_4$ and the solvent was evaporated to yield a residue which was purified by flash chromatography using chloroform/ethanol/NH$_4$OH, 94.5/5/0.5) to afford the title compound as a white solid.

EXAMPLE 471

6-[2-Fluoro-4-((3-methyl-butyl)pentylaminomethyl)phenoxy]nicotinamide

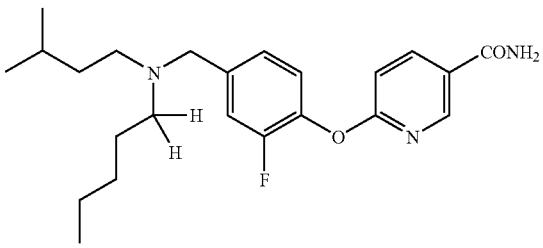

Reductive amination of N-pentyl-N-3-methylbutylamine and 6-(2-fluoro-4-formyl-phenoxy)-nicotinamide as described above afforded the title compound in 86% yield.

$^1$H NMR (CHCl$_3$-d$_3$) δ: 8.56 (d, 1H, J=2.4 Hz), 8.17 (dd, 1H, J=8.5, 2.4 Hz), 7.28-7.10 (m, 3H), 7.02 (d, 1H, J=8.7 Hz), 6.21 (bs, 2H), 3.54 (s, 2H), 2.42 (dt, 4H, J=8.7 Hz), 1.65-1.53 (m, 1H), 1.53-1.40 (m, 2H), 1.40-1.20 (m, 6H), 0.86 (t, 3H, J=7.0 Hz), 0.85 (d, 6H, J=6.5 Hz).

EXAMPLE 472

6-[2-Fluoro-4-((3-methyl-butylpropylamino)methyl)phenoxy]nicotinonamide

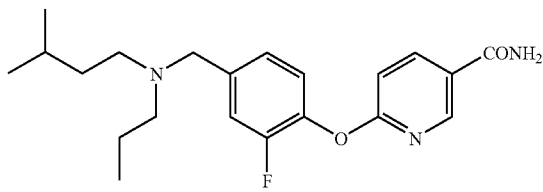

The title compound was prepared by reductive amination of 6-[2-fluoro-4-((3-methyl-butyl)aminomethyl)phenoxy]nicotinamide with propanaldehyde in 86% Yield.

$^1$H NMR (CHCl$_3$-d$_3$) δ: 8.56 (d, 1H, J=2.4 Hz), 8.17 (dd, 1H, J=8.5, 2.4 Hz), 7.28-7.10 (m, 3H), 7.02 (d, 1H, J=8.5 Hz), 6.24 (bs, 2H), 3.54 (s, 2H), 1.65-1.55 (m, 1H), 1.55-1.40 (m, 2H), 1.40-1.30 (m, 2H), 0.86 (t, 3H, J=7.0 Hz), 0.85 (d, 6H, J=6.5 Hz).

$^{13}$C NMR (CHCl$_3$-d$_3$) δ: 167.6, 165.5, 156.4, 153.1, 147.5, 139.7, 124.8, 123.5, 117.3, 117.1, 111.0, 58.2, 56.3, 52.3, 36.3, 26.6, 23.1, 20.6, 12.3. MS (Electrospray): 374.2 (M$^+$+1).

EXAMPLE 473

6-[4-Bis-((3-methyl-butylamino)-methyl)-2-fluorophenoxy]nicotinonamide

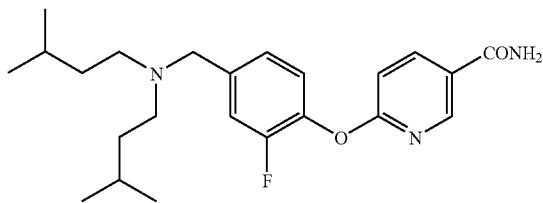

The title compound was prepared by reductive amination of 6-[2-fluoro-4-((3-methyl-butyl)aminomethyl)phenoxy]nicotinamide with 3-methylbutanaldehyde in 80% Yield.

$^1$H NMR (CHCl$_3$-d$_3$): 8.55 (d, 1H, J=2.4 Hz), 8.17 (dd, 1H, J=8.5, 2.4 Hz), 7.28-7.10 (m, 3H), 7.02 (d, 1H, J=8.7 Hz), 6.25 (bs, 2H), 3.53 (s, 2H), 2.44 (t, 4H, J=7.3 Hz), 1.58 (sept, 2H, J=7.3 Hz), 1.35 (dt, 4H, J=7.3 Hz), 0.85 (dd, 6H, J=6.7 Hz).

$^{13}$C NMR (CHCl$_3$-d$_3$) δ: 167.6, 165.5, 156.4, 153.1, 147.5, 139.7, 124.8, 123.5, 117.4, 117.1, 111.0, 58.2, 52.3, 36.3, 26.6, 23.1. MS (Electrospray): 402.2 (M$^+$+1).

EXAMPLE 474

6-[4-1-(2-Thiophen-2-ylethylaminoethyl)-phenoxy]nicotinonamide

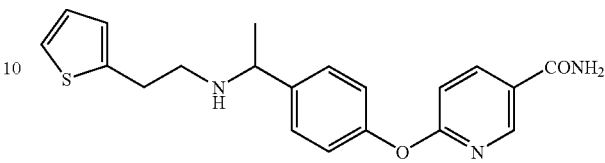

Step 1

(4-Acetyl-phenoxy)nicotinamide

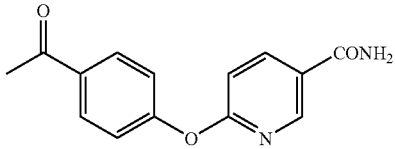

4-Hydroxyacetophenone (1 equiv), 6-chloronicotinamide (1 equiv) and K$_2$CO$_3$ (1.4 equiv) in anhydrous DMF (0.4 M) was heated at 150° C. under nitrogen during 2.5 days. After cooling down to room temperature, toluene was added and solvents were evaporated. The residue was partitioned in water/EtOAc. The aqueous layer was thoroughly extracted with EtOAc. The combined organic layer was dried over Na$_2$SO$_4$, filtered and concentrated under vacuum (toluene was added to aid DMF evaporation). The crude mixture was purified by flash chromatography using EtOAc/CH$_2$Cl$_2$/2 M NH$_3$ in MeOH (12:7:1) as eluent in 20% yield.

$^1$H NMR (MeOH-d$_4$) δ: 8.63 (d, 1H, J=2.7 Hz), 8.30 (dd, 1H, J=8.6, 2.7 Hz), 8.06 and 7.25 (AA'BB' system, 4H), 7.10 (d, 1H, J=8.6 Hz), 2.61 (s, 3H)

$^{13}$C NMR (MeOH-d$_4$): 196.2, 165.1, 163.4, 156.8, 146.9, 139.2, 132.9, 129.7, 125.3, 120.6, 110.8, 26.1 MS (Electrospray): 257.0 (M$^+$+1).

Step 2

To a mixture of the ketone (step 1) (1 equiv) and 2-thiophen-2-ylethylamine (1.5 equiv), in THF (0.04 M) was added titanium tetraisopropoxide (2 equiv) at 0° C. and the resulting solution was stirred overnight under nitrogen atmosphere at room temperature. The following day titanium tetrachloride (1.0 M solution in CH$_2$Cl$_2$, 2 equiv) was added and the reaction mixture was stirred for 2.5 hours. NaCNBH$_4$ was added (2 equiv) and stirring was kept for 2 more hours. The reaction can be monitored by electrospray MS. The reaction mixture was quenched with saturated solution of NaHCO$_3$, and diluted with EtOAc. The reaction mixture was filtered off and the filtrate was evaporated to yield a residue which was purified by SCX. Quantitative yield.

$^1$H NMR (MeOH-d$_4$) δ: 8.61 (d, 1H, J=2.4 Hz), 8.23 (dd, 1H, J=8.7, 2.4 Hz), 7.40-7.30 (m, 2H), 7.20-7.05 (m, 3H), 7.00-6.75 (m, 3H), 3.82 (q, 1H, J=7.5 Hz), 2.95 (m, 2H), 2.70 (m, 2H), 1.34 (d, 3H, J=7.5 Hz).

$^{13}$C NMR (MeOH-d$_4$): 167.2, 164.7, 151.6, 146.4, 146.3, 140.9, 138.4, 126.9, 125.5, 123.7, 122.1, 120.0, 109.5, 56.2, 36.0, 28.3, 21.4. MS (Electrospray): 368.2 (M$^+$+1).

INTERMEDIATES FOR EXAMPLES 475-480

Intermediate 1

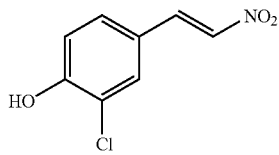

3-Chloro-4-hydroxybenzaldehyde (2 g, 12.8 mmol), nitromethane (4.68 g, 76.6 mmol) and ammonium acetate (3.93 g, 51.1 mmol) are dissolved in 20 mL acetic acid and the reaction mixture is heated at 110° C. After 3.5 h the reaction mixture is concentrated under reduced pressure and the residue is partitioned between EtOAc and water. Separate the layers and wash the organic layer with brine. Dry with sodium sulfate, filter and concentrate under reduced pressure. Silica gel chromatography using hexanes: dichloromethane:EtOAc in a 60:35:5 ratio afforded 1.26 g (49%) of the title compound.

$^1$H-NMR (CDCl$_3$, 400 MHz): 7.90 (d, 1H, J=13.6 Hz), 7.55 (d, 1H, J=1.8 Hz), 7.49 (d, 1H, J=13.6 Hz), 7.41 (d, 1H, J=8.3 Hz), 7.09 (d, 1H, J=8.3 Hz), 5.92 (s, 1H),

Intermediate 2

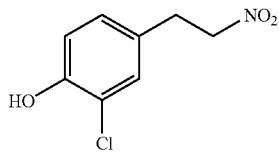

To a solution of lithium aluminum hydride (0.325 g, 8.55 mmol) in 30 mL of THF at 0° C. is added aluminum trichloride (1.14 g, 8.55 mmol). After 5 min the intermediate 1 (0.57 g, 2.85 mmol) is added dropwise in 15 mL of THF and the reaction is allowed to stir for 18 h. 100 mL of water and 10 mL of 5 N HCL are added and the reaction mixture is extracted with 3:1 n-butanol:toluene. The combined organic layers are washed with brine, dried over sodium sulfate and concentrated. SCX ion-exchange chromatography afforded 335 mg (68%) of the title compound. MS (APCI): (M$^+$+1), NH-NMR (DMSO, 400 MHz): 7.14 (m, 1H), 6.92 (m, 1H), 6.83 (m, 1H), 2.86 (d, 1H, J=7.48, 7.05 Hz), 2.69 (t, 1H, J=7.48, 7.05 Hz), 2.59 (d, 1H, J=7.48, 7.05 Hz), 2.50 (d, 1H, J=7.48, 7.05 Hz).

Intermediate 3

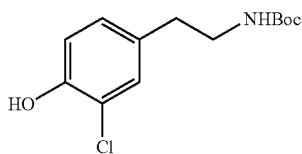

To a solution of the intermediate 2 (400 mg, 2.32 mmol) in 15 mL of THF is added di-tert-butyl dicarbonate (557 mg, 2.56 mmol) and sodium bicarbonate (234 mg, 2.79 mmol) After 18 h the reaction mixture is partitioned between EtOAc and brine. The organic layer is separated and washed with 1 M citric acid and brine. It is dried over sodium sulfate, filtered and concentrated. Silica gel chromatography using 5-10% EtOAc in dichloromethane afforded 430 mg (68%) of the title compound. MS (APCI): (M$^+$+1-Boc group), $^1$H-NMR (CDCl$_3$, 400 MHz): 7.14 (d, 1H, J=1.5 Hz), 6.99 (dd, 1H, J=8.3, 1.9 Hz), 6.94 (d, 1H, J=7.8 Hz), 3.32 (m, 2H), 2.70 (t, 2H, J=6.8 Hz), 1.43 (s, 9H).

Intermediate 4

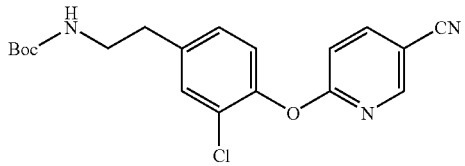

A solution of the intermediate 3 (700 mg, 2.57 mmol), 6-chloronicotinonitrile (392 mg, 2.83 mmol) and sodium hydride (113 mg, 2.83 mmol) is stirred for 18 h. The reaction mixture is partitioned between ethyl acetate and brine. The organic layer is separated, washed with water and brine, dried over sodium sulfate, filtered and concentrated. Silica gel chromatography using 0-10% ethyl acetate in dichloromethane afforded 895 mg (93%) of the title compound. MS (APCI): (M$^+$+1-Boc group) 274, $^1$H-NMR (CDCl$_3$, 400 MHz): 8.42 (d, 1H, J=1.9 Hz), 7.94 (dd, 1H, J=8.8, 2.4 Hz), 7.32 (d, 1H, J=1.5 Hz), 7.08-7.25 (m, 3H), 4.61 (bs, 1H), 3.39 (m, 2H), 2.81 (t, 2H, J=6.84 Hz), 1.43 (s, 9H).

Intermediate 5

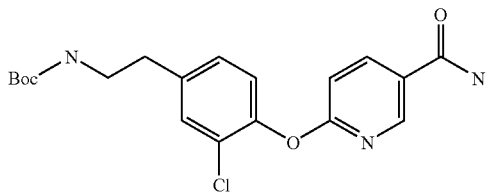

To a solution of the intermediate 4 (875 mg, 2.34 mmol) in DMSO was added potassium carbonate (161 mg, 1.17 mmol)

followed by addition of 30% hydrogen peroxide solution (10 µl) and the reaction was allowed to stir for 18 h. The reaction mixture was partitioned between ethyl acetate and brine. The organic layer was washed with water and brine before being dried over sodium sulfate, filtered and concentrated to afford 827 mg (90%) of the title compound. $^1$H-NMR (CDCl$_3$, 400 MHz): 8.55 (bs, 1H), 8.21 (dd, 1H, J=8.8, 2.4 Hz), 7.32 (bs, 1H), 7.16 (bs, 2H), 7.04 (d, 1H, J=8.8 Hz), 4.63 (bs, 1H), 3.39 (m, 2H), 2.81 (t, 2H, J=6.84 Hz), 1.44 (s, 9H).

Intermediate 6

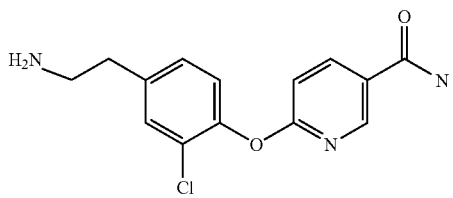

A solution of the intermediate 5 (827 mg, 2.11 mmol) in 25% TFA in methylene chloride was stirred for 18 h. The reaction mixture was concentrated under reduced pressure, and purified using SCX ion-exchange chromatography to afford 587 mg (95%) of the title compound. MS (APCI): (M$^+$+1) 292. $^1$H-NMR (CDCl$_3$ with MeOH (d-4), 400 MHz): 8.49 (d, 1H, J=2.4 Hz), 8.21 (dd, 1H, J=8.3, 2.4 Hz), 7.27 (d, 1H, J=1.5 Hz), 7.11 (m, 2H), 6.96 (d, 1H, J=8.8 Hz), 2.92 (t, 2H, J=6.9 Hz), 2.72 (t, 2H, J=6.8 Hz).

EXAMPLE 475

6-[4-(2-Benzylamino-ethyl)-2-chloro-phenoxy]-nicotinamide

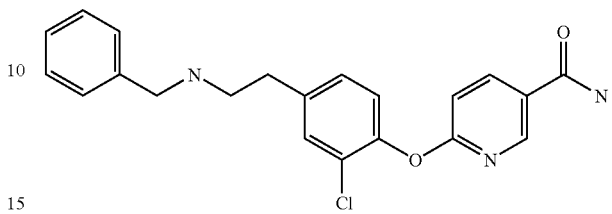

The intermediate 6 (100 mg, 0.342 mmol) and benzaldehyde (435 mg, 0.411 mmol) were dissolved in 5 mL of methanol while stirring for 18 h. NaBH$_4$ (29.4 mg, 0.68 mmol) was added and the reaction continued for an additional 4 h. The NaBH$_4$ was neutralized with a few drops of acetic acid and the reaction mixture was loaded directly onto a 2 g SCX column for purification to afford 103 mg (79%) of the title compound. MS (APCI): (M$^+$+1, M$^+$+3) 382, 384. $^1$H-NMR (CDCl$_3$, 400 MHz): 8.53 (d, 1H, J=2.44 Hz), 8.19 (dd, 1H, J=8.3, 2.4 Hz), 7.29-7.33 (m, 6H), 7.14-7.16 (m, 2H), 7.03 (d, 1H, J=8.3 Hz), 3.83 (s, 2H), 2.92 (m, 2H), 2.83 (m, 2H).  HPLC Purity: 94%,  HPLC Retention time: 1.745 minutes.

By the method outlined for the synthesis of Example 475, the following compounds were prepared.

| Example | Name | Mass | NMR/MS/LC/MS |
|---|---|---|---|
| 476 | 6-{2-Chloro-4-[2-(2-methyl-benzylamino)-ethyl]-phenoxy}-nicotinamide | 395 | (APCI): (M$^+$ + 1, M$^+$ + 3) 396, 398<br>$^1$H-NMR (CDCl$_3$, 400 MHz): 8.53 (d, 1H, J = 2.44 Hz), 8.19 (dd, 1H, J = 8.3, 2.4 Hz), 7.34 (d, 1H, J = 1.95 Hz), 7.26 (m, 1H), 7.12-7.18 (m, 5H), 7.03 (d, 1H, J = 7.8 Hz), 3.80 (s, 2H), 2.97 (t, 2H, J = 6.84 Hz), 2.84 (t, 2H, J = 6.84 Hz), 2.32 (s, 3H).<br>HPLC Purity: 94.6%<br>HPLC Retention time: 1.842 min. |
| 477 | 6-{2-Chloro-4-[2-(2-trifluoromethyl-benzylamino)-ethyl]-phenoxy}-nicotinamide | 449 | (APCI): (M$^+$ + 1) 450<br>HPLC Purity: 80.8%<br>HPLC Retention time: 2.197 min. |
| 478 | 6-{2-Chloro-4-[2-(3-fluoro-benzylamino)-ethyl]-phenoxy}-nicotinamide | 399 | (APCI): (M$^+$ + 1, M$^+$ + 3) 400, 402<br>$^1$H-NMR (CDCl$_3$ with D$_4$ MeOH, 400 MHz): 8.49 (d, 1H, J = 2.44 Hz), 8.17 (dd, 1H, J = 8.3, 2.4 Hz),<br>6.90-7.25 (m, 8H), 3.75 (s, 2H), 2.76-2.84 (m, 4H).<br>HPLC Purity: 93.8%<br>HPLC Retention time: 1.799 min. |
| 479 | 6-{2-Chloro-4-[2-(3-chloro-benzylamino)-ethyl]-phenoxy}-nicotinamide | 416 | (APCI): (M$^+$, M$^+$ + 2) 416, 418<br>$^1$H-NMR (CDCl$_3$ with D$_4$ MeOH, 400 MHz): 8.46 (d, 1H, J = 1.95 Hz), 8.12 (dd, 1H, J = 8.8, 2.4 Hz),<br>7.04-7.22 (m, 7H), 6.88 (d, 1H, J = 8.3 Hz), 3.68 (s, 2H),<br>2.73-2.78 (m, 4H). |

| Example | Name | Mass | NMR/MS/LC/MS |
|---|---|---|---|
| | | | **HPLC Purity: 93.4% |
| | | | **HPLC Retention time: 1.857 min. |
| 480 | 6-{2-Chloro-4-[2-(3-trifluoromethyl-benzylamino)-ethyl]-phenoxy}-nicotinamide | 449 | (APCI): (M⁺ + 1) 450 |
| | | | **HPLC Purity: 81.9% |
| | | | **HPLC Retention time: 2.275 min. |

**HPLC conditions: (10/90 to 90/10 ACN/(0.1% TFA in water) Water's Xterra MS C18 Column 4.6 mm × 50 mm × 5 micron.

INTERMEDIATES FOR EXAMPLES 481-482

Intermediate 1

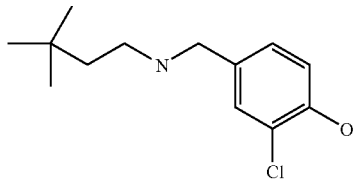

3-Chloro-4-hydroxybenzaldehyde (100 mg, 0.64 mmol) and 3,3-dimethyl-1-butylamine (56 mg, 0.55 mmol) were dissolved in 2 mL methanol containing 3 Å molecular sieves. After 18 hours, sodium borohydride (41 mg, 1.28 mmol) was added and the reaction was continued for another 4 h. The reaction was quenched by the addition of a few drops of acetic acid and purified by SCX ion-exchange chromatography to afford 50 mg (37.6%) of the title compound. MS (APCI): (M+1) 242, $^1$H-NMR (CDCl$_3$, 400 MHz): 7.29 (d, 1H, J=1.95 Hz), 7.10 (dd, 1H, J=8.3, 1.95 Hz), 6.87 (d, 1H, J=8.3 Hz), 3.72 (s, 2H), 2.67 (t, 2H, J=8.3 Hz), 1.48 (t, 2H, J=8.8 Hz), 0.89 (s, 9H).

Intermediate 2

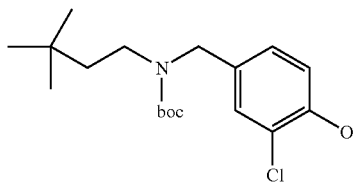

To a solution of the intermediate 1 (50 mg, 0.2 mmol) in 2 mL of THF was added di-tert-butyl dicarbonate (56.5 mg, 0.26 mmol) and sodium bicarbonate (26 mg, 0.31 mmol). After 18 h the reaction mixture was partitioned between EtOAc and brine. The organic layer is separated and washed with 1 M citric acid and brine, after which it was dried over sodium sulfate, filtered and concentrated. Silica gel chromatography using 0-5% EtOAc in dichloromethane afforded 34 mg (48%) of the title compound. $^1$H-NMR (CDCl$_3$, 400 MHz): 7.21 (s, 1H), 7.04 (m, 1H), 6.96 (d, 1H, J=8.3 Hz), 5.52 (s, 1H), 4.31 (bs, 2H), 3.14 (m, 2H), 1.56 (m, 11H), 0.85 (s, 9H).

Intermediate 3

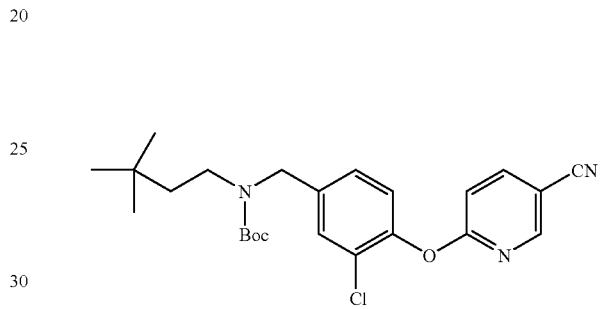

A solution of the intermediate 2 (110 mg, 0.32 mmol), 6-chloronicotinonitrile (49 mg, 0.35 mmol) and sodium hydride (14.2 mg, 0.35 mmol) was stirred for 18 h. The reaction mixture was partitioned between ethyl acetate and brine. The organic layer was separated, washed with water and brine, dried over sodium sulfate, filtered and concentrated. Silica gel chromatography using 0-5% ethyl acetate in 60:40 hexanes:dichloromethane afforded 23 mg (16%) of the title compound. MS (APCI): (M⁺+1-Boc group) 344, $^1$H-NMR (CDCl$_3$, 400 MHz): 8.42 (dd, 1H, J=2.2, 0.88 Hz), 7.95 (dd, 1H, J=8.37, 2.2 Hz), 7.36 (s, 1H), 7.15-7.20 (m, 2H), 7.09 (d, 1H, J=8.8 Hz), 4.40 (bs, 2H), 3.19 (m, 2H), 1.48 (bs, 11H), 0.89 (s, 9H).

Intermediate 4

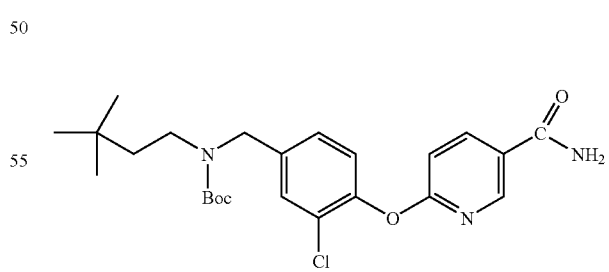

To a solution of the intermediate 3 (244 mg, 0.55 mmol) in 5 mL of DMSO was added potassium carbonate (38 mg, 0.275 mmol) followed by 30% hydrogen peroxide solution (2 mL) and the reaction was allowed to stir for 18 h. The reaction mixture was partitioned between ethyl acetate and brine. The organic layer was washed with water and brine before being dried over sodium sulfate, filtered and concentrated to afford 218 mg (86%) of the title compound. MS (APCI): (M$^+$+1-Boc group) 362.

EXAMPLE 481

6-{2-Chloro-4-[(3,3-dimethylbutylamino)-methyl]-phenoxy}-nicotinamide

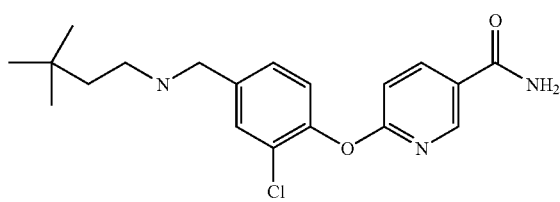

A solution of the intermediate 4 (218 mg, 0.47 mmol) in 2.5 mL of 20% TFA in methylene chloride was stirred for 18 h. After the reaction mixture was concentrated under reduced pressure, SCX ion-exchange chromatography followed by silica gel chromatography using 5-10% 2 N NH$_3$ methanol in dichloromethane afforded 151 mg (88%) of the title compound. MS (APCI): (M$^+$+1) 362, $^1$H-NMR (CDCl$_3$, 400 MHz): 8.53 (d, 1H, J=2.64 Hz), 7.95 (dd, 1H, J=8.8, 2.64 Hz), 7.48 (d, 1H, J=2.2 Hz), 7.29 (dd, 1H, J=8.36, 2.2 Hz), 7.16 (d, 1H, J=7.92 Hz), 7.02 (d, 1H, J=9.24 Hz), 5.93 (vbs, 2H), 3.80 (s, 2H), 2.67 (m, 2H), 1.45 (m, 2H), 0.91 (s, 9H). Purity: 94.2%, Retention time: 1.802 minutes.

The following compound is also prepared by the method outlined for the synthesis of the compound of Example 481.

| Example | Name | Mass | NMR/LC/MS |
|---|---|---|---|
| 482 | 6-{2-Chloro-4-[(2-thiophen-2-yl-ethylamino)-methyl]-phenoxy}-nicotinamide | 387 | MS (APCI): (M$^+$ + 1) 388, $^1$H-NMR (CDCl$_3$, 400 MHz): 8.51 (bs, 1H), 8.19 (dd, 1H, J = 8.3, 1.95 Hz), 7.43 (bs, 1 Hz), 6.81-7.24 7.29 (m, 6H), 3.79 (s, 2H), 3.03 (m, 2H), 2.91 (m, 2H). Purity: 87.1% Retention time: 1.696 minutes. |

EXAMPLE 483

3-Bromo-4-{5-[(2-thiophen-2-yl-ethylamino)-methyl]-pyridin-2-yloxy}-benzamide dihydrochloride

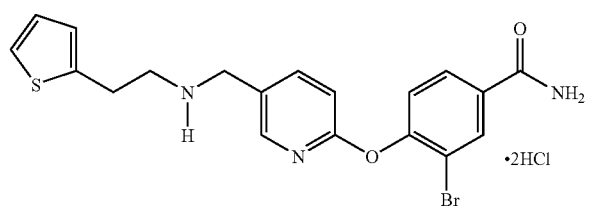

Step 1

6-Chloro-pyridine-3-carbaldehyde

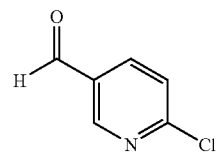

Combine 6-chloro-nicotino-nitrile ((1.00 g, 7.21 mmol) and toluene (24 mL). Cool the resulting solution at 0° C. and add DIBAL-H (1.0 M in toluene, 7.58 mL, 7.58 mmol) dropwise. Stir the resulting red solution at 0° C. for 1 h. Then, add methanol (2 mL) followed by H$_2$SO$_4$ (aq. 2.0 M, 6 mL). Stir for 1 h at rt. Add CHCl$_3$:isopropanol (3/1, 15 mL) and wash with Rochelle's salt solution (20 mL), followed by NaHCO$_3$ (20 mL) and brine. Dry the combined organic layers over magnesium sulfate, filter and concentrate. Purify by flash chromatography (EtOAc/hexanes 10%) to give the title compound (530 mg, 62%).

Step 2

3-Bromo-4-(5-formyl-pyridin-2-yloxy)-benzonitrile

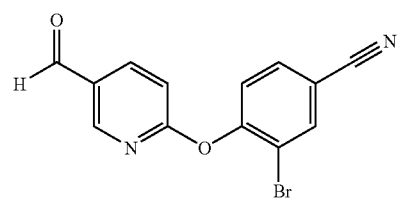

Combine 6-chloro-pyridine-3-carbaldehyde (1.00 g, 7.09 mmol), 3-bromo-4-hydroxy-benzonitrile (1.48 g, 7.80 mmol) in dimethylacetamide (40 mL). Add potassium carbonate (1.47 g, 10.64 mmol) and stir and heat the reaction at 130° C. for 2 h. Let cool down the reaction to room temperature and poured into water. Filter the precipitate formed, washing with water, to give the title compound (1.55 g, 72%)

Step 3

3-Bromo-4-(5-formyl-pyridin-2-yloxy)-benzamide

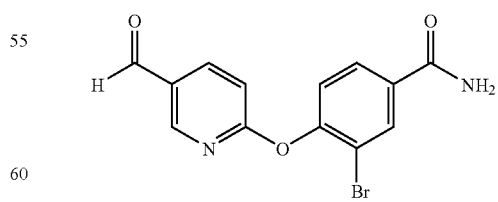

Combine 3-bromo-4-(5-formyl-pyridin-2-yloxy)-benzonitrile (1.60 g, 5.28 mmol) and potassium carbonate (365 mg, 2.64 mmol) in DMSO (40 mL). Cool the reaction mixture at 0° C. Add hydrogen peroxide (1.59 mL, 5.28 mmol) dropwise and let the reaction stir at room temperature for 2 h. Pour into water and triturate to a white solid with stirring. Filter the white solid and dry to give (852 mg, 82%) of the title compound.

Step 4

Using a method similar to example 462, using 2-thiophen-2-ylethylamine and 3-bromo-4-(5-formyl-pyridin-2-yloxy)benzamide (step 3) gives the title compound (220 mg, 92%). Mass spectrum (ion spray): m/z=433.9 (M+1); $^1$H NMR (CDCl$_3$): 8.11 (d, J=2.2 Hz, 1H), 8.05 (d, J=2.2 Hz, 1H), 7.76 (td, J=8.4 Hz, 2H), 7.22 (d, J=8.4 Hz, 1H), 7.14 (d, J=5.1 Hz, 1H), 7.00 (d, J=8.4 Hz, 1H), 6.93 (dd, J=3.2 Hz, 5.1 Hz, 1H), 6.83 (d, J=3.2 Hz, 1H), 6.14 (bs, 1H), 5.87 (bs, 1H), 3.77 (s, 2H), 3.04 (t, J=6.7 Hz, 2H), 2.93 (t, J=6.7 Hz, 2H).

EXAMPLE 484

3-Bromo-4-(5-pentylaminomethyl-pyridin-2-yloxy)-benzamide

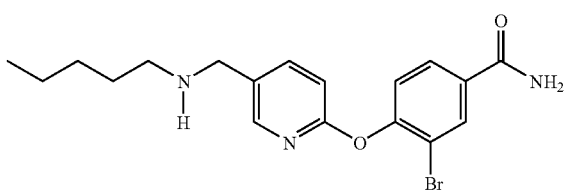

Using a method similar to example 462, using pentylamine and the benzamide in Example 483, step 3, gives the title compound (158 mg, 65%). Mass spectrum (ion spray): m/z=394.0 (M+1); $^1$H NMR (CDCl$_3$): 8.09 (d, J=2.2 Hz, 1H), 8.04 (d, J=2.1 Hz, 1H), 7.75 (d, J=8.6 Hz, 2H), 7.17 (d, J=8.6 Hz, 1H), 6.98 (d, J=8.3 Hz, 1H), 6.59 (bs, 1H), 6.34 (bs, 1H), 3.73 (s, 2H), 2.59 (t, J=6.8 Hz, 2H), 1.52-1.44 (m, 3H), 1.31-1.25 (m, 4H), 0.86 (t, J=6.8 Hz, 3H).

EXAMPLE 485

3-Bromo-4-{5-[(3,3-dimethyl-butylamino)-methyl]-pyridin-2-yloxy}-benzamide

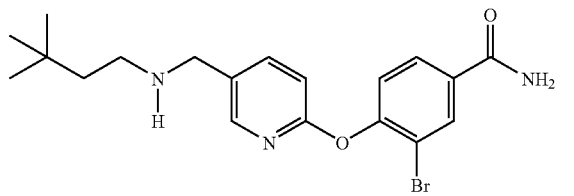

Using a method similar to example 462, using cyclohexylmethylamine and the benzamide in Example 483 step 3, gives the title compound (168 mg, 66%). Mass spectrum (ion spray): m/z=408.0 (M+1); $^1$H NMR (DMSO-d$_6$): 8.19 (s, 1H), 8.07 (bs, 1H), 8.00 (s, 1H), 7.90 (d, J=8.6 Hz, 1H), 7.83 (d, J=8.5 Hz, 1H), 7.48 (bs, 1H), 7.28 (d, J=8.5 Hz, 1H), 7.08 (d, J=8.5 Hz, 1H), 3.63 (s, 2H), 2.46 (t, J=7.8 Hz, 2H), 2.04 (bs, 1H), 1.33 (t, J=7.8 Hz, 2H), 0.84 (s, 9H).

EXAMPLE 486

3-Bromo-4-{5-[(cyclohexylmethyl-amino)-methyl]-pyridin-2-yloxy}-benzamide

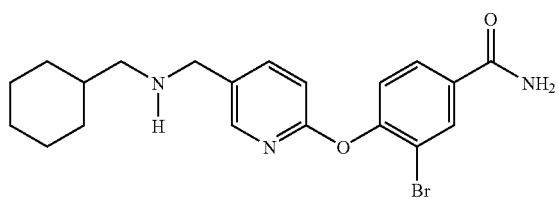

Using a method similar to example 462, using cyclohexylmethylamine and the benzamide in Example 483 step 3, affords the title compound (209 mg, 80%). Mass spectrum (ion spray): m/z=418.2 (M+1); $^1$H NMR (DMSO-d$_6$): 8.18 (s, 1H), 8.07 (bs, 1H), 7.99 (s, 1H), 7.89 (d, J=8.4 Hz, 1H), 7.83 (d, J=8.4 Hz, 1H), 7.48 (bs, 1H), 7.28 (d, J=8.4 Hz, 1H), 7.08 (d, J=8.4 Hz, 1H), 3.62 (s, 2H), 2.28 (d, J=6.5 Hz, 2H), 1.76-1.57 (m, 5H), 1.40-1.30 (m, 1H), 1.22-1.06 (m, 3H), 0.88-0.77 (m, 2H).

EXAMPLE 487

3-Methoxy-4-(5-pentylaminomethyl-pyridin-2-yloxy)-benzamide

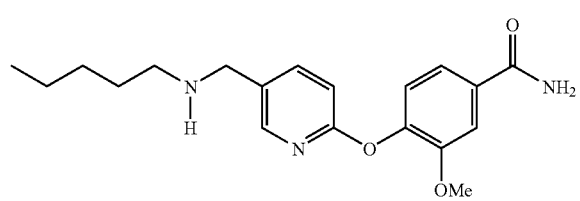

Step 1

4-(5-Formyl-pyridin-2-yl oxy)-3-methoxy-benzonitrile

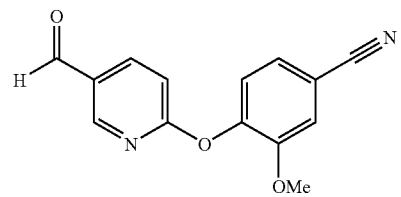

Using a method similar to example 483 (step 2), using 4-hydroxy-3-methoxy-benzonitrile (1.18 g, 7.91 mmol) gives the title compound (1.71 g, 94%).

Step 2

4-(5-Formyl-pyridin-2-yloxy)-3-methoxy-benzamide

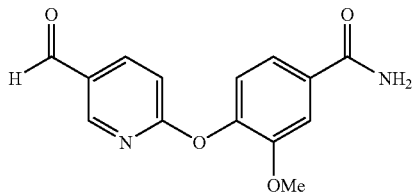

Using a method similar to example 483 (step 3), using 4-(5-formyl-pyridin-2-yloxy)-3-methoxy-benzonitrile (1.71 g, 6.74 mmol) gives the title compound (1.107 g, 60%).

Step 3

Using a method similar to example 462, using pentylamine and the benzamide in step 2, gives the title compound (174 mg, 69%). Mass spectrum (ion spray): m/z=344.3 (M+1); $^1$H NMR (CDCl$_3$): 8.02 (d, J=1.9 Hz, 1H), 7.69 (dd, J=2.1 Hz, 8.6 Hz, 1H), 7.53 (d, J=1.7 Hz, 1H), 7.32 (dd, J=1.7 Hz, 8.1 Hz, 1H), 7.10 (d, J=8.1 Hz, 1H), 6.92 (d, J=8.6 Hz, 1H), 6.51 (bs, 1H), 6.25 (bs, 1H), 3.76 (s, 3H), 3.71 (s, 2H), 2.58 (t, J=7.6 Hz, 2H), 1.51-1.43 (m, 3H), 1.31-1.24 (m, 4H), 0.86 (t, J=6.6 Hz, 3H).

EXAMPLE 488

4-{5-[(3,3-Dimethyl-butylamino)-methyl]-pyridin-2-yloxy}-3-methoxy-benzamide

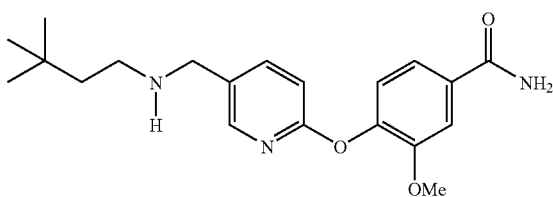

Using a method similar to example 462, using 3,3-dimethylbutylamine and the benzamide in Example 487, step 2, gives the title compound (170 mg, 65%). Mass spectrum (ion spray): m/z=358.3 (M+1); $^1$H NMR (DMSO-d$_6$): 7.98 (bs, 1H), 7.95 (s, 1H), 7.75 (d, J=8.2 Hz, 1H), 7.59 (s, 1H), 7.49 (d, J=8.5 Hz, 1H), 7.36 (bs, 1H), 7.14 (d, J=8.5 Hz, 1H), 6.94 (d, J=8.5 Hz, 1H), 3.71 (s, 3H), 3.61 (s, 2H), 2.45 (t, J=8.4 Hz, 2H), 1.32 (t, J=8.4 Hz, 2H), 0.84 (s, 9H).

EXAMPLE 489

3-Methoxy-4-{5-[(2-thiophen-2-yl-ethylamino)-methyl]-pyridin-2-yloxy}-benzamide dihydrochloride Using a method similar to example 462, using 2-thiophen-2-ylethylamine and the benzamide in Example 489, step 2, gives the title compound (188 mg, 67%). Mass spectrum (ion spray): m/z=384.2 (M+1); $^1$H NMR (CDCl$_3$): 8.01 (s, 1H), 7.67 (d, J=8.3 Hz, 1H), 7.54 (s, 1H), 7.34 (d, J=7.9 Hz, 1H), 7.13-7.08 (m, 2H), 6.94-6.86 (m, 2H), 6.81 (s, 1H), 6.67 (bs, 1H), 6.42 (bs, 1H), 3.79-3.71 (m, 5H), 3.05-2.98 (m, 2H), 2.93-2.86 (m, 2H).

EXAMPLE 490

4-{5-[(Cyclohexylmethyl-amino)-methyl]-pyridin-2-yloxy}-3-methoxy-benzamide dihydrochloride Using a method similar to example 462, using cyclohexylmethylamine and the benzamide in Example 487, step 2, gives the title compound (179 mg, 66%). Mass spectrum (ion spray): m/z=370.3 (M+1); $^1$H NMR (CDCl$_3$): 8.01 (d, J=2.0 Hz, 1H), 7.69 (dd, J=2.2 Hz, 8.2 Hz, 1H), 7.53 (d, J=1.8 Hz, 1H), 7.32 (dd, J=1.8 Hz, 8.2 Hz, 1H), 7.09 (d, J=8.0 Hz, 1H), 6.91 (d, J=8.4 Hz, 1H), 6.52 (bs, 1H), 6.27 (bs, 1H), 3.76 (s, 3H), 3.69 (s, 2H), 2.41 (d, J=6.6 Hz, 2H), 1.74-1.60 (m, 5H), 1.46-1.36 (m, 2H), 1.26-1.09 (m, 3H), 0.92-0.81 (m, 2H).

EXAMPLE 491

3-Chloro-4-(5-{[2-(3-fluoro-phenyl)-ethylamino]-methyl}-pyridin-2-yloxy)-benzamide dihydrochloride

Step 1

3-Chloro-4-(5-formyl-pyridin-2-yloxy)-benzonitrile

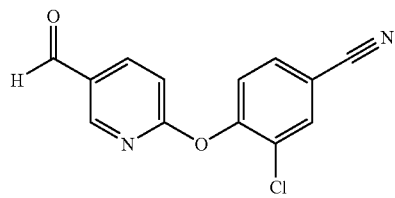

Using a method similar to example 483 (step 2), using 3-chloro-4-hydroxy-benzonitrile (527 mg, 3.43 mmol) gives the title compound (573 mg, 76%).

Step 2

3-Chloro-4-(5-formyl-pyridin-2-yloxy)-benzamide

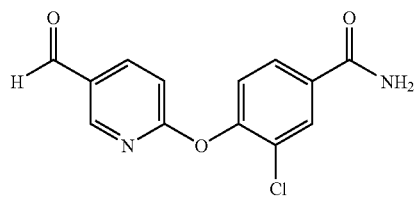

Using a method similar to example 483 (step 3) using 3-chloro-4-(5-formyl-pyridin-2-yloxy)-benzonitrile (573 mg, 2.36 mmol) gives the title compound (404 mg, 62%).

Step 3

Using a method similar to example 462, using fluorophenethylamine and the benzamide in step 2, gives the title compound (84 mg, 97%). Mass spectrum (ion spray): m/z=400.2 (M+1); $^1$H NMR (CDCl$_3$) 8.01 (s, 1H), 7.93 (d, J=2.0 Hz, 1H), 7.73-7.68 (m, 2H), 7.24-7.19 (m, 2H), 6.99-6.86 (m, 4H), 6.51 (bs, 1H), 6.33 (bs, 1H), 3.74 (s, 2H), 2.87 (t, J=6.6 Hz, 2H), 2.79 (t, J=6.6 Hz, 2H).

EXAMPLE 492

4-{2-Methyl-4-[(3-methyl-butylamino)-methyl]-phenoxy}-benzamide

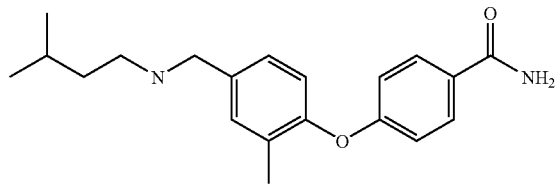

Step 1

4-(4-Formyl-2-methyl-phenoxy)-benzonitrile

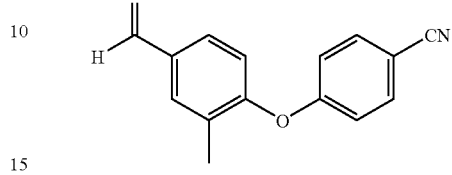

Dissolve 3-hydroxy-3-methyl-benzaldehyde (1.02 g, 7.49 mmol) in DMF (10 mL), add K$_2$CO$_3$ (1.45 g, 10.49 mmol) and 4-fluorobenzonitrile (906 mg, 7.49 mmol), heat the mixture at 130° C. overnight. Add water and extract the aqueous layer with EtOAc. Combine organic layers and dry over Na$_2$SO$_4$. Eliminate the solvent and purify by flash chromatography on silica gel (eluent: EtOAc/hexane 15/85) to give the title compound (920 mg, 52%). TLC: R$_f$ in EtOAc/hexane 20/80: 0.32. $^1$H-NMR (CDCl$_3$, 200 MHz): 9.96 (s, 1H), 7.84-7.61 (m, 4H), 7.05-6.98 (m, 3H), 2.31 (s, 3H).

Step 2

4-(4-Formyl-2-methyl-phenoxy)-benzamide

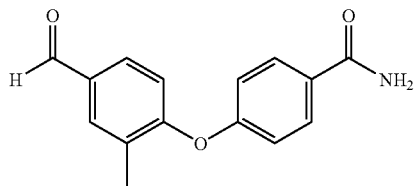

The compound of step 1 is subject to hydrolysis using hydrogen peroxide and potassium carbonate. The details of the hydrolysis procedure to form the amide form nitrile have been described exhaustively elsewhere in this document.

$^1$H-NMR (CDCl$_3$, 200 MHz): 9.94 (s, 1H), 7.87-7.65 (m, 4H), 7.04-6.95 (m, 3H), 5.92 (bs, 2H), 2.34 (s, 3H).

Step 3

Combine 3-methyl-butylamine (93 µl, 0.8 mmol), the aldehyde from Example 492, step 2 above and 3 Å molecular sieves (1.8 g) in methanol (5 mL), stir the mixture at room temperature overnight. Add NaBH$_4$ (149 mg, 4.0 mmol) and stir at room temperature for 3 hours. Filtrate the mixture over celite and eliminate the solvent. Purify crude mixture by SCX column to obtain the title compound (190 mg, 73%). Electrospray MS M+1 ion 327. $^1$H-NMR (CDCl$_3$, 200 MHz): 7.87-7.80 (m, 2H), 7.32-7.20 (m, 2H), 6.96-6.85 (m, 3H), 3.76 (s, 2H), 2.68-2.60 (m, 2H), 2.16 (s, 3H), 1.69-1.39 (m, 3H), 0.91 (d, 6H, J=7.0 Hz).

EXAMPLE 493

4-[2-Methyl-4-(phenethylamino-methyl)-phenoxy]-benzamide

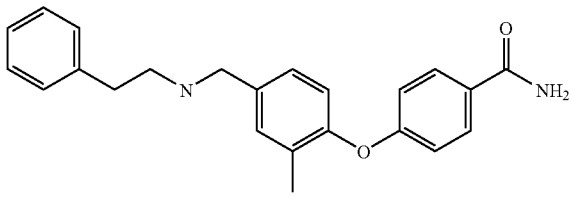

Compound 2 was prepared from aldehyde described in Example 492, step 2 and phenethylamine using the reductive amination conditions described above. Electrospray MS M+1 ion=361. $^1$H-NMR (CDCl$_3$, 200 MHz): 7.87-7.80 (m, 2H), 7.31-7.15 (m, 7H), 6.93-6.83 (m, 3H), 3.76 (s, 2H), 2.84 (s, 4H), 2.14 (s, 3H).

EXAMPLE 494

4-{2-Methyl-4-[(2-thiophen-2-yl-ethylamino)-methyl]-phenoxy}benzamide

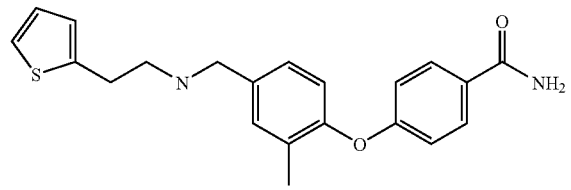

Compound 3 was prepared from aldehyde described in Example 492, step 2 and 2-thiophen-2-yl-ethylamine using the reductive animation conditions described above Electrospray MS M+1 ion=367. $^1$H-NMR (CDCl$_3$, 200 MHz): 7.85-7.81 (m, 2H), 7.26-7.17 (m, 3H), 6.95-6.85 (m, 5H), 3.76 (s, 2H), 3.10-3.02 (m, 2H), 2.91-2.84 (m, 2H), 2.15 (s, 3H).

EXAMPLE 495

4-{3-Chloro-4-[(3-methyl-butylamino)-methyl]-phenoxy}-benzamide

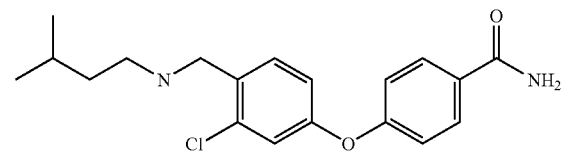

Step 1

4-(3-Chloro-4-formyl-phenoxy)-benzonitrile

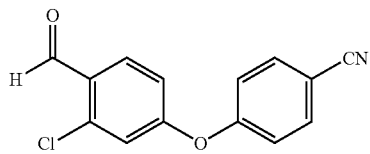

Dissolve 2-chloro-4-hydroxy-benzaldehyde (1.09 g, 7.01 mmol) in DMF (10 mL), add K$_2$CO$_3$ (1.06 g, 7.7 mmol) and 4-fluorobenzonitrile (932 mg, 7.7 mmol), heat the mixture at 130° C. overnight. Add water and extract the aqueous layer with EtOAc. Combine organic layers and dry over Na$_2$SO$_4$. Eliminate the solvent and purify by flash chromatography on silica gel (eluent: EtOAc/hexane 15/85) to give the title compound (240 mg, 14%), $^1$H-NMR (CDCl$_3$, 300 MHz): 10.40 (s, 1H), 7.98 (d, 1H, J=8.6 Hz), 7.74-7.71 (m, 2H), 7.17-7.00 (m, 4H).

Step 2

4-{3-Chloro-4-[(3-methyl-butylamino)-methyl]-phenoxy}-benzonitrile

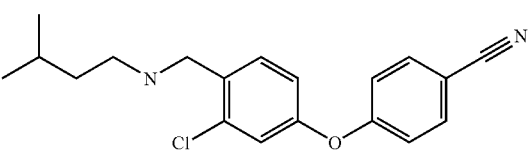

The reductive amination was done in the conditions described in Example 492, step 3 using the aldehyde described above. The crude mixture was purified by flash chromatography (EtOAc/hexane 20/80) to obtain the title compound (105 mg, 68%). Electrospray MS M+1 ion=329. $^1$H-NMR (CDCl$_3$, 200 MHz): 7.64-7.59 (m, 2H), 7.45 (d, 1H, J=8.3 Hz), 7.09-6.92 (m, 4H), 3.8 (s, 2H), 2.67 (t, 2H, J=7.5 Hz), 1.75-1.56 (m, 1H), 1.43 (q, 1H, J=7.5 Hz), 0.90 (d, 6H, J=6.8 Hz).

Step 3

The compound of step 2 above is subject to hydrolysis using hydrogen peroxide and potassium carbonate. The details of the hydrolysis procedure to form the amide form nitrile have been described exhaustively elsewhere in this document.

$^1$H-NMR (CDCl$_3$, 200 MHz): 7.92-7.89 (m, 2H), 7.47 (d, 1H, J=8.3 Hz), 7.11-6.98 (m, 4H), 3.86 (s, 2H), 2.64 (t, 2H, J=7.7 Hz), 1.66-1.55 (m, 1H), 1.44 (q, 2H, J=7.7 Hz), 0.91 (d, 6H, J=6.6 Hz). $^{13}$C-NMR (CDCl$_3$, 300 MHz): 167.6, 157.4, 153.5, 131.9, 129.9, 129.0, 127.0, 126.3, 117.5, 115.3, 115.1, 47.1, 35.5, 23.5, 19.1.

EXAMPLE 496

4-[3-Chloro-4-(phenethylamino-methyl)-phenoxy]-benzamide

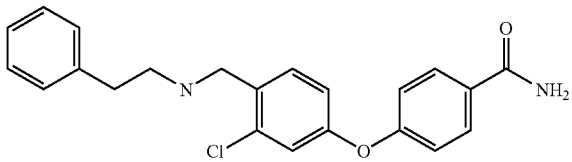

Step 1

4-[3-Chloro-4-(phenethylamino-methyl)-phenoxy]-benzonitrile

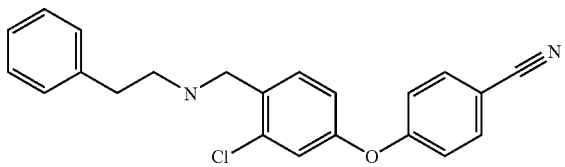

The reductive amination was done in the conditions described in Example 492, step 3 using the aldehyde described for compound 4 (step 1). The crude mixture was purified by flash chromatography (EtOAc/hexane 20/80) to obtain the title compound (101 mg, 59%). Electrospray MS M+1 ion=363. $^1$H-NMR (CDCl$_3$, 200 MHz): 7.64-7.59 (m, 2H), 7.42-7.20 (m, 6H), 7.07-6.89 (m, 4H), 3.89 (s, 2H), 2.99-2.81 (m, 4H).

Step 2

The compound of step 1 above is subject to hydrolysis using hydrogen peroxide and potassium carbonate. The details of the hydrolysis procedure to form the amide form nitrile have been described exhaustively elsewhere in this document. Electrospray MS M+1 ion=381. $^1$H-NMR (CDCl$_3$, 200 MHz): 7.92-7.85 (m, 2H), 7.39 (d, 1H, J=8.3 Hz), 7.30-7.12 (m, 5H), 7.06-6.91 (m, 4H), 3.84 (s, 2H), 2.83 (s, 4H).

EXAMPLE 497

4-{2-Ethoxy-4-[(3-methyl-butylamino)-methyl]-phenoxy}-benzamide (47J-3179-381, LSN 2120309)

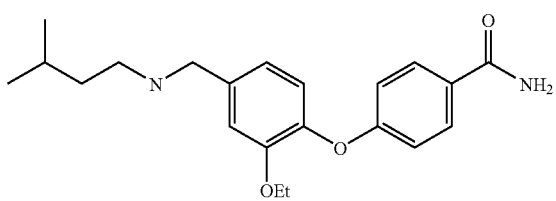

Dissolve 3-ethoxy-4-hydroxy-benzaldehyde (2.57 g, 15.45 mmol) in DMF (20 mL), add K$_2$CO$_3$ (2.33 g, 16.86 mmol) and 4-fluorobenzonitrile (1.70 g, 14.05 mmol), heat the mixture at 130° C. overnight. Add water and extract the aqueous layer with EtOAc. Combine organic layers and dry over Na$_2$SO$_4$. Eliminate the solvent and purify by flash chromatography on silica gel (eluent: EtOAc/hexane 15/85) to get a mixture of two compounds (1.45 g). This mixture (240 mg) is submitted to the reductive amination conditions described for compound 1 (step 3) using 3-methyl-butylamine to obtain a mixture of two compounds which is subject to hydrolysis using hydrogen peroxide and potassium carbonate in the conditions described elsewhere in this document. This mixture is purified by flash chromatography (EtOAc and CH$_2$Cl$_2$/MeOH 10%) and then the title compound is isolated after HPLC (Column: XTerraMSC18 (5 um, 19×100 mm). Isocratic mode: 55/45 Ammonium bicarbonate-pH 9-/Acetonitrile. Flow: 10 mL/min).

$^1$H-NMR (CDCl$_3$, 200 MHz): 7.82-7.78 (m, 2H), 7.14-6.83 (m, 5H), 4.01 (q, 2H, J=6.8 Hz), 3.76 (s, 2H), 2.66-2.58 (m, 2H), 1.70-1.39 (m, 3H), 1.17 (t, 3H, J=7.0 Hz), 0.91 (d, 6H, J=6.7 Hz). $^{13}$C-NMR (CDCl$_3$, 300 MHz): 172.2, 163.6, 152.8, 144.4, 139.4, 130.8, 128.6, 123.8, 122.8, 116.9, 116.3, 65.9, 54.6, 39.8, 27.9, 23.4, 15.3.

EXAMPLE 498

6-{4-[2-(Benzyl-methyl-amino)-ethyl]-phenoxy}-nicotinamide

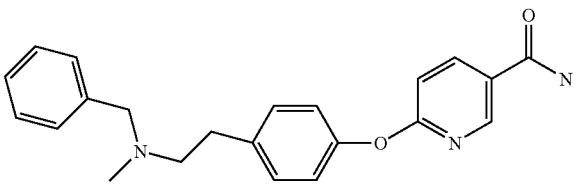

Step 1

[2-(4-Hydroxy-phenyl)-ethyl]-carbamic acid ethyl ester

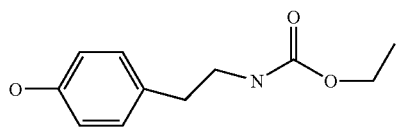

Add dropwise via an addition funnel a solution of ethyl chloroformate (0.74 mL, 7.7 mmol) in tetrahydrofuran (7 mL) to a stirred solution of tyramine (1.0 g, 7.3 mmol), sodium hydroxide (0.7 g, 17.1 mmol), and water (7 mL). Stir at room temperature for 18 hours then pour the reaction into 1 N aqueous hydrochloric acid so the pH=1-2. Extract with ethyl acetate (3×25 mL). Dry the combined ethyl acetate extracts over sodium chloride/magnesium sulfate, filter, and concentrate on a rotary evaporator to yield 1.3 g, 6.2 mmol of [2-(4-hydroxy-phenyl)-ethyl]-carbamic acid ethyl ester: $^1$H NMR (CDCl3, 300.00 MHz): 7.01 (d, 2H); 6.78 (d, 2H); 6.26

(s, 1H); 4.78 (s, 1H); 4.14-4.09 (m, 2H); 3.40-3.38 (m, 2H); 2.74-2.69 (m, 2H); 1.24-1.19 (m, 3H).

Step 2

4-(2-Methylamino-ethyl)-phenol

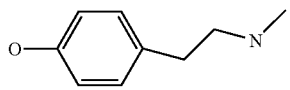

Add dropwise via an addition funnel a solution of [2-(4-Hydroxy-phenyl)-ethyl]-carbamic acid methyl ester (13.0 g, 62.2 mmol) in tetrahydrofuran (100 mL) to a stirred solution at 0° C. of 1.0M lithium aluminum hydride in tetrahydrofuran (156 mL) and tetrahydrofuran (250 mL). Reflux for 18 hours, cool to 0° C., quench with saturated aqueous ammonium chloride then stir at room temperature for 3 hours. Filter off the aluminum salts, concentrate on a rotary evaporator, and dry under vacuum to yield 6.6 g of 4-(2-methylamino-ethyl)-phenol: $^1$H NMR (DMSO-d6, 300.00 MHz): 6.97 (d, 2H); 6.65 (d, 2H); 2.65-2.55 (m, 4H); 2.28 (s, 3H).

Step 3

6-[4-(2-Methylamino-ethyl)-phenoxy]-nicotinamide

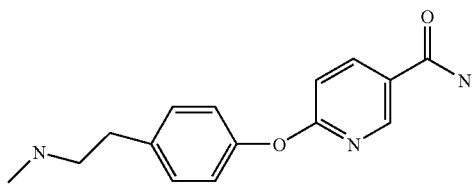

Combine 4-(2-methylamino-ethyl)-phenol (1.0 g, 6.6 mmol), 6-chloronicotinamide (1.0 g, 6.6 mmol), and cesium carbonate (4.3 g, 13.2 mmol) in N,N-dimethylformamide (30 mL), stir and heat at 85° C. for 18 hours. Cool to room temperature and evaporate on a rotary evaporator to yield the crude product (1.3 g). The crude product is purified by flash column chromatography on silica gel eluting with 1% conc. ammonium hydroxide/10% ethanol in chloroform then ethanol to yield 6-[4-(2-Methylamino-ethyl)-phenoxy]-nicotinamide (0.4 g, 1.5 mmol): $^1$H NMR (DMSO-d6, 300.00 MHz): 8.58 (d, 1H); 8.22 (dd, 1H); 7.26-7.23 (m, 2H); 7.05-7.02 (m, 3H); 3.32 (br, 2H); 2.69 (m, 5H); 2.29 (m, 4H) m/z=271.87 (M+1); HPLC=99% (5/95 to 95/5 ACN/(0.1% TFA in water) over 10 minutes, Zorbax SB-Phenyl 4.6 mm×15 cm×5 micron, λ=254 nM.

Step 4

[2-(4-Hydroxy-phenyl)-ethyl]-methyl-carbamic acid tert-butyl ester

Combine di-tert-butyl dicarbonate (9.7 g, 44.5 mmol), 4-(2-methylamino-ethyl)-phenol (5.6 g, 37.1 mmol), and tetrahydrofuran (150 mL) and stir at room temperature for 18 hours. Concentrate on a rotary evaporator to yield the crude product. The crude product is purified by flash column chromatography on silica gel eluting with 25% ethyl acetate in hexanes to yield [2-(4-hydroxy-phenyl)-ethyl]-methyl-carbamic acid tert-butyl ester (7.7 g, 30.7 mmol): $^1$H NMR (CDCl$_3$, 300.00 MHz): 7.00 (d, 2H); 6.76 (d, 2H); 6.39 (s, 1H); 3.40 (t, 2H); 2.81 (s, 3H); 2.73 (t, 2H); 1.42 (s, 9H).

Step 5

{2-[4-(5-Carbamoyl-pyridin-2-yloxy)-phenyl]-ethyl}-methyl-carbamic acid tert-butyl ester Combine [2-(4-hydroxy-phenyl)-ethyl]-methyl-carbamic acid tert-butyl ester (5.0 g, 19.9 mmol), 6-chloronicotinamide (3.1 g, 19.9 mmol), and cesium carbonate (12.9 g, 39.8 mmol), in N,N-dimethylformamide (90 mL), stir and heat at 85° C. for 18 hours. Cool to room temperature and evaporate on a rotary evaporator to yield the crude product (9.5 g). The crude product is purified by flash column chromatography on silica gel eluting with (0.5% conc. ammonium hydroxide/5% ethanol) to (1% conc. ammonium hydroxide/10% ethanol) in chloroform to yield {2-[4-(5-carbamoyl-pyridin-2-yloxy)-phenyl]-ethyl}-methyl-carbamic acid tert-butyl ester (6.5 g, 17.5 mmol): $^1$H NMR (CDCl$_3$, 300.00 MHz): 8.60 (s, 1H); 8.18-8.14 (m, 1H); 7.24-7.24 (m, 2H); 7.07 (d, 2H); 6.94 (d, 1H); 5.98 (br, 2H); 3.47-3.42 (m, 2H); 2.85-2.85 (m, 5H); 1.42 (s, 9H).

Step 6

6-[4-(2-Methylamino-ethyl)-phenoxy]-nicotinamide

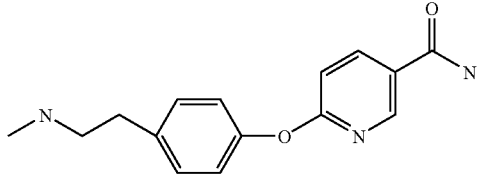

Add dropwise via an addition funnel, a solution of trifluoroacetic acid (30 mL) in dichloromethane (100 mL) to a stirred solution at 0° C. of {2-[4-(5-carbamoyl-pyridin-2-yloxy)-phenyl]-ethyl}-methyl-carbamic acid tert-butyl ester (11.4 g, 30.7 mmol) in 1,2-dichloromethane (400 mL). Warm the mixture to room temperature and stir for 18 hours. Evaporate on a rotary evaporator to yield the crude trifluoroacetic acid salt. Dissolve the salt in methanol (150 mL) and 1,2-dichloromethane (150 mL) then combine with MP-carbonate resin (50 g@2.55 eq/g) (available from Argonaut Technologies). Stir for 18 hours at room temperature, filter, wash the resin with 1,2-dichloromethane (3×75 mL), and evaporate the filtrate on a rotary evaporator to yield 6-[4-(2-Methylamino-ethyl)-phenoxy]-nicotinamide (8.1 g, 29.9 mmol).

Step 7

Combine 6-[4-(2-Methylamino-ethyl)-phenoxy]-nicotinamide (135 mg, 0.5 mmol), benzaldehyde (53 μL, 0.52 mmol), sodium triacetoxyborohydride (0.21 g, 1.0 mmol), acetic acid (30 μL, 0.52 mmol), tetrahydrofuran (1 mL), and 1,2-dichloroethane (5 mL) then stir at room temperature for 18 hours. Dilute the reaction with saturated aqueous sodium bicarbonate solution and extract with ethyl acetate (3×50 mL). Dry the combined ethyl acetate extracts with sodium chloride/magnesium sulfate, filter, and concentrate on a rotary evaporator to yield 200 mg of the crude product. The crude product is purified by flash column chromatography on silica gel eluting with (0.5% conc. ammonium hydroxide/5% ethanol) to (1% conc. ammonium hydroxide/10% ethanol) in chloroform to yield 6-{4-[2-(benzyl-methyl-amino)-ethyl]-phenoxy}-nicotinamide (106 mg, 0.29 mmol): m/z=362.07 (M+1); $^1$H NMR (CDCl3, 300.00 MHz): 8.58 (s, 1H); 8.16 (dd, 3.0 Hz, 1H); 7.33-7.22 (m, 7H); 7.05 (d, 2H); 6.95 (d, 1H); 5.86 (br s, 2H); 3.63 (s, 2H); 2.89-2.72 (m, 4H); 2.34 (s, 3H), HPLC=100% (5/95 to 95/5 ACN/(0.1% TFA in water) over 10 minutes, Zorbax® SB-Phenyl 4.6 mm×15 cm×5 micron, λ=254 nM.

By the method of Example 498 the following compounds were prepared, isolated as the free base except where noted:

| | | | Data | |
|---|---|---|---|---|
| | | Mass spectrum (ion spray): m/z (M + 1) | HPLC(5/95 to 95/5 ACN/(0.1% TFA in water) over 10 minutes, Zorbax SB-Phenyl 4.6 mm × 15 cm × 5 micron, λ = 254 nM | |
| Example | Name | | Purity | Retention Time (minutes) |
| 499 | 6-{4-[2-(Methyl-thiophen-2-ylmethyl-amino)-ethyl]-phenoxy}-nicotinamide | 367.95 | 99 | 5.86 |
| 500 | 6-(4-{2-[Methyl-(3-methyl-butyl)-amino]-ethyl}-phenoxy)-nicotinamide | 342.07 | 99 | 5.91 |
| 501 | 6-{4-[2-(Isobutyl-methyl-amino)-ethyl]-phenoxy}-nicotinamide | 327.4 | 97 | 5.73 |
| 502 | 6-{4-[2-(Bicyclo[2.2.1]hept-5-en-2-ylmethyl-methyl-amino)-ethyl]-phenoxy}-nicotinamide | 378.5 | 99 | 6.03 |
| 503 | 6-{4-[2-(Cyclohexylmethyl-methyl-amino)-ethyl]-phenoxy}-nicotinamide | 368.5 | 100 | 6.04 |
| 504 | 6-(4-{2-[Methyl-(2-phenoxy-benzyl)-amino]-ethyl}-phenoxy)-nicotinamide | 454.5 | 99 | 6.32 |
| 505 | 6-(4-{2-[Methyl-(2-methyl-benzyl)-amino]-ethyl}-phenoxy)-nicotinamide | 376.5 | 99 | 5.98 |
| 506 | 6-(4-{2-[(3-Chloro-benzyl)-methyl-amino]-ethyl}-phenoxy)-nicotinamide | 395.9 | 100 | 6.02 |
| 507 | 6-(4-{2-[(2-Chloro-benzyl)-methyl-amino]-ethyl}-phenoxy)-nicotinamide | 395.9 | 100 | 5.96 |
| 508 | 6-(4-{2-[(4-Fluoro-2-trifluoromethyl-benzyl)-methyl-amino]-ethyl}-phenoxy)-nicotinamide | 448.4 | 100 | 6.08 |

|  |  | Data | | |
|---|---|---|---|---|
|  |  | Mass spectrum | HPLC(5/95 to 95/5 ACN/(0.1% TFA in water) over 10 minutes, Zorbax SB-Phenyl 4.6 mm × 15 cm × 5 micron, λ = 254 nM | |
| Example | Name | (ion spray): m/z (M + 1) | Purity | Retention Time (minutes) |
| 509 | 6-(4-{2-[(3-Bromo-4-fluoro-benzyl)-methyl-amino]-ethyl}-phenoxy)-nicotinamide | 458.3 | 100 | 6.04 |
| 510 | 6-(4-{2-[(2-Chloro-6-fluoro-benzyl)-methyl-amino]-ethyl}-phenoxy)-nicotinamide | 413.9 | 100 | 5.93 |
| 511 | 6-{4-[2-(Cyclohexyl-methyl-amino)-ethyl]-phenoxy}-nicotinamide | 354.5 | 100 | 5.89 |
| 512 | 6-(4-{2-[Methyl-(2-trifluoromethoxy-benzyl)-amino]-ethyl}-phenoxy)-nicotinamide | 446.4 | 99 | 6.13 |
| 513 | 6-(4-{2-[(3-Fluoro-benzyl)-methyl-amino]-ethyl}-phenoxy)-nicotinamide | 380.4 | 100 | 5.90 |
| 514 | 6-(4-{2-[Methyl-(3-phenyl-1H-pyrazol-4-ylmethyl)-amino]-ethyl}-phenoxy)-nicotinamide | 428.5 | 100 | 5.79 |
| 515 | 6-(4-{2-[(1,5a,6,9,9a,9b-Hexahydro-4H-dibenzofuran-4a-ylmethyl)-methyl-amino]-ethyl}-phenoxy)-nicotinamide | 460.3 | 76 | 6.28 |
| 516 | 6-(4-{2-[Methyl-(2,4,6-trimethyl-cyclohex-3-enylmethyl)-amino]-ethyl}-phenoxy)-nicotinamide | 408.6 | 76 | 6.26 |
| 517 | 6-(4-{2-[(5-Chloro-1-methyl-3-trifluoromethyl-1H-pyrazol-4-ylmethyl)-methyl-amino]-ethyl}-phenoxy)-nicotinamide | 467.9 | 100 | 5.94 |
| 518 | 6-{4-[2-(Cyclohex-3-enylmethyl-methyl-amino)-ethyl]-phenoxy}-nicotinamide | 366.5 | 86 | 5.94 |
| 519 | 6-{4-[2-(Dec-4-enyl-methyl-amino)-ethyl]-phenoxy}-nicotinamide | 410.6 | 93 | 6.45 |
| 520 | 6-(4-{2-[Methyl-(2-phenyl-but-2-enyl)-amino]-ethyl}-phenoxy)-nicotinamide | 402.5 | 100 | 6.10 |
| 521 | 6-(4-{2-[(3-Furan-2-yl-2-phenyl-allyl)-methyl-amino]-ethyl}-phenoxy)-nicotinamide | 454.5 | 84 | 6.23 |
| 522 | 6-(4-{2-[(2-Methoxy-benzyl)-methyl-amino]-ethyl}-phenoxy)-nicotinamide | 392.2 | 98 | 5.99 |
| 523 | 6-(4-{2-[(3-Chloro-4-fluoro-benzyl)-methyl-amino]-ethyl}-phenoxy)-nicotinamide | 414.5 | 99 | 6.03 |
| 524 | 6-(4-{2-[Methyl-(3-methyl-benzyl)-amino]-ethyl}-phenoxy)-nicotinamide | 376.2 | 100 | 5.99 |
| 525 | 6-(4-{2-[Methyl-(3-trifluoromethyl-benzyl)-amino]-ethyl}-phenoxy)-nicotinamide | 430.18 | 100 | 6.07 |
| 526 | 6-(4-{2-[(2,6-Difluoro-benzyl)-methyl-amino]-ethyl}-phenoxy)-nicotinamide | 398.17 | 100 | 5.88 |
| 527 | 6-(4-{2-[Methyl-(3-methyl-thiophen-2-ylmethyl)-amino]-ethyl}-phenoxy)-nicotinamide | 382.17 | 96 | 5.93 |
| 528 | 6-(4-{2-[Methyl-(3-phenoxy-benzyl)-amino]-ethyl}-phenoxy)-nicotinamide | 454.21 | 99 | 6.28 |
| 529 | 6-(4-{2-[Methyl-(2-trifluoromethyl-benzyl)-amino]-ethyl}-phenoxy)-nicotinamide | 430.15 | 100 | 6.03 |

-continued

|  |  |  | Data |  |
|---|---|---|---|---|
|  |  |  |  | HPLC(5/95 to 95/5 ACN/(0.1% TFA in water) over 10 minutes, Zorbax SB-Phenyl 4.6 mm × 15 cm × 5 micron, λ = 254 nM |
|  |  | Mass spectrum |  |  |
| Example | Name | (ion spray): m/z (M + 1) | Purity | Retention Time (minutes) |
| 530 | 6-{4-[2-(Methyl-thiophen-3-ylmethyl-amino)-ethyl]-phenoxy}-nicotinamide | 368.13 | 100 | 6.85 |
| 531 | 6-{4-[2-(Cyclopentylmethyl-methyl-amino)-ethyl]-phenoxy}-nicotinamide | 354.2 | 100 | 5.93 |
| 532 | 6-(4-{2-[(5-Chloro-1,3-dimethyl-1H-pyrazol-4-ylmethyl)-methyl-amino]-ethyl}-phenoxy)-nicotinamide | 414.18 | 97 | 5.71 |
| 533 | 6-(4-{2-[(2,5-Bis-trifluoromethyl-benzyl)-methyl-amino]-ethyl}-phenoxy)-nicotinamide | 498.13 | 100 | 6.23 |
| 534 | 6-(4-{2-[(3-Cyclopentyloxy-4-methoxy-benzyl)-methyl-amino]-ethyl}-phenoxy)-nicotinamide | 476.24 | 100 | 6.18 |
| 535 | 6-(4-{2-[(2-Fluoro-6-trifluoromethyl-benzyl)-methyl-amino]-ethyl}-phenoxy)-nicotinamide | 448.16 | 100 | 6.02 |
| 536 | 6-(4-{2-[Methyl-(4-trifluoromethyl-cyclohexyl)-amino]-ethyl}-phenoxy)-nicotinamide | 422.21 | 100 | 6.04 |
| 537 | 6-(4-{2-[(4-Chloro-3-trifluoromethyl-benzyl)-methyl-amino]-ethyl}-phenoxy)-nicotinamide | 464.13 | 100 | 6.17 |
| 538 | 6-(4-{2-[Methyl-(6-methyl-cyclohex-3-enylmethyl)-amino]-ethyl}-phenoxy)-nicotinamide | 380.22 | 90 | 6.05 |
| 539 | 6-{4-[2-(Cyclohex-1-enylmethyl-methyl-amino)-ethyl]-phenoxy}-nicotinamide | 366.2 | 84 | 5.98 |
| 540 | 4-({2-[4-(5-Carbamoyl-pyridin-2-yloxy)-phenyl]-ethyl}-methyl-amino)-piperidine-1-carboxylic acid ethyl ester | 427.22 | 100 | 5.79 |
| 541 | 6-(4-{2-[(2-Fluoro-4-trifluoromethyl-benzyl)-methyl-amino]-ethyl}-phenoxy)-nicotinamide | 448.16 | 100 | 6.11 |
| 542 | 6-(4-{2-[(3,4-Dimethyl-cyclohexyl)-methyl-amino]-ethyl}-phenoxy)-nicotinamide | 382.26 | 99 | 6.11 |
| 543 | 6-(4-{2-[Methyl-(tetrahydro-thiophen-3-yl)-amino]-ethyl}-phenoxy)-nicotinamide | 358.16 | 99 | 5.74 |
| 544 | 6-{4-[2-(Bicyclo[2.2.1]hept-5-en-2-yl-methyl-amino)-ethyl]-phenoxy}-nicotinamide | 364.5 | 99 | 5.82 |

EXAMPLE 545

6-{2-Methyl-4-[2-(3-methyl-butylamino)-ethyl]-phenoxyl}-nicotinamide

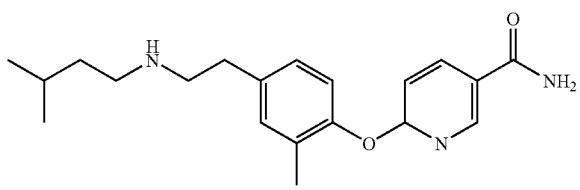

Step 1

2-Methyl-4-(2-nitro-vinyl)-phenol

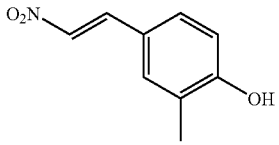

Dissolve 2-methyl-4-hydroxy-benzaldehyde (980 mg, 6.3 mmol), nitromethane (2.0 mL, 37.7 mmol) and ammonium acetate (1.9 g, 25.1 mmol) in acetic acid (9 mL). Heat the reaction mixture at 110° C. for 2 hours. Concentrate the reaction mixture under reduced pressure and partition the residue between ether and water. Separate the layers and dry with $Na_2SO_4$, filter and concentrate under reduced pressure to afford a crude product. Purify the crude by flash chromatography (eluent: EtOAc/hexane 20/80 and 30/70) to afford the title compound (1.0 g). $^1$H-NMR ($CDCl_3$, 200 MHz): 7.94 (d, 1H, J=13.4 Hz), 7.50 (d, 1H, J=13.6 Hz), 7.34-7.27 (m, 2H), 6.82 (d, 1H, J=8.1 Hz), 2.28 (s, 3H).

Step 2

4-(2-Amino-ethyl)-2-methyl-phenol

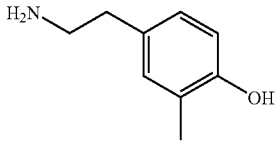

Procedure 1: Dissolve compound obtained in step 1 above (440 mg, 2.46 mmol) in methanol (10 mL) and add Pd/C 10% (272 mg) and HCl conc (1 mL). Stir the mixture at room temperature under hydrogen overnight. Filter the mixture over celite and evaporate the solvent to afford a crude product. Purify the crude product by SCX column to obtain the title compound (232 mg, 63%).

Procedure 2: To lithium aluminum hydride 1.0M in ether (1.67 mL, 1.67 mmol) at 0° C. a solution of aluminum trichloride (224 mg, 1.67 mmol) in THF (2 mL) is added. After 5 min a solution of compound obtained in step 1 above (100 mg, 0.56 mmol) in THF (2 mL) is added and the reaction is allowed to stir at room temperature overnight. Add water and then 3 N HCl, the aqueous layer is extracted with 3/1 n-butanol/toluene. The combined organic layers are dried over sodium sulfate and concentrated. SCX ion-exchange chromatography afforded 71 mg (84%) of the title compound. Electrospray MS M+1 ion=152. $^1$H-NMR (methanol-$d_4$, 200 MHz): 6.89 (bs, 1H), 6.82 (dd, 1H, J=8.3 and 2.4 Hz), 6.64 (d, 1H, J=8.1 Hz), 2.80 (t, 2H, J=6.7 Hz), 2.61 (t, 2H, J=7.0 Hz), 2.15 (s, 3H).

Step 3

[2-(4-Hydroxy-3-methyl-phenyl)-ethyl]-carbamic acid tert-butyl ester

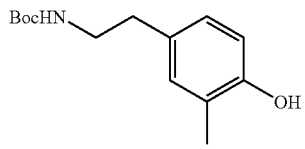

Dissolve amine obtained in step 2 above (289 mg, 1.91 mmol) in dry THF (5 mL) under $N_2$ atmosphere, add a solution of di-tertbutyl dicarbonate (439 mg, 2.0 mmol) in THF (5 mL), stir the mixture at room temperature overnight. Evaporate the solvent to obtain the title compound (462 mg, 96%). TLC $R_f$(EtOAc/hexane 20/80): 0.27. $^1$H-NMR (methanol-$d_4$, 200 MHz): 6.88 (bs, 1H), 6.82 (d, 1H, J=8.3 Hz), 6.63 (d, 1H, J=8.1 Hz), 3.17 (t, 2H, J=6.7 Hz), 2.60 (t, 2H, J=7.0 Hz), 2.14 (s, 3H), 1.50 (s, 9H).

Step 4

{2-[4-(5-Cyano-pyridin-2-yloxy)-3-methyl-phenyl]-ethyl}-carbamic acid tert-butyl ester

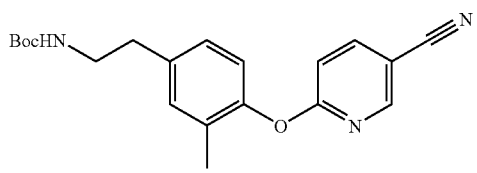

A solution of phenol obtained in step 3 above (455 mg, 1.1 mmol), 6-chloronicotinonitrile (251 mg, 1.81 mmol) and sodium hydride (87 mg, 2.17 mmol) in DMSO (10 mL) is stirred at room temperature for 18 hours. Pour the mixture into ice cold water and extract the aqueous layer with EtOAc. Dry the organic layer over $Na_2SO_4$, filter, and concentrate the filtrate to afford a crude product. Purify the crude product by flash column chromatography (eluent: EtOAc/hexane 15/85 and 20/80) to afford the title compound (358 mg, 57%). Electrospray MS $M^+$+1-Boc group ion: 298. $^1$H-NMR ($CDCl_3$, 200 MHz): 8.42 (dd, 1H, J=0.5 and 2.4 Hz), 7.90 (dd, 1H, J=2.4 and 8.6 Hz), 7.11-6.94 (m, 4H), 3.37 (q, 2H, J=7.0 Hz), 2.77 (t, 2H, J=7.2 Hz), 2.10 (s, 3H), 1.43 (s, 9H).

Step 5

{2-[4-(5-Carbamoyl-pyridin-2-yloxy)-3-methyl-phenyl]-ethyl}-carbamic acid tert-butyl ester

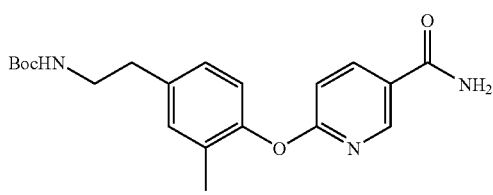

The compound of step 4 is subject to hydrolysis using hydrogen peroxide and potassium carbonate. The details of the hydrolysis procedure to form an amide form the corresponding nitrile have been described previously.

$^1$H-NMR (CDCl$_3$, 200 MHz): 8.58 (d, 1H, J=2.4 Hz), 8.17 (dd, 1H, J=2.4 and 8.6 Hz), 7.09-6.90 (m, 4H), 3.38 (q, 2H, J=6.7 Hz), 2.77 (t, 2H, J=7.0 Hz), 2.11 (s, 3H), 1.43 (s, 9H).

Step 6

6-[4-(2-Amino-ethyl)-2-methyl-phenoxy]-nicotinamide

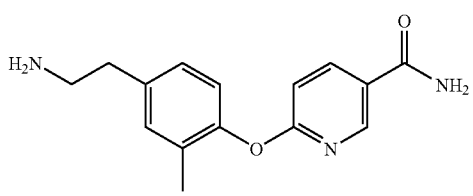

To a solution of the compound of step 5 (376 mg, 1.01 mmol) in CH$_2$Cl$_2$ (20 mL), add trifluoroacetic acid (2.03 mL, 26.4 mmol). Stir the reaction mixture at room temperature for 2 hours. Eliminate the solvent and purify by SCX column to obtain the title compound (264 mg, 96%). Electrospray MS M$^+$+1 ion: 272. $^1$H-NMR (methanol-d$_4$, 200 MHz): 8.58 (d, 1H, J=2.4 Hz), 8.24 (dd, 1H, J=2.7 and 8.9 Hz), 7.17-6.94 (m, 4H), 2.94-2.86 (m, 2H), 2.78-2.71 (m, 2H), 2.10 (s, 3H).

Step 7

Combine 3-methyl-butylaldehyde (60 µl, 0.22 mmol), amine from step 6 above (60 mg, 0.22 mmol) and 3 A molecular sieves (670 mg) in methanol (2 mL), stir the mixture at room temperature overnight. Add NaBH$_4$ (41 mg, 1.10 mmol) and stir at room temperature for 3 hours. Filter the mixture over Celite® and concentrate the filtrate to afford a crude product. Purify the crude mixture by flash chromatography (eluent: CH$_2$Cl$_2$/MeOH 80/20) to obtain the title compound (45 mg, 60%). Electrospray MS M+1 ion=342. $^1$H-NMR (methanol-d$_4$, 200 MHz): 8.59 (dd, 1H, J=0.8 and 2.7 Hz), 8.24 (dd, 1H, J=2.4 and 8.6 Hz), 7.19-7.10 (m, 2H), 7.00-6.93 (m, 2H), 2.93-2.76 (m, 4H), 2.70-2.62 (m, 2H), 2.10 (s, 3H), 1.71-1.36 (m, 3H), 0.91 (d, 6H, J=6.4 Hz).

EXAMPLES 546-552

Compounds of examples 546-552 were prepared following the method of example 545. The purification process is described in each case

EXAMPLE 546

6-{2-Methyl-4-[2-(3,3-dimethyl-butylamino)-ethyl]-phenoxy}-nicotinamide

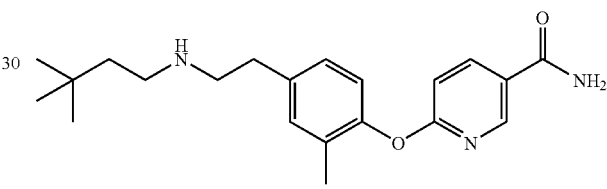

Purification: SCX column. Electrospray MS M+1 ion=356. $^1$H-NMR (metanol-d$_4$, 200 MHz): 8.59 (d, 1H, J=2.4 Hz), 8.24 (dd, 1H, J=2.4 and 8.6 Hz), 7.18-7.10 (m, 2H), 7.00-6.94 (m, 2H), 2.92-2.78 (m, 4H), 2.69-2.60 (m, 2H), 2.10 (s, 3H), 1.48-1.39 (m, 2H), 0.93 (s, 9H).

EXAMPLE 547

6-[2-Methyl-4-(2-pentylamino-ethyl)-phenoxy]-nicotinamide

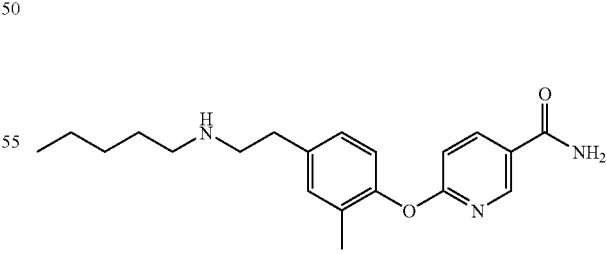

Purification: Flash chromatography (eluent: CH$_2$Cl$_2$/EtOAc/MeOH:NH$_3$ 2M 35/60/5). Electrospray MS M+1 ion=342. $^1$H-NMR (metanol-d$_4$, 200 MHz): 8.59 (dd, 1H, J=0.5 and 2.3 Hz), 8.24 (dd, 1H, J=2.6 and 8.8 Hz), 7.17-7.08 (m, 2H), 6.98-6.92 (m, 2H), 2.88-2.75 (m, 4H), 2.65-2.57 (m, 2H), 2.09 (s, 3H), 1.59-1.25 (m, 6H), 0.91 (t, 3H, J=6.4 Hz).

EXAMPLE 548

6-{4-[2-(Cyclohexylmethyl-amino)-ethyl]-2-methyl-phenoxy}-nicotinamide

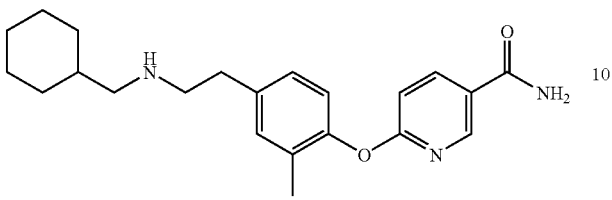

Purification: Flash chromatography (eluent: CH$_2$Cl$_2$/MeOH 90/10). Electrospray MS M+1 ion=368. $^1$H-NMR (metanol-d$_4$, 200 MHz): 8.59 (d, 1H, J=2.4 Hz), 8.24 (dd, 1H, J=2.7 and 8.6 Hz), 7.18-7.10 (m, 2H), 7.00-6.93 (m, 2H), 2.85 (bs, 4H), 2.50 (d, 2H, J=6.4 Hz), 2.10 (s, 3H), 1.77-0.84 (m, 11H).

EXAMPLE 549

6-{4-[2-(3-Fluoro-benzylamino)-ethyl]-2-methyl-phenoxy}-nicotinamide

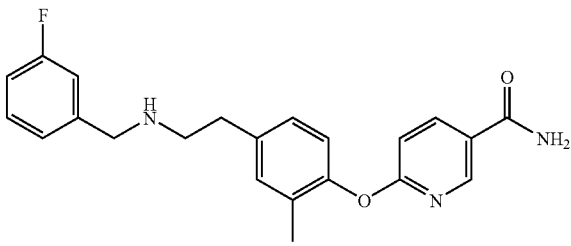

Purification: SCX column. Electrospray MS M+1 ion=380. $^1$H-NMR (metanol-d$_4$, 200 MHz): 8.59 (dd, 1H, J=0.5 and 2.4 Hz), 8.24 (dd, 1H, J=2.4 and 8.6 Hz), 7.38-6.92 (m, 8H), 3.79 (s, 2H), 2.82 (s, 4H), 2.09 (s, 3H).

EXAMPLE 550

6-{4-[2-(3-Fluoro-benzylamino)-ethyl]-2-methyl-phenoxy}-nicotinamide, mesylate salt

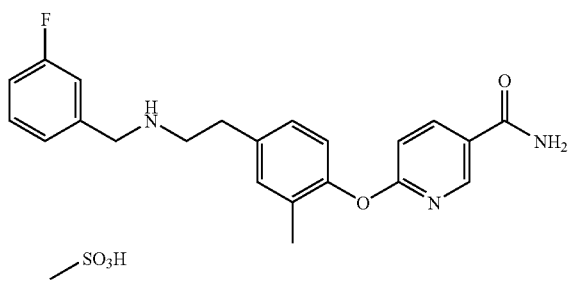

Example 5 (free amine of example 6) was dissolved in THF, then methanosulfonic acid was added (1.0 eq), the mixture was stirred for 1 hour and the solvent eliminated to give the title compound. Electrospray MS M+1 ion=380. $^1$H-NMR (metanol-d$_4$, 300 MHz): 8.59 (bs, 1H), 8.28 (dd, 1H, J=1.4 and 8.7 Hz), 7.56-7.02 (m, 8H), 4.30 (s, 2H), 3.36 (t, 2H, J=7.3 Hz), 3.06 (t, 2H, J=7.3 Hz), 2.72 (s, 3H), 2.14 (s, 3H).

EXAMPLE 551

6-(4-{2-[(Bicyclo[2.2.1]hept-5-en-2-ylmethyl)-amino]-ethyl}-2-methyl-phenoxy)-nicotinamide

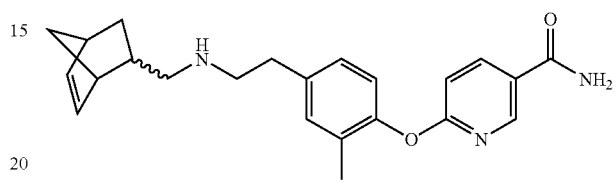

Purification: HPLC (Column: X-Terra MS C18. A=10 Mm NH$_4$HCO$_3$ pH9/B=CH$_3$CN. Gradient mode: from 30 to 99% B. Flow rate: 1 mL/min). Electrospray MS M+1 ion=378. $^1$H-NMR (metanol-d$_4$, 200 MHz): 8.59 (d, 1H, J=2.6 Hz), 8.24 (dd, 1H, J=2.4 and 8.6 Hz), 7.16-6.91 (m, 4H), 6.16-5.88 (m, 2H), 2.81-1.81 (m, 9H), 2.09 (s, 3H), 1.65-0.99 (m, 3H), 0.57-0.48 (m, 1H).

EXAMPLE 552

6-[4-(2-Cyclooctylamino-ethyl)-2-methyl-phenoxy]-nicotinamide

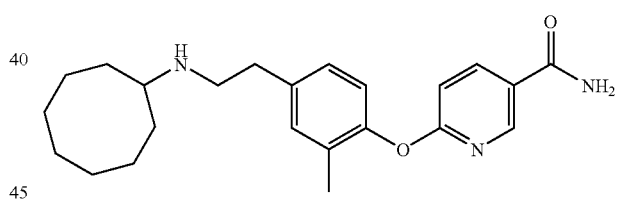

Purification: Flash chromatography (eluent: CH$_2$Cl$_2$/MeOH 70/30). Electrospray MS M+1 ion=382 $^1$H-NMR (metanol-d$_4$, 200 MHz): 8.59 (d, 1H, J=2.4 Hz), 8.24 (dd, 1H), J=2.4 and 8.6 Hz), 7.18-6.92 (m, 4H), 2.95-2.77 (m, 5H), 2.12 (m, 1H), 2.10 (s, 3H), 1.89-1.46 (m, 13H).

EXAMPLE 553

6-{3-Chloro-4-[2-(3-methyl-butylamino)-ethyl]-phenoxy}-nicotinamide

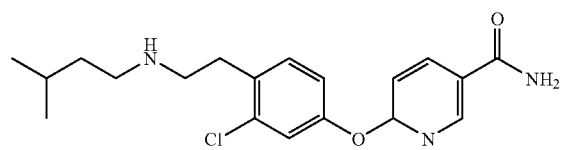

Step 1

3-Chloro-4-(2-nitro-vinyl)-phenol

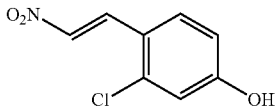

The 3-chloro-4-hydro-oxy-benzaldehyde (980 mg, 6.3 mmol), nitromethane (2.0 mL, 37.7 mmol) and ammonium acetate (1.9 g, 25.1 mmol) were dissolved in acetic acid (9 mL) and the reaction heated at 110° C. for 2 hours. The reaction is concentrated under reduced pressure and the residue partitioned between ether and water. Separate the layers and dry with $Na_2SO_4$, filter and concentrate under reduced pressure. Purify the crude product by flash chromatography (eluent: EtOAc/hexane 20/80 and 30/70) afforded the title compound (1.0 g, 80%). $^1$H-NMR ($CDCl_3$, 200 MHz): 8.34 (d, 1H, J=13.4 Hz), 7.82 (d, 1H, J=13.4 Hz), 7.71 (d, 1H, J=8.6 Hz), 6.94 (d, 1H, J=2.4 Hz), 6.80 (dd, 1H, J=2.4 and 8.6 Hz).

Step 2

4-(2-Amino-ethyl)-3-chloro-phenol

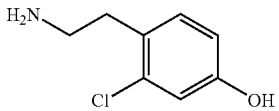

To lithium aluminum hydride 1.0 M in ether (1.50 mL, 1.50 mmol) at 0° C. a solution of aluminum trichloride (201 mg, 1.51 mmol) in THF (2 mL) is added. After 5 min a solution of compound obtained in step 1 above (100 mg, 0.50 mmol) in THF (2 mL) is added and the reaction is allowed to stir at room temperature overnight. Add water and then 3 N HCl. Extract the aqueous layer with 3/1 n-butanol/toluene. The combined organic layers are dried over sodium sulfate and concentrated. SCX ion-exchange chromatography of the concentrate afforded 70 mg (81%) of the title compound. Electrospray MS M+1 ion=172. $^1$H-NMR (methanol-$d_4$, 200 MHz): 7.06 (d, 1H, J=8.3 Hz), 6.79 (d, 1H, J=2.4 Hz), 6.65 (dd, 1H, J=2.4 and 8.3 Hz), 2.82 (m, 4H).

Step 3

[2-(4-Hydroxy-2-chloro-phenyl)-ethyl]-carbamic acid tert-butyl ester

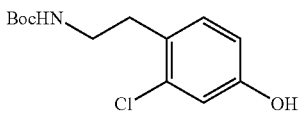

Dissolve amine obtained in step 2 above (620 mg, 3.62 mmol) in dry THF (20 mL) and DMF (1 mL) under $N_2$ atmosphere, add a solution of di-tertbutyl dicarbonate (791 mg, 3.62 mmol) in THF (10 mL), stir the mixture at room temperature overnight. Concentrate the mixture to a crude product and purify the crude product by flash chromatography (eluent: EtOAc/hexane 30/70) to obtain the title compound (670 mg, 68%). TLC $R_f$(EtOAc/hexane 20/80): 0.27. $^1$H-NMR (methanol-$d_4$, 200 MHz): 7.06 (d, 1H, J=8.3 Hz), 6.78 (d, 1H, J=2.6 Hz), 6.65 (dd, 1H, J=2.4 and 8.3 Hz), 3.21 (t, 2H, J=6.7 Hz), 2.78 (t, 2H, J=7.5 Hz), 1.41 (s, 9H).

Step 4

{2-[4-(5-Cyano-pyridin-2-yloxy)-2-chloro-phenyl]-ethyl}-carbamic acid tert-butyl ester

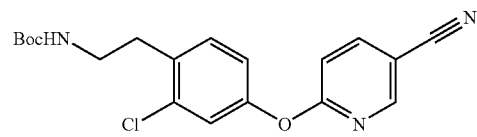

A solution of phenol obtained in step 3 above (650 mg, 2.4 mmol), 6-chloronicotinonitrile (333 mg, 2.4 mmol) and sodium hydride (115 mg, 2.9 mmol) in DMSO (12 mL) is stirred at room temperature for 18 hours. Pour the mixture into cold water (about 0° C.) and extract the aqueous layer with EtOAc. Dry the organic layer over $Na_2SO_4$, filter and concentrate the filtrate to afford a crude product. Purify the crude product by flash chromatography (eluent: EtOAc/hexane 20/80 and 30/70) to afford the title compound (810 mg, 90%). Electrospray MS $M^+$+1-Boc group ion: 318. $^1$H-NMR ($CDCl_3$, 200 MHz): 8.46 (dd, 1H, J=0.5 and 2.2 Hz), 7.94 (dd, 1H, J=2.4 and 8.6 Hz), 7.31-7.18 (m, 2H), 7.06-6.98 (m, 2H), 3.41 (q, 2H, J=6.7 Hz), 2.95 (t, 2H, J=7.3 Hz), 1.44 (s, 9H).

Step 5

{2-[4-(5-Carbamoyl-pyridin-2-yloxy)-2-chloro-phenyl]-ethyl}-carbamic acid tert-butyl ester

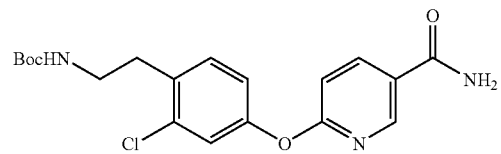

The compound of step 4 is subject to hydrolysis using hydrogen peroxide and potassium carbonate. The details of the hydrolysis procedure to form analogous amides from the corresponding nitrile have been described previously.

$^1$H-NMR (methanol-$d_4$, 200 MHz): 8.62 (dd, 1H, J=0.8 and 2.7 Hz), 8.27 (dd, 1H, J=2.4 and 8.6 Hz), 7.34 (d, 1H, J=8.3 Hz), 7.22 (d, 1H, J=2.4 Hz), 7.07-7.02 (m, 2H), 3.34 (m, 2H), 2.92 (t, 2H, J=7.3 Hz), 1.42 (s, 9H).

Step 6

6-[4-(2-Amino-ethyl)-2-chloro-phenoxy]-nicotinamide

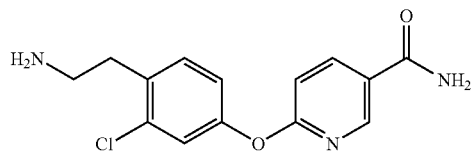

The compound of step 5 is subjected to hydrolysis using trifluoroacetic acid. The details of the hydrolysis procedure to remove the protecting group have been described previously. Electrospray MS M+1 ion=292. $^1$H-NMR (metanol-$d_4$, 200 MHz): 8.60 (dd, 1H, J=0.8 and 2.7 Hz), 8.28 (dd, 1H, J=2.7 and 8.9 Hz), 7.38 (d, 1H, J=8.3 Hz), 7.24 (d, 1H, J=2.4 Hz), 7.09-7.03 (m, 2H), 2.94 (s, 4H).

Step 7

Combine compound from step 6 (60 mg, 0.21 mmol), 3-methyl-butyraldehyde (24 µl, 0.23 mmol) and 3 A molecular sieves (670 mg) in methanol (2 mL), stir the mixture at room temperature overnight. Add NaBH$_4$ (41 mg, 1.10 mmol) and stir at room temperature for 3 hours. Filter the mixture over celite. Concentrate the filtrate to afford the crude product. Purify the crude product using an SCX column to obtain the title compound. Electrospray MS M+1 ion=362. $^1$H-NMR (metanol-$d_4$, 200 MHz): 8.61 (dd, 1H, J=0.8 and 2.7 Hz), 8.27 (dd, 1H, J=2.4 and 8.6 Hz), 7.38 (d, 1H, J=8.6 Hz), 7.22 (d, 1H, J=2.4 Hz), 7.07-7.03 (m, 2H), 3.03-2.81 (m, 4H), 2.70-2.62 (m, 2H), 1.62 (m, 1H), 1.48-1.37 (m, 2H), 0.92 (d, 6H, J=6.5 Hz).

EXAMPLES 554-558

Compounds of examples 554-558 were prepared following procedures similar to that of Example 553. The purification process is described in each case.

EXAMPLE 554

6-{3-Chloro-4-[2-(3,3-dimethyl-butylamino)-ethyl]-phenoxy}-nicotinamide

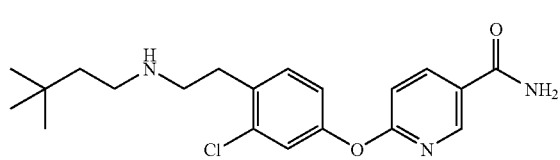

Purification: SCX column. Electrospray MS M+1 ion=376. $^1$H-NMR (metanol-$d_4$, 200 MHz): 8.61 (dd, 1H, J=0.5 and 2.4 Hz), 8.27 (dd, 1H, J=2.7 and 8.9 Hz), 7.38 (d, 1H, J=8.3 Hz), 7.22 (d, 1H, J=2.4 Hz), 7.09-7.03 (m, 2H), 3.02-2.81 (m, 4H), 2.69-2.61 (m, 2H), 1.49-1.40 (m, 2H), 0.93 (s, 9H).

EXAMPLE 555

6-[3-Chloro-4-(2-pentylamino-ethyl)-phenoxy]-nicotinamide

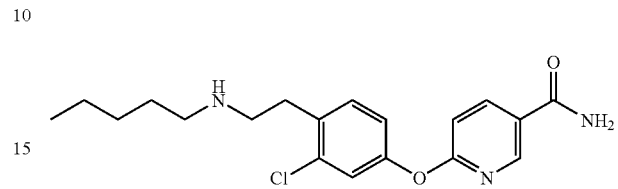

Purification: flash chromatography (eluent: CH$_2$Cl$_2$/MeOH 90/10). Electrospray MS M+1 ion=362. $^1$H-NMR (metanol-$d_4$, 200 MHz): 8.61 (dd, 1H, J=0.8 and 2.4 Hz), 8.27 (dd, 1H, J=2.4 and 8.6 Hz), 7.38 (d, 1H, J=8.3 Hz), 7.23 (d, 1H, J=2.4 Hz), 7.09-7.03 (m, 2H), 3.03-2.81 (m, 4H), 2.68-2.61 (m, 2H), 1.61-1.47 (m, 2H), 1.37-1.28 (m, 4H), 0.93 (t, 3H, J=6.7 Hz).

EXAMPLE 556

6-{3-Chloro-4-[2-(cyclohexylmethyl-amino)-ethyl]-phenoxy}-nicotinamide

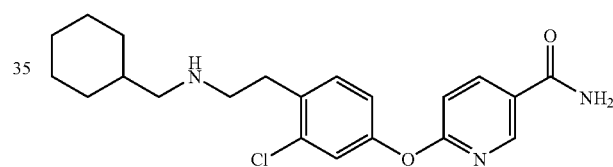

Purification: SCX column. Electrospray MS M+1 ion=388. $^1$H-NMR (metanol-$d_4$, 300 MHz): 8.63 (d, 1H, J=1.8 Hz), 8.28 (dd, 1H, J=2.4 and 8.5 Hz), 7.37 (d, 1H, J=8.2 Hz), 7.22 (d, 1H, J=2.2 Hz), 7.07-7.03 (m, 2H), 3.01-2.81 (m, 4H), 2.49 (d, 2H, J=6.7 Hz), 1.79-1.68 (m, 5H), 1.61-1.42 (m, 1H), 1.38-1.17 (m, 3H), 0.99-0.85 (m, 2H).

EXAMPLE 557

6-{3-Chloro-4-[2-(3-fluoro-benzylamino)-ethyl]-phenoxy}-nicotinamide

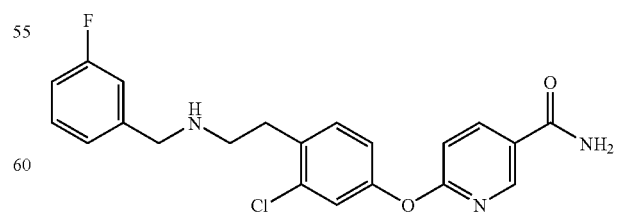

Purification: SCX column. Electrospray MS M+1 ion=400. $^1$H-NMR (metanol-$d_4$, 300 MHz): 8.63 (d, 1H, J=2.2 Hz), 8.27 (dd, 1H, J=2.4 and 8.7 Hz), 7.36-6.95 (m, 8H), 3.82 (s, 2H), 3.01-2.81 (m, 4H).

EXAMPLE 558

6-(4-{2-[(Bicyclo[2.2.1]hept-5-en-2-ylmethyl)-amino]-ethyl}-3-chloro-phenoxy)-nicotinamide

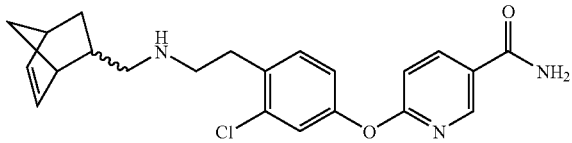

Purification: SCX column. Electrospray MS M+1 ion=398. ¹H-NMR (metanol-$d_4$, 200 MHz): 8.61 (dd, 1H, J=0.5 and 2.4 Hz), 8.26 (dd, 1H, J=2.4 and 8.6 Hz), 7.40-7.03 (m, 4H), 6.18-5.92 (m, 2H), 3.01-2.66 (m, 6H), 2.40-2.18 (m, 2H), 1.95-1.83 (m, 1H), 1.64-1.11 (m, 3H), 0.60-0.50 (m, 1H).

EXAMPLE 559

6-{2,6-Difluoro-4-[2-(3-methyl-butylamino)-ethyl]-phenoxy}-nicotinamide

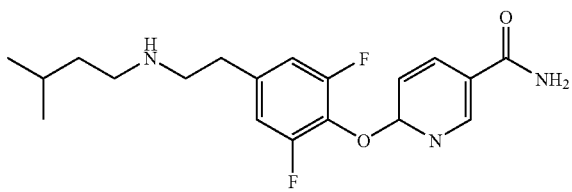

Step 1

2,6-Difluoro-4-(2-nitro-vinyl)-phenol

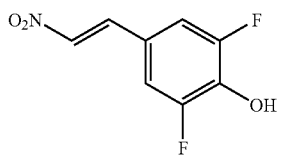

3,5-Difluoro-4-hydroxybenzaldehyde (2.27 g, 14.4 mmol), nitromethane (4.7 mL, 86.4 mmol) and ammonium acetate (4.4 g, 57.6 mmol) were dissolved in acetic acid (22 mL) and the reaction mixture was heated at 110° C. for 1 hour 30 min. The reaction was concentrated under reduced pressure and the residue partitioned between ether and water, the layers were separated and the organic layer was dried with $Na_2SO_4$. The organic mixture was filtered and the filtrate concentrated under reduced pressure to afford a crude product. The crude product was purified by flash column chromatography (eluent: EtOAc/hexane 22/78) to afford the title compound (2.05 g, yield: 71%). Electrospray MS M−1 ion=200. ¹H-NMR ($CDCl_3$, 200 MHz): 7.84 (d, 1H, J=13.7 Hz), 7.45 (d, 1H, J=13.7 Hz), 7.19-6.99 (m, 2H).

Step 2

4-(2-Amino-ethyl)-2,6-difluoro-phenol

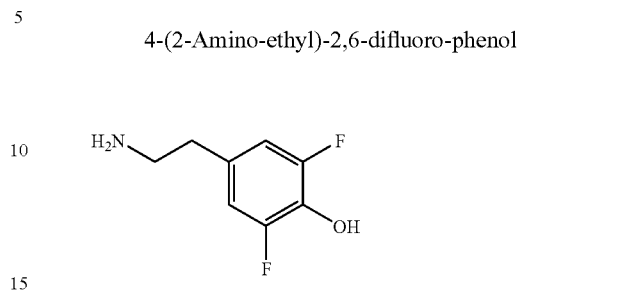

To lithium aluminum hydride 11.0M in ether (30 mL, 29.8 mmol) at 0° C. a solution of aluminum trichloride (4.0 g, 29.8 mmol) in THF (40 mL) is added. After 5 min a solution of compound obtained in step 1 above (2.0 g, 9.95 mmol) in THF (40 mL) is added and the reaction is allowed to stir at room temperature overnight. Add water and then 3 N HCL, the aqueous layer is extracted with 3/1 n-butanol/toluene. The combined organic layers are dried over sodium sulfate and concentrated. SCX ion-exchange chromatography afforded 1.50 g (87%) of the title compound. Electrospray MS M+1 ion=174. ¹H-NMR (methanol-$d_4$, 200 MHz): 6.95-6.78 (m, 2H), 3.14 (t, 2H, J=7.0 Hz), 2.86 (t, 2H, J=7.3 Hz).

Step 3

[2-(3,5-Difluoro-4-hydroxy-phenyl)-ethyl]-carbamic acid tert-butyl ester

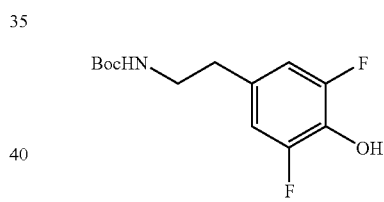

Dissolve amine obtained in step 2 above (1.5 g, 8.67 mmol) in dry THF (22 mL) under $N_2$ atmosphere, add a solution of di-tertbutyl dicarbonate (1.89 g, 8.67 mmol) in THF (22 mL), stir the mixture at room temperature overnight. Eliminate the solvent. Purify by flash chromatography (eluent: EtOAc/hexane 1/4 and 1/1) to obtain the desired compound (1.40 g). ¹H-NMR ($CDCl_3$, 200 MHz): 6.85-6.66 (m, 2H), 3.31 (q, 2H, J=6.2 Hz), 2.69 (t, 2H, J=7.0 Hz), 1.44 (s, 9H).

Step 4

{2-[4-(5-Cyano-pyridin-2-yloxy)-3,5-difluoro-phenyl]-ethyl}-carbamic acid tert-butyl ester

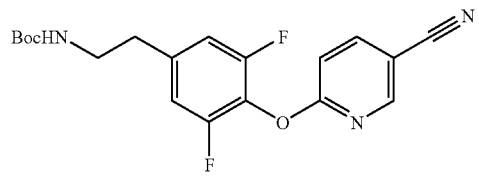

A solution of phenol obtained in step 3 above (1.31 g, 4.8 mmol), 6-chloronicotinonitrile (700 mg, 5.04 mmol) and sodium hydride (290 mg, 7.2 mmol) in DMSO (25 mL) is stinted at room temperature for 18 hours. Pour the mixture into iced water and extract the aqueous layer with EtOAc. Dry the organic layer over $Na_2SO_4$, filtrate and eliminate the solvent. Purify by flash chromatography (EtOAc/hexane 20/80 and 34/66) to get the title compound (950 mg, 51%). $^1$H-NMR (CDCl$_3$, 200 MHz): 8.41 (dd, 1H, J=0.8 and 2.1 Hz), 7.97 (dd, 1H, J=2.4 and 8.6 Hz), 7.18 (dd, 1H, J=0.8 and 8.6 Hz), 6.92-6.81 (m, 2H), 3.39 (q, 2H, J=6.9 Hz), 2.81 (t, 2H, J=6.7 Hz), 1.45 (s, 9H).

Step 5

{2-[4-(5-Carbamoyl-pyridin-2-yloxy)-3,5-difluoro-phenyl]-ethyl}-carbamic acid tert-butyl ester

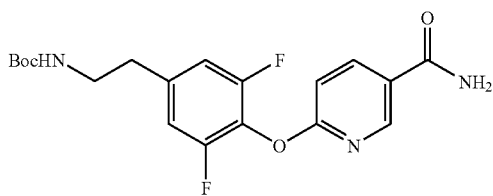

The compound of step 4 is subjected to hydrolysis using hydrogen peroxide and potassium carbonate. The details of the hydrolysis procedure to form analogous amides from the corresponding nitrile have been described previously.
$^1$H-NMR (metanol-d$_4$, 300 MHz): 8.58 (d, 1H, J=2.4 Hz), 8.31 (dd, 1H, J=2.4 and 8.7 Hz), 7.19 (d, 1H, J=8.7 Hz), 7.02-6.98 (m, 2H), 3.35-3.30 (m, 2H), 2.81 (t, 2H, J=7.1 Hz), 1.44 (s, 9H).

Step 6

6-[4-(2-Amino-ethyl)-2,6difluoro-phenoxy]-nicotinamide

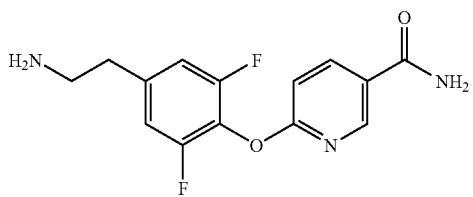

To a solution of compound of step 5 (930 mg, 2.37 mmol) in CH$_2$Cl$_2$ (50 mL), trifluoroacetic acid is added (4.7 mL, 61.5 mmol). Stir the reaction mixture at room temperature for 2 h. Eliminate the solvent and purify by SCX column to obtain the title compound (658 mg, 95%). Electrospray MS M$^+$+1 ion: 294. $^1$H-NMR (metanol-d$_4$, 200 MHz): 8.56 (d, 1H, J=2.4 Hz), 8.30 (dd, 1H, J=2.4 and 8.9 Hz), 7.18 (d, 1H, J=8.9 Hz), 7.05-6.95 (m, 2H), 2.96-2.74 (m, 4H).

Step 7

Combine 3-methyl-butylaldehyde (26 µl, 0.24 mmol) amine from step 6 above and 3 A molecular sieves (900 mg) in methanol (3 mL), stir the mixture at room temperature overnight. Add NaBH$_4$ (45 mg, 1.20 mmol) and stir at room temperature for 3 hours. Filtrate the mixture over celite and eliminate the solvent. Submit the crude to a SCX column to obtain a solid which was further purified by HPLC (Column: X-Terra MS C18. A=10 Mm NH$_4$HCO$_3$ pHB8/B=CH$_3$CN. Gradient mode: from 30 to 70% B. Flow rate: 1 mL/min) to obtain the title compound (42 mg). Electrospray MS M+1 ion=364. $^1$H-NMR (metanol-d$_4$, 300 MHz): 8.60 (d, 1H, J=2.0 Hz), 8.32 (dd, 1H, J=2.2 and 8.5 Hz), 7.19 (d, 1H, J=8.7 Hz), 7.01-6.98 (m, 2H), 2.85 (m, 4H), 2.63 (m, 2H), 1.62 (m, 1H), 1.42 (q, 1H, J=7.3 Hz), 0.92 (d, 6H, J=6.5 Hz).

By the method of example 559 the following examples (examples 560-563) were prepared. The purification process is described in each case

EXAMPLE 560

6-{4-[2-(3,3-Dimethyl-butylamino)-ethyl]-2,6-difluoro-phenoxy}-nicotinamide

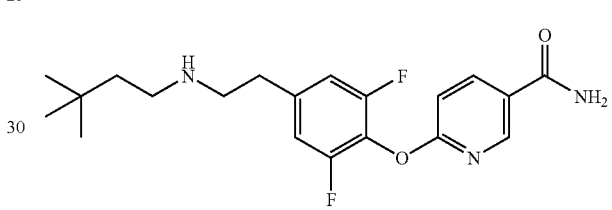

Purification: HPLC (Column: X-Terra MS C18. A=10 Mm NH$_4$HCO$_3$ pH8/B=CH$_3$CN. Gradient mode: from 30 to 99% B. Flow rate: 1 mL/min). Electrospray MS M+1 ion=378. $^1$H-NMR (metanol-d$_4$, 300 MHz): 8.48 (d, 1H, J=2.4 Hz), 8.23 (dd, 1H, J=2.4 and 8.5 Hz), 7.12 (d, 1H, J=8.5 Hz), 7.00-6.93 (m, 2H), 2.91-2.78 (m, 4H), 2.67-2.61 (m, 2H), 1.43-1.38 (m, 2H), 0.87 (s, 9H).

EXAMPLE 561

6-[2,6-Difluoro-4-(2-pentylamino-ethyl)-phenoxy]-nicotinamide

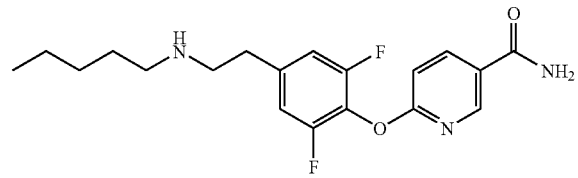

Purification: HPLC (Column: X-Terra MS C18. A=10 Mm NH$_4$HCO$_3$ pH8/B=CH$_3$CN. Gradient mode: from 25 to 70% B. Flow rate: 1 mL/min). Electrospray MS M+1 ion=364. $^1$H-NMR (metanol-d$_4$, 300 MHz): 8.59 (d, 1H, J=2.4 Hz), 8.32 (dd, 1H, J=2.4 and 8.7 Hz), 7.19 (d, 1H, J=8.7 Hz), 7.02-7.00 (m, 2H), 2.88 (m, 4H), 2.65 (t, 2H, J=7.3 Hz), 1.55 (m, 2H), 1.35 (m, 4H), 0.93 (t, 3H, J=6.7 Hz).

EXAMPLE 562

6-{4-[2-(Cyclohexylmethyl-amino)-ethyl]-2,6-difluoro-phenoxy}-nicotinamide

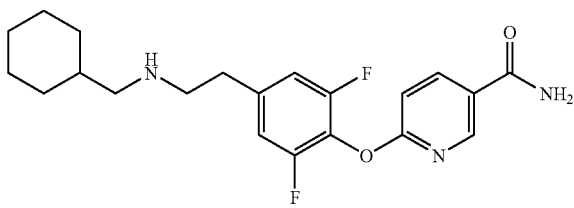

Purification: HPLC (Column: X-Terra MS C18. A=10 Mm NH₄HCO₃ pH8/B=CH₃CN. Gradient mode: from 30 to 99% B. Flow rate: 1 mL/min). Electrospray MS M+1 ion=390. ¹H-NMR (metanol-$d_4$, 300 MHz): 8.48 (d, 1H, J=2.4 Hz), 8.23 (dd, 1H, J=2.4 and 8.9 Hz), 7.11 (d, 1H, J=8.8 Hz), 6.99-6.92 (m, 2H), 2.83 (m, 4H), 2.47 (d, 2H, J=6.9 Hz), 1.72-1.59 (m, 5H), 1.55-1.41 (m, 1H), 1.31-1.05 (m, 3H), 0.94-0.81 (m, 2H).

EXAMPLE 563

6-{4-[2-(Cyclopropylmethyl-amino)-ethyl]-2,6-difluoro-phenoxy}-nicotinamide

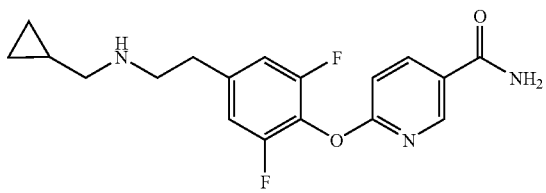

Purification: HPLC (Column: X-Terra MS C18. A=10 Mm NH₄HCO₃ pH8/B=MeOH. Gradient mode: from 35 to 80% B. Flow rate: 1 mL/min). Electrospray MS M+1 ion=348. ¹H-NMR (metanol-$d_4$, 300 MHz): 8.59 (d, 1H, J=2.4 Hz), 8.32 (dd, 1H, J=2.4 and 8.7 Hz), 7.19 (d, 1H, J=8.7 Hz), 7.02-7.00 (m, 2H), 2.93-2.83 (m, 4H), 2.50 (d, 2H, J=6.9 Hz), 1.10-0.90 (m, 1H), 0.55-0.49 (m, 2H), 0.20-0.15 (m, 2H).

EXAMPLE 564

6-(2-Pentyl-2,3,4,5-tetrahydro-1H-benzo[c]azepin-7-yloxy)nicotinamide

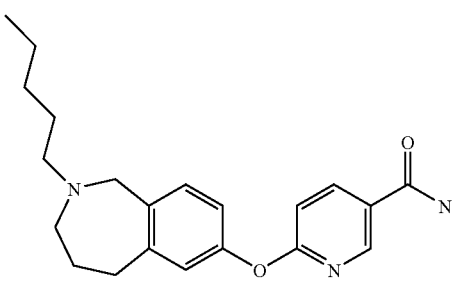

Mix 6-(2,3,4,5-tetrahydro-1H-benzo[c]azepin-7-yloxy)nicotinamide (Example 447, Part E, 0.300 g, 1.06 mmol), K₂CO₃ (0.366 g, 2.65 mmol), and 1-bromopentane (0.176 g, 1.16 mmol) in DMF (5.3 mL). Heat at 70° C. overnight and then increase the temperature to 100° C. for additional two hours. Cool the reaction mixture to room temperature and add ethyl acetate (150 mL). Wash with 1.0 N NaOH (1×50 mL), brine (1×50 mL), dry the organic layer over Na₂SO₄, filter and concentrate. Purify by flash chromatography eluting with 7% to 15% (2.0 M NH₃ in methanol) in ethyl acetate to give the title compound: MS ES⁺ 354.2 (M+H)⁺, HRMS calcd for C₂₁H₂₈N₃O₂ 354.2182 (M+H)⁺, found 354.2188, time 0.53 min; Anal. Calcd for C₂₁H₂₇N₃O₂: C, 71.36; H, 7.70; N, 11.89. Found: C, 71.14; H, 7.60; N, 11.79.

EXAMPLE 565

6-(2-Hexyl-2,3,4,5-tetrahydro-1H-benzo[c]azepin-7-yloxy)nicotinamide

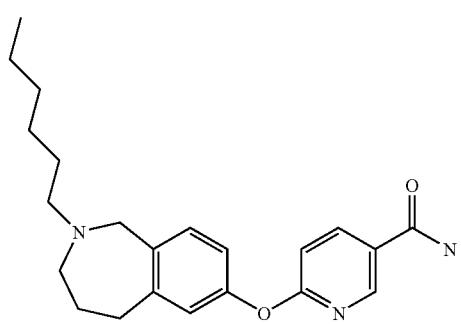

Mix 6-(2,3,4,5-tetrahydro-1H-benzo[c]azepin-7-yloxy)nicotinamide (Example 447, Part E, 0.300 g, 1.06 mmol), K₂CO₃ (0.366 g, 2.65 mmol), and 1-bromohexane (0.192 g, 1.16 mmol) in DMF (5.3 mL). Heat at 70° C. overnight, then increase the temperature to 100° C. for additional two hours. Cool the reaction mixture to room temperature and add ethyl acetate (150 mL). Wash with 1.0 N NaOH (1×50 mL), brine (1×50 mL), dry the organic layer over Na₂SO₄, filter and concentrate. Purify by flash chromatography eluting with 7% to 15% (2.0 M NH₃ in methanol) in ethyl acetate to give the title compound: MS ES⁺ 368.2 (M+H)⁺, HRMS calcd for C₂₂H₃₀N₃O₂ 368.2338 (M+H)⁺, found 368.2334, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=11.6 min, 97.8% purity.

EXAMPLE 566

6-[2-(2-Morpholin-4-ylethyl)-2,3,4,5-tetrahydro-1H-benzo[c]azepin-7-yloxy]nicotinamide

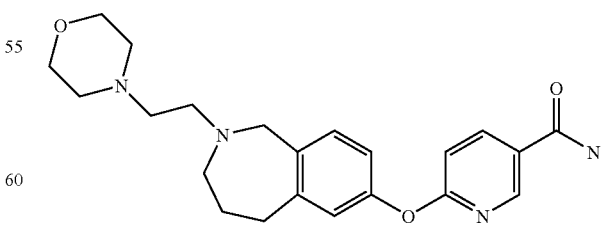

Mix 6-(2,3,4,5-tetrahydro-1H-benzo[c]azepin-7-yloxy)nicotinamide (Example 447, Part E, 0.300 g, 1.06 mmol), K₂CO₃ (0.366 g, 2.65 mmol), and 4-(2-chloroethyl)morpholine hydrochloride (0.217 g, 1.16 mmol) in DMF (5.3 mL).

Heat at 90° C. overnight. Cool the reaction mixture to room temperature and add ethyl acetate (150 mL). Wash with 1.0 N NaOH (1×50 mL), brine (1×50 mL), dry the organic layer over Na$_2$SO$_4$, filter and concentrate. Purify by flash chromatography eluting with 10% to 20% (2.0 M NH$_3$ in methanol) in acetone to give the title compound: MS ES$^+$ 397.2 (M+H)$^+$, HRMS calcd for C$_{22}$H$_{29}$N$_4$O$_3$ 397.2240 (M+H)$^+$, found 397.2223, time 0.48 min; HPLC [YMC-Pro pack C-18 (150× 4.6 mm, S-5 microm), 0.05% TFA/acetonitrile in 0.05% TFA/ water at 1.0 mL/min, 10-20% over 5 min, 20-95% over 18 min], $t_R$=5.6 min, 99.0% purity.

EXAMPLE 567

6-[2-(3-Morpholin-4-ylpropyl)-2,3,4,5-tetrahydro-1H-benzo[c]azepin-7-yloxy]nicotinamide

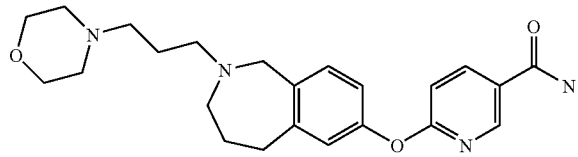

Mix 6-(2,3,4,5-tetrahydro-1H-benzo[c]azepin-7-yloxy) nicotinamide (Example 447, Part E, 0.300 g, 1.06 mmol), K$_2$CO$_3$ (0.366 g, 2.65 mmol), and 4-(3-chloropropyl)morpholine (0.191 g, 1.16 mmol) in DMF (5.3 mL). Heat at 90° C. overnight. Cool the reaction mixture to room temperature and add ethyl acetate (150 mL). Wash with 1.0 N NaOH (1×50 mL), brine (1×50 mL), dry the organic layer over Na$_2$SO$_4$, filter and concentrate. Purify by flash chromatography eluting with 10% (2.0 M NH) in methanol) in acetone to give the title compound: MS ES$^+$ 411.2 (M+H)$^+$, HRMS calcd for C$_{23}$H$_{31}$N$_4$O$_3$ 411.2396 (M+H)$^+$, found 411.2389 time 0.48 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=5.7 min, 100% purity.

EXAMPLE 568

6-(2-Heptyl-2,3,4,5-tetrahydro-1H-benzo[c]azepin-7-yloxy)nicotinamide

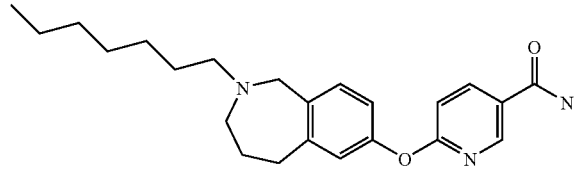

Mix 6-(2,3,4,5-tetrahydro-1H-benzo[c]azepin-7-yloxy) nicotinamide (Example 447, Part E, 0.300 g, 1.06 mmol), K$_2$CO$_3$ (0.366 g, 2.65 mmol), and 1-bromoheptane (0.199 g, 1.11 mmol) in DMF (5.3 mL). Heat at 50° C. overnight, then increase the temperature to 80° C. for 3.5 hours. Cool the reaction mixture to room temperature and add ethyl acetate (100 mL). Wash with water (1×30 mL), brine (1×30 mL), dry the organic layer over NaSO$_4$, filter and concentrate. Purify by flash chromatography eluting with 6% to 15% (2.0 M NH$_3$ in methanol) in ethyl acetate to give the title compound: MS ES$^+$ 382.2 (M+H)$^+$, HRMS calcd for C$_{23}$H$_{32}$N$_3$O$_2$ 382.2495 (M+H)$^+$, found 382.2489, time 0.46 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=12.6 min, 98.6% purity.

EXAMPLE 569

6-[2-(3-Cyclohexylpropyl)-2,3,4,5-tetrahydro-1H-benzo[c]azepin-7-yloxy]nicotinamide

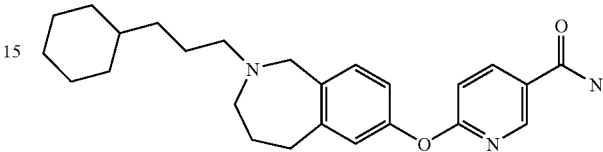

Mix 6-(2,3,4,5-tetrahydro-1H-benzo[c]azepin-7-yloxy) nicotinamide (Example 447, Part E, 0.300 g, 1.06 mmol), K$_2$CO$_3$ (0.366 g, 2.65 mmol), and (3-chloropropyl)cyclohexane (0.179 g, 1.11 mmol) in DMF (5.3 mL). Heat at 50° C. overnight, then increase the temperature to 80° C. for 3.5 hours. Cool the reaction mixture to room temperature and add ethyl acetate (100 mL). Wash with water (1×30 mL), brine (1×30 mL), dry the organic layer over Na$_2$SO$_4$, filter and concentrate. Purify by flash chromatography eluting with 6% to 15% (2.0 M NH$_3$ in methanol) in ethyl acetate to give the title compound: MS ES$^+$ 408.3 (M+H)$^+$, HRMS calcd for C$_{25}$H$_{34}$N$_3$O$_2$ 408.2651 (M+H)$^+$, found 408.2652, time 0.46 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=13.3 min, 100% purity.

EXAMPLE 570

6-[2-(3,3-Dimethylbutyl)-2,3,4,5-tetrahydro-1H-benzo[c]azepin-7-yloxy]nicotinamide

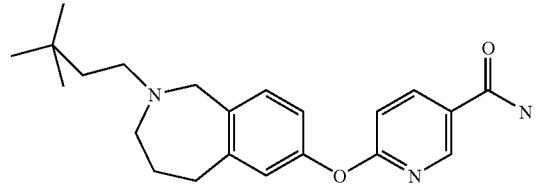

Mix 6-(2,3,4,5-tetrahydro-1H-benzo[c]azepin-7-yloxy) nicotinamide (Example 447, Part E, 0.300 g, 1.06 mmol), K$_2$CO$_3$ (0.366 g, 2.65 mmol), and 1-bromo-3,3-dimethylbutane (0.183 g, 1.11 mmol) in DMF (5.3 mL). Heat at 70° C. overnight. Cool the reaction mixture to room temperature and add ethyl acetate (100 mL). Wash with water (1×30 mL) and brine (1×30 mL). Dry the organic layer over Na$_2$SO$_4$, filter and concentrate. Purify by flash chromatography eluting with 6% to 15% (2.0 M NH$_3$ in methanol) in ethyl acetate to give the title compound: MS ES$^+$ 368.2 (M+H)$^+$, HRMS calcd for C$_{22}$H$_{30}$N$_3$O$_2$ 368.2338 (M+H)$^+$, found 368.2321, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=11.1 min, 96.8% purity.

EXAMPLE 571

6-[2-(2-Ethylbutyl)-2,3,4,5-tetrahydro-1H-benzo[c]azepin-7-yloxy]nicotinamide

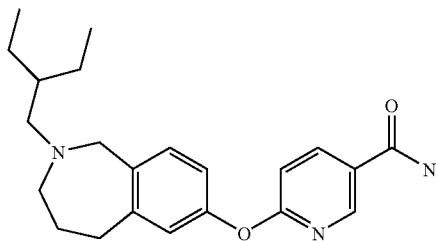

Mix 6-(2,3,4,5-tetrahydro-1H-benzo[c]azepin-7-yloxy)nicotinamide (Example 447, Part E, 0.300 g, 1.06 mmol), $K_2CO_3$ (0.366 g, 2.65 mmol), and 3-bromomethylpentane (0.183 g, 1.11 mmol) in DMF (5.3 mL). Beat at 70° C. overnight. Cool the reaction mixture to room temperature and add ethyl acetate (100 mL). Wash with water (1×30 mL) and brine (1×30 mL). Dry the organic layer over $Na_2SO_4$, filter and concentrate. Purify by flash chromatography eluting with 6% to 15% (2.0 M $NH_3$ in methanol) in ethyl acetate to give the title compound: MS ES$^+$ 368.2 (M+H)$^+$, HRMS calcd for $C_{22}H_{30}N_3O_2$ 368.2338 (M+H)$^+$, found 368.2324, time 0.55 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=10.9 min, 100% purity.

EXAMPLE 572

6-[2-(2-tert-Butoxyethyl)-2,3,4,5-tetrahydro-1H-benzo[c]azepin-7-yloxy]nicotinamide

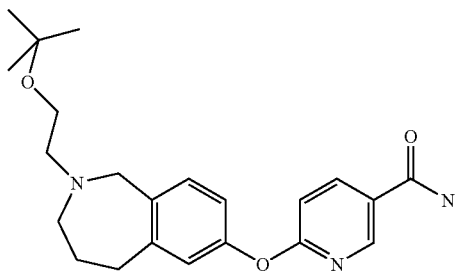

Part A: 2-tert-Butoxyethyl methanesulfonate

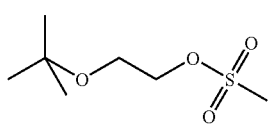

At 0° C. add triethylamine (35.4 mL, 254 mmol) to a stirring solution of 2-tert-butoxyethanol (10.0 g, 84.6 mmol) and methanesulfonic chloride (13.1 mL, 169 mmol) in dichloromethane (169 mL). Allow the reaction mixture to warm to room temperature over night. Dilute the reaction mixture with dichloromethane (200 mL) and wash it with water (1×100 mL), 1.0 N HCl (1×100 mL) and 1.0 N NaOH (1×100 mL). Dry the organic layer over $MgSO_4$, filter and concentrate to give the title compound: $^1$H NMR (CHCl$_3$-d$_6$) 4.33 (t, 2H), 3.62 (t, 2H), 3.06 (s, 3H), 1.21 (s, 9H) GC/MS, $t_R$ 13.7 min, % of total 92.9%.

Part B: 6-[2-(2-tert-Butoxyethyl)-2,3,4,5-tetrahydro-1H-benzo[c]azepin-7-yloxy]nicotinamide

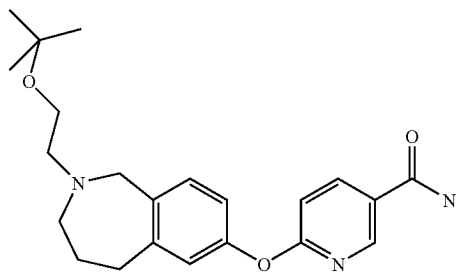

Mix 6-(2,3,4,5-tetrahydro-1H-benzo[c]azepin-7-yloxy)nicotinamide (Example 447, Part E, 0.300 g, 1.06 mmol), $K_2CO_3$ (0.366 g, 2.65 mmol), and 2-tert-butoxyethyl methanesulfonate (0.218 g, 1.11 mmol) in DMF (5.3 mL). Heat at 70° C. overnight. Cool the reaction mixture to room temperature and add ethyl acetate (100 mL). Wash with water (1×30 mL) and brine (1×30 mL). Dry the organic layer over $Na_2SO_4$, filter and concentrate. Purify by flash chromatography eluting with 6% to 15% (2.0 M $NH_3$ in methanol) in ethyl acetate to give the title compound: MS ES$^+$ 384.2 (M+H)$^+$, HRMS calcd for $C_{22}H_{30}N_3O_3$ 384.2287 (M+H)$^+$, found 384.2276, time 0.55 min; HPLC [YMC-Pro pack C-18 (150× 4.6 mm, S-5 microm), 0.05% TFA/acetonitrile in 0.05% TFA/water at 1.0 mL/min, 10-20% over 5 min, 20-95% over 18 min], $t_R$=10.5 min, 97.7% purity.

EXAMPLE 573

6-[2-(4,4,4-Trifluorobutyl)-2,3,4,5-tetrahydro-1H-benzo[c]azepin-7-yloxy]nicotinamide

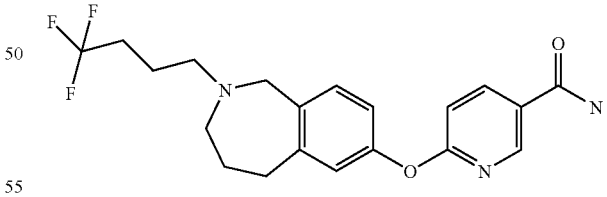

Mix 6-(2,3,4,5-tetrahydro-1H-benzo[c]azepin-7-yloxy)nicotinamide (Example 447, Part E, 0.350 g, 1.24 mmol), $K_2CO_3$ (0.427 g, 3.09 mmol), and 4-bromo-1,1,1-trifluorobutane (0.248 g, 1.30 mmol) in DMF (6.2 mL). Heat at 95° C. for 5.5 hours, then at 50° C. overnight. Cool the reaction mixture to room temperature and add ethyl acetate (100 mL). Wash with water (1×30 mL) and brine (1×30 mL). Dry the organic layer over $Na_2SO_4$, filter and concentrate. Purify by flash chromatography eluting with 6% to 20% (2.0 M $NH_3$ in methanol) in ethyl acetate to give the title compound: MS ES$^+$ 394.2 (M+H)$^+$, HRMS calcd for $C_{20}H_{23}N_3O_2F_3$ 394.1742

(M+H)+, found 394.1733, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18 min], $t_R$=10.1 min, 100% purity.

EXAMPLE 574

6-(2-Butyl-2,3,4,5-tetrahydro-1H-benzo[c]azepin-7-yloxy)nicotinamide

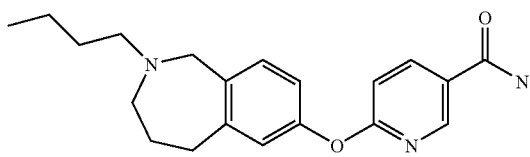

Mix 6-(2,3,4,5-tetrahydro-1H-benzo[c]azepin-7-yloxy)nicotinamide (Example 447, Part E, 0.350 g, 1.24 mmol), $K_2CO_3$ (0.427 g, 3.09 mmol), and 1-bromobutane (0.178 g, 1.30 mmol) in DMF (6.2 mL). Heat at 95° C. for 5.5 hours, then at 50° C. overnight. Cool the reaction mixture to room temperature and add ethyl acetate (100 mL). Wash with water (1×30 mL) and brine (1×30 mL). Dry the organic layer over $Na_2SO_4$, filter and concentrate. Purify by flash chromatography eluting with 6% to 20% (2.0 M $NH_3$ in methanol) in ethyl acetate to give the title compound: MS ES+ 340.2 (M+H)+, HRMS calcd for $C_{20}H_{26}N_3O_2$ 340.2025 (M+H)+, found 340.2019, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min. 20-95% over 18 min], $t_R$=9.6 min, 98.3% purity.

INTERMEDIATES FOR EXAMPLES 575-578

Intermediate 1A

6-Methoxy-1,2,3,4-tetrahydro-isoquinoline

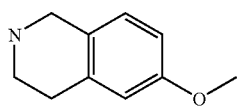

Combine 2-(3-methoxyphenol)ethylamine (10.0 g, 66.13 mmol), 88% Formic acid, and paraformaldehyde (2.05 g, 68.25 mmol) at 0° C. Stir at room temperature for 24 hours and concentrate under reduced pressure. Add acetyl chloride (5 mL) in MeOH (80 mL) at room temperature and stir for 10 minutes. After concentration, triturate the reaction mixture with ethyl acetate, cool to room temperature, and filter to afford 8.76 g, 53.7 mmol (81% yield) of the title compound as a white solid: $^1H$ NMR (500 MHz, $CD_3OD$); 3.05-13.15 (2H, m), 3.45-3.55 (2H, m), 3.70 (3H, s), 4.30 (2H, s), 4.8-5.0 (1H, br s), 6.8-6.9 (2H, m), 7.1-7.2 (1H, m); MS m/z 163 (M+).

Intermediate 2A

6-Hydroxy-1,2,3,4-tetrahydro-isoquinoline
NF7-AOO344-183

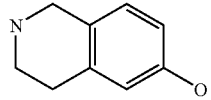

Combine 6-methoxy-1,2,3,4-tetrahydro-isoquinoline (5.0 g, 20.5 mmol) and 48% aq HBr (20 mL) at room temperature. Heat the reaction at reflux for 24 hours, cool the reaction to room temperature, and concentrate under reduced pressure. Triturate with ethyl acetate and filter to afford 5.5 g, 20.5 mmol (99% yield) of the title compound as a tan solid: $^1H$ NMR (500 MHz, DMSO-$d_6$); 2.8-2.9 (2H, m), 3.3-3.4 (2H, m), 4.1 (2H, s), 6.5-6.7 (2H, m), 6.9-7.1 (1H, m), 8.8-9.0 (2H, br s), 9.4-9.5 (1H, s).

Intermediate 3A

6-Hydroxy-3,4-dihydro-1H-isoquinoline-2-carboxylic acid tert-butyl ester

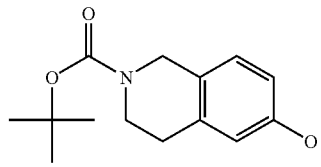

Combine 6-hydroxy-1,2,3,4-tetrahydroisoquinoline (5.5 g, 23.9 mmol), THF (100 mL), $Et_3N$ (8.3 mL, 59.8 mmol), and BOC-anhydride (8.3 g, 28.7 mmol). Stir at room temperature for 72 hours under nitrogen, concentrate under reduced pressure and then flash chromatograph using 1:1 hexanes:ethyl acetate eluent to afford 3.51 g, 14.1 mmol (59% yield) of the title compound: $^1H$ NMR (500 MHz, $CDCl_3$); 1.5 (9H, br s), 2.7-2.8 (2H, m), 3.5-3.6 (2H, m), 4.4 (2H, s), 6.5-6.8 (2H, m), 6.9-7.0 (1H, m); MS m/z 150 (M+1-$CO_2$t-Bu).

Intermediate 4A 6-(4-Cyano-phenoxy)-3,4-dihydro-1H-isoquinoline-2-carboxylic acid tert-butyl ester

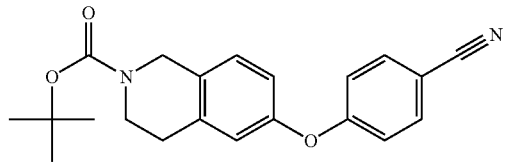

Combine in a round bottom flask equipped with a Dean Stark trap 6-hydroxy-3,4-dihydro-1H-isoquinoline-2-carboxylic acid tert-butyl ester (1.59 g, 6.36 mmol), toluene, dimethylacetamide (10 mL and 30 mL respectively), K$_2$CO$_3$ (1.25 g, 9.04 mmol), and 4-fluorobenzonitrile (0.72 g, 6.04 mmol). Reflux the reaction under a nitrogen atmosphere for 4 hours then cool to room temperature. Add water to the reaction mixture and extract the product from the water layer using ethyl acetate. The product, a white solid, precipitates out from the ethyl acetate to afford 1.93 g, 5.5 mmol (87% yield) of the title compound: $^1$H NMR (500 MHz, CDCl$_3$); 1.5 (9H, s), 2.75-2.85 (2H, m), 3.6-3.7 (2H, m), 4.5 (2H, s), 6.8-6.9 (2H, m), 6.9-7.0 (2H, m), 7.1-7.2 (1H, m), 7.5-7.6 (2H, m); MS m/z 249 (M-CO$_2$t-Bu).

Intermediate 5A 6-(4-Carbamoyl-phenoxy)-3,4-dihydro-1H-isoquinoline-2-carboxylic acid tert-butyl ester NF7-AOO344-181

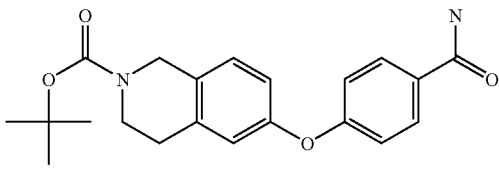

Combine 6-(4-cyano-phenoxy)-3,4-dihydro-1H-isoquinoline-2-carboxylic acid tert-butyl ester (1.93 g, 5.51 mmol), t-butyl alcohol (50 mL), and KOH (1.56 g, 27.6 mmol). Stir for 72 hours at room temperature, concentrate under reduced pressure then add ethyl acetate. Wash the ethyl acetate solution with a brine solution and dry the organic layer over Na$_2$SO$_4$. After concentrating the organic layer under reduced pressure, the reaction affords 1.93 g, 2.50 mmol (95% yield) of the title compound as a white solid:

$^1$H NMR (500 MHz, CDCl$_3$); 1.5 (9H, s), 2.75-2.85 (2H, m), 3.6-3.7 (2H, m), 4.5 (2H, s), 6.8-6.9 (2H, m), 6.9-7.0 (2H, m), 7.1-7.2 (1H, m), 7.7-7.9 (2H, m); TLC R$_f$=0.5 by 2:1 hexanes:ethyl acetate eluent.

Intermediate 6A 4-(1,2,3,4-Tetrahydro-isoquinolin-6-yloxy)-benzamide

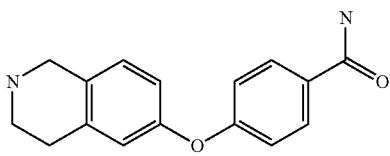

Combine 6-(4-carbamoyl-phenoxy)-3,4-dihydro-1H-isoquinoline-2-carboxylic acid tert-butyl ester (4.0 g, 10.83 mmol), CH$_2$Cl$_2$ (100 mL), and TFA (25 mL) at room temperature. Stir for 24 hours, followed by the addition of 1.0 M K$_2$CO$_3$ (aq), and extract the product out of the aqueous layer with several washings of ethyl acetate/THF. Concentrate the organic phase under reduced pressure and add to 2, 10 g SCX Columns pre-treated with 5% AcOH/MeOH. After several washings of the SCX Columns with MeOH, elute with 1.0 N NH$_3$-MeOH solution to afford 2.08 g, 7.7 mmol (71% yield) of the title compound as a white foam: $^1$H NMR (500 MHz, DMSO-d$_6$); 2.9-3.1 (2H, m), 3.10-3.25 (1H, m), 3.3-3.5 (2H, m), 4.1-4.3 (2H, m), 7.0-7.2 (3H, m), 7.2-7.4 (1H, m), 7.4-7.6 (1H, m), 8.0-8.1 (1H, m), 8.2-8.4 (1H, m), 8.5-8.65 (1H, m), 9.2-9.4 (2H, m); MS m/z 269 (M+1).

EXAMPLE 575

4-(2-Pentyl-1,2,3,4-tetrahydro-isoquinolin-6-yloxy)-benzamide

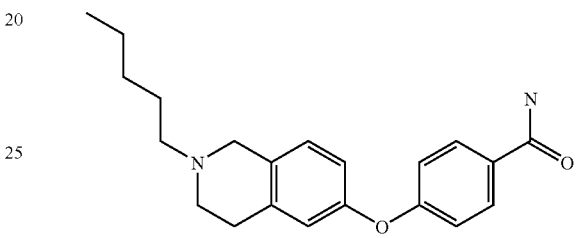

Combine 4-(1,2,3,4-tetrahydro-isoquinolin-6-yloxy)-benzamide (80.0 mg, 0.30 mmol), DMF (4 mL), Et$_3$N (0.2 mL, 1.32 mmol), and pentylbromide (0.1 mL, 0.66 mmol) in a 7 mL vial. Place the vial on a shaker at 70° C. for 72 hours and then add ethyl acetate to the reaction vial. Wash with water and several times with 10% LiCl (aq), and dry over Na$_2$SO$_4$. Concentrate the organic mixture and flash chromatograph using 2% 1.0 N NH$_3$ in MeOH, 20% THF, 78% CH$_2$Cl$_2$ to afford 78.0 mg (77% yield) of the title compound: $^1$H NMR (500 MHz, CDCl$_3$); 0.9-1.0 (3H, m), 1.3-1.4 (4H, m), 1.5-1.7 (2H, m), 2.4-2.6 (2H, m), 2.7-2.8 (2H, m), 2.8-3.0 (2H, m), 3.5-3.6 (2H, m), 6.8-6.8 (2H, m), 6.9-7.1 (3H, m), 7.7-7.9 (2H, m); MS m/z 339 (M+1).

EXAMPLE 576

4-[2-(3-Methyl-butyl)-1,2,3,4-tetrahydro-isoquinolin-6-yloxy]-benzamide

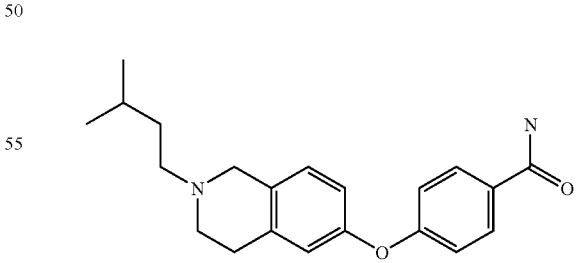

Using a method similar to Example 575, using isoamylbromide (0.1 mL, 0.66 mmol) gives 63.0 mg (62% yield) of the title compound: $^1$H NMR (500 MHz, CDCl$_3$); 0.9-1.0 (6H, m), 1.4-1.8 (3H, m), 2.5-2.6 (2H, m), 2.7-2.8 (2H, m), 2.9-3.0 (2H, m), 3.6-3.8 (2H, m), 6.8-7.1 (5H, m), 7.7-7.9 (2H, m); MS m/z 339 (M+1).

EXAMPLE 577

4-(2-Benzyl-1,2,3,4-tetrahydro-isoquinolin-6-yloxy)-benzamide

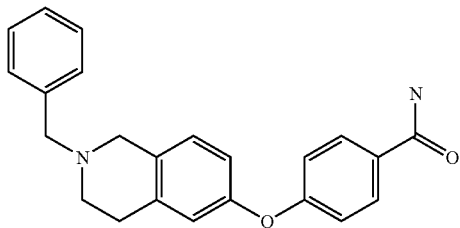

Using a method similar to Example 575, using benzylbromide (0.1 mL, 0.66 mmol) gives 81.0 mg (75% yield) of the title compound: $^1$H NMR (500 MHz, CDCl$_3$); 2.6-2.8 (2H, m), 2.8-3.0 (2H, m), 3.5-3.7 (4H, m), 5.6-6.1 (2H, br s), 6.7-6.8 (2H, m), 6.8-7.0 (3H, m), 7.2-7.4 (5H, m), 7.7-7.9 (2H, m); MS m/z 359 (M+1).

EXAMPLE 578

4-(5-Phenethyl-1,2,3,4-tetrahydro-isoquinolin-6-yloxy)-benzamide

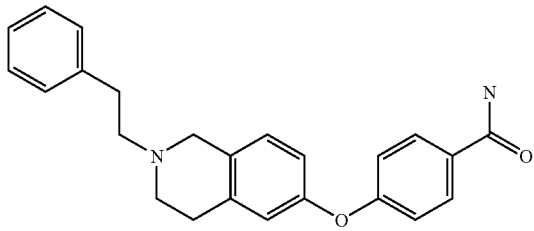

Using a method similar to Example 575, using intermediate 1A, and phenethylbromide (0.1 mL, 0.66 mmol) gives 81.9 mg (73% yield) of the title compound: $^1$H NMR (500 MHz, CDCl$_3$); 2.7-3.0 (7H, m), 3.6-3.8 (3H, m), 5.8-6.2 (2H, br s), 6.8-7.1 (5H, m), 7.2-7.4 (5H, m), 7.7-7.9 (2H, m); MS m/z 373 (M+1).

Intermediate 7A 6-(5-Carbamoyl-pyridin-2-yloxy)-3,4-dihydro-1H-isoquinoline-2-carboxylic acid tert-butyl ester

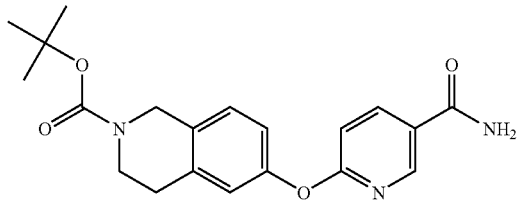

Combine in a round bottom flask equipped with a Dean Stark trap 6-hydroxy-3,4-dihydro-1H-isoquinoline-2-carboxylic acid tert-butyl ester (5.42 g, 21.74 mmol), toluene, dimethylacetamide (30 mL and 90 mL respectively), K$_2$CO$_3$ (4.51 g, 32.61 mmol), and 6-chloronicatinamide (3.40 g, 21.74 mmol). Reflux the reaction under a nitrogen atmosphere for 4 hours then cool to room temperature. Add water to the reaction mixture and extract the product from the water layer using ethyl acetate. The product, a white solid, precipitates out from the ethyl acetate to afford 5.8 g, 15.7 mmol (72% yield) of the title compound: $^1$H NMR (500 MHz, DMSO-d$_6$); 1.4 (9H, s), 2.7-2.9 (2H, m), 3.5-3.6 (2H, m), 4.4-4.6 (2H, m), 6.9-7.0 (2H, m), 7.0-7.1 (1H, m), 7.2-7.3 (1H, m), 7.5 (1H, s), 8.1 (1H, s), 8.2-8.3 (1H, m), 8.6 (1H, m).

Intermediate 8A 6-(1,2,3,4-Tetrahydro-isoquinolin-6-yloxy)-nicotinamide

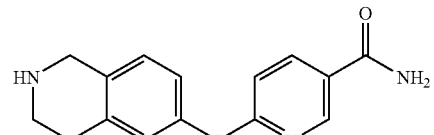

Combine 6-(5-carbamoyl-pyridin-2-yloxy)-3,4-dihydro-1H-isoquinoline-2-carboxylic acid tert-butyl ester (4.0 g, 10.83 mmol), CH$_2$Cl$_2$ (100 mL), and TFA (25 mL). Stir at room temperature for 12 hours and add 1.0 M K$_2$CO$_3$ and CHCl$_3$ to the reaction. Separate the organic layer, wash with brine, and dry over Na$_2$SO$_4$. Concentrate under reduced pressure and add mixture to 2, 10 g SCX columns, wash with MeOH, and elute with 1.0 N NH$_3$ in MeOH. Concentrate to afford 2.91 g, 10.8 mmol (71% yield) of the title compound as a white foam: $^1$H NMR (500 MHz, DMSO-d$_6$): 2.9-3.1 (2H, m), 3.2-3.5 (2H, m), 4.2-4.4 (2H, m), 6.9-7.2 (3H, m), 7.2-7.4 (1H, m), 7.4-7.6 (1H, m), 7.9-8.1 (1H, m), 8.2-8.4 (1H, m), 8.5-8.7 (1H, m), 8.2-9.4 (2H, m); MS m/z/269 (M+1).

EXAMPLE 579

6-(2-Phenethyl-1,2,3,4-tetrahydro-isoquinolin-6-yloxy)-nicotinamide

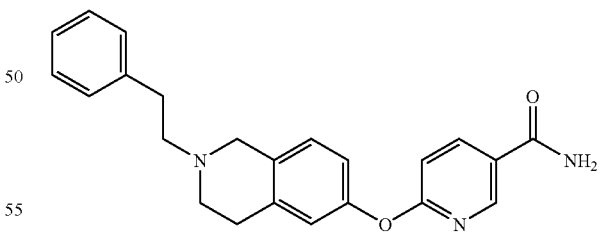

Combine 6-(1,2,3,4-tetrahydro-isoquinolin-6-yloxy)-nicotinamide (46.9 mg, 0.17 mmol), DMF (3 mL). Et$_3$N (0.1 mL, 0.77 mmol), and phenethylbromide (52 uL, 0.38 mmol) in a 7 mL vial. Place the reaction vial on a shaker at 70° C. for 72 hours, and then add water and ethyl acetate. Wash the ethyl acetate layer several times with water, 10% LiCl, and dry over Na$_2$SO$_4$. Concentrate organic mixture and flash chromatograph using 30% THF, 4% 1.0 N NH$_3$ in MeOH, 76% CH$_2$Cl$_2$ to afford 23.2 mg, (37% yield) of the title compound: MS m/z 374 (M+1).

By the method of example 579 the following compounds were prepared and isolated as the free base:

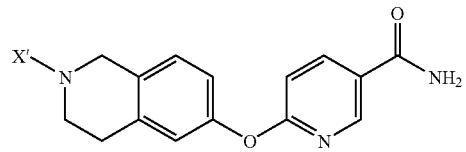

| No.: | X' | Name of the Final Compound | Data |
|---|---|---|---|
| 580 | Benzyl | 6-(2-Benzyl-1,2,3,4-tetrahydro-isoquinoline-6-yloxy)-nicotinamide | Mass spectrum (ion spray): m/z = 360 (M + 1); $^1$H NMR (500 MHz, (CDCl$_3$) 2.7-3.0 (4H, m), 3.6-3.8 (4H, m), 6.8-7.1 (3H, m), 7.2-7.5 (4H, m), 8.1-8.2 (1H, m), 8.5-8.7 (1H, s) |
| 581 | Pentyl | 6-(2-Pentyl-1,2,3,4-tetrahydro-isoquinoline-6-yloxy)-nicotinamide | Mass spectrum (ion spray): m/z = 340 (M + 1); $^1$H NMR (500 MHz, (CDCl$_3$) 0.8-1.0 (3H, m), 1.2-1.4 (4H, m), 1.5-1.7 (2H, m), 2.4-2.6 (2H, m), 2.7-2.8 (2H, m), 2.8-3.0 (2H, m), 3.6-3.7 (2H, m), 5.8-6.3 (1H, br d), 6.8-7.1 (4H, m), 8.1-8.2 (1H, m), 8.5-8.7 (1H, s) |
| 582 | 2-1H-Indol-3-yl-ethyl | 6-[2-(2-1H-Indol-3-yl-ethyl)-1,2,3,4-tetrahydro-isoquinolin-6-yloxy]-nicotinamide | Mass spectrum (ion spray): m/z = 413 (M + 1); |
| 583 | 2-(3-Chloro-benzyl) | 6-[2-(3-Chloro-benzyl)-1,2,3,4-tetrahydro-isoquinoline-6-yloxy]-nicotinamide | Mass spectrum (ion spray): m/z = 394 (M + 1) |
| 584 | 2-(2-Carbamoyl-ethyl) | 6-[2-(2-Carbamoyl-ethyl)-1,2,3,4-tetrahydro-isoquinolin-6-yloxy]-nicotinamide | Mass spectrum (ion spray): m/z = 341 (M + 1); |
| 585 | 2-(2-Phenylsulfanyl-ethyl) | 6-[2-(2-Phenylsulfanyl-ethyl)-1,2,3,4-tetrahydro-isoquinolin-6-yloxy]-nicotinamide | Mass spectrum (ion spray): m/z = 406 (M + 1); |
| 586 | 2-(3-Methyl-butyl) | 6-[2-(3-Methyl-butyl)-1,2,3,4-tetrahydro-isoquinolin-6-yloxy]-nicotinamide | Mass spectrum (ion spray): m/z = 340 (M + 1); |
| 587 | 2-(4-Trifluoromethyl-enzyl) | 6-[2-(4-Trifluoromethyl-benzyl)-1,2,3,4-tetrahydro-isoquinolin-6-yloxy]-nicotinamide | Mass spectrum (ion spray): m/z = 428 (M + 1); |
| 588 | 2-(3-Chloro-benzyl) | 6-[2-(3-Chloro-benzyl)-1,2,3,4-tetrahydro-isoquinolin-6-yloxy]-nicotinamide | Mass spectrum (ion spray): m/z = 394 (M + 1); |
| 589 | 2-(3-Phenyl-allyl) | 6-[2-(3-Phenyl-allyl)-1,2,3,4-tetrahydro-isoquinolin-6-yloxy]-nicotinamide | Mass spectrum (ion spray): m/z = 386 (M + 1); |
| 590 | 2-(5-Chloro-benzo[b]thiophen-3-ylmethyl | 6-[2-(5-Chloro-benzo[b]thiophen-3-ylmethyl-1,2,3,4-tetrahydro-isoquinolin-6-yloxy)-nicotinamide | Mass spectrum (ion spray): m/z = 450 (M + 1) |
| 591 | 2-Cyclopropylmethyl | 6-(2-Cyclopropylmethyl-1,2,3,4-tetrahydro-isoquinolin-6-yloxy)-nicotinamide | Mass spectrum (ion spray): m/z = 324 (M + 1); |
| 592 | 2-(3,5-Bis-trifluoromethyl-benzyl) | 6-[2-(3,5-Bis-trifluoromethyl-benzyl)-1,2,3,4-tetrahydro-isoquinolin-6-yloxy]-nicotinamide | Mass spectrum (ion spray): m/z = 496 (M + 1); |
| 593 | 2-(3-Bromo-benzyl) | 6-[2-(Bromo-benzyl)-1,2,3,4-tetrahydro-isoquinolin-6-yloxy]-nicotinamide | Mass spectrum (ion spray): m/z = 438 (M); |
| 594 | 2-(4-Methyl-benzyl) | 6-[2-(4-Methyl-benzyl)-1,2,3,4-tetrahydro-isoquinolin-6-yloxy]-nicotinamide | Mass spectrum (ion spray): m/z = 374 (M + 1); |
| 595 | 2-(2-Fluoro-benzyl) | 6-[2-(2-Fluoro-benzyl)-1,2,3,4-tetrahydro-isoquinolin-6-yloxy]-nicotinamide | Mass spectrum (ion spray): m/z = 378 (M + 1); |
| 596 | 2-(3-Methoxy-benzyl) | 6-[2-(3-Methoxy-benzyl)-1,2,3,4-tetrahydro-isoquinolin-6-yloxy]-nicotinamide | Mass spectrum (ion spray): m/z = 390 (M + 1); |
| 597 | 2-(1H-Benzoimidazol-2-ylmethyl) | 6-[2-(1H-Benzoimidazol-2-ylmethyl)-1,2,3,4-tetrahydro-isoquinolin-6-yloxy]-nicotinamide | Mass spectrum (ion spray): m/z = 400 (M + 1): |
| 598 | 2-(5-Chloro-thiophen-2-ylmethyl) | 6-[2-(5-Chloro-thiophen-2-ylmethyl)-1,2,3,4-tetrahydro-isoquinolin-6-yloxy]-nicotinamide | Mass spectrum (ion spray): m/z = 400 (M + 1); |
| 599 | 2-(2,6-Dichloro-benzyl) | 6-[2-(2,6-Dichloro-benzyl)-1,2,3,4-tetrahydro-isoquinolin-6-yloxy]-nicotinamide | Mass spectrum (ion spray): m/z = 428 (M): |
| 600 | 2-(3-Fluoro-benzyl) | 6-[2-(3-Fluoro-benzyl)-1,2,3,4-tetrahydro-isoquinolin-6-yloxy]-nicotinamide | Mass spectrum (ion spray): m/z = 378 (M + 1); |
| 601 | 2-[2-(4-Methoxy-phenyl)-ethyl] | 6-{2-[2-(4-Methoxy-phenyl)-ethyl]-1,2,3,4-tetrahydro-isoquinolin-6-yloxy}nicotinamide | Mass spectrum (ion spray): m/z = 404 (M + 1); |
| 602 | 3-Propionic acid | 3-[6-(5-Carbamoyl-pyridin-2-yloxy)-3,4-dihydro-1H-isoquinolin-2yl]-propionic acid | Mass spectrum (ion spray): m/z = 342 (M + 1); |
| 603 | 2-(3-Piperidin-1-yl-propyl) | 6-[2-(3-Piperidin-1-yl-propyl)-1,2,3,4-tetrahydro-isoquinolin-6-yloxy]-nicotinamide | Mass spectrum (ion spray): m/z = 395 (M + 1); |
| 604 | 2-Pent-4-ynyl | 6-(2-Pent-4-ynyl-1,2,3,4-tetrahydro-isoquinolin-6-yloxy)-nicotinamide | Mass spectrum (ion spray): m/z = 336 (M + 1); |
| 605 | 2-(2-Piperidin-1-yl-ethyl) | 6-[2-(2-Piperidin-1-yl-ethyl)-1,2,3,4-tetrahydro-isoquinolin-6-yloxy]-nicotinamide | Mass spectrum (ion spray): m/z = 381 (M + 1); |
| 606 | 2-(2-Diisopropylamino-ethyl) | 6-[2-(2-Diisopropylamino-ethyl)-1,2,3,4-tetrahydro-isoquinolin-6-yloxy]-nicotinamide | Mass spectrum (ion spray): m/z = 397 (M + 1); |
| 607 | 2-(3,3,4,4-Tetrafluoro-butyl) | 6-[2-(3,3,4,4-Tetrafluoro-butyl)-1,2,3,4-tetrahydro-isoquinolin-6-yloxy]-nicotinamide | Mass spectrum (ion spray): m/z = 398 (M + 1); |

-continued

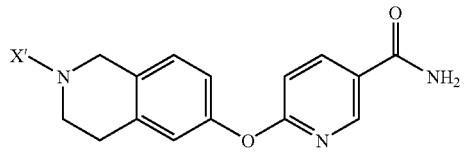

| No.: | X' | Name of the Final Compound | Data |
|---|---|---|---|
| 608 | 2-Cyclobutylmethyl | 6-(2-Cyclobutylmethyl-1,2,3,4-tetrahydro-isoquinolin-6-yloxy)-nicotinamide | Mass spectrum (ion spray): m/z = 338 (M + 1); |
| 609 | 2-(3,3-Dimethyl-butyl) | 6-[2-(3,3-Dimethyl-butyl)-1,2,3,4-tetrahydro-isoquinolin-6-yloxy]-nicotinamide | Mass spectrum (ion spray): m/z = 354 (M + 1); |
| 610 | 2-(3,4,4-Trifluoro-but-3-enyl) | 6-[2-(3,4,4-Trifluoro-but-3-enyl)-1,2,3,4-tetrahydro-isoquinolin-6-yloxy]-nicotinamide | Mass spectrum (ion spray): m/z = 378 (M + 1); |
| 611 | 2-(2-Methoxy-benzyl) | 6-[2-(2-Methoxy-benzyl)-1,2,3,4-tetrahydroisoquinolin-6-yloxy]-nicotinamide | Mass spectrum (ion spray): m/z = 390 (M + 1); |
| 612 | 2-Pyridin-3-ylmethyl | 6-(2-Pyridin-3-ylmethyl-1,2,3,4-tetrahydro-isoquinolin-6-yloxy)-nicotinamide | Mass spectrum (ion spray): m/z = 361 (M + 1); |

Intermediate 9A

[2-(3-Methoxy-phenyl)-ethyl]-carbamic acid methyl ester

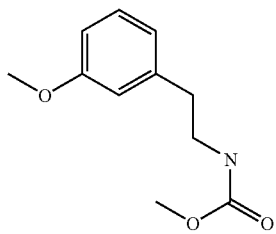

Combine 2-(3-methoxyphenyl)ethylamine (9.6 mL, 66.1 mmol), THF (300 mL), Et$_3$N (11.0 mL, 78.9 mmol), and methyl chloroformate (26.0 mL, 339 mmol) at 0° C. under nitrogen atmosphere. Stir at room temperature for 18 hours, add the mixture into water, wash with brine, and dry the organic layer over Na$_2$SO$_4$ followed by concentrating under reduced pressure. Flash chromatograph using 2:1 hexanes: ethyl acetate to afford 13.6 g, 65.0 mmol (98% yield) of the title compound: $^1$H NMR (500 MHz, CDCl$_3$); 2.8 (2H, t, J=6.7, 7.0 Hz), 3.41-3.46 (2H, m), 3.7 (3H, s), 3.8 (3H, s), 4.6-4.8 (1H, br s), 6.7-6.8 (3H, m), 7.2-7.3 (1H, m); MS m/z 210 (M+1).

Intermediate 10A

8-Methoxy-3,4-dihydro-2H-isoquinolin-1-one

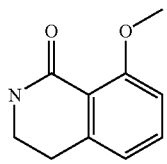

Combine polyphosphoric acid (30 g) at 180° C. and [2-(3-methoxy-phenyl)-ethyl]-carbamic acid methyl ester (3.0 g, 14.33 mmol). Stir for 15 minutes then add to a beaker of ice. Extract the product from the water using CH$_2$Cl$_2$ and CHCl$_3$. Dry the organic layer over Na$_2$SO$_4$ and then concentrate under reduced pressure. Flash chromatograph using 5% MeOH in ethyl acetate to afford 0.340 g, 1.92 mmol (13% yield) of the title compound: $^1$H NMR (500 MHz, CDCl$_3$); 2.92 (2H, t, J=6.4 Hz), 3.43-3.47 (2H, m), 3.85 (3H, s), 6.2-6.3 (1H, br s), 6.8-6.9 (2H, m), 7.3-7.4 (1H, m), 7.5-7.6 (2H, m); MS m/z 178 (M+1).

Intermediate 11A

8-Methoxy-1,2,3,4-tetrahydro-isoquinoline

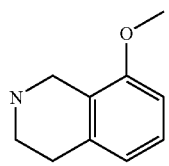

Combine 8-methoxy-3,4-dihydro-2H-isoquinolin-1-one (0.778 g, 4.40 mmol), THF (20 mL), and LiAlH$_4$ (0.333 g, 8.8 mmol) at 0° C. under nitrogen atmosphere. After 30 minutes of the reaction, reflux for 2 hours and then cool to room temperature. Quench the reaction by adding water and 1.0 M NaOH at 0° C. and stirring for 12 hours at room temperature. Filter the reaction through Celite® and elute with THF. After concentrating the filtrate under reduced pressure, add the mixture to a 10 g SCX column pre-treated with 5% AcOH/MeOH. After rinsing several times with MeOH, elute the product using 1.0 N NH$_3$-MeOH followed by concentration under reduced pressure to afford 0.665 g, 4.07 mmol (93% yield) of the title compound as a tan oil: $^1$H NMR (500 MHz, CDCl$_3$); 1.7-2.0 (1H, b s), 2.77 (2H, t, J=5.86 Hz), 3.09 (2H, t, J=5.86 Hz), 3.8 (3H, s), 3.95 (2H, s), 6.6-6.8 (2H, m), 7.0-7.15 (1H, m); TLC 5% MeOH:ethyl acetate R$_f$=0.1

Intermediate 12A 1,2,3,4-Tetrahydro-isoquinolin-8-ol

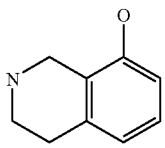

Combine 8-methoxy-tetrahydroisoquinoline (665.7 mg, 4.08 mmol) and 48% HBr at room temperature. Reflux the reaction for 3 hours and then cool to room temperature. Recrystallize the product from EtOH and diethyl ether to afford 754.2 mg, 3.28 mmol (80% yield) of the title compound as a tarnish white solid: $^1$H NMR (500 MHz, DMSO-d$_6$); 2.9 (2H, t, J=6.16, 5.86 Hz), 3.2-3.4 (2H, m), 4.0 (2H, s), 6.6-6.8 (2H, m), 7.0-7.1 (1H, m), 8.8-9.1 (2H, br m), 9.9 (1H, s); MS m/z 148 (M−1).

Intermediate 13A

8-Hydroxy-3,4-dihydro-1H-isoquinoline-2-carboxylic acid tert-butyl ester

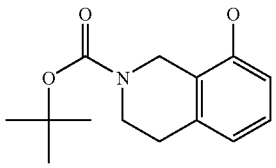

Combine 8-hydro-oxy tetrahydro-isoquinoline HBr salt (754.2 mg, 3.28 mmol), and Et$_3$N (2.8 mL, 19.68 mmol), anhydrous THF (20 mL), and BOC-anhydride (1.14 g, 3.94 mmol). Stir the reaction at room temperature for 72 hours followed by an aqueous work-up. Wash the organic layer with brine and dry over Na$_2$SO$_4$. After concentrating the organic layer under reduced pressure, flash chromatograph using 4:1 hexanes:ethyl acetate eluent to afford 249.6 mg, 1.01 mmol (31% yield) of the title compound as a white foam: $^1$H NMR (500 MHz, CDCl$_3$); 1.5 (9H, s), 2.73-2.79 (2H, m), 3.5-3.6 (2H, m), 4.45-4.61 (2H, b s), 6.6-6.9 (2H, m), 6.9-7.2 (1H, m); TLC 4:1 hexanes:ethyl acetate R$_f$=0.13

Intermediate 14A 8-(5-Carbamoyl-pyridin-2-yloxy)-3,4-dihydro-1H-isoquinoline-2-carboxylic acid tert-butyl ester

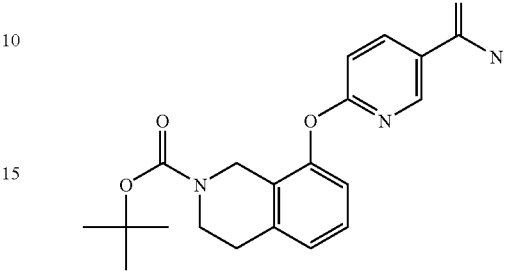

Combine in a 100 mL round bottom flask equipped with a stir bar, a Dean Stark trap, and a reflux condenser 8-hydroxy-3,4-dihydro-1H-isoquinoline-2-carboxylic acid tert-butyl ester (249.6 mg, 1.01 mmol), dimethylacetamide (30 mL), toluene (10 mL), K$_2$CO$_3$ (814.74 mg, 5.90 mmol), and 6-chloronicatinamide (626.28 mg, 4.0 mmol). Reflux the reaction under nitrogen for 5 hours. After cooling to room temperature, add water to the reaction mixture and extract the product using ethyl acetate. Wash the organic layer with brine and dry over Na$_2$SO$_4$. After concentrating under reduced pressure, flash chromatograph using 20% THF in CH$_2$C$_{12}$ to afford 245.1 mg, 0.66 mmol (66% yield) of the title compound: $^1$H NMR (500 MHz, CD$_3$OD); 1.3-1.5 (9H, m), 2.9 (2H, m), 3.5-3.7 (2H, m), 3.85 (2H, s), 6.9-7.0 (1H, m), 7.1-7.2 (1H, m), 7.2-7.3 (1H, m), 7.5-7.6 (1H, m), 8.2-8.3 (1H, n), 8.6-8.7 (H, br s), 8.8 (1H, s); MS m/z 370 (M+1).

Intermediate 15A 6-(1,2,3,4-Tetrahydro-isoquinolin-8-yloxy)-nicotinamide

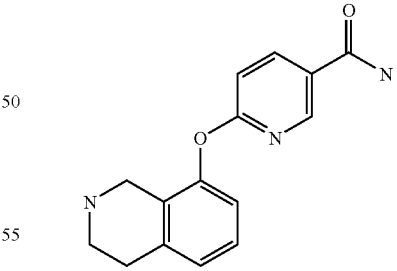

Combine S-(5-carbamoyl-pyridin-2-yloxy)-3,4-dihydro-1H-isoquinoline-2-carboxylic acid tert-butyl ester (249.6 mg, 1.01 mmol), CH$_2$Cl$_2$ (25 mL), and TFA (10 mL) at room temperature under nitrogen atmosphere. Stir for 12 hours then concentrate under reduced pressure. Solubilize the mixture in MeOH and add to a 2 g SCX Column (pre-treated with 5% AcOH-MeOH), wash several times with MeOH, and elute with 1.0 N NH$_3$ in MeOH to afford 156.1 mg, 0.58 mmol (57% yield) of the title compound.

EXAMPLE 613

6-(2-Phenethyl-1,2,3,4-tetrahydro-isoquinolin-8-yloxy)-nicotinamide

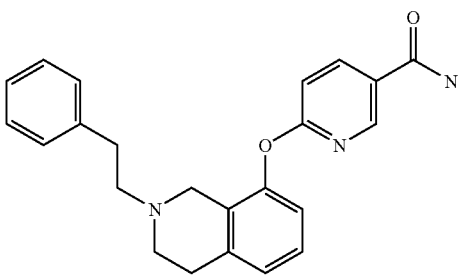

Using a method similar to Example 24, using phenethyl-bromide (40 uL, 0.28 mmol) gives 26.9 mg (55% yield) of the title compound: $^1$H NMR (500 MHz, CDCl$_3$); 1.8-2.1 (4H, m), 2.7-3.0 (6H, m), 5.9-6.3 (2H, br d), 6.8-7.4 (10H, m), 8.1-8.3 (1H, m), 8.5 (1H, s);
MS m/z 374 (M+1).

EXAMPLE 614

6-(2-Benzyl-1,2,3,4-tetrahydro-isoquinolin-8-yloxy)-nicotinamide

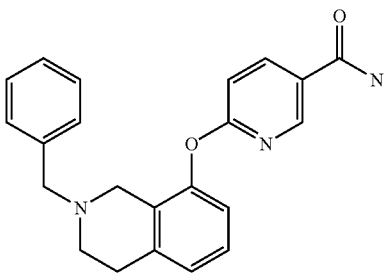

Using a method similar to Example 24, using benzylbromide (0.1 mL, 0.97 mmol) gives 45.6 mg (63% yield) of the title compound.

EXAMPLE 615

6-(2-Pentyl-1,2,3,4-tetrahydro-isoquinolin-8-yloxy)-nicotinamide

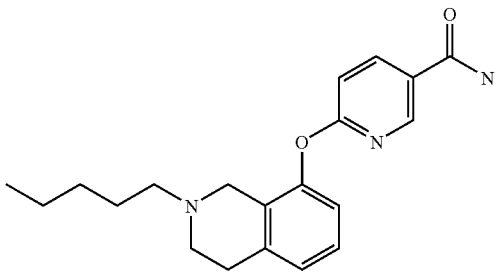

Using a method similar to Example 24, using pentylbromide (54 uL, 0.48 mmol) gives 32.5 mg (48% yield) of the title compound: $^1$H NMR (500 MHz, CD$_3$OD); 0.8 (3H, t), 1.2-1.3 (4H, m), 1.4-1.6 (2H, m), 2.3-2.5 (2H, m), 2.7 (2H, t), 2.9-3.0 (2H, m), 3.5 (2H, s), 6.8-7.2 (5H, m), 8.1-8.2 (1H, m), 8.6 (1H, s); MS m/z 340 (M+1).

Intermediate 16A 1,2-Bis-bromomethyl-4-methoxy-benzene

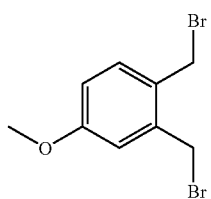

Combine 3,4-dimethylanisole (2.72 g, 20.0 mmol), CCl$_4$ (50 mL), NBS (7.12 g, 40.0 mmol), and benzoyl peroxide (40.0 mg, 0.17 mmol). Reflux the reaction for 12 hours and then cool to room temperature and concentrate under reduced pressure. Flash chromatograph using 4:1 CHCl$_3$:hexanes eluent to afford 1.90 g, 6.4 mmol (32% yield) of the title compound: $^1$H NMR (500 MHz, CDCl$_3$); 3.8 (3H, s), 4.6 (2H, s), 4.7 (2H, s), 6.8-6.9 (2H, m), 7.1-7.4 (1H, m); TLC 4:1 CHCl$_3$:hexanes R$_f$=0.67

Intermediate 17A

2-Benzyl-5-methoxy-2,3-dihydro-1H-isoindol

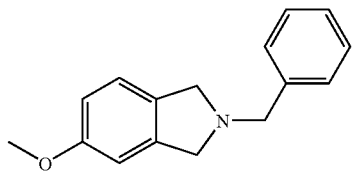

Combine in a round bottom flask 1,2-bis-bromomethyl-4-methoxy-benzene (1.0 g, 3.40 mmol), benzyltriethylammonium chloride (73.5 mg, 3.2 mmol), 50% NaOH (aq)/toluene (3.0 mL/14 mL), and then drop wise add benzylamine (0.37 mL, 3.39 mmol). Stir the reaction at room temperature for 3 hours, add to ethyl acetate, wash with water, brine, and dry over Na$_2$SO$_4$. After concentrating under reduced pressure, add the mixture to a 10 g SCX column, wash with MeOH, and elute with 1.0 N NH$_3$-MeOH. Flash chromatograph using 3:1 hexanes:ethyl acetate to afford 580.0 mg, 2.42 mmol (71% yield) of the title compound as a brown oil: $^1$H NMR (500

MHz, CDCl$_3$); 3.7 (3H, s), 3.9-4.0 (6H, m), 6.7-6.8 (2H, m), 7.1 (1H, d), 7.3-7.5 (5H, m); MS m/z 238 (M−1).

Intermediate 18A

2-Benzyl-2,3-dihydro-1H-isoindol-5-ol

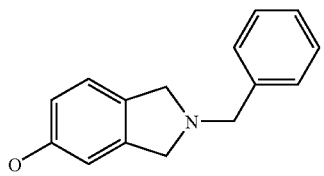

Combine 2-benzyl-5-methoxy-2,3-dihydro-1H-isoindol (580.0 mg, 2.42 mmol) and 48% HBr (aq) (20 mL). Reflux the reaction for 5 hours and then cool to room temperature. Concentrate the reaction mixture under reduced pressure then add to 5 g SCX column. Wash the column with MeOH and elute with 1.0 N NH$_3$-MeOH to afford 265.4 mg 1.17 mmol) (49% yield) of the title compound as a brown solid: $^1$H NMR (500 MHz, CD$_3$OD); 3.8-3.9 (4H, m), 3.91 (2H, s), 6.6-6.7 (2H, m), 7.0 (1H, d), 7.2-7.5 (5H, m); MS m/z 226 (M+1).

EXAMPLE 616

6-(2-Benzyl-2,3-dihydro-1H-isoindol-5-yloxy)-nicotinamide

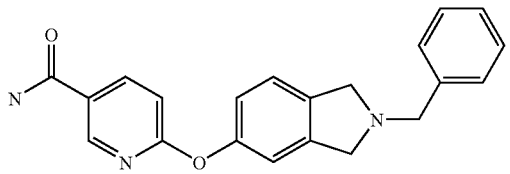

Combine in a round bottom flask equipped with a stir bar and a Dean Stark trap under a nitrogen atmosphere 2-benzyl-2,3-dihydro-1H-isoindol-5-ol (265.4 mg, 1.18 mmol), toluene (10 mL), DMA (30 mL), K$_2$CO$_3$ (244.6 mg, 1.77 mmol), and 6-chloronicatinamide (184.4 mg, 1.18 mmol). Reflux the reaction for 6 hours and then cool to room temperature. Add ethyl acetate, wash the ethyl acetate layer several times with water, brine, and dry over Na$_2$SO$_4$. After concentrating under reduced pressure, purify the mixture by reverse phase chromatography (5% to 95% (0.01% TFA buffer in acetonitrile)/water) to afford 333.4 mg, 0.97 mmol (82% yield) of the title compound as a white foam: $^1$H NMR (500 MHz, CD$_3$OD); 4.6-4.8 (6H, m), 7.0 (1H, d), 7.1-7.2 (2H, m), 7.4-7.6 (6H, m), 8.2 (1H, d), 8.6 (1H, s); MS m/z 346 (M+1).

Intermediate 19A 6-(2,3-Dihydro-1H-isoindol-5-yloxy)-nicotinamide

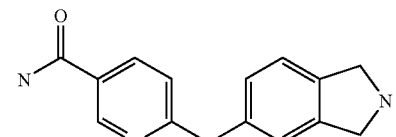

Combine 6-(2-benzyl-2,3-dihydro-1H-isoindol-5-yloxy)-nicotinamide (230.0 mg, 0.67 mmol), EtOH (5 mL), and 10% Pd—C (45.0 mg) and place under a hydrogen balloon. Stir the reaction at room temperature for 168 hours at atmospheric pressure. Filter the reaction mixture through a pad of Celite® using MeOH eluent and then concentrate the filtrate under reduced pressure. Add the mixture to a 2 g SCX column, wash with MeOH, and elute using 1.0 N NH$_3$—MeOH. After concentrating under reduced pressure, purify the mixture by flash chromatography using 10% 1.0 N NH$_3$-MeOH/DCM eluent to afford 19.2 mg, 0.08 mmol (11% yield) of the title compound as a white solid: $^1$H NMR (500 MHz, CD$_3$OD); 4.1-4.3 (4H, br m), 6.9-7.1 (3H, m), 7.3-7.4 (1H, m), 8.2-8.3 (1H, m), 8.6 (1H, s); MS m/z 254 (M−1).

EXAMPLE 617

6-(2-Phenethyl-2,3-dihydro-1H-isoindol-5-yloxy)-nicotinamide

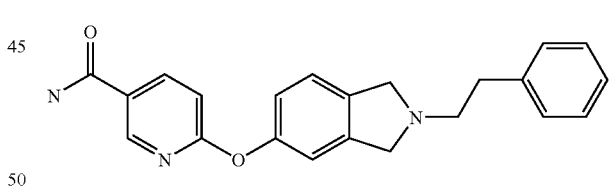

Combine 6-(2,3-dihydro-1H-isoindol-5-yloxy)-nicotinamide (19.2 mg, 0.08 mmol), DMF (3 mL), Et$_3$N (46 uL, 0.33 mmol), and 2-phenethylbromide (23 uL, 0.165 mmol). Place the reaction on a shaker for 12 hours at 70° C., then cool to room temperature and concentrate under reduced pressure. Add the mixture to a 2 g SCX column, wash with MeOH, and then elute with 1.0 N NH$_3$-MeOH. After concentrating the mixture, purify using reverse phase chromatography (5% to 95% (0.001% TFA buffer in acetonitrile)/water) to afford 9.5 mg, 0.03 mmol (33% yield) of the title compound: $^1$H NMR (500 MHz, CD$_3$OD); 2.8-3.2 (4H, m), 4.1-4.2 (4H, m), 6.8-7.1 (3H, m), 7.2-7.4 (6H, m), 8.2 (1H, d), 8.6 (1H, s); MS m/z 358 (M−1).

EXAMPLES 618-636

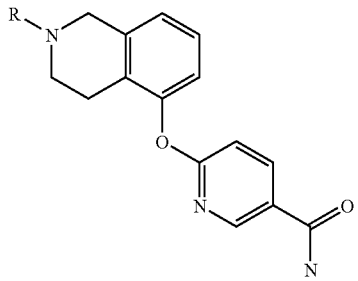

Examples 618-625

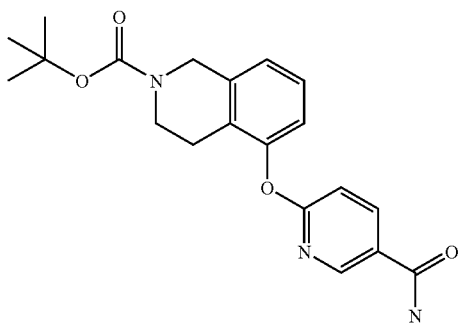

Examples 626-639

EXAMPLE 618

5-(5-Carbamoyl-pyridin-2-yloxy)-3,4-dihydro-1H-isoquinoline-2-carboxylic acid ter-butyl ester

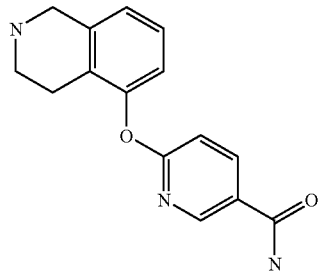

Combine 5-hydroxy, 3,4-dihydro-1H-isoquinoline-2-carboxylic acid tert-butyl ester (2.0 g, 8 mmol), cesium carbonate (5.2 g, 16 mmol) and N,N-dimethylformamide (60 mL), stir at room temperature for 30 minutes. Add 6-chloronicotinamide (1.2 g, 8 mmol) and heat at 190° C. for 2 days. Cool to room temperature, dilute with brine, and then extract with ethyl acetate (3×150 mL). Dry the ethyl acetate extracts with sodium chloride/magnesium sulfate, filter, then concentrate on a rotary evaporator to yield 3 g of the crude product. The crude product is purified by flash column chromatography on silica gel eluting with 0.5% conc. ammonium hydroxide/5% ethanol in chloroform to yield 5-(5-carbamoyl-pyridin-2-yloxy)-3,4-dihydro-1H-isoquinoline-2-carboxylic acid tert-butyl ester (2.1 g, 5.7 mmol): $^1$H NMR (DMSO-d$_6$, 300.00 MHz): 8.54 (s, 1H); 8.30-8.23 (m, 1H); 8.02-7.93 (m, 1H); 7.48 (s, 1H); 7.23 (d, 1H); 7.09-6.95 (m, 1H); 4.54 (s, 2H); 3.48-3.36 (m, 4H); 2.87-2.71 (m, 2H); 1.39 (s, 9H).

EXAMPLE 619

6-(1,2,3,4-Tetrahydro-isoquinolin-5-yloxy)-nicotinamide

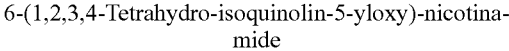

Add drop wise via an addition funnel a solution of trifluoroacetic acid (5.7 mL) in dichloromethane (25 mL) to a stirred solution of 5-(5-carbamoyl-pyridin-2-yloxy)-3,4-dihydro-1H-isoquinoline-2-carboxylic acid tert-butyl ester (2.1 g, 5.7 mmol) in dichloromethane (75 mL) at 0° C. Warm to room temperature and stir for 18 hours. Evaporate on a rotary evaporator, dissolve the residue in methanol (50 mL) and dichloromethane (50 mL), and then add MP-carbonate resin (7.9 g @2.87 eq/g). Agitate for 2 hours, filter, concentrate on a rotary evaporator, and dry under vacuum to yield 6-(1,2,3,4-tetrahydro-isoquinolin-5-yloxy)-nicotinamide (1.5 g, 5.6 mmol): HPLC=85% (50/50 to 90/10 ACN/(0.1% TFA in water), Zorbax SB-Phenyl 4.6 mm×15 cm×5 micron, λ=254 nm). $^1$H NMR (DMSO-d$_6$, 300.00 MHz): 8.55 (d, 1H), 8.23 (dd, 1H), 8.01 (s, 1H), 7.46 (s, 1H), 6.95 (m, 5H), 3.90 (s, 2H), 2.85 (m, 2H), 2.38 (m, 2H).

EXAMPLE 620

6-(2-Benzyl-1,2,3,4-tetrahydro-isoquinolin-5-yloxy)-nicotinamide

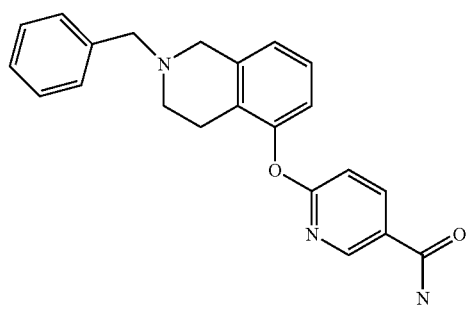

Combine 6-(1,2,3,4-tetrahydro-isoquinolin-5-yloxy)-nicotinamide (100 mg, 0.37 mmol), benzaldehyde (39 µL, 0.38 mmol), sodium triacetoxyborohydride (101 mg, 0.48 mmol), acetic acid (22 µL, 0.39 mmol), and 1,2-dichloroethane (5 mL) then stir at room temperature for 18 hours. Dilute the reaction with saturated aqueous sodium bicarbonate solution and extract with dichloromethane (3×25 mL). Dry the combined dichloromethane extracts with sodium chloride/magnesium sulfate, filter, and concentrate on a rotary evaporator to yield 45 mg of the crude product. The crude product is purified by flash column chromatography on silica gel eluting with (0.5% conc. ammonium hydroxide/5% ethanol) to (1% conc. ammonium hydroxide/10% ethanol) in chloroform to yield 6-(2-benzyl-1,2,3,4-tetrahydro isoquinolin-5-yloxy)-nicotinamide (31 mg, 0.09 mmol): m/z=360.1 (M+1); 3H NMR (DMSO-d$_6$, 300.00 MHz): 8.56 (s, 1H); 8.16-8.12 (m, 1H); 7.38-7.15 (m, 6H); 6.94-6.89 (m, 3H); 6.17 (s, 2H); 3.74-3.61 (m, 4H); 2.69-2.66 (m, 4H), HPLC=99% (30/70 to 90/10 ACN/(0.1% TFA in water), Zorbax SB-Phenyl 4.6 mm×15 cm×5 micron, λ=254 nm).

By the method of Example 620 the followings compounds were prepared and isolated as the free base except where noted:

| Example | Name | Mass spectrum (ion spray): m/z (M + 1) | Purity | HPLC (30/70 to 90/10 ACN/(0.1% TFA in water), Zorbax SB-Phenyl 4.6 mm × 15 cm × 5 micron, λ = 254 nm) Retention Time (minutes) |
|---|---|---|---|---|
| 621 | 6-(2-Butyl-1,2,3,4-tetrahydro-isoquinolin-5-yloxy)-nicotinamide | 326.16 | 96 | 2.55 |
| 622 | 6-[2-(3-Methyl-butyl)-1,2,3,4-tetrahydro-isoquinolin-5-yloxy]-nicotinamide | 340.17 | 99 | 3.16 |
| 623 | 6-(2-Thiophen-2-ylmethyl-1,2,3,4-tetrahydro-isoquinolin-5-yloxy)-nicotinamide | 366.07 | 99 | 2.57 |
| 624 | 6-(2-Phenethyl-1,2,3,4-tetrahydro-isoquinolin-5-yloxy)-nicotinamide | 374.14 | 100 | 4.19 |
| 625 | 6-(2-Hexyl-1,2,3,4-tetrahydro-isoquinolin-5-yloxy)-nicotinamide | 354.2 | 94 | |
| 626 | 6-(2-Isopropyl-1,2,3,4-tetrahydro-isoquinolin-5-yloxy)-nicotinamide | 312.13 | 60 | |
| 627 | 6-(2-Propyl-1,2,3,4-tetrahydro-isoquinolin-5-yloxy)-nicotinamide | 312.15 | 71 | 1.94 |
| 628 | 6-(2-Isobutyl-1,2,3,4-tetrahydro-isoquinolin-5-yloxy)-nicotinamide | 326.15 | 98 | 2.15 |
| 629 | 6-(2-Pentyl-1,2,3,4-tetrahydro-isoquinolin-5-yloxy)-nicotinamide | 340.17 | 99 | 3.20 |
| 630 | 6-(2-Furan-2-ylmethyl-1,2,3,4-tetrahydro-isoquinolin-5-yloxy)-nicotinamide | 350.11 | 98 | 2.17 |
| 631 | 6-(2-Cyclohexyl-1,2,3,4-tetrahydro-isoquinolin-5-yloxy)-nicotinamide | 352.16 | 96 | 2.76 |
| 632 | 6-(2-Pyridin-2-ylmethyl-1,2,3,4-tetrahydro-isoquinolin-5-yloxy)-nicotinamide | 361.13 | 76 | 1.95 |
| 633 | 6-(2-Pyridin-3-ylmethyl-1,2,3,4-tetrahydro-isoquinolin-5-yloxy)-nicotinamide | 361.13 | 99 | 1.53 |
| 634 | 6-(2-Pyridin-4-ylmethyl-1,2,3,4-tetrahydro-isoquinolin-5-yloxy)-nicotinamide | 361.13 | 99 | 1.57 |
| 635 | 6-(2-Cyclohexylmethyl-1,2,3,4-tetrahydro-isoquinolin-5-yloxy)-nicotinamide | 366.18 | 94 | 4.19 |
| 636 | 6-[2-(3-Phenyl-propyl)-1,2,3,4-tetrahydro-isoquinolin-5-yloxy]-nicotinamide | 388.16 | 94 | 5.60 |

EXAMPLE 637

7-(5-Carbamoyl-pyridin-2-yloxy)-3,4-dihydro-1H-isoquinoline-2-carboxylic acid tert-butyl ester

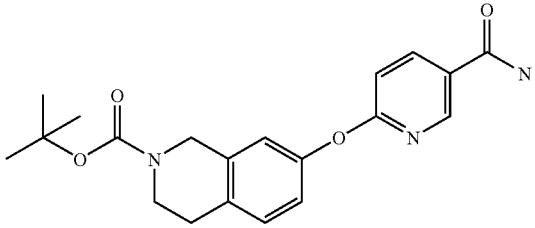

Combine 7-hydroxy-3,4-dihydro-1H-isoquinoline-2-carboxylic acid tert-butyl ester (1.7 g, 6.8 mmol, Reference *J. Med. Chem.* 1998, 41 (25), 4983-4994), cesium carbonate (4.4 g, 13.6 mmol) and N,N-dimethylformamide (75 mL) and stir at room temperature for 30 minutes. Add 6-chloronicotinamide (1.1 g, 6.8 mmol) and heat at 100° C. for 2 days. Cool to room temperature, dilute with brine then extract with ethyl acetate (3×125 mL). Dry the ethyl acetate extracts with sodium chloride/magnesium sulfate, filter, then concentrate on a rotary evaporator to yield 12 g of the crude product. The crude product is purified by flash column chromatography on silica gel eluting with (0.1% conc. ammonium hydroxide/1% ethanol) to (1% conc. ammonium hydroxide/10% ethanol) in chloroform to yield 7-(5-carbamoyl-pyridin-2-yloxy)-3,4-dihydro-1H-isoquinoline-2-carboxylic acid tert-butyl ester (1.2 g, 3.3 mmol): $^1$H NMR (CDCl$_3$, 300.00 MHz): 8.59 (s, 1H); 8.17 (d, 1H); 7.20-7.17 (m, 2H); 6.98-6.89 (m, 2H); 5.97 (s, 2H); 4.57 (s, 2H); 3.68-3.66 (m, 2H); 2.83 (t, 2H); 1.48 (s, 9H).

EXAMPLE 638

6-(1,2,3,4-Tetrahydro-isoquinolin-7-yloxy)-nicotinamide

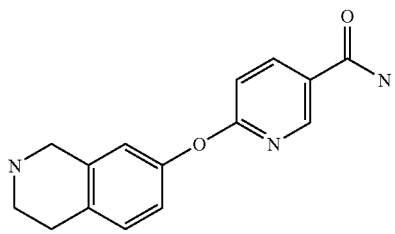

Add drop wise via an addition funnel a solution of trifluoroacetic acid (3.3 mL) in dichloromethane (10 mL) to a stirred solution of 7-(5-carbamoyl-pyridin-2-yloxy)-3,4-dihydro-1H-isoquinoline-2-carboxylic acid tert-butyl ester (1.2 g, 3.3 mmol)) in dichloromethane (50 mL) at 0° C. Warm to room temperature and stir for 18 hours. Evaporate on a rotary evaporator, dissolve the residue in methanol, and then apply in equal parts to 2-10 g SCX cartridges. Wash each cartridge with methanol until neutral pH then elute product with 2.0 M ammonia in methanol. Collect the basic eluent and concentrate on a rotary evaporator to yield 6-(1,2,3,4-tetrahydro-isoquinolin-7-yloxy)-nicotinamide (0.9 g, 3.3 mmol): $^1$H NMR (CDCl$_3$, 300.00 MHz): 8.57 (s, 1H); 8.15 (d, 1H); 7.15-7.13 (m, 1H); 6.96-6.89 (m, 2H); 6.80 (s, 1H); 5.87 (br, 2H); 4.01 (s, 2H); 3.17-3.13 (m, 2H); 2.82-2.78 (m, 2H); 1.73 (br, 1H).

EXAMPLE 639

6-(2-Benzyl-1,2,3,4-tetrahydro-isoquinolin-7-yloxy)-nicotinamide

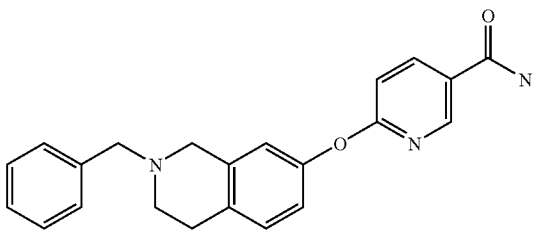

Combine 6-(1,2,3,4-tetrahydro-isoquinolin-7-yloxy)-nicotinamide (94 mg, 0.35 mmol), benzaldehyde (37 μL, 0.37 mmol), sodium triacetoxyborohydride (96 mg 0.46 mmol), acetic acid (21 μL, 0.37 mmol), and 1,2-dichloroethane (5 mL) then stir at room temperature for 18 hours. Dilute the reaction with saturated aqueous sodium bicarbonate solution and extract with 5% methanol in dichloromethane (3×25 mL). Dry the combined 5% methanol in dichloromethane extracts with sodium chloride/magnesium sulfate, filter, and concentrate on a rotary evaporator to yield 100 mg of the crude product. The crude product is purified by flash column chromatography on silica gel eluting with 1% conc. ammonium hydroxide/10% ethanol in chloroform to yield 6-(2-benzyl-1,2,3,4-tetrahydro-isoquinolin-7-yloxy)-nicotinamide 2039910 (30 mg, 0.09 mmol): m/z=360.12 (M+1); $^1$H NMR (CDCl$_3$, 300.00 MHz): 8.50 (d, 1H); 8.09-8.05 (m, 1H); 7.34-7.20 (m, 5H); 7.09 (d, 1H); 6.87-6.82 (m, 2H); 6.71 (d, 1H); 5.80 (s, 2H); 3.63-3.57 (m, 4H); 2.87-2.69 (m, 4H), HPLC=96%@2.98 m (5/95 to 95/5 ACN/(0.1% TFA in water) over 10 minutes, Zorbax SB-Phenyl 4.6 mm×15 cm×5 micron, λ=254 nm).

By the method of Example 639 the following compounds were prepared and isolated as the free base except where noted:

| | | Data | | |
|---|---|---|---|---|
| Example | Name | Mass spectrum (ion spray): m/z (M + 1) | Purity | HPLC (5/95 to 95/5 ACN/(0.1% TFA in water) over 10 minutes, Zorbax SB-Phenyl 4.6 mm × 15 cm × 5 micron, λ = 254 nm) Retention Time (minutes) |
| 640 | 6-(2-Propyl-1,2,3,4-tetrahydro-isoquinolin-7-yloxy)-nicotinamide | 312.1 | 94 | 6.08 |
| 641 | 6-(2-Cyclohexyl-1,2,3,4-tetrahydro-isoquinolin-7-yloxy)-nicotinamide | 352.1 | 96 | 6.32 |
| 642 | 6-[2-(3-Cyclohexyl-propyl)-1,2,3,4-tetrahydro-isoquinolin-7-yloxy]-nicotinamide | 394.2 | 90 | 6.84 |
| 643 | 6-(2-Pentyl-1,2,3,4-tetrahydro-isoquinolin-7-yloxy)-nicotinamide | 340.1 | 96 | 6.38 |
| 644 | 6-(2-Cyclohexylmethyl-1,2,3,4-tetrahydro-isoquinolin-7-yloxy)-nicotinamide | 366.1 | 98 | 6.45 |
| 645 | 6-(2-Phenethyl-1,2,3,4-tetrahydro-isoquinolin-7-yloxy)-nicotinamide | 374.1 | 96 | 6.46 |
| 646 | 6-[2-(3-Phenyl-propyl)-1,2,3,4-tetrahydro-isoquinolin-7-yloxy]-nicotinamide | 388.1 | 99 | 6.53 |
| 647 | 6-(2-Pyridin-3-ylmethyl-1,2,3,4-tetrahydro-isoquinolin-7-yloxy)-nicotinamide | 361.1 | 99 | 5.8 |
| 648 | 6-(2-Thiophen-2-ylmethyl-1,2,3,4-tetrahydro-isoquinolin-7-yloxy)-nicotinamide | 366 | 99 | 6.24 |
| 649 | 6-(2-Furan-2-ylmethyl-1,2,3,4-tetrahydro-isoquinolin-7-yloxy)-nicotinamide | 350.1 | 96 | 6.14 |
| 650 | 6-[2-(3-Chloro-benzyl)-1,2,3,4-tetrahydro-isoquinolin-7-yloxy]-nicotinamide | 394 | 98 | 6.47 |

EXAMPLE 651

6-{2-Methyl-4-[2-(3-methyl-butylamino)-ethyl]-phenoxy}-nicotinamide

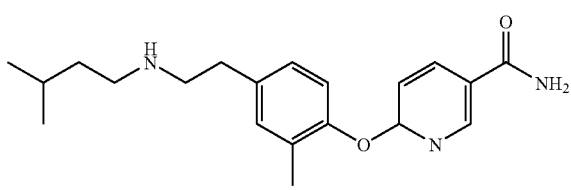

Step 1

2-Methyl-4-(2-nitro-vinyl)-phenol

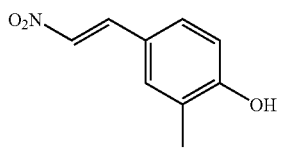

The 2-methyl-4-hydroxy-benzaldehyde (980 mg, 6.3 mmol), nitromethane (2.0 mL, 37.7 mmol) and ammonium acetate (1.9 g, 25.1 mmol) were dissolved in acetic acid (9 mL) and the reaction heated at 110° C. for 2 h. The reaction is concentrated under reduced pressure and the residue partitioned between ether and water. Separate the layers and dry with $Na_2SO_4$, filter and concentrate under reduced pressure. Purify the crude by flash chromatography (eluent: EtOAc/hexane 20/80 and 30/70) afforded the title compound (1.0 g). $^1$H-NMR (CDCl$_3$, 200 MHz): 7.94 (d, 1H, J=13.4 Hz), 7.50 (d, 1H, J=13.6 Hz), 7.34-7.27 (m, 2H), 6.82 (d, 1H, J=8.1 Hz), 2.28 (s, 3H).

Step 2

4-(2-Amino-ethyl)-2-methyl-phenol

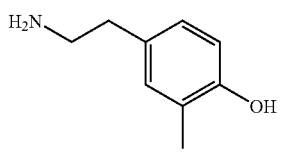

Procedure 1: Dissolve compound obtained in step 1 above (440 mg, 2.46 mmol) in methanol (10 mL) and add Pd/C 10% (272 mg) and HCl conc (1 mL). Stir the mixture at room temperature under hydrogen overnight. Filtrate over celite and eliminate the solvent. Purify by SCX column to obtain the title compound (232 mg, 63%).

Procedure 2: To lithium aluminum hydride 1.0M in ether (1.67 mL, 1.67 mmol) at 0° C. a solution of aluminum trichloride (224 mg, 1.67 mmol) in THF (2 mL) is added. After 5 mL) a solution of compound obtained in step 1 above (100 mg, 0.56 mmol) in THF (2 mL) is added and the reaction is allowed to stir at room temperature overnight. Add water and then 3 N HCl, the aqueous layer is extracted with 3/1 n-butanol/toluene. The combined organic layers are dried over sodium sulfate and concentrated. SCX ion-exchange chromatography afforded 71 mg (84%) of the title compound. Electrospray MS M+1 ion=152. $^1$H-NMR (methanol-d$_4$, 200 MHz): 6.89 (bs, 1H), 6.82 (dd, 1H, J=8.3 and 2.4 Hz), 6.64 (d, 1H, J=8.1 Hz), 2.80 (t, 2H, J=6.7 Hz), 2.61 (t, 2H, J=7.0 Hz), 2.15 (s, 3H).

Step 3

[2-(4-Hydroxy-3-methyl-phenyl)-ethyl]-carbamic acid tert-butyl ester

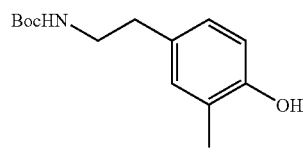

Dissolve amine obtained in step 2 above (289 mg, 1.91 mmol) in dry THF (5 mL) under $N_2$ atmosphere, add a solution of di-tertbutyl dicarbonate (439 mg, 2.0 mmol) in THF (5 mL), stir the mixture at room temperature overnight. Eliminate the solvent to obtain the title compound (462 mg, 96%). TLC R$_f$(EtOAc/hexane 20/80): 0.27. $^1$H-NMR (methanol-d$_4$, 200 MHz): 6.88 (bs, 1H), 6.82 (d, 1H, J=8.3 Hz), 6.63 (d, 1H, J=8.1 Hz), 3.17 (t, 2H, J=6.7 Hz), 2.60 (t, 2H, J=7.0 Hz), 2.14 (s, 3H), 1.50 (s, 9H).

Step 4

{2-[4-(5-Cyano-pyridin-2-yloxy)-3-methyl-phenyl]-ethyl}-carbamic acid tert-butyl ester

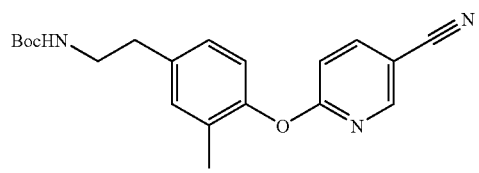

A solution of phenol obtained in step 3 above (455 mg, 1.1 mmol), 6-chloronicotinonitrile (251 mg, 1.81 mmol) and sodium hydride (87 mg, 2.17 mmol) in DMSO (10 mL) is stirred at room temperature for 18 h. Pour the mixture into iced water and extract the aqueous layer with EtOAc. Dry the organic layer over $Na_2SO_4$, filtrate and eliminate the solvent. Purify by flash chromatography (eluent: EtOAc/hexane 15/85 and 20/80) to get the title compound (358 mg, 57%). Electrospray MS M$^+$+1-Boc group ion: 298. $^1$H-NMR (CDCl$_3$, 200 MHz): 8.42 (dd, 1H, J=0.5 and 2.4 Hz), 7.90 (dd, 1H, J=2.4 and 8.6 Hz), 7.11-6.94 (m, 4H), 3.37 (q, 2H, J=7.0 Hz), 2.77 (t, 2H, J=7.2 Hz), 2.10 (s, 3H), 1.43 (s, 9H).

Step 5

{2-[4-(5-Carbamoyl-pyridin-2-yloxy)-3-methyl-phenyl]-ethyl}-carbamic acid tert-butyl ester

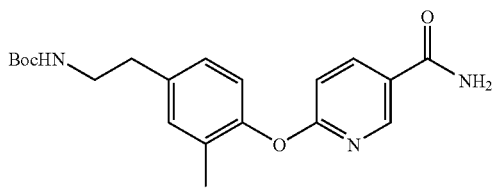

The compound of step 4 is subject to hydrolysis using hydrogen peroxide and potassium carbonate. The details of the hydrolysis procedure to form the amide form nitrile have been described exhaustively somewhere in P-15876.

$^1$H-NMR (CDCl$_3$, 200 MHz): 8.58 (d, 1H, J=2.4 Hz), 8.17 (dd, 1H, J=2.4 and 8.6 Hz), 7.09-6.90 (m, 4H), 3.38 (q, 2H, J=6.7 Hz), 2.77 (t, 2H, J=7.0 Hz), 2.11 (s, 3H), 1.43 (s, 9H).

Step 6

6-[4-(2-Amino-ethyl)-2-methyl-phenoxy]-nicotinamide

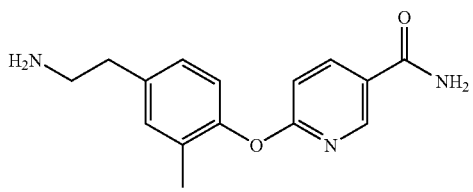

To a solution of compound of step 5 (376 mg, 1.01 mmol) in CH$_2$Cl$_2$ (20 mL), trifluoroacetic acid is added (2.03 mL, 26.4 mmol). Stir the reaction mixture at room temperature for 2 h. Eliminate the solvent and purify by SCX column to obtain the title compound (264 mg, 96%). Electrospray MS M$^+$+1 ion: 272. $^1$H-NMR (metanol-d$_4$, 200 MHz): 8.58 (d, 1H, J=2.4 Hz), 8.24 (dd, 1H, J=2.7 and 8.9 Hz), 7.17-6.94 (m, 4H), 2.94-2.86 (m, 2H), 2.78-2.71 (m, 2H), 2.10 (s, 3H).

Step 7

Combine 3-methyl-butylaldehyde (60 μl, 0.22 mmol), amine from step 6 above (60 mg, 0.22 mmol) and 3 A molecular sieves (670 mg) in methanol (2 mL), stir the mixture at room temperature overnight. Add NaBH$_4$ (41 mg, 1.10 mmol) and stir at room temperature for 3 hours. Filtrate the mixture over celite and eliminate the solvent. Purify the crude mixture by flash chromatography (eluent: CH$_2$Cl$_2$/MeOH 80/20) to obtain the title compound (45 mg, 60%). Electrospray MS M+1 ion=342. $^1$H-NMR (metanol-d$_4$, 200 MHz): 8.59 (dd, 1H, J=0.8 and 2.7 Hz), 8.24 (dd, 1H, J=2.4 and 8.6 Hz), 7.19-7.10 (m, 2H), 7.00-6.93 (m, 2H), 2.93-2.76 (m, 4H), 2.70-2.62 (m, 2H), 2.10 (s, 3H), 1.71-1.36 (m, 3H), 0.91 (d, 6H, J=6.4 Hz).

By the method of example 1 the following examples (examples 2-8) were prepared. The purification process is described in each case

EXAMPLE 652

6-{2-Methyl-4-[2-(3,3-dimethyl-butylamino)-ethyl]-phenoxy}-nicotinaide

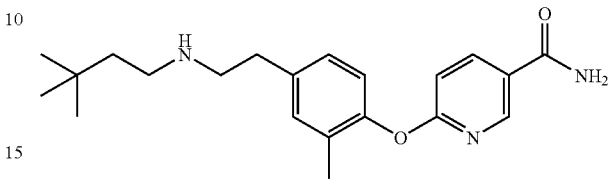

Purification: SCX column. Electrospray MS M+1 ion=356. $^1$H-NMR (metanol-d$_4$, 200 MHz): 8.59 (d, 1H, J=2.4 Hz), 8.24 (dd, 1H, J=2.4 and 8.6 Hz), 7.18-7.10 (m, 2H), 7.00-6.94 (m, 2H), 2.92-2.78 (m, 4H), 2.69-2.60 (m, 2H), 2.10 (s, 3H), 1.48-1.39 (m, 2H), 0.93 (s, 9H).

EXAMPLE 653

6-[2-Methyl-4-(2-pentylamino-ethyl)-phenoxy]-nicotinamide

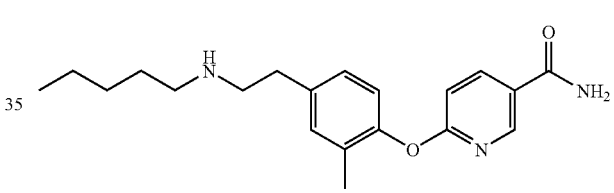

Purification: Flash chromatography (eluent: CH$_2$Cl$_2$/EtOAc/MeOH:NH$_3$ 2M 35/60/5). Electrospray MS M+1 ion=342. $^1$H-NMR (metanol-d$_4$, 200 MHz): 8.59 (dd, 1H, J=0.5 and 2.3 Hz), 8.24 (dd, 1H, J=2.6 and 8.8 Hz), 7.17-7.08 (m, 2H), 6.98-6.92 (m, 2H), 2.88-2.75 (m, 4H), 2.65-2.57 (m, 2H), 2.09 (s, 3H), 1.59-1.25 (m, 6H), 0.91 (t, 3H, J=6.4 Hz).

EXAMPLE 654

6-{4-[2-(Cyclohexylmethyl-amino)-ethyl]-2-methyl-phenoxy}-nicotinamide

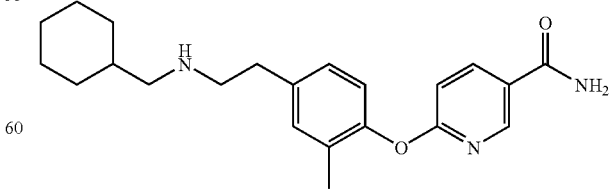

Purification: Flash chromatography (eluent: CH$_2$Cl$_2$/MeOH 90/10). Electrospray MS M+1 ion=368. $^1$H-NMR (metanol-d$_4$, 200 MHz): 8.59 (d, 1H, J=2.4 Hz), 8.24 (dd, 1H, J=2.7 and 8.6 Hz), 7.18-7.10 (m, 2H), 7.00-6.93 (m, 2H), 2.85 (bs, 4H), 2.50 (d, 2H, J=6.4 Hz), 2.10 (s, 3H), 1.77-0.84 (m, 11H).

EXAMPLE 655

6-{4-[2-(3-Fluoro-benzylamino)-ethyl]-2-methyl-phenoxy}-nicotinamide

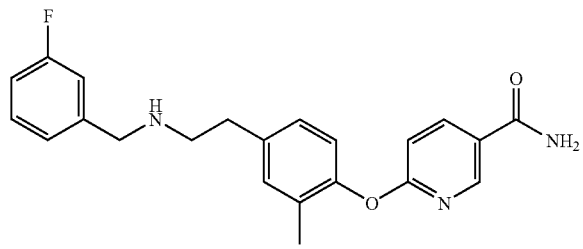

Purification: SCX column. Electrospray MS M+1 ion=380. $^1$H-NMR (metanol-d$_4$, 200 MHz): 8.59 (dd, 1H, J=0.5 and 2.4 Hz), 8.24 (dd, 1H, J=2.4 and 8.6 Hz), 7.38-6.92 (m, 8H), 3.79 (s, 2H), 2.82 (s, 4H), 2.09 (s, 3H).

EXAMPLE 656

6-{4-[2-(3-Fluoro-benzylamino)-ethyl]-2-methyl-phenoxy}-nicotinamide, mesylate salt

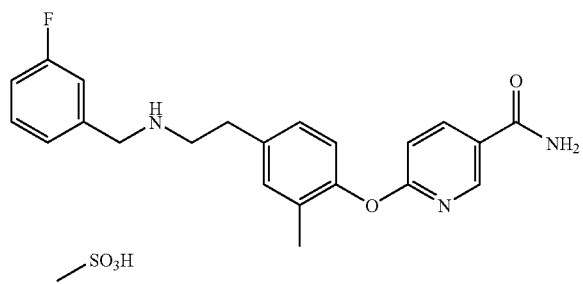

Example 655 (free amine of example 656) was dissolved in THF, then methanosulfonic acid was added (1.0 eq), the mixture was stirred for 1 hour and the solvent eliminated to give the title compound. Electrospray MS M+1 ion=380. $^1$H-NMR (metanol-d$_4$, 300 MHz): 8.59 (bs, 1H), 8.28 (dd, 1H, J=1.4 and 8.7 Hz), 7.56-7.02 (m, 5H), 4.30 (s, 2H), 3.36 (t, 2H, J=7.3 Hz), 3.06 (t, 2H, J=7.3 Hz), 2.72 (s, 3H), 2.14 (s, 3H).

EXAMPLE 657

6-(4-{2-[(Bicyclo[2.2.1]hept-5-en-2-ylmethyl)-amino]-ethyl}-2-methyl-phenoxy)-nicotinamide

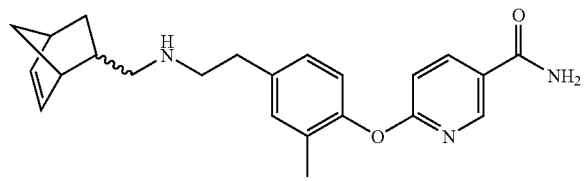

Purification: HPLC (Column: X-Terra MS C18. A=10 Mm NH$_4$HCO$_3$ pH9/B=CH$_3$CN. Gradient mode: from 30 to 99% B. Flow rate: 1 mL/min). Electrospray MS M+1 ion 378. $^1$H-NMR (metanol-d$_4$, 200 MHz): 8.59 (d, 1H, J=2.6 Hz), 8.24 (dd, 1H, J=2.4 and 8.6 Hz), 7.16-6.91 (m, 4H), 6.16-5.88 (m, 2H), 2.81-1.81 (m, 9H), 2.09 (s, 3H), 1.65-0.99 (m, 3H), 0.57-0.48 (m, 1H).

EXAMPLE 658

6-[4-(2-Cyclooctylamino-ethyl)-2-methyl-phenoxy]-nicotinamide

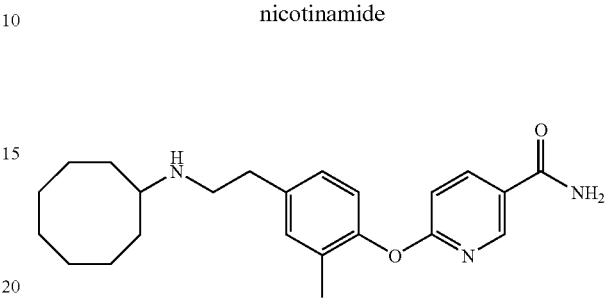

Purification: Flash chromatography (eluent: CH$_2$Cl$_2$/MeOH 70/30). Electrospray MS M+1 ion=382. $^1$H-NMR (metanol-d$_4$, 200 MHz): 8.59 (d, 1H, J=2.4 Hz), 8.24 (dd, 1H, J=2.4 and 8.6 Hz), 7.18-6.92 (m, 4H), 2.95-2.77 (m, 5H), 2.12 (m, 1H), 2.10 (s, 3H), 1.89-1.46 (m, 13H).

EXAMPLE 659

6-{3-Chloro-4-[2-(3-methyl-butylamino)-ethyl]-phenoxy}-nicotinamide

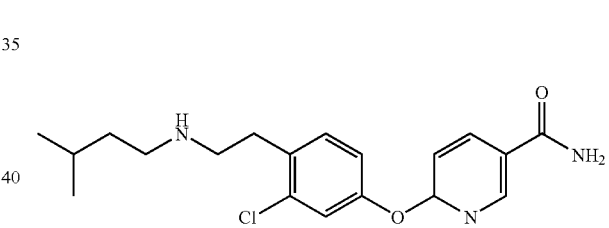

Step 1

3-Chloro-4-(2-nitro-vinyl)-phenol

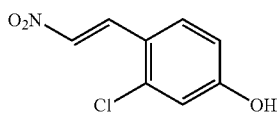

The 3-chloro-4-hydroxy-benzaldehyde (980 mg, 6.3 mmol), nitromethane (2.0 mL 37.7 mmol) and ammonium acetate (1.9 g, 25.1 mmol) were dissolved in acetic acid (9 mL) and the reaction heated at 110° C. for 2 h. The reaction is concentrated under reduced pressure and the residue partitioned between ether and water. Separate the layers and dry with Na$_2$SO$_4$, filter and concentrate under reduced pressure. Purify the crude by flash chromatography (eluent: EtOAc/hexane 20/80 and 30/70) afforded the title compound (1.0 g, 80%). $^1$H-NMR (CDCl$_3$, 200 MHz): 8.34 (d, 1H, J=13.4 Hz), 7.82 (d, 1H, J=13.4 Hz), 7.71 (d, 1H, J=8.6 Hz), 6.94 (d, 1H, J=2.4 Hz), 6.80 (dd, 1H, J=2.4 and 8.6 Hz).

Step 2

4-(2-Amino-ethyl)-3-chloro-phenol

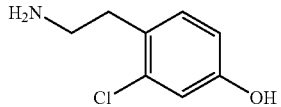

To lithium aluminum hydride 1.0M in ether (1.50 mL, 1.50 mmol) at 0° C. a solution of aluminum trichloride (201 mg, 1.51 mmol) in THF (2 mL) is added. After 5 min a solution of compound obtained in step 1 above (100 mg, 0.50 mmol) in THF (2 mL) is added and the reaction is allowed to stir at room temperature overnight. Add water and then 3 N HCl, the aqueous layer is extracted with 3/1 n-butanol/toluene. The combined organic layers are dried over sodium sulfate and concentrated. SCX ion-exchange chromatography afforded 70 mg (81%) of the title compound. Electrospray MS M+1 ion=172. $^1$H-NMR (methanol-$d_4$, 200 MHz): 7.06 (d, 1H, J=8.3 Hz), 6.79 (d, 1H, J=2.4 Hz), 6.65 (dd, 1H, J=2.4 and 8.3 Hz), 2.82 (m, 4H).

Step 3

[2-(4-Hydroxy-2-chloro-phenyl)-ethyl]-carbamic acid tert-butyl ester

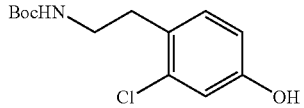

Dissolve amine obtained in step 2 above (620 mg, 3.62 mmol) in dry THF (20 mL) and DMF (1 mL) under $N_2$ atmosphere, add a solution of di-tertbutyl dicarbonate (791 mg, 3.62 mmol) in THF (10 mL), stir the mixture at room temperature overnight. Eliminate the solvent and purify the crude by flash chromatography (eluent: EtOAc/hexane 30/70) to obtain the title compound (670 mg, 68%). TLC $R_f$ (EtOAc/hexane 20/80): 0.27. $^1$H-NMR (methanol-$d_4$, 200 MHz): 7.06 (d, 1H, J=8.3 Hz), 6.78 (d, 1H, J=2.6 Hz), 6.65 (dd, 1H, J=2.4 and 8.3 Hz), 3.21 (t, 2H, J=6.7 Hz), 2.78 (t, 2H, J=7.5 Hz), 1.41 (s, 9H).

Step 4

{2-[4-(5-Cyano-pyridin-2-yloxy)-2-chloro-phenyl]-ethyl}-carbamic acid tert-butyl ester

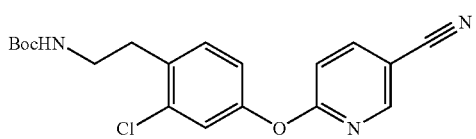

A solution of phenol obtained in step 3 above (650 mg, 2.4 mmol), 6-chloronicotinonitrile (333 mg, 2.4 mmol) and sodium hydride (115 mg, 2.9 mmol) in DMSO (12 mL) is stirred at room temperature for 18 h. Pour the mixture into iced water and extract the aqueous layer with EtOAc. Dry the organic layer over $Na_2SO_4$, filtrate and eliminate the solvent. Purify by flash chromatography (eluent: EtOAc/hexane 20/80 and 30/70) to get the title compound (810 mg, 90%). Electrospray MS M$^+$+1-Boc group ion: 318. $^1$H-NMR (CDCl$_3$, 200 MHz): 8.46 (dd, 1H, J=0.5 and 2.2 Hz), 7.94 (dd, 1H, J=2.4 and 8.6 Hz), 7.31-7.18 (m, 2H), 7.06-6.98 (m, 2H), 3.41 (q, 2H, J=6.7 Hz), 2.95 (t, 2H, J=7.3 Hz), 1.44 (s, 9H).

Step 5

{2-[4-(5-Carbamoyl-pyridin-2-yloxy)-2-chloro-phenyl]-ethyl}-carbamic acid tert-butyl ester

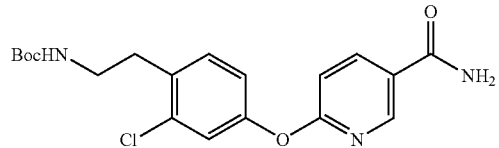

The compound of step 4 is subject to hydrolysis using hydrogen peroxide and potassium carbonate. The details of the hydrolysis procedure to form the amide form nitrile have been described previously.

$^1$H-NMR (methanol-$d_4$, 200 MHz): 8.62 (dd, 1H, J=0.8 and 2.7 Hz), 8.27 (dd, 1H, J=2.4 and 8.6 Hz), 7.34 (d, 1H, J=8.3 Hz), 7.22 (d, 1H, J=2.4 Hz), 7.07-7.02 (m, 2H), 3.34 (m, 2H), 2.92 (t, 2H, J=7.3 Hz), 1.42 (s, 9H).

Step 6

6-[4-(2-Amino-ethyl)-2-chloro-phenoxy]-nicotinamide

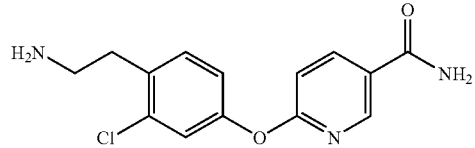

The compound of step 5 is subject to hydrolysis using trifluoroacetic acid. The details of the hydrolysis procedure to remove the protecting group have been described previously. Electrospray MS M+1 ion=292. $^1$H-NMR (metanol-$d_4$, 200 MHz): 8.60 (dd, 1H, J=0.8 and 2.7 Hz), 8.28 (dd, 1H, J=2.7 and 8.9 Hz), 7.38 (d, 1H, J=8.3 Hz), 7.24 (d, 1H, J=2.4 Hz), 7.09-7.03 (m, 2H), 2.94 (s, 4H).

Step 7

Combine compound from step 6 (60 mg, 0.21 mmol), 3-methyl-butyraldehyde (24 □l, 0.23 mmol) and 3 A molecular sieves (670 mg) in methanol (2 mL), stir the mixture at room temperature overnight. Add NaBH$_4$ (41 mg, 1.10 mmol) and stir at room temperature for 3 hours. Filtrate the mixture over celite and eliminate the solvent. Purify the crude mixture by SCX to obtain the title compound. Electrospray MS M+1 ion=362.

¹H-NMR (metanol-d₄, 200 MHz): 8.61 (dd, 1H, J=0.8 and 2.7 Hz), 8.27 (dd, 1H, J=2.4 and 8.6 Hz), 7.38 (d, 1H, J=8.6 Hz), 7.22 (d, 1H, J=2.4 Hz), 7.07-7.03 (m, 2H), 3.03-2.81 (m, 4H), 2.70-2.62 (m, 2H), 1.62 (m, 1H), 1.48-1.37 (m, 2H), 0.92 (d, 6H, J=6.5 Hz).

By the method of example 9 the following examples (examples 10-14) were prepared. The purification process is described in each case

EXAMPLE 660

6-{3-Chloro-4-[2-(3,3-dimethyl-butylamino)-ethyl]-phenoxy}-nicotinamide

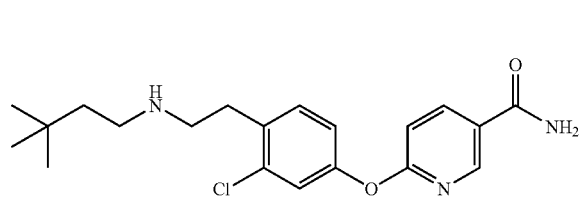

Purification: SCX column. Electrospray MS M+1 ion=376. ¹H-NMR (metanol-d₄, 200 MHz): 8.61 (dd, 1H, J=0.5 and 2.4 Hz), 8.27 (dd, 1H, J=2.7 and 8.9 Hz), 7.38 (d, 1H, J=8.3 Hz), 7.22 (d, 1H, J=2.4 Hz), 7.09-7.03 (m, 2H), 3.02-2.81 (m, 4H), 2.69-2.61 (m, 2H), 1.49-1.40 (m, 2H), 0.93 (s, 9H).

EXAMPLE 661

6-[3-Chloro-4-(2-pentylamino-ethyl)-phenoxy]-nicotinamide

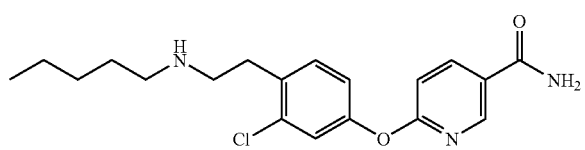

Purification: flash chromatography (eluent: CH₂Cl₂/MeOH 90/10). Electrospray MS M+1 ion=362. ¹H-NMR (metanol-d₄, 200 MHz): 8.61 (dd, 1H, J=0.8 and 2.4 Hz), 8.27 (dd, 1H, J=2.4 and 8.6 Hz), 7.38 (d, 1H, J=8.3 Hz), 7.23 (d, 1H, J=2.4 Hz), 7.09-7.03 (m, 2H), 3.03-2.81 (m, 4H), 2.68-2.61 (m, 2H), 1.61-1.47 (m, 2H), 1.37-1.28 (m, 4H), 0.93 (t, 3H, J=6.7 Hz).

EXAMPLE 662

6-{3-Chloro-4-[2-(cyclohexylmethyl-amino)-ethyl]-phenoxy}nicotinamide

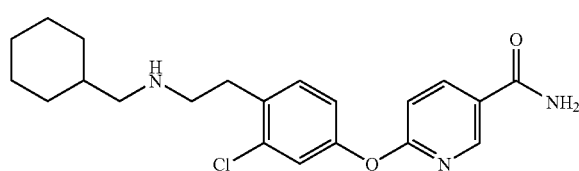

Purification: SCX column. Electrospray MS M+1 ion=388. ¹H-NMR (metanol-d₄, 300 MHz): 8.63 (d, 1H, J=1.8 Hz), 8.28 (dd, 1H, J=2.4 and 8.5 Hz), 7.37 (d, 1H, J=8.2 Hz), 7.22 (d, 1H, J=2.2 Hz), 7.07-7.03 (m, 2H), 3.01-2.81 (m, 4H), 2.49 (d, 2H, J=6.7 Hz), 1.79-1.68 (m, 5H), 1.61-1.42 (m, 1H), 1.38-1.17 (m, 3H), 0.99-0.85 (m, 2H).

EXAMPLE 663

6-{3-Chloro-4-[2-(3-fluoro-benzylamino)-ethyl]-phenoxy}-nicotinamide

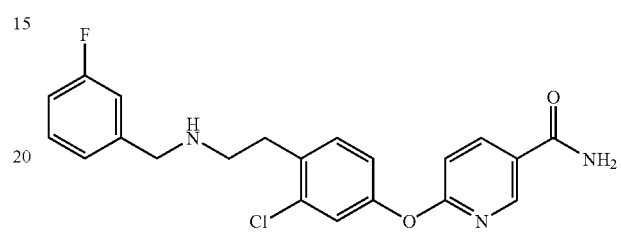

Purification: SCX column. Electrospray MS M+1 ion=400. ¹H-NMR (metanol-d₄, 300 MHz): 8.63 (d, 1H, J=2.2 Hz), 8.27 (dd, 1H, J=2.4 and 8.7 Hz), 7.36-6.95 (m, 8H), 3.82 (s, 2H), 3.01-2.81 (m, 4H).

EXAMPLE 664

6-(4-{2-[(Bicyclo[2.2.1]hept-5-en-2-ylmethyl)-amino]-ethyl}-3-chloro-phenoxy)-nicotinamide

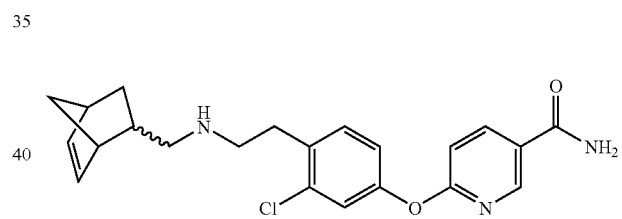

Purification: SCX column. Electrospray MS M+1 ion=398. ¹H-NMR (metanol-d₄, 200 MHz): 8.61 (dd, 1H, J=0.5 and 2.4 Hz), 8.26 (dd, 1H, J=2.4 and 8.6 Hz), 7.40-7.03 (m, 4H), 6.18-5.92 (m, 2H), 3.01-2.66 (m, 6H), 2.40-2.18 (m, 2H), 1.95-1.83 (m, 1H), 1.64-1.11 (m, 3H), 0.60-0.50 (m, 1H).

EXAMPLE 665

6-{2,6-Difluoro-4-[2-(3-methyl-butylamino)-ethyl]-phenoxy}-nicotinamide

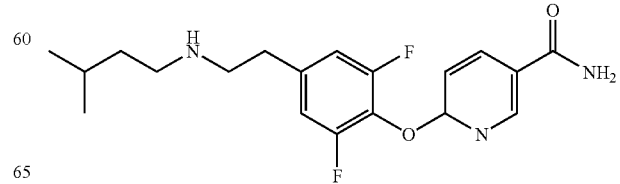

Step 1

2,6-Difluoro-4-(2-nitro-vinyl)-phenol

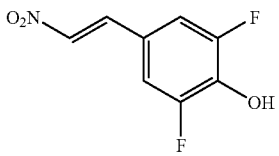

Aldehyde (2,6-difluoro-4-hydroxybenzaldehyde) (2.27 g, 14.4 mmol), nitromethane (4.7 mL, 86.4 mmol) and ammonium acetate (4.4 g, 57.6 mmol) were dissolved in acetic acid (22 mL) and the reaction heated at 110° C. for 1 h 30 min. The reaction is concentrated under reduced pressure and the residue partitioned between ether and water. Separate the layers and dry with $Na_2SO_4$, filter and concentrate under reduced pressure. Purify the rude by flash chromatography (eluent: EtOAc/hexane 22/78) afforded the title compound (2.05 g, yield: 71%). Electrospray MS M−1 ion=200. $^1$H-NMR ($CDCl_3$, 200 MHz): 7.84 (d, 1H, J=13.7 Hz), 7.45 (d, 1H, J=13.7 Hz), 7.19-6.99 (m, 2H).

Step 2

4-(2-Amino-ethyl)-2,6-difluoro-phenol

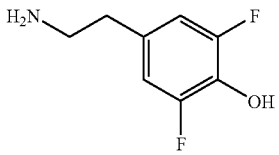

To lithium aluminum hydride 1.0M in ether (30 mL, 29.8 mmol) at 0° C. a solution of aluminum trichloride (4.0 g, 29.8 mmol) in THF (40 mL) is added. After 5 min a solution of compound obtained in step 1 above (2.0 g, 9.95 mmol) in THF (40 mL) is added and the reaction is allowed to stir at room temperature overnight. Add water and then 3 N HCL, the aqueous layer is extracted with 3/1 n-butanol/toluene. The combined organic layers are dried over sodium sulfate and concentrated. SCX ion-exchange chromatography afforded 1.50 g (87%) of the title compound. Electrospray MS M+1 ion=174. $^1$H-NMR (methanol-$d_4$, 200 MHz): 6.95-6.78 (m, 2H), 3.14 (t, 2H, J=7.0 Hz), 2.86 (t, 2H, J=7.3 Hz).

Step 3

[2-(3,5-Difluoro-4-hydroxy-phenyl)-ethyl]-carbamic acid tert-butyl ester

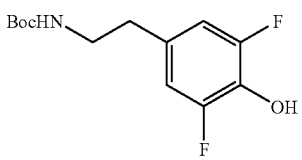

Dissolve amine obtained in step 2 above (1.5 g, 8.67 mmol) in dry THF (22 mL) under $N_2$ atmospheres add a solution of di-tertbutyl dicarbonate (1.89 g, 8.67 mmol) in THF (22 mL), stir the mixture at room temperature overnight. Eliminate the solvent. Purify by flash chromatography (eluent: EtOAc/hexane 1/4 and 1/1) to obtain the desired compound (1.40 g). $^1$H-NMR ($CDCl_3$, 200 MHz): 6.85-6.66 (m, 2H), 3.31 (q, 2H, J=6.2 Hz), 2.69 (t, 2H, J=7.0 Hz), 1.44 (s, 9H).

Step 4

{2-[4-(5-Cyano-pyridin-2-yloxy)-3,5-difluoro-phenyl]-ethyl}-carbamic acid tert-butyl ester

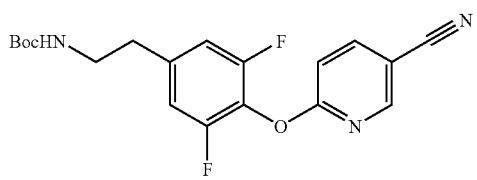

A solution of phenol obtained in step 3 above (1.31 g, 4.8 mmol), 6-chloronicotinonitrile (700 mg, 5.04 mmol) and sodium hydride (290 mg, 7.2 mmol) in DMSO (25 mL) is stirred at room temperature for 18 h. Pour the mixture into iced water and extract the aqueous layer with EtOAc. Dry the organic layer over $Na_2SO_4$, filtrate and eliminate the solvent. Purify by flash chromatography (EtOAc/hexane 20/80 and 34/66) to get the title compound (950 mg, 51%). $^1$H-NMR ($CDCl_3$, 200 MHz): 8.41 (dd, 1H, J=0.8 and 2.1 Hz), 7.97 (dd, 1H, J=2.4 and 8.6 Hz), 7.18 (dd, 1H, J=0.8 and 8.6 Hz), 6.92-6.81 (m, 2H), 3.39 (q, 2H, J=6.9 Hz), 2.81 (t, 2H, J=6.7 Hz), 1.45 (s, 9H).

Step 5

{2-[4-(5-Carbamoyl-pyridin-2-yloxy)-3,5-difluoro-phenyl]-ethyl}-carbamic acid tert-butyl ester

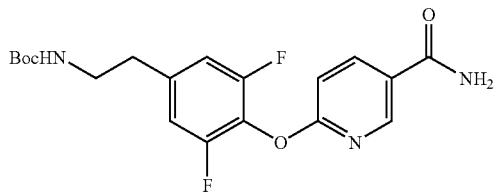

The compound of step 4 is subject to hydrolysis using hydrogen peroxide and potassium carbonate. The details of the hydrolysis procedure to form the amide form nitrile have been described exhaustively somewhere in P-15876.

$^1$H-NMR (metanol-$d_4$, 300 MHz): 8.58 (d, 1H, J=2.4 Hz), 8.31 (dd, 1H, J=2.4 and 8.7 Hz), 7.19 (d, 1H, J=8.7 Hz), 7.02-6.98 (m, 2H), 3.35-3.30 (m, 2H), 2.81 (t, 2H, J=7.1 Hz), 1.44 (s, 9H).

Step 6

6-[4-(9-Amino-ethyl)-2,6difluoro-phenoxy]-nicotinamide

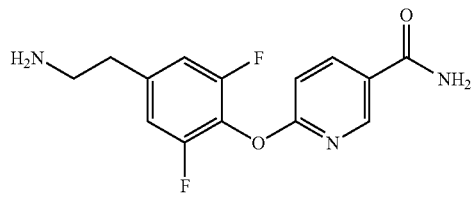

To a solution of compound of step 5 (930 mg, 2.37 mmol) in $CH_2Cl_2$ (50 mL), trifluoroacetic acid is added (4.7 mL, 61.5 mmol). Stir the reaction mixture at room temperature for 2 h. Eliminate the solvent and purify by SCX column to obtain the title compound (658 mg, 95%). Electrospray MS $M^+ +1$ ion: 294. $^1$H-NMR (metanol-$d_4$, 200 MHz): 8.56 (d, 1H, J=2.4 Hz), 8.30 (dd, 1H, J=2.4 and 8.9 Hz), 7.18 (d, 1H, J=8.9 Hz), 7.05-6.95 (m, 2H), 2.96-2.74 (m, 4H).

Step 7

Combine 3-methyl-butylaldehyde (26 µl, 0.24 mmol), amine from step 6 above and 3 A molecular sieves (900 mg) in methanol (3 mL), stir the mixture at room temperature overnight. Add $NaBH_4$ (45 mg, 1.20 mmol) and stir at room temperature for 3 hours. Filtrate the mixture over celite and eliminate the solvent. Submit the crude to a SCX column to obtain a solid which was further purified by HPLC (Column: X-Terra MS C18. A=10 Mm $NH_4HCO_3$ pH8/B=$CH_3CN$. Gradient mode: from 30 to 70% B. Flow rate: 1 mL/min) to obtain the title compound (42 mg). Electrospray MS M+1 ion=364. $^1$H-NMR (metanol-$d_4$, 300 MHz): 8.60 (d, 1H, J=2.0 Hz), 8.32 (dd, 1H, J=2.2 and 8.5 Hz), 7.19 (d, 1H, J=8.7 Hz), 7.01-6.98 (m, 2H), 2.85 (m, 4H), 2.63 (m, 2H), 1.62 (m, 1H), 1.42 (q, 1H, J=7.3 Hz), 0.92 (d, 6H, J=6.5 Hz).

By the method of example 665 the following examples (examples 666-669) were prepared. The purification process is described in each case

EXAMPLE 666

6-{4-[2-(3,3-Dimethyl-butylamino)-ethyl]-2,6-difluoro-phenoxy}-nicotinamide

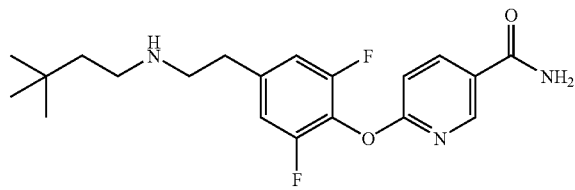

Purification: HPLC (Column: X-Terra MS C18. A=10 Mm $NH_4HCO_3$ pH8/B=$CH_3CN$. Gradient mode: from 30 to 99% B. Flow rate: 1 mL/min). Electrospray MS M+1 ion=378. $^1$H-NMR (metanol-$d_4$, 300 MHz): 8.48 (d, 1H, J=2.4 Hz), 8.23 (dd, 1H, J=2.4 and 8.5 Hz), 7.12 (d, 1H, J=8.5 Hz), 7.00-6.93 (m, 2H), 2.91-2.78 (m, 4H), 2.67-2.61 (m, 2H), 1.43-1.38 (m, 2H), 0.87 (s, 9H).

EXAMPLE 667

6-[2,6-Difluoro-4-(2-pentylamino-ethyl)-phenoxy]-nicotinamide

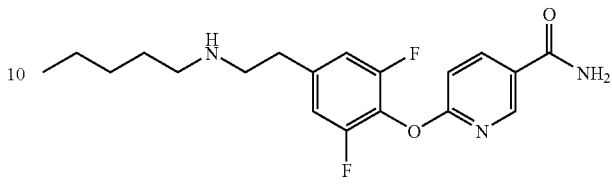

Purification: HPLC (Column: X-Terra MS C18. A=10 Mm $NH_4HCO_3$ pH8/B=$CH_3CN$. Gradient mode: from 25 to 70% B. Flow rate: 1 mL/min). Electrospray MS M+1 ion=364. $^1$H-NMR (metanol-$d_4$, 300 MHz): 8.59 (d, 1H, J=2.4 Hz), 8.32 (dd, 1H, J=2.4 and 8.7 Hz), 7.19 (d, 1H, J=8.7 Hz), 7.02-7.00 (m, 2H), 2.88 (m, 4H), 2.65 (t, 2H, J=7.3 Hz), 1.55 (m, 2H), 1.35 (m, 4H), 0.93 (t, 3H, J=6.7 Hz).

EXAMPLE 668

6-{4-[2-(Cyclohexylmethyl-amino)-ethyl]-2,6-difluoro-phenoxy}-nicotinamide

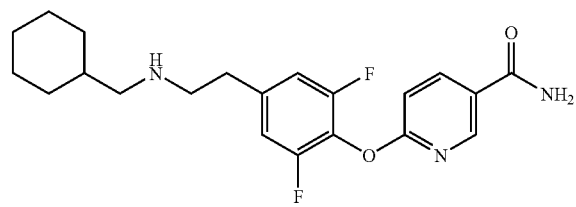

Purification: HPLC (Column: X-Terra MS C18. A=10 Mm $NH_4HCO_3$ pH8/B=$CH_3CN$. Gradient mode: from 30 to 99% B. Flow rate: 1 mL/min). Electrospray MS M+1 ion=390. $^1$H-NMR (metanol-$d_4$, 300 MHz): 8.48 (d, 1H, J=2.4 Hz), 8.23 (dd, 1H, J=2.4 and 8.9 Hz), 7.11 (d, 1H, J=8.8 Hz), 6.99-6.92 (m, 2H), 2.83 (m, 4H), 2.47 (d, 2H, J=6.9 Hz), 1.72-1.59 (m, 5H), 1.55-1.41 (m, 1H), 1.31-1.05 (m, 3H), 0.94-0.81 (m, 2H).

EXAMPLE 669

6-{4-[2-(Cyclopropylmethyl-amino)-ethyl]-2,6-difluoro-phenoxy}-nicotinamide

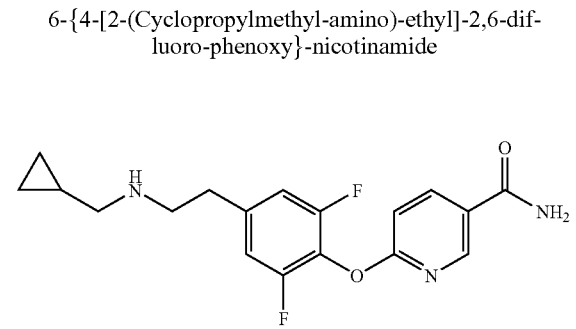

Purification: HPLC (Column: X-Terra MS C18. A=10 Mm $NH_4HCO_3$ pH8/B=MeOH. Gradient mode: from 35 to 80% B. Flow rate: 1 mL/min). Electrospray MS M+1 ion 348.

¹H-NMR (metanol-d₄, 300 MHz): 8.59 (d, 1H, J=2.4 Hz), 8.32 (dd, 1H, J=2.4 and 8.7 Hz), 7.19 (d, 1H, J=8.7 Hz), 7.02-7.00 (m, 2H), 2.93-2.83 (m, 4H), 2.50 (d, 2H, J=6.9 Hz), 1.10-0.90 (m, 1H), 0.55-0.49 (m, 2H), 0.20-0.15 (m, 2H).

General Procedure: Reductive Amination (Examples 670-693)

To a mixture of amine (1 equiv), aldehyde (1.5 equiv) in 5% AcOH/methanol (0.2 M) was added NaCNBH₄ (5 equiv) and the resulting reaction mixture was stirred for 2 hours under nitrogen atmosphere at room temperature. The reaction can be monitored by electrospray MS or TLC. Ethyl acetate was added to the reaction mixture and washed twice with saturated aqueous solution of NaHCO₃. The organic layer was separated, dried over anhydrous NaSO₄ and the solvent evaporated to yield a residue which was purified by flash chromatography using chloroform/ethanol/NH₄OH, 94.5/5/0.5) to afford the title compound as a white solid.

EXAMPLE 670

6-[4-((3-Methyl-butyl), cyclopropylmethyl amino methyl)-2-fluoro phenoxy]nicotinamide

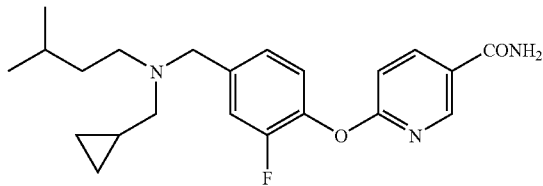

The title compound was prepared by reductive amination of 6-[2-fluoro-4-((3-methyl-butyl)aminomethyl)phenoxy]nicotinamide with cyclopropylcarboxaldehyde.

83% Yield. Mp 94-5° C.

¹H NMR (CHCl₃-d₃) δ: 8.55 (d, 1H, J=2.4 Hz), 8.15 (dd, 1H, J=8.5, 2.4 Hz), 7.28-7.10 (m, 3H), 6.98 (d, 1H, J=8.5 Hz), 6.53 (bs, 2H), 3.62 (s, 2H), 2.56 (t, 2H, J=7.4 Hz), 2.33 (d, 2H, J=7.4 Hz), 1.65-1.55 (m, 1H), 1.55-1.40 (m, 2H), 0.85 (d, 6H+1H, J=6.5 Hz), 0.47 (m, 2H), 0.53 (m, 2H). ¹³C NMR (CHCl₃-d₃) δ: 167.9, 165.4, 156.4, 153.1, 147.6, 139.7, 139.3, 125.0, 123.5, 117.3, 110.9, 59.0, 58.0, 52.3, 36.2, 26.6, 23.1, 8.9, 4.3. MS (Electrospray): 386.2 (M⁺+1).

EXAMPLE 671

6-[4-((3-Methyl-butyl), cyclohexylmethyl amino methyl)-2-fluoro phenoxy]nicotinonamide

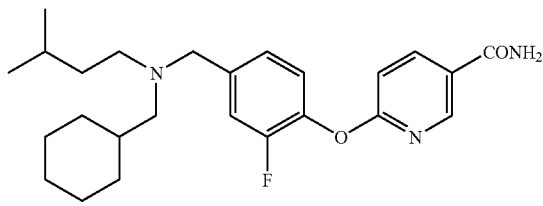

The title compound was prepared by reductive amination of 6-[2-fluoro-4-((3-methyl-butyl) aminomethyl)phenoxy] nicotinamide with cyclohexylcarboxaldehyde.

71% Yield. Mp 110-1° C. ¹H NMR (CHCl₃-d₃) δ: 8.55 (d, 1H, J=2.3 Hz), 8.15 (dd, 1H, J=8.6, 2.3 Hz), 7.28-7.10 (m, 3H), 6.98 (d, 1H, J=8.6 Hz), 6.37 (bs, 2H), 3.49 (s, 2H), 2.40 (t, 2H, J=7.2 Hz), 2.15 (d, 2H, J=7.2 Hz), 1.75-1.10 (m, 13H), 1.55-1.40 (m, 2H), 0.83 (d, 6H+1H, J=6.6 Hz). ¹³C NMR (CHCl₃-d₃) δ: 167.8, 165.5, 156.4, 153.1, 147.5, 139.7, 139.1, 124.9, 123.5, 117.2, 110.9, 69.0, 61.8, 58.9, 52.9, 43.0, 36.5, 32.2, 29.9, 26.5, 23.0. MS (Electrospray): 428.4 (M⁺+1).

EXAMPLE 672

6-[4-(((3-Pyridylethyl), ethyl amino methyl)-2-fluoro phenoxy]nicotinonamide

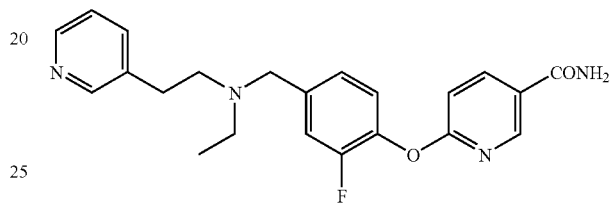

The title compound was prepared by reductive amination of 6-[2-fluoro-4-((3-methyl-butyl)aminomethyl)phenoxy]nicotinamide with acetaldehyde.

51% Yield. ¹H NMR (CHCl₃-d₃) δ: 8.58 (bs, 1H), 8.40 (bs, 2H), 8.20 (dd, 1H, J=8.9, 2.4 Hz), 7.45 (d, 1H, J=7.7 Hz), 7.25 (dd, 1H, J=7.9, 3.8 Hz), 7.15-7.00 (m, 4H), 6.80 (bs, 1H), 6.20 (bs, 1H), 3.59 (s, 2H), 2.70 (m, 4H), 2.55 (c, 2H, J=7.0 Hz), 1.04 (t, 3H, J=7.0 Hz). ¹³C NMR (CHCl₃-d₃) δ: 167.7, 165.3, 156.4, 153.1, 150.3, 147.6, 139.8, 139.5, 139.4, 139.3, 136.8, 136.4, 125.0, 124.7, 123.6, 116.9, 110.9, 57.6, 57.7, 47.7, 31.3, 12.2. MS (Electrospray): 395.4 (M⁺+1).

EXAMPLE 673

6-[4-(Cyclopropyl methyl amino methyl)-2-fluoro phenoxy]nicotinonamide

The title product was prepared following standard reductive amination techniques with cyclopropylmethyl amine and 6-(4-formyl-2-fluorophenoxy)nicotinamide.

58% Yield. MP 128-9° C. ¹H NMR (MeOH-d₄) δ: 8.60 (d, 1H, J=2.4 Hz), 8.27 (dd, 1H, J=8.7, 2.4 Hz), 7.33-7.18 (m, 3H), 6.98 (d, 1H, J=8.7 Hz), 3.81 (s, 2H), 2.44 (d, 1H, J=6.7 Hz), 1.00 (m, 1H), 0.51 (m, 2H), 0.16 (m, 2H). ¹³C NMR (MeOH-d₄) δ: 170.0, 166.6, 157.9, 154.6, 149.1, 141.0, 140.7, 126.8, 126.3, 125.3, 118.2, 111.8, 55.2, 53.7, 11.8, 4.5. MS (Electrospray): 316.1 (M⁺+1).

EXAMPLE 674

6-[4-(Cyclohexyl methyl amino methyl)-2-fluoro phenoxy]nicotinonamide

The title product was prepared following standard reductive amination techniques with cyclohexylmethyl amine and 6-(4-formyl-2-fluorophenoxy)nicotinamide.

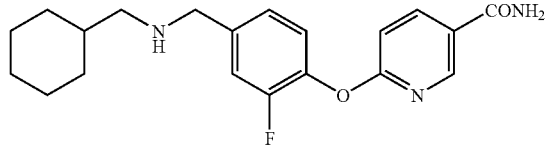

58% Yield. MP 152-3° C. $^1$H NMR (MeOH-d$_4$) δ: 8.60 (d, 1H, J=2.2 Hz), 8.26 (dd, 1H, J=8.5, 2.2 Hz), 7.35-7.15 (m, 3H), 7.01 (d, 1H, J=8.7 Hz), 3.78 (s, 2H), 2.45 (d, 1H, J=6.7 Hz), 1.90-1.65 (m, 5H), 1.55 (m, 1H), 1.45-1.15 (m, 3H), 1.00-0.80 (m, 2H). $^{13}$C NMR (MeOH-d$_4$) δ: 170.0, 166.7, 157.9, 154.6, 149.1, 141.2, 140.8, 126.8, 126.3, 125.3, 118.2, 111.7, 57.0, 54.1, 39.2, 32.9, 28.1, 27.5. MS (Electrospray): 358.1 (M⁺+1).

EXAMPLE 675

6-[4-(Cycloheptylamino methyl)-2-fluoro phenoxy]nicotinonamide

The title product was prepared following standard reductive amination techniques with cycloheptylamine and 6-(4-formyl-2-fluorophenoxy)nicotinamide.

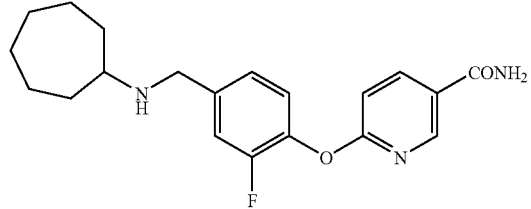

69% Yield. $^1$H NMR (MeOH-d$_4$) δ: 8.59 (d, 1H, J=2.2 Hz), 8.26 (dd, 1H, J=8.5, 2.2 Hz), 7.34-7.18 (m, 3H), 7.10 (d, 1H, J=8.7 Hz), 3.80 (s, 2H), 2.75 (bs, 1H), 1.85-1.70 (m, 5H), 1.70-1.35 (m, 7H). $^{13}$C NMR (MeOH-d$_4$) δ: 170.0, 166.7, 157.9, 154.6, 149.1, 141.2, 126.8, 126.4, 126.3, 125.3, 118.3, 111.7, 58.3, 34.9, 28.6, 27.4, 25.8. MS (Electrospray): 358.1 (M⁺+1).

EXAMPLE 676

6-[4-(Cyclooctylamino methyl)-2-fluoro phenoxy]nicotinonamide

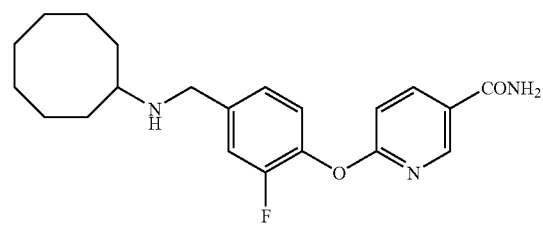

The title product was prepared following standard reductive amination techniques with cyclooctylamine and 6-(4-formyl-2-fluorophenoxy)nicotinamide in 49% Yield.

$^1$H NMR (MeOH-d$_4$) δ: 8.59 (d, 1H, J=2.4 Hz), 8.26 (dd, 1H, J=8.7, 2.4 Hz), 7.40-7.20 (m, 3H), 7.08 (d, 1H, J=8.7 Hz), 3.78 (s, 2H), 2.68 (bs, 1H), 2.00-1.85 (m, 2H), 1.80-1.40 (m, 14H). $^{13}$C NMR (MeOH-d$_4$) δ: 170.0, 166.7, 157.9, 154.6, 149.1, 141.1, 140.9, 126.8, 126.3, 125.3, 118.2, 111.7, 59.6, 51.4, 38.8, 35.6, 29.7, 26.0. MS (Electrospray): 372.3 (M⁺+1).

EXAMPLE 677

6-[4-(tert-butylamino methyl)-2-fluoro phenoxy]nicotinonamide

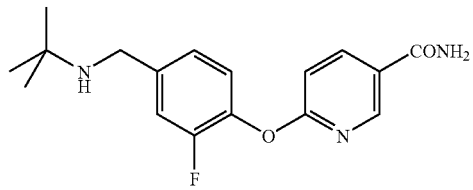

The title product was prepared following standard reductive amination techniques with tert-1-butylamine and 6-(4-formyl-2-fluorophenoxy)nicotinamide in 12% yield.

$^1$H NMR (MeOH-d$_4$) δ: 8.58 (d, 1H, J=2.4 Hz), 8.27 (dd, 1H, J=8.7, 2.4 Hz), 7.35-7.20 (m, 3H), 7.10 (d, 1H, J=8.7 Hz), 3.75 (s, 2H), 1.22 (s, 9H). $^{13}$C NMR (MeOH-d$_4$) δ: 170.1, 166.7, 157.6, 154.6, 149.0, 141.6, 141.5, 126.8, 126.4, 125.3, 118.4, 111.6, 52.4, 47.5, 29.1. MS (Electrospray): 318.1 (M⁺+1).

EXAMPLE 678

6-[4-(2-furylmethyl amino methyl)-2-fluoro phenoxy]nicotinonamide

The title product was prepared following standard reductive amination techniques with 2-furylmethyl amine and 6-(4-formyl-2-fluorophenoxy)nicotinamide.

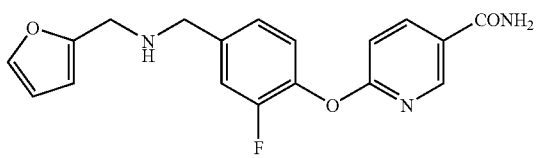

27% Yield. $^1$H NMR (MeOH-d$_4$) δ: 8.60 (d, 1H, J=2.0 Hz), 8.26 (dd, 1H, J=8.7, 2.0 Hz), 7.46 (bs, 1H), 7.30-7.15 (m 3H), 7.08 (d, 1H, J=8.5 Hz), 6.37 (bs, 1H), 6.29 (bs, 1H), 3.77 (s, 4H). $^{13}$C NMR (MeOH-d$_4$) δ: 170.0, 166.7, 158.0, 154.8, 149.1, 143.7, 141.2, 140.5, 140.4, 126.8, 126.4, 126.3, 125.3, 118.3, 111.7, 109.1, 52.9, 46.0. MS (Electrospray): 342.1 (M$^+$+1).

EXAMPLE 679

(S)-6-[4-(Methyl)benzyl amino methyl)-2-fluorophenoxy]nicotinonamide

The title compound prepared following standard reductive amination with (S)-methylbenzylamine and 6-(4-formyl-2-fluorophenoxy)nicotinamide.

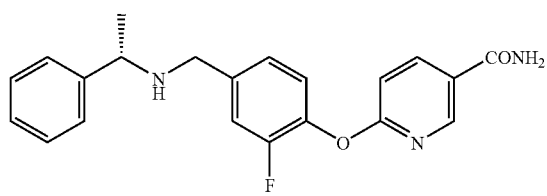

50% Yield. $^1$H NMR (MeOH-d$_4$) δ: 8.59 (d, 1H, J=2.0 Hz), 8.30 (dd, 1H, J=8.5, 2.0 Hz), 7.40-7.30 (m, 4H), 7.28 (m, 1H), 7.18 (m, 2H), 7.09 (m, 2H), 3.81 (c, 1H, J=6.7 Hz), 3.60 (AB system, 2H), 1.39 (d, 3H, J=6.7 Hz). $^{13}$C NMR (MeOH-d$_4$) δ: 170, 166.7, 157.9, 154.6, 149.0, 146.4, 141.2, 130.0, 128.4, 127.2, 126.8, 126.3, 126.2, 125.2, 118.1, 111.7, 58.9, 51.7, 24.5. MS (Electrospray): 366.1 (M$^+$+1).

EXAMPLE 680

(R)-6-[4-(Methylbenzyl amino methyl)-2-fluoro phenoxy]nicotinonamide

The title compound was prepared following standard reductive amination with (R)-methylbenzylamine and 6-(4-formyl-2-fluorophenoxy)nicotinamide.

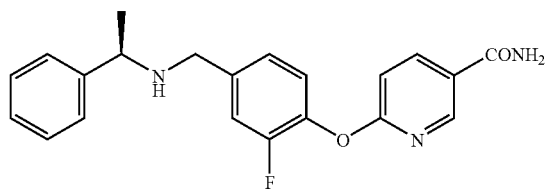

39% Yield. $^1$H NMR (MeOH-d$_4$) δ: 8.59 (d, 1H, J=2.0 Hz), 8.30 (dd, 1H, J=8.5, 2.0 Hz), 7.40-7.30 (m, 4H), 7.28 (m, 1H), 7.18 (m, 2H), 7.09 (m, 2H), 3.81 (c, 1H, J=6.7 Hz), 3.60 (AB system, 2H), 1.39 (d, 3H, J=6.7 Hz). $^{13}$C NMR (MeOH-d$_4$) δ: 170.1, 166.7, 157.9, 154.6, 149.0, 146.4, 141.2, 130.0, 128.4, 127.2, 126.8, 126.3, 126.2, 125.2, 118.1, 111.7, 58.9, 51.7, 24.5. MS (Electrospray): 366.1 (M$^+$+1).

EXAMPLE 681

Synthesis of 6-(4-Ethylaminomethyl-2-fluoro-phenoxy)-nicotinamide

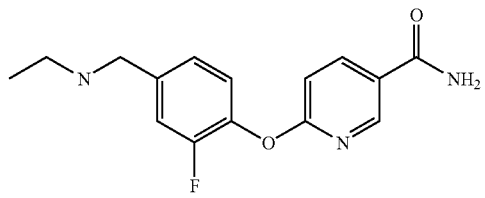

Using ethylamine and 2-fluoro-4-formylphenoxynicotinamide, the title product was obtained in 72% Yield $^1$H NMR (DMSO, 300 MHz) δ: 8.54 (dd, J=1.8, 1H), 8.27 (dd, J=7.4, 1.6 Hz, 1H), 8.00 (br s, 1H), 7.46 (br s, 1H), 7.3-7.1 (m, 4H), 3.68 (s, 2H), 2.49 (q, 2H), 1.02 (t, J=4.6 Hz, 3H). MS (Electrospray): (M$^+$+1) 290.2

EXAMPLE 682

Synthesis of 6-(2-Fluoro-4-propylaminomethyl)-phenoxy)-nicotinamide

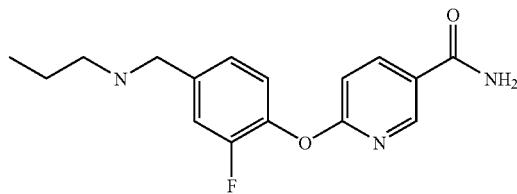

Using n-propylamine and 2-fluoro-4-formylphenoxynicotinamide, the title product was obtained.

MS (Electrospray): (M$^+$+1) 304.2 (M$^+$−1) 302.3 HPLC=90%@5.66 m (5/95 to 95/5 ACN/(0.1% TFA in water) over 10 minutes, Zorbax SB-Phenyl 4.6 mm×15 cm×5 micron, λ=254 nM.de

EXAMPLE 683

Synthesis of 6-(2-Fluoro-4-hexylaminomethyl-phenoxy)-nicotinamide

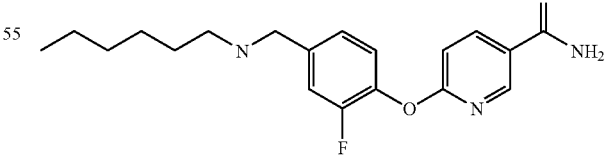

Using hexylamine and 2-fluoro-4-formylphenoxynicotinamide the title product was obtained.

MS (Electrospray): (M$^+$+1) 346.2 (M$^+$−1) 344.4 HPLC=98%@5.98 m (5/95 to 95/5 ACN/(0.1% TFA in water) over 10 minutes, Zorbax SB-Phenyl 4.6 mm×15 cm×5 micron, λ=254 nM.de

EXAMPLE 684

Synthesis of 6-[2-Fluoro-4-(isobutylamino-methyl)-phenoxy]-nicotinamide

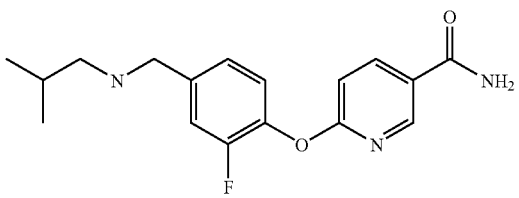

Using isopropylamine and 2-fluoro-4-formylphenoxynicotinamide, the title product was obtained.
MS (Electrospray): (M⁺+1) 318.2 HPLC=94% (5.72 m (5/95 to 95/5 ACN/(0.1% TFA in water) over 10 minutes, Zorbax SB-Phenyl 4.6 mm×15 cm×5 micron, λ=254 nM.de

EXAMPLE 685

Synthesis of 6-[2-Fluoro-4-(isobutylamino-methyl)-phenoxy]-nicotinamide

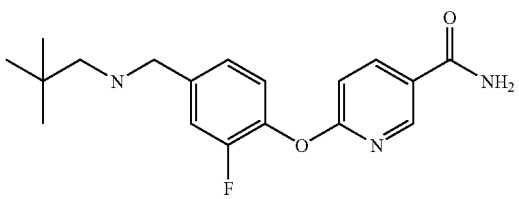

Using 2,2-dimethylpropyl amine and 2 fluoro-4-formylphenoxynicotinamide, the title product was obtained.
MS (Electrospray): (M⁺+1) 332.2 (M⁺-1) 330.4 HPLC=99%@5.79 m (5/95 to 95/5 ACN/(0.1% TFA in water) over 10 minutes, Zorbax SB-Phenyl 4.6 mm×15 cm×5 micron, λ=254 nM.de

EXAMPLE 686

Synthesis of 3-Fluoro-4-{4-[(2-pyridin-2-yl-ethylamino)-methyl]-phenoxy}-benzamide

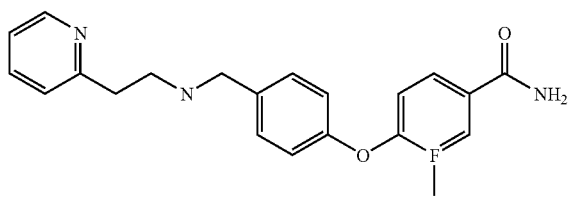

Using 2-pyridino-2-ethylamine and 4-formylphenoxy-3-fluorobenzamide (Example 243, step 3), the title product was obtained in 52% Yield.
¹H NMR (CD₃OD, 300 MHz) δ: 8.41 (d, J=1.8, 1H), 8.37 (dd, J=4.5 Hz, 1H), 7.78 (d, J=1.8, 1H), 7.74-7.64 (m, 2H), 7.38-7.33 (m, 3H), 7.07-6.97 (m, 3H), 3.77 (s, 2H), 2.85 (s, 4H). HPLC=94%@5.56 m (5/95 to 95/5 ACN/(0.1% TFA in water) over 10 minutes, Zorbax SB-Phenyl 4.6 mm×15 cm×5 micron, λ=254 nM.de MS (Electrospray): (M⁺+1) 366.1 (M⁺-1) 364.3

EXAMPLE 687

Synthesis of 2-Fluoro-4-{4-[(3-methyl-butylamino)-methyl]-phenoxy}-benzamide

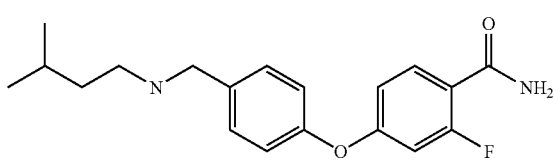

Using 3-methylbutylamine and 4-formylpheoxy-2-fluorobenzamide, the title product was obtained in 10% Yield.
¹H NMR (CD₃OD, 300 MHz) δ: 7.82 (m, 1H), 7.42 (d, J=8.7 Hz, 2H), 7.07 (d, J=8.7 Hz, 2H), 6.83 (dd, J=6.9, 2.1 Hz, 1H), 6.72 (dd, J=12.6, 2.1 Hz, 1H), 3.77 (s, 2H), 2.65-2.59 (m, 2H), 1.66-1.57 (m, 1H), 1.47-1.40 (m, 2H), 0.91 (d, J=6.6 Hz, 6H). MS (Electrospray): (M⁺+1) 331.2

EXAMPLE 688

Synthesis of 3-Methoxy-4-{4-[(3-methyl-butylamino)-methyl]-phenoxy}-benzamide

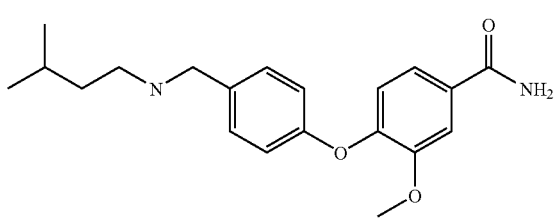

Using 3-methylbutylamine and 4-formylphenoxy-3-methoxybenzamide, the title product was obtained in 15% Yield.
¹H NMR (CD₃OD, 300 MHz) δ: 7.62 (d, J=2.4 Hz, 1H), 7.46 (dd, J=8.1, 1.8 Hz, 1H), 7.30 (d, J=8.7 Hz, 2H), 6.96 (d, J=8.1, 1H), 6.88 (d, J=8.4, 2H), 3.77 (s, 2H), 2.62-2.57 (m, 2H), 1.65-1.56 (m, 1H), 1.46-1.38 (m, 2H), 0.90 (d, J=6.6 Hz, 6H). MS (Electrospray): (M⁺+1) 343.25 HPLC=98%@5.95 m (5/95 to 95/5 ACN/(0.1% TFA in water) over 10 minutes, Zorbax SB-Phenyl 4.6 mm×15 cm×5 micron, λ=254 nM.de

EXAMPLE 689

Synthesis of 2-Methyl-4-{4-[(3-methyl-butylamino)-methyl]-phenoxy}-benzamide

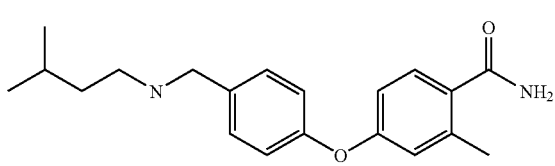

Using 3-methylbutylamine and 4-formylphenoxy-2-methylbenzamide, the title product was obtained in 71% Yield.

$^1$H NMR (CD$_3$OD, 300 MHz) δ: 7.42 (d, J=8.4 Hz, 1H), 7.36 (d, J=6.6 Hz, 2H), 6.97 (d, J=8.4, 2H), 6.67-6.83 (m, 2H), 3.74 (s, 2H), 2.65-2.58 (m, 2H), 2.40 (s, 3H), 1.63-1.59 (m, 1H), 1.47-1.39 (m, 2H), 0.91 (d, J=6.6 Hz, 6H). MS (Electrospray): (M$^+$+1) 341.3 (M$^+$−1) 239.4 HPLC=91%@6.07 nm (5/95 to 95/5 ACN/(0.1% TFA in water) over 10 minutes, Zorbax SB-Phenyl 4.6 mm×15 cm×5 micron, λ=254 nM.de

EXAMPLE 690

Synthesis of 3-Methyl-4-{4-[(3-methyl-butylamino)-methyl]-phenoxy}-benzamide

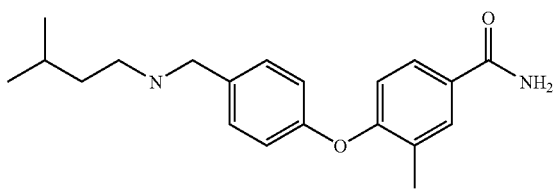

Using 3-methylbutylamine and 4-formylphenoxy-3-methylbenzamide, the title product was obtained in 60% Yield.

$^1$H NMR (CD$_3$OD, 300 MHz) δ: 7.81 (d, J=0.9 Hz, 1H), 7.68-7.64 (m 1H), 7.35 (d, J=6.6, 2H), 6.92 (d, J=6.6, 2H), 6.81 (d, J=6.6, 1H), 3.75 (s, 2H), 2.64-2.60 (m, 2H), 2.31 (s, 3H), 1.64-1.60 (m, 1H), 1.47-1.41 (m, 2H), 0.92 (d, J=6.6 Hz, 6H). MS (Electrospray): (M$^+$+1) 327.2

EXAMPLE 691

3-Fluoro-4-{4-[3-methylbutylamino)-methyl]phenoxy}-benzamide

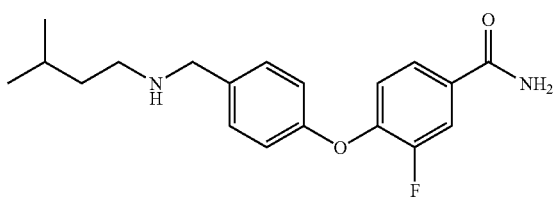

Reductive amination using the intermediate of Example 243 step 3, and 3-methylbutylamine afforded the title compound in 96% Yield $^1$H NMR (CD$_3$OD, 200 MHz) δ: 7.76 (dd, J=11.6, 2.2 Hz, 1H), 7.69-7.63 (m, 1H), 7.36 (d, J=6.7 Hz, 2H), 7.08-6.97 (m, 3H), 3.73 (s, 2H), 2.65-2.55 (m, 2H), 1.67-1.53 (m, 1H), 1.47-1.36 (m, 2H), 0.90 (d, J=6.4 Hz, 6H). HPLC=98% (6.00 m (5/95 to 95/5 ACN/(0.1% TFA in water) over 10 minutes, Zorbax SB-Phenyl 4.6 mm×15 cm×5 micron, λ=254 nM.de MS (APCI): (M$^+$+1) 331.1

EXAMPLE 692

3-Fluoro-4-{4-[(3,3-Dimethyl-butylamino)-methyl]-phenoxy}-3-fluoro-benzamide

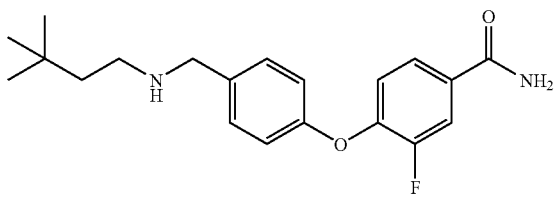

Reductive amination using the intermediate of Example 243 step 3, and 3,3-dimethylbutylamine, afforded the title compound in 62% Yield $^1$H NMR (CD$_3$OD, 200 MHz) δ: 7.76 (dd, J=11.6, 2.2 Hz, 1H), 7.74-7.64 (m, 1H), 7.36 (d, J=6.7 Hz, 2H), 7.08-6.97 (m, 3H), 3.73 (s, 2H), 2.64-2.56 (m, 2H), 1.49-1.41 (m, 2H), 2.1 (s, 9H). MS (APCI): (M$^+$+1) 345.2

EXAMPLE 693

3-Fluoro-4-(4-pentylaminomethyl-phenoxy)-benzamide

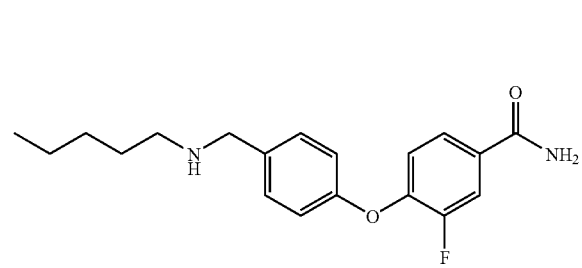

Reductive amination using the intermediate of Example 243 step 3, and pentylamine, afforded the title compound in 94% Yield.

$^1$H NMR (CD$_3$OD, 200 MHz) δ: 7.77 (dd, J=11.6, 2.2 Hz, 1H), 7.74-7.69 (m, 1H), 7.36 (d, J=6.7 Hz, 2H), 7.08-6.97 (m, 3H), 3.73 (s, 2H), 2.60-2.53 (m, 2H), 1.57-1.50 (m, 2H), 1.39-1.29 (m, 4H), 0.91 (t, J=6.7 Hz, 3H). MS (APCI): (M$^+$+1) 331.1

EXAMPLE 694

3,5-Difluoro-4-{4-[3-methyl-butylamino)-methyl]-phenoxy}-benzamide

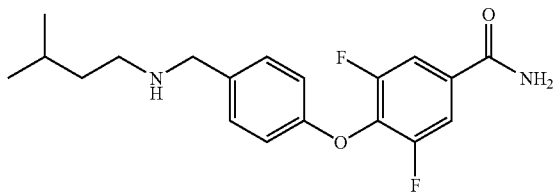

Step 1

3,5-Difluoro-4-(4-formyl-phenoxy)benzonitrile

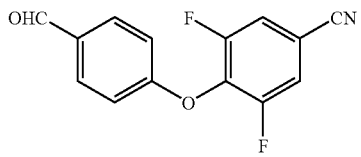

Basic displacement reaction of 4-hydroxy benzaldehyde and 3,5-difluorobenzonitrile using potassium carbonate in anhydrous DMF at reflux temperatures affords the above compound.

76% Yield $^1$H NMR (CDCl$_3$, 200 MHz) δ: 9.93 (s, 1H), 7.87 (d, J=8.8 Hz, 2H), 7.38 (d, J=6.6 Hz, 2H), 7.04 (d, J=8.4 Hz, 2H). $^{13}$C NMR (CDCl$_3$, 300 MHz) δ: 189.9, 157.4, 152.0 (d, $^1$J$_{CF}$=252.1), 146.9 (d, $^2$J$_{CF}$=11.0), 132.2, 132.0, 129.0, 128.7, 128.6, 120.3, 120.0, 119.9 (d, $^3$J$_{CF}$=1.4), 116.7, 116.3 (d, $^3$J$_{CF}$=2.3), 107.1 (d, $^2$J$_{CF}$=8.1), 15.0.

Step 2

3,5-Difluoro-4-(4-formyl-phenoxy)benzamide

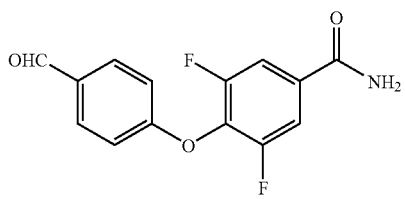

Hydrolysis of the compound of step 1 using hydrogen peroxide and potassium carbonate in DMSO as described previously afford the above compound in 99% yield.

$^1$H NMR (DMSO, 200 MHz) δ: 9.89 (s, 1H), 8.15 (brs, 1H), 7.90 (d, J=8.8 Hz, 2H), 7.80 (d, J=8.8 Hz, 2H), 7.71 (brs, 1H), 7.18 (d, J=8.8 Hz, 2H). MS (APCI): (M$^+$+1) 278.0 (M$^+$−1) 276.0

Step 3

3,5-Difluoro-4-{4-[3-methyl-butylamino)-methyl]-phenoxy}-benzamide

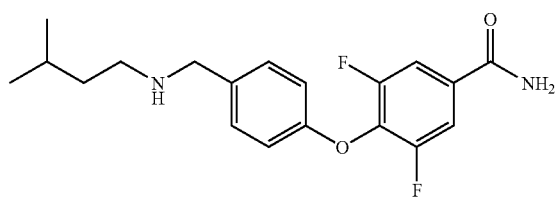

Reductive amination of the compound of step 2 with 3-methylbutylamine affords the title compound in 61% Yield $^1$H NMR (CD$_3$OD, 200 MHz) δ: 7.66 (d, J=8.9 Hz, 2H), 7.31 (d, J=8.6 Hz, 2H), 6.91 (d, J=8.6 Hz, 2H), 3.70 (s, 2H), 2.60-2.53 (m, 2H), 1.66-1.49 (m, 1H), 1.46-1.35 (m, 2H), 0.89 (d, J=6.4 Hz, 6H). MS (APCI): (M$^+$+1) 349.1

EXAMPLE 695

Synthesis of 3-Fluoro-4-(4-{[methyl-(3-methyl-butyl)-amino]-methyl}-phenoxy)-benzamide

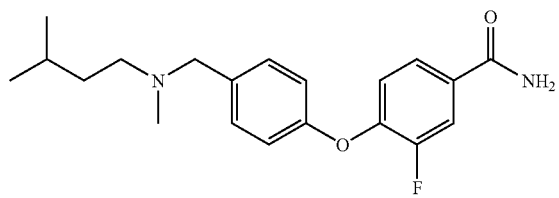

Reductive amination using formaldehyde and the compound of Example 691 affords the title product.

$^1$H NMR (CD$_2$OD, 300 MHz) δ: 7.76 (dd, J=11.4, 1.8 Hz, 1H), 7.68-7.65 (m, 1H), 7.34 (d, J=6.6 Hz, 2H), 7.08 (m, 1H), 7.00 (d, J=6.6 Hz, 2H), 3.51 (s, 2H), 2.44-2.39 (m, 2H), 2.20 (s, 3H), 1.60-1.55 (m, 1H), 1.47-1.39 (m, 2H), 0.90 (d, J=6.6 Hz, 6H). MS (Electrospray): (M$^+$+1) 345.2 (M$^+$−1) 343.3

EXAMPLE 696

Synthesis of 3,5-Difluoro-4-(4-{[methyl-(3-methyl-butyl)-amino]-methyl}-phenoxy)-benzamide

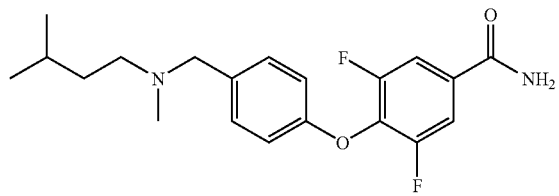

Reductive amination using formaldehyde and the compound of Example 694, step 3 affords title product in 66% Yield.

$^1$H NMR (CD$_3$OD, 300 MHz) δ: 7.66 (d, J=9.0 Hz, 2H), 7.28 (d, J=8.4 Hz, 2H), 6.90 (d, J=8.4 Hz, 2H), 3.47 (s, 2H), 2.41-2.36 (m, 2H), 2.17 (s, 3H), 1.60-1.50 (m, 1H), 1.45-1.39 (m, 2H), 0.88 (d, J=6.6 Hz, 6H). MS (Electrospray): (M$^+$+1) 363.2 (M$^+$−1) 361.3

EXAMPLE 697

Synthesis of

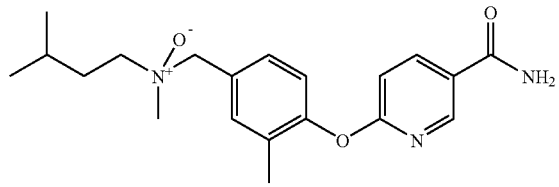

To a solution of Example 227 in chloroform was added m-CPBA (1.01 equiv) and the reaction mixture stirred for 6 hours at room temperature. It was quenched with few drops of sodium bicarbonate. The organic phase was separated and dried over magnesium sulphate, filtered and concentrated to yield a white solid. Purify by eluting through a 5 g ISCO® column CHCl$_3$: 30% (EtOH:NH$_4$OH 10%) to afford the title compound as a solid.

20% Yield $^1$H NMR (CD$_3$OD, 300 MHz) δ: 8.59 (dd, J=1.8, 0.9 Hz, 1H), 8.28-8.25 (m, 1H), 7.55 (s, 1H), 7.46 (d, J=8.4, Hz, 1H), 7.11 (d, J=8.1 Hz, 1H), 7.03 (d, J=8.7 Hz, 1H), 4.37 (q, 2H), 3.12-3.07 (m, 2H), 2.99 (s, 3H), 2.17 (s, 3H), 2.00-1.80 (m, 1H), 1.81-1.70 (m, 1H), 1.69-1.60 (m, 1H), 0.98 (dd, J=6.6, 1.2 Hz, 6H). MS (Electrospray): (M$^+$+1) 358.1 (M$^+$−1) 356.3 HPLC=90%@5.94 m (5/95 to 95/5 ACN/(0.1% TFA in water) over 10 minutes, Zorbax SB-Phenyl 4.6 mm×15 cm×5 micron, λ=254 nM.de

EXAMPLE 698

4-{2-Chloro-4-[(2-thiophen-2-yl-ethylamino)-methyl]-phenoxy}-benzamide

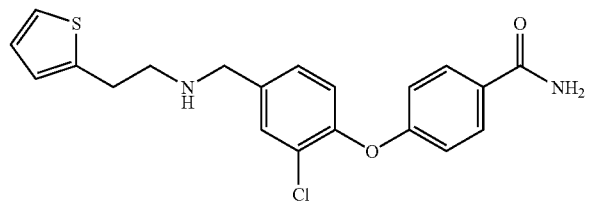

Step 1: Preparation of Intermediate 1

4-(2-Chloro-4-formyl-phenoxy)-benzamide

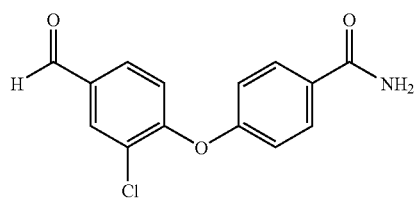

Mix 3-chloro-4-fluorobenzaldehyde (3.28 g, 20.7 mmol), 4-hydroxybenzamide (3.12 g, 22.7 mmol), potassium carbonate (4.29 g, 31.0 mmol) and dimethylacetamide (80 mL) in a flask. Heat the reaction to 100° C. for 3 hours. Let cool to ambient (room) temperature and pour into water (200 mL). After trituration, filter the solid formed and dry on a vacuum pump to obtain the product (5.35 g, 94%). $^1$H NMR (DMSO-d$_6$) 9.94 (s, 1H), 8.13 (d, J=1.7 Hz, 1H), 7.98 (bs, 1H), 7.94 (d, J=8.5 Hz, 2H), 7.88 (dd, J=1.7 Hz, 8.5 Hz, 1H), 7.36 (bs, 1H), 7.21 (d, J=8.5 Hz, 1H), 7.14 (d, J=8.5 Hz, 2H).

Step 2

Mix 4-(2-chloro-4-formyl-phenoxy)-benzamide (0.19 g, 0.70 mmol), 2-thiophen-2-yl-ethylamine (0.074 mL, 0.63 mmol), and methanol (8 mL) in a 20 mL vial. After the reaction mixture solubilizes, add 3 Å molecular sieves (0.50 g) and stir for 8 hrs. Cool in an ice bath for 10 min and add sodium borohydride (0.048 g, 1.27 mmol). Remove ice bath and stir for 2 hrs. Purify by placing directly onto an SCX column (5 g) using methanol to load and wash and 2M NH$_3$ in CH$_3$OH as eluant to obtain the product (0.23 g, 94%), serial number 2136018. Mass spectrum (ion spray): m/z=387.2 (M+1); $^1$H NMR (DMSO-d$_6$) 7.89 (bs, 1H), 7.86 (d, J=8.5 Hz, 2H), 7.57 (s, 1H), 7.34 (d, J=8.5 Hz, 1H), 7.30-7.26 (m, 2H), 7.16 (d, J=8.8 Hz, 1H), 6.95-6.84 (m, 4H), 3.74 (s, 2H), 2.94 (t, J=7.1 Hz, 2H), 2.75 (t, J=7.1 Hz, 2H).

EXAMPLE 699

4-{2-Chloro-4-[(3,3-dimethyl-butylamino)-methyl]-phenoxy}-benzamide

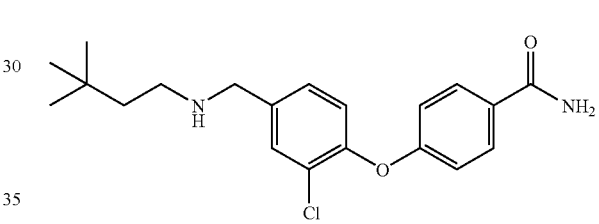

Reductive amination of the compound of Example 698, Step 1 and 3,3,dimethylbutylamine affords the title product (0.21 g, 99%). Mass spectrum (ion spray): m/z=361.3 (M+1); $^1$H NMR (DMSO-d$_6$) 7.89 (bs, 1H), 7.86 (d, J=7.7 Hz, 2H), 7.56 (s, 1H), 7.33 (d, J=8.2 Hz, 1H), 7.28 (bs, 1H), 7.16 (d, J=7.7 Hz, 1H), 6.89 (d, J=7.7 Hz, 2H), 3.69 (s, 2H), 2.49 (t, J=7.7 Hz, 2H), 1.35 (t, J=7.7 Hz, 2H), 0.85 (s, 9H).

EXAMPLE 700

4-{2-Chloro-4-[(3-methyl-butylamino)-methyl]-phenoxy}-benzamide

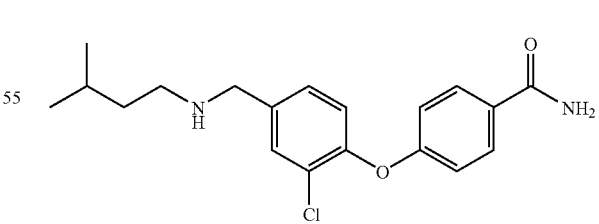

Reductive amination of the compound of Example 698, Step 1 and 3-methylbutylamine affords the title product (0.20 g, 92%). Mass spectrum (ion spray): m/z=347.3 (M+1); $^1$H NMR (DMSO-d$_6$) 7.90 (bs, 1H), 7.86 (d, J=8.3 Hz, 2H), 7.55 (s, 1H), 7.33 (d, J=8.3 Hz, 1H), 7.28 (bs, 1H), 7.15 (d, J=8.3 Hz, 1H), 6.89 (d, J=8.3 Hz, 2H), 3.67 (d, J=6.7 Hz, 2H), 2.46

(t, J=7.8 Hz, 2H), 1.61 (septet, J=6.7 Hz, 1H), 1.30 (q, J=6.7 Hz, 2H), 0.83 (d, J=6.7 Hz, 6H).

EXAMPLE 701

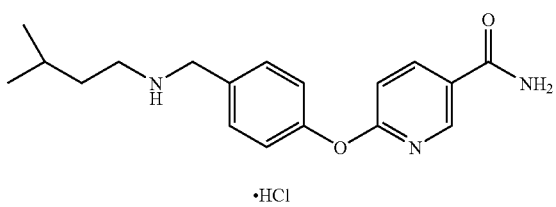

·HCl

Step 1

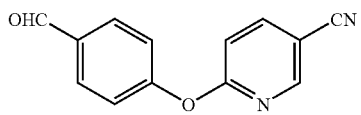

4-Hydroxybenzaldehyde (2.94 mol), 2-chloro-5-cyanopyridine (2.94 mol) and approximately 5.7 L of dimethylacetamide were stirred under nitrogen atmosphere. Potassium carbonate (6.17 mol) was added and the mixture was heated the at about 100° C. for about 4 hours or until complete as determined by HPLC analysis The mixture was The reaction mixture was stirred overnight at room temperature. The product was precipitated by adding ice water and allowing to cool with stirring. The product was filtered and the wetcake was rinsed with water. After air drying, the product was further dried under vacuum at 50° C.

Step 2

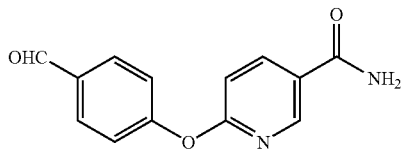

The product of step 1 (2.86 mol), potassium carbonate (1.42 mol), and DMSO (2.6 L) were stirred at room temperature. The mixture was then cooled to 18° C. in an ice-bath, followed by the dropwise addition of 30% hydrogen peroxide (321 mL, 3.14 mol). The observed exotherm was controlled to 52° C. by a slow peroxide addition rate and adding more ice to the ice-bath. The progress of the reaction was monitored by HPLC which showed consumption of the nitrile. The mixture was allowed to warm to room temperature, poured into ice water (about 13 L) and stirred for 45 minutes. The mixture was vacuum filtered and rinsed with water (2×3 L). The solid was further dried in a vacuum oven at 50° C. for 3 days to afford approximately 80% yield.

Step 3

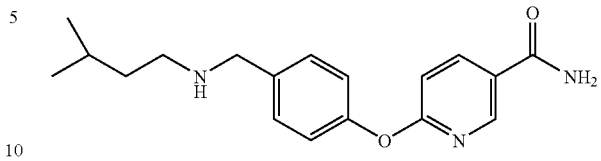

The product of step 2 (2.28 mol), 672 grams of activated molecular sieves, and isopentylamine (3.42 mol) were stirred in methanol (12.5 L) at room temperature. The mixture was stirred overnight (approximately 16 hours) at room temperature. Upon consumption of the aldehyde as determined by HPLC analysis, sodium borohydride ((34.50 g) was added as a solid in 25 gram portions until used up. The reaction mixture was stirred overnight at room temperature and worked as described previously (adjusting for larger amounts of compound) following procedures described previously. To afford about a 93% step 3 yield.

Step 4

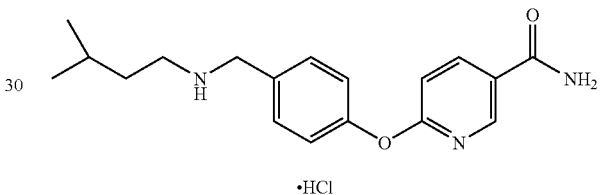

·HCl

The product of step 3 (1.66 mol) was dissolved in 95:5 EtOH/H$_2$O solvents. The solution was heated to 60° C. followed by addition 1N HCl solution (1.66 L) over 15 minutes at 60° C. An additional 500 mL of 95:5 ethanol/water was added to rinse in all of the HCl solution. The resulting mixture was stirred at 60° C. for 2 hours. The mixture was allowed to cool to room temperature. The mixture was filtered and the solid was rinsed with 4×500 mL 95:5 ethanol/water. The solid was dried in a vacuum overnight at 45 ° C. until drying loss was negligible. Step 4 yield was about 93%.

Mass spectrum (ion spray): m/z=314.7 (M+1), $^1$H NMR δ (ppm) 1.03 (d, 6H), 1.78 (s, 3H), 3.40 (s, 2H), 4.54 (s, 2H), 7.41-7.50 (m, 5H), 7.82-7.85 (m, 2H), 9.06-9.08 (m, 1H), 9.23-9.25 (m, 1H). $^{13}$C NMR: δ (ppm) 20.56, 25.78, 34.71, 48.06, 51.67, 112.88, 121.58, 125.66, 130.98, 133.30, 140.45, 148.98, 152.17, 161.58, 166.30.

EXAMPLE 702

4-(2-Chloro-4-pentylaminomethyl-phenoxy)-benzamide

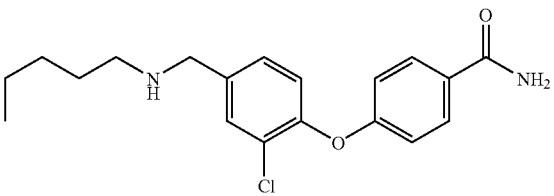

Reductive amination of the compound of Example 698, Step 1 and pentylamine affords the title product t (0.22 g, 98%). Mass spectrum (ion spray): m/z=347.3 (M+1); $^1$H NMR (DMSO-d$_6$) 7.89 (bs, 1H), 7.86 (d, J=8.9 Hz, 2H), 7.55 (s, 1H), 7.33 (d, J=8.4 Hz, 1H), 7.27 (bs, 1H), 7.15 (d, J=8.4 Hz, 1H), 6.89 (d, J=8.9 Hz, 2H), 3.67 (s, 2H), 2.45 (t, J=6.7 Hz, 2H), 1.45-1.37 (m, 2H), 1.28-1.23 (m, 4H), 0.87-0.82 (m, 3H).

EXAMPLE 703

3-Chloro-4-{4-[(2-thiophen-2-yl-ethylamino)-methyl]-phenoxy}-benzamide

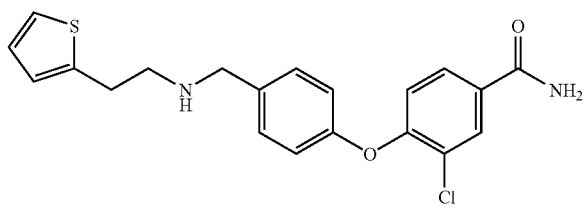

Step 1: 3-Chloro-4-(4-formyl-phenoxy)-benzonitrile

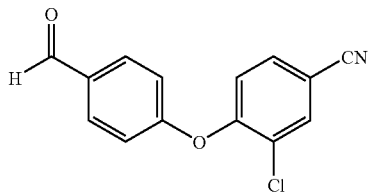

Mix 4-hydroxy-benzaldehyde (0.86 g, 7.07 mmol), 3-chloro-4-fluoro-benzonitrile (1.00 g, 6.43 mmol), cesium carbonate (3.14 g, 9.64 mmol) and dimethylacetamide (30 mL) in a flask. Heat to 100° C. for 4 hrs. Let cool to room temperature (rt) and pour into water (200 mL). After trituration, filter the solid formed and dry on a vacuum pump to obtain the product (1.57 g, 95%). $^1$H NMR (DMSO-d$_6$) 9.96 (s, 1H), 8.29 (d, J=1.8 Hz, 1H), 7.97 (d, J=8.6 Hz, 2H), 7.89 (dd, J=1.8 Hz, 8.6 Hz, 1H), 7.35 (d, J=8.6 Hz, 1H), 7.23 (d, J=8.6 Hz, 2H).

Step 2

3-Chloro-4-(4-formyl-phenoxy)-benzamide

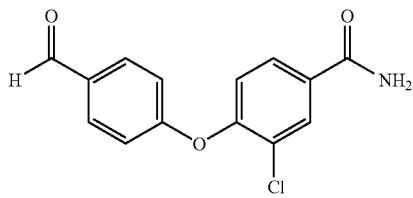

Cool a solution of 3-chloro-4-(4-formyl-phenoxy)-benzonitrile (1.57 g, 6.10 mmol) in dimethylsulfoxide (50 mL) to 0° C. Add potassium carbonate (0.42 g, 3.05 mmol) followed by 30% aqueous hydrogen peroxide (1.83 mL, 6.10 mmol). Remove the cooling bath and let stir at rt for 3 hrs. Pour into water (100 mL) and after trituration, filter the solid formed to obtain the product (1.40 g, 84%). $^1$H NMR (DMSO-d$_6$) 9.93 (s, 1H), 8.12 (d, J=1.2 Hz, 1H), 8.10 (bs, 1H), 7.95-7.90 (m, 3H), 7.53 (bs, 1H), 7.34 (d, J=8.6 Hz, 1H), 7.13 (d, J=8.6 Hz, 2H).

Step 3

Use 3-chloro-4-(4-formyl-phenoxy)-benzamide (0.20 g, 0.71 mmol), 2-thiophen-2-yl-ethylamine (0.075 mL, 0.64 mmol), sodium borohydride (0.049 g, 1.29 mmol) and methanol (8 mL) in a procedure and purification similar to that of Example 1, to obtain the product (0.24 g, 94%), serial number 2137632. Mass spectrum (ion spray): m/z=387.1 (M+1); $^1$H NMR (CDCl$_3$) 7.93 (d, J=2.1 Hz, 1H), 7.62 (dd, J=2.1 Hz, 8.7 Hz, 1H), 7.31 (d, J=8.5 Hz, 2H), 7.14 (d, J=5.2 Hz, 1H), 6.97 (d, J=8.3 Hz, 2H), 6.93 (dd, J=3.4 Hz, 5.1 Hz, 1H), 6.88 (d, J=8.7 Hz, 1H), 6.84 (d, J=3.1 Hz, 1H), 6.11 (bs, 2H), 3.81 (s, 2H), 3.05 (t, J=6.7 Hz, 2H), 2.95 (t, J=6.7 Hz, 2H).

EXAMPLE 704

3-Chloro-4-{4-[(3,3-dimethyl-butylamino)-methyl]-phenoxy}-benzamide

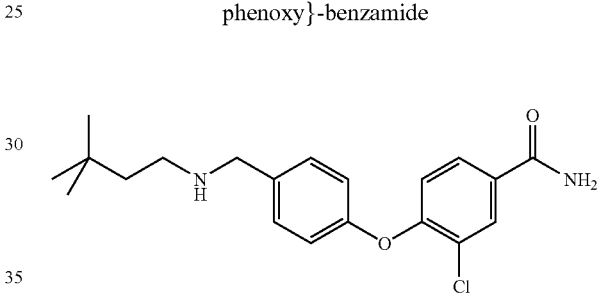

Reductive amination of the compound of Example 703, Step 2 and 3,3,dimethylbutylamine affords the title product (0.21 g, 98%). Mass spectrum (ion spray): m/z=361.2 (M+1); $^1$H NMR (CDCl$_3$) 7.93 (s, 1H), 7.61 (d, J=7.9 Hz, 1H), 7.33 (d, J=7.5 Hz, 2H), 6.97 (d, J=7.5 Hz, 2H), 6.87 (d, J=8.3 Hz, 1H), 6.24 (bs, 2H), 3.78 (s, 2H), 2.65 (t, J=6.5 Hz, 2H), 1.43 (t, J=6.5 Hz, 2H), 0.89 (s, 9H).

EXAMPLE 705

3-Chloro-4-{4-[(3-methyl-butylamino)-methyl]-phenoxy}-benzamide

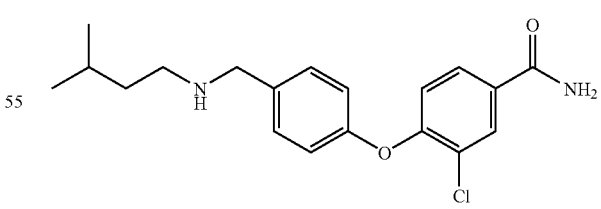

Preparation using a method similar to Example 703 yields the product (0.21 g, 93. Mass spectrum (ion spray): m/z=347.2 (M+1); $^1$H NMR (CDCl$_3$) 7.93 (s, 1H), 7.61 (d, J=8.4 Hz, 1H), 7.31 (d, J=8.4 Hz, 2H), 6.95 (d, J=8.4 Hz, 2H), 6.85 (d, J=8.6 Hz, 1H), 6.49 (bs, 2H), 3.76 (s, 2H), 2.63 (t, J=7.3 Hz, 2H), 1.61 (septet, J=6.5 Hz, 1H), 1.39 (q, J=7.3 Hz, 2H), 0.87 (d, J=6.8 Hz, 6H).

EXAMPLE 706

4-{4-[(3,3-Dimethyl-butylamino)-methyl]-2-trifluoromethyl-phenoxy}-benzamide hydrochloride

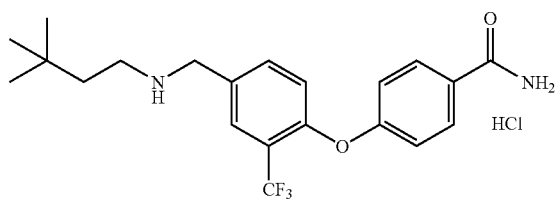

Step 1

4-(4-Formyl-2-trifluoromethyl-phenoxy)-benzamide

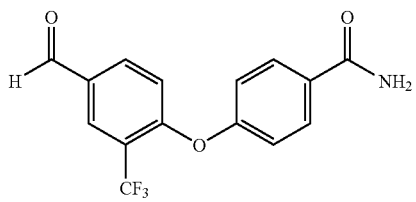

Preparation using a method similar to Example 703, step 2 yields the product (2.00 g, 88%). $^1$H NMR (DMSO-$d_6$) 10.02 (s, 1H), 8.33 (s, 1H), 8.14 (d, J=8.6 Hz, 1H), 8.00 (bs, 1H), 7.97 (d, J=8.6 Hz, 2H), 7.39 (bs, 1H), 7.22 (d, J=8.6 Hz, 2H), 7.19 (d, J=8.6 Hz, 1H).

Step 2

Preparation using a method similar to Example 697 yields the product (0.17 g, 83%). Mass spectrum (ion spray): m/z=395.2 (M+1); $^1$H NMR (CDCl$_3$) 7.79 (d, J=8.2 Hz, 2H), 7.66 (s, 1H), 7.48 (d, J=8.4 Hz, 1H), 7.00-6.94 (m, 3H), 6.33 (bs, 2H), 3.81 (s, 2H), 2.65 (t, J=8.2 Hz, 2H), 1.43 (t, J=8.2 Hz, 2H), 0.89 (s, 9H).

EXAMPLE 707

3-Chloro-4-(3-methoxy-4-pentylaminomethyl-phenoxy)-benzamide hydrochloride

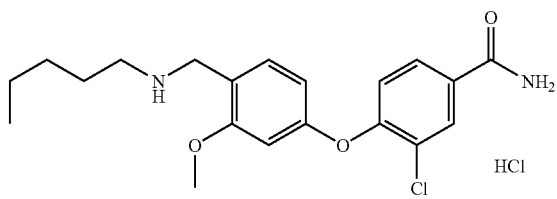

EXAMPLE 708 (cont.)

Step 1

3-Chloro-4-(4-formyl-3-methoxy-phenoxy)-benzonitrile

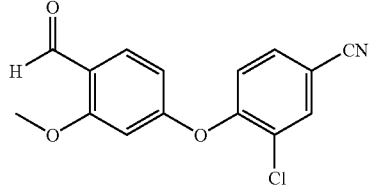

Preparation using a method similar to Example 703, step 1 yields the product (1.83 g, 94%). $^1$H NMR (DMSO-$d_6$) 10.24 (s, 1H), 8.26 (s, 1H), 7.87 (dd, J=2.0 Hz, 8.5 Hz, 1H), 7.72 (d, J=8.5 Hz, 1H), 7.33 (d, J=8.5 Hz, 1H), 6.98 (d, J=2.0 Hz, 1H), 6.61 (d, J=8.5 Hz, 1H), 3.88 (s, 3H).

Step 2

3-Chloro-4-(4-formyl-3-methoxy-phenoxy)-benzamide

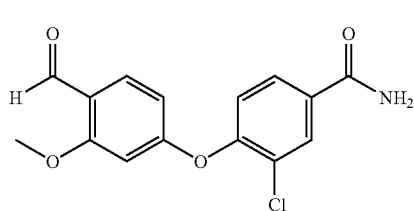

Preparation using a method similar to Example 703, step 2 yields the product (1.73 g, 89%). $^1$H NMR (DMSO-$d_6$) 10.22 (s, 1H), 8.11 (d, J=1.9 Hz, 1H), 8.1 (bs, 1H), 7.90 (dd, J=1.9 Hz, 8.5 Hz, 1H), 7.70 (d, J=8.7 Hz, 1H), 7.54 (bs, 1H), 7.32 (d, J=8.5 Hz, 1H), 6.91 (d, J=2.0 Hz, 1H), 6.49 (dd, J=2.0 Hz, 8.7 Hz, 1H), 3.88 (s, 3H).

Step 3

Reductive amination of the compound of step 2 with n-pentylamine affords the title product (0.18 g, 86%). Mass spectrum (ion spray): m/z=377.2 (M+1); $^1$H NMR (CDCl$_3$) 7.93 (d, J=2.0 Hz, 1H), 7.61 (dd, J=2.1 Hz, 8.7 Hz, 1H), 7.20 (d, J=8.2 Hz, 1H), 6.89 (d, J=8.7 Hz, 1H), 6.59 (d, J=2.1 Hz, 1H), 6.51 (dd, J=2.1 Hz, 8.2 Hz, 1H), 6.33 (bs, 1H), 6.17 (bs, 1H), 3.78 (s, 3H), 3.74 (s, 2H), 2.59 (t, J=7.2 Hz, 2H), 1.54-1.46 (m, 2H), 1.33-1.25 (m, 4H), 0.89 (t, J=6.8 Hz, 3H).

EXAMPLE 708

3-Bromo-4-{4-[(3-methyl-butylamino)-methyl]-phenoxy}-benzamide)

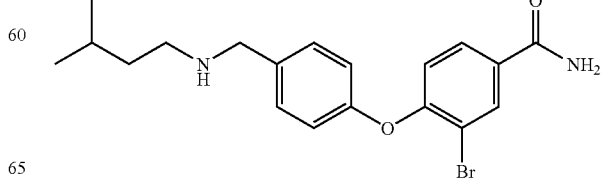

Step 1

3-Bromo-4-hydroxy-benzamide

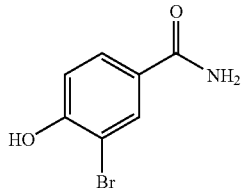

3-Bromo-4-hydroxy-benzonitrile (495 mg, 2.5 mmol) is dissolved in H$_2$SO$_4$ 98%, heat the solution at 80° C. for 1 hour. Cool the mixture at room temperature and pour it into ice-water. Extract the aqueous layer with EtOAc. Dry the organic layer over Na$_2$SO$_4$. Eliminate the solvent to obtain the title compound (450 mg, 83%). $^1$H-NMR (metanol-d$_4$, 200 MHz): 8.04 (d, 1H, J=2.0 Hz), 7.70 (dd, 1H, J=2.0 and 8.4 Hz), 6.93 (d, 1H, J=8.6 Hz)

Step 2

3-Bromo-4-(4-formyl-phenoxy)-benzamide

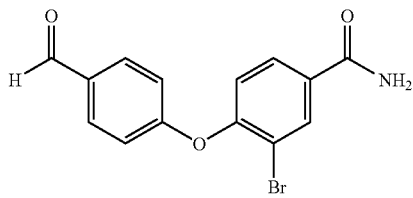

Add K$_2$CO$_3$ (1.49 g, 10.8 mmol) to a solution of 4-fluorobenzaldehyde (1.16 mL, 10.8 mmol) and 3-bromo-4-hydroxy-benzamide (1.16 g, 5.4 mmol) in DMF (20 mL). Heat the mixture under $_{N2}$ overnight. Cool the mixture at room temperature and pour it into ice-water. Extract the aqueous layer with EtOAc. Dry the organic layer over Na$_2$SO$_4$. Eliminate the solvent. Purify by flash chromatography (eluent: EtOAc/hexane 2/1 and 4/1) to get the title compound (1.0 g, 58%). $^1$H-NMR (metanol-d$_4$, 300 MHz): 9.84 (s, 1H), 8.18 (d, 1H, J=2.0 Hz), 7.88-7.83 (m, 3H), 7.13 (d, 1H, J=8.5 Hz), 7.04-7.01 (m, 2H).

Step 3

Reductive amination using the aldehyde obtained in the previous step following general procedures described previously afforded the desired compound.

Electrospray MS M+1 ion=391. $^1$H-NMR (metanol-d$_4$, 300 MHz): 8.13 (d, 1H, J=2.4 Hz), 7.73 (dd, 1H, J=2.0 and 8.5 Hz), 7.33-7.31 (m, 2H), 6.93-6.90 (m, 2H), 6.83 (d, 1H, J=8.5 Hz), 3.69 (s, 2H), 2.57-2.51 (m, 2H), 1.61-1.30 (m, 3H), 0.83 (d, 6H, J=6.4 Hz).

EXAMPLE 709

3-Bromo-4-(3-pentylaminomethyl-phenoxy}-benzamide

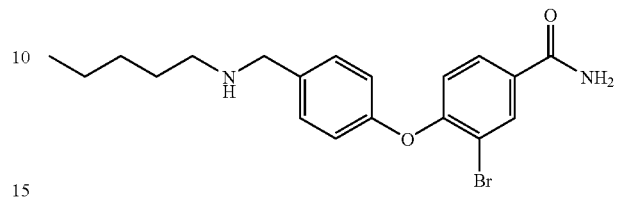

Using 77-pentylbromide and following procedures similar to that of Example 707 afforded the title compound.

Electrospray MS M+1 ion=391. $^1$H-NMR (metanol-d$_4$, 300 MHz): 8.12 (d, 1H, J=2.0 Hz), 7.73 (dd, 1H, J=2.0 and 8.5 Hz), 7.33-7.30 (m, 2H), 6.93-6.90 (m, 2H), 6.83 (d, 1H, J=8.5 Hz), 3.69 (s, 2H), 2.54-2.49 (m, 2H), 1.52-1.23 (m, 6H), 0.84 (t, 3H, J=6.4 Hz).

EXAMPLE 710

6-(2,3-Difluoro-4-pentylaminomethyl-phenoxy)-nicotinamide

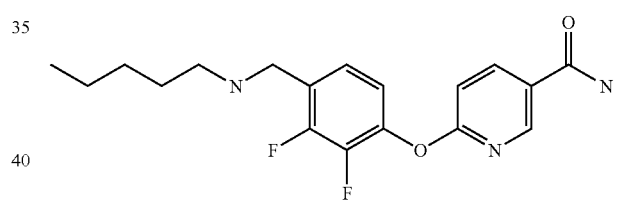

Step 1

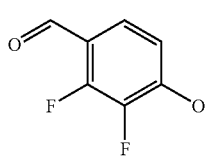

2,3-Difluoro-4-hydroxy-benzaldehyde

Combine 2,3-difluoro-4-methoxy-benzaldehyde (2.76 g, 16.0 mmol) and pyridine hydrochloride (18.5 g, 160 mmol) in a round bottom flask equipped with nitrogen inlet. Heat the mixture at 170° C. two hours, cool to near ambient temperature and dilute with water. Extract aqueous with EtOAc (2×), wash extract with 0.1 N aq. HCl (2×), water (2×) and brine, dry (MgSO$_4$) and concentrate. Purify on silica gel (20% EtOAc/Hexane) to give 2,3-difluoro-4-hydroxy-benzaldehyde (171 g) as a yellow solid. ¹HNMR (CDCl₃): 10.18 (s, 1H), 7.59 (t, 1H), 6.90 (t, 1H), 6.14 (s, 1H).

Step 2

6-(2,3-Difluoro-4-formyl-phenoxy)-nicotinonitrile

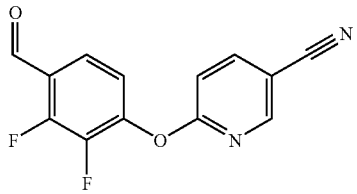

Combine 2,3-difluoro-4-hydroxy-benzaldehyde (see Canadian patent 1190093) (1.93 g, 12.2 mmol), 6-chloronicotinonitrile (1.69 g, 12.2 mmol), K₂CO₃ (2.53 g, 18.3 mmol) and DMA (30 ml) in a sealed, pressure vessel. Heat the suspension at 180° C. for five minutes in a microwave (600 Watts), cool to near ambient temperature and pour into aqueous NH₄Cl. Extract aqueous with EtOAc (2×), wash with water (2×) and brine, dry (MgSO₄) and concentrate. Purify on silica gel (20% EtOAc/Hexane) to give 6-(2,3-difluoro-4-formyl-phenoxy)-nicotinonitrile (2.07 g) as a white solid. ¹H NMR (CDCl₃): 10.33 (s, 1H), 8.42 (s, 1H), 8.02 (d, 1H), 7.73 (t, 1H), 7.20 (d, 1H), 7.15 (t, 1H).

Step 3

6-(2,3-Difluoro-4-formyl-phenoxy)-nicotinamide

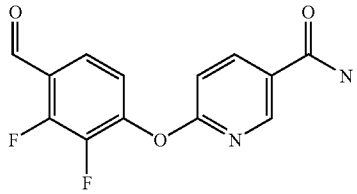

Add 30% aq. H₂O₂ (7.95 ml) to a suspension of 6-(2,3-difluoro-4-formyl-phenoxy)-nicotinonitrile (2.07 g, 7.95 mmol), K₂CO₃ (550 mg, 3.98 mmol) and DMSO (20 ml) stirring in an ice/water bath. After one hour, pour the reaction mixture into water and extract with EtOAc. Wash the extract with water and brine before drying (MgSO₄) and concentrating to give 6-(2,3-difluoro-4-formyl-phenoxy)-nicotinamide (1.64 g) as a white solid. ¹HNMR (DMSO-d₆): 10.14 (s, 1H), 8.58 (s, 1H), 8.33 (d, 1H), 8.07 (s, 1H), 7.74 (t, 1H), 7.55 (s, 1H), 7.33 (d, 1H), 7.27 (t, 1H).

Step 4

Combine 6-(2,3-difluoro-4-formyl-phenoxy)-nicotinamide (278 mg, 1.00 mmol), n-pentylamine (105 mg, 1.20 mmol), and MeOH (3 ml) in a round bottom flask equipped with nitrogen inlet and stir for two hours. Add NaBH₄ (57 mg, 1.50 mmol) and stir for an additional two hours before concentrating. Dissolve concentrate in EtOAc and wash with 5% aq. KOH and brine, dry (Na₂SO₄), and concentrate. Purify on silica gel (5% (1 M NH₃/MeOH)/DCM) to give the title compound (290 mg) as a white solid. Mass spectrum (ion spray): m/z=350 (M+1); ¹HNMR (DMSO-d₆): 8.55 (s, 1H), 8.28 (d, 1H), 8.03 (s, 1H), 7.50 (s, 1H), 7.29 (m, 1H), 7.22 (d, 1H), 7.15 (m, 1H), 3.73 (s, 2H), 2.48 (t, 2H), 1.41 (m, 2H), 1.25 (m, 4H), 0.84 (m, 3H).

EXAMPLE 711

6-{4-[(3,3-Dimethyl-butylamino)-methyl]-2-fluoro-6-methoxy-phenoxy}-nicotinamide

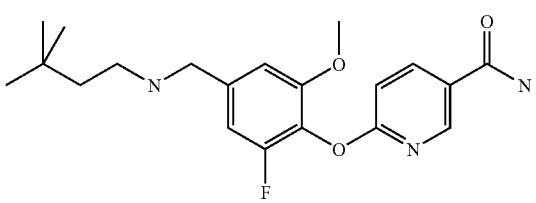

Step 1

6-(2-Fluoro-4-formyl-6-methoxy-phenoxy)-nicotinamide

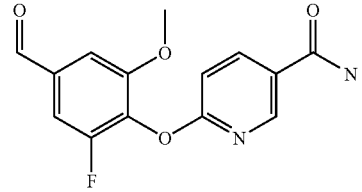

Using a method similar to Example 710, Step 2, using 3-fluoro-4-hydroxy-5-methoxy-benzaldehyde (Journal of Organic Chemistry (1986), 51(2H), 4072-3.) (2.84 g, 16.7 mmol), 6-chloronicotinonitrile (2.31 g, 16.7 mmol) and K₂CO₃ (3.46 g, 25.0 mmol) gives 6-(2-fluoro-4-formyl-6-methoxy-phenoxy)-nicotinonitrile (3.04 g) as a white solid. ¹HNMR (CDCl₃): 9.94 (s, 1H), 8.37 (s, 1H), 7.98 (d, 1H), 7.36 (m, 2H), 7.20 (d, 1H), 3.87 (s, 3H).

Hydrolysis of 6-(2-fluoro-4-formyl-6-methoxy-phenoxy)-nicotinonitrile (3.04 g, 11.1 mmol) in a similar manner as described for Example 710, Step 3, gives 6-(2-fluoro-4-formyl-6-methoxy-phenoxy)-nicotinamide (2.75 g) as a white solid. ¹HNMR (DMSO-d₆): 9.96 (s, 1H), 8.50 (s, 1H), 8.28 (d, 1H), 8.01 (s, 1H), 7.55 (m, 2H), 7.48 (s, 1H), 7.26 (d, 1H), 3.82 (s, 3H).

Step 2

Using a method similar to Example 710, Step 4, using 6-(2-fluoro-4-formyl-6-methoxy-phenoxy)-nicotinamide (250 mg, 0.861 mmol), 3,3-dimethyl-butylamine (104 mg, 1.03 mmol), and NaBH₄ (49 mg, 1.29 mmol) gave the title compound (259 mg) as a white solid. Mass spectrum (ion spray): m/z=376 (M+1); ¹HNMR (DMSO-d₆): 8.50 (s, 1H), 8.23 (d, 1H), 7.98 (s, 1H), 7.44 (s, 1H), 7.13 (d, 1H), 6.96 (s, 1H), 6.89 (d, 1H), 3.71 (s, 3H), 3.68 (s, 2H), 2.51 (t, 2H), 1.37 (t, 2H), 0.86 (s, 9H).

EXAMPLE 712

6-{4-[(3,3-Dimethyl-butylamino)-methyl]-2,6-difluoro-phenoxy}-nicotinamide

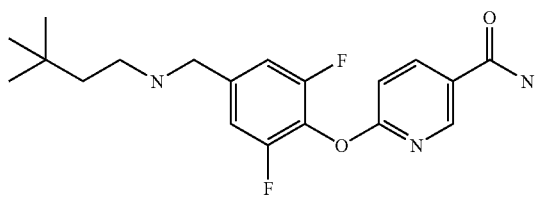

Step 1

6-(2,6-Difluoro-4-formyl-phenoxy)-nicotinamide

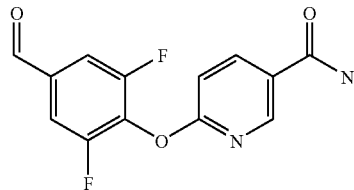

Using a method similar to Example 710, Step 2, using 3,5-difluoro-4-hydroxy-benzaldehyde (Journal of Medicinal Chemistry (1989), 32(2), 450-5.) (2.50 g, 15.8 mmol), 6-chloronicotinonitrile (2.19 g, 15.8 mmol) and $K_2CO_3$ (3.27 g, 23.7 mmol) gives 6-(4-formyl-2,6-difluoro-phenoxy)-nicotinonitrile (2.84 g) as a white solid. $^1$HNMR (CDCl$_3$): 9.95 (s, 1H), 8.39 (s, 1H), 8.02 (d, 1H), 7.58 (d, 2H), 7.25 (d, 1H).

Hydrolysis of 6-(4-formyl-2,6-difluoro-phenoxy)-nicotinonitrile (3.47 g, 13.3 mmol) in a similar manner as described for Example 710, Step 3, gives 6-(2,6-difluoro-4-formyl-phenoxy)-nicotinamide (2.87 g) as a white solid. $^1$HNMR (CDCl$_3$): 9.94 (s, 1H), 8.49 (s, 1H), 8.25 (d, 1H), 7.57 (d, 2H), 7.20 (d, 1H), 5.85 (br. s, 2H).

Step 2

Using a method similar to Example 710, Step 4, using 6-(2,6-difluoro-4-formyl-phenoxy)-nicotinamide (278 mg, 1.00 mmol), 3,3-dimethylbutylamine (105 mg, 1.20 mmol), and NaBH$_4$ (57 mg, 1.50 mmol) gave the title compound (292 mg) as a white solid. Mass spectrum (ion spray): m/z=364 (M+1); $^1$HNMR (DMSO-d$_6$): 8.54 (s, 1H), 8.30 (d, 1H), 8.04 (s, 1H), 7.51 (s, 1H), 7.29 (d, 1H), 7.22 (d, 2H), 3.71 (s, 2H), 2.49 (t, 2H), 1.36 (m, 2H), 0.86 (s, 9H).

EXAMPLE 713

6-{2,6-Difluoro-4-[(3-methyl-butylamino)-methyl]-phenoxy}-nicotinamide

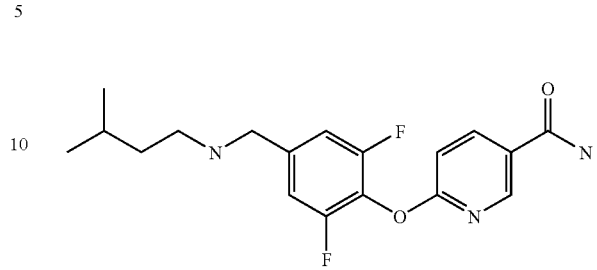

Using a method similar to Example 712, using 6-(2,6-difluoro-4-formyl-phenoxy)-nicotinamide (Example 712, Step 1) (139 mg, 0.500 mmol), isoamylamine (52 mg, 0.600 mmol), and NaBH$_4$ (28 mg, 0.750 mmol) gave the title compound (148 mg) as a white solid. Mass spectrum (ion spray): m/z=350 (M+1); $^1$HNMR (CDCl$_3$): 8.51 (s, 1H), 8.21 (d, 1H), 7.14 (d, 1H), 7.03 (d, 2H), 5.74 (br. s, 9H), 3.79 (s, 2H), 2.65 (t, 2H), 1.66 (m, 1H), 1.41 (m, 2H), 0.91 (d, 6H).

EXAMPLE 714

6-{2,3,6-Trifluoro-4-[(3-methyl-butylamino)-methyl]-phenoxy}-nicotinamide

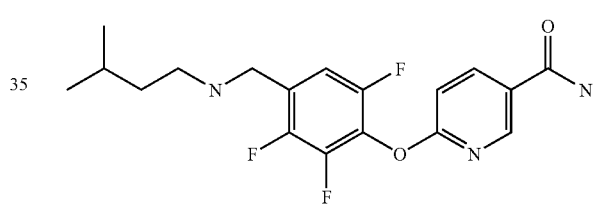

Step 1

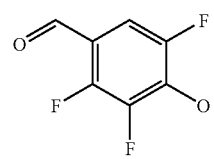

2,3,5-Trifluoro-4-hydroxy-benzaldehyde

Add hexamethylenetetramine (7.10 g, 50.6 mmol) portion wise to a solution of 2,3,6-trifluorophenol (5.00 g, 33.7 mmol) in TFA (35 ml) at ambient temperature and reflux for 15 hours. After cooling, treat the reaction mixture with water (60 ml), followed by 50% aq. H$_2$SO$_4$ (30 ml), and stir at ambient temperature for 30 minutes. Extract with EtOAc (2×) and wash with 1N aq. HCl (3×) and water. Extract the organic with 2N aq. NaOH (2×) and acidify the alkaline extract with conc. HCl while cooling in an ice/water bath. Collect the resulting solid via filtration and dry to give 2,3,5-trifluoro-4-hydroxy-benzaldehyde (2.97 g) as an off-white solid.

Step 2

6-{2,3,6-Trifluoro-4-[(3-methyl-butylamino)-methyl]-phenoxy}-nicotinonitrile

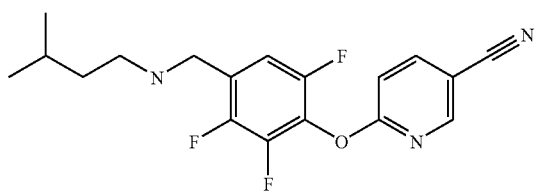

Using a method similar to Example 710, Part 2, using 2,3,5-trifluoro-4-hydroxy-benzaldehyde (1.00 g, 5.64 mmol), 6-chloronicotinonitrile (782 mg, 5.64 mmol) and $K_2CO_3$ (1.17 g, 8.47 mmol) gives 6-(2,3,6-trifluoro-4-formyl-phenoxy)-nicotinonitrile (907 mg) contaminated with 6-chloronicotinonitrile starting material. Dissolve this mixture in MeOH (15 ml) and treat with isoamylamine (194 mg, 2.23 mmol). After stirring for two hours, add $NaBH_4$ (105 mg, 2.79 mmol) and stir for an additional hour. Purification as described in Example 710, Step 4, gives 6-{2,3,6-trifluoro-4-[(3-methyl-butylamino)-methyl]-phenoxy}-nicotinonitrile (383 mg) as a colorless oil.

Step 3

Hydrolysis of 6-{2,3,6-trifluoro-4-[(3-methyl-butylamino)-methyl]-phenoxy}-nicotinonitrile (383 mg, 1.09 mmol) in a similar manner as described for Example 710, Step 3, gives the title compound (374 mg) as a white solid. Mass spectrum (ion spray): m/z=368 (M+1); $^1$HNMR ($CDCl_3$): 8.50 (s, 1H), 8.23 (d, 1H), 7.16 (d, 1H), 7.08 (m, 1H), 5.83 (br. s, 2H), 3.87 (s, 2H), 2.66 (t, 2H), 1.64 (m, 1H), 1.41 (m, 2H), 0.90 (d, 6H).

EXAMPLE 715

6-{3-[(2-Cyclohexyl-ethylamino)-methyl]-2-methyl-phenoxy}-nicotinamide

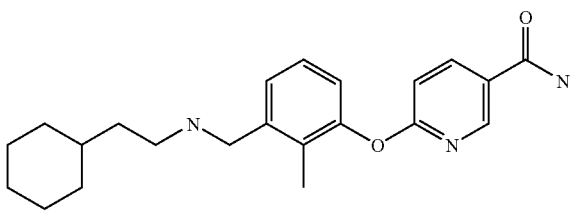

Step 1

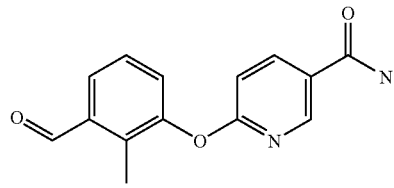

6-(3-Formyl-2-methyl-phenoxy)-nicotinamide

Using a method similar to Example 221, Step 1, using 2-methyl-3-hydroxy-benzaldehyde (see European Patent 0807621 A1) (965 mg, 6.42 mmol), 6-chloronicotinonitrile (890 mg, 6.42 mmol) and $K_2CO_3$ (1.33 g, 9.63 mmol) gives 6-(3-formyl-2-methyl-phenoxy)-nicotinonitrile (1.40 g) as a white solid. $^1$HNMR ($CDCl_3$): 10.30 (s, 1H), 8.41 (s, 1H), 7.96 (d, 1H), 7.78 (d, 1H), 7.45 (t, 1H), 7.30 (d, 1H), 7.10 (d, 1H), 2.45 (s, 3H).

Hydrolysis of 6-(3-formyl-2-methyl-phenoxy)-nicotinonitrile (1.40 g, 5.55 mmol) in a similar manner as described for Example 710, Step 3, gives 6-(3-formyl-2-methyl-phenoxy)-nicotinamide (1.27 g) as a white solid. $^1$HNMR ($CDCl_3$): 10.31 (s, 1H), 8.52 (s, 1H), 8.21 (d, 1H), 7.76 (d, 1H), 7.44 (t, 1H), 7.32 (d, 1H), 7.04 (d, 1H), 5.77 (br. s, 2H), 2.47 (s, 3H).

Step 2

Using a method similar to Example 710, Step 4, using 6-(3-formyl-2-methyl-phenoxy)-nicotinamide (256 mg, 1.00 mmol), cyclohexylethylamine (Synthesis (1983), (5), 388-9) (190 mg, 1.50 mmol), and $NaBH_4$ (57 mg, 1.50 mmol) gave the title compound (325 mg) as a white solid. Mass spectrum (ion spray): m/z=368 (M+1); $^1$HNMR (DMSO-$d_6$): 8.54 (s, 1H), 8.21 (d, 1H), 7.98 (s, 1H), 7.43 (s, 1H), 7.22-7.14 (m, 2H), 7.00 (d, 1H), 6.92 (d, 1H), 3.65 (s, 2H), 2.53 (t, 2H), 2.00 (s, 3H), 1.66-1.55 (m, 5H), 1.35-1.27 (m, 3H), 1.20-1.06 (m, 3H), 0.84 (m, 2H).

EXAMPLE 716

6-[2-Isopropyl-3-(2-pentylamino-ethyl)-phenoxy]-nicotinamide

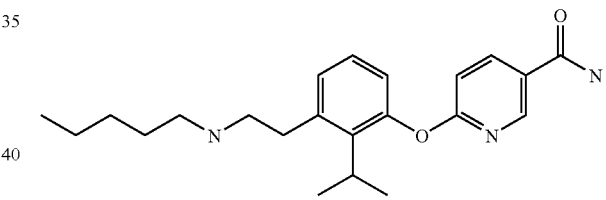

Step 1

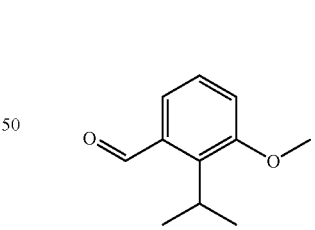

2-isopropyl-3-methoxy-benzaldehyde

Add drop wise a 1 M DIBAL-H/toluene solution (122 mmol) over two hours, to a solution of 2-isopropyl-3-methoxy-benzonitrile (see JCS 13, 489, (1948)), (10.7 g, 61.0 mmol) in toluene (200 ml), stirring under nitrogen at −78° C. After the addition is complete, allow the reaction mixture to warm to 0° C. over two hours and maintain at 0° C. for an additional two hours. Quench the reaction mixture by drop wise addition of AcOH (35 ml), followed by water (100 ml), and stir at ambient temperature for two hours. Dilute with additional water (100 ml), separate layers, extract aqueous with EtOAc (2×), and wash combined organic with water (2×) and brine. After drying (Na₂SO₄) and concentrating, purify crude on silica gel (10% EtOAc/hexane) to give 2-isopropyl-3-methoxy-benzaldehyde (8.81 g) as a yellow oil. ¹HNMR (CDCl₃): 10.45 (s, 1H), 7.42 (d, 1H), 7.27 (t, 1H), 7.07 (d, 1H), 4.03 (m, 1H), 3.85 (s, 3H), 1.39 (d, 6H).

Step 2

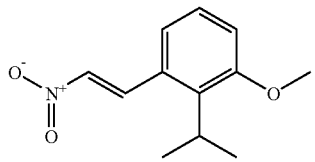

2-Isopropyl-1-methoxy-3-(2-nitro-vinyl)-benzene

Using a method similar to Example 659, Step 1, using 2-isopropyl-3-methoxy-benzaldehyde (3.56 g, 20.0 mmol), nitromethane (3.25 ml, 60.0 mmol), ammonium acetate (2.00 g, 26.0 mmol) and acetic acid (25 ml) gave 2-isopropyl-1-methoxy-3-(2-nitro-vinyl)-benzene (3.92 g) as a viscous oil. ¹HNMR (CDCl₃): 8.48 (d, 1H), 7.38 (d, 1H), 7.20 (t, 1H), 7.02-6.96 (m, 2H), 3.84 (s, 3H), 3.41 (m, 1H), 1.36 (d, 6H).

Step 3

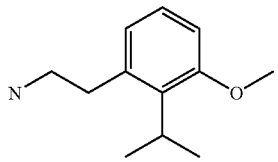

2-(2-Isopropyl-3-methoxy-phenyl)-ethylamine

Using a method similar to Example 659, Step 2, using 2-isopropyl-1-methoxy-3-(2-nitro-vinyl)-benzene (3.92 g, 17.7 mmol), LAH (53.1 mmol) and AlCl₃ (53.1 mmol) gave 2-(2-isopropyl-3-methoxy-phenyl)-ethylamine (3.4 g) as a viscous oil. ¹HNMR (CDCl₃): 7.08 (t, 1H), 6.77-6.73 (m, 2H), 3.80 (s, 3H), 3.22 (m, 1H), 2.89 (m, 2H), 2.80 (m, 2H), 1.32 (d, 6H).

Step 4

[2-(3-Hydroxy-2-isopropyl-phenyl)-ethyl]-carbamic acid tert-butyl ester

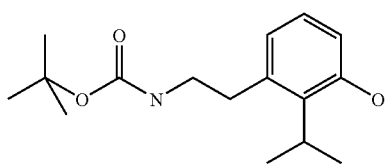

Add 1M BBr₃/DCM (44.2 mmol) drop wise, over 40 minutes, to a solution of 2-(2-isopropyl-3-methoxy-phenyl)-ethylamine (3.4 g, 17.7 mmol) in DCM (40 ml) stirring at −78° C. under nitrogen. After addition is complete, stir at ambient temperature for two hours. Cool reaction mixture back to −78° C., quench with MeOH (25 ml) and concentrate. To this crude material, add THF (50 ml), 1M aq. K₂CO₃ (45 ml) and Boc₂O (4.24 g, 19.4 mmol), and stir overnight at ambient temperature. After pouring the reaction mixture into aq. NH₄Cl, extract with EtOAc, wash extract with brine, dry (Na₂SO₄) and concentrate. Purify crude on silica gel (10% to 40% EtOAc/hexane) to give [2-(3-hydroxy-2-isopropyl-phenyl)-ethyl]-carbamic acid tert-butyl ester (4.02 g) as a viscous, amber oil. ¹HNMR (CDCl₃): 6.97 (t, 1H), 6.70 (d, 1H), 6.58 (d, 1H), 4.58 (br. s, 1H), 3.30 (m, 2H), 3.23 (m, 1H), 2.83 (t, 2H), 1.44 (s, 9H), 1.37 (d, 6H).

Step 5

{2-[3-(5-Cyano-pyridin-2-yloxy)-2-isopropyl-phenyl]-ethyl}-carbamic acid tert-butyl ester

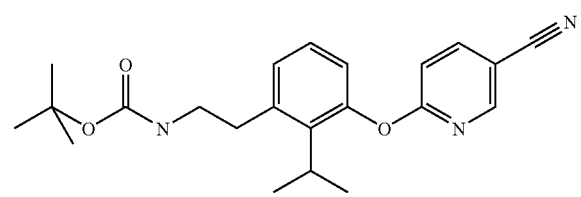

Using a method similar to Example 221, Step 1, using [2-(3-hydroxy-2-isopropyl-phenyl)-ethyl]-carbamic acid tert-butyl ester (4.02 g, 14.4 mmol), 6-chloronicotinonitrile (1.99 g, 14.4 mmol) and K₂CO₃ (2.98 g, 21.5 mmol) gives {2-[3-(5-cyano-pyridin-2-yloxy)-2-isopropyl-phenyl]-ethyl}-carbamic acid tert-butyl ester (4.11 g) as a yellow foam. ¹HNMR (CDCl₃): 8.50 (s, 1H), 7.92 (d, 1H), 7.17 (t, 1H), 7.06 (d, 1H), 7.01 (d, 1H), 6.86 (d, 1H), 4.63 (br. s, 1H), 3.34 (m, 2H), 3.27 (m, 1H), 2.91 (t, 2H), 1.44 (s, 9H), 1.24 (d, 6H).

Step 6

{2-[3-(5-Carbamoyl-pyridin-2-yloxy)-2-isopropyl-phenyl]-ethyl}-carbamic acid tert-butyl ester

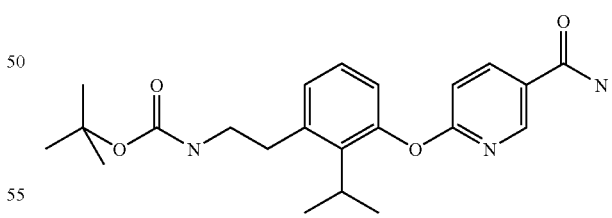

Hydrolysis of {2-[3-(5-cyano-pyridin-2-yloxy)-2-isopropyl-phenyl]-ethyl}-carbamic acid tert-butyl ester (4.11 g, 10.7 mmol) in a similar manner as described for Example 710, Step 3, gives {2-[3-(5-Carbamoyl-pyridin-2-yloxy)-2-isopropyl-phenyl]-ethyl}-carbamic acid tert-butyl ester (4.30 g) as a yellow foam. ¹HNMR (CDCl₃): 8.63 (s, 1H), 8.18 (d, 1H), 7.15 (t, 1H), 7.03 (d, 1H), 6.95 (d, 1H), 6.86 (d, 1H), 5.98 (br. s, 2H), 4.67 (br. s, 1H), 3.34 (m, 2H), 3.26 (m, 1H), 2.90 (t, 2H), 1.44 (s, 9H), 1.26 (d, 6H).

Step 7

6-[3-(2-Amino-ethyl)-2-isopropyl-phenoxy]-nicotinamide

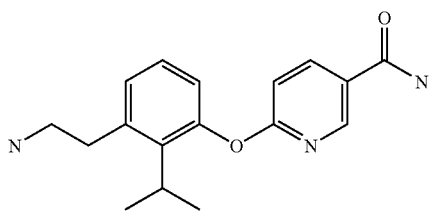

Deprotection of {2-[3-(5-Carbamoyl-pyridin-2-yloxy)-2-isopropyl-phenyl]-ethyl}-carbamic acid tert-butyl ester (4.30 g, 10.7 mmol) as described in Example 651, Step 6, gave 6-[3-(2-amino-ethyl)-2-isopropyl-phenoxy]-nicotinamide (2.72 g) as a white foam.

$^1$HNMR (DMSO-d$_6$): 8.59 (s, 1H), 8.23 (d, 1H), 8.01 (s, 1H), 7.44 (s, 1H), 7.11 (t, 1H), 7.03-6.98 (m, 2H), 6.80 (d, 1H), 3.24 (m, 1H), 2.71 (m, 4H), 1.72 (br. s, 2H), 1.17 (d, 6H).

Step 8

Using a method similar to Example 710, Step 4, using 6-[3-(2-amino-ethyl)-2-isopropyl-phenoxy]-nicotinamide (299 mg, 1.00 mmol), valeraldehyde (112 mg, 1.30 mmol), and NaBH$_4$ (57 mg, 1.50 mmol) gave the title compound (245 mg) as a colorless glass. Mass spectrum (ion spray): m/z=370 (M+1); $^1$HNMR (DMSO-d$_6$): 8.59 (s, 1H), 8.22 (d, 1H), 8.00 (s, 1H), 7.44 (s, 1H), 7.10 (t, 1H), 7.01 (m, 2H), 6.80 (d, 1H), 3.24 (m, 1H), 2.76 (m, 2H), 2.63 (m, 2H), 2.50 (m, 2H), 1.38 (m, 2H), 1.25 (m, 4H), 1.16 (d, 6H), 0.84 (t, 3H).

EXAMPLE 717

6-(2-Methoxy-4-{[2-(4-methylcyclohexyl)ethylamino]methyl}phenoxy)nicotinamide methanesulfonate

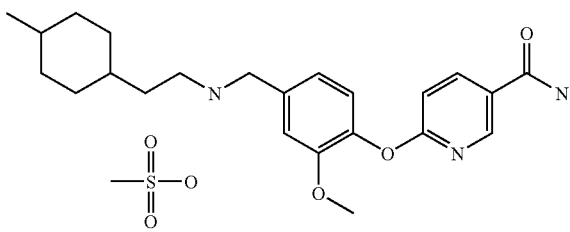

Place 6-(4-formyl-2-methoxyphenoxy)nicotinamide (Example 414, Part B) (0.100 g, 0.367 mmol), 2-(4-methylcyclohexyl)ethylamine (0.0571 g, 0.404 mmol) and 3 Å molecular sieves in a vial. Add methanol (3.6 mL), cap and stir overnight. Add NaBH$_4$ (ca. 3-5 eq in two portions) and stir until the gasses stop evolving. Load the reaction mixture directly onto a 5 g ISCO® pre-load column. Dry the column in a vacuum oven at room temperature. Purify by eluting through a 10 g ISCO® column with 6% to 15% (2.0 M NH$_3$ in methanol) in ethyl acetate to give 6-(2-methoxy-4-{[2-(4-methylcyclohexyl)ethylamino]methyl}phenoxy)nicotinamide (0.0958 g, 65.6%). Dissolve the compound in dichloromethane (2.5 mL) and add 1 equivalent of 0.50 M methanesulfonic acid in dichloromethane. Stir the solution for a short time before concentrating to afford the title compound: TOF MS ES$^+$ 398.2 (M+H)$^+$, HRMS calcd for C$_{23}$H$_{32}$N$_3$O$_3$ 398.2444 (M+H)$^+$, found 398.2440, time 0.52 min; Anal. Calcd for C$_{23}$H$_{31}$N$_3$O$_3$·0.5H$_2$O: C, 57.35; H, 7.22; N, 8.36. Found: C, 57.33; H, 6.94; N, 8.34.

EXAMPLE 718

6-(4-{[2-(2,4-Difluorophenyl)ethylamino]methyl}-2-methoxyphenoxy)nicotinamide methanesulfonate

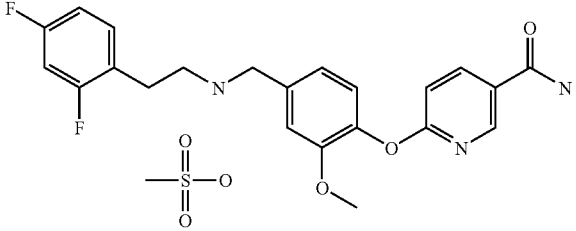

To a slurry of LiAlH$_4$ (0.417 g, 1.0 mmol) in THF (25 mL), add AlCl$_3$ (1.47 g, 11.0 mmol) in THF (10 mL). Cool the reaction mixture to 0° C. and slowly add 2,4-difluorophenylacetonitrile (0.11 g, 6.53 mmol). Quench with saturated aqueous Na$_2$CO$_2$ (10 mL) and filter through a Celite® pad. Dilute the filtrate to 150 mL with dichloromethane. Extract the product out with 1.0 N HCl (2×100 mL). Add 5.0 N NaOH to the aqueous layer until it is basic. Extract the aqueous layer with dichloromethane (2×100 mL), dry the organic layer over Na$_2$SO$_4$, filter and concentrate to afford the 2-(2,4-difluorophenyl)ethylamine as the crude amine.

Place 6-(4-formyl-2-methoxyphenoxy)nicotinamide (Example 414, Part B) (0.300 g, 1.10 mmol), 2-(2,4-difluorophenyl)ethylamine (0.343 g, 2.184 mmol) and 3 Å molecular sieves in a vial. Add methanol (4.4 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 2% to 20% (2.0 M NH$_3$ in methanol) in ethyl acetate to give 6-(4-{[2-(2,4-difluorophenyl)ethylamino]methyl}-2-methoxyphenoxy)nicotinamide. Dissolve the compound in methanol (5.0 mL) and add 1 equivalent of 0.50 M methanesulfonic acid in dichloromethane. Stir the solution for a short time before concentrating to give the title compound: TOF MS ES$^+$ 414.2 (M+H)$^+$, HRMS calcd for C$_{22}$H$_{22}$N$_3$O$_3$F, 414.1629 (M+H)$^+$, found 414.1613, time 0.52 min; HPLC [YMC-Pro pack C-18 (150×4.6 mm, S-5 microm), 0.1% TFA/acetonitrile in 0.1% TFA/water at 1.0 mL/min, 10-20% over 5 min, 20-95% over 18 min], t$_R$=11.6 min, 100% purity.

EXAMPLE 719

5-(2-Methoxy-4-pentylaminomethylphenoxy)pyrazine-2-carboxamide

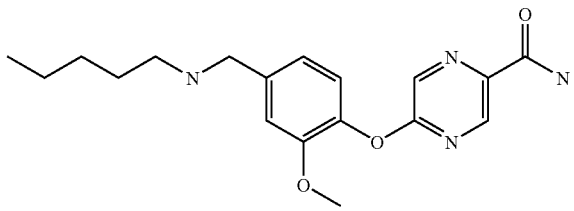

Part A: 5-(4-Formyl-2-methoxyphenoxy)pyrazine-2-carboxamide

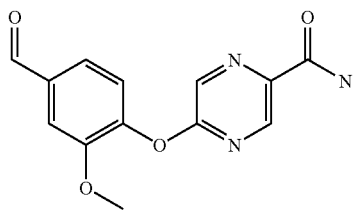

Dissolve 5-chloropyrazine-2-carboxamide (Example 387, Part A) (0.374 g, 2.34 mmol) and vanillin (0.361 g, 2.34 mmol) in DMF (23.7 mL). Add $K_2CO_3$ (0.821 g, 8.94 mmol) and heat at 100° C. for 1.5 hours. Concentrate the reaction mixture. Take the solid up in water (50 mL) and extract with dichloromethane (3×100 mL). Dry the organic layer over $Na_2SO_4$, filter and concentrate to give the title compound (0.625 g, 96.4%): TOF MS ES⁺ 274.1 (M+H)⁺, HRMS calcd for $C_{13}H_{12}N_3O_4$ 274.0828 (M+H)⁺, found 274.0829, time 0.55 min; HPLC [YMC-Pro pack C-18 (150×4.6 mm, S-5 microm), 0.1% TFA/acetonitrile in 0.1% TFA/water at 1.0 mL/min, 5-95 over 19 min], $t_R$=10.2 min, 98.1% purity.

Part B: 5-(2-Methoxy-4-pentylaminomethylphenoxy pyrazine-2-carboxamide

Place 5-(4-formyl-2-methoxyphenoxy)pyrazine-2-carboxamide (Example 719, Part A) (0.200 g, 0.732 mmol), amylamine (0.0670 g, 0.769 mmol) and 3 Å molecular sieves in a vial. Add methanol (3.6 mL), cap and stir overnight. Add $NaBH_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 60% to 90% (5% (2.0 M $NH_3$ in methanol) in ethyl acetate) in hexanes. Concentrate the fractions containing the product. Take the solid up in ethyl acetate (50 mL) and wash with 1.0 N NaOH to give the title compound (0.180 g, 71.7%): TOF MS ES⁺ 345.2 (M+H)⁺, HRMS calcd for $C_{18}H_{25}N_4O_3$ 345.1927 (M+H)⁺, found 345.1926, time 0.52 min; HPLC [Waters XTerra™ C-18 (150×4.6 mm, S-5 microm), 0.1% TFA/acetonitrile in 0.1% TFA/water at 1.0 mL/min, 5-95% over 23 min], $t_R$=10.4 min, 100% purity.

EXAMPLE 720

5-(2-Methoxy-4-{[2-(tetrahydropyran-4-yl)ethylamino]methyl}phenoxy)pyrazine-2-carboxamide

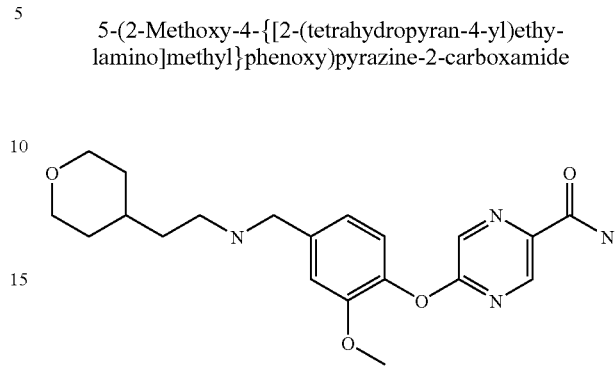

Place 5-(4-Formyl-2-methoxyphenoxy)pyrazine-2-carboxamide (Example 719, Part A) (0.200 g, 0.732 mmol), 2-(tetrahydropyran-4-yl)ethylamine (0.0993 g, 0.769 mmol) and 3 Å molecular sieves in a vial. Add methanol (3.6 mL), cap and stir overnight. Add $NaBH_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column 5% to 20% (2.0 M $NH_3$ in methanol) in ethyl acetate. Concentrate the fractions containing the product. Take the solid up in ethyl acetate (50 mL) and wash with 1.0 N NaOH to give the title compound (0.168 g, 59.4%): TOF MS ES⁺ 387.2031 (M+H)⁺, HRMS calcd for $C_{20}H_{27}N_4O_4$ 387.2032 (M+H)⁺, found 387.2031, time 0.52 min; HPLC [Waters XTerra™ C-18 (150×4.6 mm, S-5 microm), 0.1% TFA/acetonitrile in 0.1% TFA/water at 1.0 mL/min, 5-95% over 23 min], $t_R$=8.7 min, 100% purity.

EXAMPLE 721

6-{2-Methoxy-4-[(3-methylbutylamino)methyl]phenoxy}pyridazine-3-carboxamide

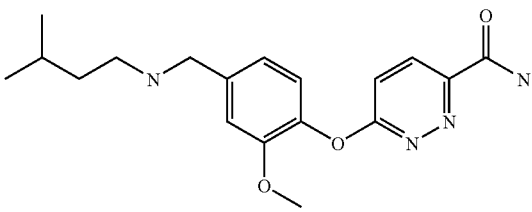

Part A: Methyl 6-chloropyridazine-3-carboxylate

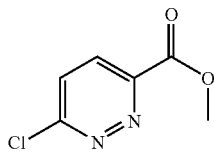

Dissolve 6-oxo-1,6-dihydropyridazine-3-carboxylic acid monohydrate (33.0 g, 209 mmol) in $SOCl_2$ (700 mL) and reflux for 2.5 hours. Concentrate the dark solution to complete dryness. Take the solid up in dichloromethane (700 mL), cool to 0° C. and add methanol (9.6 mL) and triethylamine (54.5 mL). Allow the reaction mixture to warm to room temperature as it stirs overnight. Load the reaction mixture onto a silica gel plug. Wash the plug with 20% ethyl acetate in dichloromethane. Purify the impure fractions by chromatography eluting with 50% ethyl acetate in dichloromethane to give the title compound (29.4 g, 82%): TOF MS ES$^+$ 173.0 (M+H)$^+$, HRMS calcd for $C_6H_6N_2O_2Cl$ 173.0118 (M+H)$^+$, found 173.0130, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=6.9 min, 100% purity.

Part B: 6-Chloropyridazine-3-carboxamide

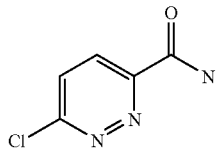

Dissolve methyl 6-chloropyridazine-3-carboxylate (0.498 g, 2.89 mmol) in methanol (28 mL). Cool the solution to 0° C. with an acetone/dry ice bath. Bubble ammonia into the reaction mixture then allow it to warm to 0° C. over 1 hour before concentrating to give the title compound (0.451 g, 99%): TOF MS ES$^+$ 157.0 (M)$^+$, HRMS calcd for $C_5H_4N_3OCl$ 157.0043 (M)$^+$, found 157.0010, time 4.45 min; HPLC [YMC-Pro pack C-18 (150×4.6 mm, S-5 microm), 0.1 TFA/acetonitrile in 0.1% TFA/water at 1.0 mL/min, 10-20% over 5 min then 20-95% over 18], $t_R$=5.2 min, 100% purity.

Part C: 6-(4-Formyl-2-methoxyphenoxy)pyridazine-3-carboxamide

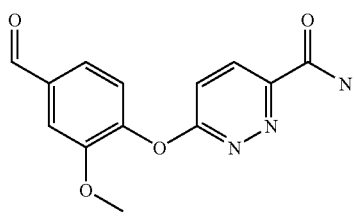

Dissolve 5-chloropyradizine-2-carboxamide (Example 721. Part B) (0.502 g, 3.18 mmol) and vanillin (0.484 g, 3.18 mmol) in DMF (16 mL). Add $K_2CO_3$ (1.10 g, 7.96 mmol) and heat at 100° C. for 3.6 hours. Concentrate the reaction mixture. Take the solid up in water (100 mL) and extract with dichloromethane (3×100 mL). Dry the organic layer over $MgSO_4$, filter and concentrate to give the title compound (0.824 g, 95%): TOF MS ES$^+$ 274.1 (M+H)$^+$, HRMS calcd for $C_{13}H_{12}N_3O_4$ 274.0828 (M+H)$^+$, found 274.0832, time 0.59 min; HPLC [YMC-Pro pack C-18 (150×4.6 mm, S-5 microm), 0.1% TFA/acetonitrile in 0.1% TFA/water at 1.0 mL/min, 5-95 over 19 min], $t_R$=11.4 ml, 96.3% purity.

Part D: 6-{2-Methoxy-4-[(3-methylbutylamino)methyl]phenoxy}pyridazine-3-carboxamide Place 6-(4-formyl-2-methoxyphenoxy)pyridazine-3-carboxamide (Example 721, Part C) (0.200 g, 0.732 mmol), isoamylamine (0.0670 g, 0.769 mmol) and 3 Å molecular sieves in a vial. Add methanol (3.6 mL), cap and stir overnight. Add $NaBH_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 10% to 20% (2.0 M $NH_3$ in methanol) in ethyl acetate. Concentrate the fractions containing the product. Take the solid up in ethyl acetate (50 mL) and wash with 1.0 N NaOH (2×10 mL). Dry the organic layer over $Na_2SO_4$, filter and concentrate to give the title compound (0.112 g, 44%): TOF MS ES$^+$ 345.2 (M+H)$^+$, HRMS calcd for $C_{18}H_{25}N_4O_3$ 345.1927 (M+H)$^+$, found 345.1926, time 0.52 min; Anal. Calcd for $C_{18}H_{24}N_4O_3$: C, 62.77; H, 7.02; N, 16.27. Found: C, 62.29; H, 7.01; N, 15.50.

EXAMPLE 722

6-(2-M ethoxy-4-{[2-(tetrahydropyran-4-yl)ethylamino]methyl}phenoxy)pyridazine-3-carboxamide

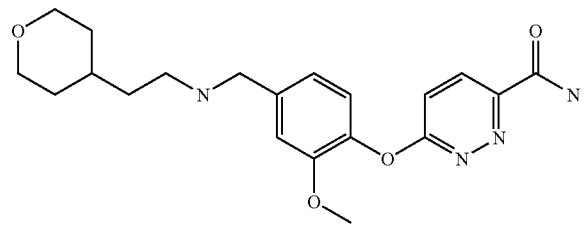

Place 6-(4-formyl-2-methoxyphenoxy)pyridazine-3-carboxamide (Example 721, Part C) (0.200 g, 0.732 mmol), 2-(tetrahydropyran-4-yl)ethylamine (0.0993 g, 0.769 mmol) and 3 Å molecular sieves in a vial. Add methanol (3.6 mL), cap and stir overnight. Add $NaBH_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 10% to 20% (2.0 M $NH_3$ in methanol) in ethyl acetate. Concentrate the fractions containing the product. Take the solid up in ethyl acetate (50 mL) and wash with 1.0 N NaOH (2×10 mL). Dry the organic layer over $Na_2SO_4$, filter and concentrate to give the title compound (0.154 g, 54%): TOF MS ES$^+$ 387.2 (M+H)$^+$, HRMS calcd for $C_{20}H_{27}N_4O_4$ 387.2032 (M+H)$^+$, found 387.2024, time 0.52 min; Anal. Calcd for $C_{20}H_{26}N_4O_4$: C, 62.16; H, 6.78; N, 14.50. Found: C, 61.58; H, 6.66; N, 14.13.

EXAMPLE 723

6-(2-Methoxy-4-propylaminomethylphenoxy)nicotinamide methanesulfonate

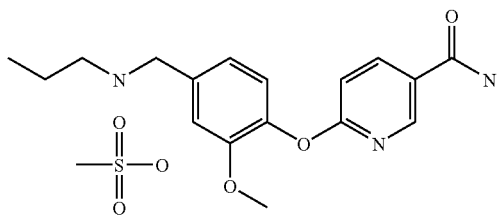

Place 6-(4-formyl-2-methoxyphenoxy)nicotinamide (Example 414, Part B) (0.250 g, 0.918 mmol), propylamine (0.060 g, 1.01 mmol) and 3 Å molecular sieves in q vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.327 g, 84%): TOF MS ES$^+$ 316.2 (M+H)$^+$, HRMS calcd for C$_{17}$H$_{22}$N$_3$O$_3$ 316.1661 (M+H)$^+$, found 316.1671, time 0.52 mm; HPLC [YMC-Pro Pack C-18 (150× 4.6 mm, S-5 microm), 0.1% TFA/acetonitrile in 0.1% TFA/water at 1.0 mL/min, 10-20% over 5 min then 20-95% over 18 min], $t_R$=8.3 min, 100% purity.

EXAMPLE 724

6-[4-(Isobutylaminomethyl)-2-methoxyphenoxy]nicotinamide methanesulfonate

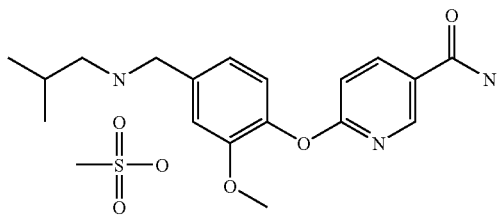

Place 6-(4-formyl-2-methoxyphenoxy)nicotinamide (Example 414, Part B) (0.250 g, 0.918 mmol), isobutylamine (0.074 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.344 g, 87%): TOF MS ES$^+$ 330.2 (M+H)$^+$, HRMS calcd for C$_{18}$H$_{24}$N$_3$O$_3$ 330.1818 (M+H)$^+$, found 330.1808, time 0.52 min; HPLC [YMC-Pro Pack C-18 (150× 4.6 mm, S-5 microm), 0.1% TFA/acetonitrile in 0.1% TFA/water at 1.0 mL/min, 10-20% over 5 min. then 20-95% over 18 min], $t_R$=9.2 min, 100% purity.

EXAMPLE 725

6-{4-[(2,2-Dimethylpropylamino)methyl]-2-methoxyphenoxy}nicotinamide methanesulfonate

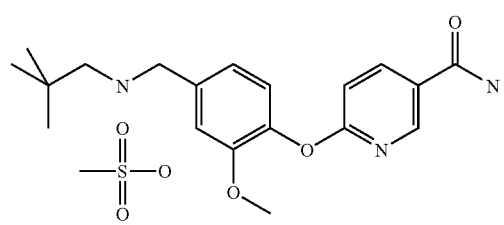

Place 6-(4-formyl-2-methoxyphenoxy)nicotinamide (Example 414, Part B) (0.250 g, 0.918 mmol), neopentylamine (0.074 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ASCOT pre-load column. Dry the column in a vacuum oven at room temperature. Purify by eluting through a 40 g ISCO® column with 5% to 20% (2.0 M NH$_3$ in methanol) in ethyl acetate to give the title compound as a free base. Dissolve the product in methanol and add one equivalent of 0.5 M methanesulfonic acid solution in dichloromethane. Concentrate to afford the title compound (0.339 g, 89%): TOF MS ES$^+$ 344.2 (M+H)$^+$, HRMS calcd for C$_{19}$H$_{26}$N$_3$O$_3$ 344.1974 (M+H)$^+$, found 344.1963, time 0.52 min; HPLC [YMC-Pro Pack C-18 (150× 4.6 mm, S-5 microm), 0.1% TFA/acetonitrile in 0.1% TFA/water at 1.0 mL/min, 10-20% over 5 min, then 20-95% over 18 min], $t_R$=9.9 min, 99.2% purity.

EXAMPLE 726

6-(2-Methoxy-4-{[(tetrahydropyran-4-ylmethyl)amino]methyl}phenoxy)nicotinamide methanesulfonate

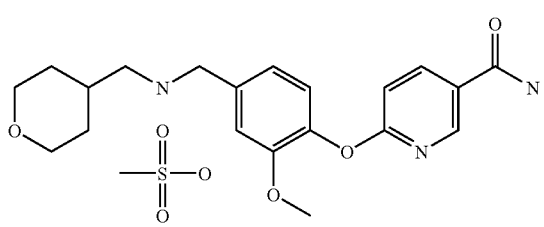

Place 6-(4-formyl-2-methoxyphenoxy)nicotinamide (Example 414, Part B) (0.250 g 0.918 mmol), 4-aminomethyltetrahydropyran (0.116 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.375 g, 85%): TOF MS ES+ 372.2 (M+H)+, HRMS calcd for $C_{20}H_{26}N_3O_4$ 372.1923 (M+H)+, found 372.1909, time 0.50 min; HPLC [YMC-Pro Pack C-18 (150×4.6 mm, S-5 microm), 0.1% TFA/acetonitrile in 0.1% TFA/water at 1.0 mL/min, 10-20% over 5 min then 20-95% over 18 min], $t_R$=8.3 min, 100% purity.

EXAMPLE 727

6-(4-Heptylaminomethyl-2-methoxyphenoxy)nicotinamide methanesulfonate

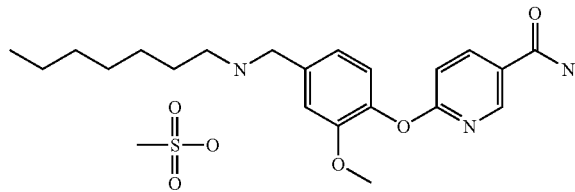

Place 6-(4-formyl-2-methoxyphenoxy)nicotinamide (Example 414, Part B) (0.250 g, 0.918 mmol), heptylamine (0.060 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.341 g, 79%): TOF MS ES+ 372.2 (M+H)+, HRMS calcd for $C_{21}H_{30}N_3O_3$ 372.2287 (M+H)+, found 372.2294, time 0.52 min; HPLC [YMC-Pro Pack C-18 (150×4.6 mm, S-5 microm), 0.1% TFA/acetonitrile in 0.1% TFA/water at 1.0 mL/min, 10-20% over 5 min. then 20-95% over 18 min], $t_R$=12.7 min. 99.0% purity.

EXAMPLE 728

6-{2-Methoxy-4-[(2-pyridin-4-ylethylamino)methyl]phenoxy}nicotinamide methanesulfonate

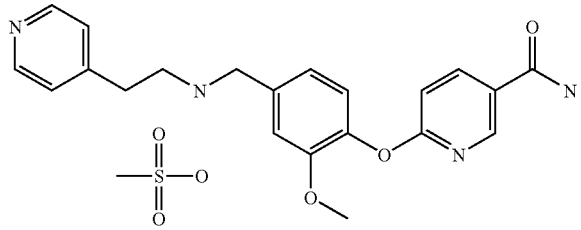

Place 6-(4-formyl-2-methoxyphenoxy)nicotinamide (Example 414, Part B) (0.250 g, 0.918 mmol), 2-pyridin-4-ylethylamine (0.060 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by outing through a 40 g ISCO® column with 5% to 25% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.339 g, 76%): TOF MS ES+ 379.2 (M+H)+, HRMS calcd for $C_{21}H_{23}N_4O_3$ 379.1770 (M+H)+, found 379.1753, time 0.32 min; IR (KBr) 3418 (N—H), 1194 (O—CH$_3$), 1668 (C=O), 1610 (H$_2$NCO—) cm$^{-1}$.

EXAMPLE 729

6-{2-Methoxy-4-[(3-methoxypropylamino)methyl]phenoxy}nicotinamide methanesulfonate

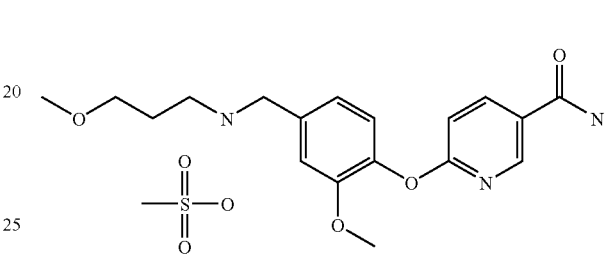

Place 6-(4-formyl-2-methoxyphenoxy)nicotinamide (Example 414, Part B) (0.250 g, 0.918 mmol), 3-methoxypropylamine (0.090 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature Purify by eluting through a 40 g ISCO® column with 5% to 15% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.328 g, 82%): TOF MS ES+ 346.2 (M+H)+, HRMS calcd for $C_{18}H_{24}N_3O_4$ 346.1767 (M+H)+, found 346.1766, time 0.52 ml; HPLC [Waters XTerra™ C-18 (150×4.6 mm, S-5 microm), 0.1% TFA/acetonitrile in 0.1% TFA/water at 1.0 mL/min, 5-95 over 23 min], $t_R$=7.7 min, 100% purity.

EXAMPLE 730

6-{4-[(3-Ethoxypropylamino)methyl]-2-methoxyphenoxy}nicotinamide methanesulfonate

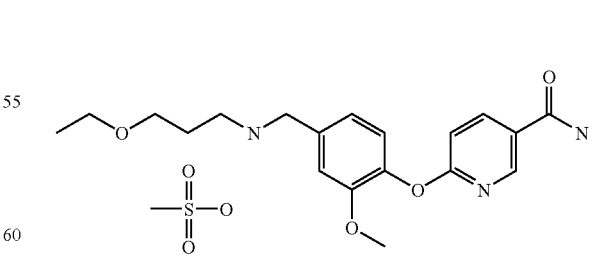

Place 6-(4-formyl-2-methoxyphenoxy)nicotinamide (Example 414, Part B) (0.250 g, 0.918 mmol), 3-ethoxypropylamine (0.060 g, 1.01 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH₃ in methanol) in ethyl acetate to give the title compound as a free base. Dissolve the product in methanol and add one equivalent of 0.5 M methanesulfonic acid solution in dichloromethane. Concentrate to give the title compound (0.325 g, 82%): TOF MS ES⁺ 360.2 (M+H)⁺, HRMS calcd for $C_{19}H_{26}N_3O_4$ 360.1923 (M+H)⁺, found 360.1920, time 0.52 min; HPLC [YMC-Pro Pack C-18 (150×4.6 mm, S-5 microm), 0.1% TFA/acetonitrile in 0.1% TFA/water at 1.0 mL/min, 10-20% over 5 ml, then 20-95% over 8 min], $t_R$=9.3 min. 100% purity.

EXAMPLE 731

6-{4-[(3-Isopropoxypropylamino)methyl]-2-methoxyphenoxy}nicotinamide methanesulfonate

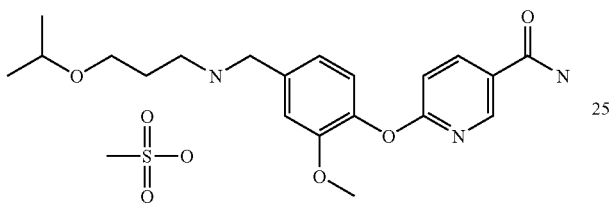

Place 6-(4-formyl-2-methoxyphenoxy)nicotinamide (Example 414, Part B) (0.250 g, 0.918 mmol), 3-isopropoxypropylamine (0.060 g, 1.01 mmol) and 3 Å molecular sieves in a vial. Add methanol (6.1 mL), cap and stir overnight. Add NaBH₄ (ca. 3-5 eq in two portions) and stir until the gasses stop evolving. Load the reaction mixture directly onto a 25 g ISCO® pre-load column. Dry the column in a vacuum oven at room, temperature. Purify by eluting through a 40 g ISCO® column with 5% to 15% (2.0 M NH₃ in methanol) in ethyl acetate to give the title compound as a free base. Dissolve the product in methanol and add one equivalent of 0.5 M methanesulfonic acid solution in dichloromethane. Concentrate to give the title compound (0.353 g, 84%): TOF MS ES⁺ 374.2 (M+H)⁺, HRMS calcd for $C_{20}H_{28}N_3O_4$ 374.2080 (M+H)⁺, found 374.2080, time 0.52 min; HPLC [YMC-Pro Pack C-18 (150×4.6 mm, S-5 microm), 0.1% TFA/acetonitrile in 0.1% TFA/water at 1.0 mL/min, 10-20% over 5 min, then 20-95% over 18 min], $t_R$=110, min, 100% purity.

EXAMPLE 732

6-{4-[(2-Isopropoxyethylamino)methyl]-2-methoxyphenoxy}nicotinamide methanesulfonate

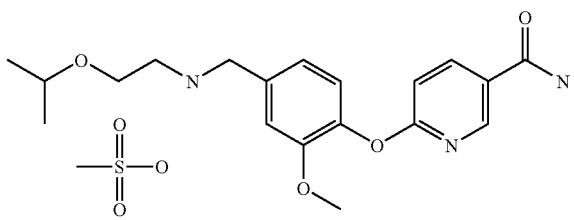

Place 6-(4-formyl-2-methoxyphenoxy)nicotinamide (Example 414, Part B) (0.250 g, 0.918 mmol), 2-aminoethyl isopropyl ether (0.060 g, 1.01 mmol) and 3 Å molecular sieves in a vial. Add methanol (6.1 mL), cap and stir overnight. Add NaBH₄ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH₃ in methanol) in ethyl acetate to give the title compound as a free base. Dissolve the product in methanol and add one equivalent of 0.5 M methanesulfonic acid solution in dichloromethane. Concentrate to give the title compound (0.333 g, 81%): TOF MS ES⁺ 360.2 (M+H)⁺, HRMS calcd for $C_{19}H_{26}N_3O_4$ 360.1923 (M+H)⁺, found 360.1939, time 0.52 min; HPLC [YMC-Pro Pack C-18 (150×4.6 mm, S-5 microm), 0.1% TFA/acetonitrile in 0.1% TFA/water at 1.0 mL/min, 10-20% over 5 min, then 20-95% over 18 min], $t_R$=9.7 min, 99.2% purity.

EXAMPLE 733

6-{4-[(3-Ethylpentylamino)methyl]-2-methoxyphenoxy}nicotinamide methanesulfonate

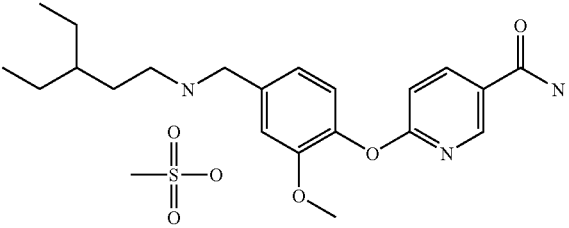

Part A: 3-Ethylpentanenitrile

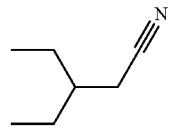

To a suspension of sodium cyanide (3.33 g, 67.8 mmol) in DMSO (24 mL) at 60° C., slowly add 1-bromo-2-ethylbutane (10 g, 60.6 mmol). Keep the internal temperature between 55-60° C. by intermittently cooling with an ice bath. Add additional DMSO (10 mL) to keep the slurry stirring. Heat at 70° C. for two hours, then cool to room temperature. Dilute the reaction mixture with water (100 mL) and extract with ether (3×50 mL). Wash the organic extracts with 5.0 N HCl (1×25 mL) and water (1×25 mL). Dry the organic layer over MgSO₄, filter and concentrate to give the title compound (6.43 g, 96%): ¹H NMR (CDCl₃, 400 MHz) δ2.34 (d, J=6.2 Hz, 2H), 1.56 (m, 1H), 1.46 (m, 4H), 0.93 (t, J=7.3 Hz, 6H).

Part B: 3-Ethylpentylamine

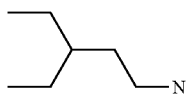

Cool a slurry of LiAlH$_4$ (4.35 g, 115 mmol) in ether (57 mL) to 0° C. Allow reaction mixture to gently reflux upon the addition of 3-ethylpentanenitrile (6.38 g, 57.3 mmol). Stir for two hours before quenching with 1.0 N NaOH. Filter the suspension through a Celite® pad. Separate the two layers and wash the organic layer with additional 1.0 N NaOH (2×25 mL), dry it over Na$_2$SO$_4$, filter and carefully concentrate to give the title compound: $^1$H NMR (DMSO-d$_6$, 400 MHz) δ 2.50 (t, J=7.3 Hz, 2H), 1.24 (m, 7H), 0.080 (t, J=7.0 Hz, 6H).

Part C: 6-{4-[(3-Ethylpentylamino)methyl]-2-methoxyphenoxy}nicotinamide methanesulfonate Place 6-(4-formyl-2-methoxyphenoxy)nicotinamide (Example 414, Part B) (0.250 g, 0.918 mmol), 3-ethylpentylamine (0.111 g, 0.964 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 15% (2.0 M NH$_3$ in methanol) in ethyl acetate to give the title compound as a free base. Dissolve the product in methanol and dichloromethane and add one equivalent of 0.5 M methanesulfonic acid solution in dichloromethane. Concentrate to give the title compound (0.371 g, 84%): TOF MS ES$^+$ 372.2 (M+H)$^+$, HRMS calcd for C$_{21}$H$_{30}$N$_3$O$_3$ 372.2287 (M+H)$^+$, found 372.2271, time 0.32 min; HPLC [Waters XTerra™ C-18 (150×4.6 mm, S-5 microm), 0.1% TFA/acetonitrile in 0.1% TFA/water at 1.0 mL/min, 5-95% over 23 min], t$_R$=11.9 min, 100% purity.

EXAMPLE 734

6-{2-Methoxy-4-[(2-morpholin-4-ylethylamino)methyl]phenoxy}nicotinamide methanesulfonate

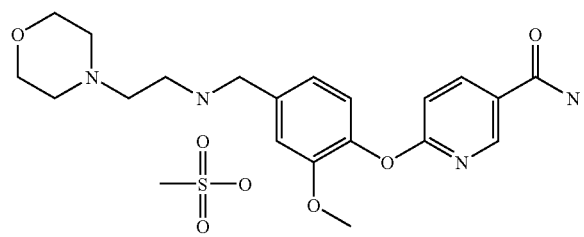

Place 6-(4-formyl-2-methoxyphenoxy)nicotinamide (Example 414, Part B) (0.250 g, 0.918 mmol), 2-morpholin-4-ylethylamine (0.126 g, 0.964 mmol) and 3 Å molecular sieves in a vial. Add methanol (6.1 mL), cap and stir overnight, Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 30% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.350 g, 74%): TOF MS ES$^+$ 387.2 (M+H)$^+$, HRMS calcd for C$_{20}$H$_{27}$N$_4$O$_4$ 387.2032 (M+H)$^+$, found 387.2032, time 0.52 min; HPLC [Waters XTerra™ C-18 (150×4.6 mm, S-5 microm), 0.1% TFA/acetonitrile in 0.1% TFA/water at 1.0 mL/min, 5-95 over 23 min], t$_R$=5.7 min. 100% purity.

EXAMPLE 735

6-{2-Methoxy-4-[(2-thiomorpholin-4-ylethylamino)methyl]phenoxy}nicotinamide methanesulfonate

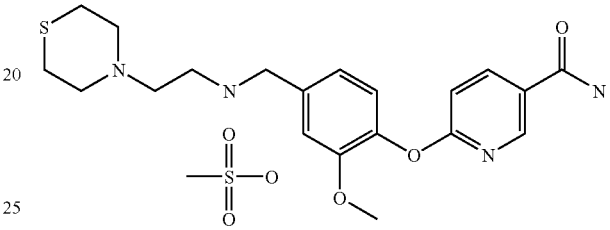

Place 6-(4-formyl-2-methoxyphenoxy)nicotinamide (Example 414, Part B) (0.250 g, 0.918 mmol), 2-thiomorpholin-4-ylethylamine (0.141 g, 0.964 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 25% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.356 g, 73%): TOF MS ES$^+$ 403.2 (M+H)$^+$, HRMS calcd for C$_{20}$H$_{27}$N$_4$O$_3$S 403.1804 (M+H)$^+$, found 403.1801, time 0.43 min; HPLC [Waters XTerra™ C-18 (150×4.6 mm, S-5 microm), 0.1% TFA/acetonitrile in 0.1% TFA/water at 1.0 mL/min, 5-95% over 23 min], t$_R$=6.2 min, 100% purity.

EXAMPLE 736

6-{2-Methoxy-4-[(3-morpholin-4-ylpropylamino)methyl]phenoxy}nicotinamide methanesulfonate

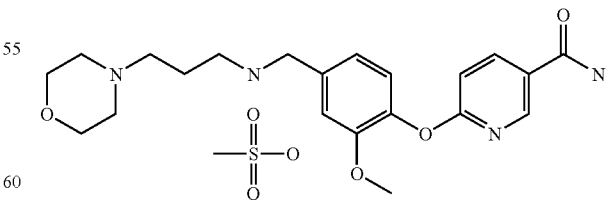

Place 6-(4-formyl-2-methoxyphenoxy)nicotinamide (Example 414, Part B) (0.250 g, 0.918 mmol), 3-morpholin-4-ylpropylamine (0.139 g, 0.964 mmol) and 3 Å molecular sieves in a vial. Add methanol (6.1 mL), cap and stir overnight. Add NaBH$_4$ (ca. 3-5 eq in two portions) and stir until the gasses stop evolving. Load the reaction mixture directly onto a 25 g ISCO® pre-load column. Dry the column in a vacuum oven at room temperature. Purify by eluting through a 40 g ISCO® column with 5% to 30% (2.0 M NH$_3$ in methanol) in ethyl acetate to give the title compound as a free base. Dissolve the product in methanol and add one equivalent of 0.5 M methanesulfonic acid solution in dichloromethane. Concentrate to give the title compound (0.340 g, 74%): TOF MS ES$^+$ 401.2 (M+H)$^+$, HRMS calcd for C$_{21}$H$_{29}$N$_4$O$_4$ 401.2189 (M+H)$^+$, found 401.2178, time 0.52 min; HPLC [Waters XTerra™ C-18 (150×4.6 mm, S-5 microm), 0.1% TFA/acetonitrile in 0.1% TFA/water at 1.0 mL/min, 5-95% over 23 min], t$_R$=5.6 min. 100% purity.

EXAMPLE 737

5-{4-[(3,3-Dimethylbutylamino)methyl]-2-fluorophenoxy}pyrazine-2-carboxamide

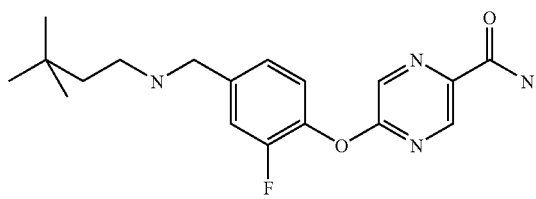

Part A:
3-Fluoro-4-triisopropylsilanyloxybenzaldehyde

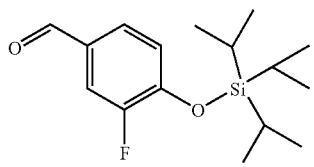

Add triisopropylsilyl chloride (74.32 g, 0.3855 mol), followed by DMF (25 mL), to a solution of 3-fluoro-4-hydroxybenzaldehyde (45.01 g, 0.3213 mol) and imidazole (43.74 g, 0.6425 mole) in DMF (313 mL) at 25-29° C. in a steady stream over 2 min. Stir for 1 hr at room temperature till the reaction complete as determined by HPLC (Column: 4.6 mm×25 cm Zorbax RX-C8; eluant: 50/50 0.1% TFA:acetonitrile, flow rate 2 mL/min; detector: 230 nm; temperature: 22° C.; injection: 10 μL). Pour the reaction mixture into saturated aqueous ammonium chloride solution (1 L) and extract with ether (3×1 L). Combine the ether layers, wash with brine (2×750 mL) and dried over sodium sulfate. Filter and concentrate to give a yellow oil (106.3 g). Purify the crude oil on 1 kg Merck silica gel grade 60 with 20:1 heptane/ethyl acetate (90.14 g, 94.6%).

Part B: (4-[1,3]Dioxolan-2-yl-2-fluorophenoxy)triisopropylsilane

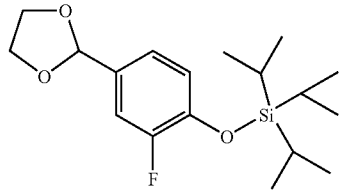

Into a 5 L 3-neck flask equipped with a condenser and a Dean-Stark trap add 3-fluoro-4-triisopropylsilanyloxybenzaldehyde (Example 737, Part A) (90.14 g, 0.3041 mol), ethylene glycol (188.75 g, 3.041 mol), and p-toluenesulfonic acid (0.58 g, 0.003041 mol) in toluene (3.155 L). Heat to boil and reflux until 130 mL of H$_2$O (lower layer) is collected in the Dean-Stark trap (5 hrs). Cool to room temperature, wash with 10% aqueous potassium carbonate solution (2×1 L) and brine (2×1 L), and dry over sodium sulfate. Filter and concentrate to give the crude produce.

Part C: 4-[1,3]Dioxolan-2-yl-2-fluorophenol

To a solution of (4-[1,3]dioxolan-2-yl-2-fluorophenoxy)triisopropylsilane (Example 93. Part B) (105.9 g, approximately 0.311 mol) in THF (1.589 L) add 1.0 M tetrabutylammonium fluoride (TBAF) in THF (311 mL) in a steady stream over 5 min at 23-27° C. without cooling. Stir for 1 hr till the reaction complete by TLC (19:1 heptane/ethyl acetate). Concentrate to a red oil and partition between ether (500 mL) and deionized water (1 L). Separate the layers and extract the aqueous layer with ether (500 mL). Combine the ether layers, wash with brine and dry over sodium sulfate. Filter and concentrate to give the crude product (92.9 g). Dissolve the crude product in dichloromethane and filter through 400 g of silica gel 60. Wash with dichloromethane (3×1 L fractions) and concentrate the combined filtrate to give an impure product. Crystallize from dichloromethane/heptane to give the title compound (29.8 g, 52%). Gas chromatography: retention time 15.96 min (30 m×0.32 mm i.d. DB-1 column, 0.25 micron film thickness; 1.2 mL/min flow rate; 55:1 split ratio; temperature profile: 35° C./3 min, 10° C. temperature increase per min; 250° C./10.5 min). $^1$H NMR (DMSO-d$_6$) δ 3.84-3.93 (m, 2H, CH$_2$), 3.93-4.04 (m, 2H, CH$_2$), 5.60 (s, 1H, CH), 6.91 (t, 11, ArH), 7.06 (dd, 1H, ArH), 7.15 (dd, 1H, ArH), 10.0 (s, 1H, OH).

Part D: 5-(4-[1,3]Dioxolan-2-yl-2-fluorophenoxy) pyrazine-2-carboxamide

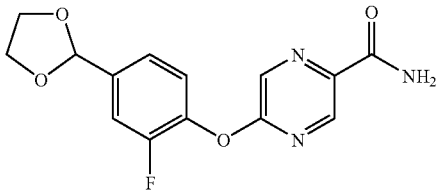

Heat a mixture of 5-chloropyrazine-2-carboxamide (14.18 g, 0.09 mol) (see S. Fujii, T. Takagi, S. Toshihisa, M. Seki, Agric. Biol. Chem., 1982, 46, (8), 2169), 4-[1,3]dioxolan-2-yl-2-fluorophenol (Example 737, Part C) (16.58 g, 0.09 mole), and powdered potassium carbonate (31.10 g, 0.225 mol) in DMF (213 mL) at 100° C. for 2 hours. Dilute the reaction mixture to 1 L with deionized water, filter at room temperature, and wash the filter cake with water. Extract the filtrate with ether (2×1 L) and dry the extracts over sodium sulfate. Combine the filter cake and ether extracts and concentrate to dryness to give a semi-solid (32.81 g) containing residual water and DMF (by $^1$H NMR). Recrystallize a portion from ethyl acetate to give a purified sample: mp 169-172° C.; $^1$H NMR (DMSO-$d_6$) δ 3.94-4.03 (m, 2H, CH$_2$), 4.03-4.11 (m, 2H, CH$_2$), 5.78 (s, 1H, CH), 7.36 (d, 1H, ArH), 7.46 (t, 2H, ArH), 7.73 (s, 1H, HetH), 8.13 (s, 1H, HetH), 8.68 (d, 2H, amide); $^{13}$C NMR (DMSO-$d_6$) δ 64.879, 101.364, 114.869, 123.251, 123.762, 132.997, 137.855, 139.454, 140.340, 140.744, 152.019, 154.475, 159.643, 164.135; MS (ES$^+$): m/z 306.0 (M+H).

Part E:
5-(2-Fluoro-4-formylphenoxy)pyrazine-2-carboxamide

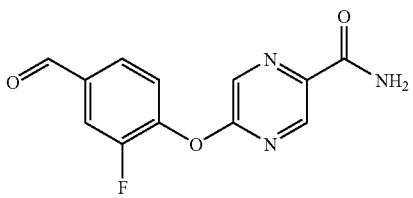

Combine formic acid (90%, 453 mL) and crude 5-(4-[1,3] dioxolan-2-yl-2-fluorophenoxy)pyrazine-2-carboxamide (Example 737, Part D) (32.81 g, approximately 0.09 mole) and stir initially a clear yellow solution, which becomes a thick slurry in an hour at room temperature. Stir overnight at room temperature till the reaction complete by HPLC. Quench the reaction with deionized water (1 L) and extract with dichloromethane (4×4 L). Combine the extracts and mix with aqueous sodium bicarbonate solution. Concentrate on a rotary evaporator to give a slurry of a solid in water (when the separation of layers not possible). Extract the mixture with ethyl acetate (4×1 L) and concentrate the combined extracts to a yellow solid (29.65 g). Form slurries successively four times with boiling methanol (1 L) and filter while hot. Combine the filter cakes and dissolve in enough boiling methanol to give a clear solution. Concentrate the solution to approximately 1 liter and allow to crystallize at 0° C. Filter the resulting slurry at 0° C. and dry the filter cake under vacuum at room temperature to give the title compound (17.79 g, 75.7%). $^1$H NMR (DMSO-$d_6$) δ 7.70 (t, 1H, ArH), 7.78 (s, 1H. HetH), 7.86-7.93 (m, 2H, ArH), 8.14 (s, 1H, HetH), 8.73 (d, 2H, amide), 10.0 S, 1H, CHO); $^{13}$C NMR (DMSO-$d_6$) δ 116.884, 124.606, 126.980, 133.186, 134.967, 140.765, 144.016, 152.493, 154.974, 159.276, 164.057, 190.777; MS (ES$^+$) m/z 262.3 (M+H).

Part F: 5-{4-[(3,3-Dimethylbutylamino)methyl]-2-fluorophenoxy}pyrazine-2-carboxamide Place 5-(2-fluoro-4-formylphenoxy)pyrazine-2-carboxamide (Example 737, Part E) (0.350 g, 1.14 mmol), 3,3-dimethylbutylamine (0.19 g, 1.41 mmol) and 3 Å molecular sieves in a vial. Add methanol (9.7 mL), cap and stir overnight. Add NaBH$_4$ (0.053 g, 1.41 mmol) and stir until the gasses stop evolving. Filter the reaction mixture, then concentrate. Purify by eluting through a 40 g ISCO® column with 6% to 30% (2.0 M NH$_3$ in methanol) in ethyl acetate to give the title compound (0.225 g, 49%): TOF MS ES$^+$ 347.2 (M+H)$^+$, HRMS calcd for C$_{18}$H$_{24}$N$_4$O$_2$F 347.1883 (M+H)$^+$, found 347.1883, time 0.53 min; HPLC [YMC-Pro pack C-18 (150×4.6 min, S-5 microm), 0.05% TFA/acetonitrile in 0.05% TFA/water at 1.0 mL/min, 10-20% over 5 min, 20-95% over 18], $t_R$=10.9 min, 100% purity.

EXAMPLE 738

5-(2-Fluoro-4-{[2-(2-fluorophenyl)ethylamino] methyl}phenoxy)pyridine-2-carboxamide

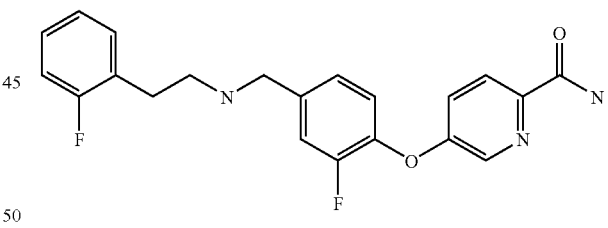

Place 5-(2-fluoro-4-formylphenoxy)pyridine-2-carboxamide (Example 403, Part B) (0.650 g, 2.50 mmol), 2-fluorophenethylamine (0.382 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.718 g, 75%): TOF MS ES$^+$ 384.2 (M+H)$^+$, HRMS calcd for C$_{21}$H$_{20}$N$_3$O$_2$F$_2$ 387.2032 (M+H)$^+$, found 387.2032, time 0.52 min; HPLC [YMC-Pro pack C-18 (150×46 mm, S-5 microm), 0.05% TFA/acetonitrile in 0.05% TFA/water at 1.0 mL/min, 10-20% over 5 min, 20-95% over 18], $t_R$=11.4 min, 100% purity.

EXAMPLE 739

5-{2-Fluoro-4-[(4-methylpentylamino)methyl]phenoxy}pyridine-2-carboxamide

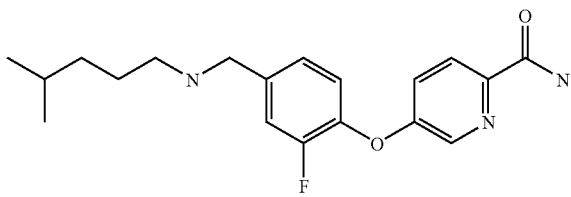

Place 5-(2-fluoro-4-formylphenoxy)pyridine-2-carboxamide (Example 403, Part B) (0.650 g, 2.50 mmol), 4-methylpentylamine (Example 433, Part A) (0.278 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.470 g, 55%): TOF MS ES$^+$ 346.2 (M+H)$^+$, HRMS calcd for C$_{19}$H$_{25}$N$_3$O$_2$F 346.1931 (M+H)$^+$, found 346.1922, time 0.48 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=11.6 min, 100% purity.

EXAMPLE 740

5-{4-[(3,3-Dimethylbutylamino)methyl]-2-fluorophenoxy}pyridine-2-carboxamide

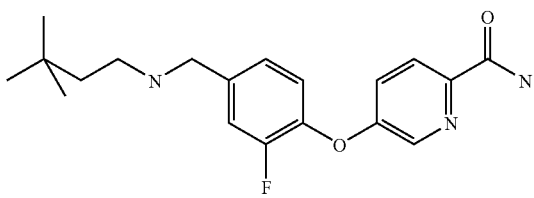

Place 5-(2-fluoro-4-formylphenoxy)pyridine-2-carboxamide (Example 403, Part B) (0.650 g, 2.50 mmol), 3,3-dimethylbutylamine (0.278 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.543 g, 63%): TOF MS ES$^+$ 346.2 (M+H)$^+$, HRMS calcd for C$_{19}$H$_{25}$N$_3$O$_2$F 346.1931 (M+H)$^+$, found 346.1921, time 0.48 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=11.3 min, 100% purity.

EXAMPLE 741

5-{4-[(4,4-Dimethylpentylamino)methyl]-2-fluorophenoxy}pyridine-2-carboxamide

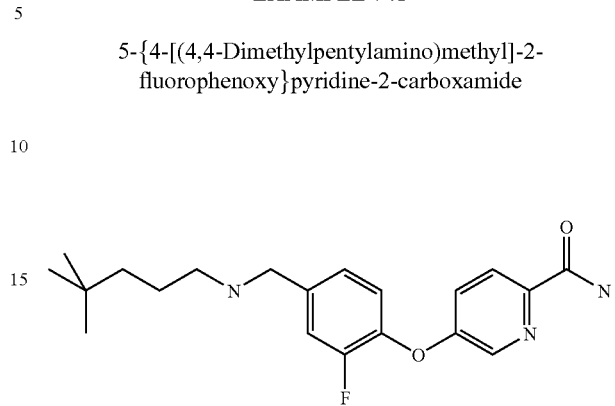

Part A: 4,4-Dimethylpentanenitrile

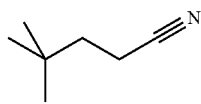

To a suspension of sodium cyanide (3.33 g, 67.8 mmol) in DMSO (34 mL) at 60° C., slowly add 1-bromo-3,3-dimethylbutane (10 g, 60.6 mmol). Keep the internal temperature between 55-65° C. by intermittently cooling with an ice bath. Heat at 70° C. for 1.5 hours, then cool to room temperature. Dilute the reaction mixture with water (100 mL) and extract with ether (3×50 mL). Wash the organic extracts with 5.0 N HCl (1×25 mL) and water (1×25 mL). Dry the organic layer over MgSO$_4$, filter and concentrate to give the title compound (6.66 g, 98%): $^1$H NMR (CDCl$_3$, 400 MHz) δ 2.29 (t, J=8.1 Hz, 2H), 1.63 (t, J=8.1 Hz, 2H), 0.94 (s, 9H).

Part B: 4,4-Dimethylpentylamine

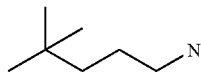

Cool a slurry of LiAlH$_4$ (4.30 g, 113 mmol) in ether (57 mL) to −30° C. Allow reaction mixture to gently reflux upon the addition of 4,4-dimethylpentanenitrile (6.29 g, 56.6 mmol). Heat at reflux for an additional 45 minutes. Cool the reaction mixture to room temperature before quenching with 1.0 N NaOH. Filter the suspension through a Celite® pad. Separate the two layers and wash the organic layer with additional 1.0 N NaOH (2×25 mL), dry it over Na$_2$SO$_4$, filter and carefully concentrate to give the title compound: $^1$H NMR (CDCl$_3$, 400 MHz) δ 2.68 (m, 2H), 2.17 (bs, 2H), 1.44 (m, 2H) 1.18 (t, J=11.0 Hz, 2H), 0.88 (s, 9H).

Part C: 5-{4-[(4,4-Dimethylpentylamino)methyl]-2-fluorophenoxy}pyridine-2-carboxamide

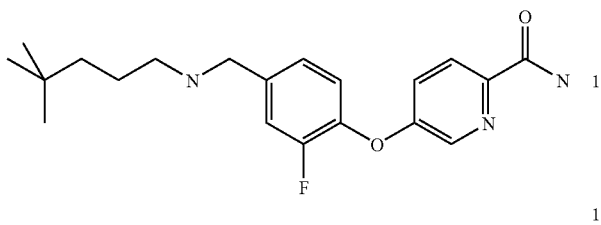

Place 5-(2-fluoro-4-formylphenoxy)pyridine-2-carboxamide (Example 403, Part B) (0.650 g, 2.50 mmol), 4,4-dimethylpentylamine (0.317 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.248 g, 28%): TOF MS ES$^+$ 360.2 (M+H)$^+$, HRMS calcd for C$_{20}$H$_{27}$N$_3$O$_2$F 360.2087 (M+H)$^+$, found 360.2076, time 0.48 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=12.3 min, 98.2% purity.

EXAMPLE 742

5-{4-[(3-Ethylpentylamino)methyl]-2-fluorophenoxy}pyridine-2-carboxamide

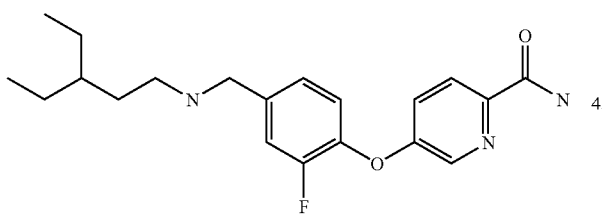

Place 5-(2-fluoro-4-formylphenoxy)pyridine-2-carboxamide (Example 403, Part B) (0.650 g, 2.50 mmol), 3-ethylpentylamine (Example 733, Part B) (0.317 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.516 g, 58%): TOF MS ES$^+$ 360.2 (M+H)$^+$, HRMS calcd for C$_{20}$H$_{27}$N$_3$O$_2$F 360.2087 (M+H)$^+$, found 360.2086, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=12.3 min, 100% purity.

EXAMPLE 743

5-{4-[(2-Cyclopentylethylamino)methyl]-2-fluorophenoxy}pyridine-2-carboxamide

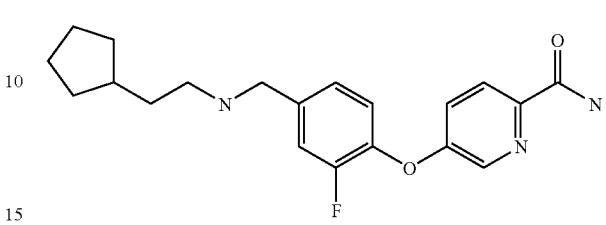

Place 5-(2-fluoro-4-formylphenoxy)pyridine-2-carboxamide (Example 403, Part B) (0.650 g, 2.50 mmol), 2-cyclopentylethylamine (0.792 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 10% (2.0 M NH$_3$ in methanol) in ethyl acetate to give the title compound (0.0850 g, 10%): TOF MS ES$^+$ 358.2 (M+H)$^+$, HRMS calcd for C$_{20}$H$_{25}$N$_3$O$_2$F 358.1931 (M+H)$^+$, found 358.1925, time 0.48 min; HPLC [YMC-Pro pack C-18 (150×4.6 mm, S-5 microm), 0.05% TFA/acetonitrile in 0.05% TFA/water at 1.0 mL/min, 10-20% over 5 ml, 20-95% over 18], t$_R$=11.8 min, 94.2% purity.

EXAMPLE 744

5-{2-Fluoro-4-[(2-thiomorpholin-4-ylethylamino)methyl]phenoxy}pyridine-2-carboxamide

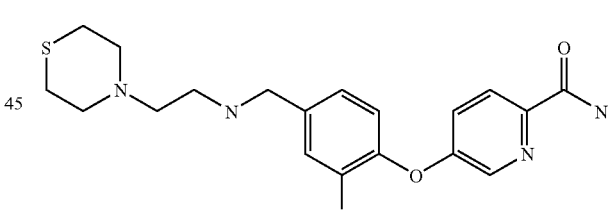

Place 5-(2-fluoro-4-formylphenoxy)pyridine-2-carboxamide (Example 403, Part B) (0.650 g, 2.50 mmol), 2-thiomorpholin-4-ylethylamine (0.402 g, 2.75 mmol) and 3 Å molecular sieves in a vial. Add methanol (12 mL), cap and stir overnight. Add NaBH$_4$ (slight excess) and stir until the gasses stop evolving. Load the reaction mixture directly onto a 25 g ISCO® pre-load column. Dry the column in a vacuum oven at room temperature. Purify by eluting through a 40 g ISCO® column with 0% to 30% (2.0 M NH$_3$ in methanol) in ethyl acetate to give the title compound (0.792 g, 81%): TOF MS ES$^+$ 391.2 (M+H)$^+$, HRMS calcd for C$_{19}$H$_{24}$N$_4$O$_2$FS 391.1604 (M+H)$^+$, found 391.1594, time 0.48 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=6.7 min, 100% purity.

EXAMPLE 745

5-{2-Fluoro-4-[(3-methyl-butylamino)-methyl]-phenoxy}-pyrazine-2-carboxylic acid amide

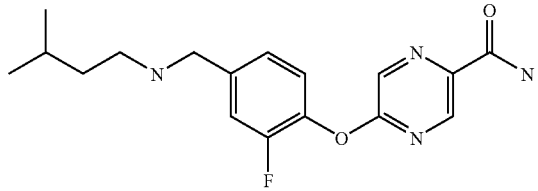

Place 5-(2-fluoro-4-formylphenoxy)pyrazine-2-carboxamide (Example 737, Part E) (0.400 g, 1.53 mmol), isoamylamine (0.147 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes) to give the title compound (0.225 g, 50%): TOF MS ES$^+$ 333.2 (M+H)$^+$, HRMS calcd for C$_{17}$H$_{22}$N$_4$O$_2$F 333.1727 (M+H)$^+$, found 333.1714, time 0.55 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=10.1 min, 100% purity.

EXAMPLE 746

5-(2-Fluoro-4-pentylaminomethylphenoxy)pyrazine-2-carboxamide

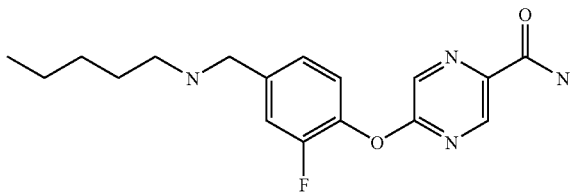

Place 5-(2-fluoro-4-formylphenoxy)pyrazine-2-carboxamide (Example 737, Part E) (0.400 g, 1.53 mmol), amylamine (0.147 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column 0% to 15% (2.0 M NH$_3$ in methanol) in 80% (ethyl acetate in hexanes) to give the title compound (0.334 g, 66%): TOF MS ES$^+$ 333.2 (M+H)$^+$, HRMS calcd for C$_{17}$H$_{22}$N$_4$O$_2$F 333.1727 (M+H)$^+$, found 333.1722, time 0.53 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=10.3 min, 96.8% purity.

EXAMPLE 747

5-{4-[(4,4-Dimethylpentylamino)methyl]-2-fluorophenoxy}pyrazine-2-carboxamide

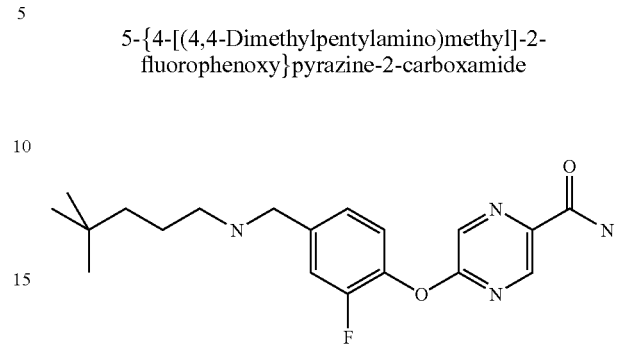

Place 5-(2-fluoro-4-formylphenoxy)pyrazine-2-carboxamide (Example 737, Part E) (0.400 g, 1.53 mmol), 4,4-dimethylpentylamine (0.194 g, 1.68 mmol) (Example 97, Part B) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes). Concentrate the fractions containing the product. Take the solid up in dichloromethane (100 mL) and wash with 1.0 N NaOH (2×25 mL) to give the title compound (0.314 g, 57%): TOF MS ES$^+$ 361.2 (M+H)$^+$, HRMS calcd for C$_{19}$H$_{26}$N$_4$O$_2$F 361.2040 (M+H)$^+$, found 361.2042, time 0.55 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=12.0 min. 100% purity.

EXAMPLE 748

5-{4-[(3-Ethylpentylamino)methyl]-2-fluorophenoxy}pyrazine-2-carboxamide

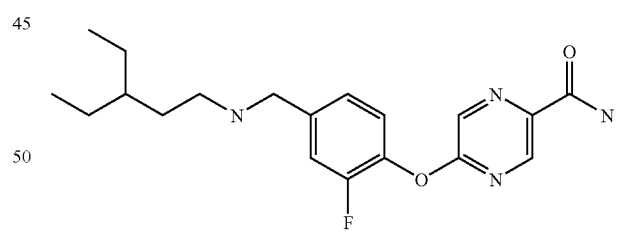

Place 5-(2-fluoro-4-formylphenoxy)pyrazine-2-carboxamide (Example 737, Part E) (0.400 g, 1.53 mmol), 3-ethylpentylamine (0.194 g, 1.68 mmol) (Example 733, Part B) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes) to give the title compound (0.342 g, 62%): TOF MS ES$^+$ 361.2 (M+H)$^+$, HRMS calcd for C$_{19}$H$_{26}$N$_4$O$_2$F 361.2040 (M+H)$^+$, found 361.2048, time 0.57 min; HPLC [YMC-Pro pack C-18 (150×

4.6 mm, S-5 microm), 0.05% TFA/acetonitrile in 0.05% TFA/water at 1.0 mL/min, 10-20% over 5 min. 20-95% over 18], $t_R$=12.0 min, 96.9% purity.

EXAMPLE 749

5-(2-Fluoro-4-{[2-(tetrahydropyran-4-yl)ethylamino]methyl}phenoxy)pyrazine-2-carboxamide

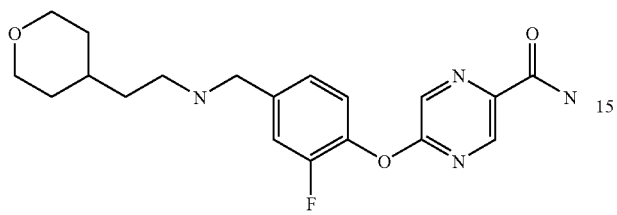

Place 5-(2-fluoro-4-formylphenoxy)pyrazine-2-carboxamide (Example 737, Part E) (0.400 g, 1.53 mmol), 2-(tetrahydropyran-4-yl)ethylamine (0.217 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 30% (2.0 M NH$_3$ in methanol) in 80% (ethyl acetate in hexanes) to give the title compound (0.385 g, 67%): TOF MS ES$^+$ 375.2 (M+H)$^+$, HRMS calcd for $C_{19}H_{24}N_4O_3F$ 375.1832 (M+H)$^+$, found 375.1847, time 0.53 min; HPLC [YMC-Pro pack C-18 (150× 4.6 mm, S-5 microm), 0.05% TFA/acetonitrile in 0.05% TFA/water at 1.0 mL/min, 10-20% over 5 min, 20-95% over 18], $t_R$ 8.6 min, 95.4% purity.

EXAMPLE 750

5-(2-Fluoro-4-{[2-(4-fluorophenyl)ethylamino]methyl}phenoxy)pyrazine-2-carboxamide

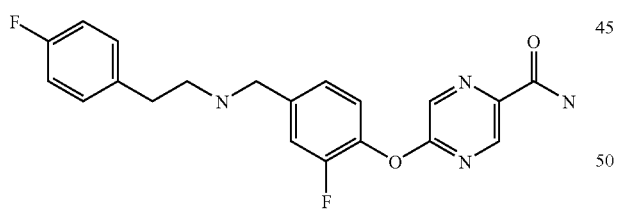

Place 5-(2-fluoro-4-formylphenoxy)pyrazine-2-carboxamide (Example 737, Part E) (0.400 g, 1.53 mmol), 4-fluorophenethylamine (0.234 g, 1.68 mmol) and 3 Å molecular-sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes). Concentrate the fractions containing the product. Take the solid up in dichloromethane (100 mL) and wash with 1.0 N NaOH (2×25 mL) to give the title compound (0.383 g, 65%): TOF MS ES$^+$ 385.1 (M+H)$^+$, HRMS calcd for $C_{20}H_{19}N_4O_2F_2$ 385.1476 (M+H)$^+$, found 385.1480, time 0.55 min; HPLC [YMC-Pro pack C-18 (150× 4.6 mm, S-5 microm), 0.05% TFA/acetonitrile in 0.05% TFA/water at 1.0 mL/min, 10-20% over 5 min. 20-95% over 18], $t_R$=11.1 min, 100% purity.

EXAMPLE 751

5-{2-Fluoro-4-[(2-thiophen-2-ylethylamino)methyl]phenoxy}pyrazine-2-carboxamide

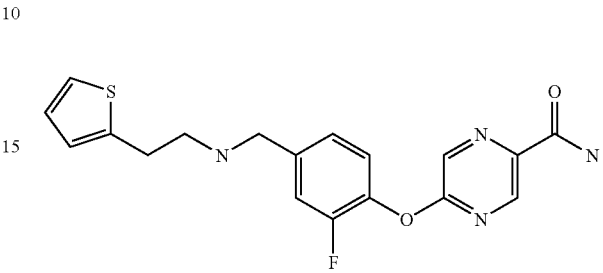

Place 5-(2-fluoro-4-formylphenoxy)pyrazine-2-carboxamide (Example 737, Part E) (0.400 g, 1.53 mmol), 2-(2-thienyl)ethylamine (0.217 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes). Concentrate the fractions containing the product. Take the solid up in dichloromethane (100 mL) and wash with 1.0 N NaOH (2×25 mL) to give the title compound (0.100 g, 18%): TOF MS ES$^+$ 373.1 (M+H)$^+$, HRMS calcd for $C_{15}H_{11}N_4O_2FS$ 373.1135 (M+H)$^+$, found 373.1150, time 0.48 min; HPLC [YMC-Pro pack C-18 (150× 4.6 mm, S-5 microm), 0.05% TFA/acetonitrile in 0.05% TFA/water at 1.0 mL/min, 10-20% over 5 min. 20-95% over 18], $t_R$=10.3 min. 100% purity.

EXAMPLE 752

5-(2-Fluoro-4-hexylaminomethylphenoxy)pyrazine-2-carboxamide

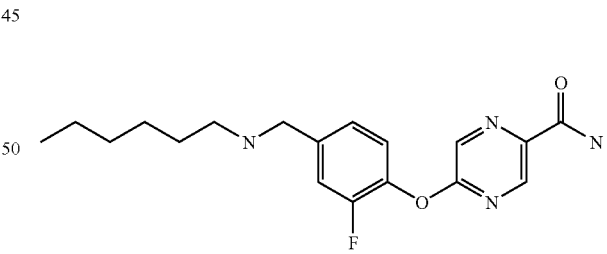

Place 5-(2-fluoro-4-formylphenoxy)pyrazine-2-carboxamide (Example 737, Part E) (0.400 g, 1.53 mmol), hexylamine (0.170 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes) to give the title compound (0.329 g, 62%): TOF MS ES$^+$ 347.2 (M+H)$^+$, HRMS calcd for $C_{18}H_{24}N_4O_2F$ 347.1883 (M+H)$^+$, found 347.1897, time 0.57

EXAMPLE 753

5-(4-{[2-(3,4-Dichlorophenyl)ethylamino]methyl}-2-fluorophenoxy)pyrazine-2-carboxamide

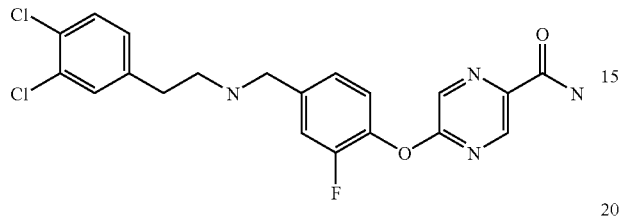

Place 5-(2-fluoro-4-formylphenoxy)pyrazine-2-carboxamide (Example 737, Part E) (0.400 g, 1.53 mmol), 3,4-dichlorophenethylamine (0.320 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 15% (2.0 M NH$_3$ in methanol) in 80% (ethyl acetate in hexanes). Concentrate the fractions containing the product. Take the solid up in dichloromethane (100 mL) and wash with 1.0 N NaOH (2×25 mL) to give the title compound (0.293 g, 44%): TOF MS ES$^+$ 435.1 (M+H)$^+$, HRMS calcd for C$_{20}$H$_{18}$N$_4$O$_2$FCl$_2$ 435.0791 (M+H)$^+$, found 435.0815, time 0.53 min; HPLC [YMC-Pro pack C-18 (150× 4.6 mm, S-5 microm), 0.05% TFA/acetonitrile in 0.05% TFA/water at 1.0 mL/min, 10-20% over 5 min, 20-95% over 18], t$_R$=12.8 min, 100% purity.

EXAMPLE 754

5-{2-Fluoro-4-[(3-isopropoxypropylamino)methyl]phenoxy}pyrazine-2-carboxamide

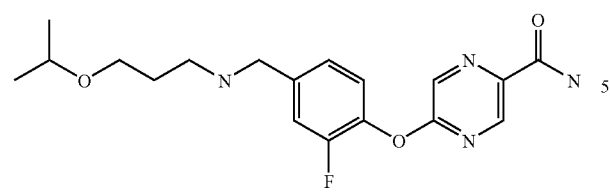

Place 5-(2-fluoro-4-formylphenoxy)pyrazine-2-carboxamide (Example 737, Part E) (0.400 g, 1.53 mmol), 3-isopropoxypropylamine (0.197 g, 1.68 mmol) and 3 Å molecular sieves in a vial. Add methanol (7.7 mL), cap and stir overnight. Add NaBH$_4$ (0.058 g, 1.53 mmol) and stir until the gasses stop evolving. Load the reaction mixture directly onto a 25 g ISCO® pre-load column. Dry the column in a vacuum oven at room temperature. Purify by eluting through a 40 g ISCO® column with 0% to 30% (2.0 M NH$_3$ in methanol) in 80% (ethyl acetate in hexanes). Concentrate the fractions containing the product. Take the solid tip in dichloromethane (100 mL) and wash with 1.0 N NaOH (2×25 mL) to give the title compound (0.395 g, 71%): TOF MS ES$^+$ 363.2 (M+H)$^+$, HRMS calcd for C$_{18}$H$_{24}$N$_4$O$_3$F 363.1832 (M+H)$^+$, found 363.1821, time 0.57 min; HPLC [YMC-Pro pack C-18 (150× 4.6 mm, S-5 microm), 0.05% TFA/acetonitrile in 0.05% TFA/water at 1.0 mL/min, 10-20% over 5 min, 20-95% over 18], t$_R$=9.8 ml, 100% purity.

EXAMPLE 755

6-(4-{[2-(2-Fluorophenyl)ethylamino]methyl}-2-methoxyphenoxy)nicotinamide methansulfonate

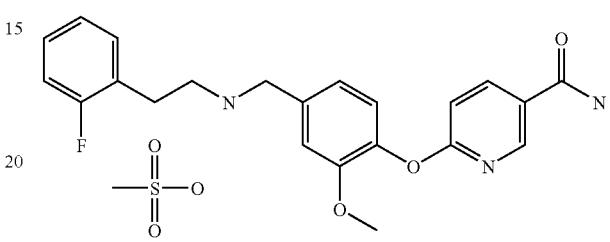

Dissolve 6-(4-{[2-(2-fluorophenyl)ethylamino]methyl}-2-methoxyphenoxy)nicotinamide (Example 431) (0.701, 1.18 mmol) in methanol (4.4 mL) and dichloromethane (4.4 mL). Add 0.5 M methanesulfonic acid (3.54 mL, 1.18 mmol) in dichloromethane. Stir for 10 minutes, then concentrate to give the title compound (0.875 g, ~100%): TOF MS ES$^+$ 396.2 (M+H)$^+$, HRMS calcd for C$_{22}$H$_{23}$N$_3$O$_3$F 396.1723 (M+H)$^+$, found 396.1739, time 0.53 min; HPLC [Waters XTerra™ MS C-18 (150×4.6 mm, S-5 microm), 0.1% TFA/acetonitrile in 0.1% TFA/water at 1.0 mL/min, 5-95% over 15 min], t$_R$=10.8 min, 100% purity.

EXAMPLE 756

6-{4-[(3,3-Dimethylbutylamino)methyl]-2-methoxyphenoxy}pyridazine-3-carboxamide methanesulfonate

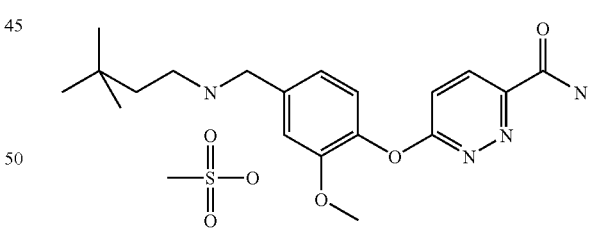

Place 6-(4-formyl-2-methoxyphenoxy)pyridazine-3-carboxamide (Example 721, Part C) (0.406 g, 1.49 mmol), 3,3-dimethylbutylamine (0.216 mL, 1.56 mmol) and 3 Å molecular sieves in a vial. Add methanol (7.4 mL), cap and stir overnight. Add NaBH$_4$ (0.060 g, 1.56 mmol) and stir until the gasses stop evolving. Filter the reaction mixture, then concentrate it. Purify by eluting through a 40 g ISCO® column with 6% to 30% (2.0 M NH$_3$ in methanol) in 80% (ethyl acetate in hexanes) to give the title compound as a free base (0.378 g, 71%). Dissolve the free base (0.357, 0.99 mmol) in methanol (2.5 mL) and dichloromethane (2.5 mL). Add 0.5 M methanesulfonic acid (1.99 mL, 0.99 mmol) in dichloromethane. Stir for 10 minutes, then concentrate to give the

EXAMPLE 757

6-(2-Fluoro-4-{[2-(tetrahydropyran-4-yl)ethylamino]methyl}phenoxy)nicotinamide methanesulfonate

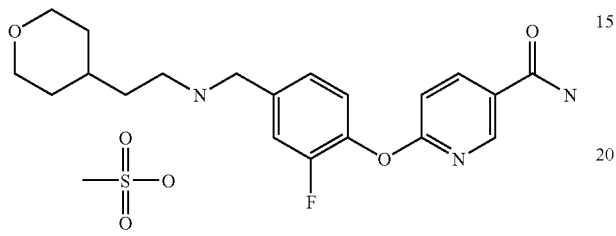

Place 6-(2-fluoro-4-formylphenoxy)nicotinamide (Example 223, step 1) (0.700 g, 2.69 mmol), 2-(tetrahydropyran-4-yl)ethylamine (0.348 g, 2.69 mmol) and 3 Å molecular sieves in a vial. Add methanol (13.5 mL), cap and stir overnight. Add NaBH$_4$ (0.204 g, 5.38 mmol) and stir until the gasses stop evolving. Filter the reaction mixture, then concentrate it. Purify by chromatography eluting with 0% to 20% (2.0 M NH$_3$ in methanol) in ethyl acetate over 1 hour at 20 mL/min to give 6-(2-fluoro-4-{[2-(tetrahydropyran-4-yl)ethylamino]methyl}phenoxy)nicotinamide. (0.717 g, 71.3%). Dissolve the compound in dichloromethane:methanol (10 mL) and add 1 equivalent of 0.50 M methanesulfonic acid in dichloromethane. Stir the solution for a short time before concentrating to give the title compound (0.904 g): TOF MS ES$^+$ 374.2 (M+H)$^+$, HRMS calcd for C$_{20}$H$_{25}$N$_3$O$_3$F 374.1880 (M+H)$^+$, found 374.1881, time 0.55 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=8.7 min, 100% purity.

EXAMPLE 758

5-(4-{[2-(4-Fluorophenyl)ethylamino]methyl}-2-methylphenoxy)pyrazine-2-carboxamide

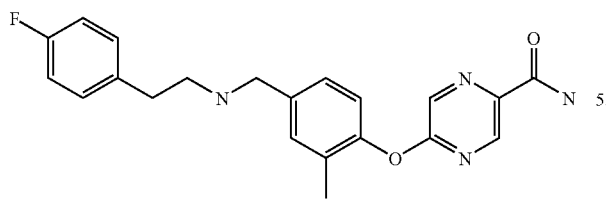

Place 5-(4-formyl-2-methylphenoxy)pyrazine-2-carboxamide (Example 404, part D) (0.600 g, 2.33 mmol), 2-(4-fluorophenyl)ethylamine (0.325 g, 2.33 mmol) and 3 Å molecular sieves in a vial. Add methanol (11.7 mL), cap and stir overnight. Add NaBH$_4$ (0.088 g, 2.33 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate. Concentrate the fraction containing the product, then take it up in EtOAc (100 mL). Wash the organic solution with 1.0 N NaOH (2×25 mL), dry it over Na$_2$SO$_4$ and concentrate it to give the title compound (0.478 g, 54.0%): TOF MS ES$^+$ 381.2 (M+H)$^+$, HRMS calcd for C$_{21}$H$_{22}$N$_4$O$_2$F 381.1727 (M+H)$^+$, found 381.1729, time 0.39 min; HPLC [YMC-Pro pack C-18 (150×4.6 mm, S-5 microm), 0.05% TFA/acetonitrile in 0.05% TFA/water at 1.0 mL/min, 10-20% over 5 min. 20-95% over 18], t$_R$=11.3 min. 97.8% purity.

EXAMPLE 759

5-{2-Methyl-4-[(2-pyridin-3-yl-ethylamino)methyl]phenoxy}pyrazine-2-carboxamide

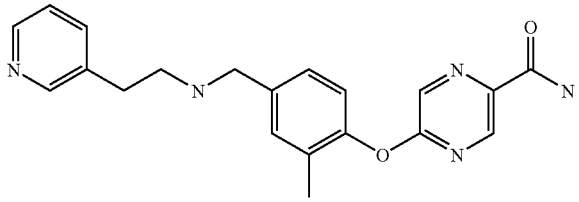

Place 5-(4-formyl-2-methylphenoxy)pyrazine-2-carboxamide (Example 404, part D) (0.600 g, 2.33 mmol), 2-pyridin-3-ylethylamine (0.285 g, 2.33 mmol) and 3 Å molecular sieves in a vial. Add methanol (11.7 mL), cap and stir overnight. Add NaBH$_4$ (0.088 g, 2.33 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 25% (2.0 M NH$_3$ in methanol) in ethyl acetate. Concentrate the fraction containing the product, then take it up in EtOAc (100 mL). Wash the organic solution with 1.0 N NaOH (2×25 mL), dry it over Na$_2$SO$_4$ and concentrate it to give the title compound (0.315 g, 37.2%): TOF MS ES$^+$ 364.2 (M+H)$^+$, HRMS calcd for C$_{20}$H$_{22}$N$_5$O$_2$ 364.1773 (M+H)$^+$, found 367.1774, time 0.39 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=6.1 min, 100% purity.

EXAMPLE 760

6-(4-{[2-(4-Fluorophenyl)ethylamino]methyl}-2-methoxyphenoxy)nicotinamide methanesulfonate

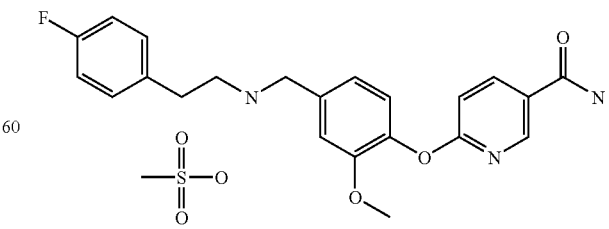

Dissolve 6-(4-{[2-(4-fluorophenyl)ethylamino]methyl}-2-methoxyphenoxy)nicotinamide (Example 430) (8.40 g, 2.12 mmol) in dichloromethane:methanol (1:1) (4.25 mL) and add 1 equivalent of 0.50 M methanesulfonic acid in dichloromethane. Stir the solution for a short time before concentrating to give the title compound (0.1.02 g): TOF MS ES+ 396.2 (M+H)+, HRMS calcd for $C_{22}H_{23}N_3O_3.F$ 396.1723 (M+H)+, found 396.1731, time 0.39 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=10.9 min, 100% purity.

EXAMPLE 761

5-(2-Methoxy-4-{[2-(tetrahydropyran-4-yl)ethylamino]methyl}phenoxy)pyridine-2-carboxamide methanesulfonate

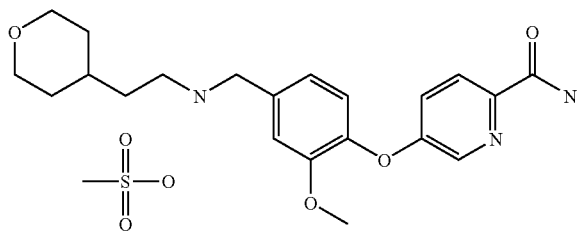

Place 5-(4-formyl-2-methoxyphenoxy)pyridine-2-carboxamide (Ex 391, Part A) (0.600 g, 2.20 mmol), 2-(tetrahydropyan-4-yl)ethylamine (0.285 g, 2.20 mmol) and 3 Å molecular sieves in a vial. Add methanol (11.0 mL), cap and stir overnight. Add NaBH4 (0.0833 g, 2.20 mmol) and stir until the gasses stop evolving. Filter the reaction mixture, then concentrate it. Purify by chromatography eluting with 5% to 30% (2.0 M NH3 in methanol) in ethyl acetate over 45 minutes to give 5-(2-methoxy-4-{[2-(tetrahydropyran-4-yl)ethylamino]methyl}phenoxy)pyridine-2-carboxamide. (0.6103 g, 71.9%). Dissolve the compound in dichloromethane:methanol (3.2 mL) and add 1 equivalent of 0.50 M methanesulfonic acid in dichloromethane. Stir the solution for a short time before concentrating to give the title compound (0.775 g): TOF MS ES+ 386.2 (M+H)+, HRMS calcd for $C_{21}H_{28}N_3O_4$ 386.2080 (M+H)+, found 386.2078, time 0.39 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=9.3 min, 100% purity.

EXAMPLE 762

5-{2-Methoxy-4-[(3-methylbutylamino)methyl]phenoxy}pyrazine-2-carboxamide

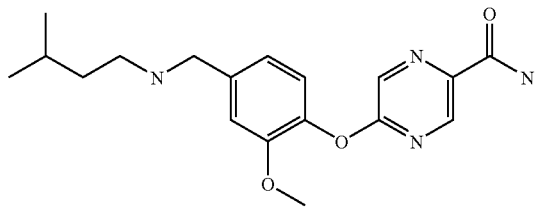

Place 5-(4-formyl-2-methoxyphenoxy)pyrazine-2-carboxamide (Example 719, Part A) (0.700 g, 2.56 mmol), isoamylamine (0.234 g, 2.69 mmol) and 3 Å molecular sieves in a vial. Add methanol (12.8 mL), cap and stir overnight. Add NaBH4 (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH3 in methanol) in ethyl acetate over 45 minutes. Concentrate the fraction containing the product, and dissolve it in EtOAc (100 mL). Wash the organic solution with 1.0 N NaOH (2×25 mL), dry it over Na2SO4, filter and concentrate to give the title compound (0.484 g, 54.9%): TOF MS ES+ 345.2 (M+H)+, HRMS calcd for $C_{18}H_{25}N_4O_3$ 345.1927 (M+H)+, found 345.1938, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=10.1 min, 95.4% purity.

EXAMPLE 763

5-{2-Methoxy-4-[(4-methylpentylamino)methyl]phenoxy}pyrazine-2-carboxamide

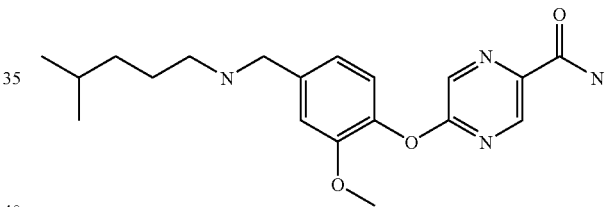

Place 5-(4-formyl-2-methoxyphenoxy)pyrazine-2-carboxamide (Example 719, Part A) (0.700 g, 2.56 mmol), 4-methylpentylamine (Example 433, Part A) (0.272 g, 2.69 mmol) and 3 Å molecular sieves in a vial. Add methanol (12.8 mL), cap and stir overnight. Add NaBH4 (0.0969 g, 2.56 mmol) and stir until the sasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH3 in methanol) in ethyl acetate over 45 minutes. Concentrate the fraction containing the product, then take it up in EtOAc (100 mL). Wash the organic solution with 1.0 N NaOH (2×25 mL), dry it over Na2SO4, filter and concentrate. Dissolve the product in ether:dichloromethane (5:1) (25 mL), add hexanes (20 mL), and then concentrate to about a quarter of the volume. Filter the precipitate to give the title compound (0.335 g, 36.5%): TOF MS ES+ 359.2 (M+H)+, HRMS calcd for $C_{19}H_{27}N_4O_3$ 359.2083 (M+H)+, found 359.2087, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], $t_R$=11.3 min, 100% purity.

EXAMPLE 764

5-{4-[(3,3-Dimethylbutylamino)methyl]-2-methoxyphenoxy}pyrazine-2-carboxamide

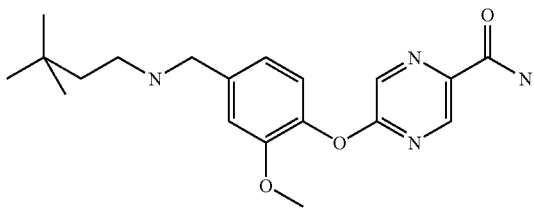

Place 5-(4-formyl-2-methoxyphenoxy)pyrazine-2-carboxamide (Example 719, Part A) (0.700 g, 2.56 mmol), 3,3-dimethylbutylamine (0.272 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting t-rough a 40 g ISCO® column with 5% to 20% (2.0 M NH$_3$ in methanol) in ethyl acetate over 45 minutes. Concentrate the fraction containing the product, then take it up in EtOAc (100 mL). Wash the organic solution with 1.0 N NaOH (2×25 mL), dry it over Na$_2$SO$_4$, filter and concentrate. Dissolve the product in ether:dichloromethane (5:1) (25 mL), add hexanes (20 mL), and then concentrate to about a quarter of the volume. Filter the precipitate to give the title compound (0.421 g, 45.9%): TOF MS ES$^+$ 359.2 (M+H)$^+$, HRMS calcd for C$_{19}$H$_{27}$N$_4$O$_3$ 359.2083 (M+H)$^+$, found 359.2093, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=11.0 min, 98.0% purity.

EXAMPLE 765

5-{4-[(4,4-Dimethylpentylamino)methyl]-2-methoxyphenoxy}pyrazine-2-carboxamide

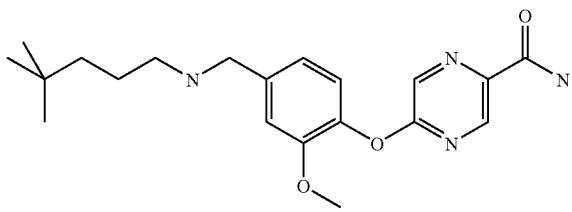

Place 5-(4-formyl-2-methoxyphenoxy)pyrazine-2-carboxamide (Example 719, Part A) (0.700 g, 2.56 mmol), 4,4-dimethylpentylamine (0.310 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes. Concentrate the fraction containing the product, then add EtOAc (100 mL). Wash the organic solution with 1.0 N NaOH (2×25 mL), dry it over Na$_2$SO$_4$, filter and concentrate. Dissolve the product in ether:dichloromethane (5:1) (25 mL), add hexanes (20 mL), and then concentrate to about a quarter of the volume. Filter the precipitate to give the title compound (0.356 g, 37.3%): TOF MS ES$^+$ 373.2 (M+H)$^+$, HRMS calcd for C$_{20}$H$_{29}$N$_4$O$_3$ 373.2240 (M+H)$^+$, found 373.2245, time 0.39 man; HPLC [YMC-Pro pack C-18 (150×4.6 mm, S-5 microm); 0.05% TFA/acetonitrile in 0.05% TFA/water at 1.0 min, 10-20% over 5 min, 20-95% over 18], t$_R$=12.0 min, 98.7% purity.

EXAMPLE 766

5-{4-[(3-Ethylpentylamino)methyl]-2-methoxyphenoxy}pyrazine-2-carboxamide

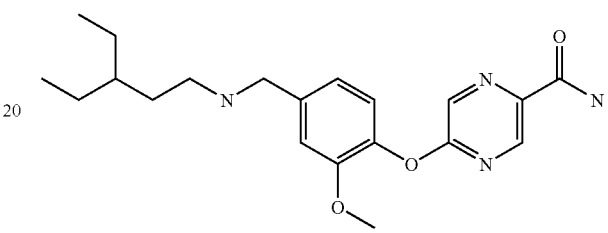

Place 5-(4-formyl-2-methoxyphenoxy)pyrazine-2-carboxamide (Example 719 Part A) (0.700 g, 2.56 mmol), 3-ethylpentylamine (Example 733, Part B) (0.310 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes. Concentrate the fraction containing the product, then add EtOAc (100 mL). Wash the organic solution with 1.0 N NaOH (2×25 mL), dry it over Na$_2$SO$_4$, filter and concentrate. Dissolve the product in ether:dichloromethane (5:1) (25 mL), add hexanes (20 mL), and then concentrate to about a quarter of the volume. Filter the precipitate to give the title compound (0.302 g, 31.7%): TOF MS ES$^+$ 373.2 (M+H)$^+$, HRMS calcd for C$_{20}$H$_{29}$N$_4$O$_3$ 373.2240 (M+H)$^+$, found 373.2247, time 0.39 min; HPLC [YMC-Pro pack C-18 (150×4.6 mm, S-5 microm), 0.05% TFA/acetonitrile in 0.05% TFA/water at 1.0 mL/min, 0-20% over 5 min, 20-95% over 18], t$_R$=12.0 min, 100% purity.

EXAMPLE 767

5-(4-{[2-(4-Fluorophenyl)ethylamino]methyl}-2-methoxyphenoxy)pyrazine-2-carboxamide

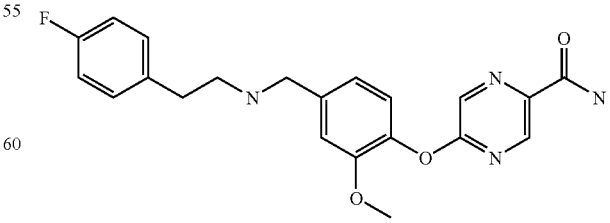

Place 5-(4-formyl-2-methoxyphenoxy)pyrazine-2-carboxamide (Example 719, Part A) (0.700 g, 2.56 mmol), 4-fluorophenethylamine (0.374 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes. Concentrate the fraction containing the product then add EtOAc (100 mL). Wash the organic solution with 1.0 N NaOH (2×25 mL), dry it over Na$_2$SO$_4$, filter and concentrate. Dissolve the product in ether:dichloromethane (5:1) (25 mL), add hexanes (20 mL), and then concentrate to about a quarter of the volume. Filter the precipitate to give the title compound (0.545 g, 53.4%): TOF MS ES$^+$ 397.2 (M+H)$^+$, HRMS calcd for C$_{21}$H$_{22}$N$_4$O$_3$F 397.1676 (M+H)$^+$, found 397.1689, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=11.2 min, 100% purity.

EXAMPLE 768

5-{4-[(2-Isopropoxyethylamino)methyl]-2-methoxyphenoxy}pyrazine-2-carboxamide

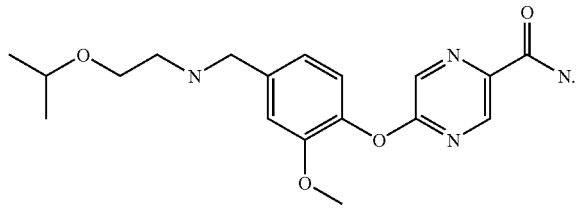

Place 5-(4-formyl-2-methoxyphenoxy)pyrazine-2-carboxamide (Example 719, Part A) (0.700 g, 2.56 mmol), 2-isopropoxyethylamine (0.278 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes. Concentrate the fraction containing the product, then take it up in EtOAc (100 mL). Wash the organic solution with 1.0 N NaOH (2×25 mL), dry it over Na$_2$SO$_4$ filter and concentrate to give the title compound (0.512 g, 55.5%): TOF MS ES$^+$ 361.2 (M+H)$^+$, HRMS calcd for C$_{18}$H$_{25}$N$_4$O$_4$ 361.1876 (M+H)$^+$, found 361.1891, time 0.38 min; HPLC [YMC-Pro pack C-18 (150×4.6 mm, S-5 microm), 0.05% TFA/acetonitrile in 0.05% TFA/water at 1.0 mL/min, 10-20% over 5 min, 20-95% over 18], t$_R$=9.4 min, 100% purity.

EXAMPLE 769

5-{2-Methoxy-4-[(3-methoxypropylamino)methyl]phenoxy}pyrazine-2-carboxamide

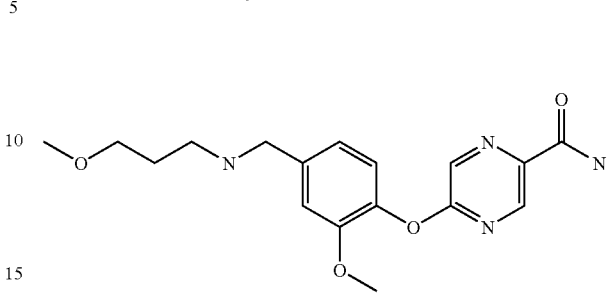

Part A: 5-(4-Formyl-2-methoxyphenoxy)pyrazine-2-carboxamide

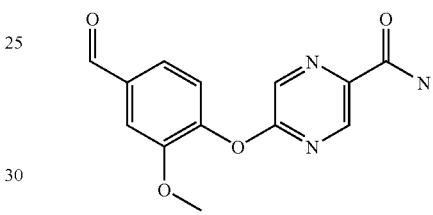

Dissolve 5-chloropyrazine-2-carboxamide (Example 387, Part A) (0.374 g, 2.34 mmol) and vanillin (0.361 g, 2.34 mmol) in DMF (23.7 mL). Add K$_2$CO$_3$ (0.821 g, 8.94 mmol) and heat at 100° C. for 1.5 hours. Concentrate the reaction mixture. Take the solid up in water (50 mL) and extract with dichloromethane (3×100 mL). Dry the organic layer over Na$_2$SO$_4$, filter and concentrate to give the title compound (0.625 g, 96.4%): TOF MS ES$^+$ 274.1 (M+H)$^+$, HRMS calcd for C$_{13}$H$_{12}$N$_3$O$_4$ 274.0828 (M+H)$^+$, found 274.0829, time 0.55 min; HPLC [YMC-Pro pack C-18 (150×4.6 mm, S-5 microm), 0.1% TFA/acetonitrile in 0.1% TFA/water at 1.0 mL/min, 5-95 over 19 min], t$_R$=10.2 min, 98.1% purity.

Part B: Place 5-(4-formyl-2-methoxyphenoxy)pyrazine-2-carboxamide (Part A) (0.700 g, 2.56 mmol), 3-methoxypropylamine (0.240 g, 2.69 mmol) and 3 Å molecular sieves in a vial. Add methanol (12.8 mL), cap and stir overnight. Add NaBH$_4$ (0.0969 g, 2.56 mmol) and stir until the gasses stop evolving. Load the reaction mixture directly onto a 25 g ISCO® pre-load column. Dry the column in a vacuum oven at room temperature. Purify by eluting through a 40 g ISCO® column with 5% to 20% (2.0 M NH$_3$ in methanol) in ethyl acetate over 45 minutes. Concentrate the fraction containing the product, then take it up in EtOAc (100 mL). Wash the organic solution with 1.0 N NaOH (2×25 mL), dry it over Na$_2$SO$_4$ filter and concentrate to give the title compound (0.484 g, 54.6%): TOF MS ES$^+$ 347.2 (M+H)$^+$, HRMS calcd for C$_{17}$H$_{23}$N$_4$O$_4$ 347.1719 (M+H)$^+$, found 347.1729, time 0.38 mm: HPLC [YMC-Pro pack C-18 (150×4.6 mm, S-5 microm), 0.05% TFA/acetonitrile in 0.05% TFA/water at 1.0 mL/min, 10-20% over 5 ml, 20-95% over 18], t$_R$=8.0 min. 100% purity.

EXAMPLE 770

N-Methyl-6-[4-(phenethylamino-methyl)-phenoxy]-nicotinamide

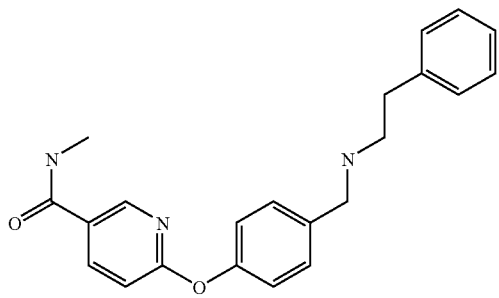

Step 1

Starting from 6-(4-Formyl-phenoxy)-nicotinic acid

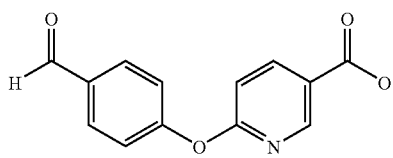

Combine 6-(4-Formyl-phenoxy)-nicotinic acid ethyl ester (1.5 g, 5.53 mmol), MeOH (5 mL), THF (5 mL), and 5N NaOH (aq) (2 mL). Reflux the reaction 18 hours and then add 1N HCl (aq) (2 mL). After concentrating the reaction on the rotovap, add Ethyl acetate to precipitate out the desired product. Filter and concentrate the ethyl acetate filtrate to afford 1.14 g (85% yield) of the title compound: TLC 1:1Hexanes:Ethyl acetate $R_f$=0.01.

Step 2

6-[4-(Phenethylamino-methyl)-phenoxy]-nicotinic acid ethyl ester

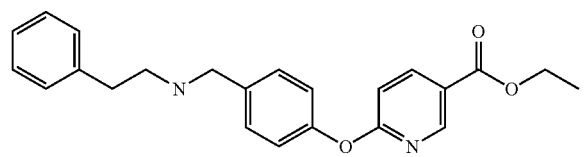

Combine 6-(4-Formyl-phenoxy)-nicotinic acid ethyl ester (0.62 g, 2.29 mmol), MeOH (12 mL), Trimethylorthoformate (8 mL), and Phenethylamine (0.26 mL, 2.06 mmol). After the reaction stirs at room temperature under a Nitrogen atmosphere for 3.5 hours, add NaBH$_4$ (251.0 mg, 2.75 mmol). After the reaction stirs at room temperature for 12 hours, concentrate under reduced pressure and add the mixture to a 5 g SCX column. Wash the column with MeOH and elute with 1N NH$_3$ MeOH to afford 854.0 mg (99% yield) of the title compound: $^1$H NMR (500 MHz, CDCl$_3$); 2.8 (2H, t), 2.8-3.0 (4H, m), 3.8 (2H, s), 3.9 (3H, s), 6.9 (1H, d), 7.1-7.4 (9H, m), 8.3 (1H, d), 8.8 (1H, s); MS m/z 377 (M+1).

Step 3

[4-(5-Ethylcarbamoyl-pyridin-2-yloxy)-benzyl]-phenethyl-carbamic acid tert-butyl ester

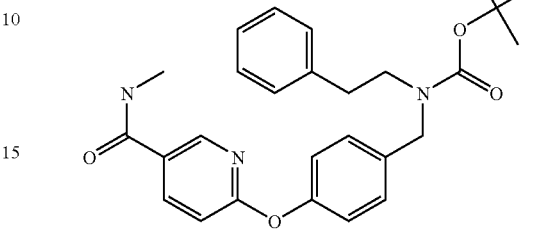

Combine 6-{4-[(tert-Butoxycarbonyl-phenethyl-amino)-methyl]-phenoxy}-nicotinic acid (0.097 g, 0.21 mmol), CH$_2$Cl$_2$ (5 mL), EDC (0.048 g, 0.25 mmol), HOBt (0.034 g, 0.25 mmol), Hunig's Base (92 uL, 0.53 mmol), and Methylamine Hydrochloride (0.014 g, 0.21 mmol) in a 7 mL reaction vial. After reactions shake for 72 hours, add 10% Citric acid, followed by 10% NaHCO$_3$, and then add the organic mixture to a Celite column. Elute with CH$_2$Cl$_2$, concentrate and flash chromatograph using 2:1 Ethyl acetate:Hexanes eluent to afford 55.4 mg (57% yield) of the title compound: $^1$H NMR (500 MHz, CDCl$_3$); 1.4 (9H, s), 2.7-2.9 (21 m), 3.0 (3H, s), 4.2-4.4 (2H, m), 4.3-4.5 (2H, m), 6.3-6.4 (1H, br s), 6.9 (1H, d), 7.0-7.4 (9H, m), 8.1 (1H, d), 8.6 (1H, s); MS m/z 362 (M−100, Boc).

Step 4

N-Methyl-6-[4-(phenethylamino-methyl)-phenoxy]-nicotinamide

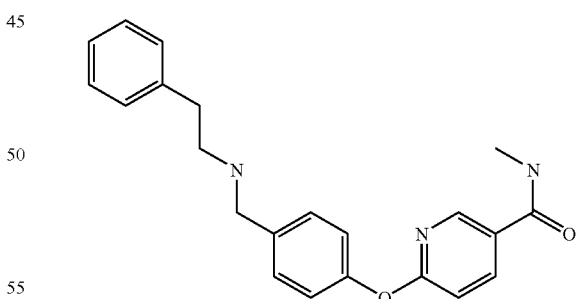

Combine [4-(5-Ethylcarbamoyl-pyridin-2-yloxy)-benzyl]-phenethyl-carbamic acid tert-butyl ester (55.4 mg, 0.12 mmol), CH$_2$Cl$_2$ (4 mL), and TFA 99% (0.8 mL) in a 7 mL reaction vial. After reaction shakes on shaker at room temperature for 24 hours, concentrate under reduced pressure. Add the reaction mixture to a 2 g SCX column, wash with MeOH, and elute with 1N NH$_3$ MeOH. Concentrate sample to afford 41.2 mg (95% yield) of the title compound: $^1$H NMR (500 MHz, CDCl$_3$); 1.5 (1H, br m), 2.7-3.0 (7H, m), 3.7 (2H, s), 6.2 (1H, br s), 6.9 (1H, d), 7.0-7.4 (9H, m), 8.0 (1H, d), 8.4 (1H, s); MS m/z 363 (M+1).

EXAMPLES 771-827

Intermediate 1

6-Methoxy-1,2,3,4-tetrahydro-isoquinoline

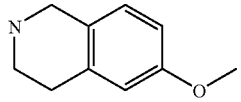

Combine 2-(3-Methoxyphenol)ethylamine (10.0 g, 66.13 mmol), 88% Formic acid, and paraformaldehyde (2.05 g, 68.25 mmol) at 0° C. After the reaction stirs at room temperature for 24 hours, concentrate under reduced pressure. Add Acetyl chloride in MeOH (5 ml in 80 ml of MeOH) at room temperature and stir for 10 minutes. After concentration, triturate the reaction mixture with ethyl acetate, cool to room temperature and filter to afford 8.76 g, 53.7 mmol (81% yield) of the title compound as a white solid:

$^1$H NMR (500 MHz, d-MeOH); 3.05-13.15 (2H, m), 3.45-3.55 (2H, m), 3.70 (3H, s), 4.30 (2H, s), 4.8-5.0 (1H, br s), 6.8-6.9 (2H, m), 7.1-7.2 (1H, m); MS m/z 163 (M+).

Intermediate 2

6-Hydroxy-1,2,3,4-tetrahydro-isoquinoline

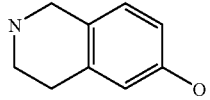

Combine 6-Methoxy-1,2,3,4-tetrahydro-isoquinoline (5.0, 20.5 mmol) and 48% HBr(aq), 20 ml at room temperature. After the reaction refluxes for 24 hours, cool the reaction to room temperature and concentrate under reduced pressure. Triturate with ethyl acetate and filter to afford 5.5 g, 20.5 mmol (99% yield) of the title compound as a tan solid: $^1$H NMR (500 MHz, DMSO); 2.8-2.9 (2H, m), 3.3-3.4 (2H, m), 4.1 (2H, s), 6.5-6.7 (2H, m), 6.9-7.1 (1H, m), 8.8-9.0 (2H, br s), 9.4-9.5 (1H, s).

Intermediate 3

6-Hydroxy-3,4-dihydro-1H-isoquinoline-2-carboxylic acid tert-butyl ester

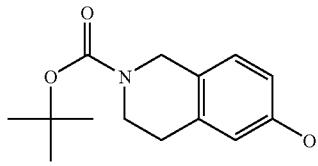

Combine 6-Hydroxy-1,2,3,4-tetrahydro-isoquinoline (5.5 g, 23.9 mmol), THF, 100 ml, Et$_3$N (8.3 ml, 59.8 mmol), and Boc-anhydride (8.3 g, 28.7 mmol). After the reaction stirs at room temperature for 72 hours under nitrogen, concentrate under reduced pressure and then flash chromatography using 1:1 Hexanes:Ethyl acetate eluent to afford 3.51 g, 14.1 mmol (59% yield) of the title compound: $^1$H NMR (500 MHz, CDCl$_3$); 1.5 (9H, br s), 2.7-2.8 (2H, m), 3.5-3.6 (2H, m), 4.4 (2H, s), 6.5-6.8 (2H, m), 6.9-7.0 (1H, m); MS m/z 150 (M+).

Intermediate 4

6-(4-Cyano-phenoxy)-3,4-dihydro-1H-isoquinoline-2-carboxylic acid tert-butyl ester

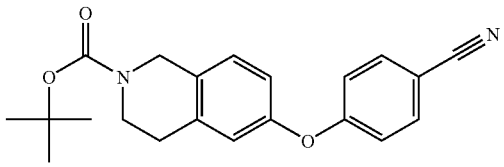

Combine in a round bottom flask equipped with a Dean Stark Trap 6-Hydroxy-3,4-dihydro-1H-isoquinoline-2-carboxylic acid tert-butyl ester (1.59 g, 6.36 mmol), toluene, dimethylacetamide (10 ml and 30 ml respectively), K$_2$CO$_3$ (1.25 g, 9.04 mmol), and 4-Fluorobenzonitrile (0.72 g, 6.04 mmol). Reflux the reaction under a Nitrogen atmosphere for 4 hours then cool to room temperature. Add water to the reaction mixture and extract the product from the water layer using ethyl acetate. The product, a white solid, precipitates out from the ethyl acetate to afford 1.93 g, 5.5 mmol (87% yield) of the title compound: $^1$H NMR (500 MHz, CDCl$_3$); 1.5 (9H, s), 2.75-2.85 (2H, m), 3.6-3.7 (2H, m), 4.5 (2H, s), 6.8-6.9 (2H, m), 6.9-7.0 (2H, m), 7.1-7.2 (1H, m), 7.5-7.6 (2H, m); MS m/z 249 (M+).

Intermediate 5

6-(4-Carbamoyl-phenoxy)-3,4-dihydro-1H-isoquinoline-2-carboxylic acid tert-butyl ester

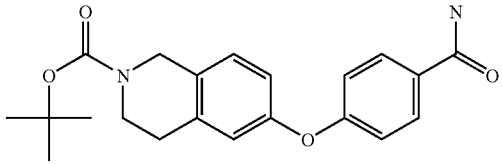

Combine 6-(4-Cyano-phenoxy)-3,4-dihydro-1H-isoquinoline-2-carboxylic acid tert-butyl ester (1.93, 5.51 mmol), t-butyl alcohol (50 ml), and KOH (1.56 g, 27.6 mmol). After the reaction stirs for 72 hours at room temperature, concentrate under reduced pressure then add ethyl acetate. Wash the ethyl acetate with a brine solution and dry the organic layer over Na$_2$SO$_4$. After concentrating the organic layer under reduced pressure, the reaction affords 1.93 g, 2.50 mmol (95% yield) of the title compound as a white solid: $^1$H NMR (500 MHz, CDCl$_3$); 1.5 (9H, s), 2.75-2.85 (2H, m), 3.6-3.7 (2H, m), 4.5 (2H, s), 6.8-6.9 (2H, m), 6.9-7.0 (2H, m), 7.1-7.2 (1H, m), 7.7-7.9 (2H, m); TLC R$_f$=0.5 2:1 Hexanes:Ethyl acetate.

Intermediate 6

4-(1,2,3,4-Tetrahydro-isoquinolin-6-yloxy)-benzamide

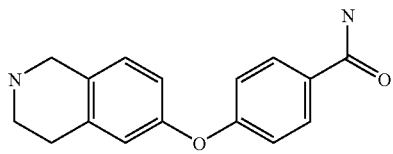

Combine 6-(4-Carbamoyl-phenoxy)-3,4-dihydro-1H-isoquinoline-2-carboxylic acid tert-butyl ester (4.0 g, 10.83 mmol), $CH_2Cl_2$ (100 ml), and TFA (25 ml) at room temperature. After the reaction stirred for 24 hours followed by the addition of 1M $K_2CO_3$ (aq), extract the product out of the aqueous layer with several washings of ethyl acetate/THF. Concentrate the organic phase under reduced pressure and add to 2, 10 g SCX Columns pre-treated with 5% AcOH/MeOH. After several washings of the SCX Columns with MeOH, the elute the product using 1N $NH_3$-MeOH solution to afford 2.00 g, 7.7 mmol (71% yield) of the title compound as a white foam: $^1H$ NMR (500 MHz, DMSO); 2.9-3.1 (2H, m), 3.10-3.25 (1H, m), 3.3-3.5 (2H, m), 4.1-4.3 (2H, m), 7.0-7.2 (3H, m), 7.2-7.4 (1H, m), 7.4-7.6 (1H, m), 8.0-8.1 (1H, m), 8.2-8.4 (1H, m), 8.5-8.65 (1H, m), 9.2-9.4 (2H, m); MS m/z 269 (M+1).

EXAMPLE 771

4-(2-Pentyl-1,2,3,4-tetrahydro-isoquinolin-6-yloxy)-benzamide

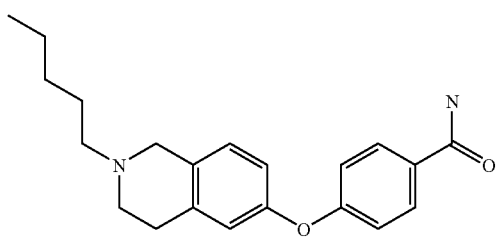

Combine 4-(1,2,3,4-Tetrahydro-isoquinolin-6-yloxy)-benzamide (80.0 mg, 0.30 mmol), DMF (4 mL), $Et_3N$ (0.2 mL, 1.32 mmol), and Pentylbromide (0.1 mL, 0.66 mmol) in a 7 mL vial. Place vial on shaker at 70° C. for 72 hours and then added Ethyl acetate to reaction vial, wash with water and several times with 10% LiCl(aq), dry over $Na_2SO_4$. Concentrate the organic mixture and flash chromatograph using 2% 1N $NH_3$ MeOH, 20% THF, 78% $CH_2Cl_2$ to afford 78.0 mg (77% yield) of the title compound: $^1H$ NMR (500 MHz, $CDCl_3$); 0.9-1.0 (3H, m), 1.3-1.4 (4H, m), 1.5-1.7 (2H, m), 2.4-2.6 (2H, m), 2.7-2.8 (2H, m), 2.8-3.0 (2H, r), 3.5-3.6 (2H, 1H), 6.8-6.8 (2H, m), 6.9-7.1 (3H, m), 7.7-7.9 (2H, m); MS m/z 339 (M+1).

EXAMPLE 772

4-[2-(3-Methyl-butyl)-1,2,3,4-tetrahydro-isoquinolin-6-yloxy]-benzamide

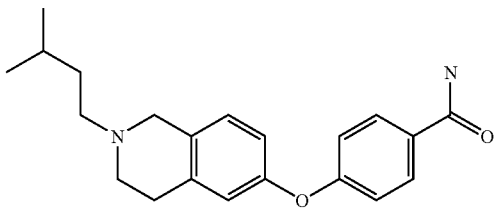

Using a method similar to Example 771, using Isoamylbromide (0.1 mL, 0.66 mmol) gives 63.0 mg (62% yield) of the title compound: $^1H$ NMR (500 MHz, $CDCl_3$); 0.9-1.0 (6H, m), 1.4-1.8 (3H, m), 2.5-2.6 (2H, m), 2.7-2.8 (2H, m), 2.9-3.0 (2H, m), 3.6-3.8 (2H, m), 6.8-7.1 (5H, m), 7.7-7.9 (2H, m), MS m/z 339 (M+1).

EXAMPLE 773

4-(2-Benzyl-1,2,3,4-tetrahydro-isoquinolin-6-yloxy)-benzamide

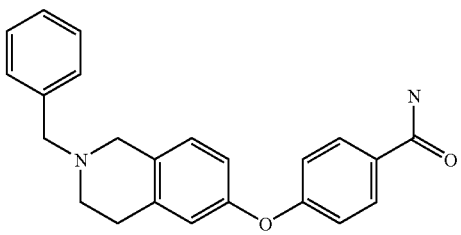

Using a method similar to Example 771, using Benzylbromide (0.1 mL, 0.66 mmol) gives 81.0 mg (75% yield) of the title compound: 3H NMR (500 MHz, $CDCl_3$); 2.6-2.8 (2H, m), 2.8-3.0 (2H, m), 3.5-3.7 (4H, m), 5.6-6.1 (2H, br s), 6.7-6.8 (2H, m), 6.8-7.0 (3H, m), 7.2-7.4 (5M, m), 7.7-7.9 (2H, m); M/S m/z 359 (M+1).

EXAMPLE 774

4-(5-Phenethyl-1,2,3,4-tetrahydro-isoquinolin-6-yloxy)-benzamide

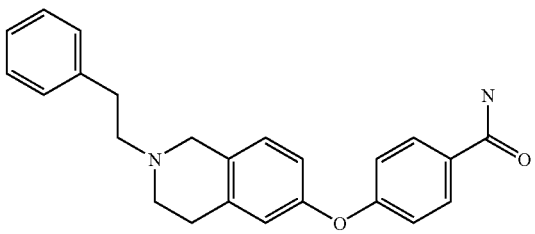

Using a method similar to Example 771, using Phenethylbromide (0.1 mL, 0.66 mmol) gives 81.9 mg (73% yield) of the title compound: $^1H$ NMR (500 MHz, $CDCl_3$); 2.7-3.0

(7H, m), 3.6-3.8 (3H, m), 5.8-6.2 (2H, br s), 6.8-7.1 (5H, m), 7.2-7.4 (5H, m), 7.7-7.9 (2H, m); MS m/z 373 (M+1).

Intermediate 7

6-(5-Carbamoyl-pyridin-2-yloxy)-3,4-dihydro-1H-isoquinoline-2-carboxylic acid tert-butyl ester

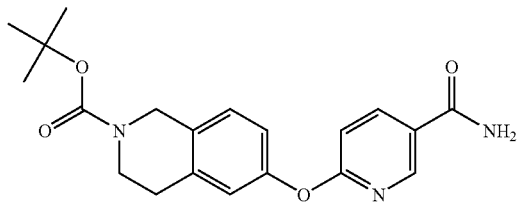

Combine in a round bottom flask equipped with a Dean Stark Trap 6-Hydroxy-3,4-dihydro-1H-isoquinoline-2-carboxylic acid tert-butyl ester (5.42 g, 21.74 mmol), Toluene, Dimethyl acetamide (30 ml and 90 ml respectively), $K_2CO_3$ (4.51 g, 32.61 mmol), and 6-Chloronicatinamide (3.40, 21.74 mmol). Reflux the reaction under a Nitrogen atmosphere for 4 hours then cool to room temperature. Add water to the reaction mixture and extract the product from the water layer using ethyl acetate. The product, a white solid, precipitates out from the ethyl acetate to afford 5.8 g, 15.7 mmol (72% yield) of the title compound: $^1$H NMR (500 MHz, DMSO); 1.4 (9H, s), 2.7-2.9 (2H, m), 3.5-3.6 (2H, m), 4.4-4.6 (2H, m), 6.9-7.0 (2H, m), 7.0-7.1 (1H, m), 7.2-7.3 (1H, m), 7.5 (1H, s), 8.1 (1H, s), 8.2-8.3 (1H, m), 8.6 (1H, m).

Intermediate 8

6-(1,2,3,4-Tetrahydro-isoquinolin-6-yloxy)-nicotinamide

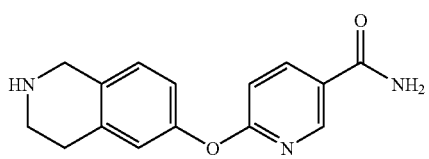

Combine 6-(5-Carbamoyl-pyridin-2-yloxy)-3,4-dihydro-1H-isoquinoline-2-carboxylic acid tert-butyl ester (4.0 g, 10.83 mmol), $CH_2Cl_2$ (100 mL), and TFA (25 mL). After reaction stirs at room temperature for 12 hours, add 1 M $K_2CO_3$ and $CHCl_3$ to the reaction. Separate the organic layer, wash with brine, and dry over $Na_2SO_4$. Concentrate under reduced pressure and add mixture to 2, 1 g SCX columns, wash with MeOH, and elute with 1N $NH_3$ MeOH. Concentrate to afford 2.91 g, 10.8 mmol (71% yield) of the title compound as a white foam: $^1$H NMR (500 MHz, DMSO); 2.9-3.1 (2H, m), 3.2-3.5 (2H, m), 4.2-4.4 (2H, m), 6.9-7.2 (3H, m), 7.2-7.4 (1H, m), 7.4-7.6 (1H, m), 7.9-8.1 (1H, m), 8.2-8.4 (1H, m), 8.5-8.7 (1H, m), 8.2-9.4 (2H, m); MS m/z 269 (M+1).

EXAMPLE 775

6-(2-Phenethyl-1,2,3,4-tetrahydro-isoquinolin-6-yloxy)-nicotinamide NF7-AOO855-011

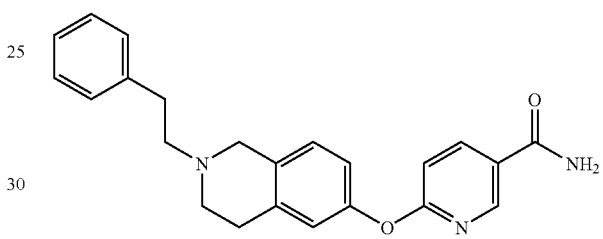

Combine 6-(1,2,3,4-Tetrahydro-isoquinolin-6-yloxy)-nicotinamide (46.9 mg, 0.17 mmol), DMF (3 mL), $Et_3N$ (0.1 mL, 0.77 mmol), and Phenethylbromide (52 uL, 0.38 mmol) in a 7 mL vial. Add reaction vial to a shaker at 70° C. for 72 hours, and then add water and Ethyl acetate. Extract the Ethyl acetate several times with water, 10% LiCl, and dry over $Na_2SO_4$. Concentrate organic mixture and flash chromatograph using 30% THF, 4% 1N $NH_3$ MeOH, 76% $CH_2Cl_2$ to afford 23.2 mg, (37% yield) of the title compound: $^1$H NMR (500 MHz, $CDCl_3$); 1.1-1.2 (1H, m), 1.6-2.1 (7H, m), 2.6-3.0 (9H, m), 3.6-4.0 (6H, m), 5.7-5.8 (1H, m), 6.8-7.3 (9H, m), 8.0-8.2 (1H, m), 8.5-8.6 (1H, m); MS m/z 374 (M+1).

By the method of example 775 the following compounds were prepared, isolated as the free base:

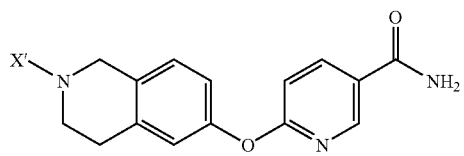

| No.: | X' | Name of the Final Compound | Data |
|---|---|---|---|
| 776 | Benzyl | 6-(2-Benzyl-1,2,3,4-tetrahydro-isoquinoline-6-yloxy)-nicotinamide | Mass spectrum (ion spray): m/z = 360 (M + 1); $^1$H NMR (500 MHz, ($CDCl_3$) 2.7-3.0 (4H, m), 3.6-3.8 (4H, m), 6.8-7.1 (3H, m), 7.2-7.5 (4H, m), 8.1-8.2 (1H, m), 8.5-8.7 (1H, s). |
| 777 | Pentyl | 6-(2-Pentyl-1,2,3,4-tetrahydro-isoquinolin-6-yloxy)-nicotinamide | Mass spectrum (ion spray): m/z = 340 (M + 1); $^1$H NMR (500 MHz, ($CDCl_3$) |

-continued

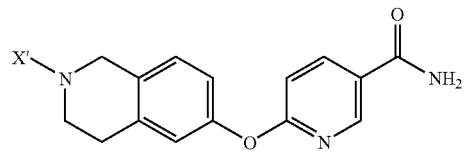

| No.: | X' | Name of the Final Compound | Data |
|---|---|---|---|
| | | | 0.8-1.0 (3H, m), 1.2-1.4 (4H, m), 1.5-1.7 (2H, m), 2.4-2.6 (2H, m), 2.7-2.8 (2H, m), 2.8-3.0 (2H, m), 3.6-3.7 (2H, m), 5.8-6.3 (1H, br d), 6.8-7.1 (4H, m), 8.1-8.2 (1H, m), 8.5-8.7 (1H, s). |
| 778 | 2-1H-Indo-3-yl-ethyl | 6-[2-(3-Phenyl-propyl)-1,2,3,4-tetrahydro-isoquinolin-6-yloxy]-nicotinamide | Mass spectrum (ion spray): m/z = 413 (M + 1); |
| 779 | 2-(3-Chloro-benzyl) | 6-[2-(3-Chloro-benzyl)-1,2,3,4-tetrahydro-isoquinoline-6-yloxy]-nicotinamide | Mass spectrum (ion spray): m/z = 388 (M + 1); |
| 780 | 2-(2-Carbamoyl-ethyl) | 6-[2-(2-Carbamoyl-ethyl)-1,2,3,4-tetrahydro-isoquinolin-6-yloxy]-nicotinamide | Mass spectrum (ion spray): m/z = 341 (M + 1); |
| 781 | 2-(2-Phenylsulfanyl-ethyl) | 6-[2-(2-Phenylsulfanyl-ethyl)-1,2,3,4-tetrahydro-isoquinolin-6-yloxy]-nicotinamide | Mass spectrum (ion spray): m/z = 406 (M + 1); |
| 782 | 2-(3-Methyl-butyl) | 6-[2-(3-Methyl-butyl)-1,2,3,4-tetrahydro-isoquinolin-6-yloxy]-nicotinamide | Mass spectrum (ion spray): m/z = 340 (M + 1); |
| 783 | 2-(4-Trifluoromethyl-benzyl) | 6-[2-(4-Trifluoromethyl-benzyl)-1,2,3,4-tetrahydro-isoquinolin-6-yloxy]-nicotinamide | Mass spectrum (ion spray): m/z = 428 (M + 1); |
| 784 | 2-(3-Chloro-benzyl) | 6-[2-(3-Chloro-benzyl)-1,2,3,4-tetrahydro-isoquinolin-6-yloxy]-nicotinamide | Mass spectrum (ion spray): m/z = 394 (M + 1); |
| 785 | 2-(3-Phenyl-allyl) | 6-[2-(3-Phenyl-allyl)-1,2,3,4-tetrahydro-isoquinolin-6-yloxy]-nicotinamide | Mass spectrum (ion spray): m/z = 386 (M + 1); |
| 786 | Benzo[b]thiopheny-3-ylmethyl | 6-(2-Benzo[b]thiophen-3-ylmethyl-1,2,3,4-tetrahydro-isoquinolin-6-yloxy)-nicotinamide | Mass spectrum (ion spray): m/z = 450 (M + 1); |
| 787 | 2-Cyclopropylmethyl | 6-(2-Cyclopropylmethyl-1,2,3,4-tetrahydro-isoquinolin-6-yloxy)-nicotinamide | Mass spectrum (ion spray): m/z = 324 (M + 1); |
| 788 | 2-(3,5-Bis-trifluoromethyl-benzyl) | 6-[2-(3,5-Bis-trifluoromethyl-benzyl)-1,2,3,4-tetrahydro-isoquinolin-6-yloxy]-nicotinamide | Mass spectrum (ion spray): m/z = 496 (M + 1); |
| 789 | 2-(3-Bromo-benzyl) | 6-[2-(Bromo-benzyl)-1,2,3,4-tetrahydro-isoquinolin-6-yloxy]-nicotinamide | Mass spectrum (ion spray): m/z = 438 (M); |
| 790 | 2-(4-Methyl-benzyl) | 6-[2-(4-Methyl-benzyl)-1,2,3,4-tetrahydro-isoquinolin-6-yloxy]-nicotinamide | Mass spectrum (ion spray): m/z = 374 (M + 1); |
| 791 | 2-(2-Fluoro-benzyl) | 6-[2-(2-Fluoro-benzyl)-1,2,3,4-tetrahydro-isoquinolin-6-yloxy]-nicotinamide | Mass spectrum (ion spray): m/z = 378 (M + 1); |
| 792 | 2-(3-Methoxy-benzyl) | 6-[2-(3-Methoxy-benzyl)-1,2,3,4-tetrahydro-isoquinolin-6-yloxy]-nicotinamide | Mass spectrum (ion spray): m/z = 390 (M + 1); |
| 793 | 2-(1H-Benzoimidazol-2-ylmethyl) | 6-[2-(1H-Benzoimidazol-2-ylmethyl)-1,2,3,4-tetrahydro-isoquinolin-6-yloxy]-nicotinamide | Mass spectrum (ion spray): m/z = 400 (M + 1); |
| 794 | 2-(5-Chloro-thiophen-2-ylmethyl) | 6-[2-(5-Chloro-thophen-2-ylmethyl)-1,2,3,4-tetrahydro-isoquinolin-6-ylozy]-nicotinamide | Mass spectrum (ion spray): m/z = 400 (M + 1); |
| 795 | 2-(2,6-Dichloro-benzyl) | 6-[2-(2,6-Dichloro-benzyl)-1,2,3,4-tetrahydro-isoquinolin-6-yloxy]-nicotinamide | Mass spectrum (ion spray): m/z = 428 (M); |
| 796 | 2-(3-Fluoro-benzyl) | 6-[2-(3-Fluoro-benzyl)-1,2,3,4-tetrahydro-isoquinolin-6-yloxy]-nicotinamide | Mass spectrum (ion spray): m/z = 378 (M + 1); |
| 797 | 2-[2-(4-Methoxy-phenyl)-ethyl] | 6-{2-[2-(4-Methoxy-phenyl)-ethyl]-1,2,3,4-tetrahydro-isoquinolin-6-yloxy}nicotinamide | Mass spectrum (ion spray): m/z = 404 (M + 1); |
| 798 | 3-Propionic acid | 3-[6-(5-Carbamoyl-pyridin-2-yloxy)-3,4-dihydro-1H-isoquinolin-2yl]-propionic acid | Mass spectrum (ion spray): m/z = 342 (M + 1); |
| 799 | 2-(3-Piperidin-1-yl-propyl) | 6-[2-(3-Piperidin-1-yl-propyl)-1,2,3,4-tetrahydro-isoquinolin-6-yloxy]-nicotinamide | Mass spectrum (ion spray): m/z = 395 (M + 1); |
| 800 | 2-Pent-4-ynyl | 6-(2-Pent-4-ynyl-1,2,3,4-tetrahydro-isoquinolin-6-yloxy)-nicotinamide | Mass spectrum (ion spray): m/z = 336 (M + 1); |
| 801 | 2-(2-Piperidin-1-yl-ethyl) | 6-[2-(2-Piperidin-1-yl-ethyl)-1,2,3,4-tetrahydro-isoquinolin-6-yloxy]-nicotinamide | Mass spectrum (ion spray): m/z = 381 (M + 1); |
| 802 | 2-(2-Diisopropylamino-ethyl) | 6-[2-(2-Diisopropylamino-ethyl)-1,2,3,4-tetrahydro-isoquinolin-6-yloxy]-nicotinamide | Mass spectrum (ion spray): m/z = 397 (M + 1); |
| 803 | 2-(3,3,4,4-Tetrafluoro-butyl) | 6-[2-(3,3,4,4-Tetrafluoro-butyl)-1,2,3,4-tetrahydro-isoquinolin-6-yloxy]-nicotinamide | Mass spectrum (ion spray): m/z = 398 (M + 1); |
| 804 | 2-Cyclobutylmethyl | 6-(2-Cyclobutylmethyl-1,2,3,4-tetrahydro-isoquinolin-6-yloxy)-nicotinamide | Mass spectrum (ion spray): m/z = 338 (M + 1); |
| 805 | 2-(3,3-Dimethyl-butyl) | 6-[2-(3,3-Dimethyl-butyl)-1,2,3,4-tetrahydro-isoquinolin-6-yloxy]-nicotinamide | Mass spectrum (ion spray): m/z = 354 (M + 1); |
| 806 | 2-(3,4,4-Trifluoro-but-3-enyl) | 6-[2-(3,4,4-Trifluoro-but-3-enyl)-1,2,3,4-tetrahydro-isoquinolin-6-yloxy]-nicotinamide | Mass spectrum (ion spray): m/z = 378 (M + 1); |
| 807 | 2-(2-Methoxy-benzyl) | 6-[2-(2-Methoxy-benzyl)-1,2,3,4-tetrahydroisoquinolin-6-yloxy]-nicotinamide | Mass spectrum (ion spray): m/z = 390 (M + 1); |
| 808 | 2-Pyridin-3-ylmethyl | 6-(2-Pyridin-3-ylmethyl-1,2,3,4-tetrahydro-isoquinolin-6-yloxy)-nicotinamide | Mass spectrum (ion spray): m/z = 361 (M + 1); |

Intermediate 9

[2-(3-Methoxy-phenyl)-ethyl]-carbamic acid methyl ester

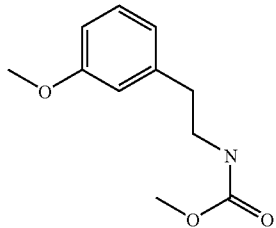

Combine Methoxyphenylethylamine (9.6 ml, 66.1 mmol), THF (300 mmol), Et₃N (11.0 ml, 78.9 mmol), and methyl chloroformate (26.0 ml, 339 mmol) at 0° C. under nitrogen atmosphere. After the reaction stirs at room temperature for 18 hours, add the mixture into water, wash with brine, and dry the organic layer over Na₂SO₄ followed by concentrating under reduced pressure. Flash chromatograph using 2:1 Hexanes:Ethyl acetate to afford 13.6 g, 65.0 mmol (98% yield) of the title compound: ¹H NMR (500 MHz, CDCl₃); 2.8 (2H, t, J=6.7, 7.0 Hz), 3.41-3.46 (2H, m), 3.7 (3H, s), 3.8 (3H, s), 4.6-4.8 (1H, b s), 6.7-6.8 (3H, m), 7.2-7.3 (1H, m); MS m/z 210 (M+1).

Intermediate 10

8-Methoxy-3,4-dihydro-2H-isoquinolin-1-one

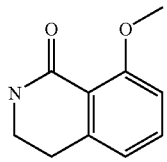

Combine polyphosphoric acid (30 g) at 180° C. and [2-(3-Methoxy-phenyl)-ethyl]-carbamic acid methyl ester (3.0 g, 14.33 mmol). After the reaction stirs for 15 minutes then add to a beaker of ice. Extract the product from the water using CH₂Cl₂ and CHCl₃. Dry the organic layer over Na₂SO₄ and then concentrate under reduced pressure. Flash chromatograph using 5% MeOH in Ethyl acetate to afford 0.340 g, 1.92 mmol (13% yield) of the title compound: ¹H NMR (500 MHz, CDCl₃); 2.92 (2H, t, J=6.4), 3.43-3.47 (2H, m), 3.85 (3H, s), 6.2-6.3 (1H, b s), 6.8-6.9 (2H, m), 7.3-7.4 (1H, m), 7.5-7.6 (2H, m); MS m/z 178 (M+1).

Intermediate 11

8-Methoxy-1,2,3,4-tetrahydro-isoquinoline

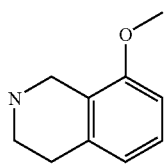

Combine 8-Methoxy-3,4-dihydro-2H-isoquinolin-1-one (0.778 g, 4.40 mmol), THF (20 ml), and LiAlH₄ (0.333 g, 8.8 mmol) at 0° C. under nitrogen atmosphere. After 30 minutes the reaction, reflux for 2 hours and then cool to room temperature. Quench the reaction by adding water and 1M NaOH at 0° C. and stirring for 12 hours at room temperature. Filter the reaction through celite and elute with THF. After concentrating the filtrate under reduced pressure, add the mixture to a 10 g SCX column pre-treated with 5% AcOH/MeOH. After rinsing several times with MeOH, elute the product using 1N NH₃-MeOH followed by concentration under reduced pressure to afford 0.665 g, 4.07 mmol (93% yield) of the title compound as a tan oil: ¹H NMR (500 MHz, CDCl₃); 1.7-2.0 (1H, b s), 2.77 (2H, t, J=5.86), 3.09 (2H, t, J=5.86), 3.8 (3H, s), 3.95 (2H, s), 6.6-6.8 (2H, m), 7.0-7.15 (1H, m); TLC 5% MeOH: Ethyl acetate R_f=0.1

Intermediate 12

1,2,3,4-Tetrahydro-isoquinolin-8-ol

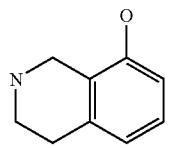

Combine 8-Methoxy-tetrahydroisoquinoline (665.7 mg, 4.08 mmol) and 48% HBr at room temperature. Reflux the reaction for 3 hours and then cool to room temperature. Recrystallize the product from EtOH and Diethyl ether to afford 754.2 mg, 3.28 mmol (80% yield) of the title compound as a tannish white solid: ¹H NMR (500 MHz, DMSO); 2.9 (2H, t, J=6.16, 5.86), 3.2-3.4 (2H, m), 4.0 (2H, s), 6.6-6.8 (2H, m), 7.0-7.1 (1H, m), 8.8-9.1 (2H, b m), 9.9 (1H, s); MS m/z 148 (M+).

Intermediate 13

8-Hydroxy-3,4-dihydro-1H-isoquinoline-2-carboxylic acid tert-butyl ester

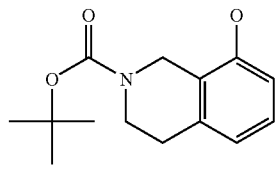

Combine 8-Hydroxy tetrahydroisoquinoline HBr salt (754.2 mg, 3.28 mmol), and Et₃N (2.8 ml, 19.68 mmol), THF anhydrous (20 ml), and Boc-anhydride (1.14 g, 3.94 mmol). Stir the reaction at room temperature for 72 hours followed by an aqueous work-up. Wash the organic layer with brine and dry over Na₂SO₄. After concentrating the organic layer under reduced pressure, flash chromatograph using 4:1 Hexanes: Ethyl acetate eluent to afford 249.6 mg, 1.01 mmol (31% yield) of the title compound as a white foam: ¹H NMR (500 MHz, CDCl₃); 1.5 (9H, s), 2.73-2.79 (2H, m), 3.5-3.6 (2H, m), 4.45-4.61 (2H, b s), 6.6-6.9 (2H, m), 6.9-7.2 (1H, m); TLC 4:1 Hexanes:Ethyl acetate R_f=0.13

Intermediate 14

8-(5-Carbamoyl-pyridin-2-yloxy)-3,4-dihydro-1H-isoquinoline-2-carboxylic acid tert-butyl ester

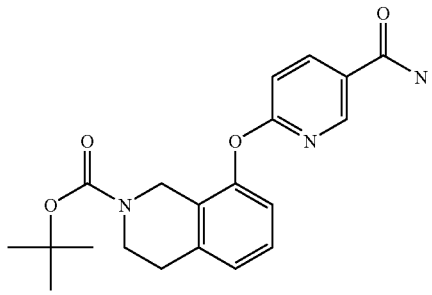

Combine in a 100 ml round bottom flask equipped with stir bar, Dean Stark trap, and reflux condenser 8-Hydroxy-3,4-dihydro-1H-isoquinoline-2-carboxylic acid tert-butyl ester (249.6 mg, 1.01 mmol), dimethylacetamide (30 ml), toluene (10 ml), $K_2CO_3$ (814.74 mg, 5.90 mmol), and 6-Chloronicatinamide (626.28 mg, 4.0 mmol). Reflux the reaction under nitrogen for 5 hours. After cooling to room temperature, add water to the reaction mixture and extract the product using ethyl acetate. Wash the organic layer with brine and dry over $Na_2SO_4$. After concentrating under reduced pressure, flash chromatograph using 20% THF in $CH_2Cl_2$ to afford 245.1 mg, 0.66 mmol (66% yield) of the title compound: $^1H$ NMR (500 MHz, d-MeOH); 1.3-1.5 (9H, m), 2.8-2.9 (2H, m), 3.5-3.7 (2H, m), 3.85 (2H, s), 6.9-7.0 (1H, m), 7.1-7.2 (1H, m), 7.2-7.3 (1H, m), 7.5-7.6 (1H, m), 8.2-8.3 (1H, m), 8.6-8.7 (1H, b s), 8.8 (1H, s); MS m/z 370 (M+1).

Intermediate 15

6-(1,2,3,4-Tetrahydro-isoquinolin-8-yloxy)-nicotinamide

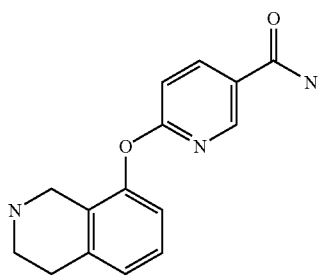

Combine 8-(5-Carbamoyl-pyridin-2-yloxy)-3,4-dihydro-1H-isoquinoline-2-carboxylic acid tert-butyl ester (249.6 mg, 1.01 mmol), $CH_2Cl_2$ (25 ml), and TFA (10 ml) at room temperature under nitrogen atmosphere. After the reaction stirs for 12 hours then concentrate under reduced pressure. Solubilize the mixture in MeOH and add to a 2 g SCX Column (pre-treated with 5% AcOH-MeOH), wash several times with MeOH, and elute the product with 1N $NH_3$ MeOH to afford 156.1 mg, 0.58 mmol (57% yield) of the title compound.

EXAMPLE 809

6-(2-Phenethyl-1,2,3,4-tetrahydro-isoquinolin-5-yloxy)-nicotinamide

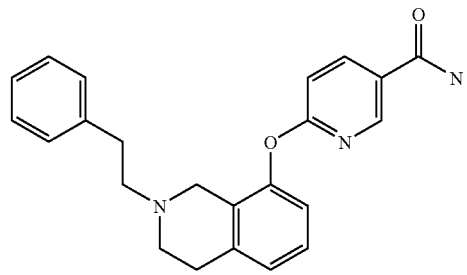

Using a method similar to Example 786, using Phenethylbromide (40 uL, 0.28 mmol) gives 26.9 mg (55% yield) of the title compound: $^1H$ NMR (500 MHz, $CDCl_3$); 1.8-2.1 (4H, m), 2.7-3.0 (6H, m), 5.9-6.3 (2H, br d), 6.8-7.4 (10H, m), 8.1-8.3 (1H, m), 8.5 (1H, s); MS m/z 374 (M+1).

EXAMPLE 810

6-(2-Benzyl-1,2,3,4-tetrahydro-isoquinolin-8-yloxy)-nicotinamide

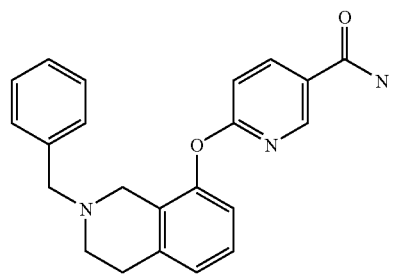

Using a method similar to Example 786, using Benzylbromide (0.1 mL, 0.97 mmol) gives 45.6 mg (63% yield) of the title compound.

EXAMPLE 811

6-(2-Pentyl-1,2,3,4-tetrahydro-isoquinolin-8-yloxy)-nicotinamide

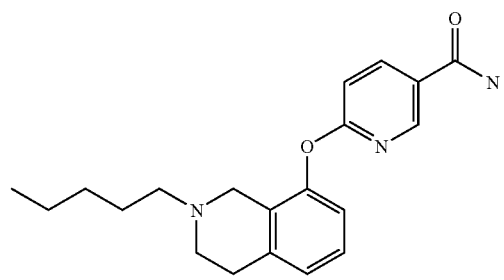

Using a method similar to Example 786, using Pentylbromide (54 uL, 0.48 mmol) gives 32.5 mg (48% yield) of the title compound: $^1H$ NMR (500 MHz, d-MeOH); 0.8 (3H, t), 1.2-1.3 (4H, m), 1.4-1.6 (2H, m), 2.3-2.5 (2H, m), 2.7 (2H, t), 2.9-3.0 (2H, m), 3.5 (2H, s), 6.8-7.2 (5H, m), 8.1-8.2 (1H, m), 8.6 (1H, s); MS m/z 340 (M+1).

Intermediate 16

1,2-Bis-bromomethyl-4-methoxy-benzene

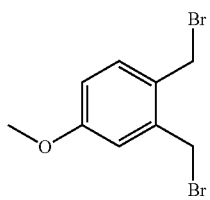

Combine 3,4-Dimethylanisole (2.72 g, 20.0 mmol), CCl$_4$ (50 mL), NBS (7.12 g, 40.0 mmol), and Benzoyl peroxide (40.0 mg, 0.17 mmol). Reflux the reaction for 12 hours and then cool to room temperature and concentrate tinder reduced pressure. Flash chromatograph using 4:1 CHCl$_3$:Hexanes eluent to afford 1.90 g, 6.4 mmol (32% yield) of the title compound: $^1$H NMR (500 MHz, CDCl$_3$); 3.8 (3H, s), 4.6 (2H, s), 4.7 (2H, s), 6.8-6.9 (2H, m), 7.1-7.4 (1H, m); TLC 4:1 CHCl$_3$:Hexanes R$_f$=0.67

Intermediate 17

2-Benzyl-5-methoxy-2,3-dihydro-1H-isoindol

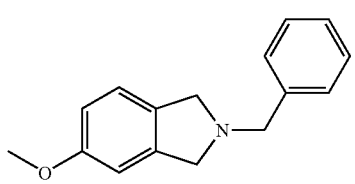

Combine in a round bottom flask 1,2-Bis-bromomethyl-4-methoxy-benzene (1.0 g, 3.40 mmol), Benzyltriethylammonium chloride (73.5 mg, 3.2 mmol), 50% NaOH(aq)/Toluene (3.0 mL/14 mL), and then dropwise addition of Benzylamine (0.37 mL, 3.39 mmol). Stir the reaction at room temperature for 3 hours, and then add to Ethyl acetate, wash with water, brine, and dry over Na$_2$SO$_4$. After concentrating under reduced pressure, the add the mixture to a 10 g SCX column, wash with MeOH, and elute with 1N NH$_3$-MeOH. Flash chromatograph using 3:1 Hexanes:Ethyl acetate to afford 580.0 mg, 2.42 mmol (71% yield) of the title compound as a brown oil: $^1$H NMR (500 MHz, CDCl$_3$); 3.7 (3H, s), 3.9-4.0 (6H, m), 6.7-6.8 (2H, m), 7.1 (1H, d), 7.3-7.5 (5H, m); MS m/z 238 (M).

Intermediate 18

2-Benzyl-2,3-dihydro-1H-isoindol-5-ol

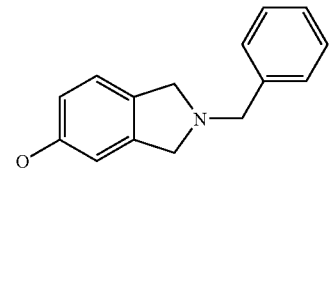

Combine 2-Benzyl-5-methoxy-2,3-dihydro-1H-isoindol (580.0 mg, 2.42 mmol) and 48% HBr (aq) (20 mL). Reflux the reaction for 5 hours and then cool to room temperature. Concentrate the reaction mixture under reduced pressure then add to 5 g a SCX column. Wash the column with MeOH and elute with 1N NH$_3$-MeOH to afford 265.4 mg, 1.17 mmol (49% yield) of the title compound as a brown solid: $^1$H NMR (500 MHz, d-Methanol); 3.8-3.9 (4H, m), 3.91 (2H, s), 6.6-6.7 (2H, m), 7.0 (1H, d), 7.2-7.5 (4H, m); MS m/z 226 (M+1).

EXAMPLE 812

6-(2-Benzyl-2,3-dihydro-1H-isoindol-5-yloxy)-nicotinamide 0

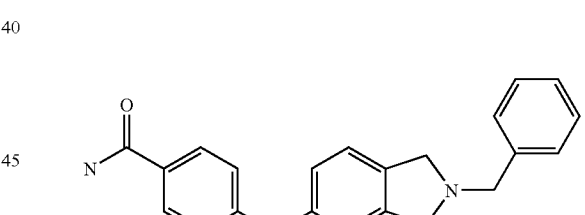

Combine in a round bottom flask equipped with stir, a Dean Stark Trap, and a nitrogen atmosphere 2-Benzyl-2,3-dihydro-1H-isoindol-5-ol (265.4 mg, 1.18 mmol), Toluene (10 mL), DMA (30 mL), K$_2$CO$_3$ (244.6 mg, 1.77 mmol), and 6-Chloronicatinamide (184.4 mg, 1.18 mmol). Reflux the reaction for 6 hours and then cool to room temperature and add ethyl acetate. Wash the Ethyl acetate layer several times with water, brine, and dry over Na$_2$SO$_4$. After concentrating under reduced pressure, Purify the mixture by reverse phase chromatography (5% to 95% 0.01% TFA buffer in acetonitrile/water) to afford 333.4 mg, 0.97 mmol (82% yield) of the title compound as a white foam: $^1$H NMR (500 MHz, d-Methanol); 4.6-4.8 (6H, m), 7.0 (1H, d), 7.1-7.2 (2H, m), 7.4-7.6 (5H, m), 8.2 (1H, d), 8.6 (1H, s); MS m/z 346 (M+1).

Intermediate 19

6-(2,3-Dihydro-1H-isoindol-5-yloxy)-nicotinamide

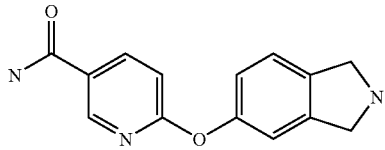

Combine 6-(2-Benzyl-2,3-dihydro-1H-isoindol-5-yloxy)-nicotinamide (230.0 mg, 0.67 mmol), EtOH (5 mL), 10% Pd—C (45.0 mg), and a Hydrogen balloon. Stir the reaction at room temperature for 168 hours at atmospheric pressure. Filter the reaction mixture through a pad of Celite using MeOH eluent and then concentrate the filtrate under reduced pressure. Add the mixture to a 2 g SCX column, wash with MeOH, and elute using 1N $NH_3$-MeOH. After concentrating under reduced pressure, purify the mixture by flash chromatography using 10% 1N $NH_3$-MeOH/DCM eluent to afford 19.2 mg, 0.08 mmol (11% yield) of the title compound as a white solid: $^1$H NMR (500 MHz, d-Methanol); 4.1-4.3 (4H, br m), 6.9-7.1 (3H, m), 7.3-7.4 (1H, m), 8.2-8.3 (1H, m), 8.6 (1H, s); MS m/z 254 (M).

EXAMPLE 813

6-(2-Phenethyl-2,3-dihydro-1H-isoindol-5-yloxy)-nicotinamide

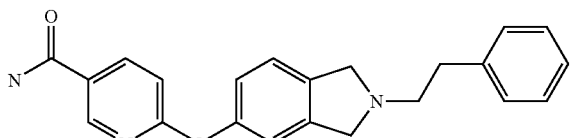

Combine 6-(2,3-Dihydro-1H-isoindol-5-yloxy)-nicotinamide (19.2 mg, 0.08 mmol), DMF (3 mL), $Et_3N$ (46 uL, 0.33 mmol), and 2-Phenethylbromide (23 uL, 0.165 mmol). Place the reaction on a shaker for 12 hours at 70° C., then cool to room temperature and concentrate under reduced pressure. Add the mixture to a 2 g SCX column, wash with MeOH, and then elute with 1 N $NH_3$-MeOH. After concentrating the mixture, purify using reverse phase chromatography (5% to 95% 0.001% TFA buffer in acetonitrile/water) to afford 9.5 mg, 0.03 mmol (33% yield) of the title compound: $^1$H NMR (500 MHz, d-Methanol); 2.8-3.2 (4H, m), 4.1-4.2 (4H, m), 6.8-7.1 (3H, m), 7.2-7.4 (6H, m), 8.2 (1H, d), 8.6 (1H, s); MS m/z 358 (M).

Intermediate 20

6-(4-Formyl-phenoxy)-nicotinic acid ethyl ester

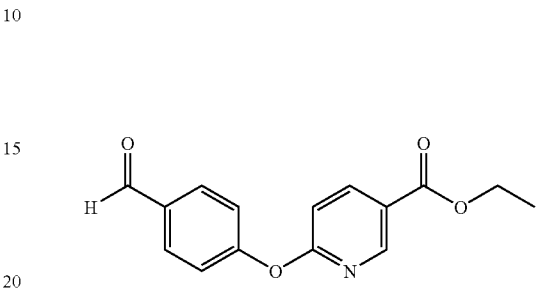

Combine in a round bottom flask equipped with a stir, Dean Stark Trap filled with toluene, and reflux condenser 4-Hydroxybenzaldehyde (2.14 g, 17.5 mmol), $K_2CO_3$ (3.63 g, 26.3 mmol), 6-Chloronicatinamide (3.25 g, 17.5 mmol) and a solution of DMA:Toluene (45:15 mL). After the reaction refluxes under nitrogen atmosphere for 3 hours, concentrate under reduced pressure and then add ethyl acetate. Wash the organic layer several times with water, then brine, and dry over $Na_2SO_4$. After concentrating under reduced pressure, flash chromatograph using 33% Hexanes, 63% Ethyl acetate eluent to afford 4.70 g, 17.4 mmol (99% yield) of the title compound: $^1$H NMR (500 MHz, $CDCl_3$); 1.4 (3H, t), 4.3-4.4 (2H, m), 7.1 (1H, d), 7.3-7.4 (2H, m), 7.9-8.0 (2H, m), 8.3 (1H, d), 9.9 (1H, s); TLC 2:1 Hexanes:Ethyl acetate $R_f$=0.55.

Intermediate 21

6-(4-Formyl-phenoxy)-nicotinic acid

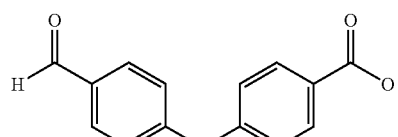

Combine 6-(4-Formyl-phenoxy)-nicotinic acid ethyl ester (1.5 g, 5.53 mmol), MeOH (5 mL), THF (5 mL), and 5N NaOH (aq) (2 mL). Reflux the reaction 18 hours and then add 1N HCl (aq) (2 mL). After concentrating the reaction on the rotovap, add Ethyl acetate to precipitate out the desired product. Filter and concentrate the ethyl acetate filtrate to afford 1.14 g (85% yield) of the title compound: TLC 1:1Hexanes: Ethyl acetate $R_f$=0.01.

Intermediate 22

4-[5-(Piperidine-1-carbonyl)-pyridin-2-yloxy]-benzaldehyde

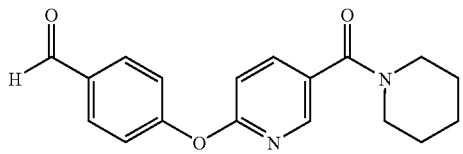

Combine 6-(4-Formyl-phenoxy)-nicotinic acid (250.0 mg, 1.03 mmol), EDC (237.0 mg, 1.23 mmol), HOBt (166.2 mg, 1.23 mmol), and Piperidine (0.10 mL, 1.03 mmol) in CH$_2$Cl$_2$ (6 mL). After reaction stirs at room temperature under a Nitrogen atmosphere for 24 hours, concentrate the reaction mixture using a rotovap, add Ethyl acetate and wash with 0.1N HCl, 10% NaHCO$_3$ Brine, and dry over Na$_2$SO$_4$. After concentrating the reaction mixture, flash chromatograph using 2:1 Ethyl acetate:Hexanes to afford 144.1 mg (45% yield) of the title compound as a white foam: $^1$H NMR (500 MHz, CDCl$_3$); 1.5-1.8 (6H, m), 3.3-3.8 (4H, m), 7.0-7.1 (1H, m), 7.3-7.4 (2H, m), 7.8-8.0 (3H, m), 8.3 (1H, m), 9.9 (1H, s); MS m/z 311 (M+1).

EXAMPLE 814

{6-[4-(Phenethylamino-methyl)-phenoxy]-pyridin-3-yl)-piperidin-1-yl-methanone

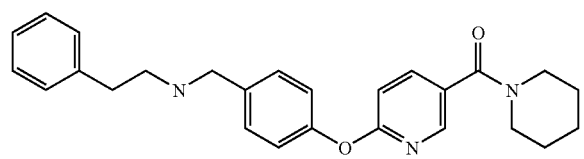

Combine 4-[5-(Piperidine-1-carbonyl)-pyridin-2-yloxy]-benzaldehyde (72.0 mg, 0.23 mmol), MeOH (2.3 mL), Trimethylorthoformate (1.6 mL), and Phenethylamine (26 uL, 0.21 mmol). After the reaction stirs for 72 hours at room temperature under a Nitrogen atmosphere, add NaBH$_4$ (10.5 mg, 0.28 mmol). After 5 hours, concentrate the reaction under reduced pressure and add the mixture to a 2 g SCX column. Wash with MeOH and then 1N NH$_3$ MeOH to afford 72.2 mg (75% yield) of the title compound: $^1$H NMR (500 MHz, CDCl$_3$); 1.5-1.8 (6H, m), 2.8-3.0 (4H, m), 3.3-3.8 (4H, m), 3.85 (2H, s), 6.8 (1H, d), 7.1-7.4 (9H, m), 8.0 (1H, d), 8.2 (1H, s); MS m/z 416 (M+1).

EXAMPLE 815

(6-{4-[(3-Methyl-butylamino)-methyl]-phenoxy}-pyridin-3-yl)-piperidin-1-yl-methanone

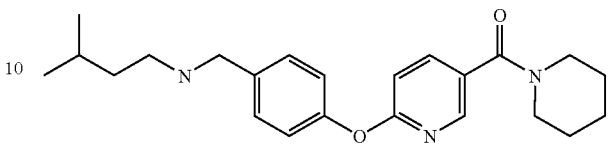

Using a method similar to Example 814, using Isoamylamine (25 uL, 0.21 mmol) gives 63.7 mg (72% yield) of the title compound: $^1$H NMR (500 MHz, CDCl$_3$); 0.9-1.0 (6H, m), 1.3-1.4 (3H, m), 1.4-1.8 (8H, br m), 2.6 (2H, t), 3.3-3.8 (4H, br m), 3.85 (2H, s), 6.8 (1H, d), 7.1 (2H, d), 7.4 (2H, d), 7.8 (1H, d), 8.2 (1H, s); MS m/z 382 (M+1).

Intermediate 23

6-[4-(Phenethylamino-methyl)-phenoxy]-nicotinic acid ethyl ester

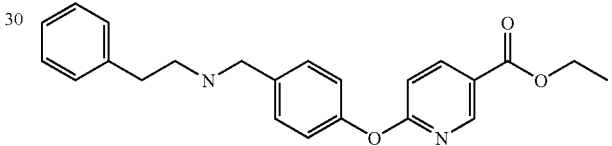

Combine 6-(4-Formyl-phenoxy)-nicotinic acid ethyl ester (0.62 g, 2.29 mmol), MeOH (12 mL), Trimethylorthoformate (8 mL), and Phenethylamine (0.26 mL, 2.06 mmol). After the reaction stirs at room temperature under a Nitrogen atmosphere for 3.5 hours, add NaBH4 (251.0 mg, 2.75 mmol). After the reaction stirs at room temperature for 12 hours, concentrate under reduced pressure and add the mixture to a 5 g SCX column. Wash the column with MeOH and elute with 1N NH$_3$ MeOH to afford 854.0 mg (99% yield) of the title compound: $^1$H NMR (500 MHz, CDCl$_3$); 2.8 (2H, t), 2.8-3.0 (4H, m), 3.8 (2H, s), 3.9 (3H, s), 6.9 (1H, d), 7.1-7.4 (9H, m), 8.3 (1H, d), 8.8 (1H, s); MS m/z 377 (M+1).

Intermediate 24

6-{4-[3-Methyl-butylamino)-methyl]-phenoxy}-nicotinic acid ethyl ester

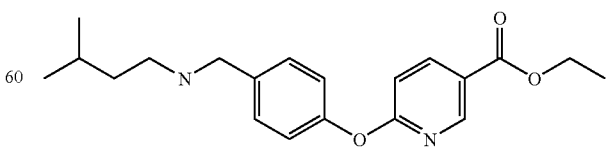

Using a method similar to Intermediate 23, using Isoamylamine (0.20 ml, 0.50 mmol) gives 854.0 mg (99% yield) of the title compound: $^1$H NMR (500 MHz CDCl$_3$); 0.8-0.9 (6H, t), 1.4-1.7 (3H, m), 2.8-3.0 (2H, m), 3.8 (2H, s), 3.9 (3H, s), 6.9 (1H, d), 7.1-7.4 (4H, m), 8.3 (1H, d), 8.8 (1H, s); MS m/z 343 (M+1).

Intermediate 25

6-{4-[(tert-Butoxycarbonyl-phenethyl-amino)-methyl]-phenoxy}-nicotinic acid ethyl ester

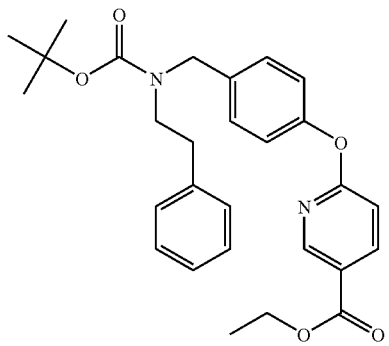

Combine 6-[4-(Phenethylamino-methyl)-phenoxy]-nicotinic acid ethyl ester (0.854 g, 2.27 mmol), THF (50 mL), Triethylamine (0.8 mL, 5.68 mmol), and Boc-anhydride (0.788 g, 2.72 mmol). After the reaction stirs at room temperature under a Nitrogen atmosphere for 2.5 hours, concentrate under reduced pressure. Add Ethyl acetate and wash with sat NH$_4$Cl (aq), brine, and then dry over Na2SO4. Concentrate the organic mixture under reduced pressure and then flash chromatograph using 8:1 to 3:1 Hexanes:Ethyl acetate gradient to afford 333.0 mg (33% yield) of title compound: $^1$H NMR (500 MHz, CDCl$_3$); 1.4 (9H, s), 2.7-2.9 (2H, m), 3.3-3.5 (2H, m), 3.9 (3H, s), 4.3-4.4 (2H, m), 6.9 (1H, d), 7.1-7.4 (9H, m), 8.3 (1H, d), 8.8 (1H, s); MS m/z 363 (M−100, Boc).

Intermediate 26

6-(4-{tert-Butoxycarbonyl-(3-methyl-butyl)-amino]-methyl}-phenoxy)-nicotinic acid ethyl ester

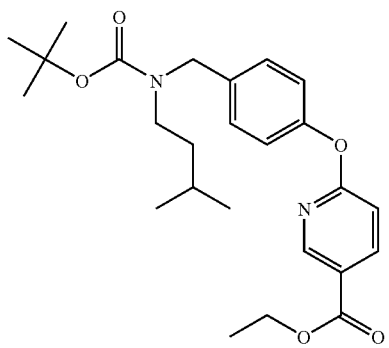

Using a method similar to Intermediate 25, using 6-{4-[3-Methyl-butylamino)-methyl]-phenoxy}-nicotinic acid ethyl ester (0.854 g, 2.27 mmol) gives 311.0 mg (31% yield) of the title compound: $^1$H NMR (500 MHz, CDCl$_3$); 0.8-0.9 (6H, m), 1.3-1.6 (12H, m), 3.0-3.3 (2H, m), 3.8 (3H, s), 4.2-4.4 (2H, m), 6.9 (1H, d), 7.0-7.3 (5H, m), 8.2 (1H, d), 8.7 (1H, s); TLC 3:1 Hexanes:Ethyl acetate R$_f$=0.34.

Intermediate 27

6-{4-[tert-Butoxycarbonyl-phenethyl-amino)-methyl]-phenoxy}-nicotinic acid

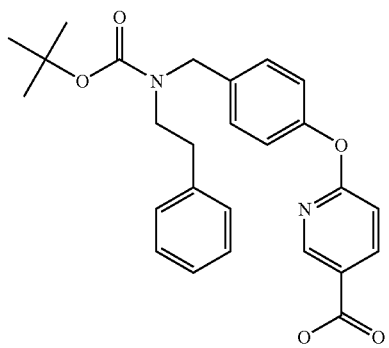

Combine 6-{4-[(tert-Butoxycarbonyl-phenethyl-amino)-methyl]-phenoxy}-nicotinic acid ethyl ester (0.333 g, 0.72 mmol), MeOH (5 mL), THF (5 mL), and 2.5N NaOH (aq) (2 mL). After the reaction refluxes under a Nitrogen atmosphere for 24 hours, concentrate under reduced pressure. Add 2.5N HCl (aq) (2 mL), Ethyl acetate, and wash with water, brine, and then dry over Na$_2$SO$_4$. Concentrate the organic mixture under reduced pressure to afford 293.0 mg (91% yield) of title compound as a white foam: $^1$H NMR (500 MHz, CDCl$_3$); 1.4 (9H, s), 2.6-2.8 (2H, m), 3.2-3.4 (2H, m), 4.2-4.4 (2H, m), 4.3-4.4 (2H, m), 6.9 (1H, d), 7.0-7.3 (9H, m), 8.3 (1H, d), 8.8 (1H, s); MS m/z 349 (M−100, Boc).

Intermediate 28

6-(4-{[tert-Butoxycarbonyl-(3-methyl-butyl)-amino]-methyl}-phenoxy)-nicotinic acid

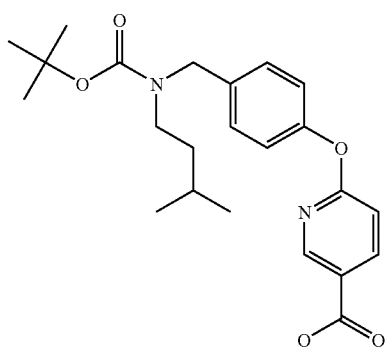

Using a method similar to Intermediate 27, using 6-(4-{tert-Butoxycarbonyl-(3-methyl-butyl)-amino]-methyl}-phenoxy)-nicotinic acid ethyl ester (0.311 g, 0.73 mmol) gives 273.4 mg (92% yield) of the title compound: $^1$H NMR (500 MHz, CDCl$_3$); 0.8-0.9 (6H, m), 1.3-1.6 (12H, m), 3.0-

Intermediate 29

[4-(5-Ethylcarbamoyl-pyridin-2-yloxy)-benzyl]-phenethyl-carbamic acid tert-butyl ester

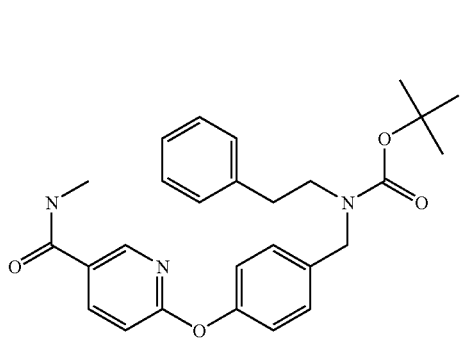

Combine 6-{4-[(tert-Butoxycarbonyl-phenethyl-amino)-methyl]-phenoxy}-nicotinic acid (0.097 g, 0.21 mmol), CH$_2$Cl$_2$ (5 mL), EDC (0.048 g, 0.25 mmol), HOBt (0.034 g, 0.25 mmol), Hunig's Base (92 uL, 0.53 mmol), and Methylamine Hydrochloride (0.014 g, 0.21 mmol) in a 7 mL reaction vial. After reactions shake for 72 hours, add 10% Citric acid, followed by 10% NaHCO$_3$, and then add the organic mixture to a Celite column. Elute with CH$_2$Cl$_2$, concentrate, and flash chromatograph using 2:1 Ethyl acetate:Hexanes eluent to afford 55.4 mg (57% yield) of the title compound: $^1$H NMR (500 MHz, CDCl$_3$); 1.4 (9H, s), 2.7-2.9 (2H, m), 3.0 (3H, s), 4.2-4.4 (2H, m), 4.3-4.5 (2H, m), 6.3-6.4 (1H, br s), 6.9 (1H, d), 7.0-7.4 (9H, m), 8.1 (1H, d), 8.6 (1H, s); MS m/z 362 (M−100, Boc).

Intermediate 30

[4-(5-Ethylcarbamoyl-pyridin-2-yloxy]-phenethyl-carbamic acid tert-butyl ester

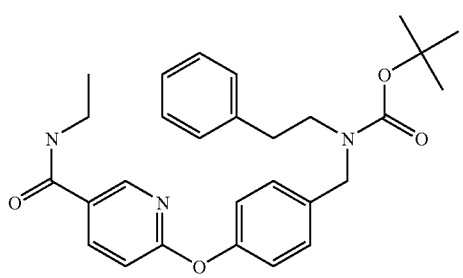

Using a method similar to Intermediate 29, using Ethylamine, 2.0 M in MeOH (0.11 mL, 0.21 mmol) gives 72.3 mg (72% yield) of the title compound: $^1$H NMR (500 MHz, CDCl$_3$); 0.2 (3H, t), 1.4 (9H, m), 2.7-2.9 (2H, m), 3.3-3.5 (4H, m), 4.2-4.4 (2H, m), 6.2 (1H, br s), 6.9 (1H, d), 7.0-7.4 (9H, m), 8.1 (1H, d), 8.6 (1H, s); MS m/z 376 (M−100, Boc).

Intermediate 31

[4-(5-Isopropylcarbamoyl-pyridin-2-yloxy)-benzyl]-phenethyl-carbamic acid tert-butyl ester

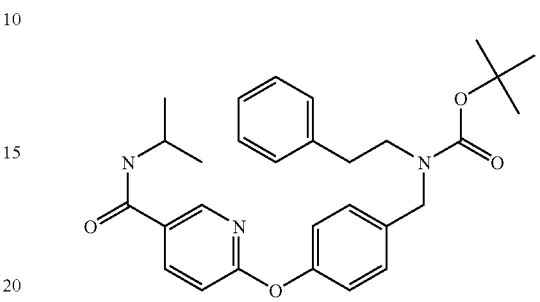

Using a method similar to Intermediate 29, using Isopropylamine, (18.0 uL, 0.21 mmol) gives 70.6 mg (69% yield) of the title compound: $^1$H NMR (500 MHz, CDCl$_3$); 1.2 (6H, d), 1.4 (9H, s), 2.6-2.8 (2H, m), 3.2-3.4 (2H, m), 4.2-4.4 (3H, m), 5.9 (1H, ds), 6.8 (1H, d), 6.9-7.0 (9H, m), 8.0 (1H, d), 8.4 (1H, s); MS m/z 390 (M−100, Boc).

Intermediate 32

(3-Methyl-butyl)-[4-(5-methylcarbamoyl-pyridin-2-yloxy)-benzyl]-carbamic acid tert-butyl ester

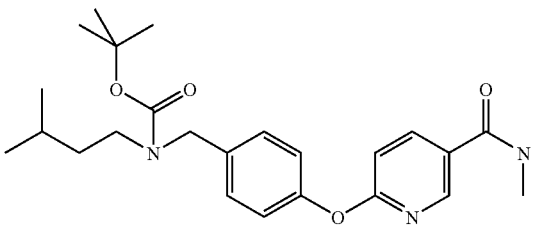

Combine 6-(4-{[tert-Butoxycarbonyl-(3-methyl-butyl)-amino]-methyl}-phenoxy)-nicotinic acid (0.090 g, 0.21 mmol), CH$_2$Cl$_2$ (5 mL), EDC (0.048 g, 0.25 mmol), HOBt (0.034 g, 0.25 mmol), Hunig's Base (92 uL, 0.53 mmol), and Methylamine Hydrochloride (0.014 g, 0.21 mmol) in a 7 mL reaction vial. After reactions shake for 72 hours, add 10% Citric acid, followed by 10% NaHCO$_3$, and then add the organic mixture to a Celite column. Elute with CH$_2$Cl$_2$, concentrate, and flash chromatograph using 2:1 Ethyl acetate: Hexanes eluent to afford 56.2 mg (63% yield) of the title compound: $^1$H NMR (500 MHz, CDCl$_3$); 0.9 (6H, d), 1.3-1.6 (12H, m), 3.0 (3H, s), 3.1-3.3 (2H, m), 4.3-4.5 (2H, m), 6.3

(1H, br s), 6.9 (1H, d), 7.1 (2H, d), 7.2-7.4 (2H, m), 8.1 (1H, d), 8.5 (1H, s); MS m/z 328 (M−100, Boc).

Intermediate 33

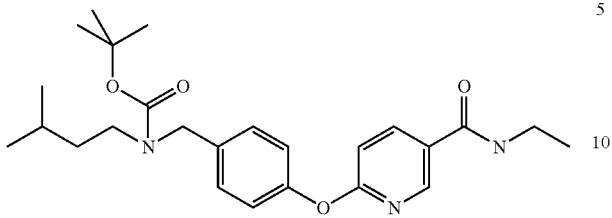

[4-(5-Ethylcarbamoyl-pyridin-2-yloxy)-benzyl]-(3-methyl-butyl)-carbamic acid tert-butyl ester Using a method similar to Intermediate 42, using Ethylamine, 2.0 M in MeOH (0.11 mL, 0.21 mmol) gives 66.7 mg (72% yield) of the title compound: $^1$H NMR (500 MHz, CDCl$_3$); 0.9 (6H, d), 1.2 (3H, t), 1.3-1.6 (12H, m), 3.1-3.3 (2H, m), 3.4-3.5 (2H, m), 4.3-4.5 (2H, m), 6.2 (1H, br s), 6.9 (1H, d), 7.1 (2H, d), 7.2-7.4 (2H, m), 8.1 (1H, d), 8.5 (1H, s); MS m/z 328 (M−10, Boc).

Intermediate 34

[4-(5-Isopropylcarbamoyl-pyridin-2-yloxy)-benzyl]-(3-methyl-butyl)-carbamic acid tert-butyl ester

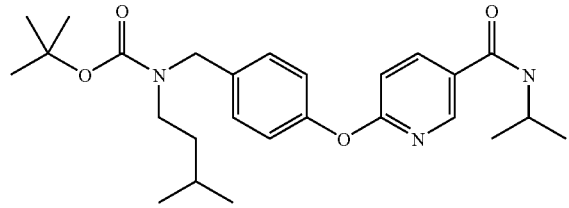

Using a method similar to Intermediate 42, using Isopropylamine, (18.0 uL, 0.21 mmol) gives 66.7 mg (41% yield) of the title compound: $^1$H NMR (500 MHz, CDCl$_3$); 0.9 (6H, d), 1.3 (6H, d), 1.3-1.6 (12H, m), 3.1-3.4 (2H, m), 4.2-4.3 (1H, d), 4.3-4.5 (2H, m), 5.9 (2H, br s), 6.9 (1H, d), 7.1 (2H, d), 7.2-7.4 (3H, m), 8.1 (1H, d), 8.5 (1H, s); MS m/z 328 (M−100, Boc).

EXAMPLE 816

N-Ethyl-6-[4-(phenethylamino-methyl)-phenoxy]-nicotinamide

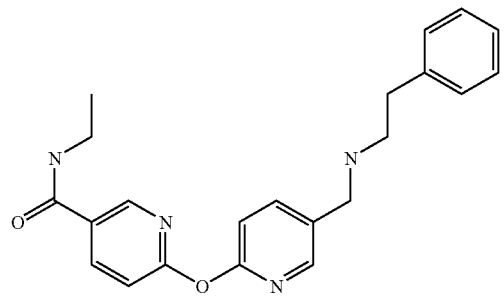

Using a method similar to Example 770, using [4-(5-Ethylcarbamoyl-pyridin-2-yloxy]-phenethyl-carbamic acid tert-butyl ester (72.3 mg, 0.15 mmol) gives 45.6 mg (80% yield) of the title compound: $^1$H NMR (500 MHz, CDCl$_3$); 1.2 (3H, t), 2.8-3.0 (4H, m), 3.4-3.6 (2H, m), 3.8 (2H, s), 6.1 (1H, br s), 6.9 (1H, d), 7.0-7.4 (9H, m), 8.1 (1H, d), 8.5 (1H, s); MS m/z 376 (M+1).

EXAMPLE 817

N-Isopropyl-6-[4-(phenethylamino-methyl)-phenoxy]-nicotinamide

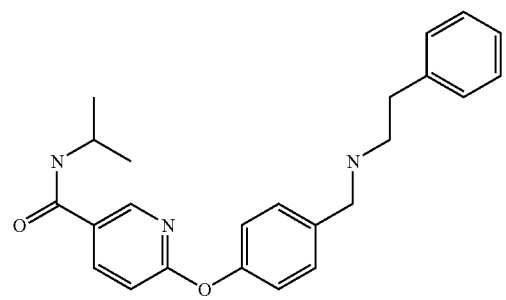

Using a method similar to Example 770, using [4-(5-Isopropylcarbamoyl-pyridin-2-yloxy)-benzyl]-phenethyl-carbamic acid tert-butyl ester (70.6 mg, 0.14 mmol) gives 64.5 mg (99% yield) of the title compound: $^1$H NMR (500 MHz, CDCl$_3$); 1.3 (6H, d), 2.8-3.0 (4H, m), 3.8 (2H, s), 4.2-4.4 (1H, m), 5.9 (1H, ds), 6.9 (1H, d), 7.0-7.4 (9H, m), 8.1 (1H, d), 8.5 (1H, s); MS m/z 390 (M+1).

EXAMPLE 818

N-Methyl-6-{4-[(3-methyl-butylamino)-methyl]-phenoxy}-nicotinamide

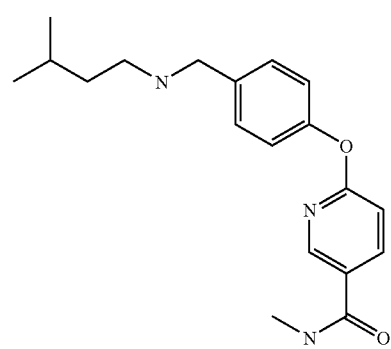

Using a method similar to Example 770, using (3-Methyl-butyl)-[4-(5-methylcarbamoyl-pyridin-2-yloxy)-benzyl]-carbamic acid tert-butyl ester (56.2 mg, 0.13 mmol) gives 33.9 mg (79% yield) of the title compound: $^1$H NMR (500 MHz, CDCl$_3$); 0.9 (6H, d), 1.3-1.5 (2H, m), 1.5-1.8 (2H, br m), 2.7 (2H, t), 2.9-3.0 (4H, m), 3.8 (2H, s), 6.2 (1H, br s), 6.9 (1H, d), 7.1 (2H, d), 7.2-7.4 (2H, m), 8.1 (1H, d), 8.5 (1H, s); MS m/z 328 (M+1).

EXAMPLE 819

N-Ethyl-6-{4-[(3-methyl-butylamino)-methyl]-phenox}-nicotinamide

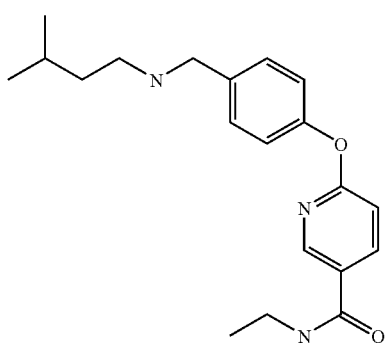

Using a method similar to Example 770, using [4-(5-Ethylcarbamoyl-pyridin-2-yloxy)-benzyl]-(3-methyl-butyl)-carbamic acid tert-butyl ester (66.7 mg, 0.15 mmol) gives 44.4 mg (86% yield) of the title compound: $^1$H NMR (500 MHz, CDCl$_3$); 0.9 (6H, d), 1.2 (3H, t), 1.3-1.5 (2H, m), 1.6-1.7 (1H, m), 2.6 (2H, t), 3.4-3.6 (2H, m), 3.8 (2H, s), 6.2 (1H, br s), 6.9 (1H, d), 7.1 (2H, d), 7.2-7.4 (2H, m), 8.1 (1H, d), 8.5 (1H, s); MS m/z 342 (M+1).

EXAMPLE 820

N-Isopropyl-6-{4-[(3-methyl-butylamino)-methyl]-phenoxy}-nicotinamide

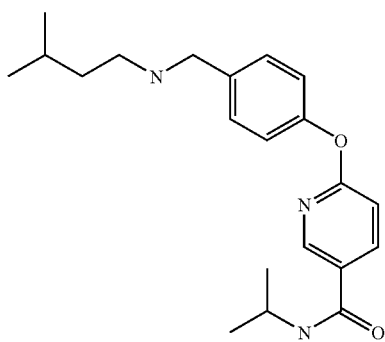

Using a method similar to Example 770 using [4-(5-Isopropylcarbamoyl-pyridin-2-yloxy)-benzyl]-(3-methyl-butyl)-carbamic acid tert-butyl ester (39.6 mg, 0.09 mmol) gives 26.0 mg (84% yield) of the title compound: $^1$H NMR (500 MHz, CDCl$_3$); 0.9 (6H, d), 1.3 (6H, d), 1.4-1.5 (2H, m), 1.5-1.7 (2H, m), 2.7 (2H, t), 3.8 (2H, s), 4.2-4.3 (1H, m), 5.9 (1H, br s), 6.9 (1H, d), 7.1 (2H, d), 7.2-7.4 (3H, m), 8.1 (1H, d), 8.5 (1H, s); MS m/z 356 (M+1).

Intermediate 35

1-(4-Methoxy-benzyl)-piperidine-3-carboxylic acid ethyl ester

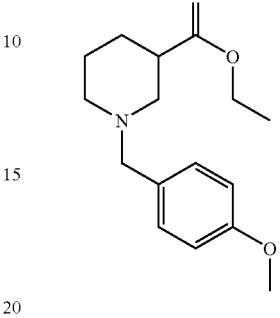

Combine Ethyl nipecotate (9.9 mL, 63.6 mmol), K$_2$CO$_3$ (13.2 g, 95.4 mmol), and DMF (300 mL) at room temperature under a Nitrogen atmosphere. Heat reaction mixture to 70° C. for 30 minutes then add 4-Methoxybenzyl chloride (9.5 mL, 69.9 mmol). Stir the reaction for 5 hours at 70° C. then cool the reaction mixture to room temperature and stir for an additional 12 hours. Add Ethyl acetate to the reaction mixture and extract with water and then brine. Dry the organic layer over Na$_2$SO$_4$. Concentrate under reduced pressure and flash chromatograph using 3:1 Hexanes:Ethyl acetate to give 14.6 g (82% yield) of the title compound: $^1$H NMR (500 MHz, CDCl$_3$); 1.2 (3H, t), 1.4-1.6 (2H, m), 1.6-1.7 (1H, m), 1.9-2.1 (2H, m), 2.2 (1H, t), 1.5-1.8 (2H, m), 2.9 (1H, d), 3.5 (2H, q), 3.8 (3H, s), 4.1 (2H, dd), 6.8 (2H, d), 7.2 (2H, d); MS m/z 278 (M+1).

Intermediate 36

1-(4-Methoxy-benzyl)-piperidine-3-carboxylic acid methoxy-methyl-amide

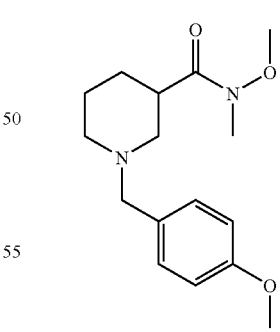

Combine 1-(4-Methoxy-benzyl)-piperidine-3-carboxylic acid ethyl ester (9.3 g, 33.5 mmol), THF (200 mL), N,O-Dimethylhydroxylamine hydrochloride (4.9 g, 50.3 mmol) at −10° C. (Acetone/ice bath) under a Nitrogen atmosphere. By dropwise addition, add Isopropylmagnesium chloride (50.3 mL, 100.6 mmol). Stir the reaction for 6 hours allowing the reaction mixture to warm to room temperature. Quench the reaction mixture with sat NH$_4$Cl (aq) and extract product from the water using Ethyl acetate. Wash the organic layer with brine and then dry over Na$_2$SO$_4$. Concentrate under reduced pressure and flash chromatograph using 1:1 Hexanes:Ethyl acetate and then 1:1 Hexanes:Ethyl acetate with 3% 1N NH$_3$ MeOH to give 9.13 g (93% yield) of the title compound: $^1$H NMR (500 MHz, CDCl$_3$); 1.4-1.7 (3H, m), 1.8 (1H, d), 1.9 (1H, t), 2.1 (1H, t), 2.8-3.0 (3H, m), 3.1 (3H, s), 3.5 (2H, d), 3.6 (3H, s), 3.8 (3H, s), 6.8 (2H, d), 7.2 (2H, d); MS m/z 293 (M+1).

Intermediate 37

1-[1-(4-Methoxy-benzyl)-piperidin-3-yl]-propan-1-one NF7-AOO855-198

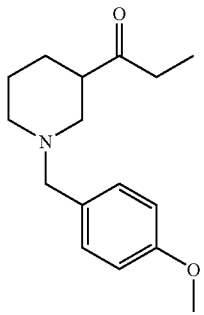

Combine 1-(4-Methoxy-benzyl)-piperidine-3-carboxylic acid methoxy-methyl-amide (416.0 mg, 1.42 mmol) and THF (10 mL) at −78° C. under a Nitrogen atmosphere. By dropwise addition, add Ethylmagnesium bromide (0.56 mL, 1.7 mmol). Stir the reaction for 12 hours allowing the reaction mixture to warm to room temperature and then add another addition of Ethylmagnesium bromide (0.56 ml, 1.7 mmol) at room temperature. After the reaction stirs for 1 hour, quench the reaction mixture with sat NH$_4$Cl (aq) and extract product from the water using Ethyl acetate. Wash the organic layer with brine and then dry over Na$_2$SO$_4$. Concentrate under reduced pressure and add to an SCX (5 g) column pre-treated with 5% AcOH/MeOH. Wash with MeOH and elute product using 1N NH$_3$ MeOH to give 280.6 mg (76% yield) of the title compound: $^1$H NMR (500 MHz, d-MeOH); 0.9 (3H, q), 1.2-1.4 (1H, m), 1.5-1.7 (1H, m), 1.7-1.8 (1H, m), 1.9 (1H, d), 1.9-2.1 (2H, m), 2.4-2.5 (2H, m), 2.6-2.7 (1H, m), 2.8 (1H, d), 2.9 (1H, d), 3.5 (2H, s), 3.8 (3H, s), 6.8 (2H, d), 7.2 (2H, d); MS m/z 262 (M+1).

Intermediate 38

1-(4-Methoxy-benzyl)-3-propyl-piperidine

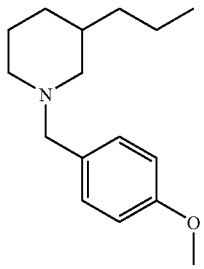

Combine 1-[1-(4-Methoxy-benzyl)-piperidin-3-yl]-propan-1-one (277.3 mg, 1.07 mmol), Diethylene glycol (10 mL), KOH (178.0 mg, 3.18 mmol), and Hydrazine-monohydrate (1.0 mL) at room temperature under a Nitrogen atmosphere. Heat the reaction mixture to 120° C. for 2 hours and then 220° C. for 4 hours. Cool reaction to room temperature and then pour the reaction mixture over sat NH$_4$Cl (aq). Extract with Ethyl acetate, wash with brine, and dry over Na$_2$SO$_4$. Concentrate under reduced pressure and flash chromatograph using 3% 1N NH$_3$ MeOH in CH$_2$Cl$_2$ to give 105.2 mg (40% yield) of the title compound: $^1$H NMR (500 MHz, CDCl$_3$); 0.9 (3H, t), 1.1-1.4 (4H, m), 1.5-1.7 (3H, m), 1.7 (1H, d), 1.9 (1H, td), 2.7-2.9 (2H, m), 3.5 (2H, dd), 3.8 (3H, s), 6.8 (2H, d), 7.2 (2H, d); MS m/z 248 (M+1).

EXAMPLE 821

6-[4-(3-Propyl-piperidin-1-ylmethyl)-phenoxy]-nicotinamide

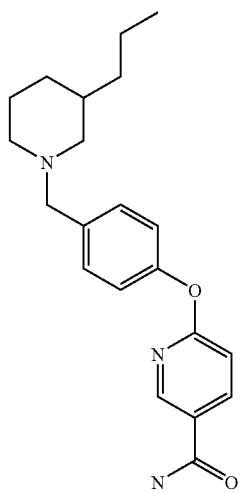

Combine 1-(4-Methoxy-benzyl)-3-propyl-piperidine (105.2 mg, 0.43 mmol), Ethanol (50 mL), 20% Pd(OH)$_2$/C (75.0 mg), and a Hydrogen at 30° C. under 50-60 psi for 12 hours on a Parr shaker. Filter the reaction mixture and then add 5% AcOH/MeOH (3 mL), 6-(4-Formyl-phenoxy)-nicotinonitrile (Intermediate 51) (40.0 mg, 0.31 mmol), and NaCNBH$_3$ (83.7 mg, 0.34 mmol). Stir the reaction at room temperature for 72 hours and then concentrate the reaction mixture under reduced pressure. Add the reaction mixture to an SCX Column (2 g), wash with methanol, and elute with 1N NH$_3$ MeOH. Concentrate under reduced pressure and flash chromatograph using 3% 1N NH$_3$ MeOH in CH$_2$Cl$_2$ to give 19.8 mg (18% yield) of the title compound: $^1$H NMR (500 MHz, CDCl$_3$); 0.8-0.9 (4H, m), 1.0-1.4 (5H, m), 1.5-1.8 (4H, m), 1.9-2.1 (1H, br s), 2.8-3.0 (2H, br s), 3.4-3.7 (2H, br d), 6.9 (1H, d), 7.1 (2H, d), 7.3-7.5 (2H, m), 8.1 (1H, d), 8.6 (1H, s); MS m/z 354 (M+1).

Intermediate 39

6-(4-Formyl-phenoxy)-nicotinonitrile

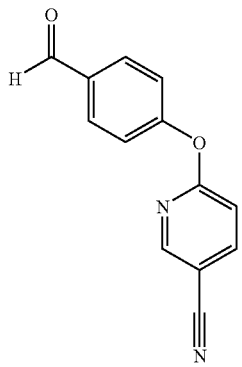

Combine 4-Hydroxybenzaldehyde (8.0 g, 65.5 mmol), 6-Chloronicotinonitrile (9.07 g, 65.5 mmol), powdered $K_2CO_3$ (13.6 g, 98.3 mmol), and DMA/Toluene (80/240 mL) in a 500 mL RB flask equipped with a stir, reflux condenser and a Dean Stark Trap. Reflux the reaction mixture for several hours under a Nitrogen atmosphere then cool to room temperature and quench with sat $NH_4Cl$ (aq). Add Ethyl acetate to extract the product and wash several times with water and then brine. Dry the organic layer over $Na_2SO_4$. Concentrate and flash chromatograph using 2:1 Hexanes:Ethyl acetate to give 13.2 g (88% yield) of the title compound: $^1H$ NMR (500 MHz, $CDCl_3$); 7.1 (1H, d), 7.3-7.4 (2H, m), 7.9-8.0 (3H, m), 8.5 (1H, d), 10.0 (1H, s); MS m/z 225 (M+1).

Intermediate 40

6-(4-Formyl-phenoxy)-nicotinamide

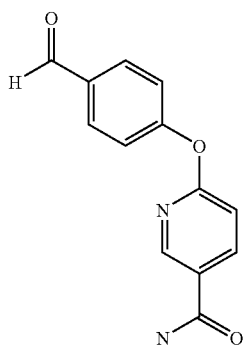

Combine 6-(4-Formyl-phenoxy)-nicotinonitrile (3.02 g, 13.5 mmol), powdered $K_2CO_3$ (0.93 g, 6.7 mmol), and DMSO (100 mL) in a RB flask and add $H_2O_2$, 30% wt. Aq (4.05 mL, 13.5 mmol) by dropwise addition at 0° C. Stir the reaction mixture for 3 hours allowing it to come to room temperature then quench the reaction slowly at 0° C. with water. Extract the product out of the water layer with ethyl acetate several times and then wash with brine. Dry over $Na_2SO_4$ and concentrate under reduced pressure to give 2.78 g (95% yield) of the title compound: $^1H$ NMR (500 MHz, DMSO); 7.2 (1H, d), 7.3-7.4 (2H, m), 7.5 (1H, br s), 7.9-8.0 (2H, m), 8.1 (1H, br s), 8.3 (1H, d), 8.7 (1H, s), 10.0 (1H, s); MS m/z 243 (M+1).

Intermediate 41

2-{1-(4-Methoxy-benzyl)-piperidin-3-yl]-propan-2-ol

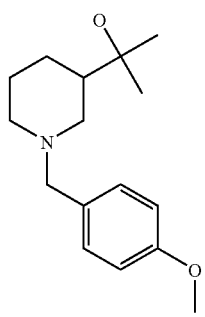

Combine 1-(4-Methoxy-benzyl)-piperidine-3-carboxylic acid ethyl ester (1.36 g, 4.9 mmol) and THF (10 mL) at −10° C. (Acetone/ice bath) under a Nitrogen atmosphere. By dropwise addition, add Methylmagnesium bromide (6.5 mL, 19.6 mmol). Stir the reaction for 3 hours at room temperature and then quench the reaction mixture with sat $NH_4Cl$ (aq) and extract product from the water using Ethyl acetate. Wash the organic layer with brine and then dry over $Na_2SO_4$. Concentrate under reduced pressure and flash chromatograph using 3% 1N $NH_3$-MeOH in $CH_2Cl_2$ to give 832.0 mg (65% yield) of the title compound: $^1H$ NMR (500 MHz, d-MeOH); 1.1 (6H, d), 1.4-1.7 (2H, m), 1.7-2.0 (4H, m), 2.8 (1H, d), 3.1 (1H, d), 3.4 (1H, s), 3.5 (2H, d), 3.8 (2H, s), 4.8 (3H, s), 6.8 (2H, d), 7.2 (2H, d); MS m/z 264 (M+1).

Intermediate 42

3-Isopropylidene-1-(4-methoxy-benzyl)-piperidine

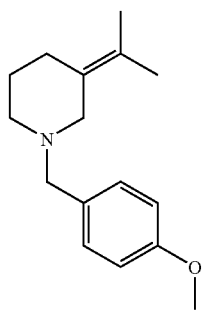

Combine 2-1{-(4-Methoxy-benzyl)-piperidin-3-yl]-propan-2-ol (0.564 g, 2.14 mmol) and 1:1 $Et_3SiH:TFA$ (8 mL) at room temperature. Reflux the reaction for 72 hours under a Nitrogen atmosphere and then concentrate under reduced pressure and flash chromatograph using 3% 1N $NH_3$-MeOH in $CH_2Cl_2$ to give 400.0 mg (76% yield) of the title compound: $^1H$ NMR (500 MHz, $CDCl_3$); 1.5-1.6 (8H, d), 2.2 (2H, t), 2.5 (2H, br s), 3.0 (2H, br s), 3.5 (2H, br s), 3.8 (3H, s), 6.8 (2H, d), 7.2 (2H, d); MS m/z 246 (M+1).

EXAMPLE 822

6-[4-(3-Isopropyl-piperidin-1-ylmethyl)-phenoxy]-nicotinamide

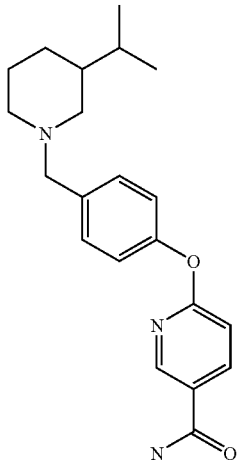

Combine 3-Isopropylidene-1-(4-methoxy-benzyl)-piperidine (227.0 mg, 0.92 mmol), Ethanol (50 mL), 20% Pd(OH)$_2$/C (75.0 mg), and a Hydrogen at 30° C. under 50-60 psi for 12 hours on a Parr shaker. Filter the reaction mixture and then add 5% AcOH/MeOH (3 mL), 6-(4-Formyl-phenoxy)-nicotinonitrile (Intermediate 51) (104.0 mg, 0.43 mmol), and NaCNBH$_3$ (49.0 mg, 0.78 mmol). Stir the reaction at room temperature for 72 hours and then concentrate the reaction mixture under reduced pressure. Add the reaction mixture to an SCX Column (2 g), wash with methanol, and elute with 1N NH$_3$ MeOH. Concentrate under reduced pressure and purify by reverse phase chromatography using 5 to 95% 0.001% TFA in CH$_3$CN/H$_2$O to give 37.2 mg (11% yield) of the title compound: $^1$H NMR (500 MHz, d-MeOH); 0.9 (6H, dd), 0.9-1.1 (1H, m), 1.3-1.6 (3H, m), 1.7-1.9 (3H, m), 1.9-2.0 (1H, m), 2.9 (1H, d), 3.0 (1H, d), 3.5 (2H, dd), 6.9 (1H, d), 7.1 (2H, d), 7.4 (2H, d), 8.2 (1H, d), 8.6 (1H, s); MS m/z 354 (M+1).

Intermediate 43

1-[1-(4-Methoxy-benzyl)-piperidin-3-yl]-butan-1-one

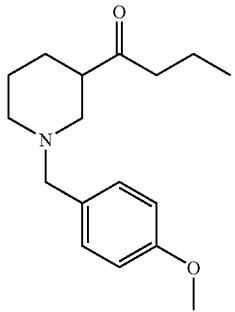

Combine 1-(4-Methoxy-benzyl)-piperidine-3-carboxylic acid methoxy-methyl-amide (401.0 mg, 1.37 mmol) and THF (10 mL) at 0° C. under a Nitrogen atmosphere. By dropwise addition, add Propylmagesium chloride (4.0 mL, 8.22 mmol). Reflux the reaction for 5 hours then cool the reaction to room temperature and quench the reaction mixture with sat NH$_4$Cl (aq) and extract product from the water using Ethyl acetate. Wash the organic layer with brine and then dry over Na$_2$SO$_4$. Concentrate under reduced pressure and add to an SCX (5 g) column pre-treated with 5% AcOH/MeOH. Wash with MeOH and elute product using 1N NH$_3$ MeOH to give 356.0 mg (94% yield) of the title compound: $^1$H NMR (500 MHz, CDCl$_3$); 0.8 (3H, t), 1.3 (1H, qd), 1.4-1.5 (3H, m), 1.6-1.8 (1H, n), 1.9 (1H, dd), 2.0 (1H, td), 2.1 (1H, t), 2.4 (2H, t), 2.5-2.6 (1H, m), 2.7 (1H, d), 2.9 (1H, d), 3.4 (2H, dd), 3.8 (3H, s), 6.8 (2H, d), 7.2 (2H, d); TLC 4% 1N NH$_3$ MeOH:CH$_2$Cl$_2$ R$_f$=0.42.

Intermediate 44

3-Butyl-1-(4-methoxy-benzyl)-piperidine

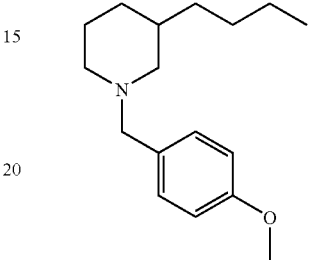

Combine 1-[1-(4-Methoxy-benzyl)-piperidin-3-yl]-butan-1-one (356.0 mg, 0.95 mmol), Diethylene glycol (15 mL), KOH (479.0 mg, 8.54 mmol), and Hydrazine-monohydrate (1.8 mL) at room temperature under a Nitrogen atmosphere. Heat the reaction mixture to 120° C. for 2 hours and then 220° C. for 24 hours. Cool reaction to room temperature and then pour the reaction mixture over sat NH$_4$Cl (aq). Extract with Ethyl acetate, wash with brine, and dry over Na$_2$SO$_4$. Concentrate under reduced pressure and flash chromatograph using 3% 1N NH$_3$ MeOH in CH$_2$Cl$_2$ to give 220.7 mg (89% yield) of the title compound: $^1$H NMR (500 MHz, CDCl$_3$); 0.7-0.9 (3H, m), 1.1-1.4 (4H, m), 1.5-1.7 (4H, m), 1.7 (1H, d), 1.9 (1H, t), 2.8 (2H, t), 3.4 (2H, dd), 3.6-3.7 (3H, m), 3.8 (3H, s), 6.8 (2H, d), 7.2 (2H, d); MS m/z 262 (M+1).

EXAMPLE 822

6-[4-(3-Butyl-piperidin-1-ylmethyl)-phenoxy]-nicotinamide

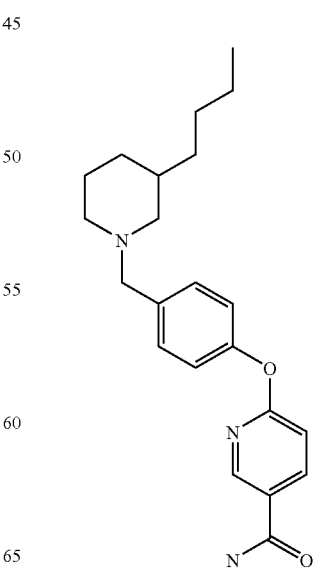

Using a method similar to Example 822, using 3-Butyl-1-(4-methoxy-benzyl)-piperidine (220.7 mg, 0.89 mmol) gives 24.6 mg (9% yield) of the title compound: ¹H NMR (500 MHz, CDCl₃); 0.8-0.9 (4H, m), 1.1-1.4 (6H, m), 1.5-1.7 (4H, m), 1.8 (1H, d), 1.9 (1H, t), 2.9-3.0 (2H, m), 3.5 (2H, dd), 5.9-6.2 (2H, br s), 6.9 (1H, d), 7.1 (2H, d), 7.3-7.4 (2H, m), 8.2 (1H, d), 8.5 (1H, s); MS m/z 368 (M+1).

Intermediate 45

1-[1-(Methoxy-benzyl)-piperidin-3-yl]-ethanone

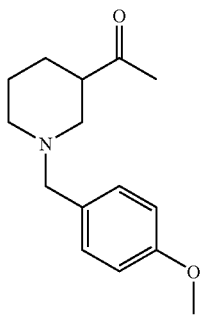

Using a method similar to Intermediate 43, using Methylmagnesium bromide (7.4 mL, 22.16 mmol) gives 1.37 g (73% yield) of the title compound: ¹H NMR (500 MHz, CDCl₃); 1.4 (1H, qd), 1.5-1.6 (1H, m), 1.6-1.7 (1H, m), 1.8-1.9 (1H, m), 2.0 (1H, td), 2.1 (3H, s), 2.5-2.6 (1H, m), 2.7 (2H, d), 2.9 (1H, d), 3.5 (2H, dd), 3.8 (3H, s), 6.8 (2H, d), 7.2 (2H, d); MS m/z 248 (M+1).

Intermediate 46

3-Ethyl-1-(4-methoxy-benzyl)-piperidine

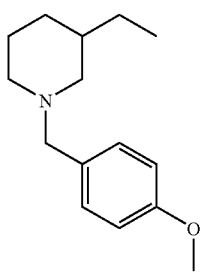

Using a method similar to Intermediate 44, using 1-[1-(Methoxy-benzyl)-piperidin-3-yl]-ethanone (1.0 g, 4.03 mmol) gives 388.3 mg (42% yield) of the title compound: ¹H NMR (500 MHz, CDCl₃); 0.8-0.9 (4H, m), 1.1-1.2 (2H, m), 1.4-1.6 (4H, m), 1.7 (1H, d), 1.9 (1H, td), 2.8 (2H, t), 3.4 (2H, dd), 3.8 (3H, s), 6.8 (2H, d), 7.2 (2H, d); MS m/z 234 (M+1).

EXAMPLE 824

6-[4-(3-Ethyl-piperidin-1-ylmethyl)-phenoxy]-nicotinamide

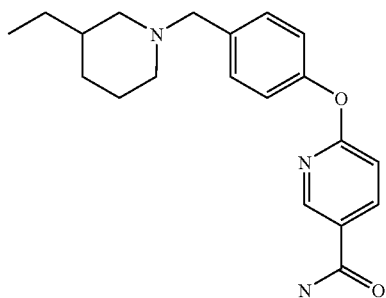

Using a method similar to Example 822, using 3-Ethyl-1-(4-methoxy-benzyl)-piperidine (388.3 mg, 1.66 mmol) gives 45.8 mg (21% yield) of the title compound: ¹H NMR (500 MHz, CDCl₃); 0.8-0.9 (4H, m), 1.1-1.3 (2H, m), 1.4-1.6 (4H, m), 1.7 (1H, d), 1.9 (1H, t), 2.8 (2H, t), 3.5 (2H, dd), 6.0-6.2 (2H, br s), 6.9 (1H, d), 7.1 (2H, d), 7.3-7.4 (2H, m), 8.2 (1H, d), 8.5 (1H, s); MS m/z 340 (M+1).

EXAMPLE 825

6-[4-(3,3-Dimethyl-piperidin-1-ylmethyl)-phenoxy]-nicotinamide

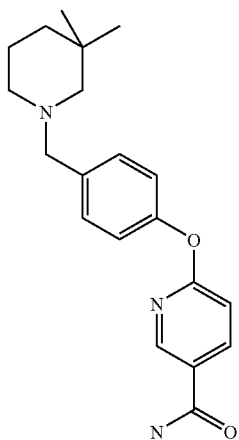

Combine 5% AcOH/MeOH (3 mL), 6-(4-Formyl-phenoxy)-nicotinonitrile (Intermediate 51) (242.24 mg, 1.0 mmol), and NaCNBH₃ (113.1 mg, 1.8 mmol). Stir the reaction at room temperature for 3 hours and then concentrate the reaction mixture under reduced pressure. Add the reaction mixture to an SCX Column (2 g), wash with methanol, and elute with 1N NH, MeOH. Concentrate under reduced pressure and purify by reverse phase chromatography using 5 to 95% 0.001% TFA in CH₃CN/H₂O to give 168.0 mg (55% yield) of the title compound: ¹H NMR (500 MHz, CDCl₃); 0.9 (6H, s), 1.2-1.3 (2H, m), 1.1.5-1.8 (4H, m), 2.0-2.1 (2H, m), 2.2-2.4 (2H, m), 3.4-3.5 (2H, m), 6.9 (1H, d), 7.1 (1H, d), 7.2 (1H, d), 7.4 (1H, d), 7.5 (1H, d), 8.2 (1H, d), 8.6 (1H, d); MS m/z 340 (M+1).

EXAMPLE 826

6-[4-(3-Trifluoromethyl-piperidin-1-ylmethyl)-phenoxy]-nicotinamide

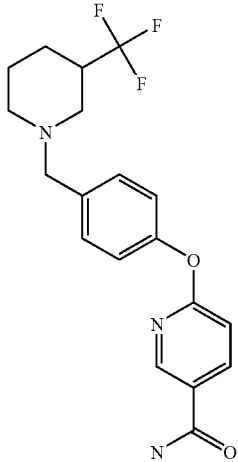

Combine 5% AcOH/MeOH (3 mL), 6-(4-Formyl-phenoxy)-nicotinonitrile (Intermediate 51) (120.0 mg, 0.33 mmol), and NaCNBH$_3$ (184.0 mg, 0.46 mmol). Stir the reaction at room temperature for 12 hours and then concentrate the reaction mixture under reduced pressure. Add the reaction mixture to an SCX Column (2 g), wash with methanol, and elute with 1N NH$_3$ MeOH. Concentrate under reduced pressure and purify by reverse phase chromatography using 5 to 95% 0.001% TFA in CH$_3$CN/H$_2$O to give 46.6 mg (26% yield) of the title compound: $^1$H NMR (500 MHz, d-MeOH); 1.2-1.4 (1H, m), 1.5-1.7 (1H, m), 1.7-1.9 (1H, m), 1.9-2.1 (2H, m), 2.3-2.5 (1H, m), 2.9 (1H, d), 3.1 (1H, d), 3.6 (2H, s), 6.9 (1H, d), 7.1 (2H, d), 7.4 (2H, d), 8.2 (1H, d), 8.6 (1H, d); MS m/z 380 (M+1).

EXAMPLE 827

6-[4-(3-Spiro-[1-(3,4-dihydro)naphthalene]-piperidin-1-ylmethyl)-phenoxy]-nicotinamide

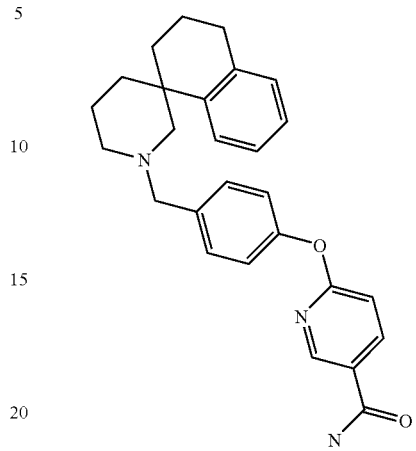

Combine 5% AcOH/MeOH (3 mL), 6-(4-Formyl-phenoxy)-nicotinonitrile (Intermediate 51) (126.4 mg, 0.52 mmol), and NaCNBH$_3$ (65.3 mg, 1.04 mmol). Stir the reaction at room temperature for 12 hours and then concentrate the reaction mixture under reduced pressure. Add the reaction mixture to an SCX Column (2 g), wash with methanol, and elute with 1N NH$_3$ MeOH. Concentrate under reduced pressure and purify by reverse phase chromatography using 5 to 95% 0.001% TFA in CH$_3$CN/H$_2$O to give 105.2 mg (47% yield) of the title compound: $^1$H NMR (500 MHz, d-MeOH); 1.5-1.8 (5H, m), 1.9-2.0 (2H, m), 2.1-2.2 (2H, m), 2.3-2.4 (1H, m), 2.5-2.8 (3H, m), 2.9 (1H, d), 3.3-3.4 (2H, m), 3.5-3.6 (1H, m), 6.9-7.2 (7H, m), 7.3-7.5 (2H, m), 8.2 (1H, d), 8.6 (1H, d); MS m/z 428 (M+1).

We claim:

1. A method of treating irritable bowel syndrome in a patient in need thereof, which comprises administering a therapeutically effective amount of 5-(2-Methoxy-4-{[2-(tetrahydro-pyran-4-yl)-ethylamino]-methyl}-phenoxy)-pyrazine-2-carboxamide, or a pharmaceutically acceptable salt thereof, to said patient.

2. The method of claim 1 wherein said patient is human.

* * * * *

UNITED STATES PATENT AND TRADEMARK OFFICE
CERTIFICATE OF CORRECTION

PATENT NO. : 7,560,463 B2 Page 1 of 1
APPLICATION NO. : 12/052994
DATED : July 14, 2009
INVENTOR(S) : Charles Howard Mitch It is certified that error appears in the above-identified patent and that said Letters Patent is hereby corrected as shown below:

First Page, Col. 2, Line 10 (Other Publications): Delete "Gilmans's" and insert -- Gilman's --, therefor.

First Page, Col. 2, Line 29 (Other Publications): Delete "-4(3" and insert -- -4-(3 --, therefor.

First Page, Col. 2, Line 33 (Other Publications): Delete "adminstration" and insert -- administration --, therefor.

Signed and Sealed this

Fifth Day of January, 2010

David J. Kappos
*Director of the United States Patent and Trademark Office*